US008716445B2

(12) United States Patent
Lal et al.

(10) Patent No.: US 8,716,445 B2
(45) Date of Patent: May 6, 2014

(54) COMPOSITIONS COMPRISING SIGNAL PEPTIDE-CONTAINING PROTEINS

(75) Inventors: Preeti G. Lal, Santa Clara, CA (US); Y. Tom Tang, San Jose, CA (US); Gina A. Gorgone Simone, Earleville, MD (US); Neil C. Corley, Castro Valley, CA (US); Karl J. Guegler, Menlo Park, CA (US); Mariah R. Baughn, Los Angeles, CA (US); Ingrid E. Akerblom, Lansdale, PA (US); Janice K. Au-Young, Brisbane, IL (US); Henry Yue, Sunnyvale, CA (US); Chandra S. Arvizu, San Diego, CA (US); Roopa M. Reddy, Fremont, CA (US); Jennifer L. Hillman, Santa Cruz, CA (US); Olga Bandman, Mountain View, CA (US)

(73) Assignee: Incyte Corporation, Palo Alto, CA (US)

( * ) Notice: Subject to any disclaimer, the term of this patent is extended or adjusted under 35 U.S.C. 154(b) by 79 days.

(21) Appl. No.: 13/397,592

(22) Filed: Feb. 15, 2012

(65) Prior Publication Data

US 2013/0244927 A1    Sep. 19, 2013

Related U.S. Application Data

(60) Division of application No. 12/457,389, filed on Jun. 9, 2009, now Pat. No. 8,153,398, which is a continuation of application No. 11/905,820, filed on Oct. 4, 2007, now abandoned, which is a division of application No. 10/820,474, filed on Apr. 7, 2004, now abandoned, which is a division of application No. 09/720,533, filed as application No. PCT/US99/14484 on Jun. 25, 1999, now abandoned.

(60) Provisional application No. 60/090,762, filed on Jun. 26, 1998, provisional application No. 60/094,983, filed on Jul. 31, 1998, provisional application No. 60/102,686, filed on Oct. 1, 1998, provisional application No. 60/112,129, filed on Dec. 11, 1998.

(51) Int. Cl.
*C07K 1/00*    (2006.01)
*C07K 14/00*   (2006.01)
*C07K 17/00*   (2006.01)

(52) U.S. Cl.
USPC ......................................................... 530/350

(58) Field of Classification Search
None
See application file for complete search history.

(56) References Cited

U.S. PATENT DOCUMENTS 5,474,796 A    12/1995   Brennan
5,605,662 A    2/1997    Heller et al.
6,084,088 A    7/2000    Sheppard et al.
7,368,531 B2   5/2008    Rosen et al.
2004/0018980 A1  1/2004  Gurney et al.

FOREIGN PATENT DOCUMENTS

| WO | WO 94/01548 | 1/1994 |
| WO | WO 95/25116 | 9/1995 |
| WO | WO 84/03564 | 12/1995 |
| WO | WO 95/35505 | 12/1995 |
| WO | WO 99/31117 | 6/1999 |
| WO | WO 00/55350 | 9/2000 |

OTHER PUBLICATIONS

U.S. Appl. No. 60/090,762, filed Jun. 26, 1998, Preeti et al.
U.S. Appl. No. 60/094,983, filed Jul. 31, 1998, Akerblom.
U.S. Appl. No. 60/102,686, filed Oct. 1, 1998, Tang et al.
U.S. Appl. No. 60/112,129, filed Dec. 11, 1998, Tang.
Alberts, B. et al., "Signal Peptides and Signal Patches Direct Proteins to the Correct Cellular Address," (1994), *Molecular Biology of the Cell*, Garland Publishing, New York, NY, pp. 557-560,582-592.
Ayad, S. et al., (1994), The Extracellular Matrix Facts Book, Academic Press, San Diego, CA, pp. 2-16.
Bolton, A.E. and W.M. Hunter, "The Labelling of Proteins to High Specific Radioactivates by Conjugation to a $^{125}$I-Containing Acylating Agent," (1973) *Biochem. J.* 133:529-539.
Broglie, R. et al., "Light-Regulated Expression of a Pea Ribulose-1,5-Bisphosphate Carboxylase Small Subunit Gene in Transformed Plant Cells," (1984) *Science* 224: 838-843.
Burton, D.R., "A large array of human monoclonal antibodies to type 1 human immunodeficiency virus from combinatorial libraries of asymptomatic seropositive individuals," (1991) *Proc. Natl. Acad. Sci. USA* 88:10134-10137.
Caruthers, M.H. et al., "New chemical methods for synthesizing polynucleotides," (1980) *Nucleic Acids Symp. Ser.* 7:215-223.
Chicsz, R.M. and F.Z. Regnier, "High-Performance Liquid Chromatography: Effective Proteins Purification by Various Chromatographic Modes," (1990) *Methods Enzymol.* 182:392-421.
Colbere-Garapin, F. et al., "A New Dominant Hybrid Selective Marker for Higher Eukaryotic Cells," (1981) *J. Mol. Biol.* 150:1-14.
Cole, S.P. et al., "Human monoclonal antibodies," (1984) *Mol. Cell Biol.* 62:109-120.
Coruzzi, G. et al., "Tissue-Specific and Light-Regulated Expression of a Pea Nuclear Gene Encoding the Small Subunit of rebulose-I,5-Bisphosphate Carboxylate," (1984) *EMBO J.* 3:1671-1680.
Cote, R.J. et al., "Generation of human monoclonal antibodies reactive with cellular antig," (1983) *Proc. Natl. Acad. Sci. USA* 80:2026-2030.
Creighton, "Proteins, Structure and Molecular Properties," *W.H. Freeman, NY*, pp. 28-60 (2008).
Duplaa, C. et al., "Quantitative analysis of polymerase chain reaction products using biotinylated dUTP incorporation," (1993) *Anal. Biochem.* 212:229-236.
Eddy, S.R., "Hidden Markov Models," (1996) *Curr. Opin. Struct. Biol.* 6:361-365.

(Continued)

Primary Examiner — Robert Landsman
(74) Attorney, Agent, or Firm — Foley & Lardner LLP

(57) ABSTRACT

The invention provides human signal peptide-containing proteins (HSPP) and polynucleotides which identify and encode HSPP. The invention also provides expression vectors, host cells, antibodies, agonists, and antagonists. The invention also provides methods for diagnosing, treating, or preventing disorders associated with expression of HSPP.

9 Claims, No Drawings

(56) References Cited

OTHER PUBLICATIONS

Engelhard, E.K. et al., "The insect tracheal system: a conduit for the systemic spread of *Autographa californica* M nuclear polyhedrosis virus," (1994) *Proc. Natl. Acad. Sci. USA* 91:3224-3227.

Gatti, R.A. et al., "Localization of an Ataxi-Telangiectasia Gene to Chromosome," (1998) *Nature* 336:577-580.

Gee et al., "Potential Therapeutic Usefulness of Intermolecular Triplex DNA," *Mol. & Immuno. Approaches*, pp. 163-177 (1994).

Goldman, C.K. et al., "In Vitro and In Vivo Gene Delivery Mediated by a Synthethic Polycationic Amino Polymer," (1997) *Nat. Biotechnol.* 15:462-466.

Harrington, J.J. et al., "Formation of *De Novo* Centromere and Construction of First-Generation Human Artificial Microchromosomes," (1997) *Nat. Genet.* 15:345-355.

Harrington, M. G., "Elution of Protein from Gels," *Methods Enzymol.*, 182: 488-495.

Hartman, S.C. and R.C. Mulligan, "Two dominant-acting selectable markers for gene transfer studies in mammalian cells," (1988) *Proc. Natl. Acad. Sci. USA* 85:8047-8051.

Heller, R.A. et al., "Discovery and analysis of inflammatory disease-related genes using cDNA microarrays," (1997) *Proc. Natl. Acad. Sci. USA* 94:2150-2155.

Horn, T. et al., "Synthesis of oligonucleotides on cellulose. Part II: design and synthetic strategy to the synthesis of 22 oligodeoxynucleotides coding for Gastric Inhibitory Polypeptide (GIP)," (1980) *Nucleic Acids Symp. Ser.* 7:225-232.

Huse, W.D. et al., "Generation of a Large Combinatorial Library of the Immunoglobulin Repertoire in Phage Lambda," (1989) *Science* 246:1275-1281.

Kimmel, A.R., "Identification and Characterization of Specific Clones: Strategy for Confirming the Validity of Presumptive Clones," (1987) *Methods Enzymol.* 152:507-511.

Kohler, G. et al., "Continuous Cultures of Fused Cells Secreting Antibody of Predefined Specificity," (1975) *Nature* 256:495-497.

Kozbor, D. et al., "Specific Immunoglobulin Productions and Enhanced Tumorigenicity Following Ascites Growth of Human Hybridomas," (1985), *J. Immunol. Methods*, 81: 31-42.

Lagerstrom, M. et al., "Capture PCR: efficient amplification of DNA fragments adjacent to a known sequence in human and YAC DNA," *PCR Methods Applic.* 1:111-119.

Lodish et al., "Cell to Cell Signaling: Hormones and Receptors," (1995), *Molecular Cell Biology*, pp. 856-864, Scientific American Books Inc., New York, NY.

Logan, J. and T. Shenk, "Adenovirus tripartite leader sequence enhances translation of mRNAs late after infection," (1984) *Proc. Natl. Acad. Sci. USA* 81:3655-3659.

Lowry, I. et al., "Isolation of Tranforming DNA: Cloning the Hamster aprt Gene," (1980) *Cell* 22:817-823.

Martin, C. R. et al., "Neuroendocrine Systems," *Endocrine Physiology*, pp. 57-62, Oxford University Press, New York, NY.

Melby, P.C. et al., "Quantitative Measurement of Human Cytokine Gene Expression by Polymerase Chain Reaction," (1993) *J. Immunol. Methods* 159:235-244.

Morrison, S.L. et al., "Chimeric human antibody molecules: mouse antigen-binding domains with human constant region domainss," (1984) *Proc. Natl. Acad. Sci. USA* 81:6851-6855.

Neuberger, M.S. et al., "Recombinant Antibodies Possessing Novel Effector Functions," (1984) *Nature* 312:604-608.

Orlandi, R. et al., Cloning immunoglobulin variable domains for expression by the polymerase chain reaction, (1989) *Proc. Natl. Acad. Sci. USA* 86:3833-3837.

Parker, J.D. et al., "Targeted Gene Walking Polymerase Chain Reaction," (1991), *Nucleic Acids Res.*, 19: pp. 3055-3060.

Price, C. M., "Fluorescence In Situ Hybridization," (1993) *Blood Rev.*, 7: 127-134.

Rao, V.B., "Direct Sequencing of Polymerase Chain Reaction-Amplified DNA," (1994) *Anal. Biochem.* 216:1-14.

Rhodes, C.A., "Transformation of Maize by electroporation of Embryos," (1995) *Methods Mol. Biol.* 55:121-131.

Roberge, J.Y. et al., "A Strategy for a Convergent Synthesis of N-Linked Glycopeptides on a Solid Support ," *Science* 269:202-204.

Ruoslahti, E., "Integrins as Signaling Molecules and Targets for Tumor Therapy," (1997), *Kidney Int.* 51: 1413-1417.

Sandig, V. et al., "Gene Transfer into Hepatocytes and Human Liver Tissue by Baculorirus Vectors," (1996) *Hum. Gene Ther.* 7:1937-1945.

Sarkar, G., "Restriction-Site PCR: A Direct Method of Unknown Sequence Retrieval Adjacent to a Known Locus by Using Universal Primers," (1993) *PCR Methods Applic.* 2:318-322.

Scharf, D. et al., "Heat Stress Promoters and Transcription Factors," (1994) *Results Probl. Cell Differ.* 20:125-162.

Schena, M. et al., "Quantitative Monitoring of Gene Expression Patterns with a Complementary DNA Microarray," (1995) *Science* 270:467-470.

Schena et al., "Parallel Human Genome Analysis: Microarray-based Expression Monitoring of 1000 Genes," *Proc. Natl. Acad. Sci.*, vol. 93, pp. 10614-10619 (1996).

Scorer, C.A. et al., "Rapid Selection Using G418 of High Copy Number Transformants of *Pichia pastoris* for High-Level Foreign Gene Expression," (1994) *Bio/Technology* 12:181-184.

Shalon, D. et al., "A DNA Microarray System for Analyzing Complex DNA Samples Using Two-Color Fluorescent Probe Hybridization," (1996) *Genome Res.* 6:639-645.

Sjaastad, M. D. et al., "Integrin-Mediated Calcium Signaling and Regulation of Cell Adhesion by Intracellular Calcium," (1997), *BioEssays*, 19: 47-55.

Takamatsu, N., "Expression of Bacterial Chloramphenicol Acetyltransferase Gene in Tobacco Plants Mediated by TRV-RNA," (1987) *EMBO J.* 6:307-311.

Takeda, S. et al., "Construction of Chimaeric Processed Immunoglobulin Genes Containing Mouse Variable and Human Constant Region Sequences," (1985) *Nature* 314:452-454.

Murry, "Agrobacterium-Mediated Plant Transformation," *The McGraw Hill Yearbook of Science and Technology*, (1992), pp. 191-196, McGraw Hill, New York NY.

Trask, B.J., "Fluorescence in situ Hybridization," (1991) *Trends Genet.* 7:149-154.

Triglia, T. et al., "A procedure for in vitro amplification of DNA segments that lie outside the boundaries of known sequences," (1988) *Nucleic Acids Res.* 16:8186.

Vans Heeke, G. and S.M. Schuster, "Expression of Human Synthetase in *Escherichia coli*," (1989) *J. Biol. Chem.* 264:5503-5509.

Wahl, G.M. and S.L. Berger, "Molecular Hybridization of Immobilized Nucleic AcidsL Theoretical Concepts and Practical Considerations," (1987) *Methods Enzymol.* 152:399-407.

Wigler, M. et al., "Transfer of Purified Herpes Virus Thymidine Kinase Gene to Cultured Mouse Cells," (1977) *Cell* 11:223-232.

Wigler, M. et al., "Transformation of mammalian cells with an amplifiable dominant-acting gene," (1980) *Proc. Natl. Acad. Sci. USA* 77:3567-3570.

Winter, G. et al., "Man-Made Antibodies," (1991) *Nature* 349:293-299.

Winter, J. et al., "The Expression of Heat Shock Protein and Cognate Genes During Plant Development," (1991), *Results Probl. Cell Differ.*, 17: 85-105.

Alberts, B. et al., "Control of Gene Expression," *Molecular Biology of the Cell*, (1994), pp. 104-474, Garland Publishing Co, New York, NY.

Alberts, B. et al., "Ion Channels are Ion Selective and Fluctuate between Open and Closed States," *Molecular Biology of the Cell*, (1994), pp. 523-546, Garland Publishing, New York, NY.

Alberts, B. et al., Molecular Biology of the Cell, (1994), pp. 85, 211, 239-240, 642-645, Garland Publishing, Inc., New York, NY.

Barclay, A. N. et al., The Leucocyte Antigen Facts Book, (1993), pp. 144-145, Academic Press, San Diego, CA.

Beavo, J.A., "Cyclic Nucleotide Phosphodiesterases: Functional Implications of Multiple Isoforms," *Physiological Reviews*, (1995), pp. 725-748, vol. 75.

Bolander, F.F., "Membrane Receptors," *Molecular Endocrinology*, (1994), pp. 162-176, Academic Press, San Diego, CA.

(56) References Cited

OTHER PUBLICATIONS

Boll, M. et al,. "Expression cloning and functional characterization of the kidney cortex high-affinity proton-coupled peptide transporter," *Proc. Natl. Acad. Sci.*, (1996), pp. 284-289, vol. 93.

Callard, R. et al., "The Chemokine Family," *The Cytokine Facts Book*, (1994), pp. 181-190, 210-213, 223-227, Academic Press, New York, NY.

Charbonneau, H. et al., "1002 protein Phosphatases," *Annu. Rev. Cell Biol*, (1992), pp. 463-493, vol. 8.

Diamond, R.H. et al., "PRL-1, A Unique Nuclear Protein Tyrosine Phosphatases, Affects Cell Growth," *Mol Cell Biol*, (1994), pp. 3752-3762, vol. 14.

Duprat, F. et al., "TASK, a human background K+ channel to sense external pH variations near physiological pH," *EMBO J.*, (1997), pp. 5464-5471, vol. 16.

Grant et al., "Vectors for Expression of Cloned Genes," *Methods Enzymol.*, (1987), pp. 516-544, vol. 153.

Hardie, G. et al., "The Eukaryotic Protein Kinase Superfamily," *The Protein Kinase Facts Book*, (1995), pp. 7-47, vol. I, Academic Press, San Diego, CA.

Hein, J., "Phylogenetic Trees," *Methods Enzymol.*, (1990), pp. 626-645, vol. 183.

Higgins, D.G. et al., "CLUSTAL: a package for performing multiple sequence alignment on a microcomputer," *Gene*, (1988), pp. 237-244, vol. 73.

Ito, K. et al., "A New Member of the Cationic Amino Acid Transporter Family is Preferentially Expressed in Adult Mouse Brain," *J. Biol. Chem.*, (1997), pp. 26780-26786, vol. 272.

Kishore, U. et al., "Modular Organization of Carbohydrate Recognition Domains in Animal Lectins," *Matrix Biol.*, (1997), pp. 583-592, vol. 15.

Maecker, H.T. et al., "The Tetraspanin Superfamily: Molecular Facilitators," *FASEB J.*, (1997), pp. 428-442, vol. 11.

Meyers, R.A., "Sceleroderma Diagnosis with Recombinant Protein," *Molecular Biology and Biotechnology*, (1995), Wiley VCH, New York NY, pp. 853-859.

Noel, L. S. et al., "Robo-1, a Novel Member of the Urokinase Plasminogen Activator Receptor/CD59/Ly-6/Snake Toxin Family Selectively Expressed in Rat Bone and Growth Plate Cartilage," *J. Biol. Chem.*, (1998), pp. 3878-3883, vol. 273.

Ormerod, M. G., *Flow Cytometry*, (1994), Oxford, New York NY, 7 pgs. [PREFACE].

Pabo, C.O. et al., "Transcription FactorsL Structural Families and Principles of DNA Recognition," *Ann. Rev. Biochem.*, (1992), pp. 1053-1095, vol. 61.

Pessin, J. E et al., "Mammalian Facilitative Glucose Transporter Family: Structure and Molecular Regulation," *Annu. Rev. Physiol.*, (1992), pp. 911-930, vol. 54.

Pimentel, E., "Regulation of Cell Functions," *Handbook of Growth Factors*, (1994), pp. 1-9, CRC Press, Ann Arbor, MI.

Pound, J.D., *Immunochemical Protocols*, (1998), Humana Press, Totowa NJ., 5 pgs. [PREFACE].

Rossiter, H. et al., "Selectins, T-cell rolling and inflammation," *Mol. Med. Today*, (1997) pp. 214-222, vol. 3.

Stryer, L., "Hormone Action," *Biochemistry*, (1988), pp. 975-980, 1029-1035, W. H. Freeman and Co., New York.

Tanaka, T. et al., "Lipocalin-type Prostaglandin D Synthase (β-Trace) is a Newly Recognized Type of Retinoid Transporter," *J. Biol. Chem.* (1997), pp. 15789-15795, vol. 272.

Van't Hof, W. et al., "The Salivary Lipocalin von Ebner's Gland Protein is a Proteinase Inhibitor," *J. Biol. Chem.*, (1997). pp. 1837-1841, vol. 272.

Watson, S. et al., "Introduction: Seven Transmembrane Proteins," *The G-protein Linked Receptor Facts Book*, (1994), pp. 2-6, Academic Press, San Diego, CA.

Carninci et al., (Direct Submission), GenBank Sequence Database (Accession BAC33411), National Center for Biotechnology Information, National Library of Medicine, Bethesda, Maryland 20894 (GI 26339480) Dec. 5, 2002.

Conklin, et al., (Direct Submission), GenBank Sequence Database (Accession CAC88605), Nathional center for Biotechnology Information, National Library of Medicine, Bethesda, Maryland 20894 (GI 15862412) Sep. 28, 2001.

Fujita et al., (Direct Submission), GenBank Sequence Database (Accession AB056722), National Center for Biotechnology Information, National Library of Medicine, Bethesda, Maryland, 20894 (GI 22779233) Sep. 11, 2002.

Hudson, (Direct Submission), Nucleotide Sequence Database (Accession HS578357), European Molecular Biology Laboratory—European Bioinformatics Institute Apr. 27, 2000.

Koehrer et al, (Direct Submission), GenBank Sequence Database (Accession AL110199), National Center for Biotechnology Information, National Library of Medicine, Bethesda, Maryland 20894 (GI 5817118) Feb. 18, 2000.

Database EST. Accession No. AA524300, Aug. 21, 1997.

Bonaldo et al., Genome Research 6: 791-806, 1996.

Blattner et al, Science 277: 1453-1462, 1997.

COMPOSITIONS COMPRISING SIGNAL PEPTIDE-CONTAINING PROTEINS

CROSS-REFERENCE TO RELATED APPLICATION(S)

This application is a divisional of U.S. patent application Ser. No. 12/457,389, filed Jun. 9, 2009, now U.S. Pat. No. 8,153,398, which is a continuation of U.S. patent application Ser. No. 11/905,820, filed Oct. 4, 2007, now abandoned, which is a divisional application of U.S. patent application Ser. No. 10/820,474, filed Apr. 7, 2004, now abandoned, which is a divisional of U.S. patent application Ser. No. 09/720,533, filed Mar. 20, 2001, now abandoned, which is the National Phase of International Application No. PCT/US99/14484, filed Jun. 25, 1999, which claims benefit under 35 U.S.C. §119(e) to U.S. Provisional Patent Application No. 60/090,762, filed Jun. 26, 1998, U.S. Provisional Patent Application No. 60/094,983, filed Jul. 31, 1998, U.S. Provisional Patent Application No. 60/102,686, filed Oct. 1, 1998, and U.S. Provisional Patent Application No. 60/112,129, filed Dec. 11, 1998. These applications are all incorporated herein by reference in their entirety.

TECHNICAL FIELD

This invention relates to nucleic acid and amino acid sequences of human signal peptide-containing proteins and to the use of these sequences in the diagnosis, treatment, and prevention of cell proliferative disorders including cancer; inflammation; and cardiovascular, neurological, reproductive, and developmental disorders.

BACKGROUND OF THE INVENTION

Protein transport is essential for cellular function. Transport of a protein may be mediated by a signal peptide located at the amino terminus of the protein itself. The signal peptide is comprised of about ten to twenty hydrophobic amino acids which target the nascent protein from the ribosome to a particular membrane bound compartment such as the endoplasmic reticulum (ER). Proteins targeted to the ER may either proceed through the secretory pathway or remain in any of the secretory organelles such as the ER, Golgi apparatus, or lysosomes. Proteins that transit through the secretory pathway are either secreted into the extracellular space or retained in the plasma membrane. Secreted proteins are often synthesized as inactive precursors that are activated by post-translational processing events during transit through the secretory pathway. Such events include glycosylation, phosphorylation, proteolysis, and removal of the signal peptide by a signal peptidase. Other events that may occur during protein transport include chaperone-dependent unfolding and folding of the nascent protein and interaction of the protein with a receptor or pore complex. Examples of secreted proteins with amino terminal signal peptides are discussed below and include receptors, extracellular matrix molecules, cytokines, hormones, growth and differentiation factors, neuropeptides, vasomediators, phosphokinases, phosphatases, phospholipases, phosphodiesterases, G and Ras-related proteins, ion channels, transporters/pumps, proteases, and transcription factors. (Reviewed in Alberts, B. et al. (1994) *Molecular Biology of The Cell*, Garland Publishing, New York, N.Y., pp. 557-560, 582-592.)

G-protein coupled receptors (GPCRs) comprise a superfamily of integral membrane proteins which transduce extracellular signals. GPCRs include receptors for biogenic amines such as dopamine, epinephrine, histamine, glutamate (metabotropic effect), acetylcholine (muscarinic effect), and serotonin; for lipid mediators of inflammation such as prostaglandins, platelet activating factor, and leukotrienes; for peptide hormones such as calcitonin, C5a anaphylatoxin, follicle stimulating hormone, gonadotropin releasing hormone, neurokinin, oxytocin, and thrombin; and for sensory signal mediators such as retinal photopigments and olfactory stimulatory molecules. The structure of these highly conserved receptors consists of seven hydrophobic transmembrane regions, cysteine disulfide bridges between the second and third extracellular loops, an extracellular N-terminus, and a cytoplasmic C-terminus. The N-terminus interacts with ligands, the disulfide bridges interact with agonists and antagonists, and the large third intracellular loop interacts with G proteins to activate second messengers such as cyclic AMP, phospholipase C, inositol triphosphate, or ion channels. (Reviewed in Watson, S, and Arkinstall, S. (1994) *The G-protein Linked Receptor Facts Book*, Academic Press, San Diego, Calif., pp. 2-6; and Bolander, F. F. (1994) *Molecular Endocrinology*, Academic Press, San Diego, Calif., pp. 162-176.)

Other types of receptors include cell surface antigens identified on leukocytic cells of the immune system. These antigens have been identified using systematic, monoclonal antibody (mAb)-based "shot gun" techniques. These techniques have resulted in the production of hundreds of mAbs directed against unknown cell surface leukocytic antigens. These antigens have been grouped into "clusters of differentiation" based on common immunocytochemical localization patterns in various differentiated and undifferentiated leukocytic cell types. Antigens in a given cluster are presumed to identify a single cell surface protein and are assigned a "CD" number. Some of the genes encoding proteins identified by CD antigens have been isolated and characterized as both transmembrane proteins and cell surface proteins anchored to the plasma membrane via covalent attachment to fatty acid-containing glycolipids such as glycosylphosphatidylinositol (GPI). (Reviewed in Barclay, A. N. et al. (1993) *The Leucocyte Antigen Facts Book*, Academic Press, San Diego, Calif., pp. 144-145; Noel, L. S. et al. (1998) J. Biol. Chem. 273: 3878-3883.)

Tetraspanins are a superfamily of membrane proteins which facilitate the formation and stability of cell-surface signaling complexes containing lineage-specific proteins, integrins, and other tetraspanins. They are involved in cell activation, proliferation (including cancer), differentiation, adhesion, and motility. These proteins cross the membrane four times, have conserved intracellular—and C-termini and an extracellular, non-conserved hydrophilic domain. Tetraspanins include, e.g., platelet and endothelial cell membrane proteins, leukocyte surface proteins, tissue specific and tumorous antigens, and the retinitis pigmentosa-associated gene peripherin. (Maecker, H. T. et al. (1997) FASEB J. 11:428-442.)

Matrix proteins (MPs) are transmembrane and extracellular proteins which function in formation, growth, remodeling, and maintenance of tissues and as important mediators and regulators of the inflammatory response. The expression and balance of MPs may be perturbed by biochemical changes that result from congenital, epigenetic, or infectious diseases. In addition, MPs affect leukocyte migration, proliferation, differentiation, and activation in the immune response. MPs are frequently characterized by the presence of one or more domains which may include collagen-like domains, EGF-like domains, immunoglobulin-like domains, and fibronectin-like domains. In addition, some MPs are heavily glycosylated.

MPs include extracellular proteins such as fibronectin, collagen, and galectin and cell adhesion receptors such as cell adhesion molecules (CAMs), cadherins, and integrins. (Reviewed in Ayad, S. et al. (1994) *The Extracellular Matrix Facts Book*, Academic Press, San Diego, Calif., pp. 2-16; Ruoslahti, E. (1997) Kidney Int. 51:1413-1417; Sjaastad, M. D. and Nelson, W. J. (1997) BioEssays 19:47-55.)

Lectins are proteins characterized by their ability to bind carbohydrates on cell membranes by means of discrete, modular carbohydrate recognition domains, CRDs. (Kishore, U. et al. (1997) Matrix Biol. 15:583-592.) Certain cytokines and membrane-spanning proteins have CRDs which may enhance interactions with extracellular or intracellular ligands, with proteins in secretory pathways, or with molecules in signal transduction pathways. The lipocalin superfamily constitutes a phylogenetically conserved group of more than forty proteins that function by binding to and transporting a variety of physiologically important ligands. (Tanaka, T. et al. (1997) J. Biol. Chem. 272:15789-15795; and van't Hof, W. et al. (1997) J. Biol. Chem. 272:1837-1841.) Selectins are a family of calcium ion-dependent lectins expressed on inflamed vascular endothelium and the surface of some leukocytes. (Rossiter, H. et al. (1997) Mol. Med. Today 3:214-222.)

Protein kinases regulate many different cell proliferation, differentiation, and signaling processes by adding phosphate groups to proteins. Reversible protein phosphorylation is a key strategy for controlling protein functional activity in eukaryotic cells. The high energy phosphate which drives this activation is generally transferred from adenosine triphosphate molecules (ATP) to a particular protein by protein kinases and removed from that protein by protein phosphatases. Phosphorylation occurs in response to extracellular signals, cell cycle checkpoints, and environmental or nutritional stresses. Protein kinases may be roughly divided into two groups; protein tyrosine kinases (PTKs) which phosphorylate tyrosine residues, and serine/threonine kinases (STKs) which phosphorylate serine or threonine residues. A few protein kinases have dual specificity. A majority of kinases contain a similar 250-300 amino acid catalytic domain. (Hardie, G. and Hanks, S. (1995) *The Protein Kinase Facts Book*, Vol I, pp. 7-47, Academic Press, San Diego, Calif.)

Protein phosphatases remove phosphate groups from molecules previously modified by protein kinases thus participating in cell signaling, proliferation, differentiation, contacts, and oncogenesis. Protein phosphorylation is a key strategy used to control protein functional activity in eukaryotic cells. The high energy phosphate is transferred from ATP to a protein by protein kinases and removed by protein phosphatases. There appear to be three, evolutionarily-distinct protein phosphatase gene families: protein phosphatases (PPs); protein tyrosine phosphatases (PTPs); and acid/alkaline phosphatases (APs). PPs dephosphorylate phosphoserine/threonine residues and are an important regulator of many cAMP mediated, hormone responses in cells. PTPs reverse the effects of protein tyrosine kinases and therefore play a significant role in cell cycle and cell signaling processes. Although APs dephosphorylate substrates in vitro, their role in vivo is not well known. (Charbonneau, H. and Tonks, N. K. (1992) Annu. Rev. Cell Biol. 8:463-493.)

Cyclic nucleotides (cAMP and cGMP) function as intracellular second messengers to transduce a variety of extracellular signals, including hormones, light and neurotransmitters. Cyclic nucleotide phosphodiesterases (PDEs) degrade cyclic nucleotides to their corresponding monophosphates, thereby regulating the intracellular concentrations of cyclic nucleotides and their effects on signal transduction. At least seven families of mammalian PDEs have been identified based on substrate specificity and affinity, sensitivity to cofactors and sensitivity to inhibitory drugs. (Beavo, J. A. (1995) Physiological Reviews 75: 725-748.)

Phospholipases (PLs) are enzymes that catalyze the removal of fatty acid residues from phosphoglycerides. PLs play an important role in transmembrane signal transduction and are named according to the specific ester bond in phosphoglycerides that is hydrolyzed, i.e., $A_1$, $A_2$, C or D. $PLA_2$ cleaves the ester bond at position 2 of the glycerol moiety of membrane phospholipids giving rise to arachidonic acid. Arachidonic acid is the common precursor to four major classes of eicosanoids, namely prostaglandins, prostacyclins, thromboxanes and leukotrienes. Eicosanoids are signaling molecules involved in the contraction of smooth muscle, platelet aggregation, and pain and inflammatory responses. (Alberts, B. et al. (1994) *Molecular Biology of The Cell*, Garland Publishing, Inc., New York, N.Y., pp. 85, 211, 239-240, 642-645.)

The nucleotide cyclases, i.e., adenylate and guanylate cyclase, catalyze the synthesis of the cyclic nucleotides, cAMP and cGMP, from ATP and GTP, respectively. They act in concert with phosphodiesterases, which degrade cAMP and cGMP, to regulate the cellular levels of these molecules and their functions. cAMP and cGMP function as intracellular second messengers to transduce a variety of extracellular signals, e.g., hormones, and light and neurotransmitters. (Stryer, L. (1988) *Biochemistry* W.H. Freeman and Co., New York, pp. 975-980, 1029-1035.)

Cytokines are produced in response to cell perturbation. Some cytokines are produced as precursor forms, and some form multimers in order to become active. They are produced in groups and in patterns characteristic of the particular stimulus or disease, and the members of the group interact with one another and other molecules to produce an overall biological response. Interleukins, neurotrophins, growth factors, interferons, and chemokines are all families of cytokines which work in conjunction with cellular receptors to regulate cell proliferation and differentiation and to affect such activities as leukocyte migration and function, hematopoietic cell proliferation, temperature regulation, acute response to infections, tissue remodeling, apoptosis, and cell survival. Studies using antibodies or other drugs that modify the activity of a particular cytokine are used to elucidate the roles of individual cytokines in pathology and physiology.

Chemokines, in particular, are small chemoattractant cytokines involved in inflammation, leukocyte proliferation and migration, angiogenesis and angiostasis, regulation of hematopoiesis, HIV infectivity, and stimulation of cytokine secretion. Chemokines generally contain 70-100 amino acids and are subdivided into four subfamilies based on the presence of conserved cysteine-based motifs. (Callard, R. and Gearing, A. (1994) *The Cytokine Facts Book*, Academic Press, New York, N.Y., pp. 181-190, 210-213, 223-227.)

Growth and differentiation factors are secreted proteins which function in intercellular communication. Some factors require oligomerization or association with MPs for activity. Complex interactions among these factors and their receptors trigger intracellular signal transduction pathways that stimulate or inhibit cell division, cell differentiation, cell signaling, and cell motility. Most growth and differentiation factors act on cells in their local environment (paracrine signaling). There are three broad classes of growth and differentiation factors. The first class includes the large polypeptide growth factors such as epidermal growth factor, fibroblast growth factor, transforming growth factor, insulin-like growth factor, and platelet-derived growth factor. The second class includes the hematopoietic growth factors such as the colony stimulating factors (CSFs). Hematopoietic growth factors stimulate the proliferation and differentiation of blood cells such as B-lymphocytes, T-lymphocytes, erythrocytes, platelets, eosinophils, basophils, neutrophils, macrophages, and their stem cell precursors. The third class includes small peptide factors such as bombesin, vasopressin, oxytocin, endothelin, transferrin, angiotensin II, vasoactive intestinal peptide, and bradykinin which function as hormones to regulate cellular functions other than proliferation.

Growth and differentiation factors play critical roles in neoplastic transformation of cells in vitro and in tumor progression in vivo. Inappropriate expression of growth factors by tumor cells may contribute to vascularization and metastasis of melanotic tumors. During hematopoiesis, growth factor misregulation can result in anemias, leukemias, and lymphomas. Certain growth factors such as interferon are cytotoxic to tumor cells both in vivo and in vitro. Moreover, some growth factors and growth factor receptors are related both structurally and functionally to oncoproteins. In addition, growth factors affect transcriptional regulation of both proto-oncogenes and oncosuppressor genes. (Reviewed in Pimentel, E. (1994) *Handbook of Growth Factors*, CRC Press, Ann Arbor, Mich., pp. 1-9.)

Proteolytic enzymes or proteases either activate or deactivate proteins by hydrolyzing peptide bonds. Proteases are found in the cytosol, in membrane-bound compartments, and in the extracellular space. The major families are the zinc, serine, cysteine, thiol, and carboxyl proteases.

Zinc proteases, e.g., carboxypeptidase A, have a zinc ion bound to the active site. These proteases recognize C-terminal residues that contain an aromatic or bulky aliphatic side chain, and hydrolyze the peptide bond adjacent to the C-terminal residues. Serine proteases have an active site serine residue and include digestive enzymes, e.g., trypsin and chymotrypsin, components of the complement and blood-clotting cascades, and enzymes that control the degradation and turnover of extracellular matrix (ECM) molecules. Cysteine proteases (e.g. cathepsin) are produced by monocytes, macrophages and other immune cells, and are involved in diverse cellular processes ranging from the processing of precursor proteins to intracellular degradation. Overproduction of these enzymes can cause the tissue destruction associated with rheumatoid arthritis and asthma. Thiol proteases, e.g., papain, contain an active site cysteine and are widely distributed within tissues. Carboxyl proteases, e.g., pepsin, are active only under acidic conditions (pH 2 to 3).

Guanosine triphosphate-binding proteins (G proteins) can be grouped into two major classes: heterotrimeric G proteins and small G proteins. Heterotrimeric G proteins interact with GPCRs that respond to hormones, growth factors, neuromodulators, or other signaling molecules. The interaction between GPCR and G protein allows the G protein to exchange GTP for guanosine diphosphate (GDP). This exchange activates the G protein, allowing it to dissociate from the receptor and interact with the its cognate second messenger-generating protein, e.g., adenylate cyclase, guanylate cyclase, phospholipase C, or ion channels. The hydrolysis of GTP to GDP by the G protein acts as an on-off switch, terminating the action of the G protein and preparing it to interact with another receptor molecule, thus beginning another round of signal transduction.

The small G proteins consist of single 21-30 kDa polypeptides. They can be classified into five subfamilies: Ras, Rho, Ran, Rab, and ADP-ribosylation factor. These proteins regulate cell growth, cell cycle control, protein secretion, and intracellular vesicle interaction. In particular, the Ras proteins are essential in transducing signals from receptor tyrosine kinases to serine/threonine kinases which control cell growth and differentiation. Mutant Ras proteins, which bind but can not hydrolyze GTP, are permanently activated and cause continuous cell proliferation or cancer. All five subfamilies share common structural features and four conserved motifs. Most of the membrane-bound G proteins require a carboxy terminal isoprenyl group (CAAX), added posttranslationally, for membrane association and biological activity. The G proteins also have a variable effector region, located between motifs I and II, which is characterized as the interaction site for guanine nucleotide exchange factors or GTPase-activating proteins.

Eukaryotic cells are bound by a membrane and subdivided into membrane-bound compartments. Membranes are impermeable to many ions and polar molecules, therefore transport of these molecules is mediated by ion channels, ion pumps, transport proteins, or pumps. Symporters and antiporters regulate cytosolic pH by transporting ions and small molecules, e.g., amino acids, glucose, and drugs, across membranes; symporters transport small molecules and ions in the same direction, and antiporters, in the opposite direction. Transporter superfamilies include facilitative transporters and active ATP binding cassette transporters involved in multiple-drug resistance and the targeting of antigenic peptides to MHC Class I molecules. These transporters bind to a specific ion or other molecule and undergo conformational changes in order to transfer the ion or molecule across a membrane. Transport can occur by a passive, concentration-dependent mechanism or can be linked to an energy source such as ATP hydrolysis or an ion gradient.

Ion channels, ion pumps, and transport proteins mediate the transport of molecules across cellular membranes. Symporters and antiporters regulate cytosolic pH by transporting ions and small molecules such as amino acids, glucose, and drugs. Symporters transport small molecules and ions unidirectionally, and antiporters, bidirectionally. Transporter superfamilies include facilitative transporters and active ATP-binding cassette transporters which are involved in multiple-drug resistance and the targeting of antigenic peptides to MHC Class I molecules. These transporters bind to a specific ion or other molecule and undergo a conformational change in order to transfer the ion or molecule across the membrane. Transport can occur by a passive, concentration-dependent mechanism or can be linked to an energy source such as ATP hydrolysis. (Reviewed in Alberts, B. et al. (1994) *Molecular Biology of The Cell*, Garland Publishing, New York, N.Y., pp. 523-546.)

Ion channels are formed by transmembrane proteins which create a lined passageway across the membrane through which water and ions, such as $Na^+$, $K^+$, $Ca^{2+}$, and $Cl^-$, enter and exit the cell. For example, chloride channels are involved in the regulation of the membrane electric potential as well as absorption and secretion of ions across the membrane. Chloride channels also regulate the internal pH of membrane-bound organelles.

Ion pumps are ATPases which actively maintain membrane gradients. Ion pumps are classified as P, V, or F according to their structure and function. All have one or more binding sites for ATP in their cytosolic domains. The P-class ion pumps include $Ca^{2+}$ ATPase and $Na^+/K^+$ ATPase and function in transporting $H^+$, $Na^+$, $K^+$, and $Ca^{2+}$ ions. P-class pumps consist of two ÿ and two ÿ transmembrane subunits. The V- and F-class ion pumps have similar structures and but transport only $H^+$. F class $H^+$ pumps mediate transport across the membranes of mitochondria and chloroplasts, while V-class H⁺ pumps regulate acidity inside lysosomes, endosomes, and plant vacuoles.

A family of structurally related intrinsic membrane proteins known as facilitative glucose transporters catalyze the movement of glucose and other selected sugars across the plasma membrane. The proteins in this family contain a highly conserved, large transmembrane domain comprised of 12 ÿ-helices, and several weakly conserved, cytoplasmic and exoplasmic domains (Pessin, J. E., and Bell, G. I. (1992) Annu. Rev. Physiol. 54:911-930).

Amino acid transport is mediated by Na⁺ dependent amino acid transporters. These transporters are involved in gastrointestinal and renal uptake of dietary and cellular amino acids and in neuronal reuptake of neurotransmitters. Transport of cationic amino acids is mediated by the system y+ family and the cationic amino acid transporter (CAT) family. Members of the CAT family share a high degree of sequence homology, and each contains 12-14 putative transmembrane domains (Ito, K. and Groudine, M. (1997) J. Biol. Chem. 272:26780-26786).

Proton-coupled, 12 membrane-spanning domain transporters such as PEPT 1 and PEPT 2 are responsible for gastrointestinal absorption and for renal reabsorbtion of peptides using an electrochemical H⁺ gradient as the driving force. A heterodimeric peptide transporter, consisting of TAP 1 and TAP 2, is associated with antigen processing. Peptide antigens are transported across the membrane of the endoplasmic reticulum so they can be presented to the major histocompatibility complex class I molecules. Each TAP protein consists of multiple hydrophobic membrane spanning segments and a highly conserved ATP-binding cassette. (Boll, M. et al. (1996) Proc. Natl. Acad. Sci. 93:284-289.)

Hormones are secreted molecules that travel through the circulation and bind to specific receptors on the surface of, or within, target cells. Although they have diverse biochemical compositions and mechanisms of action, hormones can be grouped into two categories. One category consists of small lipophilic hormones that diffuse through the plasma membrane of target cells, bind to cytosolic or nuclear receptors, and form a complex that alters gene expression. Examples of these molecules include retinoic acid, thyroxine, and the cholesterol-derived steroid hormones such as progesterone, estrogen, testosterone, cortisol, and aldosterone. The second category consists of hydrophilic hormones that function by binding to cell surface receptors that transduce signals across the plasma membrane. Examples of such hormones include amino acid derivatives such as catecholamines and peptide hormones such as glucagon, insulin, gastrin, secretin, cholecystokinin, adrenocorticotropic hormone, follicle stimulating hormone, luteinizing hormone, thyroid stimulating hormone, and vasopressin. (See, for example, Lodish et al. (1995) *Molecular Cell Biology*, Scientific American Books Inc., New York, N.Y., pp. 856-864.)

Neuropeptides and vasomediators (NP/VM) comprise a large family of endogenous signaling molecules. Included in this family are neuropeptides and neuropeptide hormones such as bombesin, neuropeptide Y, neurotensin, neuromedin N, melanocortins, opioids, galanin, somatostatin, tachykinins, urotensin II and related peptides involved in smooth muscle stimulation, vasopressin, vasoactive intestinal peptide, and circulatory system-borne signaling molecules such as angiotensin, complement, calcitonin, endothelins, formylmethionyl peptides, glucagon, cholecystokinin and gastrin. NP/VMs can transduce signals directly, modulate the activity or release of other neurotransmitters and hormones, and act as catalytic enzymes in cascades. The effects of NP/VMs range from extremely brief to long-lasting. (Reviewed in Martin, C. R. et al. (1985) Endocrine Physiology, Oxford University Press, New York, N.Y., pp. 57-62.)

Regulatory molecules turn individual genes or groups of genes on and off in response to various inductive mechanisms of the cell or organism; act as transcription factors by determining whether or not transcription is initiated, enhanced, or repressed; and splice transcripts as dictated in a particular cell or tissue. Although they interact with short stretches of DNA scattered throughout the entire genome, most gene expression is regulated near the site at which transcription starts or within the open reading frame of the gene being expressed. Many of the transcription factors incorporate one of a set of DNA-binding structural motifs, each of which contains either ÿ helices or β sheets and binds to the major groove of DNA. (Pabo, C. O. and R. T. Sauer (1992) Ann. Rev. Biochem. 61:1053-95.) Other domains of transcription factors may form crucial contacts with the DNA. In addition, accessory proteins provide important interactions which may convert a particular protein complex to an activator or a repressor or may prevent binding. (Alberts, B. et al. (1994) *Molecular Biology of the Cell*, Garland Publishing Co, New York, N.Y. pp. 401-474.)

The discovery of new human signal peptide-containing proteins and the polynucleotides encoding them satisfies a need in the art by providing new compositions which are useful in the diagnosis, prevention, and treatment of cell proliferative disorders including cancer; inflammation; and cardiovascular, neurological, reproductive, and developmental disorders.

SUMMARY OF THE INVENTION

The invention features substantially purified polypeptides, proteins with signal peptides, referred to collectively as "HSPP" and individually as "HSPP-1", "HSPP-2", "HSPP-3", "HSPP-4", "HSPP-5", "HSPP-6", "HSPP-7", "HSPP-8", "HSPP-9", "HSPP-10", "HSPP-11", "HSPP-12", "HSPP-13", "HSPP-14", "HSPP-15", "HSPP-16", "HSPP-17", "HSPP-18", "HSPP-19", "HSPP-20", "HSPP-21", "HSPP-22", "HSPP-23", "HSPP-24", "HSPP-25", "HSPP-26", "HSPP-27", "HSPP-28", "HSPP-29", "HSPP-30", "HSPP-31", "HSPP-32", "HSPP-33", "HSPP-34", "HSPP-35", "HSPP-36", "HSPP-37", "HSPP-38", "HSPP-39", "HSPP-40", "HSPP-41", "HSPP-42", "HSPP-43", "HSPP-44", "HSPP-45", "HSPP-46", "HSPP-47", "HSPP-48", "HSPP-49", "HSPP-50", "HSPP-51", "HSPP-52", "HSPP-53", "HSPP-54", "HSPP-55", "HSPP-56", "HSPP-57", "HSPP-58", "HSPP-59", "HSPP-60", "HSPP-61", "HSPP-62", "HSPP-63", "HSPP-64", "HSPP-65", "HSPP-66", "HSPP-67", "HSPP-68", "HSPP-69", "HSPP-70", "HSPP-71", "HSPP-72", "HSPP-73", "HSPP-74", "HSPP-75", HSPP-76", "HSPP-77", "HSPP-78", "HSPP-79", "HSPP-80", "HSPP-81", "HSPP-82", "HSPP-83", "HSPP-84", "HSPP-85", "HSPP-86", "HSPP-87", "HSPP-88", "HSPP-89", "HSPP-90", "HSPP-91", "HSPP-92", "HSPP-93", "HSPP-94", "HSPP-95", "HSPP-96", "HSPP-97", "HSPP-98", "HSPP-99", "HSPP-100", "HSPP-101", "HSPP-102", "HSPP-103", "HSPP-104", "HSPP-105", "HSPP-106", "HSPP-107", "HSPP-108", "HSPP-109", "HSPP-110", HSPP-111", "HSPP-112", "HSPP-113", "HSPP-114", "HSPP-115", "HSPP-116", "HSPP-117", "HSPP-118", "HSPP-119", "HSPP-120", "HSPP-121", "HSPP-122", "HSPP-123", "HSPP-124", "HSPP-125", "HSPP-126", "HSPP-127", "HSPP-128", "HSPP-129", "HSPP-130", "HSPP-131", "HSPP-132", "HSPP-133", and "HSPP-134".

In one aspect, the invention provides a substantially purified polypeptide comprising an amino acid sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO: 28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134 (SEQ ID NO:1-134), and fragments thereof.

The invention further provides a substantially purified variant having at least 90% amino acid identity to at least one of the amino acid sequences selected from the group consisting of SEQ ID NO:1-134, and fragments thereof. The invention also provides an isolated and purified polynucleotide encoding the polypeptide comprising an amino acid sequence selected from the group consisting of SEQ ID NO:1-134, and fragments thereof. The invention also includes an isolated and purified polynucleotide variant having at least 90% polynucleotide sequence identity to the polynucleotide encoding the polypeptide comprising an amino acid sequence selected from the group consisting of SEQ ID NO:1-134, and fragments thereof.

Additionally, the invention provides an isolated and purified polynucleotide which hybridizes under stringent conditions to the polynucleotide encoding the polypeptide comprising an amino acid sequence selected from the group consisting of SEQ ID NO:1-134, and fragments thereof. The invention also provides an isolated and purified polynucleotide having a sequence which is complementary to the polynucleotide encoding the polypeptide comprising the amino acid sequence selected from the group consisting of SEQ ID NO:1-134, and fragments thereof.

The invention also provides an isolated and purified polynucleotide comprising a polynucleotide sequence selected from the group consisting of SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:147, SEQ ID NO:148, SEQ ID NO:149, SEQ ID NO:150, SEQ ID NO:151, SEQ ID NO:152, SEQ ID NO:153, SEQ ID NO:154, SEQ ID NO:155, SEQ ID NO:156, SEQ ID NO:157, SEQ ID NO:158, SEQ ID NO:159, SEQ ID NO:160, SEQ ID NO:161, SEQ ID NO:162, SEQ ID NO:163, SEQ ID NO:164, SEQ ID NO:165, SEQ ID NO:166, SEQ ID NO:167, SEQ ID NO:168, SEQ ID NO:169, SEQ ID NO:170, SEQ ID NO:171, SEQ ID NO:172, SEQ ID NO:173, SEQ ID NO:174, SEQ ID NO:175, SEQ ID NO:176, SEQ ID NO:177, SEQ ID NO:178, SEQ ID NO:179, SEQ ID NO:180, SEQ ID NO:181, SEQ ID NO:182, SEQ ID NO:183, SEQ ID NO:184, SEQ ID NO:185, SEQ ID NO:186, SEQ ID NO:187, SEQ ID NO:188, SEQ ID NO:189, SEQ ID NO:190, SEQ ID NO:191, SEQ ID NO:192, SEQ ID NO:193, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:222, SEQ ID NO:223, SEQ ID NO:224, SEQ ID NO:225, SEQ ID NO:226, SEQ ID NO:227, SEQ ID NO:228, SEQ ID NO:229, SEQ ID NO:230, SEQ ID NO:231, SEQ ID NO:232, SEQ ID NO:233, SEQ ID NO:234, SEQ ID NO:235, SEQ ID NO:236, SEQ ID NO:237, SEQ ID NO:238, SEQ ID NO:239, SEQ ID NO:240, SEQ ID NO:241, SEQ ID NO:242, SEQ ID NO:243, SEQ ID NO:244, SEQ ID NO:245, SEQ ID NO:246, SEQ ID NO:247, SEQ ID NO:248, SEQ ID NO:249, SEQ ID NO:250, SEQ ID NO:251, SEQ ID NO:252, SEQ ID NO:253, SEQ ID NO:254, SEQ ID NO:255, SEQ ID NO:256, SEQ ID NO:257, SEQ ID NO:258, SEQ ID NO:259, SEQ ID NO:260, SEQ ID NO:261, SEQ ID NO:262, SEQ ID NO:263, SEQ ID NO:264, SEQ ID NO:265, SEQ ID NO:266, SEQ ID NO:267, SEQ ID NO:268 (SEQ ID NO:135-268), and fragments thereof. The invention further provides an isolated and purified polynucleotide variant having at least 90% polynucleotide sequence identity to the polynucleotide sequence selected from the group consisting of SEQ ID NO:135-268, and fragments thereof. The invention also provides an isolated and purified polynucleotide having a sequence which is complementary to the polynucleotide comprising a polynucleotide sequence selected from the group consisting of SEQ ID NO:135-268, and fragments thereof.

The invention also provides a method for detecting a polynucleotide in a sample containing nucleic acids, the method comprising the steps of (a) hybridizing the complement of the polynucleotide sequence to at least one of the polynucleotides of the sample, thereby forming a hybridization complex; and (b) detecting the hybridization complex, wherein the presence of the hybridization complex correlates with the presence of a polynucleotide in the sample. In one aspect, the method further comprises amplifying the polynucleotide prior to hybridization.

The invention further provides an expression vector containing at least a fragment of the polynucleotide encoding the polypeptide comprising an amino acid sequence selected from the group consisting of SEQ ID NO:1-134, and fragments thereof. In another aspect, the expression vector is contained within a host cell.

The invention also provides a method for producing a polypeptide, the method comprising the steps of: (a) culturing the host cell containing an expression vector containing at least a fragment of a polynucleotide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1-134, and fragments thereof, in conjunction with a suitable pharmaceutical carrier.

The invention further includes a purified antibody which binds to a polypeptide selected from the group consisting of SEQ ID NO:1-134, and fragments thereof. The invention also provides a purified agonist and a purified antagonist to the polypeptide.

The invention also provides a method for treating or preventing a disorder associated with decreased expression or activity of HSPP, the method comprising administering to a subject in need of such treatment an effective amount of a pharmaceutical composition comprising a substantially purified polypeptide having the amino acid sequence selected from the group consisting of SEQ ID NO:1-134, and fragments thereof, in conjunction with a suitable pharmaceutical carrier.

The invention also provides a method for treating or preventing a disorder associated with increased expression or activity of HSPP, the method comprising administering to a subject in need of such treatment an effective amount of an antagonist of a polypeptide having an amino acid sequence selected from the group consisting of SEQ ID NO:1-134, and fragments thereof.

BRIEF DESCRIPTION OF THE TABLES

Table 1 shows nucleotide and polypeptide sequence identification numbers (SEQ ID NO), clone identification numbers (clone ID), cDNA libraries, and cDNA fragments used to assemble full-length sequences encoding HSPP.

Table 2 shows features of each polypeptide sequence, including predicted signal peptide sequences, and methods and algorithms used for identification of HSPP.

Table 3 shows the tissue-specific expression patterns of each nucleic acid sequence as determined by northern analysis, diseases, disorders, or conditions associated with these tissues, and the vector into which each cDNA was cloned.

Table 4 describes the tissues used to construct the cDNA libraries from which Incyte cDNA clones encoding HSPP were isolated.

Table 5 shows the programs, their descriptions, references, and threshold parameters used to analyze HSPP.

Table 6 shows the regions of the full-length nucleotide sequences of HSPP to which cDNA fragments of Table 1 correspond.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

DEFINITIONS

"HSPP" refers to the amino acid sequences of substantially purified HSPP obtained from any species, particularly a mammalian species, including bovine, ovine, porcine, murine, equine, and preferably the human species, from any source, whether natural, synthetic, semi-synthetic, or recombinant.

The term "agonist" refers to a molecule which, when bound to HSPP, increases or prolongs the duration of the effect of HSPP. Agonists may include proteins, nucleic acids, carbohydrates, or any other molecules which bind to and modulate the effect of HSPP.

An "allelic variant" is an alternative form of the gene encoding HSPP. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding HSPP include those sequences with deletions, insertions, or substitutions of different nucleotides, resulting in a polynucleotide the same as HSPP or a polypeptide with at least one functional characteristic of HSPP. Included within this definition are polymorphisms which may or may not be readily detectable using a particular oligonucleotide probe of the polynucleotide encoding HSPP, and improper or unexpected hybridization to allelic variants, with a locus other than the normal chromosomal locus for the polynucleotide sequence encoding HSPP. The encoded protein may also be "altered," and may contain deletions, insertions, or substitutions of amino acid residues which produce a silent change and result in a functionally equivalent HSPP. Deliberate amino acid substitutions may be made on the basis of similarity in polarity, charge, solubility, hydrophobicity, hydrophilicity, and/or the amphipathic nature of the residues, as long as the biological or immunological activity of HSPP is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence" refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of HSPP which are preferably at least 5 to about 15 amino acids in length, most preferably at least 14 amino acids, and which retain some biological activity or immunological activity of HSPP. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which, when bound to HSPP, decreases the amount or the duration of the effect of the biological or immunological activity of HSPP. Antagonists may include proteins, nucleic acids, carbohydrates, antibodies, or any other molecules which decrease the effect of HSPP.

The term "antibody" refers to intact molecules as well as to fragments thereof, such as Fab, F(ab')$_2$, and Fv fragments, which are capable of binding the epitopic determinant. Antibodies that bind HSPP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense" refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

The term "biologically active," refers to a protein having structural, regulatory, or biochemical functions of a naturally occurring molecule. Likewise, "immunologically active" refers to the capability of the natural, recombinant, or synthetic HSPP, or of any oligopeptide thereof, to induce a specific immune response in appropriate animals or cells and to bind with specific antibodies.

The terms "complementary" or "complementarity" refer to the natural binding of polynucleotides by base pairing. For example, the sequence "5' A-G-T 3'" bonds to the complementary sequence "3' T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence" refer broadly to any composition containing the given polynucleotide or amino acid sequence. The composition may comprise a dry formulation or an aqueous solution. Compositions comprising polynucleotide sequences encoding HSPP or fragments of HSPP may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution, dry milk, salmon sperm DNA, etc.).

"Consensus sequence" refers to a nucleic acid sequence which has been resequenced to resolve uncalled bases, extended using XL-PCR kit (Perkin-Elmer, Norwalk Conn.) in the 5' and/or the 3' direction, and resequenced, or which has been assembled from the overlapping sequences of more than one Incyte Clone using a computer program for fragment assembly, such as the GELVIEW Fragment Assembly system (GCG, Madison Wis.). Some sequences have been both extended and assembled to produce the consensus sequence.

The term "correlates with expression of a polynucleotide" indicates that the detection of the presence of nucleic acids, the same or related to a nucleic acid sequence encoding HSPP, by northern analysis is indicative of the presence of nucleic acids encoding HSPP in a sample, and thereby correlates with expression of the transcript from the polynucleotide encoding HSPP.

A "deletion" refers to a change in the amino acid or nucleotide sequence that results in the absence of one or more amino acid residues or nucleotides.

The term "derivative" refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity" refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR, Madison Wis.) which creates alignments between two or more sequences according to methods selected by the user, e.g., the clustal method. (See, e.g., Higgins, D. G. and P. M. Sharp (1988) Gene 73:237-244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626-645.) Identity between sequences can also be determined by other methods known in the art, e.g., by varying hybridization conditions.

"Human artificial chromosomes" (HACs) are linear microchromosomes which may contain DNA sequences of about 6 kb to 10 Mb in size, and which contain all of the elements required for stable mitotic chromosome segregation and maintenance.

The term "humanized antibody" refers to antibody molecules in which the amino acid sequence in the non-antigen binding regions has been altered so that the antibody more closely resembles a human antibody, and still retains its original binding ability.

"Hybridization" refers to any process by which a strand of nucleic acid binds with a complementary strand through base pairing.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition" refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray" refers to an arrangement of distinct polynucleotides on a substrate.

The terms "element" or "array element" in a microarray context, refer to hybridizable polynucleotides arranged on the surface of a substrate.

The term "modulate" refers to a change in the activity of HSPP. For example, modulation may cause an increase or a decrease in protein activity, binding characteristics, or any other biological, functional, or immunological properties of HSPP.

The phrases "nucleic acid" or "nucleic acid sequence," as used herein, refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, comprise a region of unique polynucleotide sequence that specifically identifies SEQ ID NO:135-268, for example, as distinct from any other sequence in the same genome. For example, a fragment of SEQ ID NO:135-268 is useful in hybridization and amplification technologies and in analogous methods that distinguish SEQ ID NO:135-268 from related polynucleotide sequences. A fragment of SEQ ID NO:135-268 is at least about 15-20 nucleotides in length. The precise length of the fragment of SEQ ID NO:135-268 and the region of SEQ ID NO:135-268 to which the fragment corresponds are routinely determinable by one of ordinary skill in the art based on the intended purpose for the fragment. In some cases, a fragment, when translated, would produce polypeptides retaining some functional characteristic, e.g., antigenicity, or structural domain characteristic, e.g., ATP-binding site, of the full-length polypeptide.

The terms "operably associated" or "operably linked" refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide" refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. "Oligonucleotide" is substantially equivalent to the terms "amplimer," "primer," "oligomer," and "probe," as these terms are commonly defined in the art.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

The term "sample" is used in its broadest sense. A sample suspected of containing nucleic acids encoding HSPP, or fragments thereof, or HSPP itself, may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

The term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified" refers to nucleic acid or amino acid sequences that are removed from their natural environment and are isolated or separated, and are at least about 60% free, preferably about 75% free, and most preferably about 90% free from other components with which they are naturally associated.

A "substitution" refers to the replacement of one or more amino acids or nucleotides by different amino acids or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

"Transformation" describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of HSPP polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The term "variant," when used in the context of a polynucleotide sequence, may encompass a polynucleotide sequence related to HSPP. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

The Invention

The invention is based on the discovery of new human signal peptide-containing proteins (HSPP), the polynucleotides encoding HSPP, and the use of these compositions for the diagnosis, treatment, or prevention of cell proliferative disorders including cancer; inflammation; and cardiovascular, neurological, reproductive, and developmental disorders.

Table 1 lists the Incyte Clones used to derive full length nucleotide sequences encoding HSPP. Columns 1 and 2 show the sequence identification numbers (SEQ ID NO) of the amino acid and nucleic acid sequences, respectively. Column 3 shows the Clone ID of the Incyte Clone in which nucleic acids encoding each HSPP were identified, and column 4, the cDNA libraries from which these clones were isolated. Column 5 shows Incyte clones, their corresponding cDNA libraries, and shotgun sequences. The clones and shotgun sequences are part of the consensus nucleotide sequence of each HSPP and are useful as fragments in hybridization technologies.

Table 6 shows the regions of the full-length nucleotide sequences of HSPP to which cDNA fragments of Table 1 correspond. Column 1 lists nucleotide sequence identifiers and column 2 shows the clone ID of the Incyte clone in which nucleic acids encoding each HSPP were identified. Column 3 shows Incyte clones and shotgun sequences which are part of the consensus nucleotide sequence of each HSPP and are useful as fragments in hybridization technologies. Column 4 lists the starting nucleotide position and column 5 the ending nucleotide position of the region of the full-length HSPP to which the cDNA fragment corresponds.

The columns of Table 2 show various properties of the polypeptides of the invention: column 1 references the SEQ ID NO; column 2 shows the number of amino acid residues in each polypeptide; column 3, potential phosphorylation sites; column 4, potential glycosylation sites; column 5, the amino acid residues comprising signature sequences and motifs; column 6, the identity of each protein; and column 7, analytical methods used to identify each HSPP as a signal peptide-containing protein. Note that in column 5, the first line of each cell lists the amino acid residues comprising predicted signal peptide sequences. Additional identifying motifs or signatures are also listed in column 5. Of particular note is the presence of a glycosyl hydrolase family 9 active site signature in SEQ ID NO:126, a ribosomal protein S18 signature in SEQ ID NO:127, an adrenodoxin family iron-sulfur binding region signature and a cytochrome c family heme-binding site signature in SEQ ID NO:132, and a urotensin II signature sequence in SEQ ID NO:96.

Using BLAST, SEQ ID NO:68 (HSPP-68) has been identified as a TWIK-related acid-sensitive K$^+$ channel, and SEQ ID NO:92 (HSPP-92) has been identified as a tyrosine-specific protein phosphatase. The tyrosine-specific protein phosphatases signature in SEQ ID NO:92 (HSPP-92) from about V328 through about F340 (including the putative active site cysteine residue at C330) was identified using BLOCKS and PRINTS. Also of note is the identification of SEQ ID NO:66 (HSPP-66) as a steroid binding protein using BLAST.

The columns of Table 3 show the tissue-specificity and diseases, disorders, or conditions associated with nucleotide sequences encoding HSPP. The first column of Table 3 lists the nucleotide sequence identifiers. The second column lists tissue categories which express HSPP as a fraction of total tissue categories expressing HSPP. The third column lists the diseases, disorders, or conditions associated with those tissues expressing HSPP. The fourth column lists the vectors used to subclone the cDNA library. Of particular note is the expression of SEQ ID NO:200, SEQ ID NO:203, and SEQ ID NO:225 in lung tissues; the expression of SEQ ID NO:212, SEQ ID NO:216, and SEQ ID NO:220 in reproductive tissues; the expression of SEQ ID NO:223 in cancerous tissues; the expression of SEQ ID NO:232 in gastrointestinal tissue, specifically the small intestine or colon (fifteen out of sixteen (93.8%) cDNA libraries); and the expression of SEQ ID NO:224 in cancerous and proliferating tissues. Also of particular interest is the tissue-specific expression of SEQ ID NO:252 and SEQ ID NO:257. SEQ ID NO:252 is derived from OVARTUT01, an ovarian tumor cDNA library and is exclusively expressed in reproductive tumor tissue. SEQ ID NO:257 is derived from THP1AZT01, a 5-aza-2'-deoxycytidine treated human promonocyte cDNA library and is exclusively expressed in hematopoietic tissue.

The following fragments of the nucleotide sequences encoding HSPP are useful in hybridization or amplification technologies to identify SEQ ID NO:135-268 and to distinguish between SEQ ID NO:135-268 and related polynucleotide sequences. The useful fragments are the fragment of SEQ ID NO:230 from about nucleotide 75 to about nucleotide 104; the fragment of SEQ ID NO:231 from about nucleotide 210 to about nucleotide 239; the fragment of SEQ ID NO:232 from about nucleotide 157 to about nucleotide 186; the fragment of SEQ ID NO:233 from about nucleotide 268 to about nucleotide 297; the fragment of SEQ ID NO:234 from about nucleotide 160 to about nucleotide 186; the fragment of SEQ ID NO:235 from about nucleotide 201 to about nucleotide 230; the fragment of SEQ ID NO:236 from about nucleotide 165 to about nucleotide 194; the fragment of SEQ ID NO:237 from about nucleotide 366 to about nucleotide 395; the fragment of SEQ ID NO:238 from about nucleotide 714 to about nucleotide 743; the fragment of SEQ ID NO:239 from about nucleotide 1731 to about nucleotide 1760; the fragment of SEQ ID NO:240 from about nucleotide 419 to about nucleotide 448; the fragment of SEQ ID NO:241 from about nucleotide 494 to about nucleotide 523; the fragment of SEQ ID NO:242 from about nucleotide 100 to about nucleotide 129; the fragment of SEQ ID NO:243 from about nucleotide 104 to about nucleotide 133; the fragment of SEQ ID NO:244 from about nucleotide 136 to about nucleotide 165; the fragment of SEQ ID NO:245 from about nucleotide 140 to about nucleotide 169; the fragment of SEQ ID NO:246 from about nucleotide 125 to about nucleotide 154; the fragment of SEQ ID NO:247 from about nucleotide 687 to about nucleotide 758; the fragment of SEQ ID NO:248 from about nucleotide 327 to about nucleotide 398; the fragment of SEQ ID NO:249 from about nucleotide 741 to about nucleotide 785; the fragment of SEQ ID NO:250 from about nucleotide 184 to about nucleotide 255; the fragment of SEQ ID NO:251 from about nucleotide 165 to about nucleotide 242; the fragment of SEQ ID NO:252 from about nucleotide 271 to about nucleotide 342; the fragment of SEQ ID NO:253 from about nucleotide 1081 to about nucleotide 1152; the fragment of SEQ ID NO:254 from about nucleotide 781 to about nucleotide 852; the fragment of SEQ ID NO:255 from about nucleotide 620 to about nucleotide 691; the fragment of SEQ ID NO:256 from about nucleotide 872 to about nucleotide 916; the fragment of SEQ ID NO:257 from about nucleotide 242 to about nucleotide 313; the fragment of SEQ ID NO:258 from about nucleotide 595 to about nucleotide 648; the fragment of SEQ ID NO:259 from about nucleotide 163 to about nucleotide 216; the fragment of SEQ ID NO:260 from about nucleotide 244 to about nucleotide 315; the fragment of SEQ ID NO:261 from about nucleotide 75 to about nucleotide 128; the fragment of SEQ ID NO:262 from about nucleotide 650 to about nucleotide 703; the fragment of SEQ ID NO:263 from about nucleotide 143 to about nucleotide 214; the fragment of SEQ ID NO:264 from about nucleotide 434 to about nucleotide 487; the fragment of SEQ ID NO:265 from about nucleotide 218 to about nucleotide 271; the fragment of SEQ ID NO:266 from about nucleotide 89 to about nucleotide 145; the fragment of SEQ ID NO:267 from about nucleotide 198 to about nucleotide 254; and the fragment of SEQ ID NO:268 from about nucleotide 10 to about nucleotide 54.

The invention also encompasses HSPP variants. A preferred HSPP variant is one which has at least about 80%, more preferably at least about 90%, and most preferably at least about 95% amino acid sequence identity to the HSPP amino acid sequence, and which contains at least one functional or structural characteristic of HSPP.

The invention also encompasses polynucleotides which encode HSPP. In a particular embodiment, the invention encompasses a polynucleotide sequence comprising a sequence selected from the group consisting of SEQ ID NO:135-268, which encodes HSPP.

The invention also encompasses a variant of a polynucleotide sequence encoding HSPP. In particular, such a variant polynucleotide sequence will have at least about 80%, more preferably at least about 90%, and most preferably at least about 95% polynucleotide sequence identity to the polynucleotide sequence encoding HSPP. A particular aspect of the invention encompasses a variant of a polynucleotide sequence comprising a sequence selected from the group consisting of SEQ ID NO: 135-268 which has at least about 80%, more preferably at least about 90%, and most preferably at least about 95% polynucleotide sequence identity to a nucleic acid sequence selected from the group consisting of SEQ ID NO:135-268. Any one of the polynucleotide variants described above can encode an amino acid sequence which contains at least one functional or structural characteristic of HSPP.

It will be appreciated by those skilled in the art that as a result of the degeneracy of the genetic code, a multitude of polynucleotide sequences encoding HSPP, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HSPP, and all such variations are to be considered as being specifically disclosed.

Although nucleotide sequences which encode HSPP and its variants are preferably capable of hybridizing to the nucleotide sequence of the naturally occurring HSPP under appropriately selected conditions of stringency, it may be advantageous to produce nucleotide sequences encoding HSPP or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HSPP and its derivatives without altering the encoded amino acid sequences include the production of RNA transcripts having more desirable properties, such as a greater half-life, than transcripts produced from the naturally occurring sequence.

The invention also encompasses production of DNA sequences which encode HSPP and HSPP derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding HSPP or any fragment thereof.

Also encompassed by the invention are polynucleotide sequences that are capable of hybridizing to the claimed polynucleotide sequences, and, in particular, to those shown in SEQ ID NO:135-268 and fragments thereof under various conditions of stringency. (See, e.g., Wahl, G. M. and S. L. Berger (1987) Methods Enzymol. 152:399-407; Kimmel, A. R. (1987) Methods Enzymol. 152:507-511.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing are well known in the art and may be used to practice any of the embodiments of the invention. The methods may employ such enzymes as the Klenow fragment of DNA polymerase I, SEQUENASE (US Biochemical, Cleveland Ohio), Taq polymerase (Perkin-Elmer), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the Hamilton MICROLAB 2200 (Hamilton, Reno Nev.), Peltier Thermal Cycler 200 (PTC200; MJ Research, Watertown Mass.) and the ABI CATALYST 800 (Perkin-Elmer). Sequencing is then carried out using either ABI 373 or 377 DNA sequencing systems (Perkin-Elmer) or the MEGABACE 1000 DNA sequencing system (Molecular Dynamics, Sunnyvale Calif.). The resulting sequences are analyzed using a variety of algorithms which are well known in the art. (See, e.g., Ausubel, F. M. (1997) *Short Protocols in Molecular Biology*, John Wiley & Sons, New York N.Y., unit 7.7; Meyers, R. A. (1995) *Molecular Biology and Biotechnology*, Wiley VCH, New York N.Y., pp. 856-853.)

The nucleic acid sequences encoding HSPP may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318-322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111-119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055-306). Additionally, one may use PCR, nested primers, and PROMOTERFINDER libraries (Clontech, Palo Alto Calif.) to walk genomic DNA. This procedure avoids the need to screen libraries and is useful in finding intron/exon junctions. For all PCR-based methods, primers may be designed using commercially available software, such as OLIGO 4.06 Primer Analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Perkin-Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode HSPP may be cloned in recombinant DNA molecules that direct expression of HSPP, or fragments or functional equivalents thereof, in appropriate host cells. Due to the inherent degeneracy of the genetic code, other DNA sequences which encode substantially the same or a functionally equivalent amino acid sequence may be produced and used to express HSPP.

The nucleotide sequences of the present invention can be engineered using methods generally known in the art in order to alter HSPP-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding HSPP may be synthesized, in whole or in part, using chemical methods well known in the art. (See, e.g., Caruthers, M. H. et al. (1980) Nucl. Acids Res. Symp. Ser. 215-223, and Horn, T. et al. (1980) Nucl. Acids Res. Symp. Ser. 225-232.) Alternatively, HSPP itself or a fragment thereof may be synthesized using chemical methods. For example, peptide synthesis can be performed using various solid-phase techniques. (See, e.g., Roberge, J. Y. et al. (1995) Science 269:202-204.) Automated synthesis may be achieved using the ABI 431A Peptide Synthesizer (Perkin-Elmer). Additionally, the amino acid sequence of HSPP, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392-421.) The composition of the synthetic peptides may be confirmed by amino acid analysis or by sequencing. (See, e.g., Creighton, T. (1984) *Proteins, Structures and Molecular Properties*, WH Freeman, New York N.Y.)

In order to express a biologically active HSPP, the nucleotide sequences encoding HSPP or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding HSPP. Such elements may vary in their strength and specificity. Specific initiation signals may also be used to achieve more efficient translation of sequences encoding HSPP. Such signals include the ATG initiation codon and adjacent sequences, e.g. the Kozak sequence. In cases where sequences encoding HSPP and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125-162.)

Methods which are well known to those skilled in the art may be used to construct expression vectors containing sequences encoding HSPP and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, Cold Spring Harbor Press, Plainview N.Y., ch. 4, 8, and 16-17; Ausubel, F. M. et al. (1995) *Current Protocols in Molecular Biology*, John Wiley & Sons, New York N.Y., ch. 9, 13, and 16.)

A variety of expression vector/host systems may be utilized to contain and express sequences encoding HSPP. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding HSPP. For example, routine cloning, subcloning, and propagation of polynucleotide sequences encoding HSPP can be achieved using a multifunctional *E. coli* vector such as PBLUESCRIPT (Stratagene, La Jolla Calif.) or pSPORT1 plasmid (Life Technologies). Ligation of sequences encoding HSPP into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503-5509.) When large quantities of HSPP are needed, e.g. for the production of antibodies, vectors which direct high level expression of HSPP may be used. For example, vectors containing the strong, inducible T5 or T7 bacteriophage promoter may be used.

Yeast expression systems may be used for production of HSPP. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, 1995, supra; Grant et al. (1987) Methods Enzymol. 153:516-54; and Scorer, C. A. et al. (1994) Bio/Technology 12:181-184.)

Plant systems may also be used for expression of HSPP. Transcription of sequences encoding HSPP may be driven viral promoters, e.g., the 35S and 19S promoters of CaMV used alone or in combination with the omega leader sequence from TMV (Takamatsu, N. (1987) EMBO J. 6:307-311). Alternatively, plant promoters such as the small subunit of RUBISCO or heat shock promoters may be used. (See, e.g., Coruzzi, G. et al. (1984) EMBO J. 3:1671-1680; Broglie, R. et al. (1984) Science 224:838-843; and Winter, J. et al. (1991) Results Probl. Cell Differ. 17:85-105.) These constructs can be introduced into plant cells by direct DNA transformation or pathogen-mediated transfection. (See, e.g., *The McGraw Hill Yearbook of Science and Technology* (1992) McGraw Hill, New York N.Y., pp. 191-196.)

In mammalian cells, a number of viral-based expression systems may be utilized. In cases where an adenovirus is used as an expression vector, sequences encoding HSPP may be ligated into an adenovirus transcription/translation complex consisting of the late promoter and tripartite leader sequence. Insertion in a non-essential E1 or E3 region of the viral genome may be used to obtain infective virus which expresses HSPP in host cells. (See, e.g., Logan, J. and T. Shenk (1984) Proc. Natl. Acad. Sci. 81:3655-3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat. Genet. 15:345-355.)

For long term production of recombinant proteins in mammalian systems, stable expression of HSPP in cell lines is preferred. For example, sequences encoding HSPP can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk$^-$ or apr$^-$ cells, respectively. (See, e.g., Wigler, M. et al. (1977) Cell 11:223-232; Lowy, I. et al. (1980) Cell 22:817-823.) Also, antimetabolite, antibiotic, or herbicide resistance can be used as the basis for selection. For example, dhfr confers resistance to methotrexate; neo confers resistance to the aminoglycosides, neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567-3570; Colbere-Garapin, F. et al. (1981) J. Mol. Biol. 150:1-14.)

Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047-8051.) Visible markers, e.g., anthocyanins, green fluorescent proteins (GFP; Clontech), β glucuronidase and its substrate β-glucuronide, or luciferase and its substrate luciferin may be used. These markers can be used not only to identify transformants, but also to quantify the amount of transient or stable protein expression attributable to a specific vector system. (See, e.g., Rhodes, C. A. (1995) Methods Mol. Biol. 55:121-131.)

Although the presence/absence of marker gene expression suggests that the gene of interest is also present, the presence and expression of the gene may need to be confirmed. For example, if the sequence encoding HSPP is inserted within a marker gene sequence, transformed cells containing sequences encoding HSPP can be identified by the absence of marker gene function. Alternatively, a marker gene can be placed in tandem with a sequence encoding HSPP under the control of a single promoter. Expression of the marker gene in response to induction or selection usually indicates expression of the tandem gene as well.

In general, host cells that contain the nucleic acid sequence encoding HSPP and that express HSPP may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of HSPP using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HSPP is preferred, but a competitive binding assay may be employed. These and other assays are well known in the art. (See, e.g., Hampton, R. et al. (1990) *Serological Methods, a Laboratory Manual*, APS Press, St Paul Minn., Sect. IV; Coligan, J. E. et al. (1997) *Current Protocols in Immunology*, Greene Pub. Associates and Wiley-Interscience, New York N.Y.; and Pound, J. D. (1998) *Immunochemical Protocols*, Humana Press, Totowa N.J.).

A wide variety of labels and conjugation techniques are known by those skilled in the art and may be used in various nucleic acid and amino acid assays. Means for producing labeled hybridization or PCR probes for detecting sequences related to polynucleotides encoding HSPP include oligolabeling, nick translation, end-labeling, or PCR amplification using a labeled nucleotide. Alternatively, the sequences encoding HSPP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech, Promega (Madison Wis.), and US Biochemical. Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HSPP may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode HSPP may be designed to contain signal sequences which direct secretion of HSPP through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and WI38), are available from the American Type Culture Collection (ATCC, Manassas, Va.) and may be chosen to ensure the correct modification and processing of the foreign protein.

In another embodiment of the invention, natural, modified, or recombinant nucleic acid sequences encoding HSPP may be ligated to a heterologous sequence resulting in translation of a fusion protein in any of the aforementioned host systems. For example, a chimeric HSPP protein containing a heterologous moiety that can be recognized by a commercially available antibody may facilitate the screening of peptide libraries for inhibitors of HSPP activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His (SEQ ID NO: 269), FLAG, c-myc, and hemagglutinin (HA). GST, MBP, Trx, CBP, and 6-His (SEQ ID NO: 269) enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the HSPP encoding sequence and the heterologous protein sequence, so that HSPP may be cleaved away from the heterologous moiety following purification. Methods for fusion protein expression and purification are discussed in Ausubel (1995, supra, ch 10). A variety of commercially available kits may also be used to facilitate expression and purification of fusion proteins.

In a further embodiment of the invention, synthesis of radiolabeled HSPP may be achieved in vitro using the TNT rabbit reticulocyte lysate or wheat germ extract systems (Promega). These systems couple transcription and translation of protein-coding sequences operably associated with the T7, T3, or SP6 promoters. Translation takes place in the presence of a radiolabeled amino acid precursor, preferably $^{35}$S-methionine.

Fragments of HSPP may be produced not only by recombinant production, but also by direct peptide synthesis using solid-phase techniques. (See, e.g., Creighton, supra, pp. 55-60.) Protein synthesis may be performed by manual techniques or by automation. Automated synthesis may be achieved, for example, using the ABI 431A Peptide Synthesizer (Perkin-Elmer). Various fragments of HSPP may be synthesized separately and then combined to produce the full length molecule.

Therapeutics

Chemical and structural similarity, e.g., in the context of sequences and motifs, exists between regions of HSPP and signal peptide sequences. In addition, chemical and structural similarity, in the context of sequences and motifs, exists between HSPP-66 and prostatic steriod-binding C3 precursor from rat (GI 206453); between HSPP-68 and TWIK-related acid-sensitive K+ channel from human (GI 2465542); and between HSPP-92 and tyrosine specific protein phosphatases (PROSITE PDOC00323). In addition, the expression of HSPP is closely associated with proliferative, cancerous, inflamed, cardiovascular, nervous, reproductive, hematopoietic/immune, and developmental tissue. Therefore, HSPP appears to play a role in cell proliferative disorders including cancer; inflammation; and cardiovascular, neurological, reproductive, and developmental disorders. In the treatment of cell proliferative disorders including cancer; inflammation; and cardiovascular, neurological, reproductive, and developmental disorders associated with increased HSPP expression or activity, it is desirable to decrease the expression or activity of HSPP. In the treatment of the above conditions associated with decreased HSPP expression or activity, it is desirable to increase the expression or activity of HSPP.

Therefore, in one embodiment, HSPP or a fragment or derivative thereof may be administered to a subject to treat or prevent a disorder associated with decreased expression or activity of HSPP. Examples of such disorders include, but are not limited to, cell proliferative disorders such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; inflammatory disorders, such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyenodocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; cardiovascular disorders including disorders of the blood vessels such as arteriovenous fistula, atherosclerosis, hypertension, vasculitis, Raynaud's disease, aneurysms, arterial dissections, varicose veins, thrombophlebitis and phlebothrombosis, and vascular tumors; disorders of the heart such as congestive heart failure, ischemic heart disease, angina pectoris, myocardial infarction, hypertensive heart disease, degenerative valvular heart disease, calcific aortic valve stenosis, congenitally bicuspid aortic valve, mitral annular calcification, mitral valve prolapse, rheumatic fever and rheumatic heart disease, infective endocarditis, nonbacterial thrombotic endocarditis, endocarditis of systemic lupus erythematosus, carcinoid heart disease, cardiomyopathy, myocarditis, pericarditis, neoplastic heart disease, and congenital heart disease; and disorders of the lungs such as congenital lung anomalies, atelectasis, pulmonary congestion and edema, pulmonary embolism, pulmonary hemorrhage, pulmonary infarction, pulmonary hypertension, vascular sclerosis, obstructive pulmonary disease, restrictive pulmonary disease, chronic obstructive pulmonary disease, emphysema, chronic bronchitis, bronchial asthma, bronchiectasis, bacterial pneumonia, viral and mycoplasmal pneumonia, lung abscess, pulmonary tuberculosis, diffuse interstitial diseases, pneumoconioses, sarcoidosis, idiopathic pulmonary fibrosis, desquamative interstitial pneumonitis, hypersensitivity pneumonitis, pulmonary eosinophilia bronchiolitis obliterans-organizing pneumonia, diffuse pulmonary hemorrhage syndromes, Goodpasture's syndromes, idiopathic pulmonary hemosiderosis, pulmonary involvement in collagen-vascular disorders, pulmonary alveolar proteinosis, lung tumors, inflammatory and noninflammatory pleural effusions, pneumothorax, and pleural tumors; neurological disorders such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease; prion diseases including kuru, Creutzfeldt-Jakob disease, and Gerstmann-Straussler-Scheinker syndrome; fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis; inherited, metabolic, endocrine, and toxic myopathies; myasthenia gravis, periodic paralysis; mental disorders including mood, anxiety, and schizophrenic disorders; akathesia, amnesia, catatonia, diabetic neuropathy, tardive dyskinesia, dystonias, paranoid psychoses, postherpetic neuralgia, and Tourette's disorder; reproductive disorders such as disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, Peyronie's disease, carcinoma of the male breast, and gynecomastia; and developmental disorders, such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, and sensorineural hearing loss.

In another embodiment, a vector capable of expressing HSPP or a fragment or derivative thereof may be administered to a subject to treat or prevent a disorder associated with decreased expression or activity of HSPP including, but not limited to, those described above.

In a further embodiment, a pharmaceutical composition comprising a substantially purified HSPP in conjunction with a suitable pharmaceutical carrier may be administered to a subject to treat or prevent a disorder associated with decreased expression or activity of HSPP including, but not limited to, those provided above.

In still another embodiment, an agonist which modulates the activity of HSPP may be administered to a subject to treat or prevent a disorder associated with decreased expression or activity of HSPP including, but not limited to, those listed above.

In a further embodiment, an antagonist of HSPP may be administered to a subject to treat or prevent a disorder associated with increased expression or activity of HSPP. Examples of such disorders include, but are not limited to, those described above. In one aspect, an antibody which specifically binds HSPP may be used directly as an antagonist or indirectly as a targeting or delivery mechanism for bringing a pharmaceutical agent to cells or tissue which express HSPP.

In an additional embodiment, a vector expressing the complement of the polynucleotide encoding HSPP may be administered to a subject to treat or prevent a disorder associated with increased expression or activity of HSPP including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HSPP may be produced using methods which are generally known in the art. In particular, purified HSPP may be used to produce antibodies or to screen libraries of pharmaceutical agents to identify those which specifically bind HSPP. Antibodies to HSPP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HSPP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HSPP have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HSPP amino acids may be fused with those of another protein, such as KLH, and antibodies to the chimeric molecule may be produced.

Monoclonal antibodies to HSPP may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495-497; Kozbor, D. et al. (1985) J. Immunol. Methods 81:31-42; Cote, R. J. et al. (1983) Proc. Natl. Acad. Sci. 80:2026-2030; and Cole, S. P. et al. (1984) Mol. Cell. Biol. 62:109-120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851-6855; Neuberger, M. S. et al. (1984) Nature 312:604-608; and Takeda, S. et al. (1985) Nature 314:452-454.) Alternatively, techniques described for the production of single chain antibodies may be adapted, using methods known in the art, to produce HSPP-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134-10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833-3837; Winter, G. et al. (1991) Nature 349:293-299.)

Antibody fragments which contain specific binding sites for HSPP may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275-1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HSPP and its specific antibody. A two-site, monoclonal-based immunoassay utilizing monoclonal antibodies reactive to two non-interfering HSPP epitopes is preferred, but a competitive binding assay may also be employed (Pound, supra).

Various methods such as Scatchard analysis in conjunction with radioimmunoassay techniques may be used to assess the affinity of antibodies for HSPP. Affinity is expressed as an association constant, $K_a$, which is defined as the molar concentration of HSPP-antibody complex divided by the molar concentrations of free antigen and free antibody under equilibrium conditions. The $K_a$ determined for a preparation of polyclonal antibodies, which are heterogeneous in their affinities for multiple HSPP epitopes, represents the average affinity, or avidity, of the antibodies for HSPP. The $K_a$ determined for a preparation of monoclonal antibodies, which are monospecific for a particular HSPP epitope, represents a true measure of affinity. High-affinity antibody preparations with $K_a$ ranging from about $10^9$ to $10^{12}$ L/mole are preferred for use in immunoassays in which the HSPP-antibody complex must withstand rigorous manipulations. Low-affinity antibody preparations with $K_a$ ranging from about $10^6$ to $10^7$ L/mole are preferred for use in immunopurification and similar procedures which ultimately require dissociation of HSPP, preferably in active form, from the antibody (Catty, D. (1988) *Antibodies, Volume I: A Practical Approach*, IRL Press, Washington, D.C.; Liddell, J. E. and Cryer, A. (1991) *A Practical Guide to Monoclonal Antibodies*, John Wiley & Sons, New York N.Y.).

The titer and avidity of polyclonal antibody preparations may be further evaluated to determine the quality and suitability of such preparations for certain downstream applications. For example, a polyclonal antibody preparation containing at least 1-2 mg specific antibody/ml, preferably 5-10 mg specific antibody/ml, is preferred for use in procedures requiring precipitation of HSPP-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding HSPP, or any fragment or complement thereof, may be used for therapeutic purposes. In one aspect, the complement of the polynucleotide encoding HSPP may be used in situations in which it would be desirable to block the transcription of the mRNA. In particular, cells may be transformed with sequences complementary to polynucleotides encoding HSPP. Thus, complementary molecules or fragments may be used to modulate HSPP activity, or to achieve regulation of gene function. Such technology is now well known in the art, and sense or antisense oligonucleotides or larger fragments can be designed from various locations along the coding or control regions of sequences encoding HSPP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding HSPP. (See, e.g., Sambrook, supra; Ausubel, 1995, supra.)

Genes encoding HSPP can be turned off by transforming a cell or tissue with expression vectors which express high levels of a polynucleotide, or fragment thereof, encoding HSPP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HSPP. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing, Mt. Kisco N.Y., pp. 163-177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding HSPP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HSPP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462-466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HSPP, antibodies to HSPP, and mimetics, agonists, antagonists, or inhibitors of HSPP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HSPP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HSPP or fragments thereof, antibodies of HSPP, and agonists, antagonists or inhibitors of HSPP, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 µg to 100,000 µg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HSPP may be used for the diagnosis of disorders characterized by expression of HSPP, or in assays to monitor patients being treated with HSPP or agonists, antagonists, or inhibitors of HSPP. Antibodies useful for diagnostic purposes may be prepared in the same manner as described above for therapeutics. Diagnostic assays for HSPP include methods which utilize the antibody and a label to detect HSPP in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring HSPP, including ELISAs, RIAs, and FACS, are known in the art and provide a basis for diagnosing altered or abnormal levels of HSPP expression. Normal or standard values for HSPP expression are established by combining body fluids or cell extracts taken from normal mammalian subjects, preferably human, with antibody to HSPP under conditions suitable for complex formation. The amount of standard complex formation may be quantitated by various methods, preferably by photometric means. Quantities of HSPP expressed in subject, control, and disease samples from biopsied tissues are compared with the standard values. Deviation between standard and subject values establishes the parameters for diagnosing disease.

In another embodiment of the invention, the polynucleotides encoding HSPP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HSPP may be correlated with disease. The diagnostic assay may be used to determine absence, presence, and excess expression of HSPP, and to monitor regulation of HSPP levels during therapeutic intervention.

In one aspect, hybridization with PCR probes which are capable of detecting polynucleotide sequences, including genomic sequences, encoding HSPP or closely related molecules may be used to identify nucleic acid sequences which encode HSPP. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding HSPP, allelic variants, or related sequences.

Probes may also be used for the detection of related sequences, and should preferably have at least 50% sequence identity to any of the HSPP encoding sequences. The hybridization probes of the subject invention may be DNA or RNA and may be derived from the sequence of SEQ ID NO:135-268 or from genomic sequences including promoters, enhancers, and introns of the HSPP gene.

Means for producing specific hybridization probes for DNAs encoding HSPP include the cloning of polynucleotide sequences encoding HSPP or HSPP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding HSPP may be used for the diagnosis of disorders associated with expression of HSPP. Examples of such disorders include, but are not limited to, cell proliferative disorders such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; inflammatory disorders, such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyenodocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; cardiovascular disorders including disorders of the blood vessels such as arteriovenous fistula, atherosclerosis, hypertension, vasculitis, Raynaud's disease, aneurysms, arterial dissections, varicose veins, thrombophlebitis and phlebothrombosis, and vascular tumors; disorders of the heart such as congestive heart failure, ischemic heart disease, angina pectoris, myocardial infarction, hypertensive heart disease, degenerative valvular heart disease, calcific aortic valve stenosis, congenitally bicuspid aortic valve, mitral annular calcification, mitral valve prolapse, rheumatic fever and rheumatic heart disease, infective endocarditis, nonbacterial thrombotic endocarditis, endocarditis of systemic lupus erythematosus, carcinoid heart disease, cardiomyopathy, myocarditis, pericarditis, neoplastic heart disease, and congenital heart disease; and disorders of the lungs such as congenital lung anomalies, atelectasis, pulmonary congestion and edema, pulmonary embolism, pulmonary hemorrhage, pulmonary infarction, pulmonary hypertension, vascular sclerosis, obstructive pulmonary disease, restrictive pulmonary disease, chronic obstructive pulmonary disease, emphysema, chronic bronchitis, bronchial asthma, bronchiectasis, bacterial pneumonia, viral and mycoplasmal pneumonia, lung abscess, pulmonary tuberculosis, diffuse interstitial diseases, pneumoconioses, sarcoidosis, idiopathic pulmonary fibrosis, desquamative interstitial pneumonitis, hypersensitivity pneumonitis, pulmonary eosinophilia bronchiolitis obliterans-organizing pneumonia, diffuse pulmonary hemorrhage syndromes, Goodpasture's syndromes, idiopathic pulmonary hemosiderosis, pulmonary involvement in collagen-vascular disorders, pulmonary alveolar proteinosis, lung tumors, inflammatory and noninflammatory pleural effusions, pneumothorax, and pleural tumors; neurological disorders such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease; prion diseases including kuru, Creutzfeldt-Jakob disease, and Gerstmann-Straussler-Scheinker syndrome; fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis; inherited, metabolic, endocrine, and toxic myopathies; myasthenia gravis, periodic paralysis; mental disorders including mood, anxiety, and schizophrenic disorders; akathesia, amnesia, catatonia, diabetic neuropathy, tardive dyskinesia, dystonias, paranoid psychoses, postherpetic neuralgia, and Tourette's disorder; reproductive disorders such as disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, Peyronie's disease, carcinoma of the male breast, and gynecomastia; and developmental disorders, such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, and sensorineural hearing loss. The polynucleotide sequences encoding HSPP may be used in Southern or northern analysis, dot blot, or other membrane-based technologies; in PCR technologies; in dipstick, pin, and multiformat ELISA-like assays; and in microarrays utilizing fluids or tissues from patients to detect altered HSPP expression. Such qualitative or quantitative methods are well known in the art.

In a particular aspect, the nucleotide sequences encoding HSPP may be useful in assays that detect the presence of associated disorders, particularly those mentioned above. The nucleotide sequences encoding HSPP may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding HSPP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of HSPP, a normal or standard profile for expression is established. This may be accomplished by combining body fluids or cell extracts taken from normal subjects, either animal or human, with a sequence, or a fragment thereof, encoding HSPP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or overexpressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HSPP may involve the use of PCR. These oligomers may be chemically synthesized, generated enzymatically, or produced in vitro. Oligomers will preferably contain a fragment of a polynucleotide encoding HSPP, or a fragment of a polynucleotide complementary to the polynucleotide encoding HSPP, and will be employed under optimized conditions for identification of a specific gene or condition. Oligomers may also be employed under less stringent conditions for detection or quantitation of closely related DNA or RNA sequences.

Methods which may also be used to quantitate the expression of HSPP include radiolabeling or biotinylating nucleotides, coamplification of a control nucleic acid, and interpolating results from standard curves. (See, e.g., Melby, P. C. et al. (1993) J. Immunol. Methods 159:235-244; Duplaa, C. et al. (1993) Anal. Biochem. 212:229-236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614-10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150-2155; and Heller, M. J. et al. (1997) U.S. Pat. No. 5,605,662.)

In another embodiment of the invention, nucleic acid sequences encoding HSPP may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Harrington, J. J. et al. (1997) Nat. Genet. 15:345-355; Price, C. M. (1993) Blood Rev. 7:127-134; and Trask, B. J. (1991) Trends Genet. 7:149-154.)

Fluorescent in situ hybridization (FISH) may be correlated with other physical chromosome mapping techniques and genetic map data. (See, e.g., Heinz-Ulrich, et al. (1995) in Meyers, supra, pp. 965-968.) Examples of genetic map data can be found in various scientific journals or at the Online Mendelian Inheritance in Man (OMIM) site. Correlation between the location of the gene encoding HSPP on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22-23, any sequences mapping to that area may represent associated or regulatory genes for further investigation. (See, e.g., Gatti, R. A. et al. (1988) Nature 336:577-580.) The nucleotide sequence of the subject invention may also be used to detect differences in the chromosomal location due to translocation, inversion, etc., among normal, carrier, or affected individuals.

In another embodiment of the invention, HSPP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HSPP and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate. The test compounds are reacted with HSPP, or fragments thereof, and washed. Bound HSPP is then detected by methods well known in the art. Purified HSPP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HSPP specifically compete with a test compound for binding HSPP. In this manner, antibodies can be used to detect the presence of any peptide which shares one or more antigenic determinants with HSPP.

In additional embodiments, the nucleotide sequences which encode HSPP may be used in any molecular biology techniques that have yet to be developed, provided the new techniques rely on properties of nucleotide sequences that are currently known, including, but not limited to, such properties as the triplet genetic code and specific base pair interactions.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

The disclosures of all applications, patents, and publications, mentioned above and below, in particular U.S. Ser. No. 60/090,762, U.S. Ser. No. 60/094,983, U.S. Ser. No. 60/102,686, and U.S. Ser. No. 60/112,129, are hereby expressly incorporated by reference.

EXAMPLES

I. Construction of cDNA Libraries

RNA was purchased from Clontech or isolated from tissues described in Table 4. Some tissues were homogenized and lysed in guanidinium isothiocyanate, while others were homogenized and lysed in phenol or in a suitable mixture of denaturants, such as TRIZOL (Life Technologies), a monophasic solution of phenol and guanidine isothiocyanate. The resulting lysates were centrifuged over CsCl cushions or extracted with chloroform. RNA was precipitated from the lysates with either isopropanol or sodium acetate and ethanol, or by other routine methods.

Phenol extraction and precipitation of RNA were repeated as necessary to increase RNA purity. In some cases, RNA was treated with DNase. For most libraries, poly(A+) RNA was isolated using oligo d(T)-coupled paramagnetic particles (Promega), OLIGOTEX latex particles (QIAGEN, Valencia Calif.), or an OLIGOTEX mRNA purification kit (QIAGEN). Alternatively, RNA was isolated directly from tissue lysates using other RNA isolation kits, e.g., the POLY(A) PURE mRNA purification kit (Ambion, Austin Tex.).

In some cases, Stratagene was provided with RNA and constructed the corresponding cDNA libraries. Otherwise, cDNA was synthesized and cDNA libraries were constructed with the UNIZAP vector system (Stratagene) or SUPERSCRIPT plasmid system (Life Technologies), using the recommended procedures or similar methods known in the art. (See, e.g., Ausubel, 1997, supra, units 5.1-6.6). Reverse transcription was initiated using oligo d(T) or random primers. Synthetic oligonucleotide adapters were ligated to double stranded cDNA, and the cDNA was digested with the appropriate restriction enzyme or enzymes. For most libraries, the cDNA was size-selected (300-1000 bp) using SEPHACRYL S1000, SEPHAROSE CL2B, or SEPHAROSE CL4B column chromatography (Amersham Pharmacia Biotech) or preparative agarose gel electrophoresis. cDNAs were ligated into compatible restriction enzyme sites of the polylinker of a suitable plasmid, e.g., PBLUESCRIPT plasmid (Stratagene), PSPORT1 plasmid (Life Technologies), or pINCY (Incyte Corporation, Palo Alto Calif.). Recombinant plasmids were transformed into competent E. coli cells including XL1-Blue, XL1-BlueMRF, or SOLR from Stratagene or DH5ÿ, DH10B, or ElectroMAX DH10B from Life Technologies.

II. Isolation of cDNA Clones

Plasmids were recovered from host cells by in vivo excision, using the UNIZAP vector system (Stratagene) or cell lysis. Plasmids were purified using at least one of the following: a MAGIC or WIZARD minipreps DNA purification system (Promega); an AGTC miniprep purification kit (Edge Biosystems, Gaithersburg Md.); and QIAWELL 8 Plasmid, QIAWELL 8 Plus Plasmid, QIAWELL 8 Ultra Plasmid purification systems or the REAL Prep 96 plasmid kit from QIAGEN. Following precipitation, plasmids were resuspended in 0.1 ml of distilled water and stored, with or without lyophilization, at 4° C.

Alternatively, plasmid DNA was amplified from host cell lysates using direct link PCR in a high-throughput format (Rao, V. B. (1994) Anal. Biochem. 216:1-14). Host cell lysis and thermal cycling steps were carried out in a single reaction mixture. Samples were processed and stored in 384-well plates, and the concentration of amplified plasmid DNA was quantified fluorometrically using PICOGREEN dye (Molecular Probes, Eugene Oreg.) and a Fluoroskan II fluorescence scanner (Labsystems Oy, Helsinki, Finland).

III. Sequencing and Analysis

The cDNAs were prepared for sequencing using the ABI CATALYST 800 (Perkin-Elmer) or the HYDRA microdispenser (Robbins Scientific) or MICROLAB 2200 (Hamilton) systems in combination with the PTC-200 thermal cyclers (MJ Research). The cDNAs were sequenced using the ABI PRISM 373 or 377 sequencing systems (Perkin-Elmer) and standard ABI protocols, base calling software, and kits. In one alternative, cDNAs were sequenced using the MEGABACE 1000 DNA sequencing system (Molecular Dynamics). In another alternative, the cDNAs were amplified and sequenced using the ABI PRISM BIGDYE terminator cycle sequencing ready reaction kit (Perkin-Elmer). In yet another alternative, cDNAs were sequenced using solutions and dyes from Amersham Pharmacia Biotech. Reading frames for the ESTs were determined using standard methods (reviewed in Ausubel, 1997, supra, unit 7.7). Some of the cDNA sequences were selected for extension using the techniques disclosed in Example V.

The polynucleotide sequences derived from cDNA, extension, and shotgun sequencing were assembled and analyzed using a combination of software programs which utilize algorithms well known to those skilled in the art. Table 5 summarizes the software programs, descriptions, references, and threshold parameters used. The first column of Table 5 shows the tools, programs, and algorithms used, the second column provides a brief description thereof, the third column presents the references which are incorporated by reference herein, and the fourth column presents, where applicable, the scores, probability values, and other parameters used to evaluate the strength of a match between two sequences (the higher the probability the greater the homology). Sequences were analyzed using MACDNASIS PRO software (Hitachi Software Engineering, South San Francisco Calif.) and LASERGENE software (DNASTAR).

The polynucleotide sequences were validated by removing vector, linker, and polyA sequences and by masking ambiguous bases, using algorithms and programs based on BLAST, dynamic programming, and dinucleotide nearest neighbor analysis. The sequences were then queried against a selection of public databases such as GenBank primate, rodent, mammalian, vertebrate, and eukaryote databases, and BLOCKS to acquire annotation, using programs based on BLAST, FASTA, and BLIMPS. The sequences were assembled into full length polynucleotide sequences using programs based on Phred, Phrap, and Consed, and were screened for open reading frames using programs based on GeneMark, BLAST, and FASTA. The full length polynucleotide sequences were translated to derive the corresponding full length amino acid sequences, and these full length sequences were subsequently analyzed by querying against databases such as the GenBank databases (described above), SwissProt, BLOCKS, PRINTS, Prosite, and Hidden Markov Model (HMM)-based protein family databases such as PFAM. HMM is a probabilistic approach which analyzes consensus primary structures of gene families. (See, e.g., Eddy, S. R. (1996) Cur. Opin. Str. Biol. 6:361-365.)

The programs described above for the assembly and analysis of full length polynucleotide and amino acid sequences were also used to identify polynucleotide sequence fragments from SEQ ID NO:135-268. Fragments from about 20 to about 4000 nucleotides which are useful in hybridization and amplification technologies were described in The Invention section above.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; Ausubel, 1995, supra, ch. 4 and 16.)

Analogous computer techniques applying BLAST were used to search for identical or related molecules in nucleotide databases such as GenBank or LIFESEQ database (Incyte Corporation). This analysis is much faster than multiple membrane-based hybridizations. In addition, the sensitivity of the computer search can be modified to determine whether any particular match is categorized as exact or similar. The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of northern analyses are reported as a percentage distribution of libraries in which the transcript encoding HSPP occurred. Analysis involved the categorization of cDNA libraries by organ/tissue and disease. The organ/tissue categories included cardiovascular, dermatologic, developmental, endocrine, gastrointestinal, hematopoietic/immune, musculoskeletal, nervous, reproductive, and urologic. The disease/condition categories included cancer, inflammation/trauma, cell proliferation, neurological, and pooled. For each category, the number of libraries expressing the sequence of interest was counted and divided by the total number of libraries across all categories. Percentage values of tissue-specific and disease- or condition-specific expression are reported in Table 3.

V. Extension of HSPP Encoding Polynucleotides

Full length nucleic acid sequences of SEQ ID NOs:135-229 were produced by extension of the component fragments described in Table 1, column 5, using oligonucleotide primers based on these fragments. For each nucleic acid sequence, one primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 (National Biosciences, Plymouth, Minn.), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO BRL) were used to extend the sequence. If more than one extension is necessary or desired, additional sets of primers are designed to further extend the known region.

High fidelity amplification was obtained by following the instructions for the XL-PCR kit (The Perkin-Elmer Corp., Norwalk, Conn.) and thoroughly mixing the enzyme and reaction mix. PCR was performed using the PTC-200 thermal cycler (MJ Research, Inc., Watertown, Mass.), beginning with 40 pmol of each primer and the recommended concentrations of all other components of the kit, with the following parameters:

| Step 1  | 94° C. for 1 min (initial denaturation)            |
|---------|----------------------------------------------------|
| Step 2  | 65° C. for 1 min                                   |
| Step 3  | 68° C. for 6 min                                   |
| Step 4  | 94° C. for 15 sec                                  |
| Step 5  | 65° C. for 1 min                                   |
| Step 6  | 68° C. for 7 min                                   |
| Step 7  | Repeat steps 4 through 6 for an additional 15 cycles |
| Step 8  | 94° C. for 15 sec                                  |
| Step 9  | 65° C. for 1 min                                   |
| Step 10 | 68° C. for 7:15 min                                |
| Step 11 | Repeat steps 8 through 10 for an additional 12 cycles |
| Step 12 | 72° C. for 8 min                                   |
| Step 13 | 4° C. (and holding)                                |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK (QIAGEN Inc.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent E. coli cells (in 40 µl of appropriate media) were transformed with 3 µl of ligation mixture and cultured in 80 µl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing carbenicillin (2× carb). The following day, several colonies were randomly picked from each plate and cultured in 150 µl of liquid LB/2× carb medium placed in an individual well of an appropriate commercially-available sterile 96-well microtiter plate. The following day, 5 µl of each overnight culture was transferred into a non-sterile 96-well plate and, after dilution 1:10 with water, 5 µl from each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec                                  |
|--------|----------------------------------------------------|
| Step 2 | 94° C. for 20 sec                                  |
| Step 3 | 55° C. for 30 sec                                  |
| Step 4 | 72° C. for 90 sec                                  |
| Step 5 | Repeat steps 2 through 4 for an additional 29 cycles |
| Step 6 | 72° C. for 180 sec                                 |
| Step 7 | 4° C. (and holding)                                |

Aliquots of the PCR reactions were run on agarose gels together with molecular weight markers. The sizes of the PCR products were compared to the original partial cDNAs, and appropriate clones were selected, ligated into plasmid, and sequenced.

The full length nucleic acid sequences of SEQ ID NO:230-268 were produced by extension of an appropriate fragment of the full length molecule using oligonucleotide primers designed from this fragment. One primer was synthesized to initiate 5' extension of the known fragment, and the other primer, to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the PTC-200 thermal cycler (MJ Research, Inc.). The reaction mix contained DNA template, 200 nmol of each primer, reaction buffer containing $Mg^{2+}$, $(NH_4)_2SO_4$, and ÿ-mercaptoethanol, Taq DNA polymerase (Amersham Pharmacia Biotech), ELONGASE enzyme (Life Technologies), and Pfu DNA polymerase (Stratagene), with the following parameters for primer pair PCI A and PCI B: Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, the parameters for primer pair T7 and SK+ were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 ÿl PICOGREEN quantitation reagent (0.25% (v/v) PICOGREEN; Molecular Probes, Eugene Oreg.) dissolved in 1×TE and 0.5 ÿl of undiluted PCR product into each well of an opaque fluorimeter plate (Corning Costar, Acton Mass.), allowing the DNA to bind to the reagent. The plate was scanned in a Fluoroskan II (Labsystems Oy, Helsinki, Finland) to measure the fluorescence of the sample and to quantify the concentration of DNA. A 5 µl to 10 µl aliquot of the reaction mixture was analyzed by electrophoresis on a 1% agarose mini-gel to determine which reactions were successful in extending the sequence.

The extended nucleotides were desalted and concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with Agar ACE (Promega).

Extended clones were religated using T4 ligase (New England Biolabs, Beverly Mass.) into pUC 18 vector (Amersham Pharmacia Biotech), treated with Pfu DNA polymerase (Stratagene) to fill-in restriction site overhangs, and transfected into competent E. coli cells. Transformed cells were selected on antibiotic-containing media, individual colonies were picked and cultured overnight at 37° C. in 384-well plates in LB/2× carb liquid media.

The cells were lysed, and DNA was amplified by PCR using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the same conditions as described above. Samples were diluted with 20% dimethysulphoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (Perkin-Elmer).

In like manner, the nucleotide sequences of SEQ ID NO:135-268 are used to obtain 5' regulatory sequences using the procedure above, oligonucleotides designed for such extension, and an appropriate genomic library.

VI. Labeling and Use of Individual Hybridization Probes

Hybridization probes derived from SEQ ID NO:135-268 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 µCi of [ÿ-$^{32}$P] adenosine triphosphate (Amersham Pharmacia Biotech), and T4 polynucleotide kinase (DuPont NEN, Boston Mass.). The labeled oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba1, or Pvu II (DuPont NEN).

The DNA from each digest is fractionated on a 0.7% agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT-AR film (Eastman Kodak, Rochester N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE software (DNASTAR). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking followed by thermal and chemical treatments and subsequent drying. (See, e.g., Schena, M. et al. (1995) Science 270:467-470; Shalon, D. et al. (1996) Genome Res. 6:639-645.) Fluorescent probes are prepared and used for hybridization to the elements on the substrate. The substrate is analyzed by procedures described above.

VIII. Complementary Polynucleotides

Sequences complementary to the HSPP-encoding sequences, or any parts thereof, are used to detect, decrease, or inhibit expression of naturally occurring HSPP. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of HSPP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HSPP-encoding transcript.

IX. Expression of HSPP

Expression and purification of HSPP is achieved using bacterial or virus-based expression systems. For expression of HSPP in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express HSPP upon induction with isopropyl beta-D-thiogalactopyranoside (IPTG). Expression of HSPP in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding HSPP by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224-3227; Sandig, V. et al. (1996) Hum. Gene Ther. 7:1937-1945.)

In most expression systems, HSPP is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from Schistosoma japonicum, enables the purification of fusion proteins on immobilized glutathione under conditions that maintain protein activity and antigenicity (Amersham Pharmacia Biotech). Following purification, the GST moiety can be proteolytically cleaved from HSPP at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, supra, ch 10 and 16). Purified HSPP obtained by these methods can be used directly in the following activity assay.

X. Demonstration of HSPP Activity

HSPP-68

HSPP-68 activity is measured by determining the potassium current using voltage clamp analysis on single *Xenopus laevis* oocytes injected with HSPP-68 cRNA. HSPP-68 cRNA is synthesized in vitro from linearized HSPP-68 encoding plasmids using the T7 RNA polymerase and injected into oocytes. Injected oocytes are used two to four days after injection. In a 0.3 ml perfusion chamber, a single oocyte is impaled with two standard microelectrodes (1-2.5 Mÿ) filled with 3 M KCl. The oocyte is maintained under voltage clamp by using a Dagan TEV 200 amplifier, in buffer containing 96 mM NaCl, 2 mM KCl, 1.8 mM $CaCl_2$, 2 mM $MgCl_2$, 5 mM HEPES, pH 7.4 with NaOH. Stimulation of the preparation, data acquisition, and analysis is performed using a computer. All experiments are performed at room temperature (21-22° C.). Following a depolarizing pulse, the characteristics of the resulting potassium current are measured via the recording electrode. The amount of potassium current that flows in response to a unit depolarization is proportional to the activity of HSPP-68 in the cell. (Duprat, F. et al. (1997) EMBO J. 16:5464-5471.)

HSPP-92

HSPP-92 protein phosphatase activity is measured by the hydrolysis of P-nitrophenyl phosphate (PNPP). HSPP-92 is incubated together with PNPP in HEPES buffer pH 7.5, in the presence of 0.1% b-mercaptoethanol at 37° C. for 60 min. The reaction is stopped by the addition of 6 ml of 10 N NaOH and the increase in light absorbance at 410 nm resulting from the hydrolysis of PNPP is measured using a spectrophotometer. The increase in light absorbance is proportional to the activity of PP in the assay. (Diamond R. H. et al (1994) Mol Cell Biol 14:3752-62.)

Alternatively, HSPP, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled HSPP, washed, and any wells with labeled HSPP complex are assayed. Data obtained using different concentrations of HSPP are used to calculate values for the number, affinity, and association of HSPP with the candidate molecules.

Alternatively, an assay for HSPP activity measures the expression of HSPP on the cell surface. cDNA encoding HSPP is subcloned into an appropriate mammalian expression vector suitable for high levels of cDNA expression. The resulting construct is transfected into a nonhuman cell line such as NIH3T3. Cell surface proteins are labeled with biotin using methods known in the art. Immunoprecipitations are performed using HSPP-specific antibodies, and immunoprecipitated samples are analyzed using SDS-PAGE and immunoblotting techniques. The ratio of labeled immunoprecipitant to unlabeled immunoprecipitant is proportional to the amount of HSPP expressed on the cell surface.

Alternatively, an assay for HSPP activity measures the amount of HSPP in secretory, membrane-bound organelles. Transfected cells as described above are harvested and lysed. The lysate is fractionated using methods known to those of skill in the art, for example, sucrose gradient ultracentrifugation. Such methods allow the isolation of subcellular components such as the Golgi apparatus, ER, small membrane-bound vesicles, and other secretory organelles. Immunoprecipitations from fractionated and total cell lysates are performed using HSPP-specific antibodies, and immunoprecipitated samples are analyzed using SDS-PAGE and immunoblotting techniques. The concentration of HSPP in secretory organelles relative to HSPP in total cell lysate is proportional to the amount of HSPP in transit through the secretory pathway.

XI. Functional Assays

HSPP function is assessed by expressing the sequences encoding HSPP at physiologically elevated levels in mammalian cell culture systems. cDNA is subcloned into a mammalian expression vector containing a strong promoter that drives high levels of cDNA expression. Vectors of choice include pCMV SPORT (Life Technologies) and pCR3.1 (Invitrogen, Carlsbad Calif.), both of which contain the cytomegalovirus promoter. 5-10 μg of recombinant vector are transiently transfected into a human cell line, preferably of endothelial or hematopoietic origin, using either liposome formulations or electroporation. 1-2 μg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York N.Y.

The influence of HSPP on gene expression can be assessed using highly purified populations of cells transfected with sequences encoding HSPP and either CD64 or CD64-GFP.

CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding HSPP and other genes of interest can be analyzed by northern analysis or microarray techniques.

XII. Production of HSPP Specific Antibodies

HSPP substantially purified using polyacrylamide gel electrophoresis (PAGE; see, e.g., Harrington, M. G. (1990) Methods Enzymol. 182:488-495), or other purification techniques, is used to immunize rabbits and to produce antibodies using standard protocols.

Alternatively, the HSPP amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel, 1995, supra, ch. 11.)

Typically, oligopeptides 15 residues in length are synthesized using an ABI 431A Peptide Synthesizer (Perkin-Elmer) using fmoc-chemistry and coupled to KLH (Sigma-Aldrich, St. Louis Mo.) by reaction with N-maleimidobenzoyl-N-hydroxysuccinimide ester (MBS) to increase immunogenicity. (See, e.g., Ausubel, 1995, supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring HSPP Using Specific Antibodies

Naturally occurring or recombinant HSPP is substantially purified by immunoaffinity chromatography using antibodies specific for HSPP. An immunoaffinity column is constructed by covalently coupling anti-HSPP antibody to an activated chromatographic resin, such as CNBr-activated SEPHAROSE (Amersham Pharmacia Biotech). After the coupling, the resin is blocked and washed according to the manufacturer's instructions.

Media containing HSPP are passed over the immunoaffinity column, and the column is washed under conditions that allow the preferential absorbance of HSPP (e.g., high ionic strength buffers in the presence of detergent). The column is eluted under conditions that disrupt antibody/HSPP binding (e.g., a buffer of pH 2 to pH 3, or a high concentration of a chaotrope, such as urea or thiocyanate ion), and HSPP is collected.

XIV. Identification of Molecules which Interact with HSPP

HSPP, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled HSPP, washed, and any wells with labeled HSPP complex are assayed. Data obtained using different concentrations of HSPP are used to calculate values for the number, affinity, and association of HSPP with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Protein SEQ ID NO: | Nucleotide SEQ ID NO: | Clone ID | Library | Fragments |
|---|---|---|---|---|
| 1 | 135 | 443531 | MPHGNOT03 | 443531H1 (MPHGNOT03), 1406807F6 (LATRTUT02), 443531T6 (MPHGNOT03), SBBA00451F1, SBBA00676F1 |
| 2 | 136 | 632860 | NEUTGMT01 | 632860H1 (NEUTGMT01), 784715R3 (PROSNOT05), 509590H1 (MPHGNOT03) |
| 3 | 137 | 670010 | CRBLNOT01 | 670010H1 (CRBLNOT01), 669971R1 (CRBLNOT01), 1553045F1 (BLADTUT04) |
| 4 | 138 | 726498 | SYNOOAT01 | 726498H1 (SYNOOAT01), 726498R6 (SYNOOAT01), 866599R3 (BRAITUT03) |
| 5 | 139 | 795064 | OVARNOT03 | 795064H1 (OVARNOT03), 4339458H1 (BRAUNOT02), 937605R3 (CERVNOT01), 2381151F6 (ISLTNOT01), 1466346F6 (PANCTUT02) |
| 6 | 140 | 924925 | BRAINOT04 | 924925H1 (BRAINOT04), 3268330H1 (BRAINOT20), 759120R3 (BRAITUT02) |
| 7 | 141 | 962390 | BRSTTUT03 | 962390H1 (BRSTTUT03), 1907958F6 (CONNTUT01), 023569F1 (ADENINB01), 167282F1 (LIVRNOT01), 1309211F1 (COLNFET02), SAUA00696F1, SAUA02860F1 |
| 8 | 142 | 1259405 | MENITUT03 | 1259405H1 (MENITUT03), 2472425H1 (THP1NOT03), 774303R1 (COLNNOT05), 1520779F1 (BLADTUT04), 1693833F6 (COLNNOT23), 1831858T6.comp (THP1AZT01), 1527737T6.comp (UCMCL5T01) |
| 9 | 143 | 1297384 | BRSTNOT07 | 1297384H1 (BRSTNOT07), 1269310F6 (BRAINOT09), 1457367F1 (COLNFET02), 415587R1 (BRSTNOT01), SANA02967F1 |
| 10 | 144 | 1299627 | BRSTNOT07 | 1299627H1 (BRSTNOT07), 1359140F6 (LUNGNOT09), 1349224F1 (LATRTUT02), SBAA01431F1, SBAA02909F1, SBAA01156F1 |
| 11 | 145 | 1306026 | PLACNOT02 | 1306026H1 (PLACNOT02), 1464088R6 (PANCNOT04), SBAA02496F1, SBAA04305F1 |
| 12 | 146 | 1316219 | BLADTUT02 | 1316219H1 (BLADTUT02), 2458603F6 (ENDANOT01), 2504756T6 (CONUTUT01) |
| 13 | 147 | 1329031 | PANCNOT07 | 1329031H1 (PANCNOT07), 1329031T6 (PANCNOT07), 1329031F6 (PANCNOT07) |

TABLE 1-continued

| Protein SEQ ID NO: | Nucleotide SEQ ID NO: | Clone ID | Library | Fragments |
|---|---|---|---|---|
| 14 | 148 | 1483050 | CORPNOT02 | 1483050H1 (CORPNOT02), 855049H1 (NGANNOT01), 077017F1 (SYNORAB01), 1483050F6 (CORPNOT02), 1480024T6 (CORPNOT02), 1483050T6 (CORPNOT02), 759486R1 (BRAITUT02) |
| 15 | 149 | 1514160 | PANCTUT01 | 1514160H1 (PANCTUT01), 1866765T7 (SKINBIT01), 782676R1 (MYOMNOT01), 008055X4 (HMC1NOT01), 008055X5 (HMC1NOT01), 1866765F6 (SKINBIT01), SAOA03127F1 |
| 16 | 150 | 1603403 | LUNGNOT15 | 1603403H1 (LUNGNOT15), 372910F1 (LUNGNOT02), 733299R7 (LUNGNOT03) |
| 17 | 151 | 1652303 | PROSTUT08 | 1652303H1 (PROSTUT08), 1671806H1 (BLADNOT05), 1341743T1 (COLNTUT03), 3803812H1 (BLADTUT03), 1878546F6 (LEUKNOT03), 1428640F1 (SINTBST01), 2058609R6 (OVARNOT03), 1331621F1 (PANCNOT07), 1306331T1 (PLACNOT02) |
| 18 | 152 | 1693358 | COLNNOT23 | 1693358H1 (COLNNOT23), 2498265H1 (ADRETUT05), 1867125F6 (SKINBIT01), 1693358T6 (COLNNOT23), 2245848R6 (HIPONON02) |
| 19 | 153 | 1707711 | DUODNOT02 | 1707711H1 (DUODNOT02), 1484609T1 (CORPNOT02), 1707711F6 (DUODNOT02), 1267959F1 (BRAINOT09), 1484609F1 (CORPNOT02), SAJA00930F1, SAJA01300R1, SAJA00999R1 |
| 20 | 154 | 1738735 | COLNNOT22 | 1738735H1 (COLNNOT22), SAJA00944R1, SAJA00137F1, SAJA03629F1 |
| 21 | 155 | 1749147 | STOMTUT02 | 1749147H1 (STOMTUT02), 1749147F6 (STOMTUT02), 1749147T6 (STOMTUT02) |
| 22 | 156 | 1817722 | PROSNOT20 | 1817722H1 (PROSNOT20), 2011085H1 (TESTNOT03) |
| 23 | 157 | 1831290 | THP1AZT01 | 1831290H1 (THP1AZT01), 3473958H1 (LUNGNOT27), 1972268F6 (UCMCL5T01), 1301277F1 (BRSTNOT07), 1521574F1 (BLADTUT04), 1561690T6 (SPLNNOT04), 891461R1 (STOMTUT01) |
| 24 | 158 | 1831477 | THP1AZT01 | 1831477H1 (THP1AZT01), 1582867H1 (DUODNOT01), 1336769T1 (COLNNOT13), 1933092H1 (COLNNOT16), 1519909F1 (BLADTUT04), 1220946H1 (NEUTGMT01), 809556T1 (LUNGNOT04), 1217559T1 (NEUTGMT01), 1309225F1 (COLNFET02) |
| 25 | 159 | 1841607 | COLNNOT07 | 1841607H1 (COLNNOT07), SBHA03588F1 |
| 26 | 160 | 1852391 | LUNGFET03 | 1852391H1 (LUNGFET03), 734140H1 (TONSNOT01), 1852391F6 (LUNGFET03) |
| 27 | 161 | 1854555 | HNT3AZT01 | 1854555H1 (HNT3AZT01), 2511711H1 (CONUTUT01), 782453R1 (MYOMNOT01), 1854555F6 (HNT3AZT01), 1840675T6 (COLNNOT07), 2109736H1 (BRAITUT03) |
| 28 | 162 | 1855755 | PROSNOT18 | 1855755H1 (PROSNOT18), 3040236H1 (BRSTNOT16), 1283207F1 (COLNNOT16), 833763T1 (PROSNOT07), 1920926R6 (BRSTTUT01) |
| 29 | 163 | 1861434 | PROSNOT19 | 1861434H1 (PROSNOT19), 980291R1 (TONGTUT01), 1861434T6 (PROSNOT19), SARA01525F1, SARA02548F1 |
| 30 | 164 | 1872334 | LEUKNOT02 | 1872334H1 (LEUKNOT02), 1872334F6 (LEUKNOT02), SBGA03684F1 |
| 31 | 165 | 1877230 | LEUKNOT03 | 1877230H1 (LEUKNOT03), 2519841H1 (BRAITUT21), 1877230T6 (LEUKNOT03), 1254693F1 (LUNGFET03), 077020R1 (SYNORAB01), 1232336F1 (LUNGFET03), 1004952R6 (BRSTNOT03), SARA01879F1, SARA02654F1 |
| 32 | 166 | 1877885 | LEUKNOT03 | 1877885H1 (LEUKNOT03), 508020F1 (TMLR3DT01), 2751126R6 (THP1AZS08), SARA02571F1 |
| 33 | 167 | 1889269 | BLADTUT07 | 1889269H1 (BLADTUT07), 1915551H1 (PROSTUT04), 629493X12 (KIDNNOT05), 1441289F1 (THYRNOT03), 1215274X34F1 (BRSTTUT01), 1818447F6 (PROSNOT20), 1208463R1 (BRSTNOT02) |
| 34 | 168 | 1890243 | BLADTUT07 | 1890243H1 (BLADTUT07), SARA01884F1, SATA00046F1, SARA03294F1, SARA02790F1 |
| 35 | 169 | 1900433 | BLADTUT06 | 1900433H1 (BLADTUT06), SATA00396F1, SATA02742F1 |
| 36 | 170 | 1909441 | CONNTUT01 | 1909441H1 (CONNTUT01), 1398811F1 (BRAITUT08), 3039939H1 (BRSTNOT16), 3324740H1 (PTHYNOT03), 1442131F6 (THYRNOT03), 2254056H1 (OVARTUT01), 2199453T6 (SPLNFET02), 1692610F6 (COLNNOT23), 1698531H1 (BLADTUT05) |
| 37 | 171 | 1932226 | COLNNOT16 | 1932226H1 (COLNNOT16), 2320569H1 (OVARNOT02), 1932226F6 (COLNNOT16), 2469455T6 (THP1NOT03), 2469455F6 (THP1NOT03), 1907140F6 (OVARNOT07), SATA02592F1 |
| 38 | 172 | 1932647 | COLNNOT16 | 1932647H1 (COLNNOT16), 1492745T1 (PROSNON01), 1492745H1 (PROSNON01), SASA02355F1, SASA00117F1, SASA00192F1 |
| 39 | 173 | 2124245 | BRSTNOT07 | 2124245H1 (BRSTNOT07), 1235393F1 (LUNGFET03), 1402264F6 (LATRTUT02), 1303990F1 (PLACNOT02), 1402264T6 (LATRTUT02) |
| 40 | 174 | 2132626 | OVARNOT03 | 2132626H1 (OVARNOT03), 1723432T6 (BLADNOT06), 2132626R6 (OVARNOT03), 1736723T6 (COLNNOT22), 1504738F1 (BRAITUT07) |
| 41 | 175 | 2280639 | PROSNON01 | 2280639H1 (PROSNON01), 1435330H1 (PANCNOT08), 1377560F6 (LUNGNOT10) |
| 42 | 176 | 2292356 | BRAINON01 | 2292356H1 (BRAINON01), 4086827H1 (LIVRNOT06), 1754442F6 (LIVRTUT01), 3571126H1 (HEAPNOT01), 1601305F6 (BLADNOT03) |
| 43 | 177 | 2349310 | COLSUCT01 | 2349310H1 (COLSUCT01), 2349310T6 (COLSUCT01) |
| 44 | 178 | 2373227 | ADRENOT07 | 2373227H1 (ADRENOT07), 3316444H1 (PROSBPT03), 302685R6 (TESTNOT04), SASA02181F1, SASA01923F1, SASA03516F1 |
| 45 | 179 | 2457682 | ENDANOT01 | 2457682H1 (ENDANOT01), 2457682F6 (ENDANOT01) |
| 46 | 180 | 2480426 | SMCANOT01 | 2480426H1 (SMCANOT01), 2480426F6 (SMCANOT01) |
| 47 | 181 | 2503743 | CONUTUT01 | 2503743H1 (CONUTUT01), 1853909H1 (HNT3AZT01), 1517619F1 (PANCTUT01), 1467896F6 (PANCTUT02), 490031F1 (HNT2AGT01), 1208654R1 (BRSTNOT02), 880544R1 (THYRNOT02) |

TABLE 1-continued

| Protein SEQ ID NO: | Nucleotide SEQ ID NO: | Clone ID | Library | Fragments |
|---|---|---|---|---|
| 48 | 182 | 2537684 | BONRTUT01 | 2537684H1 (BONRTUT01), 2005493H1 (TESTNOT03), 730969H1 (LUNGNOT03), 2537601F6 (BONRTUT01), 916487H1 (BRSTNOT04), 996135R1 (KIDNTUT01), 1920738R6 (BRSTTUT01), 1957710F6 (CONNNOT01) |
| 49 | 183 | 2593853 | OVARTUT02 | 2593853H1 (OVARTUT02), 807497H1 (STOMNOT02), 914020R6 (STOMNOT02), 889992R1 (STOMTUT01) |
| 50 | 184 | 2622354 | KERANOT02 | 2622354H1 (KERANOT02), 2623992H1 (KERANOT02), 1556510F6 (BLADTUT04) |
| 51 | 185 | 2641377 | LUNGTUT08 | 2641377H1 (LUNGTUT08), 4341415H2 (BRAUNOT02), SBCA07049F3 |
| 52 | 186 | 2674857 | KIDNNOT19 | 2674857H1 (KIDNNOT19), 1872373H1 (LEUKNOT02), 470512R6 (MMLR1DT01), 1728547H1 (PROSNOT14), 3013651F6 (MUSCNOT07), SBCA01366F1, SBCA00694F1 |
| 53 | 187 | 2758485 | THP1AZS08 | 2758485H1 (THP1AZS08), 3097533H1 (CERVNOT03), 1578959F6 (DUODNOT01) |
| 54 | 188 | 2763296 | BRSTNOT12 | 2763296H1 (BRSTNOT12), 3486025F6 (KIDNNOT31), SBDA07002F3 |
| 55 | 189 | 2779436 | OVARTUT03 | 2779436H1 (OVARTUT03), 2779436F6 (OVARTUT03), SBDA07009F3 |
| 56 | 190 | 2808528 | BLADTUT08 | 2808528H1 (BLADTUT08), 2611513F6 (THYMNOT04), SBDA07021T3 |
| 57 | 191 | 2809230 | BLADTUT08 | 2809230H1 (BLADTUT08), 2213849H1 (SINTFET03), 711706R6 (SYNORAT04), 958323R1 (KIDNNOT05), 030732F1 (THP1NOB01) |
| 58 | 192 | 2816821 | BRSTNOT14 | 2816821H1 (BRSTNOT14), 3746964H1 (THYMNOT08), 2816821F6 (BRSTNOT14), 948722T6 (PANCNOT05), 807947R6 (STOMNOT02) |
| 59 | 193 | 2817268 | BRSTNOT14 | 2817268H1 (BRSTNOT14), 3591308H1 (293TF5T01), 419522R1 (BRSTNOT01), 2073028F6 (ISLTNOT01), 1308781F6 (COLNFET02) |
| 60 | 194 | 2923165 | SININOT04 | 2923165H1 (SININOT04), 2011630H1 (TESTNOT03), 1457250F1 (COLNFET02), 754668R1 (BRAITUT02), 1406510F6 (LATRTUT02) |
| 61 | 195 | 2949822 | KIDNFET01 | 2949822H1 (KIDNFET01), SBDA07078F3 |
| 62 | 196 | 2992192 | KIDNFET02 | 2992192H1 (KIDNFET02), 2534324H2 (BRAINOT18), 2815255T6 (OVARNOT10), 1551107T6 (PROSNOT06), 1551107R6 (PROSNOT06) |
| 63 | 197 | 2992458 | KIDNFET02 | 2992458H1 (KIDNFET02), 2618951H1 (GBLANOT01), 1479252F1 (CORPNOT02), 1879054H1 (LEUKNOT03), 1879054F6 (LEUKNOT03), 2215240H1 (SINTFET03), 1535968T1 (SPLNNOT04) |
| 64 | 198 | 3044710 | HEAANOT01 | 3044710H1 (HEAANOT01), 3741773H1 (MENTNOT01), 859906X42C1 (BRAITUT03), 1534347F1 (SPLNNOT04), 1421122F1 (KIDNNOT09), 1303865F1 (PLACNOT02), 1704452F6 (DUODNOT02), 1251642F1 (LUNGFET03), 1781694R6 (PGANNON02) |
| 65 | 199 | 3120415 | LUNGTUT13 | 3120415H1 (LUNGTUT13), 1360123T1 (LUNGNOT12), 1375015H1 (LUNGNOT10) |
| 66 | 200 | 126758 | LUNGNOT01 | 126758H1 (LUNGNOT01), 126758X11 (LUNGNOT01), 811864T1 (LUNGNOT04) |
| 67 | 201 | 674760 | CRBLNOT01 | 674760H1 (CRBLNOT01), 3253976H1 (OVARTUN01), SAUA03387F1 |
| 68 | 202 | 1229438 | BRAITUT01 | 1229438H1 (BRAITUT01), 1230616H1 (BRAITUT01), 1461187R1 (PANCNOT04), 2493039H1 (ADRETUT05), 2891628H1 (LUNGFET04) |
| 69 | 203 | 1236935 | LUNGFET03 | 1236935H1 (LUNGFET03), SBAA00983F1, SBAA02057F1, SBAA00170F1 |
| 70 | 204 | 1359283 | LUNGNOT12 | 1359283H1 (LUNGNOT12), SBAA01213F1, SBAA03934F1 |
| 71 | 205 | 1450703 | PENITUT01 | 551298F1 (BEPINOT01), 551298R1 (BEPINOT01), 1450703H1 (PENITUT01), 2748715H1 (LUNGTUT11) |
| 72 | 206 | 1910668 | CONNTUT01 | 1269346H1 (BRAINOT09), 1380872F1 (BRAITUT08), 1910668F6 (CONNTUT01), 1910668H1 (CONNTUT01), SATA02800F1, SATA03799F1, SARA02035F1 |
| 73 | 207 | 1955143 | CONNNOT01 | 1955143F6 (CONNNOT01), 1955143H1 (CONNNOT01) |
| 74 | 208 | 1961637 | BRSTNOT04 | 867025H1 (BRAITUT03), 1961637H1 (BRSTNOT04), 2809064T6 (BLADTUT08), 2938714H1 (THYMFET02), 2956402H1 (KIDNFET01), 3808735T6 (CONTTUT01) |
| 75 | 209 | 1990762 | CORPNOT02 | 1990762H1 (CORPNOT02), 1990762T3 (CORPNOT02), SBGA04911F1, SBGA01201F1, SBGA02205F1 |
| 76 | 210 | 1994131 | CORPNOT02 | 1994131H1 (CORPNOT02), 2645984F6 (OVARTUT04) |
| 77 | 211 | 1997745 | BRSTTUT03 | 1752307F6 (LIVRTUT01), 1853730H1 (HNT3AZT01), 1997745H1 (BRSTTUT03), SAZA00953F1 |
| 78 | 212 | 2009035 | TESTNOT03 | 2009035H1 (TESTNOT03), 2009035R6 (TESTNOT03) |
| 79 | 213 | 2009152 | TESTNOT03 | 2009152H1 (TESTNOT03), 2009152R6 (TESTNOT03), 2783263H1 (BRSTNOT13) |
| 80 | 214 | 2061752 | OVARNOT03 | 2061752H1 (OVARNOT03), 2061752T6 (OVARNOT03), 2732805H1 (OVARTUT04), SAZA01310F1, SAZA00830F1 |
| 81 | 215 | 2061933 | OVARNOT03 | 046580R1 (CORNNOT01), 746061R1 (BRAITUT01), 826996R1 (PROSNOT06), 2061933H1 (OVARNOT03) |
| 82 | 216 | 2081422 | UTRSNOT08 | 2081422F6 (UTRSNOT08), 2081422H1 (UTRSNOT08), SBCA04793F1, SBCA05657F1, SBDA00065F1 |
| 83 | 217 | 2101278 | BRAITUT02 | 2101278H1 (BRAITUT02), SAXA00399F1, SAXA01284F1, SAXA01227F1 |
| 84 | 218 | 2121353 | BRSTNOT07 | 341437H1 (NEUTFMT01), 687136H1 (UTRSNOT02), 2121353H1 (BRSTNOT07), SASA01311F1 |
| 85 | 219 | 2241736 | PANCTUT02 | 833263H1 (PROSTUT04), 2241736H1 (PANCTUT02), SAZA01148F1, SASA03299F1, SASA01349F1 |
| 86 | 220 | 2271935 | PROSNON01 | 2271935H1 (PROSNON01), 2276774H1 (PROSNON01), 2760171T6 (THP1AZS08) |
| 87 | 221 | 2295344 | BRSTNOT05 | 2295344H1 (BRSTNOT05), 3288561F6 (BONRFET01), SBGA01801F1 |
| 88 | 222 | 2303994 | BRSTNOT05 | 905482T1 (COLNNOT08), 1858636F6 (PROSNOT18), 2303994H1 (BRSTNOT05) |
| 89 | 223 | 2497805 | ADRETUT05 | 2497805F6 (ADRETUT05), 2497805H1 (ADRETUT05) |
| 90 | 224 | 2646362 | LUNGTUT11 | 1754702H1 (LIVRTUT01), 2640776T6 (LUNGTUT08), 2646362H1 (LUNGTUT11), 3356773H1 (PROSTUT16) |

TABLE 1-continued

| Protein SEQ ID NO: | Nucleotide SEQ ID NO: | Clone ID | Library | Fragments |
|---|---|---|---|---|
| 91 | 225 | 2657146 | LUNGTUT09 | 2657146F6 (LUNGTUT09), 2657146H1 (LUNGTUT09) |
| 92 | 226 | 2755786 | THP1AZS08 | 288436R1 (EOSIHET02), 1252824F6 (LUNGFET03), 1305549H1 (PLACNOT02), 1364975R1 (SCORNON02), 2018293H1 (THP1NOT01), 2047320H1 (THP1T7T01), 2184537F6 (SININOT01), 2755786H1 (THP1AZS08), 4111022H1 (PROSBPT07) |
| 93 | 227 | 2831245 | TLYMNOT03 | 2831245H1 (TLYMNOT03), SBMA01396F1 |
| 94 | 228 | 3116250 | LUNGTUT13 | 126263F1 (LUNGNOT01), 2729942H1 (OVARTUT04), 3116250H1 (LUNGTUT13) |
| 95 | 229 | 3129630 | LUNGTUT12 | 3129630F6 (LUNGTUT12), 3129630H1 (LUNGTUT12), SBDA06436F1 |
| 96 | 230 | 007632 | HMC1NOT01 | 007632H1 (HMC1NOT01), 007632R6 (HMC1NOT01), 007632T6 (HMC1NOT01) |
| 97 | 231 | 1236968 | LUNGFET03 | 1236968H1 (LUNGFET03), SBAA02713F1, SBAA03203F1, SBAA04196F1 |
| 98 | 232 | 1334153 | COLNNOT13 | 776410R1 (COLNNOT05), 1334153H1 (COLNNOT13), 1334153T1 (COLNNOT13), 1800085F6 (COLNNOT27), 2701948H1 (OVARTUT10) |
| 99 | 233 | 1396975 | BRAITUT08 | 864113H1 (BRAITUT03), 876139R1 (LUNGAST01), 1268313F1 (BRAINOT09), 1351348T1 (LATRTUT02), 1396975H1 (BRAITUT08), 1485768F6 (CORPNOT02), 1815364F6 (PROSNOT20) |
| 100 | 234 | 1501749 | SINTBST01 | 079080R1 (SYNORAB01), 1501749H1 (SINTBST01), 1724970H1 (PROSNOT14) |
| 101 | 235 | 1575240 | LNODNOT03 | 081858R1 (SYNORAB01), 1575240H1 (LNODNOT03), 3451462R6 (UTRSNON03) |
| 102 | 236 | 1647884 | PROSTUT09 | 1647884H1 (PROSTUT09), 1647884T6 (PROSTUT09), 3998922R6 (HNT2AZS07) |
| 103 | 237 | 1661144 | BRSTNOT09 | 720941X17 (SYNOOAT01), 1661144H1 (BRSTNOT09), 2181782H1 (SININOT01) |
| 104 | 238 | 1685409 | PROSNOT15 | 755203R1 (BRAITUT02), 1226185T1 (COLNNOT03), 1300837F1 (BRSTNOT07), 1685409H1 (PROSNOT15), 1705256H1 (DUODNOT02) |
| 105 | 239 | 1731419 | BRSTTUT08 | 1731419H1 (BRSTTUT08), 1731419X319T3 (BRSTTUT08), 1731419X322F1 (BRSTTUT08), 1731419X326F1 (BRSTTUT08), 1731419X329F1 (BRSTTUT08), 1733786F6 (BRSTTUT08), SZAH01494F1 |
| 106 | 240 | 2650265 | BRSTNOT14 | 1680316T6 (STOMFET01), 2650265H1 (BRSTNOT14), 2650265T6 (BRSTNOT14), 2760588R6 (BRAINOS12) |
| 107 | 241 | 2677129 | KIDNNOT19 | 1592129H1 (CARGNOT01), 2645962H1 (OVARTUT04), 2677129F6 (KIDNNOT19), 2677129H1 (KIDNNOT19), 2910973H1 (KIDNTUT15), 4571722H1 (PROSTMT02), 4906791H2 (TLYMNOT08) |
| 108 | 242 | 3151073 | ADRENON04 | 3150857T6 (ADRENON04), 3151073H1 (ADRENON04), 3151073R6 (ADRENON04) |
| 109 | 243 | 3170095 | BRSTNOT18 | 3170095F6 (BRSTNOT18), 3170095H1 (BRSTNOT18) |
| 110 | 244 | 3475168 | LUNGNOT27 | 079680F1 (SYNORAB01), 443811T6 (MPHGNOT03), 1509356T6 (LUNGNOT14), 1873596F6 (LEUKNOT02), 2440867H1 (EOSITXT01), 3475168H1 (LUNGNOT27) |
| 111 | 245 | 3836893 | DENDTNT01 | 446637H1 (MPHGNOT03), 1219376R6 (NEUTGMT01), 3735467F6 (SMCCNOS01), 3735467T6 (SMCCNOS01), 3836893H1 (DENDTNT01) |
| 112 | 246 | 4072159 | KIDNNOT26 | 2129415T6 (KIDNNOT05), 4072159F6 (KIDNNOT26), 4072159H1 (KIDNNOT26) |
| 113 | 247 | 1003916 | BRSTNOT03 | 620937R6 (PGANNOT01), 1003916H1 and 1003916R6 (BRSTNOT03), 1413623H1 (BRAINOT12), 1435945F1 (PANCNOT08), 1479127F1 (CORPNOT02), 1969146R6 (BRSTNOT04), 2517587F6 (BRAITUT21), 2967848H1 (SCORNOT04) |
| 114 | 248 | 2093492 | PANCNOT04 | 489651H1 (HNT2AGT01), 1265353T1 (SYNORAT05), 1431505R6 (BEPINON01), 1605237F6 (LUNGNOT15), 2093492H1 and 2093492T6 (PANCNOT04), 4195560H1 (COLITUT02) |
| 115 | 249 | 2108789 | BRAITUT03 | 2108789H1 and 2108789R6 (BRAITUT03), 2182008T6 (SININOT01), 3255751R6 and 3255751T6 (OVARTUN01) |
| 116 | 250 | 2171401 | ENDCNOT03 | 037241F1 (HUVENOB01), 1821492F6 (GBLATUT01), 2055814T6 (BEPINOT01), 2171401F6 and 2171401H1 (ENDCNOT03), 2668952F6 (ESOGTUT02), 3140313H1 and 3140313T6 (SMCCNOT02), 5031775H1 (EPIBTXT01) |
| 117 | 251 | 2212530 | SINTFET03 | 187596R6 and 187596T6 (CARDNOT01), 919634R6 (RATRNOT02), 1992331H1 (CORPNOT02), 2062034H1 (OVARNOT03), 2212530F6 and 2212530H1 (SINTFET03), 2520479H1 (BRAITUT21), 2878284F6 (THYRNOT10), 2992354H1 (KIDNFET02), 4020719F6 (BRAXNOT02) |
| 118 | 252 | 2253036 | OVARTUT01 | 2253036H1 and 2253036R6 (OVARTUT01) |
| 119 | 253 | 2280161 | PROSNON01 | 482326H1 (HNT2RAT01), 934345H1 (CERVNOT01), 1379358F1 and 1379358T1 (LUNGNOT10), 1438562T1 (PANCNOT08), 1467511F6 (PANCTUT02), 1568138F1 (UTRSNOT05), 1636106T6 (UTRSNOT06), 2134534F6 (ENDCNOT01), 2280161H1 and 2280161X19F1 (PROSNON01), 2789845F6 (COLNTUT16), 3096938H1 (CERVNOT03), 3774621F6 (BRSTNOT25), 4222971H1 (PANCNOT07), 5111983H1 (ENDITXT01), 5324177H1 (FIBPFEN06) |
| 120 | 254 | 2287485 | BRAINON01 | 1454588F1 (PENITUT01), 1593332F6 (BRAINOT14), 2287485H1 and 2287485R6 (BRAINON01), 3765992H1 (BRSTNOT24), 4374293H1 (CONFNOT03), 4937931H1 (PROSTUS18), SBCA01722F1 |
| 121 | 255 | 2380344 | ISLTNOT01 | 2380344F6 and 2380344H1 (ISLTNOT01), 2888536T3 (LUNGFET04), SASA03644F1, SASA03689F1 |
| 122 | 256 | 2383171 | ISLTNOT01 | 956296R1 (KIDNNOT05), 1342250F1 (COLNTUT03), 1468046F1 and 1468046T1 (PANCTUT02), 2383171H1 (ISLTNOT01), SBYA05452U1, SBYA01369U1 |
| 123 | 257 | 2396046 | THP1AZT01 | 2396046F6, 2396046H1 and 2396118T6 (THP1AZT01) |
| 124 | 258 | 2456587 | ENDANOT01 | 2456587H1 and 2456587T6 (ENDANOT01), 2872569H1 (THYRNOT10), SBCA03778F1, SBDA00115F1, SBCA02401F1, SBCA03351F1, SBCA05164F1, SBCA04783F1, SBCA00155F1, SBCA04141F1 |

TABLE 1-continued

| Protein SEQ ID NO: | Nucleotide SEQ ID NO: | Clone ID | Library | Fragments |
|---|---|---|---|---|
| 125 | 259 | 2484813 | BONRTUT01 | 1234970T1 (LUNGFET03), 1338090F6 (COLNNOT13), 2484813H1 (BONRTUT01), SBCA00053F1, SBCA02064F1, SBCA02151F1, SBCA03770F1, SBCA04866F1, SBCA03406F1 |
| 126 | 260 | 2493851 | ADRETUT05 | 2493851H1 (ADRETUT05), 3805916F6 (BLADTUT03), 4500439H1 and 4500748H1 (BRAVTXT02), 5120601H1 (SMCBUNT01) |
| 127 | 261 | 2495719 | ADRETUT05 | 603447R1 (BRSTTUT01), 2495719H1 (ADRETUT05), 2917493F6 (THYMFET03), 4647103H1 (PROSTUT20), SBRA04984D1 |
| 128 | 262 | 2614153 | GBLANOT01 | 1833135R6 (BRAINON01), 1966515R6 (BRSTNOT04), 2331103R6 (COLNNOT11), 2614153H1 (GBLANOT01), 2656691F6 (LUNGTUT09), 3951176H1 (DRGCNOT01) |
| 129 | 263 | 2655184 | THYMNOT04 | 2655184H1 (THYMNOT04), SBDA05215F1, SBDA05213F1, SBDA01516F1 |
| 130 | 264 | 2848362 | BRSTTUT13 | 1297974F1 and 1297974T6 (BRSTNOT07), 2630138F6 (COLNTUT15), 2848362H1 (BRSTTUT13) |
| 131 | 265 | 2849906 | BRSTTUT13 | 1541617R1 and 1541617T1 (SINTTUT01), 2684504F6 and 2684504T6 (LUNGNOT23), 2796805H1 (NPOLNOT01), 2849906H1 (BRSTTUT13) |
| 132 | 266 | 2899137 | DRGCNOT01 | 2899137H1 (DRGCNOT01), 3026490F6 and 3026490T6 (HEARFET02), 3483359H1 (KIDNNOT31) |
| 133 | 267 | 2986229 | CARGDIT01 | 1740227T6 (HIPONON01), 2986229H1 (CARGDIT01) |
| 134 | 268 | 3222081 | COLNNON03 | 1754079F6 (LIVRTUT01), 3222081H1 (COLNNON03), 4053813T6 (SPLNNOT13), 4230282H1 (BRAMDIT01), SBDA07029F3 |

TABLE 2

| Protein SEQ ID NO: | Amino Acid Residues | Potential Phosphorylation Sites | Potential Glycosylation Sites | Signature Sequences | Identification | Analytical Methods |
|---|---|---|---|---|---|---|
| 1 | 88 | T83 S38 T76 | | M1-A21 | | Signal Peptide HMM |
| 2 | 128 | S30 S40 T47 T119 W125 | | M1-F28 | | Signal Peptide HMM |
| 3 | 111 | T70 | | M1-T18 | | Signal Peptide HMM |
| 4 | 110 | S32 T64 | N58 | M1-A29 | | Signal Peptide HMM |
| 5 | 78 | T27 S39 S39 S44 S22 T27 S28 S57 | | M1-R24 | | Signal Peptide HMM |
| 6 | 88 | T55 S30 S40 T55 | N34 | M1-N21 | | Signal Peptide HMM |
| 7 | 227 | S220 S70 S83 T131 S134 S141 T158 Y123 | N100 | M1-Q20 | | Signal Peptide HMM |
| 8 | 198 | S62 T123 S142 S189 S62 T100 Y85 | N60 | M1-A28 | | Signal Peptide HMM |
| 9 | 65 | T48 | | M1-A29 | | Signal Peptide HMM |
| 10 | 154 | | | M1-A29 | | Signal Peptide HMM |
| 11 | 237 | T116 T26 T79 T85 T182 T188 T194 T206 S60 S123 S176 S213 | N128 | M1-A19 | | Signal Peptide HMM |
| 12 | 225 | T158 S128 | N166 | M1-G27 | | Signal Peptide HMM |
| 13 | 117 | S41 | | M1-A23 | | Signal Peptide HMM |
| 14 | 253 | S49 T63 S92 T110 S127 T239 | N42 N47 N72 N207 | M1-T20 | | Signal Peptide HMM |
| 15 | 171 | S43 S94 T114 | | M88-R112 | | Signal Peptide HMM |
| 16 | 78 | S38 S43 | N37 | M1-G19 | | Signal Peptide HMM |
| 17 | 71 | T64 T67 | | M1-C19 | | Signal Peptide HMM |
| 18 | 188 | S36 T58 T133 Y31 | N121 N171 | M1-A21 | | Signal Peptide HMM |
| 19 | 80 | S76 | | M1-C19 | | Signal Peptide HMM |
| 20 | 80 | | | M1-G25 | | Signal Peptide HMM |
| 21 | 84 | S39 S53 S60 | | M1-G21 | | Signal Peptide HMM |

TABLE 2-continued

| Protein SEQ ID NO: | Amino Acid Residues | Potential Phosphorylation Sites | Potential Glycosylation Sites | Signature Sequences | Identification | Analytical Methods |
|---|---|---|---|---|---|---|
| 22 | 171 | S41 T150 | | M3-A21 | | Signal Peptide HMM |
| 23 | 243 | S3 S44 T75 S86 S183 S223 S36 S92 S205 Y40 Y110 | N97 | M1-C25 | | Signal Peptide HMM |
| 24 | 311 | T5 S76 T82 T93 T109 S121 T137 T170 S184 S11 T53 S75 S84 T132 S223 S274 Y69 | N49 N91 N108 N128 N135 N190 | M1-A32 | | Signal Peptide HMM |
| 25 | 57 | | | M1-L29 | | Signal Peptide HMM |
| 26 | 82 | S46 Y26 | | M1-S18 | | Signal Peptide HMM |
| 27 | 115 | | | M1-G34 | | Signal Peptide HMM |
| 28 | 327 | S93 S50 S167 S233 S89 T105 T214 S302 T318 | N138 N206 | M1-E25 | | Signal Peptide HMM |
| 29 | 133 | S63 | N105 | M1-E29 | | Signal Peptide HMM |
| 30 | 129 | S21 S65 T93 | | M1-G20 | | Signal Peptide HMM |
| 31 | 472 | S164 T32 S42 T141 T154 S155 T235 T262 T271 T334 T376 S402 S421 S435 T441 S19 S29 T327 S378 | N61 N179 N353 N356 N396 | M1-G20 | hematopoietic lineage switch 2 (g3169729) | Signal Peptide HMM BLAST-GenBank |
| 32 | 93 | T21 | | M1-A18 | | Signal Peptide HMM |
| 33 | 92 | S57 S5 | | M1-G47 | | SPScan |
| 34 | 143 | T6 T14 T135 | | M9-G40 | | Signal Peptide HMM |
| 35 | 89 | T15 S58 S66 | | M1-A19 | | Signal Peptide HMM |
| 36 | 560 | T7 T76 S150 T224 S228 S257 S358 S474 S529 S539 T186 S219 S368 Y523 | N163 N184 N379 | M1-E34 | | SPScan |
| 37 | 197 | T80 S163 | | M1-G28 | | Signal Peptide HMM |
| 38 | 437 | T47 T146 S233 S391 S403 T43 S130 S273 S339 S364 | N46 N189 N382 | M1-A21 | | Signal Peptide HMM |
| 39 | 330 | S197 T49 T150 S193 T214 T215 T49 S111 S237 | N46 N64 N166 N191 | M1-G28 | | Signal Peptide HMM |
| 40 | 148 | T73 S141 | N29 N58 N71 N103 | M1-R24 | receptor-activity-modifying protein (RAMP; g4165368) | Signal Peptide HMM BLAST-GenBank |
| 41 | 188 | S49 | | M1-V25 | | Signal Peptide HMM |
| 42 | 222 | S89 S165 T174 T182 T83 S155 | | M1-S24 | | Signal Peptide HMM |
| 43 | 111 | S54 S29 S98 S50 S57 T104 | | M1-T23 | | Signal Peptide HMM |
| 44 | 341 | T29 S106 T120 S161 S195 S37 S47 T51 S136 S223 S230 S281 | | M1-G22 | | Signal Peptide HMM |
| 45 | 148 | S21 T63 T63 A146 | N40 | M1-G23 | | Signal Peptide HMM |
| 46 | 87 | S65 | | M1-P18 | | Signal Peptide HMM |
| 47 | 383 | T77 S95 S108 S280 S351 S121 S124 S153 T187 | N93 N207 | M1-P23 | | Signal Peptide HMM |
| 48 | 109 | S25 S22 | | M1-L18 | | Signal Peptide HMM |
| 49 | 185 | S62 | | M1-A20 | | Signal Peptide HMM |
| 50 | 110 | T100 T73 S97 Y48 | N71 | M1-C21 | | Signal Peptide HMM |

TABLE 2-continued

| Protein SEQ ID NO: | Amino Acid Residues | Potential Phosphorylation Sites | Potential Glycosylation Sites | Signature Sequences | Identification | Analytical Methods |
|---|---|---|---|---|---|---|
| 51 | 126 | S17 S110 | | M1-G18 | | Signal Peptide HMM |
| 52 | 488 | S205 T31 S86 T236 S7 T447 | N250 N321 N463 | M1-L25 | putative involvement in cell wall structure or biosynthesis (g3738170) | Signal Peptide HMM BLAST-GenBank |
| 53 | 197 | T55 S34 S46 S69 T98 S108 T119 T167 S194 S2 S34 T153 | | M1-A26 | | Signal Peptide HMM |
| 54 | 84 | S65 S36 T41 S51 S69 S81 | N39 | M1-G25 | | Signal Peptide HMM |
| 55 | 97 | S56 | | M1-A22 | | Signal Peptide HMM |
| 56 | 140 | S29 | | M1-P23 | | Signal Peptide HMM |
| 57 | 285 | S53 S108 T216 S253 S277 | N153 | M1-A25 | | Signal Peptide HMM |
| 58 | 262 | S62 T166 S62 S71 Y246 | N190 | M1-G28 | 3-acylating enzyme (Q44449) | Signal Peptide HMM BLAST-GENESEQ |
| 59 | 189 | S120 T154 T34 T37 S174 | | M1-C22 | | Signal Peptide HMM |
| 60 | 257 | S98 T136 T67 S112 S234 S237 | | M55-E84β | | SPScan |
| 61 | 82 | T68 | N67 | M1-G18 | | Signal Peptide HMM |
| 62 | 202 | T21 S117 S120 | | M1-G27 | | Signal Peptide HMM |
| 63 | 450 | S107 S97 S146 S339 S440 S245 T303 S304 S399 | | M1-G18 | | Signal Peptide HMM |
| 64 | 322 | T145 T214 T16 S24 S35 S45 T145 T269 S297 T300 T314 Y87 | N53 N130 N289 | M1-G23 | | Signal Peptide HMM |
| 65 | 104 | S38 S25 S75 | | M1-A18 | | Signal Peptide HMM |
| 66 | 93 | | | M1 through about S18 Transmembrane: M1 through about Y17 | | SPscan HMM |
| 67 | 71 | S23 S64 | | M1 through about A24 | | SPscan HMM MOTIFS |
| 68 | 394 | S392 S393 S31 S127 S179 S334 T338 S358 T383 Y323 | N53 | M1 through about S31 Transmembrane: about M159 through about F178 about F109 through about S127 about F225 through about V243 | | SPScan HMM MOTIFS |
| 69 | 72 | S59 | N69 | M1 through about S23 Transmembrane: M1 through about L16 | | SPscan HMM MOTIFS |
| 70 | 71 | S11 T26 | | M1 through about Q18 | | SPscan HMM MOTIFS |
| 71 | 247 | S41 T79 | | M1 through about S25 | | SPscan HMM MOTIFS |
| 72 | 73 | S56 | | M1 through about G27 | | SPscan HMM MOTIFS |
| 73 | 70 | | | M1 through about G20 | | SPscan HMM |
| 74 | 67 | | | M1 through about G30 | | SPscan HMM |
| 75 | 91 | | | M1 through about G26 | | SPscan |
| 76 | 56 | T29 S46 T51 | | M1 through about S19 | | SPscan HMM MOTIFS |
| 77 | 112 | S62 S65 | | M1 through about G27 Transmembrane: about W79 through about H97 | | SPscan HMM MOTIFS |
| 78 | 54 | | N48 | M1 through about N34 | | SPscan HMM MOTIFS |

TABLE 2-continued

| Protein SEQ ID NO: | Amino Acid Residues | Potential Phosphorylation Sites | Potential Glycosylation Sites | Signature Sequences | Identification | Analytical Methods |
|---|---|---|---|---|---|---|
| 79 | 57 | T33 R55 | | M1 through about C18 | | SPscan HMM MOTIFS |
| 80 | 52 | S34 | | M1 through about S30 | | SPscan HMM MOTIFS |
| 81 | 64 | T43 Y27 | | M1 through about S41 | | SPscan HMM MOTIFS |
| 82 | 65 | S45 | | M1 through about A31 Transmembrane: about L38 through about F55 | | SPscan HMM MOTIFS |
| 83 | 56 | | | M1 through about E23 | | SPscan HMM |
| 84 | 120 | S69 S109 | N89 N95 | M1 through about A38 Transmembrane: about L23 through about T41 | | SPscan HMM MOTIFS |
| 85 | 67 | S28 | | M1 through about K30 Microbodies C-terminal targetting signal: A65KV | | SPscan HMM MOTIFS |
| 86 | 62 | S29 S42 S46 | N40 | M1 through about S29 | | SPscan HMM MOTIFS |
| 87 | 75 | S25 S46 | | M1 through about L19 Transmembrane: about I3 through about G20 | | SPscan HMM MOTIFS |
| 88 | 80 | T28 | | M1 through about A20 | | SPscan HMM MOTIFS |
| 89 | 50 | S11 | | M1 through about C48 | | SPscan HMM MOTIFS |
| 90 | 116 | S38 | | M1 through about G22 | | SPscan HMM MOTIFS |
| 91 | 67 | S43 | | M1 through about P21 | | SPscan HMM MOTIFS |
| 92 | 538 | S415 S52 T77 S97 T178 T228 S282 S320 S332 S384 T401 T424 S483 S207 S230 S357 T410 Y263 Y365 | N226 | M1 through about S18 Tyrosine specific protein phosphatases signature: about V328 through about F340 | | SPScan BLOCKS PRINTS MOTIFS |
| 93 | 58 | | | M1 through about S25 | | SPscan HMM |
| 94 | 119 | S39 | | M1 through about S22 Transmembrane: about V3 through about S21 | | SPscan HMM MOTIFS |
| 95 | 128 | S91 | | M1 through about G31 Transmembrane: about F108 through about L126 | | SPscan HMM MOTIFS |
| 96 | 124 | T115 T43 S91 | | M1-S20 P116-V124 (urotensin II signature) | | SPscan HMM Motifs BLOCKS BLAST |
| 97 | 182 | S28 T70 S172 S25 S32 S48 S108 S131 | | M1-S23, M1-S25 | | SPscan HMM Motifs |
| 98 | 237 | S55 S88 S121 S135 | N45 N73 N107 N118 N132 N172 N175 N185 | M1-A16, M1-S21 C40-C198 (cysteine spacing pattern similar to that of RoBo-1) | | SPScan HMM Motifs BLAST |
| 99 | 160 | S36 S59 T143 | | M1-A27 | | SPScan HMM Motifs |
| 100 | 148 | T76 S64 Y103 | | M1-S30, M1-G31 | | SPScan HMM Motifs |
| 101 | 170 | S78 T4 T30 S130 S25 S29 T122 | | M1-A23, M1-L28 | | SPScan HMM Motifs |

TABLE 2-continued

| Protein SEQ ID NO: | Amino Acid Residues | Potential Phosphorylation Sites | Potential Glycosylation Sites | Signature Sequences | Identification | Analytical Methods |
|---|---|---|---|---|---|---|
| 102 | 150 | S50 S78 S91 | | M1-A26, M1-S28 | | SPScan HMM Motifs |
| 103 | 142 | T57 T80 | | M1-A25, M1-G26 | | SPScan HMM Motifs |
| 104 | 110 | T3 | | M1-G18, M1-T25 | | SPScan HMM Motifs |
| 105 | 120 | T29 S40 S72 | | M1-G22, M1-A20 | | SPScan HMM Motifs |
| 106 | 135 | T115 S38 T41 | N32 N101 | M1-G26, M1-C25 | | SPScan HMM Motifs |
| 107 | 301 | S53 S217 S240 S283 T224 | | M1-A22 | | SPScan HMM Motifs |
| 108 | 103 | S88 T73 S84 | | M1-P19, M1-L22 | | SPScan HMM Motifs |
| 109 | 95 | T82 S52 S77 | N50 | M1-T15, M1-P19 | | SPScan HMM Motifs |
| 110 | 113 | T84 S4 | | M1-P19, M1-A24 | | SPScan HMM Motifs |
| 111 | 234 | S179 S184 S51 T70 T158 S168 T228 Y29 | N146 N191 N194 | M1-A20 | NK cell activating receptor (g4493702) | SPScan HMM Motifs BLAST-GenBank |
| 112 | 119 | S39 T61 | | M1-G30, M1-G27 | | SPScan HMM Motifs |
| 113 | 200 | S51 T46 S191 | | M1-G26 Signal Peptide | Signal Peptide Containing Protein, Homology with KIAA0206 | SPScan Motifs BLAST |
| 114 | 225 | | | M1-Q29 Signal Peptide | Signal Peptide Containing Protein | SPScan |
| 115 | 155 | S29 | | M1-A20 Signal Peptide | Signal Peptide Containing Protein | HMM Motifs |
| 116 | 468 | S143 T156 T227 S235 T271 T293 T436 S453 S117 T148 T213 S263 S417 Y73 | N280 N384 | M1-G23 Signal Peptide | Signal Peptide Containing Protein | SPScan Motifs |
| 117 | 403 | S19 S320 S69 S151 T171 T97 S393 Y193 Y378 | N87 | M1-A24 Signal Peptide | Signal Peptide Containing Protein | HMM Motifs |
| 118 | 131 | T131 S24 T79 T118 T123 T127 | N116 | M1-G25 Signal Peptide | Signal Peptide Containing Protein | SPScan Motifs |
| 119 | 556 | T176 S192 S196 T220 S344 S369 S476 T501 S529 S541 T548 T553 S48 S115 S121 T386 T424 S500 Y104 | N62 N79 N127 N157 N160 | M1-P21 Signal Peptide L226-W244, Y402-W422, V375-L392 and Y355-I376 Transmembrane Domains | Signal Peptide Containing Protein, Weakly similar to Putative Transmembrane Protein (PTM1) Precursor | SPScan Motifs HMM BLAST |
| 120 | 514 | T457 T80 S86 T141 T372 T420 S447 S94 T102 S112 T240 S297 S353 S470 | N100 N168 N319 | M1-G24 Signal Peptide | Signal Peptide Containing Protein, | SPScan Motifs |
| 121 | 109 | T46 S78 T12 | | M1-S15 Signal Peptide | Signal Peptide Containing Protein | SPScan MotifS |
| 122 | 431 | S57 T320 S339 S396 S100 S239 | | M1-L25 Signal Peptide | Signal Peptide Containing Protein, Weakly similar to OXA1L | SPScan Motifs BLAST |
| 123 | 142 | | | M1-W16 Signal Peptide | Signal Peptide Containing Protein | SPScan |
| 124 | 643 | T8 S28 S77 T169 T199 T235 S252 T320 S402 T413 S414 S558 S22 T25 S56 S62 S120 T184 S329 S423 S475 S574 Y226 | N251 | M1-S28 Signal Peptide, D37-C81, W380-C437, W440-C492 and F526-C583 Thrombospondin Type 1 Domains | Signal Peptide Containing Protein, Thrombospondin Type 1 Protein | SPScan Motifs Pfam BLAST |

TABLE 2-continued

| Protein SEQ ID NO: | Amino Acid Residues | Potential Phosphorylation Sites | Potential Glycosylation Sites | Signature Sequences | Identification | Analytical Methods |
|---|---|---|---|---|---|---|
| 125 | 568 | S510 T24 T80 S91 T153 T165 S232 S248 S262 T300 T334 S380 S446 S16 T19 T60 S127 S273 T436 T531 S554 T564 Y135 Y489 | N322 | M1-T19 Signal Peptide | Signal Peptide Containing Protein | SPScan Motifs |
| 126 | 125 | T62 S27 T36 | | M1-R32 Signal Peptide, V4-L53 Glycosyl Hydrolase Family 9 Active Site Signature | Signal Peptide Containing Protein, Glycosyl Hydrolase Protein | SPScan Motifs PROFILE-SCAN |
| 127 | 196 | T105 T47 T56 S158 | | M1-S26 Signal Peptide, H79-H123 Ribosomal Protein S18 Signature | Signal Peptide Containing Protein, Ribosomal Protein S18 | SPScan Motifs BLAST Pfam PROFILE-SCAN |
| 128 | 214 | S112 S131 | N37 N92 | M1-S35 Signal Peptide | Signal Peptide Containing Protein, Homology with GTP Binding Protein | SPScan Motifs BLAST |
| 129 | 88 | | | M1-S24 Signal Peptide | Signal Peptide Containing Protein | HMM |
| 130 | 260 | S146 S179 S192 S239 S70 T126 T150 | N50 N109 | M1-A48 Signal Peptide, G59-S142 Immunoglobulin Domain | Signal Peptide Containing Protein, Immunoglobulin Superfamily Protein | SPScan Motifs Pfam |
| 131 | 295 | T176 T56 S72 S179 S256 S87 | | M1-A30 Signal Peptide | Signal Peptide Containing Protein | SPScan Motifs |
| 132 | 183 | S11 T41 T42 S83 | | M1-W24 Signal Peptide, E131-K168 and C105-H115 Adrenodoxin Iron-Sulfur Binding Signature, C111-V116 Cytochrome C Heme Binding Signature, N69-A162 Iron-Sulfur Cluster Binding Domain | Signal Peptide Containing Protein, Adrenodoxin Family Iron-Sulfur Binding Protein, and Cytochrome C Family Heme Binding Protein | HMM Motifs BLOCKS PRINTS Pfam |
| 133 | 113 | S93 T89 Y9 | | M1-G30 Signal Peptide, V28-L74 PF00646 F-Box Domain | Signal Peptide Containing Protein, PF00646 F-Box Protein | SPScan Motifs Pfam |
| 134 | 160 | T46 T55 S65 S124 T125 T46 | | M1-A27 Signal Peptide | Signal Peptide Containing Protein, F45G2.10 and Yhr122wp Homology | SPScan Motifs BLAST |

TABLE 3

| Nucleotide SEQ ID NO: | Tissue Expression (Fraction of Total) | Disease/Condition-Specific Expression (Total of Fraction) | Vector |
|---|---|---|---|
| 135 | Hematopoietic/Immune (1.000) | Inflammation (1.000) | pBLUESCRIPT |
| 136 | Hematopoietic/Immune (0.750) Cardiovascular (0.250) | Inflammation (0.750) Cancer (0.250) | pSPORT1 |
| 137 | Nervous (1.000) | Trauma (1.000) | pSPORT1 |
| 138 | Musculoskeletal (1.000) | Inflammation (1.000) | pSPORT1 |
| 139 | Gastrointestinal (0.714) Cardiovascular (0.143) Reproductive (0.143) | Cancer (0.714) Trauma (0.143) | pSPORT1 |
| 140 | Nervous (1.000) | Neurological (0.500) Trauma (0.500) | pSPORT1 |
| 141 | Reproductive (0.293) Gastrointestinal (0.146) Hematopoietic/Immune (0.146) | Cancer (0.524) Inflammation (0.256) Fetal (0.146) | pSPORT1 |
| 142 | Reproductive (0.266) Gastrointestinal (0.170) Nervous (0.138) | Cancer (0.479) Inflammation (0.277) Fetal (0.181) | pINCY |
| 143 | Reproductive (0.417) Nervous (0.292) Developmental (0.125) | Cancer (0.417) Inflammation (0.250) Fetal (0.167) | pINCY |
| 144 | Reproductive (0.321) Cardiovascular (0.143) Developmental (0.143) | Cancer (0.464) Fetal (0.214) Inflammation (0.143) | pINCY |
| 145 | Reproductive (0.600) Gastrointestinal (0.400) | Cancer (0.400) Trauma (0.400) Inflammation (0.200) | pINCY |
| 146 | Cardiovascular (0.400) Dermatologic (0.200) Nervous (0.200) | Cancer (0.600) Fetal (0.600) | pINCY |
| 147 | Developmental (0.667) Gastrointestinal (0.333) | Fetal (0.667) Cancer (0.333) | pINCY |
| 148 | Reproductive (0.256) Nervous (0.248) Cardiovascular (0.137) | Cancer (0.479) Inflammation (0.214) Fetal (0.145) | pINCY |
| 149 | Reproductive (0.244) Nervous (0.178) Hematopoietic/Immune (0.167) | Cancer (0.433) Inflammation (0.322) Fetal (0.156) | pINCY |
| 150 | Cardiovascular (0.923) Developmental (0.077) | Cancer (0.692) Fetal (0.154) Inflammation (0.154) | pINCY |
| 151 | Reproductive (0.215) Nervous (0.190) Gastrointestinal (0.177) | Cancer (0.494) Inflammation (0.278) Trauma (0.152) | pINCY |

TABLE 3-continued

| Nucleotide SEQ ID NO: | Tissue Expression (Fraction of Total) | Disease/Condition-Specific Expression (Total of Fraction) | Vector |
|---|---|---|---|
| 152 | Reproductive (0.200) Nervous (0.171) Hematopoietic/Immune (0.143) | Inflammation (0.371) Cancer (0.229) Fetal (0.200) | pINCY |
| 153 | Reproductive (0.333) Nervous (0.157) Hematopoietic/Immune (0.137) | Cancer (0.549) Inflammation (0.176) Fetal (0.137) | pINCY |
| 154 | Gastrointestinal (0.500) Urologic (0.167) | Inflammation (0.667) Cancer (0.167) Trauma (0.167) | pINCY |
| 155 | Gastrointestinal (0.429) Reproductive (0.286) Nervous (0.143) | Inflammation (0.429) Cancer (0.286) Trauma (0.143) | pINCY |
| 156 | Reproductive (1.000) | Cancer (0.500) Inflammation (0.500) | pINCY |
| 157 | Hematopoietic/Immune (0.346) Reproductive (0.154) Gastrointestinal (0.115) | Cancer (0.404) Inflammation (0.404) Fetal (0.212) | pINCY |
| 158 | Reproductive (0.236) Hematopoietic/Immune (0.217) Gastrointestinal (0.132) | Cancer (0.415) Inflammation (0.358) Fetal (0.142) | pINCY |
| 159 | Gastrointestinal (1.000) | Cancer (1.000) | pSPORT1 |
| 160 | Developmental (0.500) Hematopoietic/Immune (0.250) Nervous (0.250) | Fetal (0.500) Inflammation (0.250) Trauma (0.250) | pINCY |
| 161 | Hematopoietic/Immune (0.250) Reproductive (0.250) Nervous (0.208) | Cancer (0.583) Fetal (0.292) Inflammation (0.250) | pINCY |
| 162 | Gastrointestinal (0.412) Reproductive (0.412) Cardiovascular (0.088) | Cancer (0.735) Inflammation (0.176) Fetal (0.029) | pINCY |
| 163 | Reproductive (0.298) Cardiovascular (0.170) Nervous (0.149) | Cancer (0.532) Inflammation (0.213) Fetal (0.191) | pINCY |
| 164 | Gastrointestinal (0.333) Hematopoietic/Immune (0.333) Reproductive (0.333) | Cancer (0.667) Inflammation (0.333) | pINCY |
| 165 | Reproductive (0.295) Gastrointestinal (0.159) Nervous (0.148) | Cancer (0.534) Inflammation (0.284) Fetal (0.091) | pINCY |
| 166 | Hematopoietic/Immune (0.538) Cardiovascular (0.077) Reproductive (0.077) | Inflammation (0.731) Cancer (0.154) Fetal (0.154) | pINCY |
| 167 | Reproductive (0.483) Gastrointestinal (0.121) Nervous (0.103) | Cancer (0.672) Inflammation (0.155) | pINCY |
| 168 | Gastrointestinal (0.222) Hematopoietic/Immune (0.222) Nervous (0.148) | Cancer (0.519) Inflammation (0.370) Fetal (0.259) | pINCY |
| 169 | Urologic (1.000) | Cancer (0.333) Fetal (0.333) Inflammation (0.333) | pINCY |
| 170 | Reproductive (0.214) Gastrointestinal (0.179) Nervous (0.143) | Cancer (0.643) Inflammation (0.143) Fetal (0.107) | pINCY |
| 171 | Reproductive (0.261) Developmental (0.174) Nervous (0.174) | Cancer (0.391) Fetal (0.304) Inflammation (0.217) | pINCY |
| 172 | Reproductive (0.357) Gastrointestinal (0.321) Cardiovascular (0.071) | Cancer (0.571) Inflammation (0.286) Fetal (0.107) | pINCY |
| 173 | Reproductive (0.306) Nervous (0.161) Cardiovascular (0.129) | Cancer (0.387) Inflammation (0.323) Fetal (0.226) | pINCY |
| 174 | Reproductive (0.229) Nervous (0.188) Cardiovascular (0.167) | Cancer (0.521) Inflammation (0.312) Trauma (0.146) | pSPORT1 |
| 175 | Reproductive (0.444) Developmental (0.167) Cardiovascular (0.111) | Cancer (0.556) Fetal (0.278) Trauma (0.111) | pSPORT1 |
| 176 | Reproductive (0.294) Gastrointestinal (0.176) Cardiovascular (0.118) | Cancer (0.765) Fetal (0.118) Inflammation (0.118) | pSPORT1 |
| 177 | Gastrointestinal (1.000) | Cancer (0.667) Inflammation (0.333) | pINCY |
| 178 | Reproductive (0.385) Nervous (0.231) Gastrointestinal (0.154) | Cancer (0.385) Inflammation (0.385) | pINCY |
| 179 | Reproductive (0.500) Cardiovascular (0.167) Gastrointestinal (0.167) | Cancer (0.667) Fetal (0.167) Inflammation (0.167) | pBLUESCRIPT |
| 180 | Cardiovascular (0.231) Reproductive (0.231) Gastrointestinal (0.154) | Cancer (0.615) Inflammation (0.308) Fetal (0.154) | pINCY |
| 181 | Reproductive (0.324) Gastrointestinal (0.176) Cardiovascular (0.130) | Cancer (0.519) Inflammation (0.222) Fetal (0.157) | pINCY |
| 182 | Reproductive (0.320) Nervous (0.180) Gastrointestinal (0.120) | Cancer (0.580) Inflammation (0.160) Fetal (0.100) | pINCY |
| 183 | Gastrointestinal (0.667) Reproductive (0.333) | Cancer (1.000) | pINCY |
| 184 | Urologic (0.667) Dermatologic (0.333) | Cancer (0.667) Fetal (0.333) | pSPORT1 |
| 185 | Cardiovascular (0.500) Reproductive (0.500) | Cancer (1.000) | pINCY |
| 186 | Reproductive (0.393) Developmental (0.107) Urologic (0.107) | Cancer (0.607) Fetal (0.179) Inflammation (0.107) | pINCY |
| 187 | Cardiovascular (0.400) Reproductive (0.333) Gastrointestinal (0.133) | Inflammation (0.467) Cancer (0.267) Fetal (0.267) | pSPORT1 |
| 188 | Nervous (0.318) Reproductive (0.227) Urologic (0.136) | Cancer (0.636) Inflammation (0.136) Trauma (0.091) | pINCY |
| 189 | Cardiovascular (0.500) Reproductive (0.500) | Cancer (1.000) | pINCY |
| 190 | Reproductive (0.318) Nervous (0.227) Hematopoietic/Immune (0.136) | Cancer (0.500) Fetal (0.227) Inflammation (0.227) | pINCY |
| 191 | Reproductive (0.253) Cardiovascular (0.158) Gastrointestinal (0.147) | Cancer (0.463) Inflammation (0.232) Fetal (0.200) | pINCY |
| 192 | Reproductive (0.333) Gastrointestinal (0.286) Cardiovascular (0.095) | Cancer (0.571) Inflammation (0.333) Fetal (0.095) | pINCY |
| 193 | Reproductive (0.304) Cardiovascular (0.217) Gastrointestinal (0.130) | Cancer (0.435) Inflammation (0.391) Fetal (0.174) | pINCY |
| 194 | Reproductive (0.312) Nervous (0.188) Cardiovascular (0.125) | Cancer (0.438) Inflammation (0.250) Fetal (0.188) | pINCY |
| 195 | Developmental (1.000) | Fetal (1.000) | pINCY |

TABLE 3-continued

| Nucleotide SEQ ID NO: | Tissue Expression (Fraction of Total) | Disease/Condition-Specific Expression (Total of Fraction) | Vector |
|---|---|---|---|
| 196 | Reproductive (0.233) Cardiovascular (0.209) Nervous (0.140) | Cancer (0.605) Fetal (0.186) Inflammation (0.116) | pINCY |
| 197 | Reproductive (0.182) Gastrointestinal (0.136) Hematopoietic/Immune (0.136) | Cancer (0.477) Inflammation (0.341) Fetal (0.182) | pINCY |
| 198 | Gastrointestinal (0.205) Reproductive (0.205) Cardiovascular (0.114) | Inflammation (0.341) Cancer (0.250) Fetal (0.227) | pINCY |
| 199 | Cardiovascular (0.520) Reproductive (0.280) Developmental (0.160) | Cancer (0.720) Fetal (0.200) Inflammation (0.080) | pINCY |
| 200 | Lung (0.958) Developmental (0.25) Musculoskeletal (0.042) | Cancer (0.583) Fetal or Proliferating (0.292) Inflammation (0.167) | pBLUESCRIPT |
| 201 | Reproductive (0.571) Musculoskeletal (0.143) Nervous (0.143) Urologic (0.143) | Cancer (0.429) Inflammation (0.571) | pSPORT1 |
| 202 | Endocrine (0.250) Nervous (0.250) Cardiovascular (0.125) Developmental (0.125) Gastrointestinal (0.125) Reproductive (0.125) | Cancer (0.375) Inflammation (0.625) Fetal or Proliferating (0.125) | pSPORT1 |
| 203 | Lung (1.000) | Fetal or Proliferating (1.000) | pINCY |
| 204 | Lung (0.500) Penis (0.500) | Cancer (0.500) | pINCY |
| 205 | Cardiovascular (0.231) Dermatologic (0.231) Reproductive (0.231) | Fetal or Proliferating (0.385) Cancer (0.308) | pINCY |
| 206 | Nervous (0.596) Reproductive (0.154) Gastrointestinal (0.077) | Cancer (0.442) Neurological (0.192) Inflammation (0.231) | pINCY |
| 207 | Gastrointestinal (1.000) | Inflammation (1.000) | pINCY |
| 208 | Reproductive (0.300) Hematopoietic/Immune (0.200) Nervous (0.150) | Cancer (0.450) Inflammation (0.400) Fetal or Proliferating (0.250) | pSPORT1 |
| 209 | Heart (0.500) Brain (0.500) | Neurological (0.500) Inflammation (0.500) | pINCY |
| 210 | Nervous (0.625) Reproductive (0.250) Musculoskeletal (0.125) | Cancer (0.750) Fetal or Proliferating (0.250) Neurological (0.125) | pINCY |
| 211 | Nervous (0.261) Reproductive (0.304) Gastrointestinal (0.174) | Cancer (0.522) Fetal or Proliferating (0.174) Inflammation (0.130) | pSPORT1 |
| 212 | Testis (1.000) | Inflammation (1.000) | pBLUESCRIPT |
| 213 | Nervous (0.400) Reproductive (0.400) Gastrointestinal (0.200) | Cancer (0.400) Inflammation (0.400) Neurological (0.200) | pBLUESCRIPT |
| 214 | Reproductive (0.476) Gastrointestinal (0.286) Cardiovascular (0.095) | Cancer (0.714) Inflammation (0.286) Neurological (0.048) | pSPORT1 |
| 215 | Reproductive (0.284) Gastrointestinal (0.216) Nervous (0.176) Hematopoietic/Immune (0.108) Cardiovascular (0.108) | Cancer (0.486) Inflammation (0.351) Fetal or Proliferating (0.122) | pSPORT1 |
| 216 | Uterus (0.500) Prostate (0.500) | Cancer (0.500) Inflammation (0.500) | pINCY |
| 217 | Nervous (0.429) Cardiovascular (0.143) Gastrointestinal (0.143) Hematopoietic/Immune (0.143) Reproductive (0.143) | Cancer (0.571) Inflammation (0.429) Fetal or Proliferating (0.285) | pSPORT1 |
| 218 | Reproductive (0.450) Hematopoietic/Immune (0.200) Nervous (0.100) Gastrointestinal (0.100) | Cancer (0.650) Inflammation (0.200) Fetal or Proliferating (0.050) | pINCY |
| 219 | Reproductive (0.364) Cardiovascular (0.182) Nervous (0.182) | Cancer (0.636) Fetal or Proliferating (0.182) Inflammation (0.273) | pINCY |
| 220 | Prostate (1.000) | Inflammation (1.000) | pSPORT1 |
| 221 | Developmental (0.333) Nervous (0.333) Reproductive (0.333) | Cancer (0.667) Fetal or Proliferating (0.667) | pSPORT1 |
| 222 | Reproductive (0.393) Hematopoietic/Immune (0.180) Nervous (0.098) Cardiovascular (0.098) | Cancer (0.508) Inflammation (0.344) Fetal or Proliferating (0.066) | pSPORT1 |
| 223 | Endocrine (0.333) Gastrointestinal (0.333) Reproductive (0.333) | Cancer (1.000) | pINCY |
| 224 | Cardiovascular (0.200) Developmental (0.200) Gastrointestinal (0.200) Reproductive (0.200) Urologic (0.200) | Cancer (0.800) Fetal or Proliferating (0.200) | pINCY |
| 225 | Lung (1.000) | Cancer (1.000) | pINCY |
| 226 | Reproductive (0.302) Hematopoietic/Immune (0.254) Cardiovascular (0.111) | Cancer (0.381) Inflammation (0.381) Fetal or Proliferating (0.286) | pSPORT1 |
| 227 | Lymphocytes (1.000) | Inflammation (1.000) | pINCY |
| 228 | Cardiovascular (0.531) Reproductive (0.250) Urologic (0.094) | Cancer (0.656) Inflammation (0.250) Fetal or Proliferating (0.094) | pINCY |
| 229 | Reproductive (0.333) Cardiovascular (0.167) Gastrointestinal (0.167) Endocrine (0.167) Hematopoietic/Immune (0.167) | Cancer (0.500) Fetal or Proliferating (0.167) Inflammation (0.333) | pINCY |
| 230 | Hematopoietic/Immune (0.500) Reproductive (0.500) | Cell Proliferation (0.500) Inflammation (0.500) | pBLUESCRIPT |
| 231 | Cardiovascular (0.333) Nervous (0.333) Developmental (0.167) | Cancer (0.500) Cell Proliferation (0.333) Inflammation (0.167) | pINCY |
| 232 | Gastrointestinal (0.938) Reproductive (0.062) | Cancer (0.500) Inflammation (0.500) | pINCY |
| 233 | Nervous (0.324) Reproductive (0.235) Hematopoietic/Immune (0.118) | Cancer (0.456) Inflammation (0.235) Trauma (0.147) | pINCY |
| 234 | Nervous (0.255) Reproductive (0.255) Musculoskeletal (0.182) | Cancer (0.545) Inflammation (0.255) Trauma (0.109) | pINCY |
| 235 | Musculoskeletal (0.308) Reproductive (0.231) Gastrointestinal (0.154) | Cancer (0.538) Inflammation (0.231) Trauma (0.154) | pINCY |
| 236 | Nervous (1.000) | Cancer (1.000) | pINCY |

TABLE 3-continued

| Nucleotide SEQ ID NO: | Tissue Expression (Fraction of Total) | Disease/Condition-Specific Expression (Total of Fraction) | Vector |
|---|---|---|---|
| 237 | Gastrointestinal (0.429) Hematopoietic/Immune (0.143) Nervous (0.143) | Cancer (0.571) Cell Proliferation (0.143) Trauma (0.143) | pINCY |
| 238 | Reproductive (0.254) Gastrointestinal (0.160) Nervous (0.128) | Cancer (0.453) Inflammation (0.241) Cell Proliferation (0.175) | pINCY |
| 239 | Nervous (0.333) Dermatologic (0.167) Endocrine (0.167) | Trauma (0.333) Cancer (0.167) Cell Proliferation (0.167) | pINCY |
| 240 | Nervous (0.273) Reproductive (0.227) Endocrine (0.136) | Cancer (0.545) Cell Proliferation (0.182) Inflammation (0.182) | pINCY |
| 241 | Reproductive (0.273) Hematopoietic/Immune (0.182) Urologic (0.182) | Cancer (0.455) Cell Proliferation (0.273) Inflammation (0.273) | pINCY |
| 242 | Endocrine (1.000) | Trauma (1.000) | pSPORT1 |
| 243 | Reproductive (1.000) | Cancer (1.000) | pINCY |
| 244 | Hematopoietic/Immune (0.545) Musculoskeletal (0.182) Cardiovascular (0.091) | Inflammation (0.636) Trauma (0.182) Cancer (0.091) | pINCY |
| 245 | Hematopoietic/Immune (0.400) Musculoskeletal (0.300) Cardiovascular (0.150) | Inflammation (0.650) Cancer (0.300) | pINCY |
| 246 | Urologic (1.000) | Cancer (0.500) Cell Proliferation (0.500) | pINCY |
| 247 | Nervous (0.292) Reproductive (0.222) Musculoskeletal (0.125) | Cell Proliferation (0.625) Inflammation/Trauma (0.181) | pSPORT1 |
| 248 | Reproductive (0.211) Developmental (0.132) Nervous (0.132) | Cell Proliferation (0.658) Inflammation/Trauma (0.184) | pSPORT1 |
| 249 | Nervous (0.500) Gastrointestinal (0.300) Hematopoietic/Immune (0.100) | Cell Proliferation (0.900) Inflammation/Trauma (0.300) | pSPORT1 |
| 250 | Cardiovascular (0.209) Gastrointestinal (0.140) Hematopoietic/Immune (0.140) | Cell Proliferation (0.605) Inflammation/Trauma (0.256) | pINCY |
| 251 | Nervous (0.308) Cardiovascular (0.154) Gastrointestinal (0.154) | Cell Proliferation (0.616) Inflammation/Trauma (0.269) | pINCY |
| 252 | Reproductive (1.000) | Cell Proliferation (1.000) | pSPORT1 |
| 253 | Reproductive (0.324) Nervous (0.162) Gastrointestinal (0.113) | Cell Proliferation (0.641) Inflammation/Trauma (0.197) | pSPORT1 |
| 254 | Reproductive (0.315) Nervous (0.296) Developmental (0.093) | Cell Proliferation (0.630) Inflammation/Trauma (0.278) | pSPORT1 |
| 255 | Nervous (0.211) Reproductive (0.211) Gastrointestinal (0.158) | Cell Proliferation (0.579) Inflammation/Trauma (0.298) | pINCY |
| 256 | Reproductive (0.250) Gastrointestinal (0.148) Hematopoietic/Immune (0.148) | Cell Proliferation (0.705) Inflammation/Trauma (0.193) | pINCY |
| 257 | Hematopoietic/Immune (1.000) | Cell Proliferation (0.400) Inflammation/Trauma (0.600) | pINCY |
| 258 | Cardiovascular (0.333) Reproductive (0.333) Developmental (0.167) | Cell Proliferation (0.833) Inflammation/Trauma (0.333) | pBLUESCRIPT |
| 259 | Cardiovascular (0.333) Reproductive (0.250) Developmental (0.167) | Cell Proliferation (0.625) Inflammation/Trauma (0.208) | pINCY |
| 260 | Endocrine (0.500) Cardiovascular (0.250) Nervous (0.250) | Cell Proliferation (0.750) Inflammation/Trauma (0.500) | pINCY |
| 261 | Reproductive (0.252) Cardiovascular (0.155) Hematopoietic/Immune (0.136) | Cell Proliferation (0.728) Inflammation/Trauma (0.194) | pINCY |
| 262 | Reproductive (0.274) Cardiovascular (0.177) Nervous (0.145) | Cell Proliferation (0.742) Inflammation/Trauma (0.210) | pINCY |
| 263 | Reproductive (0.267) Cardiovascular (0.160) Hematopoietic/Immune (0.127) | Cell Proliferation (0.654) Inflammation/Trauma (0.193) | pINCY |
| 264 | Nervous (0.229) Hematopoietic/Immune (0.200) Reproductive (0.200) | Cell Proliferation (0.743) Inflammation/Trauma (0.286) | pINCY |
| 265 | Hematopoietic/Immune (0.333) Gastrointestinal (0.167) Nervous (0.133) | Cell Proliferation (0.600) Inflammation/Trauma (0.333) | pINCY |
| 266 | Nervous (0.290) Reproductive (0.258) Cardiovascular (0.129) | Cell Proliferation (0.677) Inflammation/Trauma (0.194) | pINCY |
| 267 | Reproductive (0.261) Hematopoietic/Immune (0.217) Cardiovascular (0.087) | Cell Proliferation (0.652) Inflammation/Trauma (0.391) | pINCY |
| 268 | Gastrointestinal (0.227) Reproductive (0.193) Hematopoietic/Immune (0.168) | Cell Proliferation (0.731) Inflammation/Trauma (0.227) | pSPORT1 |

TABLE 4

| Polynucleotide SEQ ID NO: | Clone ID | Library | Library Description |
|---|---|---|---|
| 135 | 443531 | MPHGNOT03 | The library was constructed using RNA isolated from plastic adherent mononuclear cells isolated from buffy coat units obtained from unrelated male and female donors. |
| 136 | 632860 | NEUTGMT01 | The library was constructed using RNA isolated from peripheral blood granulocytes collected by density gradient centrifugation through Ficoll-Hypaque. The cells were isolated from buffy coat units obtained from 20 unrelated male and female donors. Cells were cultured in 10 nM GM-CSF for 1 hour before washing and harvesting for RNA preparation. |

TABLE 4-continued

| Poly-nucleo-tide SEQ ID NO: | Clone ID | Library | Library Description |
|---|---|---|---|
| 137 | 670010 | CRBLNOT01 | The library was constructed using RNA isolated from the cerebellum tissue of a 69-year-old Caucasian male who died from chronic obstructive pulmonary disease. Patient history included myocardial infarction, hypertension, and osteoarthritis. |
| 138 | 726498 | SYNOOAT01 | The library was constructed using RNA isolated from the knee synovial membrane tissue of an 82-year-old female with osteoarthritis. |
| 139 | 795064 | OVARNOT03 | The library was constructed using RNA isolated from ovarian tissue removed from a 43-year-old Caucasian female during removal of the fallopian tubes and ovaries. Pathology for the associated tumor tissue indicated grade 2 mucinous cystadenocarcinoma. Patient history included mitral valve disorder, pneumonia, and viral hepatitis. Family history included atherosclerotic coronary artery disease, pancreatic cancer, cerebrovascular disease, breast cancer, and uterine cancer. |
| 140 | 924925 | BRAINOT04 | The library was constructed using RNA isolated from the brain tissue of a 44-year-old Caucasian male with a cerebral hemorrhage. The tissue, which contained coagulated blood, came from the choroid plexus of the right anterior temporal lobe. Family history included coronary artery disease and myocardial infarction. |
| 141 | 962390 | BRSTTUT03 | The library was constructed using RNA isolated from breast tumor tissue removed from a 58-year-old Caucasian female during a unilateral extended simple mastectomy. Pathology indicated multicentric invasive grade 4 lobular carcinoma. The mass was identified in the upper outer quadrant, and three separate nodules were found in the lower outer quadrant of the left breast. Patient history included skin cancer, rheumatic heart disease, osteoarthritis, and tuberculosis. Family history included cerebrovascular disease, coronary artery aneurysm, breast cancer, prostate cancer, atherosclerotic coronary artery disease, and type I diabetes. |
| 142 | 1259405 | MENITUT03 | The library was constructed using RNA isolated from brain meningioma tissue removed from a 35-year-old Caucasian female during excision of a cerebral meningeal lesion. Pathology indicated a benign neoplasm in the right cerebellopontine angle of the brain. Patient history included hypothyroidism. Family history included myocardial infarction and breast cancer. |
| 143 | 1297384 | BRSTNOT07 | The library was constructed using RNA isolated from diseased breast tissue removed from a 43-year-old Caucasian female during a unilateral extended simple mastectomy. Pathology indicated mildly proliferative fibrocystic changes with epithelial hyperplasia, papillomatosis, and duct ectasia. Pathology for the associated tumor tissue indicated invasive grade 4, nuclear grade 3 mammary adenocarcinoma with extensive comedo necrosis. Family history included epilepsy, atherosclerotic coronary artery disease, and type II diabetes. |
| 144 | 1299627 | BRSTNOT07 | The library was constructed using RNA isolated from diseased breast tissue removed from a 43-year-old Caucasian female during a unilateral extended simple mastectomy. Pathology indicated mildly proliferative fibrocystic changes with epithelial hyperplasia, papillomatosis, and duct ectasia. Pathology for the associated tumor tissue indicated invasive grade 4, nuclear grade 3 mammary adenocarcinoma with extensive comedo necrosis. Family history included epilepsy, atherosclerotic coronary artery disease, and type II diabetes. |
| 145 | 1306026 | PLACNOT02 | The library was constructed using RNA isolated from the placental tissue of a Hispanic female fetus, who was prematurely delivered at 21 weeks' gestation. Serologies of the mother's blood were positive for CMV (cytomegalovirus). |
| 146 | 1316219 | BLADTUT02 | The library was constructed using RNA isolated from bladder tumor tissue removed from an 80-year-old Caucasian female during a radical cystectomy and lymph node excision. Pathology indicated grade 3 invasive transitional cell carcinoma. Family history included osteoarthritis and atherosclerosis. |
| 147 | 1329031 | PANCNOT07 | The library was constructed using RNA isolated from the pancreatic tissue of a Caucasian male fetus, who died at 23 weeks' gestation. |
| 148 | 1483050 | CORPNOT02 | The library was constructed using RNA isolated from diseased corpus callosum tissue removed from the brain of a 74-year-old Caucasian male who died from Alzheimer's disease. |
| 149 | 1514160 | PANCTUT01 | The library was constructed using RNA isolated from pancreatic tumor tissue removed from a 65-year-old Caucasian female during radical subtotal pancreatectomy. Pathology indicated an invasive grade 2 adenocarcinoma. Patient history included type II diabetes, osteoarthritis, cardiovascular disease, benign neoplasm in the large bowel, and a cataract. Family history included cardiovascular disease, type II diabetes, and stomach cancer. |
| 150 | 1603403 | LUNGNOT15 | The library was constructed using RNA isolated from lung tissue removed from a 69-year-old Caucasian male during a segmental lung resection. Pathology for the associated tumor tissue indicated residual grade 3 invasive squamous cell carcinoma. Patient history included acute myocardial infarction, prostatic hyperplasia, and malignant skin neoplasm. Family history included cerebrovascular disease, type I diabetes, acute myocardial infarction, and arteriosclerotic coronary disease. |
| 151 | 1652303 | PROSTUT08 | The library was constructed using RNA isolated from prostate tumor tissue removed from a 60-year-old Caucasian male during radical prostatectomy and regional lymph node excision. Pathology indicated an adenocarcinoma (Gleason grade 3 + 4). Adenofibromatous hyperplasia was also present. The patient presented with elevated prostate specific antigen (PSA). Patient history included a kidney cyst. Family history included tuberculosis, cerebrovascular disease, and arteriosclerotic coronary artery disease. |
| 152 | 1693358 | COLNNOT23 | The library was constructed using RNA isolated from diseased colon tissue removed from a 16-year-old Caucasian male during a total colectomy with abdominal/perineal resection. Pathology indicated gastritis and pancolonitis consistent with the acute phase of ulcerative colitis. There was only mild involvement of the ascending and sigmoid colon, and no significant involvement of the cecum, rectum, or terminal ileum. Family history included irritable bowel syndrome. |
| 153 | 1707711 | DUODNOT02 | The library was constructed using RNA isolated from duodenal tissue of a 8-year-old Caucasian female, who died from head trauma. Serology was positive for cytomegalovirus (CMV). |

TABLE 4-continued

| Poly-nucleotide SEQ ID NO: | Clone ID | Library | Library Description |
|---|---|---|---|
| 154 | 1738735 | COLNNOT22 | The library was constructed using RNA isolated from colon tissue removed from a 56-year-old Caucasian female with Crohn's disease during a partial resection of the small intestine. Pathology indicated Crohn's disease of the ileum and ileal-colonic anastomosis, causing a fistula at the anastomotic site that extended into pericolonic fat. The ileal mucosa showed linear and puncture ulcers with intervening normal tissue. Previous surgeries included a partial ileal resection and permanent ileostomy. Family history included irritable bowel syndrome. |
| 155 | 1749147 | STOMTUT02 | The library was constructed using RNA isolated from stomach tumor tissue obtained from a 68-year-old Caucasian female during a partial gastrectomy. Pathology indicated a malignant lymphoma of diffuse large-cell type. Patient history included thalassemia. Family history included acute leukemia, malignant neoplasm of the esophagus, malignant stomach neoplasm, and atherosclerotic coronary artery disease. |
| 156 | 1817722 | PROSNOT20 | The library was constructed using RNA isolated from diseased prostate tissue removed from a 65-year-old Caucasian male during a radical prostatectomy. Pathology indicated adenofibromatous hyperplasia. Pathology for the associated tumor tissue indicated an adenocarcinoma. |
| 157 | 1831290 | THP1AZT01 | The library was constructed using 1 microgram of polyA RNA isolated from THP-1 promonocyte cells treated for three days with 0.8 micromolar 5-aza-2'-deoxycytidine. THP-1 (ATCC TIB 202) is a human promonocyte line derived from peripheral blood of a 1-year-old Caucasian male with acute monocytic leukemia. |
| 158 | 1831477 | THP1AZT01 | The library was constructed using 1 microgram of polyA RNA isolated from THP-1 promonocyte cells treated for three days with 0.8 micromolar 5-aza-2'-deoxycytidine. THP-1 (ATCC TIB 202) is a human promonocyte line derived from peripheral blood of a 1-year-old Caucasian male with acute monocytic leukemia. |
| 159 | 1841607 | COLNNOT07 | The library was constructed using RNA isolated from colon tissue removed from a 60-year-old Caucasian male during a left hemicolectomy. |
| 160 | 1852391 | LUNGFET03 | The library was constructed using RNA isolated from lung tissue removed from a Caucasian female fetus, who died at 20 weeks' gestation. |
| 161 | 1854555 | HNT3AZT01 | Library was constructed using RNA isolated from the hNT2 cell line (derived from a human teratocarcinoma that exhibited properties characteristic of a committed neuronal precursor). Cells were treated for three days with 0.35 micromolar 5-aza-2'-deoxycytidine (AZT). |
| 162 | 1855755 | PROSNOT18 | The library was constructed using RNA isolated from diseased prostate tissue removed from a 58-year-old Caucasian male during a radical cystectomy, radical prostatectomy, and gastrostomy. Pathology indicated adenofibromatous hyperplasia. This tissue was associated with a grade 3 transitional cell carcinoma. Patient history included angina and emphysema. Family history included acute myocardial infarction, atherosclerotic coronary artery disease, and type II diabetes. |
| 163 | 1861434 | PROSNOT19 | The library was constructed using RNA isolated from diseased prostate tissue removed from a 59-year-old Caucasian male during a radical prostatectomy with regional lymph node excision. Pathology indicated adenofibromatous hyperplasia. Pathology for the associated tumor tissue indicated an adenocarcinoma (Gleason grade 3 + 3). The patient presented with elevated prostate-specific antigen (PSA). Patient history included colon diverticuli and thrombophlebitis. Family history included benign hypertension, multiple myeloma, hyperlipidemia and rheumatoid arthritis. |
| 164 | 1872334 | LEUKNOT02 | The library was constructed using RNA isolated from white blood cells of a 45-year-old female with blood type O+. The donor tested positive for cytomegalovirus (CMV). |
| 165 | 1877230 | LEUKNOT03 | The library was constructed using RNA isolated from white blood cells of a 27-year-old female with blood type A+. The donor tested negative for cytomegalovirus (CMV). |
| 166 | 1877885 | LEUKNOT03 | The library was constructed using RNA isolated from white blood cells of a 27-year-old female with blood type A+. The donor tested negative for cytomegalovirus (CMV). |
| 167 | 1889269 | BLADTUT07 | The library was constructed using RNA isolated from bladder tumor tissue removed from the anterior bladder wall of a 58-year-old Caucasian male during a radical cystectomy, radical prostatectomy, and gastrostomy. Pathology indicated a grade 3 transitional cell carcinoma in the left lateral bladder. Patient history included angina and emphysema. Family history included acute myocardial infarction, atherosclerotic coronary artery disease, and type II diabetes. |
| 168 | 1890243 | BLADTUT07 | The library was constructed using RNA isolated from bladder tumor tissue removed from the anterior bladder wall of a 58-year-old Caucasian male during a radical cystectomy, radical prostatectomy, and gastrostomy. Pathology indicated a grade 3 transitional cell carcinoma in the left lateral bladder. Patient history included angina and emphysema. Family history included acute myocardial infarction, atherosclerotic coronary artery disease, and type II diabetes. |
| 169 | 1900433 | BLADTUT06 | The library was constructed using RNA isolated from bladder tumor tissue removed from the posterior bladder wall of a 58-year-old Caucasian male during a radical cystectomy, radical prostatectomy, and gastrostomy. Pathology indicated grade 3 transitional cell carcinoma in the left lateral bladder wall. Patient history included angina and emphysema. Family history included acute myocardial infarction, atherosclerotic coronary artery disease, and type II diabetes. |
| 170 | 1909441 | CONNTUT01 | The library was constructed using RNA isolated from a soft tissue tumor removed from the clival area of the skull of a 30-year-old Caucasian female. Pathology indicated chondroid chordoma with neoplastic cells reactive for keratin. |
| 171 | 1932226 | COLNNOT16 | The library was constructed using RNA isolated from sigmoid colon tissue removed from a 62-year-old Caucasian male during a sigmoidectomy and permanent colostomy. |
| 172 | 1932647 | COLNNOT16 | The library was constructed using RNA isolated from sigmoid colon tissue removed from a 62-year-old Caucasian male during a sigmoidectomy and permanent colostomy. |
| 173 | 2124245 | BRSTNOT07 | The library was constructed using RNA isolated from diseased breast tissue removed from a 43-year-old Caucasian female during a unilateral extended simple mastectomy. Pathology indicated mildly proliferative fibrocystic changes with epithelial hyperplasia, papillomatosis, and duct ectasia. Pathology for the associated tumor tissue indicated invasive grade 4, nuclear grade 3 mammary adenocarcinoma with extensive comedo necrosis. Family history included epilepsy, atherosclerotic coronary artery disease, and type II diabetes. |

TABLE 4-continued

| Poly-nucleotide SEQ ID NO: | Clone ID | Library | Library Description |
|---|---|---|---|
| 174 | 2132626 | OVARNOT03 | The library was constructed using RNA isolated from ovarian tissue removed from a 43-year-old Caucasian female during removal of the fallopian tubes and ovaries. Pathology for the associated tumor tissue indicated grade 2 mucinous cystadenocarcinoma. Patient history included mitral valve disorder, pneumonia, and viral hepatitis. Family history included atherosclerotic coronary artery disease, pancreatic cancer, cerebrovascular disease, breast cancer, and uterine cancer. |
| 175 | 2280639 | PROSNON01 | The library was constructed and normalized from 4.4 million independent clones from the PROSNOT11 library. Starting RNA was made from prostate tissue removed from a 28-year-old Caucasian male who died from a gunshot wound. The normalization and hybridization conditions were adapted from Soares, M. B. et al. (1994) Proc. Natl. Acad. Sci. USA 91: 9228-9232, using a longer (19 hour) reannealing hybridization period. |
| 176 | 2292356 | BRAINON01 | The library was constructed and normalized from 4.88 million independent clones from the BRAINOT03 library. Starting RNA was made from brain tissue removed from a 26-year-old Caucasian male during cranioplasty and excision of a cerebral meningeal lesion. Pathology for the associated tumor tissue indicated a grade 4 oligoastrocytoma in the right fronto-parietal part of the brain. |
| 177 | 2349310 | COLSUCT01 | The library was constructed using RNA isolated from diseased sigmoid colon tissue obtained from a 70-year-old Caucasian male during colectomy with permanent ileostomy. Pathology indicated chronic ulcerative colitis. Patient history included benign neoplasm of the colon. Family history included atherosclerotic coronary artery disease and myocardial infarctions. |
| 178 | 2373227 | ADRENOT07 | The library was constructed using RNA isolated from adrenal tissue removed from a 61-year-old female during a bilateral adrenalectomy. Patient history included an unspecified disorder of the adrenal glands. |
| 179 | 2457682 | ENDANOT01 | The library was constructed using RNA isolated from aortic endothelial cell tissue from an explanted heart removed from a male during a heart transplant. |
| 180 | 2480426 | SMCANOT01 | The library was constructed using RNA isolated from an aortic smooth muscle cell line derived from the explanted heart of a male during a heart transplant. |
| 181 | 2503743 | CONUTUT01 | The library was constructed using RNA isolated from sigmoid mesentery tumor tissue obtained from a 61-year-old female during a total abdominal hysterectomy and bilateral salpingo-oophorectomy with regional lymph node excision. Pathology indicated a metastatic grade 4 malignant mixed mullerian tumor present in the sigmoid mesentery at two sites. |
| 182 | 2537684 | BONRTUT01 | The library was constructed using RNA isolated from rib tumor tissue removed from a 16-year-old Caucasian male during a rib osteotomy and a wedge resection of the lung. Pathology indicated a metastatic grade 3 (of 4) osteosarcoma, forming a mass involving the chest wall. |
| 183 | 2593853 | OVARTUT02 | The library was constructed using RNA isolated from ovarian tumor tissue removed from a 51-year-old Caucasian female during an exploratory laparotomy, total abdominal hysterectomy, salpingo-oophorectomy, and an incidental appendectomy. Pathology indicated mucinous cystadenoma presenting as a multiloculated neoplasm involving the entire left ovary. The right ovary contained a follicular cyst and a hemorrhagic corpus luteum. The uterus showed proliferative endometrium and a single intramural leiomyoma. The peritoneal biopsy indicated benign glandular inclusions consistent with endosalpingiosis. Family history included atherosclerotic coronary artery disease, benign hypertension, breast cancer, and uterine cancer. |
| 184 | 2622354 | KERANOT02 | The library was constructed using RNA isolated from epidermal breast keratinocytes (NHEK). NHEK (Clontech #CC-2501) is a human breast keratinocyte cell line derived from a 30-year-old black female during breast-reduction surgery. |
| 185 | 2641377 | LUNGTUT08 | The library was constructed using RNA isolated from lung tumor tissue removed from a 63-year-old Caucasian male during a right upper lobectomy with fiberoptic bronchoscopy. Pathology indicated a grade 3 adenocarcinoma. Patient history included atherosclerotic coronary artery disease, an acute myocardial infarction, rectal cancer, an asymptomatic abdominal aortic aneurysm, and cardiac dysrhythmia. Family history included congestive heart failure, stomach cancer, and lung cancer, type II diabetes, atherosclerotic coronary artery disease, and an acute myocardial infarction. |
| 186 | 2674857 | KIDNNOT19 | The library was constructed using RNA isolated from kidney tissue removed a 65-year-old Caucasian male during an exploratory laparotomy and nephroureterectomy. Pathology for the associated tumor tissue indicated a grade 1 renal cell carcinoma within the upper pole of the left kidney. Patient history included malignant melanoma of the abdominal skin, benign neoplasm of colon, cerebrovascular disease, and umbilical hernia. Family history included myocardial infarction, atherosclerotic coronary artery disease, cerebrovascular disease, prostate cancer, myocardial infarction, and atherosclerotic coronary artery disease. |
| 187 | 2758485 | THP1AZS08 | The subtracted THP-1 promonocyte cell line library was constructed using 5.76 million clones from a 5-aza-2'-deoxycytidine (AZT) treated THP-1 cell library. Starting RNA was made from THP-1 promonocyte cells treated for three days with 0.8 micromolar AZT. The library was oligo(dT)-primed, and cDNAs were cloned directionally into the pSPORT1 vectoring system using SalI (5') and NotI (3'). The hybridization probe for subtraction was derived from a similarly constructed library, made from 1 microgram of polyA RNA isolated from untreated THP-1 cells. 5.76 million clones from the AZ-treated THP-1 cell library were then subjected to two rounds of subtractive hybridization with 5 million clones from the untreated THP-1 cell library. Subtractive hybridization conditions were based on the methodologies of Swaroop et al. (Nucl. Acids Res. (1991) 19: 1954) and Bonaldo et al. (Genome Res (1996) 6: 791-806). |
| 188 | 2763296 | BRSTNOT12 | The library was constructed using RNA isolated from diseased breast tissue removed from a 32-year-old Caucasian female during a bilateral reduction mammoplasty. Pathology indicated nonproliferative fibrocystic disease. Family history included benign hypertension and atherosclerotic coronary artery disease. |

TABLE 4-continued

| Poly-nucleo-tide SEQ ID NO: | Clone ID | Library | Library Description |
|---|---|---|---|
| 189 | 2779436 | OVARTUT03 | The library was constructed using RNA isolated from ovarian tumor tissue removed from the left ovary of a 52-year-old mixed ethnicity female during a total abdominal hysterectomy, bilateral salpingo-oophorectomy, peritoneal and lymphatic structure biopsy, regional lymph node excision, and peritoneal tissue destruction. Pathology indicated an invasive grade 3 (of 4) seroanaplastic carcinoma forming a mass in the left ovary. The endometrium was atrophic. Multiple (2) leiomyomata were identified, one subserosal and 1 intramural. Pathology also indicated a metastatic grade 3 seroanaplastic carcinoma involving the omentum, cul-de-sac peritoneum, left broad ligament peritoneum, and mesentery colon. Patient history included breast cancer, chronic peptic ulcer, and joint pain. Family history included colon cancer, cerebrovascular disease, breast cancer, type II diabetes, esophagus cancer, and depressive disorder. |
| 190 | 2808528 | BLADTUT08 | The library was constructed using RNA isolated from bladder tumor tissue removed from a 72-year-old Caucasian male during a radical cystectomy and prostatectomy. Pathology indicated an invasive grade 3 (of 3) transitional cell carcinoma in the right bladder base. Family history included myocardial infarction, cerebrovascular disease, brain cancer, and myocardial infarction. |
| 191 | 2809230 | BLADTUT08 | The library was constructed using RNA isolated from bladder tumor tissue removed from a 72-year-old Caucasian male during a radical cystectomy and prostatectomy. Pathology indicated an invasive grade 3 (of 3) transitional cell carcinoma in the right bladder base. Patient history included pure hypercholesterolemia and tobacco abuse. Family history included myocardial infarction, cerebrovascular disease, brain cancer, and myocardial infarction. |
| 192 | 2816821 | BRSTNOT14 | The library was constructed using RNA isolated from breast tissue removed from a 62-year-old Caucasian female during a unilateral extended simple mastectomy. Pathology for the associated tumor tissue indicated an invasive grade 3 (of 4), nuclear grade 3 (of 3) adenocarcinoma, ductal type. Ductal carcinoma in situ, comedo type, comprised 60% of the tumor mass. Metastatic adenocarcinoma was identified in one (of 14) axillary lymph nodes with no perinodal extension. The tumor cells were strongly positive for estrogen receptors and weakly positive for progesterone receptors. Patient history included a benign colon neoplasm, hyperlipidemia, and cardiac dysrhythmia. Family history included atherosclerotic coronary artery disease, myocardial infarction, colon cancer, ovarian cancer, lung cancer, and cerebrovascular disease. |
| 193 | 2817268 | BRSTNOT14 | The library was constructed using RNA isolated from breast tissue removed from a 62-year-old Caucasian female during a unilateral extended simple mastectomy. Pathology for the associated tumor tissue indicated an invasive grade 3 (of 4), nuclear grade 3 (of 3) adenocarcinoma, ductal type. Ductal carcinoma in situ, comedo type, comprised 60% of the tumor mass. Metastatic adenocarcinoma was identified in one (of 14) axillary lymph nodes with no perinodal extension. The tumor cells were strongly positive for estrogen receptors and weakly positive for progesterone receptors. Patient history included a benign colon neoplasm, hyperlipidemia, and cardiac dysrhythmia. Family history included atherosclerotic coronary artery disease, myocardial infarction, colon cancer, ovarian cancer, lung cancer, and cerebrovascular disease. |
| 194 | 2923165 | SININOT04 | The library was constructed using RNA isolated from diseased ileum tissue obtained from a 26-year-old Caucasian male during a partial colectomy, permanent colostomy, and an incidental appendectomy. Pathology indicated moderately to severely active Crohn's disease. Family history included enteritis of the small intestine. |
| 195 | 2949822 | KIDNFET01 | The library was constructed using RNA isolated from kidney tissue removed from a Caucasian female fetus, who died at 17 weeks' gestation from anencephalus. |
| 196 | 2992192 | KIDNFET02 | The library was constructed using RNA isolated from kidney tissue removed from a Caucasian male fetus, who was stillborn with a hypoplastic left heart and died at 23 weeks' gestation. |
| 197 | 2992458 | KIDNFET02 | The library was constructed using RNA isolated from kidney tissue removed from a Caucasian male fetus, who was stillborn with a hypoplastic left heart and died at 23 weeks' gestation. |
| 198 | 3044710 | HEAANOT01 | The library was constructed using RNA isolated from right coronary and right circumflex coronary artery tissue removed from the explanted heart of a 46-year-old Caucasian male during a heart transplantation. Patient history included myocardial infarction from total occlusion of the left anterior descending coronary artery, atherosclerotic coronary artery disease, hyperlipidemia, myocardial ischemia, dilated cardiomyopathy, and left ventricular dysfunction. Previous surgeries included cardiac catheterization. Family history included atherosclerotic coronary artery disease. |
| 199 | 3120415 | LUNGTUT13 | The library was constructed using RNA isolated from tumorous lung tissue removed from the right upper lobe of a 47-year-old Caucasian male during a segmental lung resection. Pathology indicated invasive grade 3 (of 4) adenocarcinoma. Family history included atherosclerotic coronary artery disease, and type II diabetes. |
| 200 | 126758 | LUNGNOT01 | The library was constructed at Stratagene using RNA isolated from the lung tissue of a 72-year-old male. |
| 201 | 674760 | CRBLNOT01 | The library was constructed using RNA isolated from the cerebellum tissue of a 69-year-old Caucasian male who died from chronic obstructive pulmonary disease. Patient history included myocardial infarction, hypertension, and osteoarthritis. |
| 202 | 1229438 | BRAITUT01 | The library was constructed using RNA isolated from brain tumor tissue removed from a 50-year-old Caucasian female during a frontal lobectomy. Pathology indicated recurrent grade 3 oligoastrocytoma with focal necrosis and extensive calcification. Patient history included a speech disturbance and epilepsy. The patient's brain had also been irradiated with a total dose of 5,082 cyg (Fraction 8). Family history included a brain tumor. |
| 203 | 1236935 | LUNGFET03 | The library was constructed using RNA isolated from lung tissue removed from a Caucasian female fetus who died at 20 weeks' gestation. |

TABLE 4-continued

| Polynucleotide SEQ ID NO: | Clone ID | Library | Library Description |
|---|---|---|---|
| 204 | 1359283 | LUNGNOT12 | The library was constructed using RNA isolated from lung tissue removed from a 78-year-old Caucasian male during a segmental lung resection and regional lymph node resection. Pathology indicated fibrosis pleura was puckered, but not invaded. Pathology for the associated tumor tissue indicated an invasive pulmonary grade 3 adenocarcinoma. Patient history included cerebrovascular disease, arteriosclerotic coronary artery disease, thrombophlebitis, chronic obstructive pulmonary disease, and asthma. Family history included intracranial hematoma, cerebrovascular disease, arteriosclerotic coronary artery disease, and type I diabetes. |
| 205 | 1450703 | PENITUT01 | The library was constructed using RNA isolated from tumor tissue removed from the penis of a 64-year-old Caucasian male during penile amputation. Pathology indicated a fungating invasive grade 4 squamous cell carcinoma involving the inner wall of the foreskin and extending onto the glans penis. Patient history included benign neoplasm of the large bowel, atherosclerotic coronary artery disease, angina pectoris, gout, and obesity. Family history included malignant pharyngeal neoplasm, chronic lymphocytic leukemia, and chronic liver disease. |
| 206 | 1910668 | CONNTUT01 | The library was constructed using RNA isolated from a soft tissue tumor removed from the clival area of the skull of a 30-year-old Caucasian female. Pathology indicated chondroid chordoma with neoplastic cells reactive for keratin. |
| 207 | 1955143 | CONNNOT01 | The library was constructed using RNA isolated from mesentery fat tissue obtained from a 71-year-old Caucasian male during a partial colectomy and permanent colostomy. Family history included atherosclerotic coronary artery disease, myocardial infarction, and extrinsic asthma. |
| 208 | 1961637 | BRSTNOT04 | The library was constructed using RNA isolated from breast tissue removed from a 62-year-old East Indian female during a unilateral extended simple mastectomy. Pathology for the associated tumor tissue indicated an invasive grade 3 ductal carcinoma. Patient history included benign hypertension, hyperlipidemia, and hematuria. Family history included cerebrovascular and cardiovascular disease, hyperlipidemia, and liver cancer. |
| 209 | 1990762 | CORPNOT02 | The library was constructed using RNA isolated from diseased corpus callosum tissue removed from the brain of a 74-year-old Caucasian male who died from Alzheimer's disease. |
| 210 | 1994131 | CORPNOT02 | The library was constructed using RNA isolated from diseased corpus callosum tissue removed from the brain of a 74-year-old Caucasian male who died from Alzheimer's disease. |
| 211 | 1997745 | BRSTTUT03 | The library was constructed using RNA isolated from breast tumor tissue removed from a 58-year-old Caucasian female during a unilateral extended simple mastectomy. Pathology indicated multicentric invasive grade 4 lobular carcinoma. The mass was identified in the upper outer quadrant, and three separate nodules were found in the lower outer quadrant of the left breast. Patient history included skin cancer, rheumatic heart disease, osteoarthritis, and tuberculosis. Family history included cerebrovascular disease, coronary artery aneurysm, breast cancer, prostate cancer, atherosclerotic coronary artery disease, and type I diabetes. |
| 212 | 2009035 | TESTNOT03 | The library was constructed using polyA RNA isolated from testicular tissue removed from a 37-year-old Caucasian male who died from liver disease. Patient history included cirrhosis, jaundice, and liver failure. |
| 213 | 2009152 | TESTNOT03 | The library was constructed using polyA RNA isolated from testicular tissue removed from a 37-year-old Caucasian male who died from liver disease. Patient history included cirrhosis, jaundice, and liver failure. |
| 214 | 2061752 | OVARNOT03 | The library was constructed using RNA isolated from ovarian tissue removed from a 43-year-old Caucasian female during removal of the fallopian tubes and ovaries. Pathology for the associated tumor tissue indicated grade 2 mucinous cystadenocarcinoma. Patient history included mitral valve disorder, pneumonia, and viral hepatitis. Family history included atherosclerotic coronary artery disease, pancreatic cancer, stress reaction, cerebrovascular disease, breast cancer, and uterine cancer. |
| 215 | 2061933 | OVARNOT03 | The library was constructed using RNA isolated from ovarian tissue removed from a 43-year-old Caucasian female during removal of the fallopian tubes and ovaries. Pathology for the associated tumor tissue indicated grade 2 mucinous cystadenocarcinoma. Patient history included mitral valve disorder, pneumonia, and viral hepatitis. Family history included atherosclerotic coronary artery disease, pancreatic cancer, stress reaction, cerebrovascular disease, breast cancer, and uterine cancer. |
| 216 | 2081422 | UTRSNOT08 | The library was constructed using RNA isolated from uterine tissue removed from a 35-year-old Caucasian female during a vaginal hysterectomy with dilation and curettage. Pathology indicated that the endometrium was secretory phase with a benign endometrial polyp 1 cm in diameter. The cervix showed mild chronic cervicitis. Family history included atherosclerotic coronary artery disease and type II diabetes. |
| 217 | 2101278 | BRAITUT02 | The library was constructed using RNA isolated from brain tumor tissue removed from the frontal lobe of a 58-year-old Caucasian male during excision of a cerebral meningeal lesion. Pathology indicated a grade 2 metastatic hypernephroma. Patient history included a grade 2 renal cell carcinoma, insomnia, and chronic airway obstruction. Family history included a malignant neoplasm of the kidney. |
| 218 | 2121353 | BRSTNOT07 | The library was constructed using RNA isolated from diseased breast tissue removed from a 43-year-old Caucasian female during a unilateral extended simple mastectomy. Pathology indicated mildly proliferative fibrocystic changes with epithelial hyperplasia, papillomatosis, and duct ectasia. Pathology for the associated tumor tissue indicated invasive grade 4, nuclear grade 3 mammary adenocarcinoma with extensive comedo necrosis. Family history included epilepsy, cardiovascular disease, and type II diabetes. |
| 219 | 2241736 | PANCTUT02 | The library was constructed using RNA isolated from pancreatic tumor tissue removed from a 45-year-old Caucasian female during radical pancreaticoduodenectomy. Pathology indicated a grade 4 anaplastic carcinoma. Family history included benign hypertension, hyperlipidemia and atherosclerotic coronary artery disease. |

TABLE 4-continued

| Polynucleotide SEQ ID NO: | Clone ID | Library | Library Description |
|---|---|---|---|
| 220 | 2271935 | PROSNON01 | This normalized prostate library was constructed from 4.4 M independent clones from the PROSNOT11 library. Starting RNA was made from prostate tissue removed from a 28-year-old Caucasian male who died from a self-inflicted gunshot wound. The normalization and hybridization conditions were adapted from Soares, M. B. et al. (1994) Proc. Natl. Acad. Sci. USA 91: 9228-9232, using a longer (19 hour) reannealing hybridization period. |
| 221 | 2295344 | BRSTNOT05 | The library was constructed using RNA isolated from breast tissue removed from a 58-year-old Caucasian female during a unilateral extended simple mastectomy. Pathology for the associated tumor tissue indicated multicentric invasive grade 4 lobular carcinoma. Patient history included skin cancer, rheumatic heart disease, osteoarthritis, and tuberculosis. Family history included cerebrovascular and cardiovascular disease, breast and prostate cancer, and type I diabetes. |
| 222 | 2303994 | BRSTNOT05 | The library was constructed using RNA isolated from breast tissue removed from a 58-year-old Caucasian female during a unilateral extended simple mastectomy. Pathology for the associated tumor tissue indicated multicentric invasive grade 4 lobular carcinoma. Patient history included skin cancer, rheumatic heart disease, osteoarthritis, and tuberculosis. Family history included cerebrovascular and cardiovascular disease, breast and prostate cancer, and type I diabetes. |
| 223 | 2497805 | ADRETUT05 | The library was constructed RNA isolated from adrenal tumor tissue removed from a 52-year-old Caucasian female during a unilateral adrenalectomy. Pathology indicated a pheochromocytoma. |
| 224 | 2646362 | LUNGTUT11 | The library was constructed using RNA isolated from lung tumor tissue removed from the right lower lobe a 57-year-old Caucasian male during a segmental lung resection. Pathology indicated an infiltrating grade 4 squamous cell carcinoma. Multiple intrapulmonary peribronchial lymph nodes showed metastatic squamous cell carcinoma. Patient history included a benign brain neoplasm and tobacco abuse. Family history included spinal cord cancer, type II diabetes, cerebrovascular disease, and malignant prostate neoplasm. |
| 225 | 2657146 | LUNGTUT09 | The library was constructed using RNA isolated from lung tumor tissue removed from a 68-year-old Caucasian male during segmental lung resection. Pathology indicated invasive grade 3 squamous cell carcinoma and a metastatic tumor. Patient history included type II diabetes, thyroid disorder, depressive disorder, hyperlipidemia, esophageal ulcer, and tobacco use. |
| 226 | 2755786 | THP1AZS08 | This subtracted THP-1 promonocyte cell line library was constructed using 5.76 million clones from a 5-aza-2'-deoxycytidine (AZ) treated THP-1 cell library. Starting RNA was made from THP-1 promonocyte cells treated for three days with 0.8 micromolar AZ. The hybridization probe for subtraction was derived from a similarly constructed library, made from RNA isolated from untreated THP-1 cells. 5.76 million clones from the AZ-treated THP-1 cell library were then subjected to two rounds of subtractive hybridization with 5 million clones from the untreated THP-1 cell library. Subtractive hybridization conditions were based on the methodologies of Swaroop et al., NAR (1991) 19: 1954, and Bonaldo et al., Genome Research (1996) 6: 791. THP-1 (ATCC TIB 202) is a human promonocyte line derived from peripheral blood of a 1-year-old Caucasian male with acute monocytic leukemia. |
| 227 | 2831245 | TLYMNOT03 | The library was constructed using RNA isolated from nonactivated Th1 cells. These cells were differentiated from umbilical cord CD4 T cells with IL-12 and B7-transfected COS cells. |
| 228 | 3116250 | LUNGTUT13 | The library was constructed using RNA isolated from tumorous lung tissue removed from the right upper lobe of a 47-year-old Caucasian male during a segmental lung resection. Pathology indicated invasive grade 3 (of 4) adenocarcinoma. Family history included atherosclerotic coronary artery disease, and type II diabetes. |
| 229 | 3129630 | LUNGTUT12 | The library was constructed using RNA isolated from tumorous lung tissue removed from a 70-year-old Caucasian female during a lung lobectomy of the left upper lobe. Pathology indicated grade 3 (of 4) adenocarcinoma and vascular invasion. Patient history included tobacco abuse, depressive disorder, anxiety state, and skin cancer. Family history included cerebrovascular disease, congestive heart failure, colon cancer, depressive disorder, and primary liver. |
| 230 | 007632 | HMC1NOT01 | The library was constructed using RNA isolated from the HMC-1 human mast cell line derived from a 52-year-old female. Patient history included mast cell leukemia. |
| 231 | 1236968 | LUNGFET03 | The library was constructed using RNA isolated from lung tissue removed from a Caucasian female fetus who died at 20 weeks' gestation. |
| 232 | 1334153 | COLNNOT13 | The library was constructed using RNA isolated from ascending colon tissue of a 28-year-old Caucasian male with moderate chronic ulcerative colitis. |
| 233 | 1396975 | BRAITUT08 | The library was constructed using RNA isolated from brain tumor tissue removed from the left frontal lobe of a 47-year-old Caucasian male during excision of cerebral meningeal tissue. Pathology indicated grade 4 fibrillary astrocytoma with focal tumoral radionecrosis. Patient history included cerebrovascular disease, deficiency anemia, hyperlipidemia, epilepsy, and tobacco use. Family history included cerebrovascular disease and malignant prostate neoplasm. |
| 234 | 1501749 | SINTBST01 | The library was constructed using RNA isolated from ileum tissue removed from an 18-year-old Caucasian female during bowel anastomosis. Pathology indicated Crohn's disease of the ileum. Family history included cerebrovascular disease and atherosclerotic coronary artery disease. |
| 235 | 1575240 | LNODNOT03 | The library was constructed using RNA isolated from lymph node tissue removed from a 67-year-old Caucasian male during a segmental lung resection and bronchoscopy. This tissue was extensively necrotic with 10% viable tumor. Pathology for the associated tumor tissue indicated invasive grade 3-4 squamous cell carcinoma. Patient history included hemangioma. Family history included atherosclerotic coronary artery disease, benign hypertension, and congestive heart failure. |
| 236 | 1647884 | PROSTUT09 | The library was constructed using RNA isolated from prostate tumor tissue removed from a 66-year-old Caucasian male during a radical prostatectomy, radical cystectomy, and urinary diversion. Pathology indicated grade 3 transitional cell carcinoma. Patient history included lung neoplasm, and benign hypertension. Family history included malignant breast neoplasm, tuberculosis, cerebrovascular disease, atherosclerotic coronary artery disease, and lung cancer. |

TABLE 4-continued

| Poly-nucleo-tide SEQ ID NO: | Clone ID | Library | Library Description |
|---|---|---|---|
| 237 | 1661144 | BRSTNOT09 | The library was constructed using RNA isolated from breast tissue removed from a 45-year-old Caucasian female during unilateral extended simple mastectomy. Pathology for the associated tumor tissue indicated invasive nuclear grade 2-3 adenocarcinoma. Patient history included valvuloplasty of mitral valve and rheumatic heart disease. Family history included cardiovascular disease and type II diabetes. |
| 238 | 1685409 | PROSNOT15 | The library was constructed using RNA isolated from diseased prostate tissue removed from a 66-year-old Caucasian male during radical prostatectomy and regional lymph node excision. Pathology indicated adenofibromatous hyperplasia. Pathology for the associated tumor tissue indicated adenocarcinoma (Gleason grade 2 + 3). The patient presented with elevated prostate specific antigen (PSA). Family history included prostate cancer, secondary bone cancer, and benign hypertension. |
| 239 | 1731419 | BRSTTUT08 | The library was constructed using RNA isolated from breast tumor tissue removed from a 45-year-old Caucasian female during unilateral extended simple mastectomy. Pathology indicated invasive nuclear grade 2-3 adenocarcinoma. Patient history included valvuloplasty of mitral valve and rheumatic heart disease. Family history included cardiovascular disease and type II diabetes. |
| 240 | 2650265 | BRSTNOT14 | The library was constructed using RNA isolated from breast tissue removed from a 62-year-old Caucasian female during a unilateral extended simple mastectomy. Pathology for the associated tumor tissue indicated an invasive grade 3 (of 4), nuclear grade 3 (of 3) adenocarcinoma. Patient history included a benign colon neoplasm, hyperlipidemia, cardiac dysrhythmia, and obesity. Family history included cardiovascular and cerebrovascular disease and colon, ovary and lung cancer. |
| 241 | 2677129 | KIDNNOT19 | The library was constructed using RNA isolated from kidney tissue removed a 65-year-old Caucasian male during an exploratory laparotomy and nephroureterectomy. Pathology for the associated tumor tissue indicated grade 1 renal cell carcinoma within the upper pole of the left kidney. Patient history included malignant melanoma of the abdominal skin, benign neoplasm of colon, cerebrovascular disease, and umbilical hernia. Family history included myocardial infarction, atherosclerotic coronary artery disease, cerebrovascular disease, and prostate cancer. |
| 242 | 3151073 | ADRENON04 | The normalized adrenal gland library was constructed from 1.36 × 1e6 independent clones from an adrenal tissue library. Starting RNA was made from adrenal gland tissue removed from a 20-year-old Caucasian male who died from head trauma. The library was normalized in two rounds using conditions adapted from Soares et al. (PNAS (1994) 91: 9228-9232) and Bonaldo et al. (Genome Res (1996) 6: 791-806) using a significantly longer (48-hours/round) reannealing hybridization period. |
| 243 | 3170095 | BRSTNOT18 | The library was constructed using RNA isolated from diseased breast tissue removed from a 57-year-old Caucasian female during a unilateral simple extended mastectomy. Pathology indicated mildly proliferative breast disease. Patient history included breast cancer and osteoarthritis. Family history included type II diabetes, gallbladder and breast cancer, and chronic lymphocytic leukemia. |
| 244 | 3475168 | LUNGNOT27 | The library was constructed using RNA isolated from lung tissue removed from a 17-year-old Hispanic female. |
| 245 | 3836893 | DENDTNT01 | The library was constructed using RNA isolated from treated dendritic cells from peripheral blood. |
| 246 | 4072159 | KIDNNOT26 | The library was constructed using RNA isolated from left kidney medulla and cortex tissue removed from a 53-year-old Caucasian female during a nephroureterectomy. Pathology for the associated tumor tissue indicated grade 2 renal cell carcinoma involving the lower pole of the kidney. Patient history included hyperlipidemia, cardiac dysrhythmia, menorrhagia, cerebrovascular disease, atherosclerotic coronary artery disease, and tobacco abuse. Family history included cerebrovascular disease and atherosclerotic coronary artery disease. |
| 247 | 1003916 | BRSTNOT03 | The library was constructed using RNA isolated from diseased breast tissue removed from a 54-year-old Caucasian female during a bilateral radical mastectomy. Pathology for the associated tumor tissue indicated residual invasive grade 3 mammary ductal adenocarcinoma. Patient history included kidney infection and condyloma acuminatum. Family history included benign hypertension, hyperlipidemia and a malignant neoplasm of the colon. |
| 248 | 2093492 | PANCNOT04 | The library was constructed using RNA isolated from the pancreatic tissue of a 5-year-old Caucasian male who died in a motor vehicle accident. |
| 249 | 2108789 | BRAITUT03 | The library was constructed using RNA isolated from brain tumor tissue removed from the left frontal lobe a 17-year-old Caucasian female during excision of a cerebral meningeal lesion. Pathology indicated a grade 4 fibrillary giant and small-cell astrocytoma. Family history included benign hypertension and cerebrovascular disease. |
| 250 | 2171401 | ENDCNOT03 | The library was constructed using RNA isolated from dermal microvascular endothelial cells removed from a neonatal Caucasian male. |
| 251 | 2212530 | SINTFET03 | The library was constructed using RNA isolated from small intestine tissue removed from a Caucasian female fetus, who died at 20 weeks' gestation. |
| 252 | 2253036 | OVARTUT01 | The library was constructed using RNA isolated from ovarian tumor tissue removed from a 43-year-old Caucasian female during removal of the fallopian tubes and ovaries. Pathology indicated grade 2 mucinous cystadenocarcinoma involving the entire left ovary. Patient history included mitral valve disorder, pneumonia, and viral hepatitis. Family history included atherosclerotic coronary artery disease, pancreatic cancer, stress reaction, cerebrovascular disease, breast cancer, and uterine cancer. |
| 253 | 2280161 | PROSNON01 | The normalized prostate library was constructed from 4.4 M independent clones from the PROSNOT11 library. Starting RNA was made from prostate tissue removed from a 28-year-old Caucasian male who died from a self-inflicted gunshot wound. The normalization and hybridization conditions were adapted from Soares, M. B. et al. (1994) Proc. Natl. Acad. Sci. USA 91: 9228-9232, using a longer (19 hour) reannealing hybridization period. |

TABLE 4-continued

| Polynucleotide SEQ ID NO: | Clone ID | Library | Library Description |
|---|---|---|---|
| 254 | 2287485 | BRAINON01 | The library was constructed and normalized from 4.88 million independent clones from the BRAINOT03 library. RNA was made from brain tissue removed from a 26-year-old Caucasian male during cranioplasty and excision of a cerebral meningeal lesion. Pathology for the associated tumor tissue indicated a grade 4 oligoastrocytoma in the right fronto-parietal part of the brain. |
| 255 | 2380344 | ISLTNOT01 | The library was constructed using RNA isolated from a pooled collection of pancreatic islet cells. |
| 256 | 2383171 | ISLTNOT01 | The library was constructed using RNA isolated from a pooled collection of pancreatic islet cells. |
| 257 | 2396046 | THP1AZT01 | The library was constructed using RNA isolated from THP-1 promonocyte cells treated for three days with 0.8 micromolar 5-aza-2'-deoxycytidine. THP-1 (ATCC TIB 202)is a human promonocyte line derived from peripheral blood of a 1-year-old Caucasian male with acute monocytic leukemia. |
| 258 | 2456587 | ENDANOT01 | The library was constructed using RNA isolated from aortic endothelial cell tissue from an explanted heart removed from a male during a heart transplant. |
| 259 | 2484813 | BONRTUT01 | The library was constructed using RNA isolated from rib tumor tissue removed from a 16-year-old Caucasian male during a rib osteotomy and a wedge resection of the lung. Pathology indicated a metastatic grade 3 (of 4) osteosarcoma, forming a mass involving the chest wall. |
| 260 | 2493851 | ADRETUT05 | The library was constructed RNA isolated from adrenal tumor tissue removed from a 52-year-old Caucasian female during a unilateral adrenalectomy. Pathology indicated a pheochromocytoma. |
| 261 | 2495719 | ADRETUT05 | The library was constructed RNA isolated from adrenal tumor tissue removed from a 52-year-old Caucasian female during a unilateral adrenalectomy. Pathology indicated a pheochromocytoma. |
| 262 | 2614153 | GBLANOT01 | The library was constructed using RNA isolated from diseased gallbladder tissue removed from a 53-year-old Caucasian female during a cholecystectomy. Pathology indicated mild chronic cholecystitis and cholelithiasis with approximately 150 mixed gallstones. Family history included benign hypertension. |
| 263 | 2655184 | THYMNOT04 | The library was constructed using RNA isolated from thymus tissue removed from a 3-year-old Caucasian male, who died from anoxia. Serologies were negative. The patient was not taking any medications. |
| 264 | 2848362 | BRSTTUT13 | The library was constructed using RNA isolated from breast tumor tissue removed from the right breast of a 46-year-old Caucasian female during a unilateral extended simple mastectomy with breast reconstruction. Pathology indicated an invasive grade 3 adenocarcinoma, ductal type with apocrine features and greater than 50% intraductal component. Patient history included breast cancer. |
| 265 | 2849906 | BRSTTUT13 | The library was constructed using RNA isolated from breast tumor tissue removed from the right breast of a 46-year-old Caucasian female during a unilateral extended simple mastectomy with breast reconstruction. Pathology indicated an invasive grade 3 adenocarcinoma, ductal type with apocrine features and greater than 50% intraductal component. Patient history included breast cancer. |
| 266 | 2899137 | DRGCNOT01 | The library was constructed using RNA isolated from dorsal root ganglion tissue removed from the cervical spine of a 32-year-old Caucasian male who died from acute pulmonary edema and bronchopneumonia, bilateral pleural and pericardial effusions, and malignant lymphoma (natural killer cell type). Patient history included probable cytomegalovirus, infection, hepatic congestion and steatosis, splenomegaly, hemorrhagic cystitis, thyroid hemorrhage, and Bell's palsy. Surgeries included colonoscopy, large intestine biopsy, adenotonsillectomy, and nasopharyngeal endoscopy and biopsy; treatment included radiation therapy. |
| 267 | 2986229 | CARGDIT01 | The library was constructed using RNA isolated from diseased cartilage tissue. Patient history included osteoarthritis. |
| 268 | 3222081 | COLNNON03 | The normalized colon library was constructed from $2.84 \times 10^6$ independent clones from the COLNNOT07 library. Starting RNA was made from colon tissue removed from a 60-year-old Caucasian male during a left hemicolectomy. The normalization and hybridization conditions were adapted from Soares et al. (PNAS (1994) 91: 9228-9232), Swaroop et al. (Nucl. Acids Res. (1991) 19: 1954) and Bonaldo et al. (Genome Res (1996) 6: 791-806), using a significantly longer (48 hour) reannealing hybridization period. |

TABLE 5

| Program | Description | Reference | Parameter Threshold |
|---|---|---|---|
| ABI FACTURA | A program that removes vector sequences and masks ambiguous bases in nucleic acid sequences. | Perkin-Elmer Applied Biosystems, Foster City, CA. | |
| ABI/PARACEL FDF | A Fast Data Finder useful in comparing and annotating amino acid or nucleic acid sequences. | Perkin-Elmer Applied Biosystems, Foster City, CA; Paracel Inc., Pasadena, CA. | Mismatch <50% |
| ABI AutoAssembler | A program that assembles nucleic acid sequences. | Perkin-Elmer Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol. 215: 403-410; Altschul, S. F. et al. (1997) Nucleic Acids Res. 25: 3389-3402. | ESTs: Probability value = 1.0E−8 or less Full Length sequences: Probability value = 1.0E−10 or less |

TABLE 5-continued

| Program | Description | Reference | Parameter Threshold |
|---|---|---|---|
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. 85: 2444-2448; Pearson, W. R. (1990) Methods Enzymol. 183: 63-98; and Smith, T. F. and M. S. Waterman (1981) Adv. Appl. Math. 2: 482-489. | ESTs: fasta E value = 1.06E−6 Assembled ESTs: fasta Identity = 95% or greater and Match length = 200 bases or greater; fastx E value = 1.0E−8 or less Full Length sequences: fastx score = 100 or greater |
| BLIMPS | A BLocks IMProved Searcher that matches a sequence against those in BLOCKS, PRINTS, DOMO, PRODOM, and PFAM databases to search for gene families, sequence homology, and structural fingerprint regions. | Henikoff, S and J. G. Henikoff, Nucl. Acid Res., 19: 6565-72, 1991. J. G. Henikoff and S. Henikoff (1996) Methods Enzymol. 266: 88-105; and Attwood, T. K. et al. (1997) J. Chem. Inf. Comput. Sci. 37: 417-424. | Score = 1000 or greater; Ratio of Score/Strength = 0.75 or larger; and, if applicable, Probability value = 1.0E−3 or less |
| PFAM | An algorithm for searching a query sequence against hidden Markov model (HMM)-based databases of protein family consensus sequences, such as PFAM. | Krogh, A. et al. (1994) J. Mol. Biol., 235: 1501-1531; Sonnhammer, E. L. L. et al. (1988) Nucleic Acids Res. 26: 320-322. | Score = 10-50 bits for PFAM hits, depending on individual protein families |
| ProfileScan | An algorithm that searches for structural and sequence motifs in protein sequences that match sequence patterns defined in Prosite. | Gribskov, M. et al. (1988) CABIOS 4: 61-66; Gribskov, et al. (1989) Methods Enzymol. 183: 146-159; Bairoch, A. et al. (1997) Nucleic Acids Res. 25: 217-221. | Score = 4.0 or greater |
| Phred | A base-calling algorithm that examines automated sequencer traces with high sensitivity and probability. | Ewing, B. et al. (1998) Genome Res. 8: 175-185; Ewing, B. and P. Green (1998) Genome Res. 8: 186-194. | |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2: 482-489; Smith, T. F. and M. S. Waterman (1981) J. Mol. Biol. 147: 195-197; and Green, P., University of Washington, Seattle, WA. | Score = 120 or greater; Match length = 56 or greater |
| Consed | A graphical tool for viewing and editing Phrap assemblies | Gordon, D. et al. (1998) Genome Res. 8: 195-202. | |
| SPScan | A weight matrix analysis program that scans protein sequences for the presence of secretory signal peptides. | Nielson, H. et al. (1997) Protein Engineering 10: 1-6; Claverie, J. M. and S. Audic (1997) CABIOS 12: 431-439. | Score = 5 or greater |
| Motifs | A program that searches amino acid sequences for patterns that matched those defined in Prosite. | Bairoch et al. supra; Wisconsin Package Program Manual, version 9, page M51-59, Genetics Computer Group, Madison, WI. | |

TABLE 6

| Nucleotide SEQ ID NO: | Clone ID | Fragment of SEQ ID NO | Starting Nucleotide of Fragment | Ending Nucleotide of Fragment |
|---|---|---|---|---|
| 135 | 443531 | 443531H1 | 1 | 253 |
| | | 1406807F6 | 152 | 336 |
| | | 443531T6 | 847 | 355 |
| | | SBBA00451F1 | 396 | 856 |
| | | SBBA00676F1 | 546 | 865 |
| 136 | 632860 | 632860H1 | 13 | 253 |
| | | 784715R3 | 17 | 666 |
| | | 509590H1 | 455 | 706 |
| 137 | 670010 | 670010H1 | 1 | 263 |
| | | 669971R1 | 1 | 633 |
| 138 | 726498 | 726498H1 | 13 | 263 |
| | | 726498R6 | 13 | 489 |
| | | 866599R3 | 7 | 660 |
| 139 | 795064 | 795064H1 | 86 | 323 |
| | | 4339458H1 | 4 | 284 |
| | | 937605R3 | 86 | 505 |
| | | 2381151F6 | 592 | 1057 |
| | | 1466346F6 | 857 | 1241 |
| 140 | 924925 | 924925H1 | 111 | 412 |
| | | 3268330H1 | 2 | 239 |
| | | 759120R3 | 111 | 629 |
| 141 | 962390 | 1907958F6 | 1 | 478 |
| | | 023569F1 | 1122 | 470 |
| | | 167282F1 | 1216 | 543 |
| | | 1309211F1 | 911 | 1224 |
| 142 | 1259405 | 1259405H1 | 46 | 277 |
| | | 2472425H1 | 331 | 354 |
| | | 774303R1 | 190 | 743 |
| | | 1520779F1 | 418 | 1001 |
| | | 1693833F6 | 914 | 1467 |
| | | 1831858T6.comp | 1336 | 1742 |
| | | 1527737T6.comp | 1386 | 1829 |

TABLE 6-continued

| Nucleotide SEQ ID NO: | Clone ID | Fragment of SEQ ID NO | Starting Nucleotide of Fragment | Ending Nucleotide of Fragment |
|---|---|---|---|---|
| 143 | 1297384 | 1297384H1 | 402 | 641 |
| | | 1269310F6 | 1 | 492 |
| | | 1457367F1 | 792 | 1380 |
| | | 415587R1 | 1358 | 1712 |
| | | SANA02967F1 | 1143 | 614 |
| 144 | 1299627 | 1299627H1 | 1 | 250 |
| | | 1359140F6 | 1004 | 1573 |
| | | 1349224F1 | 1330 | 1731 |
| | | SBAA01431F1 | 46 | 397 |
| | | SBAA02909F1 | 868 | 262 |
| | | SBAA01156F1 | 901 | 1266 |
| 145 | 1306026 | 1306026H1 | 1 | 223 |
| | | 1464088R6 | 302 | 829 |
| | | SBAA02496F1 | 92 | 568 |
| | | SBAA04305F1 | 366 | 883 |
| 146 | 1316219 | 1316219H1 | 246 | 491 |
| | | 2458603F6 | 1 | 402 |
| | | 2504756T6 | 980 | 380 |
| 147 | 1329031 | 1329031H1 | 1 | 264 |
| | | 1329031T6 | 505 | 1 |
| | | 1329031F6 | 1 | 523 |
| 148 | 1483050 | 1483050H1 | 722 | 931 |
| | | 855049H1 | 1 | 267 |
| | | 077017F1 | 1069 | 679 |
| | | 1483050F6 | 722 | 1215 |
| | | 1480024T6 | 2063 | 1315 |
| | | 1483050T6 | 2068 | 1535 |
| | | 759486R1 | 1762 | 2089 |
| 149 | 1514160 | 1514160H1 | 1640 | 1838 |
| | | 1866765T7 | 2383 | 2210 |
| | | 782676R1 | 1652 | 1875 |
| | | 008055X4 | 1090 | 1804 |
| | | 008055X5 | 1316 | 1952 |
| | | 1866765F6 | 2209 | 2391 |
| | | SAOA03127F1 | 2129 | 1703 |
| 150 | 1603403 | 1603403H1 | 7 | 224 |
| | | 372910F1 | 420 | 44 |
| | | 733299R7 | 219 | 420 |
| 151 | 1652303 | 1652303H1 | 4 | 256 |
| | | 1671806H1 | 1 | 224 |
| | | 1341743T1 | 2069 | 1900 |
| | | 3803812H1 | 389 | 697 |
| | | 1878546F6 | 747 | 1344 |
| | | 1428640F1 | 1081 | 1664 |
| | | 2058609R6 | 1715 | 2098 |
| | | 1331621F1 | 1780 | 2096 |
| | | 1306331T1 | 1897 | 2098 |
| 152 | 1693358 | 1693358H1 | 41 | 125 |
| | | 2498265H1 | 1 | 252 |
| | | 1867125F6 | 205 | 373 |
| | | 1693358T6 | 1094 | 416 |
| | | 2245848R6 | 737 | 1103 |
| 153 | 1707711 | 1707711H1 | 408 | 626 |
| | | 1484609T1 | 2165 | 1855 |
| | | 1707711F6 | 408 | 987 |
| | | 1267959F1 | 1721 | 2182 |
| | | 1484609F1 | 1855 | 2178 |
| | | SAJA00930F1 | 544 | 1132 |
| | | SAJA01300R1 | 1675 | 1212 |
| | | SAJA00999R1 | 1675 | 1142 |
| 154 | 1738735 | 1738735H1 | 7 | 236 |
| | | SAJA00944R1 | 393 | 5 |
| | | SAJA00137F1 | 913 | 685 |
| | | SAJA03629F1 | 435 | 42 |
| 155 | 1749147 | 1749147H1 | 1 | 276 |
| 155 | | 1749147F6 | 47 | 457 |
| 155 | | 1749147T6 | 479 | 1 |
| 156 | 1817722 | 1817722H1 | 1 | 268 |
| | | 2011085H1 | 344 | 545 |
| 157 | 1831290 | 1831290H1 | 10 | 257 |
| | | 3473958H1 | 70 | 242 |
| | | 1972268F6 | 163 | 617 |
| | | 1301277F1 | 413 | 852 |
| | | 1521574F1 | 1024 | 1602 |
| | | 1561690T6 | 1729 | 1058 |
| | | 891461R1 | 1261 | 1738 |
| 158 | 1831477 | 1831477H1 | 59 | 337 |
| | | 1582867H1 | 1 | 199 |
| | | 1336769T1 | 1986 | 1639 |
| | | 1933092H1 | 525 | 789 |
| | | 1519909F1 | 841 | 1296 |
| | | 1220946H1 | 1061 | 1318 |
| | | 809556T1 | 1983 | 1687 |
| | | 1217559T1 | 2002 | 1445 |
| | | 1309225F1 | 1747 | 2001 |
| 159 | 1841607 | 1841607H1 | 13 | 192 |
| | | SBHA03588F1 | 13 | 172 |
| 160 | 1852391 | 1852391H1 | 98 | 367 |
| | | 734140H1 | 1 | 225 |
| | | 1852391F6 | 98 | 542 |
| 161 | 1854555 | 1854555H1 | 1 | 265 |
| | | 2511711H1 | 37 | 58 |
| | | 782453R1 | 223 | 712 |
| | | 1854555F6 | 1 | 346 |
| | | 1840675T6 | 1046 | 860 |
| | | 2109736H1 | 938 | 1054 |
| 162 | 1855755 | 1855755H1 | 17 | 224 |
| | | 3040236H1 | 1 | 179 |
| | | 1283207F1 | 306 | 816 |
| | | 833763T1 | 1148 | 835 |
| | | 1920926R6 | 854 | 1161 |
| 163 | 1861434 | 1861434H1 | 13 | 253 |
| | | 1861434T6 | 872 | 261 |
| | | SARA01525F1 | 426 | 808 |
| | | SARA02548F1 | 587 | 889 |
| 164 | 1872334 | 1872334H1 | 1 | 229 |
| | | 1872334F6 | 1 | 424 |
| | | SBGA03684F1 | 358 | 425 |
| 165 | 1877230 | 1877230H1 | 1405 | 1677 |
| | | 2519841H1 | 1 | 251 |
| | | 1877230T6 | 1903 | 1405 |
| | | 1254693F1 | 335 | 716 |
| | | 077020R1 | 682 | 1414 |
| | | 1232336F1 | 906 | 1507 |
| | | 1004952R6 | 1451 | 1904 |
| | | SARA01879F1 | 1545 | 1921 |
| | | SARA02654F1 | 1545 | 1923 |
| 166 | 1877885 | 1877885H1 | 68 | 323 |
| | | 508020F1 | 499 | 51 |
| | | 2751126R6 | 219 | 516 |
| | | SARA02571F1 | 407 | 499 |
| 167 | 1889269 | 1889269H1 | 757 | 1020 |
| | | 1915551H1 | 1 | 191 |
| | | 629493X12 | 481 | 865 |
| | | 1441289F1 | 693 | 865 |
| | | 1215274X34F1 | 1106 | 1631 |
| | | 1818447F6 | 1307 | 1540 |
| | | 1208463R1 | 1372 | 1493 |
| 168 | 1890243 | 1890243H1 | 9 | 268 |
| | | SARA01884F1 | 521 | 168 |
| | | SATA00046F1 | 1057 | 851 |
| | | SARA03294F1 | 1329 | 910 |
| | | SARA02790F1 | 1138 | 1535 |
| 169 | 1900433 | 1900433H1 | 1 | 242 |
| | | SATA00396F1 | 409 | 124 |
| | | SATA02742F1 | 1 | 294 |
| 170 | 1909441 | 1909441H1 | 786 | 1048 |
| | | 1398811F1 | 1 | 550 |
| | | 3039939H1 | 607 | 876 |
| | | 3324740H1 | 685 | 944 |
| | | 1442131F6 | 787 | 1232 |
| | | 2254056H1 | 1423 | 1522 |
| | | 2199453T6 | 1955 | 1351 |
| | | 1698531H1 | 1968 | 1796 |
| 171 | 1932226 | 1932226H1 | 294 | 510 |
| | | 2320569H1 | 1 | 266 |
| | | 1932226F6 | 294 | 685 |
| | | 2469455T6 | 1475 | 1071 |
| | | 2469455F6 | 1034 | 1492 |
| | | 1907140F6 | 1158 | 1482 |
| | | SATA02592F1 | 857 | 518 |

TABLE 6-continued

| Nucleotide SEQ ID NO: | Clone ID | Fragment of SEQ ID NO | Starting Nucleotide of Fragment | Ending Nucleotide of Fragment |
|---|---|---|---|---|
| 172 | 1932647 | 1932647H1 | 17 | 246 |
| | | 1492745T1 | 1582 | 1418 |
| | | 1492745H1 | 1418 | 1599 |
| | | SASA02355F1 | 386 | 19 |
| | | SASA00117F1 | 250 | 569 |
| | | SASA00192F1 | 515 | 816 |
| 173 | 2124245 | 2124245H1 | 45 | 190 |
| | | 1235393F1 | 495 | 895 |
| | | 1402264F6 | 323 | 925 |
| | | 1303990F1 | 682 | 1240 |
| | | 1402264T6 | 1613 | 950 |
| 174 | 2132626 | 2132626H1 | 406 | 651 |
| | | 1723432T6 | 1299 | 746 |
| | | 2132626R6 | 406 | 904 |
| | | 1736723T6 | 1292 | 857 |
| | | 1504738F1 | 868 | 1320 |
| 175 | 2280639 | 2280639H1 | 28 | 303 |
| | | 1377560F6 | 261 | 777 |
| 176 | 2292356 | 2292356H1 | 717 | 968 |
| | | 4086827H1 | 1 | 275 |
| | | 1754442F6 | 232 | 577 |
| | | 3571126H1 | 497 | 808 |
| | | 1601305F6 | 808 | 1464 |
| 177 | 2349310 | 2349310H1 | 1 | 236 |
| | | 2349310T6 | 682 | 2 |
| 178 | 2373227 | 2373227H1 | 298 | 524 |
| | | 3316444H1 | 801 | 1053 |
| | | 302685R6 | 1141 | 1496 |
| | | SASA02181F1 | 577 | 1 |
| | | SASA01923F1 | 963 | 466 |
| | | SASA03516F1 | 1102 | 1249 |
| 179 | 2457682 | 2457682H1 | 1 | 226 |
| | | 2457682F6 | 1 | 554 |
| 180 | 2480426 | 2480426H1 | 1 | 213 |
| | | 2480426F6 | 1 | 501 |
| 181 | 2503743 | 2503743H1 | 6 | 222 |
| | | 1853909H1 | 1 | 272 |
| | | 1517619F1 | 172 | 830 |
| | | 1467896F6 | 540 | 1112 |
| | | 490031F1 | 1647 | 1068 |
| | | 1208654R1 | 1382 | 1633 |
| | | 880544R1 | 1450 | 1648 |
| 182 | 2537684 | 2537684H1 | 434 | 682 |
| | | 2005493H1 | 1 | 194 |
| | | 730969H1 | 307 | 547 |
| | | 916487H1 | 723 | 989 |
| | | 996135R1 | 997 | 1598 |
| | | 1920738R6 | 1306 | 1692 |
| | | 1957710F6 | 1472 | 1692 |
| 183 | 2593853 | 2593853H1 | 1 | 252 |
| | | 807497H1 | 2 | 217 |
| | | 914020R6 | 284 | 740 |
| | | 889992R1 | 416 | 729 |
| 184 | 2622354 | 2622354H1 | 3 | 266 |
| | | 2623992H1 | 1 | 246 |
| | | 1556510F6 | 81 | 258 |
| 185 | 2641377 | 2641377H1 | 126 | 369 |
| | | 4341415H2 | 10 | 345 |
| | | SBCA07049F3 | 126 | 599 |
| 186 | 2674857 | 2674857H1 | 139 | 393 |
| | | 1872373H1 | 1 | 270 |
| | | 470512R6 | 1486 | 1502 |
| | | 1728547H1 | 1285 | 1508 |
| | | 3013651F6 | 1423 | 1987 |
| | | SBCA01366F1 | 819 | 385 |
| | | SBCA00694F1 | 973 | 1198 |
| 187 | 2758485 | 2758485H1 | 20 | 267 |
| | | 3097533H1 | 1 | 158 |
| | | 1578959F6 | 291 | 771 |
| 188 | 2763296 | 2763296H1 | 63 | 301 |
| | | 3486025F6 | 1 | 130 |
| | | SBDA07002F3 | 63 | 687 |
| 189 | 2779436 | 2779436H1 | 1 | 233 |
| | | 2779436F6 | 1 | 577 |
| | | SBDA07009F3 | 1 | 608 |
| 190 | 2808528 | 2808528H1 | 25 | 335 |
| | | 2611513F6 | 2 | 489 |
| | | SBDA07021T3 | 1058 | 443 |
| 191 | 2809230 | 2809230H1 | 409 | 630 |
| | | 2213849H1 | 1 | 133 |
| | | 711706R6 | 396 | 691 |
| | | 958323R1 | 407 | 800 |
| | | 030732F1 | 1366 | 623 |
| 192 | 2816821 | 2816821H1 | 210 | 501 |
| | | 3746964H1 | 1 | 307 |
| | | 2816821F6 | 210 | 682 |
| | | 948722T6 | 959 | 527 |
| 193 | 2817268 | 2817268H1 | 42 | 282 |
| | | 3591308H1 | 13 | 264 |
| | | 419522R1 | 179 | 808 |
| | | 2073028F6 | 446 | 924 |
| | | 1308781F6 | 869 | 1112 |
| 194 | 2923165 | 2923165H1 | 8 | 295 |
| | | 2011630H1 | 18 | 238 |
| | | 1457250F1 | 268 | 856 |
| | | 754668R1 | 327 | 878 |
| | | 1406510F6 | 558 | 901 |
| 195 | 2949822 | 2949822H1 | 1 | 280 |
| | | SBDA07078F3 | 1 | 606 |
| 196 | 2992192 | 2992192H1 | 25 | 321 |
| | | 2534324H2 | 1 | 240 |
| | | 2815255T6 | 690 | 219 |
| | | 1551107T6 | 893 | 471 |
| | | 1551107F6 | 471 | 690 |
| 197 | 2992458 | 2992458H1 | 48 | 362 |
| | | 2618951H1 | 1 | 247 |
| | | 1479252F1 | 163 | 610 |
| | | 1879054H1 | 563 | 840 |
| | | 1879054F6 | 563 | 1096 |
| | | 2215240H1 | 951 | 1202 |
| | | 1535968T1 | 1729 | 1173 |
| 198 | 3044710 | 3044710H1 | 652 | 952 |
| | | 3741773H1 | 1 | 283 |
| | | 859906X42C1 | 94 | 192 |
| | | 1534347F1 | 90 | 268 |
| | | 1421122F1 | 830 | 1392 |
| | | 1303865F1 | 1033 | 1487 |
| | | 1704452F6 | 1432 | 1934 |
| | | 1251642F1 | 2006 | 1544 |
| | | 1781694R6 | 1894 | 2017 |
| 199 | 3120415 | 3120415H1 | 72 | 363 |
| | | 1360123T1 | 523 | 141 |
| | | 1375015H1 | 380 | 526 |

We claim:

1. A composition comprising an isolated polypeptide comprising an amino acid sequence at least 95% identical to the amino acid sequence of SEQ ID NO: 43, wherein the polypeptide is expressed in colon tissue.

2. The composition of claim 1, wherein the polypeptide consists of the amino acid sequence of SEQ ID NO: 43.

3. The composition of claim 1, wherein the polypeptide has been modified by:

(a) replacement of hydrogen by an alkyl, acyl, or amino group;
(b) glycosylation;
(c) pegylation; or
(d) any combination thereof.

4. The composition of claim 1, further comprising at least one stabilizing compound.

5. The composition of claim 1, further comprising at least one active agent, drug, or hormone.

6. The composition of claim 1, wherein the polypeptide comprises the amino acid sequence of SEQ ID NO: 43.

7. The composition of claim 1, wherein the polypeptide consists essentially of the amino acid sequence of SEQ ID NO: 43.

8. The composition of claim 1, wherein the polypeptide is a naturally occurring amino acid sequence.

9. The composition of claim 1, further comprising at least one carrier selected from the group consisting of saline, buffered saline, dextrose, and water.

* * * * *

SEQUENCE LISTING

<160> NUMBER OF SEQ ID NOS: 269

<210> SEQ ID NO 1
<211> LENGTH: 88
<212> TYPE: PRT
<213> ORGANISM: Homo sapiens

```
<220> FEATURE:
<221> NAME/KEY: misc_feature
<223> OTHER INFORMATION: Incyte Clone No: 443531

<400> SEQUENCE: 1

Met Ser Trp Trp Leu Cys Leu Pro Leu Gly Leu Phe Gly Ser Cys Leu
1               5                   10                  15

Ala Pro Ala Ala Ala Ala Leu Ser Glu Phe Thr Gln Glu Gln His
            20                  25                  30

Asp Gly Ala Gln Pro Ser Pro Lys Cys Leu Ala Glu Glu Leu Gly Asp
            35                  40                  45

Ala Trp Thr Ile Gln Ile Glu Ala Asn Trp Lys Tyr Arg Ala Val Asn
50                  55                  60

Thr Asn Gln Arg Gly Lys Leu Leu Ala Ser Glu Thr Trp Lys Gly Arg
65                  70                  75                  80

Arg Asn Thr Phe Phe Phe Leu Pro
                85

<210> SEQ ID NO 2
<211> LENGTH: 128
<212> TYPE: PRT
<213> ORGANISM: Homo sapiens
<220> FEATURE:
<221> NAME/KEY: misc_feature
<223> OTHER INFORMATION: Incyte Clone No: 632860

<400> SEQUENCE: 2

Met Trp Pro Ala Gly Leu Gly Arg Ser Leu Leu Ala Gln Pro Ala Leu
1               5                   10                  15

Cys Ser Phe Met Gly Pro Gln Trp Ile Leu Gln Phe Cys Ser Trp Leu
            20                  25                  30

Glu Pro Arg Gln Leu Arg Trp Ser Trp Thr Glu Pro Pro Phe Thr Leu
            35                  40                  45

Leu Asp Ser Leu Gly Leu Arg Ala Ala Gln Asp Ser Cys Ser Phe Thr
50                  55                  60

Thr Leu Val Pro Leu Thr Leu Asp Ser Ser Phe Met Thr Val Asn Val
65                  70                  75                  80

Val Pro Phe Val Trp Thr Ser Ser Phe Phe Arg Ala Phe Gln Tyr Pro
            85                  90                  95

Val Thr Ser Pro Cys Arg Thr Lys Asn Thr Pro Leu Leu Ile Asp Gly
            100                 105                 110

Val Thr Arg Ile Gln Ala Thr Trp Pro Glu Ala Arg Ser Gln His Glu
            115                 120                 125

<210> SEQ ID NO 3
<211> LENGTH: 111
<212> TYPE: PRT
<213> ORGANISM: Homo sapiens
<220> FEATURE:
<221> NAME/KEY: misc_feature
<223> OTHER INFORMATION: Incyte Clone No: 670010

<400> SEQUENCE: 3

Met Gly Leu Leu Leu Leu Val Leu Phe Leu Ser Leu Pro Val Ala
1               5                   10                  15

Tyr Thr Ile Met Ser Leu Pro Ser Phe Asp Cys Gly Pro Phe Arg
            20                  25                  30

Cys Arg Val Ser Val Ala Arg Glu His Leu Pro Ser Arg Gly Ser Leu
            35                  40                  45

Leu Arg Gly Pro Arg Pro Arg Ile Pro Val Leu Val Ser Cys Gln Pro
```

```
              50                   55                   60
Val  Lys  Gly  His  Gly  Thr  Leu  Gly  Glu  Ser  Pro  Met  Pro  Phe  Lys  Arg
 65                        70                        75                        80

Val  Phe  Cys  Gln  Asp  Gly  Asn  Val  Arg  Ser  Phe  Cys  Val  Cys  Ala  Val
                          85                        90                        95

His  Phe  Ser  Ser  His  Gln  Pro  Pro  Val  Ala  Val  Glu  Cys  Leu  Lys
                         100                       105                       110
```

<210> SEQ ID NO 4
<211> LENGTH: 110
<212> TYPE: PRT
<213> ORGANISM: Homo sapiens
<220> FEATURE:
<221> NAME/KEY: misc_feature
<223> OTHER INFORMATION: Incyte Clone No: 726498

<400> SEQUENCE: 4

```
Met  Trp  Arg  Leu  Arg  Arg  Asn  Leu  Ala  Leu  Pro  Pro  Gly  Lys  Leu  Ala
 1                    5                        10                        15

Trp  Leu  Tyr  Leu  Ser  Val  Phe  Ser  Gln  Gly  Ser  Arg  Ala  Met  Met  Ser
                         20                        25                        30

Leu  Thr  Glu  Ile  Arg  Leu  Lys  His  Met  Leu  Glu  Ile  Trp  His  Gly  Arg
               35                        40                        45

Gln  Ala  Arg  Ala  Cys  Glu  Asn  Leu  Arg  Asn  Gln  Thr  Arg  Val  Ala  Thr
 50                        55                        60

Lys  Val  Glu  Pro  Gln  Lys  Gly  Arg  Ser  Thr  Glu  Ile  Cys  Cys  Leu  Ala
 65                        70                        75                        80

Val  Val  Pro  Leu  Asn  Glu  Val  Val  Gln  Ser  Ile  Leu  Trp  Trp  Val
                         85                        90                        95

Trp  Ser  Cys  Cys  Gln  His  Gln  Glu  Asp  Lys  Leu  Gly  Ala  Lys
                        100                       105                       110
```

<210> SEQ ID NO 5
<211> LENGTH: 78
<212> TYPE: PRT
<213> ORGANISM: Homo sapiens
<220> FEATURE:
<221> NAME/KEY: misc_feature
<223> OTHER INFORMATION: Incyte Clone No: 795064

<400> SEQUENCE: 5

```
Met  Ala  Glu  Ser  Gly  Leu  Thr  Ser  Leu  Pro  Gly  Thr  Ala  Ser  Trp  Phe
 1                    5                        10                        15

Cys  Phe  Leu  Pro  Val  Ser  Gln  Arg  Lys  Ala  Thr  Ser  Lys  Lys  Leu  Leu
                         20                        25                        30

Leu  Lys  Ala  Arg  Lys  Lys  Ser  Gly  Phe  Glu  Leu  Ser  Val  Thr  Asp  Ser
               35                        40                        45

Ser  Glu  Cys  Phe  Arg  Val  Thr  Ala  Ser  Val  Arg  Gly  Met  Lys  Asn  Arg
 50                        55                        60

His  Ala  Lys  Gly  Asn  Gly  Cys  Thr  Arg  Asp  Pro  Cys  Phe  Gly
 65                        70                        75
```

<210> SEQ ID NO 6
<211> LENGTH: 88
<212> TYPE: PRT
<213> ORGANISM: Homo sapiens
<220> FEATURE:
<221> NAME/KEY: misc_feature
<223> OTHER INFORMATION: Incyte Clone No: 924925

<400> SEQUENCE: 6

```
Met Trp Pro Ser Gln Val Pro Leu Leu Ala Phe Cys Phe Leu Leu Val
1               5                   10                  15

Lys Ser Thr Ser Asn Ile Asn Leu Pro Thr Pro Pro Ser Ser Leu
                20                  25                  30

Glu Asn Ser Ser Phe Val Val Ser Gln Arg Gly Asn Leu Ile Val Phe
            35                  40                  45

Gly Gly Gln Lys Lys Ala Thr Phe Arg Tyr His Phe Tyr Leu Asp Arg
        50                  55                  60

Met Pro Phe Tyr Ser Gln Ile Ser Val Tyr Phe Val Asn Gly Phe Arg
65                  70                  75                  80

Val Asn Gly Tyr Leu Cys Asn Asn
                85
```

<210> SEQ ID NO 7
<211> LENGTH: 227
<212> TYPE: PRT
<213> ORGANISM: Homo sapiens
<220> FEATURE:
<221> NAME/KEY: misc_feature
<223> OTHER INFORMATION: Incyte Clone No: 962390

<400> SEQUENCE: 7

```
Met Gly Arg Pro Leu Leu Pro Leu Leu Leu Leu Gln Pro Pro
1               5                   10                  15

Ala Phe Leu Gln Pro Gly Gly Ser Thr Gly Ser Gly Pro Ser Tyr Leu
                20                  25                  30

Tyr Gly Val Thr Gln Pro Lys His Leu Ser Ala Ser Met Gly Gly Ser
            35                  40                  45

Val Glu Ile Pro Phe Ser Phe Tyr Tyr Pro Trp Glu Leu Ala Ile Val
50                  55                  60

Pro Asn Val Arg Ile Ser Trp Arg Arg Gly His Phe His Gly Gln Ser
65                  70                  75                  80

Phe Tyr Ser Thr Arg Pro Pro Ser Ile His Lys Asp Tyr Val Asn Arg
                85                  90                  95

Leu Phe Leu Asn Trp Thr Glu Gly Gln Glu Ser Gly Phe Leu Arg Ile
                100                 105                 110

Ser Asn Leu Arg Lys Glu Asp Gln Ser Val Tyr Phe Cys Arg Val Glu
            115                 120                 125

Leu Asp Thr Arg Arg Ser Gly Arg Gln Gln Leu Gln Ser Ile Lys Gly
        130                 135                 140

Thr Lys Leu Thr Ile Thr Gln Ala Val Thr Thr Thr Thr Thr Trp Arg
145                 150                 155                 160

Pro Ser Ser Thr Thr Thr Ile Ala Gly Leu Arg Val Thr Glu Ser Lys
                165                 170                 175

Gly His Ser Glu Ser Trp His Leu Ser Leu Asp Thr Ala Ile Arg Val
                180                 185                 190

Ala Leu Ala Val Ala Val Leu Lys Thr Val Ile Leu Gly Leu Leu Cys
            195                 200                 205

Leu Leu Leu Leu Trp Trp Arg Arg Arg Lys Gly Ser Arg Ala Pro Ser
        210                 215                 220

Ser Asp Phe
225
```

<210> SEQ ID NO 8
<211> LENGTH: 198
<212> TYPE: PRT
<213> ORGANISM: Homo sapiens
<220> FEATURE:

```
<221> NAME/KEY: misc_feature
<223> OTHER INFORMATION: Incyte Clone No: 1259405

<400> SEQUENCE: 8

Met Ala Thr Leu Trp Gly Gly Leu Leu Arg Leu Gly Ser Leu Leu Ser
1               5                   10                  15

Leu Ser Cys Leu Ala Leu Ser Val Leu Leu Ala Gln Leu Ser Asp
            20                  25                  30

Ala Ala Lys Asn Phe Glu Asp Val Arg Cys Lys Cys Ile Cys Pro Pro
            35                  40                  45

Tyr Lys Glu Asn Ser Gly His Ile Tyr Asn Lys Asn Ile Ser Gln Lys
    50                  55                  60

Asp Cys Asp Cys Leu His Val Val Glu Pro Met Pro Val Arg Gly Pro
65                  70                  75                  80

Asp Val Glu Ala Tyr Cys Leu Arg Cys Glu Cys Lys Tyr Glu Glu Arg
                85                  90                  95

Ser Ser Val Thr Ile Lys Val Thr Ile Ile Tyr Leu Ser Ile Leu
            100                 105                 110

Gly Leu Leu Leu Leu Tyr Met Val Tyr Leu Thr Leu Val Glu Pro Ile
            115                 120                 125

Leu Lys Arg Arg Leu Phe Gly His Ala Gln Leu Ile Gln Ser Asp Asp
    130                 135                 140

Asp Ile Gly Asp His Gln Pro Phe Ala Asn Ala His Asp Val Leu Ala
145                 150                 155                 160

Arg Ser Arg Ser Arg Ala Asn Val Leu Asn Lys Val Glu Tyr Ala Gln
                165                 170                 175

Gln Arg Trp Lys Leu Gln Val Gln Glu Gln Arg Lys Ser Val Phe Asp
            180                 185                 190

Arg His Val Val Leu Ser
            195

<210> SEQ ID NO 9
<211> LENGTH: 65
<212> TYPE: PRT
<213> ORGANISM: Homo sapiens
<220> FEATURE:
<221> NAME/KEY: misc_feature
<223> OTHER INFORMATION: Incyte Clone No: 1297384

<400> SEQUENCE: 9

Met Met Pro Arg Leu Leu Gly Leu Gly Gly Leu Phe Ser Phe Gly Gly
1               5                   10                  15

Leu Pro Leu Leu Leu Leu Phe Phe Gln Arg Ser Arg Ala Ser Leu Ala
            20                  25                  30

Ser Ser Ser Thr Gly Leu Trp Ile Asn Gln Leu Pro Lys Gly Cys Thr
            35                  40                  45

Cys Arg Val Val Trp Ala Cys Ile Pro Asp Val Leu Glu Tyr Ala Trp
    50                  55                  60

Met
65

<210> SEQ ID NO 10
<211> LENGTH: 154
<212> TYPE: PRT
<213> ORGANISM: Homo sapiens
<220> FEATURE:
<221> NAME/KEY: misc_feature
<223> OTHER INFORMATION: Incyte Clone No: 1299627

<400> SEQUENCE: 10
```

```
Met Asp Ala Pro Arg Leu Pro Val Arg Pro Gly Val Leu Leu Pro Lys
1               5                   10                  15

Leu Val Leu Leu Phe Val Tyr Ala Asp Asp Cys Leu Ala Gln Cys Gly
            20                  25                  30

Lys Asp Cys Lys Ser Tyr Cys Cys Asp Gly Thr Thr Pro Tyr Cys Cys
                35                  40                  45

Ser Tyr Tyr Ala Tyr Ile Gly Asn Ile Leu Ser Gly Thr Ala Ile Ala
        50                  55                  60

Gly Ile Val Phe Gly Ile Val Phe Ile Met Gly Val Ile Ala Gly Ile
65                  70                  75                  80

Ala Ile Cys Ile Cys Met Cys Met Lys Asn His Arg Ala Thr Arg Val
                85                  90                  95

Gly Ile Leu Arg Thr Thr His Ile Asn Thr Val Ser Ser Tyr Pro Gly
            100                 105                 110

Pro Pro Pro Tyr Gly His Asp His Glu Met Glu Tyr Cys Ala Asp Leu
        115                 120                 125

Pro Pro Pro Tyr Ser Pro Thr Pro Gln Gly Pro Ala Gln Arg Ser Pro
        130                 135                 140

Pro Pro Pro Tyr Pro Gly Asn Ala Arg Lys
145                 150

<210> SEQ ID NO 11
<211> LENGTH: 237
<212> TYPE: PRT
<213> ORGANISM: Homo sapiens
<220> FEATURE:
<221> NAME/KEY: misc_feature
<223> OTHER INFORMATION: Incyte Clone No: 1306026

<400> SEQUENCE: 11

Met Lys Pro Leu Val Leu Leu Ala Leu Leu Trp Pro Ser Ser
1               5                   10                  15

Val Pro Ala Tyr Pro Ser Ile Thr Val Thr Pro Asp Glu Glu Gln Asn
            20                  25                  30

Leu Asn His Tyr Ile Gln Val Leu Glu Asn Leu Val Arg Ser Val Pro
        35                  40                  45

Ser Gly Glu Pro Gly Arg Glu Lys Lys Ser Asn Ser Pro Lys His Val
    50                  55                  60

Tyr Ser Ile Ala Ser Lys Gly Ser Lys Phe Lys Glu Leu Val Thr His
65                  70                  75                  80

Gly Asp Ala Ser Thr Glu Asn Asp Val Leu Thr Asn Pro Ile Ser Glu
                85                  90                  95

Glu Thr Thr Thr Phe Pro Thr Gly Gly Phe Thr Pro Gly Ile Gly Lys
            100                 105                 110

Lys Lys His Thr Glu Ser Thr Pro Phe Trp Ser Ile Lys Pro Asn Asn
        115                 120                 125

Val Ser Ile Val Leu His Ala Glu Glu Pro Tyr Ile Glu Asn Glu Glu
    130                 135                 140

Pro Glu Pro Glu Pro Glu Pro Ala Ala Lys Gln Thr Glu Ala Pro Arg
145                 150                 155                 160

Met Leu Pro Val Val Thr Glu Ser Ser Thr Ser Pro Tyr Val Thr Ser
            165                 170                 175

Tyr Lys Ser Pro Val Thr Thr Leu Asp Lys Ser Thr Gly Ile Glu Ile
        180                 185                 190

Ser Thr Glu Ser Glu Asp Val Pro Gln Leu Ser Gly Gly Thr Ala Ile
    195                 200                 205
```

```
Glu Lys Pro Glu Ser Trp Lys His Gln Arg Val Gly Tyr Asp Ala Phe
    210                 215                 220
Glu Lys Asn Leu Val Leu Ile Thr Met His Arg His Phe
225                 230                 235
```

<210> SEQ ID NO 12
<211> LENGTH: 225
<212> TYPE: PRT
<213> ORGANISM: Homo sapiens
<220> FEATURE:
<221> NAME/KEY: misc_feature
<223> OTHER INFORMATION: Incyte Clone No: 1316219

<400> SEQUENCE: 12

```
Met Thr Pro Glu Gly Val Gly Leu Thr Thr Ala Leu Arg Val Leu Cys
1               5                   10                  15
Asn Val Ala Cys Pro Pro Pro Val Glu Gly Gln Gln Lys Asp Leu
            20                  25                  30
Lys Trp Asn Leu Ala Val Ile Gln Leu Phe Ser Ala Glu Gly Met Asp
        35                  40                  45
Thr Phe Ile Arg Val Leu Gln Lys Leu Asn Ser Ile Leu Thr Gln Pro
    50                  55                  60
Trp Arg Leu His Val Asn Met Gly Thr Thr Leu His Arg Val Thr Thr
65                  70                  75                  80
Ile Ser Met Ala Arg Cys Thr Leu Thr Leu Leu Lys Thr Met Leu Thr
                85                  90                  95
Glu Leu Leu Arg Gly Gly Ser Phe Glu Phe Lys Asp Met Arg Val Pro
            100                 105                 110
Ser Ala Leu Val Thr Leu His Met Leu Leu Cys Ser Ile Pro Leu Ser
        115                 120                 125
Gly Arg Leu Asp Ser Asp Glu Gln Lys Ile Gln Asn Asp Ile Ile Asp
    130                 135                 140
Ile Leu Leu Thr Phe Thr Gln Gly Val Asn Glu Lys Leu Thr Ile Ser
145                 150                 155                 160
Glu Glu Thr Leu Ala Asn Asn Thr Trp Ser Leu Met Leu Lys Glu Val
                165                 170                 175
Leu Ser Ser Ile Leu Lys Val Pro Glu Gly Phe Phe Ser Gly Leu Ile
            180                 185                 190
Leu Leu Ser Glu Leu Leu Pro Leu Pro Leu Pro Met Gln Thr Thr Gln
        195                 200                 205
Val Ser Leu Pro Tyr Asn Met His Leu Ile Asn Asp Cys Ser Asn Thr
    210                 215                 220
Phe
225
```

<210> SEQ ID NO 13
<211> LENGTH: 117
<212> TYPE: PRT
<213> ORGANISM: Homo sapiens
<220> FEATURE:
<221> NAME/KEY: misc_feature
<223> OTHER INFORMATION: Incyte Clone No: 1329031

<400> SEQUENCE: 13

```
Met Pro Ser Pro Gly Thr Val Cys Ser Leu Leu Leu Gly Met Leu
1               5                   10                  15
Trp Leu Asp Leu Ala Met Ala Gly Ser Ser Phe Leu Ser Pro Glu His
            20                  25                  30
```

```
Gln Arg Val Gln Gln Arg Lys Glu Ser Lys Lys Pro Pro Ala Lys Leu
             35                  40                  45

Gln Pro Arg Ala Leu Ala Gly Trp Leu Arg Pro Glu Asp Gly Gly Gln
         50                  55                  60

Ala Glu Gly Ala Glu Asp Glu Leu Glu Val Arg Phe Asn Ala Pro Phe
 65                  70                  75                  80

Asp Val Gly Ile Lys Leu Ser Gly Val Gln Tyr Gln Gln His Ser Gln
                 85                  90                  95

Ala Leu Gly Lys Phe Leu Gln Asp Ile Leu Trp Glu Ala Lys Glu
                100                 105                 110

Ala Pro Ala Asp Lys
            115

<210> SEQ ID NO 14
<211> LENGTH: 253
<212> TYPE: PRT
<213> ORGANISM: Homo sapiens
<220> FEATURE:
<221> NAME/KEY: misc_feature
<223> OTHER INFORMATION: Incyte Clone No: 1483050

<400> SEQUENCE: 14

Met Asp Asn Arg Phe Ala Thr Ala Phe Val Ile Ala Cys Val Leu Ser
 1               5                  10                  15

Leu Ile Ser Thr Ile Tyr Met Ala Ala Ser Ile Gly Thr Asp Phe Trp
                 20                  25                  30

Tyr Glu Tyr Arg Ser Pro Val Gln Glu Asn Ser Ser Asp Leu Asn Lys
             35                  40                  45

Ser Ile Trp Asp Glu Phe Ile Ser Asp Glu Ala Asp Glu Lys Thr Tyr
         50                  55                  60

Asn Asp Ala Leu Phe Arg Tyr Asn Gly Thr Val Gly Leu Trp Arg Arg
 65                  70                  75                  80

Cys Ile Thr Ile Pro Lys Asn Met His Trp Tyr Ser Pro Pro Glu Arg
                 85                  90                  95

Thr Glu Ser Phe Asp Val Val Thr Lys Cys Val Ser Phe Thr Leu Thr
            100                 105                 110

Glu Gln Phe Met Glu Lys Phe Val Asp Pro Gly Asn His Asn Ser Gly
            115                 120                 125

Ile Asp Leu Leu Arg Thr Tyr Leu Trp Arg Cys Gln Phe Leu Leu Pro
130                 135                 140

Phe Val Ser Leu Gly Leu Met Cys Phe Gly Ala Leu Ile Gly Leu Cys
145                 150                 155                 160

Ala Cys Ile Cys Arg Ser Leu Tyr Pro Thr Ile Ala Thr Gly Ile Leu
                165                 170                 175

His Leu Leu Ala Gly Leu Cys Thr Leu Gly Ser Val Ser Cys Tyr Val
            180                 185                 190

Ala Gly Ile Glu Leu Leu His Gln Lys Leu Glu Leu Pro Asp Asn Val
            195                 200                 205

Ser Gly Glu Phe Gly Trp Ser Phe Cys Leu Ala Cys Val Ser Ala Pro
210                 215                 220

Leu Gln Phe Met Ala Ser Ala Leu Phe Ile Trp Ala Ala His Thr Asn
225                 230                 235                 240

Arg Lys Glu Tyr Thr Leu Met Lys Ala Tyr Arg Val Ala
                245                 250

<210> SEQ ID NO 15
<211> LENGTH: 171
```

```
<212> TYPE: PRT
<213> ORGANISM: Homo sapiens
<220> FEATURE:
<221> NAME/KEY: misc_feature
<223> OTHER INFORMATION: Incyte Clone No: 1514160

<400> SEQUENCE: 15

Met Ser Leu Pro Ile Pro Trp Leu Ser Leu Pro Cys Pro Ile Leu
1               5                   10                  15

Gly Gln Pro Ala Gly Leu Leu Trp Leu Phe Arg Pro Phe Ser Gln
                20                  25                  30

Cys Cys Gln Cys Pro Trp Glu Gly Arg Ala Ser Leu Arg His Pro Asn
                35                  40                      45

Gly Pro Ser Gly Cys Arg Glu Ala Glu Ala Trp Pro Gln Arg Ser Leu
        50                  55                      60

Leu Arg Gln Gln Leu Gln Gln Ala His Pro Leu Pro Thr Leu Pro Thr
65                  70                      75                  80

Pro Glu Arg Leu Pro Glu Gln Met Leu Phe Pro Ser Ser Ser Ser Lys
                85                      90                  95

Pro Phe Ser Leu Leu Ser Leu Thr Ile Trp Ala Arg Leu Val Gly Arg
                100                     105                 110

Leu Thr Asn Arg Ile Cys Pro Val Pro Pro Gly Ser Val Ala Ser Ser
            115                 120                 125

Met Ser Leu Gln Ala Gly Arg Cys Gly Asn Pro Val Val Leu Pro Gln
    130                 135                 140

Pro Met Pro Pro Gly Leu Leu Cys Met Asn Glu Cys Ser Leu Val Pro
145                 150                 155                 160

Gly Leu Gly Arg Gly Gln Val Asn Ser Arg Val
                165                 170

<210> SEQ ID NO 16
<211> LENGTH: 78
<212> TYPE: PRT
<213> ORGANISM: Homo sapiens
<220> FEATURE:
<221> NAME/KEY: misc_feature
<223> OTHER INFORMATION: Incyte Clone No: 1603403

<400> SEQUENCE: 16

Met Gly Ser Gly Leu Pro Leu Val Leu Leu Thr Leu Leu Gly Ser
1               5                   10                  15

Ser His Gly Thr Gly Pro Gly Met Thr Leu Gln Leu Lys Leu Lys Glu
                20                  25                      30

Ser Phe Leu Thr Asn Ser Ser Tyr Glu Ser Ser Phe Leu Glu Leu Leu
            35                  40                      45

Glu Lys Leu Cys Leu Leu Leu His Leu Pro Ser Gly Thr Ser Val Thr
    50                  55                      60

Leu His His Ala Arg Ser Gln His His Val Val Cys Asn Thr
65                  70                      75

<210> SEQ ID NO 17
<211> LENGTH: 71
<212> TYPE: PRT
<213> ORGANISM: Homo sapiens
<220> FEATURE:
<221> NAME/KEY: misc_feature
<223> OTHER INFORMATION: Incyte Clone No: 1652303

<400> SEQUENCE: 17

Met Lys Leu Leu Ser Cys Leu Leu Phe Leu Lys Ala Pro Leu Tyr Pro
1               5                   10                      15
```

-continued

Thr Leu Cys Ser Lys Asp Pro Arg Ala Gly His Ser Leu Ile Cys Gly
              20                  25                  30

Gln Ala Gly Gln Ile Pro Glu Ala Gln Leu Gly Phe Ser Ser Asp Phe
          35                  40                  45

Lys Leu Cys Trp Cys Trp Asp Gln Gln Lys Ala Asn Val Gln Pro Thr
 50                  55                  60

His Arg Thr Val Arg Gly Leu
 65                  70

<210> SEQ ID NO 18
<211> LENGTH: 188
<212> TYPE: PRT
<213> ORGANISM: Homo sapiens
<220> FEATURE:
<221> NAME/KEY: misc_feature
<223> OTHER INFORMATION: Incyte Clone No: 1693358

<400> SEQUENCE: 18

Met Val Pro Gly Ala Ala Gly Trp Cys Cys Leu Val Leu Trp Leu Pro
 1               5                  10                  15

Ala Cys Val Ala Ala His Gly Phe Arg Ile His Asp Tyr Leu Tyr Phe
              20                  25                  30

Gln Val Leu Ser Pro Gly Asp Ile Arg Tyr Ile Phe Thr Ala Thr Pro
          35                  40                  45

Ala Lys Asp Phe Gly Gly Ile Phe His Thr Arg Tyr Glu Gln Ile His
 50                  55                  60

Leu Val Pro Ala Glu Pro Pro Glu Ala Cys Gly Glu Leu Ser Asn Gly
 65                  70                  75                  80

Phe Phe Ile Gln Asp Gln Ile Ala Leu Val Glu Arg Gly Gly Cys Ser
              85                  90                  95

Phe Leu Ser Lys Thr Arg Val Val Gln Glu His Gly Gly Arg Ala Val
             100                 105                 110

Ile Ile Ser Asp Asn Ala Val Asp Asn Asp Ser Phe Tyr Val Glu Met
             115                 120                 125

Ile Gln Asp Ser Thr Gln Arg Thr Ala Asp Ile Pro Ala Leu Phe Leu
         130                 135                 140

Leu Gly Arg Asp Gly Tyr Met Ile Arg Arg Ser Leu Glu Gln His Gly
145                 150                 155                 160

Leu Pro Trp Ala Ile Ile Ser Ile Pro Val Asn Val Thr Ser Ile Pro
             165                 170                 175

Thr Phe Glu Leu Leu Gln Pro Pro Trp Thr Phe Trp
             180                 185

<210> SEQ ID NO 19
<211> LENGTH: 80
<212> TYPE: PRT
<213> ORGANISM: Homo sapiens
<220> FEATURE:
<221> NAME/KEY: misc_feature
<223> OTHER INFORMATION: Incyte Clone No: 1707711

<400> SEQUENCE: 19

Met Lys Ala Gln Pro Leu Glu Ala Leu Leu Val Ala Leu Val Leu
 1               5                  10                  15

Ser Phe Cys Gly Val Trp Phe Glu Asp Trp Leu Ser Lys Trp Arg Phe
              20                  25                  30

Gln Cys Ile Phe Gln Leu Ala His Gln Pro Ala Leu Val Asn Ile Gln
          35                  40                  45

```
Phe Arg Gly Thr Val Leu Gly Ser Glu Thr Phe Leu Gly Ala Glu Glu
            50                  55                  60

Asn Ser Ala Asp Val Arg Ser Trp Gln Thr Leu Ser Tyr Phe Glu Leu
 65                  70                  75                  80
```

```
<210> SEQ ID NO 20
<211> LENGTH: 80
<212> TYPE: PRT
<213> ORGANISM: Homo sapiens
<220> FEATURE:
<221> NAME/KEY: misc_feature
<223> OTHER INFORMATION: Incyte Clone No: 1738735

<400> SEQUENCE: 20

Met Ile Asp Leu Trp Leu Pro Ala Leu Phe Val Leu Val Ala Leu Glu
 1               5                  10                  15

Ser Leu Leu Leu Ser Pro Cys Pro Gly Thr Ser Ser Leu Thr Thr Arg
                20                  25                  30

Thr Phe Phe Pro Ser Leu Val Ser Cys Val Gln Val Pro Phe Ser Trp
            35                  40                  45

Ile Pro Cys Leu Glu Cys Phe Leu Ile Tyr Phe Leu Ile Leu Ala Glu
 50                  55                  60

Asp Val Leu Gln Leu Phe Ser Gly Asn Ala Asn Met Gln Val Asn Gln
 65                  70                  75                  80
```

```
<210> SEQ ID NO 21
<211> LENGTH: 84
<212> TYPE: PRT
<213> ORGANISM: Homo sapiens
<220> FEATURE:
<221> NAME/KEY: misc_feature
<223> OTHER INFORMATION: Incyte Clone No: 1749147

<400> SEQUENCE: 21

Met Gln Arg Pro Phe Leu Ser Val Pro Cys Leu Leu Leu Pro Ala
 1               5                  10                  15

Arg Val Val Trp Gly Cys Trp Cys Phe Leu Pro Gly Glu Asp Gly Gly
                20                  25                  30

Gly Cys Pro Thr Pro Ser Ser Gly Arg Ile Lys Leu Leu Gln Gln Cys
            35                  40                  45

Leu Leu His Pro Ser Leu Arg Ser Ile Thr Val Ser Arg Arg Ser Ala
 50                  55                  60

Gln Leu Leu Cys Arg Leu Lys Leu Gln Asn His Ile Pro Lys Val Pro
 65                  70                  75                  80

Gly Lys Asn Val
```

```
<210> SEQ ID NO 22
<211> LENGTH: 171
<212> TYPE: PRT
<213> ORGANISM: Homo sapiens
<220> FEATURE:
<221> NAME/KEY: misc_feature
<223> OTHER INFORMATION: Incyte Clone No: 1817722

<400> SEQUENCE: 22

Met His Met Ile Leu Lys Val Leu Thr Thr Ala Leu Leu Gln Ala
 1               5                  10                  15

Ala Ser Ala Leu Ala Asn Tyr Ile His Phe Ser Ser Tyr Ser Lys Asp
                20                  25                  30

Gly Ile Gly Val Pro Phe Met Gly Ser Leu Ala Glu Phe Phe Asp Ile
            35                  40                  45
```

```
Ala Ser Gln Ile Gln Met Leu Tyr Leu Leu Ser Leu Cys Met Gly
         50                  55                  60

Trp Thr Ile Val Arg Met Lys Lys Ser Gln Ser Arg Pro Leu Gln Trp
 65                  70                  75                  80

Asp Ser Thr Pro Ala Ser Thr Gly Ile Ala Val Phe Ile Val Met Thr
                 85                  90                  95

Gln Ser Val Leu Leu Leu Trp Glu Gln Phe Glu Asp Ile Ser His His
                100                 105                 110

Ser Tyr His Ser His His Asn Leu Ala Gly Ile Leu Leu Ile Val Leu
            115                 120                 125

Arg Ile Cys Leu Ala Leu Ser Leu Gly Cys Gly Leu Tyr Gln Ile Ile
        130                 135                 140

Thr Val Glu Arg Ser Thr Leu Lys Arg Glu Phe Tyr Ile Thr Phe Ala
145                 150                 155                 160

Lys Val Trp Val Trp Lys Glu Asn Gly Leu Phe
                165                 170
```

<210> SEQ ID NO 23
<211> LENGTH: 243
<212> TYPE: PRT
<213> ORGANISM: Homo sapiens
<220> FEATURE:
<221> NAME/KEY: misc_feature
<223> OTHER INFORMATION: Incyte Clone No: 1831290

<400> SEQUENCE: 23

```
Met Ser Ser Gly Thr Glu Leu Leu Trp Pro Gly Ala Ala Leu Leu Val
  1               5                  10                  15

Leu Leu Gly Val Ala Ala Ser Leu Cys Val Arg Cys Ser Arg Pro Gly
                 20                  25                  30

Ala Lys Arg Ser Glu Lys Ile Tyr Gln Gln Arg Ser Leu Arg Glu Asp
             35                  40                  45

Gln Gln Ser Phe Thr Gly Ser Arg Thr Tyr Ser Leu Val Gly Gln Ala
         50                  55                  60

Trp Pro Gly Pro Leu Ala Asp Met Ala Pro Thr Arg Lys Asp Lys Leu
 65                  70                  75                  80

Leu Gln Phe Tyr Pro Ser Leu Glu Asp Pro Ala Ser Ser Arg Tyr Gln
                 85                  90                  95

Asn Phe Ser Lys Gly Ser Arg His Gly Ser Glu Ala Tyr Ile Asp
            100                 105                 110

Pro Ile Ala Met Glu Tyr Tyr Asn Trp Gly Arg Phe Ser Lys Pro Pro
        115                 120                 125

Glu Asp Asp Asp Ala Asn Ser Tyr Glu Asn Val Leu Ile Cys Lys Gln
130                 135                 140

Lys Thr Thr Glu Thr Gly Ala Gln Gln Glu Gly Ile Gly Gly Leu Cys
145                 150                 155                 160

Arg Gly Asp Leu Ser Leu Ser Leu Ala Leu Lys Thr Gly Pro Thr Ser
                165                 170                 175

Gly Leu Cys Pro Ser Ala Ser Pro Glu Glu Asp Glu Glu Ser Glu Asp
            180                 185                 190

Tyr Gln Asn Ser Ala Ser Ile His Gln Trp Arg Glu Ser Arg Lys Val
        195                 200                 205

Met Gly Gln Leu Gln Arg Glu Ala Ser Pro Gly Pro Val Gly Ser Pro
210                 215                 220

Asp Glu Glu Asp Gly Glu Pro Asp Tyr Val Asn Gly Glu Val Ala Ala
225                 230                 235                 240
```

Thr Glu Ala

<210> SEQ ID NO 24
<211> LENGTH: 311
<212> TYPE: PRT
<213> ORGANISM: Homo sapiens
<220> FEATURE:
<221> NAME/KEY: misc_feature
<223> OTHER INFORMATION: Incyte Clone No: 1831477

<400> SEQUENCE: 24

Met Gly Val Pro Thr Ala Pro Glu Ala Gly Ser Trp Arg Trp Gly Ser
1               5                   10                  15

Leu Leu Phe Ala Leu Phe Leu Ala Ala Ser Leu Gly Pro Val Ala Ala
                20                  25                  30

Phe Lys Val Ala Thr Pro Tyr Ser Leu Tyr Val Cys Pro Glu Gly Gln
            35                  40                  45

Asn Val Thr Leu Thr Cys Arg Leu Leu Gly Pro Val Asp Lys Gly His
    50                  55                  60

Asp Val Thr Phe Tyr Lys Thr Trp Tyr Arg Ser Ser Arg Gly Glu Val
65                  70                  75                  80

Gln Thr Cys Ser Glu Arg Arg Pro Ile Arg Asn Leu Thr Phe Gln Asp
                85                  90                  95

Leu His Leu His His Gly Gly His Gln Ala Ala Asn Thr Ser His Asp
            100                 105                 110

Leu Ala Gln Arg His Gly Leu Glu Ser Ala Ser Asp His His Gly Asn
        115                 120                 125

Phe Ser Ile Thr Met Arg Asn Leu Thr Leu Leu Asp Ser Gly Leu Tyr
    130                 135                 140

Cys Cys Leu Val Val Glu Ile Arg His His Ser Glu His Arg Val
145                 150                 155                 160

His Gly Ala Met Glu Leu Gln Val Gln Thr Gly Lys Asp Ala Pro Ser
                165                 170                 175

Asn Cys Val Val Tyr Pro Ser Ser Ser Gln Glu Ser Glu Asn Ile Thr
            180                 185                 190

Ala Ala Ala Leu Ala Thr Gly Ala Cys Ile Val Gly Ile Leu Cys Leu
        195                 200                 205

Pro Leu Ile Leu Leu Leu Val Tyr Lys Gln Arg Gln Ala Ala Ser Asn
    210                 215                 220

Arg Arg Ala Gln Glu Leu Val Arg Met Asp Ser Asn Ile Gln Gly Ile
225                 230                 235                 240

Glu Asn Pro Gly Phe Glu Ala Ser Pro Pro Ala Gln Gly Ile Pro Glu
                245                 250                 255

Ala Lys Val Arg His Pro Leu Ser Tyr Val Ala Gln Arg Gln Pro Ser
            260                 265                 270

Glu Ser Gly Arg His Leu Leu Ser Glu Pro Ser Thr Pro Leu Ser Pro
        275                 280                 285

Pro Gly Pro Gly Asp Val Phe Phe Pro Ser Leu Asp Pro Val Pro Asp
    290                 295                 300

Ser Pro Asn Phe Glu Val Ile
305                 310

<210> SEQ ID NO 25
<211> LENGTH: 57
<212> TYPE: PRT
<213> ORGANISM: Homo sapiens
<220> FEATURE:
<221> NAME/KEY: misc_feature
<223> OTHER INFORMATION: Incyte Clone No: 1841607

<400> SEQUENCE: 25

Met Ala Ser Ser Cys Phe Ser Leu Ser Phe Pro Pro Leu Ser Leu Ala
1               5                   10                  15

Gly Ser Leu Ala Leu Trp Gly His Cys Cys Val Arg Leu Gly Cys Ser
            20                  25                  30

Phe Trp Ser Val Ser Ala Met Ala Gln Arg Leu Pro Ser Gln Asn Thr
        35                  40                  45

Tyr Asn Pro Pro Leu Cys Trp Ala Trp
    50                  55

<210> SEQ ID NO 26
<211> LENGTH: 82
<212> TYPE: PRT
<213> ORGANISM: Homo sapiens
<220> FEATURE:
<221> NAME/KEY: misc_feature
<223> OTHER INFORMATION: Incyte Clone No: 1852391

<400> SEQUENCE: 26

Met Phe Ser Leu Phe Ser Cys Leu Leu Ala Cys Leu Leu Asp Leu Leu
1               5                   10                  15

Leu Ser Arg Val Ala Asp Glu Ala Phe Tyr Lys Gln Pro Phe Ala Asp
            20                  25                  30

Val Ile Gly Tyr Val Tyr Val Ala Lys Leu Ile Pro Phe Ser Thr Ser
        35                  40                  45

Asp Ser Phe Tyr Phe Cys Leu Glu Leu Met Leu Leu Cys His Gln
    50                  55                  60

Leu Leu Cys Phe Leu Asn Tyr Phe Lys Leu Ala Leu Trp Gly Leu Pro
65                  70                  75                  80

Lys Asn

<210> SEQ ID NO 27
<211> LENGTH: 115
<212> TYPE: PRT
<213> ORGANISM: Homo sapiens
<220> FEATURE:
<221> NAME/KEY: misc_feature
<223> OTHER INFORMATION: Incyte Clone No: 1854555

<400> SEQUENCE: 27

Met Ala Gly Thr Val Leu Gly Val Gly Ala Gly Val Phe Ile Leu Ala
1               5                   10                  15

Leu Leu Trp Val Ala Val Leu Leu Cys Val Leu Leu Ser Arg Ala
            20                  25                  30

Ser Gly Ala Ala Arg Phe Ser Val Ile Phe Leu Phe Gly Ala Val
        35                  40                  45

Ile Ile Thr Ser Val Leu Leu Leu Phe Pro Arg Ala Gly Glu Phe Pro
    50                  55                  60

Ala Pro Glu Val Glu Val Lys Ile Val Asp Asp Phe Ile Gly Arg
65                  70                  75                  80

Tyr Val Leu Leu Ala Phe Leu Ser Ala Ile Phe Leu Gly Gly Leu Phe
            85                  90                  95

Leu Val Leu Ile His Tyr Val Leu Glu Pro Ile Tyr Ala Lys Pro Leu
            100                 105                 110

His Ser Tyr
        115

```
<210> SEQ ID NO 28
<211> LENGTH: 327
<212> TYPE: PRT
<213> ORGANISM: Homo sapiens
<220> FEATURE:
<221> NAME/KEY: misc_feature
<223> OTHER INFORMATION: Incyte Clone No: 1855755

<400> SEQUENCE: 28

Met Ala Glu Leu Pro Gly Pro Phe Leu Cys Gly Ala Leu Leu Phe
 1               5                  10                  15

Leu Cys Leu Ser Gly Leu Ala Val Glu Val Lys Val Pro Thr Glu Pro
                 20                  25                  30

Leu Ser Thr Pro Leu Gly Lys Thr Ala Glu Leu Thr Cys Thr Tyr Ser
             35                  40                  45

Thr Ser Val Gly Asp Ser Phe Ala Leu Glu Trp Ser Phe Val Gln Pro
 50                  55                  60

Gly Lys Pro Ile Ser Glu Ser His Pro Ile Leu Tyr Phe Thr Asn Gly
 65                  70                  75                  80

His Leu Tyr Pro Thr Gly Ser Lys Ser Lys Arg Val Ser Leu Leu Gln
                 85                  90                  95

Asn Pro Pro Thr Val Gly Val Ala Thr Leu Lys Leu Thr Asp Val His
                100                 105                 110

Pro Ser Asp Thr Gly Thr Tyr Leu Cys Gln Val Asn Asn Pro Pro Asp
             115                 120                 125

Phe Tyr Thr Asn Gly Leu Gly Leu Ile Asn Leu Thr Val Leu Val Pro
130                 135                 140

Pro Ser Asn Pro Leu Cys Ser Gln Ser Gly Gln Thr Ser Val Gly Gly
145                 150                 155                 160

Ser Thr Ala Leu Arg Cys Ser Ser Glu Gly Ala Pro Lys Pro Val
                165                 170                 175

Tyr Asn Trp Val Arg Leu Gly Thr Phe Pro Thr Pro Ser Pro Gly Ser
                180                 185                 190

Met Val Gln Asp Glu Val Ser Gly Gln Leu Ile Leu Thr Asn Leu Ser
            195                 200                 205

Leu Thr Ser Ser Gly Thr Tyr Arg Cys Val Ala Thr Asn Gln Met Gly
    210                 215                 220

Ser Ala Ser Cys Glu Leu Thr Leu Ser Val Thr Glu Pro Ser Gln Gly
225                 230                 235                 240

Arg Val Ala Gly Ala Leu Ile Gly Val Leu Leu Gly Val Leu Leu Leu
                245                 250                 255

Ser Val Ala Ala Phe Cys Leu Val Arg Phe Gln Lys Glu Arg Gly Lys
            260                 265                 270

Lys Pro Lys Glu Thr Tyr Gly Gly Ser Asp Leu Arg Glu Asp Ala Ile
    275                 280                 285

Ala Pro Gly Ile Ser Glu His Thr Cys Met Arg Ala Asp Ser Ser Lys
290                 295                 300

Gly Phe Leu Glu Arg Pro Ser Ser Ala Ser Thr Val Thr Thr Thr Lys
305                 310                 315                 320

Ser Lys Leu Pro Met Val Val
                325

<210> SEQ ID NO 29
<211> LENGTH: 133
<212> TYPE: PRT
<213> ORGANISM: Homo sapiens
<220> FEATURE:
<221> NAME/KEY: misc_feature
```

-continued

<223> OTHER INFORMATION: Incyte Clone No: 1861434

<400> SEQUENCE: 29

Met Arg Met Ser Leu Ala Gln Arg Val Leu Leu Thr Trp Leu Phe Thr
1               5                   10                  15

Leu Leu Phe Leu Ile Met Leu Val Leu Lys Leu Asp Glu Lys Ala Pro
            20                  25                  30

Trp Asn Trp Phe Leu Ile Phe Ile Pro Val Trp Ile Phe Asp Thr Ile
        35                  40                  45

Leu Leu Val Leu Leu Ile Val Lys Met Ala Gly Arg Cys Lys Ser Gly
    50                  55                  60

Phe Asp Pro Arg His Gly Ser His Asn Ile Lys Lys Ala Trp Tyr
65                  70                  75                  80

Leu Ile Ala Met Leu Leu Lys Leu Ala Phe Cys Leu Ala Leu Cys Ala
                85                  90                  95

Lys Leu Glu Gln Phe Thr Thr Met Asn Leu Ser Tyr Val Phe Ile Pro
            100                 105                 110

Leu Trp Ala Leu Leu Ala Gly Ala Leu Thr Glu Leu Gly Tyr Asn Val
        115                 120                 125

Phe Phe Val Arg Asp
    130

<210> SEQ ID NO 30
<211> LENGTH: 129
<212> TYPE: PRT
<213> ORGANISM: Homo sapiens
<220> FEATURE:
<221> NAME/KEY: misc_feature
<223> OTHER INFORMATION: Incyte Clone No: 1872334

<400> SEQUENCE: 30

Met Gly Leu Thr Leu Leu Leu Leu Leu Gly Leu Glu Gly Gln
1               5                   10                  15

Gly Ile Val Gly Ser Leu Pro Glu Val Leu Gln Ala Pro Val Gly Ser
            20                  25                  30

Ser Ile Leu Val Gln Cys His Tyr Arg Leu Gln Asp Val Lys Ala Gln
        35                  40                  45

Lys Val Trp Cys Arg Phe Leu Pro Glu Gly Cys Gln Pro Leu Val Ser
    50                  55                  60

Ser Ala Val Asp Arg Arg Ala Pro Ala Gly Arg Arg Thr Phe Leu Thr
65                  70                  75                  80

Asp Leu Gly Gly Gly Leu Leu Gln Val Glu Met Val Thr Leu Gln Glu
                85                  90                  95

Glu Asp Ala Gly Glu Tyr Gly Cys Met Val Asp Gly Ala Arg Gly Pro
            100                 105                 110

Gln Ile Leu His Arg Val Ser Leu Asn Ile Leu Pro Pro Gly Glu Leu
        115                 120                 125

Ser

<210> SEQ ID NO 31
<211> LENGTH: 472
<212> TYPE: PRT
<213> ORGANISM: Homo sapiens
<220> FEATURE:
<221> NAME/KEY: misc_feature
<223> OTHER INFORMATION: Incyte Clone No: 1877230

<400> SEQUENCE: 31

Met Lys Phe Leu Ile Phe Ala Phe Phe Gly Gly Val His Leu Leu Ser

-continued

```
1               5               10              15
Leu Cys Ser Gly Lys Ala Ile Cys Lys Asn Gly Ile Ser Lys Arg Thr
                20              25              30

Phe Glu Glu Ile Lys Glu Ile Ala Ser Cys Gly Asp Val Ala Lys
                35              40              45

Ala Ile Ile Asn Leu Ala Val Tyr Gly Lys Ala Gln Asn Arg Ser Tyr
50              55              60

Glu Arg Leu Ala Leu Leu Val Asp Thr Val Gly Pro Arg Leu Ser Gly
65              70              75              80

Ser Lys Asn Leu Glu Lys Ala Ile Gln Ile Met Tyr Gln Asn Leu Gln
                85              90              95

Gln Asp Gly Leu Glu Lys Val His Leu Glu Pro Val Arg Ile Pro His
                100             105             110

Trp Glu Arg Gly Glu Ser Ala Val Met Leu Glu Pro Arg Ile His
                115             120             125

Lys Ile Ala Ile Leu Gly Leu Gly Ser Ser Ile Gly Thr Pro Pro Glu
                130             135             140

Gly Ile Thr Ala Glu Val Leu Val Val Thr Ser Phe Asp Glu Leu Gln
145             150             155             160

Arg Arg Ala Ser Glu Ala Arg Gly Lys Ile Val Val Tyr Asn Gln Pro
                165             170             175

Tyr Ile Asn Tyr Ser Arg Thr Val Gln Tyr Arg Thr Gln Gly Ala Val
                180             185             190

Glu Ala Ala Lys Val Gly Ala Leu Ala Ser Leu Ile Arg Ser Val Ala
                195             200             205

Ser Phe Ser Ile Tyr Ser Pro His Thr Gly Ile Gln Glu Tyr Gln Asp
                210             215             220

Gly Val Pro Lys Ile Pro Thr Ala Cys Ile Thr Val Glu Asp Ala Glu
225             230             235             240

Met Met Ser Arg Met Ala Ser His Gly Ile Lys Ile Val Ile Gln Leu
                245             250             255

Lys Met Gly Ala Lys Thr Tyr Pro Asp Thr Asp Ser Phe Asn Thr Val
                260             265             270

Ala Glu Ile Thr Gly Ser Lys Tyr Pro Glu Gln Val Val Leu Val Ser
                275             280             285

Gly His Leu Asp Ser Trp Asp Val Gly Gln Gly Ala Met Asp Asp Gly
                290             295             300

Gly Gly Ala Phe Ile Ser Trp Glu Ala Leu Ser Leu Ile Lys Asp Leu
305             310             315             320

Gly Leu Arg Pro Lys Arg Thr Leu Arg Leu Val Leu Trp Thr Ala Glu
                325             330             335

Glu Gln Gly Gly Val Gly Ala Phe Gln Tyr Tyr Gln Leu His Lys Val
                340             345             350

Asn Ile Ser Asn Tyr Ser Leu Val Met Glu Ser Asp Ala Gly Thr Phe
                355             360             365

Leu Pro Thr Gly Leu Gln Phe Thr Gly Ser Glu Lys Ala Arg Ala Ile
                370             375             380

Met Glu Glu Val Met Ser Leu Leu Gln Pro Leu Asn Ile Thr Gln Val
385             390             395             400

Leu Ser His Gly Glu Gly Thr Asp Ile Asn Phe Trp Ile Gln Ala Gly
                405             410             415

Val Pro Gly Ala Ser Leu Leu Asp Leu Tyr Lys Tyr Phe Phe
                420             425             430
```

```
His His Ser His Gly Asp Thr Met Thr Val Met Asp Pro Lys Gln Met
            435                 440                 445

Asn Val Ala Ala Ala Val Trp Ala Val Val Ser Tyr Val Val Ala Asp
450                 455                 460

Met Glu Glu Met Leu Pro Arg Ser
465                 470

<210> SEQ ID NO 32
<211> LENGTH: 93
<212> TYPE: PRT
<213> ORGANISM: Homo sapiens
<220> FEATURE:
<221> NAME/KEY: misc_feature
<223> OTHER INFORMATION: Incyte Clone No: 1877885

<400> SEQUENCE: 32

Met Ile His Leu Gly His Ile Leu Phe Leu Leu Leu Leu Pro Val Ala
1               5                   10                  15

Ala Ala Gln Thr Thr Pro Gly Glu Arg Ser Ser Leu Pro Ala Phe Tyr
            20                  25                  30

Pro Gly Thr Ser Gly Ser Cys Ser Gly Cys Gly Ser Leu Ser Leu Pro
        35                  40                  45

Leu Leu Ala Gly Leu Val Ala Ala Asp Ala Val Ala Ser Leu Leu Ile
    50                  55                  60

Val Gly Ala Val Phe Leu Cys Ala Arg Pro Arg Arg Ser Pro Ala Gln
65                  70                  75                  80

Glu Asp Gly Lys Val Tyr Ile Asn Met Pro Gly Arg Gly
                85                  90

<210> SEQ ID NO 33
<211> LENGTH: 92
<212> TYPE: PRT
<213> ORGANISM: Homo sapiens
<220> FEATURE:
<221> NAME/KEY: misc_feature
<223> OTHER INFORMATION: Incyte Clone No: 1889269

<400> SEQUENCE: 33

Met Asn Arg Pro Ser Ala Arg Asn Ala Leu Gly Asn Val Phe Val Ser
1               5                   10                  15

Glu Leu Leu Glu Thr Leu Ala Gln Leu Arg Glu Asp Arg Gln Val Arg
            20                  25                  30

Val Leu Leu Phe Arg Ser Gly Val Lys Gly Val Phe Cys Ala Gly Ala
        35                  40                  45

Asp Leu Lys Glu Arg Glu Gln Met Ser Glu Ala Glu Val Gly Val Phe
    50                  55                  60

Val Gln Arg Leu Arg Gly Leu Met Asn Asp Ile Gly Glu Asp Leu Gly
65                  70                  75                  80

Val Gly Trp Arg Arg Gly Phe Gly Gly Pro Cys Arg
                85                  90

<210> SEQ ID NO 34
<211> LENGTH: 143
<212> TYPE: PRT
<213> ORGANISM: Homo sapiens
<220> FEATURE:
<221> NAME/KEY: misc_feature
<223> OTHER INFORMATION: Incyte Clone No: 1890243

<400> SEQUENCE: 34

Met Trp Ile Lys Gly Thr Met Lys Met Arg Gly Gly Lys Thr Ser Arg
1               5                   10                  15
```

```
Ser Ala Val Leu Pro Val Ala Gln Leu Thr Leu Ile Ala Ser Cys Phe
            20                  25                  30

Pro Asn Ser Gln Thr Val Leu Gly Thr Glu Gly Thr Leu Asp Val Glu
            35                  40                  45

Ser Ser Pro Leu Ala Leu Leu Thr Gly Leu Trp Ala Ser Pro Glu Ser
 50                  55                  60

Leu Ser Leu Tyr Leu Val Thr Leu Leu Cys Val Cys Pro Ala Leu Gln
 65                  70                  75                  80

Ser Cys Gln Gly Gln Gln Ala Asp Val Thr Leu Ala Pro Cys Glu Ile
                85                  90                  95

Phe Ile Pro Gln Thr Leu Ala Cys Glu Pro Phe Pro Ser Gln Trp Arg
            100                 105                 110

Ala Leu Lys Gly Ala Ser Leu Glu Ser Ser Ser Val Leu Trp Val Ala
            115                 120                 125

Pro Cys Arg Trp Pro Leu Thr Leu Arg Cys Ser Arg Val His Leu
            130                 135                 140

<210> SEQ ID NO 35
<211> LENGTH: 89
<212> TYPE: PRT
<213> ORGANISM: Homo sapiens
<220> FEATURE:
<221> NAME/KEY: misc_feature
<223> OTHER INFORMATION: Incyte Clone No: 1900433

<400> SEQUENCE: 35

Met Glu Arg Val Thr Leu Ala Leu Leu Leu Ala Gly Leu Thr Ala
 1               5                  10                  15

Leu Glu Ala Asn Asp Pro Phe Ala Asn Lys Asp Asp Pro Phe Tyr Tyr
            20                  25                  30

Asp Trp Lys Asn Leu Gln Leu Ser Gly Leu Ile Cys Gly Gly Leu Leu
            35                  40                  45

Ala Ile Ala Gly Ile Ala Ala Val Leu Ser Gly Lys Cys Lys Tyr Lys
 50                  55                  60

Ser Ser Gln Lys Gln His Ser Pro Val Pro Glu Lys Ala Ile Pro Leu
 65                  70                  75                  80

Ile Thr Pro Gly Ser Ala Thr Thr Cys
                85

<210> SEQ ID NO 36
<211> LENGTH: 560
<212> TYPE: PRT
<213> ORGANISM: Homo sapiens
<220> FEATURE:
<221> NAME/KEY: misc_feature
<223> OTHER INFORMATION: Incyte Clone No: 1909441

<400> SEQUENCE: 36

Met Ala Lys Lys Lys Leu Thr Glu Met Ile Pro Leu Cys Asn His Pro
 1               5                  10                  15

Ala Ser Phe Val Lys Leu Phe Val Ala Leu Gly Pro Ile Ala Gly Pro
            20                  25                  30

Glu Glu Lys Lys Gln Leu Lys Ser Thr Met Leu Leu Met Ser Glu Asp
            35                  40                  45

Leu Thr Gly Glu Gln Ala Leu Ala Val Leu Gly Ala Met Gly Asp Met
 50                  55                  60

Glu Ser Arg Asn Ser Cys Leu Ile Lys Arg Val Thr Ser Val Leu His
 65                  70                  75                  80
```

```
Lys His Leu Asp Gly Tyr Lys Pro Leu Glu Leu Leu Lys Ile Thr Gln
                85                  90                  95
Glu Leu Thr Phe Leu His Phe Gln Arg Lys Glu Phe Ala Lys Leu
            100                 105                 110
Arg Glu Leu Leu Leu Ser Tyr Leu Lys Asn Ser Phe Ile Pro Thr Glu
            115                 120                 125
Val Ser Val Leu Val Arg Ala Ile Ser Leu Leu Pro Ser Pro His Leu
        130                 135                 140
Asp Glu Val Gly Ile Ser Arg Ile Glu Ala Val Leu Pro Gln Cys Asp
145                 150                 155                 160
Leu Asn Asn Leu Ser Ser Phe Ala Thr Ser Val Leu Arg Trp Ile Gln
                165                 170                 175
His Asp His Met Tyr Leu Asp Asn Met Thr Ala Lys Gln Leu Lys Leu
            180                 185                 190
Leu Gln Lys Leu Asp His Tyr Gly Arg Gln Arg Leu Gln His Ser Asn
        195                 200                 205
Ser Leu Asp Leu Leu Arg Lys Glu Leu Lys Ser Leu Lys Gly Asn Thr
210                 215                 220
Phe Pro Glu Ser Leu Leu Glu Glu Met Ile Ala Thr Leu Gln His Phe
225                 230                 235                 240
Met Asp Asp Ile Asn Tyr Ile Asn Val Gly Glu Ile Ala Ser Phe Ile
                245                 250                 255
Ser Ser Thr Asp Tyr Leu Ser Thr Leu Leu Asp Arg Ile Ala Ser
                260                 265                 270
Val Ala Val Gln Gln Ile Glu Lys Ile His Pro Phe Thr Ile Pro Ala
        275                 280                 285
Ile Ile Arg Pro Phe Ser Val Leu Asn Tyr Asp Pro Pro Gln Arg Asp
290                 295                 300
Glu Phe Leu Gly Thr Cys Val Gln His Leu Asn Ser Tyr Leu Gly Ile
305                 310                 315                 320
Leu Asp Pro Phe Ile Leu Val Phe Leu Gly Phe Ser Leu Ala Thr Leu
                325                 330                 335
Glu Tyr Phe Pro Glu Asp Leu Leu Lys Ala Ile Phe Asn Ile Lys Phe
            340                 345                 350
Leu Ala Arg Leu Asp Ser Gln Leu Glu Ile Leu Ser Pro Ser Arg Ser
        355                 360                 365
Ala Arg Val Gln Phe His Leu Met Glu Leu Asn Arg Ser Val Cys Leu
370                 375                 380
Glu Cys Pro Glu Phe Gln Ile Pro Trp Phe His Asp Arg Phe Cys Gln
385                 390                 395                 400
Gln Tyr Asn Lys Gly Ile Gly Gly Met Asp Gly Thr Gln Gln Gln Ile
                405                 410                 415
Phe Lys Met Leu Ala Glu Val Leu Gly Gly Ile Asn Cys Val Lys Ala
            420                 425                 430
Ser Val Leu Thr Pro Tyr Tyr His Lys Val Asp Phe Glu Cys Ile Leu
        435                 440                 445
Asp Lys Arg Lys Pro Leu Pro Tyr Gly Ser His Asn Ile Ala Leu
450                 455                 460
Gly Gln Leu Pro Glu Met Pro Trp Glu Ser Asn Ile Glu Ile Val Gly
465                 470                 475                 480
Ser Arg Leu Pro Pro Gly Ala Glu Arg Ile Ala Leu Glu Phe Leu Asp
                485                 490                 495
Ser Lys Ala Leu Cys Arg Asn Ile Pro His Met Lys Gly Lys Ser Ala
            500                 505                 510
```

```
Met Lys Lys Arg His Leu Glu Ile Leu Gly Tyr Arg Val Ile Gln Ile
        515                 520                 525

Ser Gln Phe Glu Trp Asn Ser Met Ala Leu Ser Thr Lys Asp Ala Arg
        530                 535                 540

Met Asp Tyr Leu Arg Glu Cys Ile Phe Gly Glu Val Lys Ser Cys Leu
545                 550                 555                 560

<210> SEQ ID NO 37
<211> LENGTH: 197
<212> TYPE: PRT
<213> ORGANISM: Homo sapiens
<220> FEATURE:
<221> NAME/KEY: misc_feature
<223> OTHER INFORMATION: Incyte Clone No: 1932226

<400> SEQUENCE: 37

Met Gly Val Pro Leu Gly Leu Gly Ala Ala Trp Leu Ala Trp Pro
1               5                   10                  15

Gly Leu Ala Leu Pro Leu Val Ala Met Ala Ala Gly Gly Arg Trp Val
            20                  25                  30

Arg Gln Gln Gly Pro Arg Val Arg Gly Ile Ser Arg Leu Trp Leu
        35                  40                  45

Arg Val Leu Leu Arg Leu Ser Pro Met Ala Phe Arg Ala Leu Gln Gly
50                  55                  60

Cys Gly Ala Val Gly Asp Arg Gly Leu Phe Ala Leu Tyr Pro Lys Thr
65                  70                  75                  80

Asn Lys Asp Gly Phe Arg Ser Arg Leu Pro Val Pro Gly Pro Arg Arg
                85                  90                  95

Arg Asn Pro Arg Thr Thr Gln His Pro Leu Ala Leu Leu Ala Arg Val
            100                 105                 110

Trp Val Leu Cys Lys Gly Trp Asn Trp Arg Leu Ala Arg Ala Ser Gln
        115                 120                 125

Gly Leu Ala Ser His Leu Pro Pro Trp Ala Ile His Thr Leu Ala Ser
    130                 135                 140

Trp Gly Leu Leu Arg Gly Glu Arg Pro Thr Arg Ile Pro Arg Leu Leu
145                 150                 155                 160

Pro Arg Ser Gln Arg Gln Leu Gly Pro Ala Ser Arg Gln Pro Leu
                165                 170                 175

Pro Gly Thr Leu Ala Gly Arg Arg Ser Arg Thr Arg Gln Ser Arg Ala
            180                 185                 190

Leu Pro Pro Trp Arg
        195

<210> SEQ ID NO 38
<211> LENGTH: 437
<212> TYPE: PRT
<213> ORGANISM: Homo sapiens
<220> FEATURE:
<221> NAME/KEY: misc_feature
<223> OTHER INFORMATION: Incyte Clone No: 1932647

<400> SEQUENCE: 38

Met Ser Ala Val Leu Leu Leu Ala Leu Leu Gly Phe Ile Leu Pro Leu
1               5                   10                  15

Pro Gly Val Gln Ala Leu Leu Cys Gln Phe Gly Thr Val Gln His Val
            20                  25                  30

Trp Lys Val Ser Asp Leu Pro Arg Gln Trp Thr Pro Asn Thr Ser
        35                  40                  45
```

```
Cys Asp Ser Gly Leu Gly Cys Gln Asp Thr Leu Met Leu Ile Glu Ser
 50                  55                  60

Gly Pro Gln Val Ser Leu Val Leu Ser Lys Gly Cys Thr Glu Ala Lys
 65                  70                  75                  80

Asp Gln Glu Pro Arg Val Thr Glu His Arg Met Gly Pro Gly Leu Ser
                 85                  90                  95

Leu Ile Ser Tyr Thr Phe Val Cys Arg Gln Glu Asp Phe Cys Asn Asn
                100                 105                 110

Leu Val Asn Ser Leu Pro Leu Trp Ala Pro Gln Pro Ala Asp Pro
            115                 120                 125

Gly Ser Leu Arg Cys Pro Val Cys Leu Ser Met Glu Gly Cys Leu Glu
            130                 135                 140

Gly Thr Thr Glu Glu Ile Cys Pro Lys Gly Thr Thr His Cys Tyr Asp
145                 150                 155                 160

Gly Leu Leu Arg Leu Arg Gly Gly Ile Phe Ser Asn Leu Arg Val
                165                 170                 175

Gln Gly Cys Met Pro Gln Pro Gly Cys Asn Leu Leu Asn Gly Thr Gln
                180                 185                 190

Glu Ile Gly Pro Val Gly Met Thr Glu Asn Cys Asn Arg Lys Asp Phe
            195                 200                 205

Leu Thr Cys His Arg Gly Thr Thr Ile Met Thr His Gly Asn Leu Ala
            210                 215                 220

Gln Glu Pro Thr Asp Trp Thr Thr Ser Asn Thr Glu Met Cys Glu Val
225                 230                 235                 240

Gly Gln Val Cys Gln Glu Thr Leu Leu Leu Ile Asp Val Gly Leu Thr
                245                 250                 255

Ser Thr Leu Val Gly Thr Lys Gly Cys Ser Thr Val Gly Ala Gln Asn
            260                 265                 270

Ser Gln Lys Thr Thr Ile His Ser Ala Pro Pro Gly Val Leu Val Ala
            275                 280                 285

Ser Tyr Thr His Phe Cys Ser Ser Asp Leu Cys Asn Ser Ala Ser Ser
            290                 295                 300

Ser Ser Val Leu Leu Asn Ser Leu Pro Pro Gln Ala Ala Pro Val Pro
305                 310                 315                 320

Gly Asp Arg Gln Cys Pro Thr Cys Val Gln Pro Leu Gly Thr Cys Ser
                325                 330                 335

Ser Gly Ser Pro Arg Met Thr Cys Pro Arg Gly Ala Thr His Cys Tyr
                340                 345                 350

Asp Gly Tyr Ile His Leu Ser Gly Gly Leu Ser Thr Lys Met Ser
            355                 360                 365

Ile Gln Gly Cys Val Ala Gln Pro Ser Ser Phe Leu Leu Asn His Thr
370                 375                 380

Arg Gln Ile Gly Ile Phe Ser Ala Arg Glu Lys Arg Asp Val Gln Pro
385                 390                 395                 400

Pro Ala Ser Gln His Glu Gly Gly Ala Glu Gly Leu Glu Ser Leu
                405                 410                 415

Thr Trp Gly Val Gly Leu Ala Leu Ala Pro Ala Leu Trp Trp Gly Val
                420                 425                 430

Val Cys Pro Ser Cys
            435

<210> SEQ ID NO 39
<211> LENGTH: 330
<212> TYPE: PRT
<213> ORGANISM: Homo sapiens
```

```
<220> FEATURE:
<221> NAME/KEY: misc_feature
<223> OTHER INFORMATION: Incyte Clone No: 2124245

<400> SEQUENCE: 39
```

| | | | | | | | | | | | | | | | |
|---|---|---|---|---|---|---|---|---|---|---|---|---|---|---|---|
| Met | Glu | Gly | Ala | Pro | Gly | Ser | Leu | Ala | Leu | Arg | Leu | Leu | Leu | Phe |
| 1 | | | | 5 | | | | | 10 | | | | | 15 |
| Val | Ala | Leu | Pro | Ala | Ser | Gly | Trp | Leu | Thr | Thr | Gly | Ala | Pro | Glu | Pro |
| | | | 20 | | | | | 25 | | | | | 30 | | |
| Pro | Pro | Leu | Ser | Gly | Ala | Pro | Gln | Asp | Gly | Ile | Arg | Ile | Asn | Val | Thr |
| | | | 35 | | | | | 40 | | | | | 45 | | |
| Thr | Leu | Lys | Asp | Asp | Gly | Asp | Ile | Ser | Lys | Gln | Gln | Val | Val | Leu | Asn |
| 50 | | | | | 55 | | | | | 60 | | | | | |
| Ile | Thr | Tyr | Glu | Ser | Gly | Gln | Val | Tyr | Val | Asn | Asp | Leu | Pro | Val | Asn |
| 65 | | | | | 70 | | | | | 75 | | | | | 80 |
| Ser | Gly | Val | Thr | Arg | Ile | Ser | Cys | Gln | Thr | Leu | Ile | Val | Lys | Asn | Glu |
| | | | | 85 | | | | | 90 | | | | | 95 | |
| Asn | Leu | Glu | Asn | Leu | Glu | Glu | Lys | Glu | Tyr | Phe | Gly | Ile | Val | Ser | Val |
| | | | 100 | | | | | 105 | | | | | 110 | | |
| Arg | Ile | Leu | Val | His | Glu | Trp | Pro | Met | Thr | Ser | Gly | Ser | Ser | Leu | Gln |
| | | | 115 | | | | | 120 | | | | | 125 | | |
| Leu | Ile | Val | Ile | Gln | Glu | Glu | Val | Val | Glu | Ile | Asp | Gly | Lys | Gln | Val |
| 130 | | | | | 135 | | | | | 140 | | | | | |
| Gln | Gln | Lys | Asp | Val | Thr | Glu | Ile | Asp | Ile | Leu | Val | Lys | Asn | Arg | Gly |
| 145 | | | | | 150 | | | | | 155 | | | | | 160 |
| Val | Leu | Arg | His | Ser | Asn | Tyr | Thr | Leu | Pro | Leu | Glu | Glu | Ser | Met | Leu |
| | | | | 165 | | | | | 170 | | | | | 175 | |
| Tyr | Ser | Ile | Ser | Arg | Asp | Ser | Asp | Ile | Leu | Phe | Thr | Leu | Pro | Asn | Leu |
| | | | 180 | | | | | 185 | | | | | 190 | | |
| Ser | Lys | Lys | Glu | Ser | Val | Ser | Ser | Leu | Gln | Thr | Thr | Ser | Gln | Tyr | Leu |
| | | | 195 | | | | | 200 | | | | | 205 | | |
| Ile | Arg | Asn | Val | Glu | Thr | Thr | Val | Asp | Glu | Asp | Val | Leu | Pro | Gly | Lys |
| | 210 | | | | | 215 | | | | | 220 | | | | |
| Leu | Pro | Glu | Thr | Pro | Leu | Arg | Ala | Glu | Pro | Pro | Ser | Ser | Tyr | Lys | Val |
| 225 | | | | | 230 | | | | | 235 | | | | | 240 |
| Met | Cys | Gln | Trp | Met | Glu | Lys | Phe | Arg | Lys | Asp | Leu | Cys | Arg | Phe | Trp |
| | | | | 245 | | | | | 250 | | | | | 255 | |
| Ser | Asn | Val | Phe | Pro | Val | Phe | Phe | Gln | Phe | Leu | Asn | Ile | Met | Val | Val |
| | | | 260 | | | | | 265 | | | | | 270 | | |
| Gly | Ile | Thr | Gly | Ala | Ala | Val | Val | Ile | Thr | Ile | Leu | Lys | Val | Phe | Phe |
| | | | 275 | | | | | 280 | | | | | 285 | | |
| Pro | Val | Ser | Glu | Tyr | Lys | Gly | Ile | Leu | Gln | Leu | Asp | Lys | Val | Asp | Val |
| | | | 290 | | | | | 295 | | | | | 300 | | |
| Ile | Pro | Val | Thr | Ala | Ile | Asn | Leu | Tyr | Pro | Asp | Gly | Pro | Glu | Lys | Arg |
| 305 | | | | | 310 | | | | | 315 | | | | | 320 |
| Ala | Glu | Asn | Leu | Glu | Asp | Lys | Thr | Cys | Ile | | | | | | |
| | | | | 325 | | | | | 330 | | | | | | |

```
<210> SEQ ID NO 40
<211> LENGTH: 148
<212> TYPE: PRT
<213> ORGANISM: Homo sapiens
<220> FEATURE:
<221> NAME/KEY: misc_feature
<223> OTHER INFORMATION: Incyte Clone No: 2132626

<400> SEQUENCE: 40
```

-continued

```
Met Glu Thr Gly Ala Leu Arg Arg Pro Gln Leu Leu Pro Leu Leu Leu
1               5                   10                  15

Leu Leu Cys Gly Gly Cys Pro Arg Ala Gly Gly Cys Asn Glu Thr Gly
            20                  25                  30

Met Leu Glu Arg Leu Pro Leu Cys Gly Lys Ala Phe Ala Asp Met Met
                35                  40                  45

Gly Lys Val Asp Val Trp Lys Trp Cys Asn Leu Ser Glu Phe Ile Val
    50                  55                  60

Tyr Tyr Glu Ser Phe Thr Asn Cys Thr Glu Met Glu Ala Asn Val Val
65                  70                  75                  80

Gly Cys Tyr Trp Pro Asn Pro Leu Ala Gln Gly Phe Ile Thr Gly Ile
                85                  90                  95

His Arg Gln Phe Phe Ser Asn Cys Thr Val Asp Arg Val His Leu Glu
                100                 105                 110

Asp Pro Pro Asp Glu Val Leu Ile Pro Leu Ile Val Ile Pro Val Val
                115                 120                 125

Leu Thr Val Ala Met Ala Gly Leu Val Val Trp Ser Lys Arg Thr
    130                 135                 140

Asp Thr Leu Leu
145
```

<210> SEQ ID NO 41
<211> LENGTH: 188
<212> TYPE: PRT
<213> ORGANISM: Homo sapiens
<220> FEATURE:
<221> NAME/KEY: misc_feature
<223> OTHER INFORMATION: Incyte Clone No: 2280639

<400> SEQUENCE: 41

```
Met Ala Pro Pro Pro Ser Pro Gln Leu Leu Leu Ala Ala Leu
1               5                   10              15

Ala Arg Leu Leu Gly Pro Ser Glu Val Met Ala Gly Pro Ala Glu Glu
            20                  25                  30

Ala Gly Ala His Cys Pro Glu Ser Leu Trp Pro Leu Pro Pro Gln Val
                35                  40                  45

Ser Pro Arg Val Thr Tyr Thr Arg Val Ser Pro Gly Gln Ala Glu Asp
    50                  55                  60

Val Thr Phe Leu Tyr His Pro Cys Ala His Pro Trp Leu Lys Leu Gln
65                  70                  75                  80

Leu Ala Leu Leu Ala Tyr Ala Cys Met Ala Asn Pro Ser Leu Thr Pro
                85                  90                  95

Asp Phe Ser Leu Thr Gln Asp Arg Pro Leu Val Leu Thr Ala Trp Gly
                100                 105                 110

Leu Ala Leu Glu Met Ala Trp Val Glu Pro Ala Trp Ala Ala His Trp
                115                 120                 125

Leu Met Arg Arg Arg Arg Lys Gln Arg Lys Lys Ala Trp Ile
                130                 135                 140

Tyr Cys Glu Ser Leu Ser Gly Pro Ala Pro Ser Glu Pro Thr Pro Gly
145                 150                 155                 160

Arg Gly Arg Leu Cys Arg Arg Gly Cys Val Gln Ala Leu Ala Leu Ala
                165                 170                 175

Phe Ala Leu Arg Thr Gly Gly Pro Leu Ala Gln Arg
                180                 185
```

<210> SEQ ID NO 42
<211> LENGTH: 222

```
<212> TYPE: PRT
<213> ORGANISM: Homo sapiens
<220> FEATURE:
<221> NAME/KEY: misc_feature
<223> OTHER INFORMATION: Incyte Clone No: 2292356

<400> SEQUENCE: 42

Met Ala Ala Ala Leu Thr Ser Leu Ser Thr Pro Leu Leu Leu
1               5                   10                  15

Gly Ala Pro Val Ala Ala Phe Ser Pro Glu Pro Gly Leu Glu Pro Trp
                20                  25                  30

Lys Glu Ala Leu Val Arg Pro Pro Gly Ser Tyr Ser Ser Ser Ser Asn
                35                  40                  45

Ser Gly Asp Trp Gly Trp Asp Leu Ala Ser Asp Gln Ser Ser Pro Ser
        50                  55                  60

Thr Pro Ser Pro Pro Leu Pro Pro Glu Ala Ala His Phe Leu Phe Gly
65                  70                  75                  80

Glu Pro Thr Leu Arg Lys Arg Lys Ser Pro Ala Gln Val Met Phe Gln
                85                  90                  95

Cys Leu Trp Lys Ser Cys Gly Lys Val Leu Ser Thr Ala Ser Ala Met
                100                 105                 110

Gln Arg His Ile Arg Leu Val His Leu Gly Cys Gly Gly Ala Trp Gly
                115                 120                 125

Ala Ala Gly Pro Ala Gly Trp Leu Gly Leu Leu Gly Pro Ala Arg Pro
        130                 135                 140

Pro Leu Gln Leu Pro Leu Ala Gly Cys Val Ser Arg Arg Arg Gln Ala
145                 150                 155                 160

Glu Pro Glu Gln Ser Asp Gly Glu Glu Asp Phe Tyr Tyr Thr Glu Leu
                165                 170                 175

Asp Val Gly Val Asp Thr Leu Thr Asp Gly Leu Ser Ser Leu Thr Pro
                180                 185                 190

Val Phe Pro Glu Gly Phe His Ala Ser Leu Pro Ser Pro Ala Leu Lys
                195                 200                 205

Leu Arg Arg Leu Gly Gly Thr Arg Gln Pro Arg Gln Tyr Pro
210                 215                 220

<210> SEQ ID NO 43
<211> LENGTH: 111
<212> TYPE: PRT
<213> ORGANISM: Homo sapiens
<220> FEATURE:
<221> NAME/KEY: misc_feature
<223> OTHER INFORMATION: Incyte Clone No: 2349310

<400> SEQUENCE: 43

Met Gly Pro Ser Ser Cys Leu Leu Leu Ile Leu Ile Pro Leu Leu Gln
1               5                   10                  15

Leu Ile Asn Leu Gly Ser Thr Gln Cys Ser Leu Asp Ser Val Met Asp
                20                  25                  30

Lys Lys Ile Lys Asp Val Leu Asn Ser Leu Glu Tyr Ser Pro Ser Pro
                35                  40                  45

Ile Ser Lys Lys Leu Ser Cys Ala Ser Val Lys Ser Gln Gly Arg Pro
        50                  55                  60

Ser Ser Cys Pro Ala Gly Met Ala Val Thr Gly Cys Ala Cys Gly Tyr
65                  70                  75                  80

Gly Cys Gly Ser Trp Asp Val Gln Leu Glu Thr Thr Cys His Cys Gln
                85                  90                  95

Cys Ser Val Val Asp Trp Thr Thr Ala Arg Cys Cys His Leu Thr
```

```
                         100                 105                 110

<210> SEQ ID NO 44
<211> LENGTH: 341
<212> TYPE: PRT
<213> ORGANISM: Homo sapiens
<220> FEATURE:
<221> NAME/KEY: misc_feature
<223> OTHER INFORMATION: Incyte Clone No: 2373227

<400> SEQUENCE: 44

Met Val Pro Ala Ala Gly Ala Leu Leu Trp Val Leu Leu Asn Leu
 1               5                  10                  15

Gly Pro Arg Ala Ala Gly Ala Gln Gly Leu Thr Gln Thr Pro Thr Glu
                20                  25                  30

Met Gln Arg Val Ser Leu Arg Phe Gly Gly Pro Met Thr Arg Ser Tyr
            35                  40                  45

Arg Ser Thr Ala Arg Thr Gly Leu Pro Arg Lys Thr Arg Ile Ile Leu
    50                  55                  60

Glu Asp Glu Asn Asp Ala Met Ala Asp Ala Asp Arg Leu Ala Gly Pro
65                  70                  75                  80

Ala Ala Ala Glu Leu Leu Ala Ala Thr Val Ser Thr Gly Phe Ser Arg
                85                  90                  95

Ser Ser Ala Ile Asn Glu Glu Asp Gly Ser Ser Glu Glu Gly Val Val
                100                 105                 110

Ile Asn Ala Gly Lys Asp Ser Thr Ser Arg Glu Leu Pro Ser Ala Thr
                115                 120                 125

Pro Asn Thr Ala Gly Ser Ser Thr Arg Phe Ile Ala Asn Ser Gln
    130                 135                 140

Glu Pro Glu Ile Arg Leu Thr Ser Ser Leu Pro Arg Ser Pro Gly Arg
145                 150                 155                 160

Ser Thr Glu Asp Leu Pro Gly Ser Gln Ala Thr Leu Ser Gln Trp Ser
                165                 170                 175

Thr Pro Gly Ser Thr Pro Ser Arg Trp Pro Ser Pro Ser Pro Thr Ala
                180                 185                 190

Met Pro Ser Pro Glu Asp Leu Arg Leu Val Leu Met Pro Trp Gly Pro
            195                 200                 205

Trp His Cys His Cys Lys Ser Gly Thr Met Ser Arg Ser Arg Ser Gly
    210                 215                 220

Lys Leu His Gly Leu Ser Gly Arg Leu Arg Val Gly Ala Leu Ser Gln
225                 230                 235                 240

Leu Arg Thr Glu His Lys Pro Cys Thr Tyr Gln Gln Cys Pro Cys Asn
                245                 250                 255

Arg Leu Arg Glu Glu Cys Pro Leu Asp Thr Ser Leu Cys Thr Asp Thr
                260                 265                 270

Asn Cys Ala Ser Gln Ser Thr Thr Ser Thr Arg Thr Thr Thr Thr Pro
            275                 280                 285

Phe Pro Thr Ile His Leu Arg Ser Ser Pro Ser Leu Pro Pro Ala Ser
    290                 295                 300

Pro Cys Pro Ala Leu Ala Phe Trp Lys Arg Val Arg Ile Gly Leu Glu
305                 310                 315                 320

Asp Ile Trp Asn Ser Leu Ser Ser Val Phe Thr Glu Met Gln Pro Ile
                325                 330                 335

Asp Arg Asn Gln Arg
            340
```

```
<210> SEQ ID NO 45
<211> LENGTH: 148
<212> TYPE: PRT
<213> ORGANISM: Homo sapiens
<220> FEATURE:
<221> NAME/KEY: misc_feature
<223> OTHER INFORMATION: Incyte Clone No: 2457682

<400> SEQUENCE: 45

Met Ala Gly Leu Ala Ala Arg Leu Val Leu Ala Gly Ala Ala Ala
1               5                   10                  15

Leu Ala Ser Gly Ser Gln Gly Asp Arg Glu Pro Val Tyr Arg Asp Cys
            20                  25                  30

Val Leu Gln Cys Glu Glu Gln Asn Cys Ser Gly Gly Ala Leu Asn His
        35                  40                  45

Phe Arg Ser Arg Gln Pro Ile Tyr Met Ser Leu Ala Gly Trp Thr Cys
    50                  55                  60

Arg Asp Asp Cys Lys Tyr Glu Cys Met Trp Val Thr Val Gly Leu Tyr
65                  70                  75                  80

Leu Gln Glu Gly His Lys Val Pro Gln Phe His Gly Lys Trp Pro Phe
                85                  90                  95

Ser Arg Phe Leu Phe Phe Gln Glu Pro Ala Ser Ala Val Ala Ser Phe
            100                 105                 110

Leu Asn Gly Leu Ala Ser Leu Val Met Leu Cys Arg Tyr Arg Thr Phe
        115                 120                 125

Val Pro Ala Ser Ser Pro Met Tyr His Thr Cys Val Ala Phe Ala Trp
    130                 135                 140

Leu Ser Gly Arg
145

<210> SEQ ID NO 46
<211> LENGTH: 87
<212> TYPE: PRT
<213> ORGANISM: Homo sapiens
<220> FEATURE:
<221> NAME/KEY: misc_feature
<223> OTHER INFORMATION: Incyte Clone No: 2480426

<400> SEQUENCE: 46

Met Arg Pro Leu Leu Val Leu Leu Leu Gly Leu Ala Ala Gly Ser
1               5                   10                  15

Pro Pro Leu Asp Asp Asn Lys Ile Pro Ser Leu Cys Pro Gly Leu Pro
            20                  25                  30

Gly Pro Arg Gly Asp Pro Gly Arg Gly Glu Ala Gly Pro Ala Gly
            35                  40                  45

Pro Thr Gly Leu Ala Gly Glu Cys Ser Val Pro Pro Arg Ser Ala Phe
    50                  55                  60

Ser Ala Lys Arg Ser Glu Ile Arg Val Pro Pro Leu Ser Asp Ala Pro
65                  70                  75                  80

Leu Pro Ser Thr Ala Cys Trp
                85

<210> SEQ ID NO 47
<211> LENGTH: 383
<212> TYPE: PRT
<213> ORGANISM: Homo sapiens
<220> FEATURE:
<221> NAME/KEY: misc_feature
<223> OTHER INFORMATION: Incyte Clone No: 2503743

<400> SEQUENCE: 47
```

```
Met Ala Gly Ile Pro Gly Leu Leu Phe Leu Leu Phe Phe Leu Leu Cys
1               5                   10                  15

Ala Val Gly Gln Val Ser Pro Tyr Ser Ala Pro Trp Lys Pro Thr Trp
            20                  25                  30

Pro Ala Tyr Arg Leu Pro Val Val Leu Pro Gln Ser Thr Leu Asn Leu
            35                  40                  45

Ala Lys Pro Asp Phe Gly Ala Glu Ala Lys Leu Glu Val Ser Ser Ser
50                  55                  60

Cys Gly Pro Gln Cys His Lys Gly Thr Pro Leu Pro Thr Tyr Glu Glu
65                  70                  75                  80

Ala Lys Gln Tyr Leu Ser Tyr Glu Thr Leu Tyr Ala Asn Gly Ser Arg
            85                  90                  95

Thr Glu Thr Gln Val Gly Ile Tyr Ile Leu Ser Ser Ser Gly Asp Gly
            100                 105                 110

Ala Gln His Arg Asp Ser Gly Ser Gly Lys Ser Arg Arg Lys Arg
            115                 120                 125

Gln Ile Tyr Gly Tyr Asp Ser Arg Phe Ser Ile Phe Gly Lys Asp Phe
            130                 135                 140

Leu Leu Asn Tyr Pro Phe Ser Thr Ser Val Lys Leu Ser Thr Gly Cys
145                 150                 155                 160

Thr Gly Thr Leu Val Ala Glu Lys His Val Leu Thr Ala Ala His Cys
            165                 170                 175

Ile His Asp Gly Lys Thr Tyr Val Lys Gly Thr Gln Lys Leu Arg Val
            180                 185                 190

Gly Phe Leu Lys Pro Lys Phe Lys Asp Gly Arg Gly Ala Asn Asp
            195                 200                 205

Ser Thr Ser Ala Met Pro Glu Gln Met Lys Phe Gln Trp Ile Arg Val
210                 215                 220

Lys Arg Thr His Val Pro Lys Gly Trp Ile Lys Gly Asn Ala Asn Asp
225                 230                 235                 240

Ile Gly Met Asp Tyr Asp Tyr Ala Leu Leu Glu Leu Lys Lys Pro His
            245                 250                 255

Lys Arg Lys Phe Met Lys Ile Gly Val Ser Pro Pro Ala Lys Gln Leu
            260                 265                 270

Pro Gly Gly Arg Ile His Phe Ser Gly Tyr Asp Asn Asp Arg Pro Gly
            275                 280                 285

Asn Leu Val Tyr Arg Phe Cys Asp Val Lys Asp Glu Thr Tyr Asp Leu
290                 295                 300

Leu Tyr Gln Gln Cys Asp Ala Gln Pro Gly Ala Ser Gly Ser Gly Val
305                 310                 315                 320

Tyr Val Arg Met Trp Lys Arg Gln Gln Gln Lys Trp Glu Arg Lys Ile
            325                 330                 335

Ile Gly Ile Phe Ser Gly His Gln Trp Val Asp Met Asn Gly Ser Pro
            340                 345                 350

Gln Asp Phe Asn Val Ala Val Arg Ile Thr Pro Leu Lys Tyr Ala Gln
            355                 360                 365

Ile Cys Tyr Trp Ile Lys Gly Asn Tyr Leu Asp Cys Arg Glu Gly
            370                 375                 380

<210> SEQ ID NO 48
<211> LENGTH: 109
<212> TYPE: PRT
<213> ORGANISM: Homo sapiens
<220> FEATURE:
<221> NAME/KEY: misc_feature
<223> OTHER INFORMATION: Incyte Clone No: 2537684
```

-continued

```
<400> SEQUENCE: 48

Met Leu Leu Pro Ala Leu Cys Ala Trp Leu Leu Trp Val Pro Trp Cys
1               5                   10                  15

Leu Leu Val Ala Gly Ser Gly Arg Ser Gly Gly Glu Leu Cys Cys Ser
            20                  25                  30

Ser Tyr Gly Val Ser Val Ile Ser Val Trp Ser Lys Cys Ser Val Cys
        35                  40                  45

Arg Cys Leu Met Gly Ser Val Pro Arg Ile Phe Phe Ala Phe Tyr Pro
    50                  55                  60

Ile Ala Trp Leu Pro Leu Pro Gly Ser Gln Gly Cys Trp Ser Arg Ser
65                  70                  75                  80

Trp Glu Trp Pro Leu Val Glu Pro Ala Ser Cys Leu Val Cys Leu Cys
                85                  90                  95

Phe Thr Phe Gly Val Leu Ser Gly Val Val Ala Val Lys
            100                 105

<210> SEQ ID NO 49
<211> LENGTH: 185
<212> TYPE: PRT
<213> ORGANISM: Homo sapiens
<220> FEATURE:
<221> NAME/KEY: misc_feature
<223> OTHER INFORMATION: Incyte Clone No: 2593853

<400> SEQUENCE: 49

Met Lys Phe Thr Ile Val Phe Ala Gly Leu Leu Gly Val Phe Leu Ala
1               5                   10                  15

Pro Ala Leu Ala Asn Tyr Asn Ile Asn Val Asn Asp Asp Asn Asn Asn
            20                  25                  30

Ala Gly Ser Gly Gln Gln Ser Val Ser Val Asn Asn Glu His Asn Val
        35                  40                  45

Ala Asn Val Asp Asn Asn Asn Gly Trp Asp Ser Trp Asn Ser Ile Trp
    50                  55                  60

Asp Tyr Gly Asn Gly Phe Ala Ala Thr Arg Leu Phe Gln Lys Lys Thr
65                  70                  75                  80

Cys Ile Val His Lys Met Asn Lys Glu Val Met Pro Ser Ile Gln Ser
                85                  90                  95

Leu Asp Ala Leu Val Lys Glu Lys Leu Gln Gly Lys Gly Pro Gly
            100                 105                 110

Gly Pro Pro Pro Lys Gly Leu Met Tyr Ser Val Asn Pro Asn Lys Val
        115                 120                 125

Asp Asp Leu Ser Lys Phe Gly Lys Asn Ile Ala Asn Met Cys Arg Gly
    130                 135                 140

Ile Pro Thr Tyr Met Ala Glu Glu Met Gln Glu Ala Ser Leu Phe Phe
145                 150                 155                 160

Tyr Ser Gly Thr Cys Tyr Thr Thr Ser Val Leu Trp Ile Val Asp Ile
                165                 170                 175

Ser Phe Cys Gly Asp Thr Val Glu Asn
            180                 185

<210> SEQ ID NO 50
<211> LENGTH: 110
<212> TYPE: PRT
<213> ORGANISM: Homo sapiens
<220> FEATURE:
<221> NAME/KEY: misc_feature
<223> OTHER INFORMATION: Incyte Clone No: 2622354
```

-continued

```
<400> SEQUENCE: 50

Met Ala Pro Arg Gly Cys Ile Val Ala Val Phe Ala Ile Phe Cys Ile
1               5                   10                  15

Ser Arg Leu Leu Cys Ser His Gly Ala Pro Val Ala Pro Met Thr Pro
            20                  25                  30

Tyr Leu Met Leu Cys Gln Pro His Lys Arg Cys Gly Asp Lys Phe Tyr
        35                  40                  45

Asp Pro Leu Gln His Cys Cys Tyr Asp Asp Ala Val Val Pro Leu Ala
    50                  55                  60

Arg Thr Gln Thr Cys Gly Asn Cys Thr Phe Arg Val Cys Phe Glu Gln
65                  70                  75                  80

Cys Cys Pro Trp Thr Phe Met Val Lys Leu Ile Asn Gln Asn Cys Asp
                85                  90                  95

Ser Ala Arg Thr Ser Asp Asp Arg Leu Cys Arg Ser Val Ser
            100                 105                 110

<210> SEQ ID NO 51
<211> LENGTH: 126
<212> TYPE: PRT
<213> ORGANISM: Homo sapiens
<220> FEATURE:
<221> NAME/KEY: misc_feature
<223> OTHER INFORMATION: Incyte Clone No: 2641377

<400> SEQUENCE: 51

Met Trp Leu Gly Ser Trp Leu Thr Ser Leu Leu Ser Pro Tyr Gly
1               5                   10                  15

Ser Gly Trp Glu Lys Val Pro Cys Cys Val Thr Gly His Leu Arg Ser
            20                  25                  30

Cys Ser Cys Leu Leu Gly Leu Ala Gly Val Gln Ser Asp His Phe
        35                  40                  45

Ser Glu Gly Phe Phe Ser Glu Tyr Ser Ser Asp Val Leu Pro Trp Gly
    50                  55                  60

Arg Arg Ser Phe Leu Pro Gln Gly Asp Ala Ser Leu Leu Ala Cys Glu
65                  70                  75                  80

Cys Phe Leu His Leu Gln Val Val Trp Gly Phe Cys Leu Leu Glu
                85                  90                  95

Ala Trp Ala Gly Phe Thr Glu Ser Met Pro Ala Pro Ser Cys Arg
            100                 105                 110

Val His Phe Trp Cys Arg Val Asn Thr Cys Ala Phe Met Ser
        115                 120                 125

<210> SEQ ID NO 52
<211> LENGTH: 488
<212> TYPE: PRT
<213> ORGANISM: Homo sapiens
<220> FEATURE:
<221> NAME/KEY: misc_feature
<223> OTHER INFORMATION: Incyte Clone No: 2674857

<400> SEQUENCE: 52

Met Ala Gly Lys Gly Ser Ser Gly Arg Arg Pro Leu Leu Leu Gly Leu
1               5                   10                  15

Leu Val Ala Val Ala Thr Val His Leu Val Ile Cys Pro Tyr Thr Lys
            20                  25                  30

Val Glu Glu Ser Phe Asn Leu Gln Ala Thr His Asp Leu Leu Tyr His
        35                  40                  45

Trp Gln Asp Leu Glu Gln Tyr Asp His Leu Glu Phe Pro Gly Val Val
    50                  55                  60
```

```
Pro Arg Thr Phe Leu Gly Pro Val Val Ile Ala Val Phe Ser Ser Pro
 65                  70                  75                  80

Ala Val Tyr Val Leu Ser Leu Leu Glu Met Ser Lys Phe Tyr Ser Gln
                 85                  90                  95

Leu Ile Val Arg Gly Val Leu Gly Leu Gly Val Ile Phe Gly Leu Trp
            100                 105                 110

Thr Leu Gln Lys Glu Val Arg Arg His Phe Gly Ala Met Val Ala Thr
            115                 120                 125

Met Phe Cys Trp Val Thr Ala Met Gln Phe His Leu Met Phe Tyr Cys
            130                 135                 140

Thr Arg Thr Leu Pro Asn Val Leu Ala Leu Pro Val Val Leu Leu Ala
145                 150                 155                 160

Leu Ala Ala Trp Leu Arg His Glu Trp Ala Arg Phe Ile Trp Leu Ser
                165                 170                 175

Ala Phe Ala Ile Ile Val Phe Arg Val Glu Leu Cys Leu Phe Leu Gly
            180                 185                 190

Leu Leu Leu Leu Leu Ala Leu Gly Asn Arg Lys Val Ser Val Val Arg
            195                 200                 205

Ala Leu Arg His Ala Val Pro Ala Gly Ile Leu Cys Leu Gly Leu Thr
210                 215                 220

Val Ala Val Asp Ser Tyr Phe Trp Arg Gln Leu Thr Trp Pro Glu Gly
225                 230                 235                 240

Lys Val Leu Trp Tyr Asn Thr Val Leu Asn Lys Ser Ser Asn Trp Gly
                245                 250                 255

Thr Ser Pro Leu Leu Trp Tyr Phe Tyr Ser Ala Leu Pro Arg Gly Leu
            260                 265                 270

Gly Cys Ser Leu Leu Phe Ile Pro Leu Gly Leu Val Asp Arg Arg Thr
            275                 280                 285

His Ala Pro Thr Val Leu Ala Leu Gly Phe Met Ala Leu Tyr Ser Leu
            290                 295                 300

Leu Pro His Lys Glu Leu Arg Phe Ile Ile Tyr Ala Phe Pro Met Leu
305                 310                 315                 320

Asn Ile Thr Ala Ala Arg Gly Cys Ser Tyr Leu Leu Asn Asn Tyr Lys
            325                 330                 335

Lys Ser Trp Leu Tyr Lys Ala Gly Ser Leu Leu Val Ile Gly His Leu
            340                 345                 350

Val Val Asn Ala Ala Tyr Ser Ala Thr Ala Leu Tyr Val Ser His Phe
            355                 360                 365

Asn Tyr Pro Gly Gly Val Ala Met Gln Arg Leu His Gln Leu Val Pro
            370                 375                 380

Pro Gln Thr Asp Val Leu Leu His Ile Asp Val Ala Ala Ala Gln Thr
385                 390                 395                 400

Gly Val Ser Arg Phe Leu Gln Val Asn Ser Ala Trp Arg Tyr Asp Lys
            405                 410                 415

Arg Glu Asp Val Gln Pro Gly Thr Gly Met Leu Ala Tyr Thr His Ile
            420                 425                 430

Leu Met Glu Ala Ala Pro Gly Leu Leu Ala Leu Tyr Arg Asp Thr His
            435                 440                 445

Arg Val Leu Ala Ser Val Val Gly Thr Thr Gly Val Ser Leu Asn Leu
            450                 455                 460

Thr Gln Leu Pro Pro Phe Asn Val His Leu Gln Thr Lys Leu Val Leu
465                 470                 475                 480

Leu Glu Arg Leu Pro Arg Pro Ser
```

-continued

```
                485

<210> SEQ ID NO 53
<211> LENGTH: 197
<212> TYPE: PRT
<213> ORGANISM: Homo sapiens
<220> FEATURE:
<221> NAME/KEY: misc_feature
<223> OTHER INFORMATION: Incyte Clone No: 2758485

<400> SEQUENCE: 53

Met Ser Pro Arg Arg Thr Leu Pro Arg Pro Leu Ser Leu Cys Leu Ser
1               5                   10                  15

Leu Cys Leu Cys Leu Cys Leu Ala Ala Ala Leu Gly Ser Ala Gln Ser
                20                  25                  30

Gly Ser Cys Arg Asp Lys Lys Asn Cys Lys Val Val Phe Ser Gln Gln
            35                  40                  45

Glu Leu Arg Lys Arg Leu Thr Pro Leu Gln Tyr His Val Thr Gln Glu
    50                  55                  60

Lys Gly Thr Glu Ser Ala Phe Glu Gly Glu Tyr Thr His His Lys Asp
65                  70                  75                  80

Pro Gly Ile Tyr Lys Cys Val Val Cys Gly Thr Pro Leu Phe Lys Ser
                85                  90                  95

Glu Thr Lys Phe Asp Ser Gly Ser Gly Trp Pro Ser Phe His Asp Val
                100                 105                 110

Ile Asn Ser Glu Ala Ile Thr Phe Thr Asp Asp Phe Ser Tyr Gly Met
            115                 120                 125

His Arg Val Glu Thr Ser Cys Ser Gln Cys Gly Ala His Leu Gly His
    130                 135                 140

Ile Phe Asp Asp Gly Pro Arg Pro Thr Gly Lys Arg Tyr Cys Ile Asn
145                 150                 155                 160

Ser Ala Ala Leu Ser Phe Thr Pro Ala Asp Ser Ser Gly Thr Ala Glu
                165                 170                 175

Gly Gly Ser Gly Val Ala Ser Pro Ala Gln Ala Asp Lys Ala Asp Ser
            180                 185                 190

Glu Ser Asn Gly Glu
        195

<210> SEQ ID NO 54
<211> LENGTH: 84
<212> TYPE: PRT
<213> ORGANISM: Homo sapiens
<220> FEATURE:
<221> NAME/KEY: misc_feature
<223> OTHER INFORMATION: Incyte Clone No: 2763296

<400> SEQUENCE: 54

Met Thr Pro Gln Ser Leu Leu Gln Thr Thr Leu Phe Leu Leu Ser Leu
1               5                   10                  15

Leu Phe Leu Val Gln Gly Ala His Gly Arg Gly His Arg Glu Asp Phe
                20                  25                  30

Arg Phe Cys Ser Gln Arg Asn Gln Thr His Arg Ser Ser Leu His Tyr
            35                  40                  45

Tyr Trp Ser Met Arg Leu Gln Ala Arg Gly Gly Pro Ser Pro Leu Lys
    50                  55                  60

Ser Asn Ser Asp Ser Ala Arg Leu Pro Ile Ser Ser Gly Ser Thr Ser
65                  70                  75                  80

Ser Ser Arg Ile
```

-continued

<210> SEQ ID NO 55
<211> LENGTH: 97
<212> TYPE: PRT
<213> ORGANISM: Homo sapiens
<220> FEATURE:
<221> NAME/KEY: misc_feature
<223> OTHER INFORMATION: Incyte Clone No: 2779436

<400> SEQUENCE: 55

Met Gln Leu Gly Thr Gly Leu Leu Ala Ala Val Leu Ser Leu Gln
1               5                   10                  15

Leu Ala Ala Ala Glu Ala Ile Trp Cys His Gln Cys Thr Gly Phe Gly
            20                  25                  30

Gly Cys Ser His Gly Ser Arg Cys Leu Arg Asp Ser Thr His Cys Val
        35                  40                  45

Thr Thr Ala Thr Arg Val Leu Ser Asn Thr Glu Asp Leu Pro Leu Val
    50                  55                  60

Thr Lys Met Cys His Ile Gly Cys Pro Asp Ile Pro Ser Leu Gly Leu
65                  70                  75                  80

Gly Pro Tyr Val Ser Ile Ala Cys Cys Gln Thr Ser Leu Cys Asn His
                85                  90                  95

Asp

<210> SEQ ID NO 56
<211> LENGTH: 140
<212> TYPE: PRT
<213> ORGANISM: Homo sapiens
<220> FEATURE:
<221> NAME/KEY: misc_feature
<223> OTHER INFORMATION: Incyte Clone No: 2808528

<400> SEQUENCE: 56

Met Ala Ala Ser Leu Gly Gln Val Leu Ala Leu Val Leu Val Ala Ala
1               5                   10                  15

Leu Trp Gly Gly Thr Gln Pro Leu Leu Lys Arg Ala Ser Ala Gly Leu
            20                  25                  30

Gln Arg Val His Glu Pro Thr Trp Ala Gln Gly Leu Leu Gln Glu Met
        35                  40                  45

Lys Thr Leu Phe Leu Asn Thr Glu Tyr Leu Met Pro Phe Leu Leu Asn
    50                  55                  60

Gln Cys Gly Ser Leu Leu Tyr Tyr Leu Thr Leu Ala Ser Thr Asp Leu
65                  70                  75                  80

Thr Leu Ala Val Pro Ile Cys Asn Ser Leu Ala Ile Ile Phe Thr Leu
                85                  90                  95

Ile Val Gly Lys Ala Leu Gly Glu Asp Ile Gly Gly Lys Arg Ala Val
            100                 105                 110

Ala Gly Met Val Leu Thr Val Ile Gly Ile Ser Leu Cys Ile Thr Ser
        115                 120                 125

Ser Val Ser Lys Thr Gln Gly Gln Gln Ser Thr Leu
    130                 135                 140

<210> SEQ ID NO 57
<211> LENGTH: 285
<212> TYPE: PRT
<213> ORGANISM: Homo sapiens
<220> FEATURE:
<221> NAME/KEY: misc_feature
<223> OTHER INFORMATION: Incyte Clone No: 2809230

<400> SEQUENCE: 57

```
Met Glu Val Pro Pro Ala Pro Arg Ser Phe Leu Cys Arg Ala Leu
1               5                   10                  15

Cys Leu Phe Pro Arg Val Phe Ala Ala Glu Ala Val Thr Ala Asp Ser
            20                  25                  30

Glu Val Leu Glu Glu Arg Gln Lys Arg Leu Pro Tyr Val Pro Glu Pro
            35                  40                  45

Tyr Tyr Pro Glu Ser Gly Trp Asp Arg Leu Arg Glu Leu Phe Gly Lys
        50                  55                  60

Asp Glu Gln Gln Arg Ile Ser Lys Asp Leu Ala Asn Ile Cys Lys Thr
65                  70                  75                  80

Ala Ala Thr Ala Gly Ile Ile Gly Trp Val Tyr Gly Gly Ile Pro Ala
                85                  90                  95

Phe Ile His Ala Lys Gln Gln Tyr Ile Glu Gln Ser Gln Ala Glu Ile
                100                 105                 110

Tyr His Asn Arg Phe Asp Ala Val Gln Ser Ala His Arg Ala Ala Thr
            115                 120                 125

Arg Gly Phe Ile Arg Tyr Gly Trp Arg Trp Gly Trp Arg Thr Ala Val
        130                 135                 140

Phe Val Thr Ile Phe Asn Thr Val Asn Thr Ser Leu Asn Val Tyr Arg
145                 150                 155                 160

Asn Lys Asp Ala Leu Ser His Phe Val Ile Ala Gly Ala Val Thr Gly
                165                 170                 175

Ser Leu Phe Arg Ile Asn Val Gly Leu Arg Gly Leu Val Ala Gly Gly
                180                 185                 190

Ile Ile Gly Ala Leu Leu Gly Thr Pro Val Gly Gly Leu Leu Met Ala
        195                 200                 205

Phe Gln Lys Tyr Ser Gly Glu Thr Val Gln Glu Arg Lys Gln Lys Asp
210                 215                 220

Arg Lys Ala Leu His Glu Leu Lys Leu Glu Trp Lys Gly Arg Leu
225                 230                 235                 240

Gln Val Thr Glu His Leu Pro Glu Lys Ile Glu Ser Ser Leu Gln Glu
            245                 250                 255

Asp Glu Pro Glu Asn Asp Ala Lys Lys Ile Glu Ala Leu Leu Asn Leu
            260                 265                 270

Pro Arg Asn Pro Ser Val Ile Asp Lys Gln Asp Lys Asp
        275                 280                 285

<210> SEQ ID NO 58
<211> LENGTH: 262
<212> TYPE: PRT
<213> ORGANISM: Homo sapiens
<220> FEATURE:
<221> NAME/KEY: misc_feature
<223> OTHER INFORMATION: Incyte Clone No: 2816821

<400> SEQUENCE: 58

Met Thr Gln Pro Val Pro Arg Leu Ser Val Pro Ala Ala Leu Ala Leu
1               5                   10                  15

Gly Ser Ala Ala Leu Gly Ala Ala Phe Ala Thr Gly Leu Phe Leu Gly
            20                  25                  30

Arg Arg Cys Pro Pro Trp Arg Gly Arg Glu Gln Cys Leu Leu Pro
            35                  40                  45

Pro Glu Asp Ser Arg Leu Trp Gln Tyr Leu Leu Ser Arg Ser Met Arg
        50                  55                  60

Glu His Pro Ala Leu Arg Ser Leu Arg Leu Leu Thr Leu Glu Gln Pro
65                  70                  75                  80
```

```
Gln Gly Asp Ser Met Met Thr Cys Glu Gln Ala Gln Leu Leu Ala Asn
                85                  90                  95

Leu Ala Arg Leu Ile Gln Ala Lys Lys Ala Leu Asp Leu Gly Thr Phe
            100                 105                 110

Thr Gly Tyr Ser Ala Leu Ala Leu Ala Leu Ala Leu Pro Ala Asp Gly
        115                 120                 125

Arg Val Val Thr Cys Glu Val Asp Ala Gln Pro Pro Glu Leu Gly Arg
    130                 135                 140

Pro Leu Trp Arg Gln Ala Glu Ala Glu His Lys Ile Asp Leu Arg Leu
145                 150                 155                 160

Lys Pro Ala Leu Glu Thr Leu Asp Glu Leu Leu Ala Ala Gly Glu Ala
                165                 170                 175

Gly Thr Phe Asp Val Ala Val Val Asp Ala Asp Lys Glu Asn Cys Ser
            180                 185                 190

Ala Tyr Tyr Glu Arg Cys Leu Gln Leu Leu Arg Pro Gly Gly Ile Leu
        195                 200                 205

Ala Val Leu Arg Val Leu Trp Arg Gly Lys Val Leu Gln Pro Pro Lys
    210                 215                 220

Gly Asp Val Ala Ala Glu Cys Val Arg Asn Leu Asn Glu Arg Ile Arg
225                 230                 235                 240

Arg Asp Val Arg Val Tyr Ile Ser Leu Leu Pro Leu Gly Asp Gly Leu
                245                 250                 255

Thr Leu Ala Phe Lys Ile
                260

<210> SEQ ID NO 59
<211> LENGTH: 189
<212> TYPE: PRT
<213> ORGANISM: Homo sapiens
<220> FEATURE:
<221> NAME/KEY: misc_feature
<223> OTHER INFORMATION: Incyte Clone No: 2817268

<400> SEQUENCE: 59

Met Ala Leu Leu Ser Arg Pro Ala Leu Thr Leu Leu Leu Leu Leu Met
1               5                   10                  15

Ala Ala Val Val Arg Cys Gln Glu Gln Ala Gln Thr Thr Asp Trp Arg
            20                  25                  30

Ala Thr Leu Lys Thr Ile Arg Asn Gly Val His Lys Ile Asp Thr Tyr
        35                  40                  45

Leu Asn Ala Ala Leu Asp Leu Leu Gly Gly Glu Asp Gly Leu Cys Gln
    50                  55                  60

Tyr Lys Cys Ser Asp Gly Ser Lys Pro Phe Pro Arg Tyr Gly Tyr Lys
65                  70                  75                  80

Pro Ser Pro Pro Asn Gly Cys Gly Ser Pro Leu Phe Gly Val His Leu
                85                  90                  95

Asn Ile Gly Ile Pro Ser Leu Thr Lys Cys Cys Asn Gln His Asp Arg
            100                 105                 110

Cys Tyr Glu Thr Cys Gly Lys Ser Lys Asn Asp Cys Asp Glu Glu Phe
        115                 120                 125

Gln Tyr Cys Leu Ser Lys Ile Cys Arg Asp Val Gln Lys Thr Leu Gly
    130                 135                 140

Leu Thr Gln His Val Gln Ala Cys Glu Thr Thr Val Glu Leu Leu Phe
145                 150                 155                 160

Asp Ser Val Ile His Leu Gly Cys Lys Pro Tyr Leu Asp Ser Gln Arg
                165                 170                 175
```

-continued

```
Ala Ala Cys Arg Cys His Tyr Glu Glu Lys Thr Asp Leu
            180                 185

<210> SEQ ID NO 60
<211> LENGTH: 257
<212> TYPE: PRT
<213> ORGANISM: Homo sapiens
<220> FEATURE:
<221> NAME/KEY: misc_feature
<223> OTHER INFORMATION: Incyte Clone No: 2923165

<400> SEQUENCE: 60

Met Thr Ala Ala Val Phe Phe Gly Cys Ala Phe Ile Ala Phe Gly Pro
1               5                   10                  15

Ala Leu Ala Leu Tyr Val Phe Thr Ile Ala Thr Glu Pro Leu Arg Ile
            20                  25                  30

Ile Phe Leu Ile Ala Gly Ala Phe Trp Leu Val Ser Leu Leu Ile
        35                  40                  45

Ser Ser Leu Val Trp Phe Met Ala Arg Val Ile Asp Asn Lys Asp
    50                  55                  60

Gly Pro Thr Gln Lys Tyr Leu Leu Ile Phe Gly Ala Phe Val Ser Val
65                  70                  75                  80

Tyr Ile Gln Glu Met Phe Arg Phe Ala Tyr Tyr Lys Leu Leu Lys Lys
                85                  90                  95

Ala Ser Glu Gly Leu Lys Ser Ile Asn Pro Gly Glu Thr Ala Pro Ser
            100                 105                 110

Met Arg Leu Leu Ala Tyr Val Ser Gly Leu Gly Phe Gly Ile Met Ser
        115                 120                 125

Gly Val Phe Ser Phe Val Asn Thr Leu Ser Asp Ser Leu Gly Pro Gly
130                 135                 140

Thr Val Gly Ile His Gly Asp Ser Pro Gln Phe Phe Leu Tyr Ser Ala
145                 150                 155                 160

Phe Met Thr Leu Val Ile Ile Leu Leu His Val Phe Trp Gly Ile Val
                165                 170                 175

Phe Phe Asp Gly Cys Glu Lys Lys Lys Trp Gly Ile Leu Leu Ile Val
            180                 185                 190

Leu Leu Thr His Leu Leu Val Ser Ala Gln Thr Phe Ile Ser Ser Tyr
        195                 200                 205

Tyr Gly Ile Asn Leu Ala Ser Ala Phe Ile Ile Leu Val Leu Met Gly
    210                 215                 220

Thr Trp Ala Phe Leu Ala Ala Gly Gly Ser Cys Arg Ser Leu Lys Leu
225                 230                 235                 240

Cys Leu Leu Cys Gln Asp Lys Asn Phe Leu Tyr Asn Gln Arg Ser
                245                 250                 255

Arg

<210> SEQ ID NO 61
<211> LENGTH: 82
<212> TYPE: PRT
<213> ORGANISM: Homo sapiens
<220> FEATURE:
<221> NAME/KEY: misc_feature
<223> OTHER INFORMATION: Incyte Clone No: 2949822

<400> SEQUENCE: 61

Met Pro Phe Ser Trp Met Val Ile Ile Leu Gly Phe Leu Cys Gly Leu
1               5                   10                  15

Ser Gly Gln Leu Gln Ile Met Asn Thr Leu Ser Ser Leu Pro Ile Val
            20                  25                  30
```

Leu Leu Val Ser Ser Cys Leu Ile Leu Ala Arg Met Ser Tyr Ser
            35                  40                  45

Ile Leu Thr Ser Ser Tyr Gly Gly Val Phe Ile Leu Leu Asp Leu
    50                  55                  60

Lys Arg Asn Thr Ser Lys Val Ser Pro Leu Met Met Met Phe Ala Ile
65                  70                  75                  80

Gly His

<210> SEQ ID NO 62
<211> LENGTH: 202
<212> TYPE: PRT
<213> ORGANISM: Homo sapiens
<220> FEATURE:
<221> NAME/KEY: misc_feature
<223> OTHER INFORMATION: Incyte Clone No: 2992192

<400> SEQUENCE: 62

Met Ala Ala Pro Trp Arg Arg Trp Pro Thr Gly Leu Leu Ala Val Leu
1               5                   10                  15

Arg Pro Leu Leu Thr Cys Arg Pro Leu Gln Gly Thr Thr Leu Gln Arg
            20                  25                  30

Asp Val Leu Leu Phe Glu His Asp Arg Gly Arg Phe Phe Thr Ile Leu
        35                  40                  45

Gly Leu Phe Cys Ala Gly Gln Gly Val Phe Trp Ala Ser Met Ala Val
    50                  55                  60

Ala Ala Val Ser Arg Pro Pro Val Pro Val Gln Pro Leu Asp Ala Glu
65                  70                  75                  80

Val Pro Asn Arg Gly Pro Phe Asp Leu Arg Ser Ala Leu Trp Arg Tyr
                85                  90                  95

Gly Leu Ala Val Gly Cys Gly Ala Ile Gly Ala Leu Val Leu Gly Ala
            100                 105                 110

Gly Leu Leu Phe Ser Leu Arg Ser Val Arg Ser Val Val Leu Arg Ala
            115                 120                 125

Gly Gly Gln Gln Val Thr Leu Thr Thr His Ala Pro Phe Gly Leu Gly
        130                 135                 140

Ala His Phe Thr Val Pro Leu Lys Gln Val Ser Cys Met Ala His Arg
145                 150                 155                 160

Gly Glu Val Pro Ala Met Leu Pro Leu Lys Val Lys Gly Arg Arg Phe
                165                 170                 175

Tyr Phe Leu Leu Asp Lys Thr Gly His Phe Pro Asn Thr Lys Leu Phe
            180                 185                 190

Asp Asn Thr Val Gly Ala Tyr Arg Ser Leu
        195                 200

<210> SEQ ID NO 63
<211> LENGTH: 450
<212> TYPE: PRT
<213> ORGANISM: Homo sapiens
<220> FEATURE:
<221> NAME/KEY: misc_feature
<223> OTHER INFORMATION: Incyte Clone No: 2992458

<400> SEQUENCE: 63

Met Leu Val Thr Ala Tyr Leu Ala Phe Val Gly Leu Leu Ala Ser Cys
1               5                   10                  15

Leu Gly Leu Glu Leu Ser Arg Cys Arg Ala Lys Pro Pro Gly Arg Ala
            20                  25                  30

Cys Ser Asn Pro Ser Phe Leu Arg Phe Gln Leu Asp Phe Tyr Gln Val

```
                35                  40                  45
Tyr Phe Leu Ala Leu Ala Ala Asp Trp Leu Gln Ala Pro Tyr Leu Tyr
 50                  55                  60

Lys Leu Tyr Gln His Tyr Tyr Phe Leu Glu Gly Gln Ile Ala Ile Leu
 65                  70                  75                  80

Tyr Val Cys Gly Leu Ala Ser Thr Val Leu Phe Gly Leu Val Ala Ser
                 85                  90                  95

Ser Leu Val Asp Trp Leu Gly Arg Lys Asn Ser Cys Val Leu Phe Ser
                100                 105                 110

Leu Thr Tyr Ser Leu Cys Cys Leu Thr Lys Leu Ser Gln Asp Tyr Phe
                115                 120                 125

Val Leu Leu Val Gly Arg Ala Leu Gly Gly Leu Ser Thr Ala Leu Leu
            130                 135                 140

Phe Ser Ala Phe Glu Ala Trp Tyr Ile His Glu His Val Glu Arg His
145                 150                 155                 160

Asp Phe Pro Ala Glu Trp Ile Pro Ala Thr Phe Ala Arg Ala Ala Phe
                165                 170                 175

Trp Asn His Val Leu Ala Val Val Ala Gly Val Ala Ala Glu Ala Val
                180                 185                 190

Ala Ser Trp Ile Gly Leu Gly Pro Val Ala Pro Phe Val Ala Ala Ile
            195                 200                 205

Pro Leu Leu Ala Leu Ala Gly Ala Leu Ala Leu Arg Asn Trp Gly Glu
210                 215                 220

Asn Tyr Asp Arg Gln Arg Ala Phe Ser Arg Thr Cys Ala Gly Gly Leu
225                 230                 235                 240

Arg Cys Leu Leu Ser Asp Arg Arg Val Leu Leu Leu Gly Thr Ile Gln
                245                 250                 255

Ala Leu Phe Glu Ser Val Ile Phe Ile Phe Val Phe Leu Trp Thr Pro
                260                 265                 270

Val Leu Asp Pro His Gly Ala Pro Leu Gly Ile Ile Phe Ser Ser Phe
                275                 280                 285

Met Ala Ala Ser Leu Leu Gly Ser Ser Leu Tyr Arg Ile Ala Thr Ser
290                 295                 300

Lys Arg Tyr His Leu Gln Pro Met His Leu Leu Ser Leu Ala Val Leu
305                 310                 315                 320

Ile Val Val Phe Ser Leu Phe Met Leu Thr Phe Ser Thr Ser Pro Gly
                325                 330                 335

Gln Glu Ser Pro Val Glu Ser Phe Ile Ala Phe Leu Leu Ile Glu Leu
                340                 345                 350

Ala Cys Gly Leu Tyr Phe Pro Ser Met Ser Phe Leu Arg Arg Lys Val
                355                 360                 365

Ile Pro Glu Thr Glu Gln Ala Gly Val Leu Asn Trp Phe Arg Val Pro
370                 375                 380

Leu His Ser Leu Ala Cys Leu Gly Leu Leu Val Leu His Asp Ser Asp
385                 390                 395                 400

Arg Lys Thr Gly Thr Arg Asn Met Phe Ser Ile Cys Ser Ala Val Met
                405                 410                 415

Val Met Ala Leu Leu Ala Val Val Gly Leu Phe Thr Val Val Arg His
                420                 425                 430

Asp Ala Glu Leu Arg Val Pro Ser Pro Thr Glu Pro Tyr Ala Pro
                435                 440                 445

Glu Leu
    450
```

```
<210> SEQ ID NO 64
<211> LENGTH: 322
<212> TYPE: PRT
<213> ORGANISM: Homo sapiens
<220> FEATURE:
<221> NAME/KEY: misc_feature
<223> OTHER INFORMATION: Incyte Clone No: 3044710

<400> SEQUENCE: 64

Met Ala Arg Cys Phe Ser Leu Val Leu Leu Thr Ser Ile Trp Thr
1               5                   10                  15

Thr Arg Leu Leu Val Gln Gly Ser Leu Arg Ala Glu Glu Leu Ser Ile
            20                  25                  30

Gln Val Ser Cys Arg Ile Met Gly Ile Thr Leu Val Ser Lys Lys Ala
                35                  40                  45

Asn Gln Gln Leu Asn Phe Thr Glu Ala Lys Glu Ala Cys Arg Leu Leu
    50                  55                  60

Gly Leu Ser Leu Ala Gly Lys Asp Gln Val Glu Thr Ala Leu Lys Ala
65                  70                  75                  80

Ser Phe Glu Thr Cys Ser Tyr Gly Trp Val Gly Asp Gly Phe Val Val
                85                  90                  95

Ile Ser Arg Ile Ser Pro Asn Pro Lys Cys Gly Lys Asn Gly Val Gly
                100                 105                 110

Val Leu Ile Trp Lys Val Pro Val Ser Arg Gln Phe Ala Ala Tyr Cys
            115                 120                 125

Tyr Asn Ser Ser Asp Thr Trp Thr Asn Ser Cys Ile Pro Glu Ile Ile
    130                 135                 140

Thr Thr Lys Asp Pro Ile Phe Asn Thr Gln Thr Ala Thr Gln Thr Thr
145                 150                 155                 160

Glu Phe Ile Val Ser Asp Ser Thr Tyr Ser Val Ala Ser Pro Tyr Ser
                165                 170                 175

Thr Ile Pro Ala Pro Thr Thr Thr Pro Pro Ala Pro Ser Thr Ser
            180                 185                 190

Ile Pro Arg Arg Lys Lys Leu Ile Cys Val Thr Glu Val Phe Met Glu
            195                 200                 205

Thr Ser Thr Met Ser Thr Glu Thr Glu Pro Phe Val Glu Asn Lys Ala
210                 215                 220

Ala Phe Lys Asn Glu Ala Gly Phe Gly Gly Val Pro Thr Ala Leu
225                 230                 235                 240

Leu Val Leu Ala Leu Leu Phe Phe Gly Ala Ala Ala Gly Leu Gly Phe
            245                 250                 255

Cys Tyr Val Lys Arg Tyr Val Lys Ala Phe Pro Phe Thr Asn Lys Asn
            260                 265                 270

Gln Gln Lys Glu Met Ile Glu Thr Lys Val Val Lys Glu Glu Lys Ala
        275                 280                 285

Asn Asp Ser Asn Pro Asn Glu Glu Ser Lys Lys Thr Asp Lys Asn Pro
    290                 295                 300

Glu Glu Ser Lys Ser Pro Ser Lys Thr Thr Val Arg Cys Leu Glu Ala
305                 310                 315                 320

Glu Val

<210> SEQ ID NO 65
<211> LENGTH: 104
<212> TYPE: PRT
<213> ORGANISM: Homo sapiens
<220> FEATURE:
<221> NAME/KEY: misc_feature
```

<223> OTHER INFORMATION: Incyte Clone No: 3120415

<400> SEQUENCE: 65

Met Lys Leu Ala Ala Leu Leu Gly Leu Cys Val Ala Leu Ser Cys Ser
1               5                   10                  15

Ser Ala Ala Ala Phe Leu Val Gly Ser Ala Lys Pro Val Ala Gln Pro
            20                  25                  30

Val Ala Ala Leu Glu Ser Ala Ala Glu Ala Gly Ala Gly Thr Leu Ala
        35                  40                  45

Asn Pro Leu Gly Thr Leu Asn Pro Leu Lys Leu Leu Ser Ser Leu
    50                  55                  60

Gly Ile Pro Val Asn His Leu Ile Glu Gly Ser Gln Lys Cys Val Ala
65                  70                  75                  80

Glu Leu Gly Pro Gln Ala Val Gly Val Lys Ala Leu Lys Ala Leu
                85                  90                  95

Leu Gly Ala Leu Thr Val Phe Gly
            100

<210> SEQ ID NO 66
<211> LENGTH: 93
<212> TYPE: PRT
<213> ORGANISM: Homo sapiens
<220> FEATURE:
<221> NAME/KEY: misc_feature
<223> OTHER INFORMATION: Incyte Clone No: 126758

<400> SEQUENCE: 66

Met Lys Leu Val Thr Ile Phe Leu Leu Val Thr Ile Ser Leu Cys Ser
1               5                   10                  15

Tyr Ser Ala Thr Ala Phe Leu Ile Asn Lys Val Pro Leu Pro Val Asp
            20                  25                  30

Lys Leu Ala Pro Leu Pro Leu Asp Asn Ile Leu Pro Phe Met Asp Pro
        35                  40                  45

Leu Lys Leu Leu Leu Lys Thr Leu Gly Ile Ser Val Glu His Leu Val
    50                  55                  60

Glu Gly Leu Arg Lys Cys Val Asn Glu Leu Gly Pro Glu Ala Ser Glu
65                  70                  75                  80

Ala Val Lys Lys Leu Leu Glu Ala Leu Ser His Leu Val
                85                  90

<210> SEQ ID NO 67
<211> LENGTH: 71
<212> TYPE: PRT
<213> ORGANISM: Homo sapiens
<220> FEATURE:
<221> NAME/KEY: misc_feature
<223> OTHER INFORMATION: Incyte Clone No: 674760

<400> SEQUENCE: 67

Met Thr Ala Gly Gln Phe Pro Ala Leu Val Ser Leu Ala Leu Leu Leu
1               5                   10                  15

Asp Gly Gly Arg Arg Ala Ser Ala Arg Arg Asn Arg Gly His Leu Trp
            20                  25                  30

Val Phe Cys Thr Ser Phe Leu Leu Ala Pro Trp Glu Val Glu Asp Val
        35                  40                  45

Gly Trp Lys Lys Gly Leu Asp Leu Pro Pro Ser Ser Pro Pro Ser
    50                  55                  60

Pro Lys Glu Leu Ala Leu Gln
65                  70

<210> SEQ ID NO 68
<211> LENGTH: 394
<212> TYPE: PRT
<213> ORGANISM: Homo sapiens
<220> FEATURE:
<221> NAME/KEY: misc_feature
<223> OTHER INFORMATION: Incyte Clone No: 1229438

<400> SEQUENCE: 68

```
Met Lys Arg Gln Asn Val Arg Thr Leu Ala Leu Ile Val Cys Thr Phe
1               5                   10                  15

Thr Tyr Leu Leu Val Gly Ala Val Phe Asp Ala Leu Glu Ser Glu
            20                  25                  30

Pro Glu Leu Ile Glu Arg Gln Arg Leu Glu Leu Arg Gln Gln Glu Leu
            35                  40                  45

Arg Ala Arg Tyr Asn Leu Ser Gln Gly Gly Tyr Glu Glu Leu Glu Arg
        50                  55                  60

Val Val Leu Arg Leu Lys Pro His Lys Ala Gly Val Gln Trp Arg Phe
65                  70                  75                  80

Ala Gly Ser Phe Tyr Phe Ala Ile Thr Val Ile Thr Thr Ile Gly Tyr
                85                  90                  95

Gly His Ala Ala Pro Ser Thr Asp Gly Gly Lys Val Phe Cys Met Phe
            100                 105                 110

Tyr Ala Leu Leu Gly Ile Pro Leu Thr Leu Val Met Phe Gln Ser Leu
            115                 120                 125

Gly Glu Arg Ile Asn Thr Leu Val Arg Tyr Leu Leu His Arg Ala Lys
        130                 135                 140

Lys Gly Leu Gly Met Arg Arg Ala Asp Val Ser Met Ala Asn Met Val
145                 150                 155                 160

Leu Ile Gly Phe Phe Ser Cys Ile Ser Thr Leu Cys Ile Gly Ala Ala
                165                 170                 175

Ala Phe Ser His Tyr Glu His Trp Thr Phe Phe Gln Ala Tyr Tyr Tyr
            180                 185                 190

Cys Phe Ile Thr Leu Thr Thr Ile Gly Phe Gly Asp Tyr Val Ala Leu
            195                 200                 205

Gln Lys Asp Gln Ala Leu Gln Thr Gln Pro Gln Tyr Val Ala Phe Ser
        210                 215                 220

Phe Val Tyr Ile Leu Thr Gly Leu Thr Val Ile Gly Ala Phe Leu Asn
225                 230                 235                 240

Leu Val Val Leu Arg Phe Met Thr Met Asn Ala Glu Asp Glu Lys Arg
                245                 250                 255

Asp Ala Glu His Arg Ala Leu Leu Thr Arg Asn Gly Gln Ala Gly Gly
            260                 265                 270

Gly Gly Gly Gly Gly Ser Ala His Thr Thr Asp Thr Ala Ser Ser Thr
        275                 280                 285

Ala Ala Ala Gly Gly Gly Phe Arg Asn Val Tyr Ala Glu Val Leu
        290                 295                 300

His Phe Gln Ser Met Cys Ser Cys Leu Trp Tyr Lys Ser Arg Glu Lys
305                 310                 315                 320

Leu Gln Tyr Ser Ile Pro Met Ile Ile Pro Arg Asp Leu Ser Thr Ser
                325                 330                 335

Asp Thr Cys Val Glu Gln Ser His Ser Ser Pro Gly Gly Gly Arg
            340                 345                 350

Tyr Ser Asp Thr Pro Ser Arg Arg Cys Leu Cys Ser Gly Ala Pro Arg
        355                 360                 365
```

```
Ser Ala Ile Ser Ser Val Ser Thr Gly Leu His Ser Leu Ser Thr Phe
        370                 375                 380

Arg Gly Leu Met Lys Arg Arg Ser Ser Val
385                 390
```

<210> SEQ ID NO 69
<211> LENGTH: 72
<212> TYPE: PRT
<213> ORGANISM: Homo sapiens
<220> FEATURE:
<221> NAME/KEY: misc_feature
<223> OTHER INFORMATION: Incyte Clone No: 1236935

<400> SEQUENCE: 69

```
Met Cys Pro Phe Phe Pro Leu Thr Ser Leu Ile Val Phe Leu Ile Leu
1               5                   10                  15

Phe Phe Lys Thr Ile Ala Ser Ser Gly Ser Gly Ser Cys Leu Gly
            20                  25                  30

Leu Pro Lys Cys Trp Asp Tyr Arg Arg Glu His Arg Ala Arg Pro Thr
            35                  40                  45

Ile Val Phe Ser Lys His Val Tyr Thr Tyr Ser Met Arg Met Gln Ile
    50                  55                  60

Glu Ile Ser Thr Asn Ile Ser Gln
65                  70
```

<210> SEQ ID NO 70
<211> LENGTH: 71
<212> TYPE: PRT
<213> ORGANISM: Homo sapiens
<220> FEATURE:
<221> NAME/KEY: misc_feature
<223> OTHER INFORMATION: Incyte Clone No: 1359283

<400> SEQUENCE: 70

```
Met Arg Leu Thr Gly Leu Thr Leu Leu Ser Leu Met Glu Ser Leu
1               5                   10                  15

Gly Gln Val Glu Asp Arg Phe Phe Ser Thr His Arg Arg Phe Pro His
            20                  25                  30

His Thr Pro Ile Ser Gly Leu Leu Cys Arg Glu Phe Ser Leu Pro Lys
            35                  40                  45

Arg Ser Gly Val Pro Trp Thr Arg Val Leu Ile Ser Cys Ile Trp Arg
    50                  55                  60

Ser Gly Ala Gly Lys Arg Met
65                  70
```

<210> SEQ ID NO 71
<211> LENGTH: 247
<212> TYPE: PRT
<213> ORGANISM: Homo sapiens
<220> FEATURE:
<221> NAME/KEY: misc_feature
<223> OTHER INFORMATION: Incyte Clone No: 1450703

<400> SEQUENCE: 71

```
Met His Leu Ala Arg Leu Val Gly Ser Cys Leu Leu Leu Leu Leu
1               5                   10                  15

Gly Ala Leu Ser Gly Trp Ala Ala Ser Asp Asp Pro Ile Glu Lys Val
            20                  25                  30

Ile Glu Gly Ile Asn Arg Gly Leu Ser Asn Ala Glu Arg Glu Val Gly
            35                  40                  45

Lys Ala Leu Asp Gly Ile Asn Ser Gly Ile Thr His Ala Gly Arg Glu
    50                  55                  60
```

```
Val Glu Lys Val Phe Asn Gly Leu Ser Asn Met Gly Ser His Thr Gly
 65                  70                  75                  80

Lys Glu Leu Asp Lys Gly Val Gln Gly Leu Asn His Gly Met Asp Lys
                 85                  90                  95

Val Ala His Glu Ile Asn His Gly Ile Gly Gln Ala Gly Lys Glu Ala
            100                 105                 110

Glu Lys Leu Gly His Gly Val Asn Asn Ala Ala Gly Gln Ala Gly Lys
        115                 120                 125

Glu Ala Asp Lys Ala Val Gln Gly Phe His Thr Gly Val His Gln Ala
    130                 135                 140

Gly Lys Glu Ala Glu Lys Leu Gly Gln Gly Val Asn His Ala Ala Asp
145                 150                 155                 160

Gln Ala Gly Lys Glu Val Glu Lys Leu Gly Gln Gly Ala His His Ala
                165                 170                 175

Ala Gly Gln Ala Gly Lys Glu Leu Gln Asn Ala His Asn Gly Val Asn
            180                 185                 190

Gln Ala Ser Lys Glu Ala Asn Gln Leu Leu Asn Gly Asn His Gln Ser
        195                 200                 205

Gly Ser Ser His Gln Gly Gly Ala Thr Thr Pro Leu Ala Ser
    210                 215                 220

Gly Ala Ser Val Asn Thr Pro Phe Ile Asn Leu Pro Ala Leu Trp Arg
225                 230                 235                 240

Ser Val Ala Asn Ile Met Pro
                245

<210> SEQ ID NO 72
<211> LENGTH: 73
<212> TYPE: PRT
<213> ORGANISM: Homo sapiens
<220> FEATURE:
<221> NAME/KEY: misc_feature
<223> OTHER INFORMATION: Incyte Clone No: 1910668

<400> SEQUENCE: 72

Met Thr Cys Trp Met Leu Pro Pro Ile Ser Phe Leu Ser Tyr Leu Pro
 1               5                  10                  15

Leu Trp Leu Gly Pro Ile Trp Pro Cys Ser Gly Ser Thr Leu Gly Lys
             20                  25                  30

Pro Asp Pro Gly Val Trp Pro Ser Leu Phe Arg Pro Trp Asp Ala Ala
         35                  40                  45

Ser Pro Gly Asn Tyr Ala Leu Ser Arg Gly Glu Asn Gln Tyr Glu Lys
     50                  55                  60

Trp Gly Gln Gly Thr His Ser Ser Leu
 65                  70

<210> SEQ ID NO 73
<211> LENGTH: 70
<212> TYPE: PRT
<213> ORGANISM: Homo sapiens
<220> FEATURE:
<221> NAME/KEY: misc_feature
<223> OTHER INFORMATION: Incyte Clone No: 1955143

<400> SEQUENCE: 73

Met Gly Arg Leu Arg Tyr Phe Phe Ser Leu Leu Leu Arg Trp Gly
 1               5                  10                  15

Gln Leu Leu Gly Ala Asp Glu Phe Cys Cys His Lys Ser Tyr Ile Ala
             20                  25                  30
```

-continued

```
His Leu Val Cys Thr Glu Ser Ala Ile Leu Asn Pro Gly His Ala Leu
        35                  40                  45

Glu Leu Tyr Lys Lys Asn Leu Gln Val Ser Ile Leu Ser Pro Tyr Pro
 50                  55                  60

Thr Asp Pro Ile His Leu
 65                  70

<210> SEQ ID NO 74
<211> LENGTH: 67
<212> TYPE: PRT
<213> ORGANISM: Homo sapiens
<220> FEATURE:
<221> NAME/KEY: misc_feature
<223> OTHER INFORMATION: Incyte Clone No: 1961637

<400> SEQUENCE: 74

Met Met Phe Thr Ser Leu Ser Leu Ala Leu Pro Phe Leu Leu Gln Thr
 1               5                  10                  15

Met Leu Cys Leu Arg Ala Leu Leu Ile Ala Val Pro His Gly His Asp
             20                  25                  30

Trp Asn Arg Asp Ala Thr Ser Phe Tyr Thr Ser Thr Val Ser Trp Val
        35                  40                  45

Lys Ser Phe Phe Leu Phe Val Leu Asp Gly Val Ser Leu Leu Leu Pro
 50                  55                  60

Arg Leu Glu
 65

<210> SEQ ID NO 75
<211> LENGTH: 91
<212> TYPE: PRT
<213> ORGANISM: Homo sapiens
<220> FEATURE:
<221> NAME/KEY: misc_feature
<223> OTHER INFORMATION: Incyte Clone No: 1990762

<400> SEQUENCE: 75

Met Trp Pro Thr Thr Trp Ala Trp Ser Trp Val Gln Thr Leu Thr Leu
 1               5                  10                  15

Ala Leu Leu Ile Ser Cys Val Thr Leu Gly Gln Leu Ile Thr Thr Leu
             20                  25                  30

Gln Val Ser Phe Leu Ile Cys Glu Met Asp Val Ile Ile Gly Cys Asp
        35                  40                  45

Glu Met Ile Pro Ser Gly Ser Leu Val Leu Leu Trp Pro Pro Pro Leu
 50                  55                  60

Leu Leu Leu Gly Glu Phe Trp Ile Trp Asn Pro Val Ser Arg Ile Leu
 65                  70                  75                  80

Phe Trp Leu Cys His Val Pro Ala Gly Gln Leu
             85                  90

<210> SEQ ID NO 76
<211> LENGTH: 56
<212> TYPE: PRT
<213> ORGANISM: Homo sapiens
<220> FEATURE:
<221> NAME/KEY: misc_feature
<223> OTHER INFORMATION: Incyte Clone No: 1994131

<400> SEQUENCE: 76

Met Asn Glu Trp Trp Leu Leu Leu Leu His Leu His Pro Pro Arg
 1               5                  10                  15

Val Ile Ser Pro Phe Trp Phe Ile Val Ser Val Leu Thr Ala Cys Asp
             20                  25                  30
```

```
Asn Arg Lys Tyr Ile Leu Leu Arg Thr Val Pro Val Phe Ser Phe Pro
            35                  40                  45

Glu Asn Thr Tyr Phe Asp Val Gly
    50                  55

<210> SEQ ID NO 77
<211> LENGTH: 112
<212> TYPE: PRT
<213> ORGANISM: Homo sapiens
<220> FEATURE:
<221> NAME/KEY: misc_feature
<223> OTHER INFORMATION: Incyte Clone No: 1997745

<400> SEQUENCE: 77

Met Pro Leu Phe Leu Ser Ile Pro Ser Leu Phe Leu Thr Leu Ser Gly
1               5                   10                  15

Leu Gly Leu Ala Val Gln Ser Pro Ala Gly Gly Cys Trp Gly Leu Ser
            20                  25                  30

Leu Cys Arg His Cys Val Phe Leu Arg Gly Cys Pro Gln Asn Thr Pro
            35                  40                  45

Pro Ala Pro Trp Gly Ser Ser Gly Ser His Phe Ser Trp Ser Leu Arg
    50                  55                  60

Ser Gln Lys Gln Leu Leu Gln Glu Ala Lys Lys Arg Leu Gly Trp Leu
65                  70                  75                  80

Leu Val Leu Met Met Ala Phe Ile Leu Leu Gly His Phe Gly Tyr Ile
                85                  90                  95

His Gly His Cys Phe His Leu Ser Phe Leu Pro Val Pro Pro Leu Pro
            100                 105                 110

<210> SEQ ID NO 78
<211> LENGTH: 54
<212> TYPE: PRT
<213> ORGANISM: Homo sapiens
<220> FEATURE:
<221> NAME/KEY: misc_feature
<223> OTHER INFORMATION: Incyte Clone No: 2009035

<400> SEQUENCE: 78

Met Met Leu Gln Pro Val Asp Leu Leu Gln Ser Tyr Leu Leu Leu Leu
1               5                   10                  15

Tyr Cys Trp Ser Phe Ser Leu Leu Phe Thr Leu Leu Cys Asn Ala Val
            20                  25                  30

Arg Asn Asp Phe Phe His Lys Leu Phe Ser Ile Tyr Trp Met Tyr Asn
            35                  40                  45

Leu Thr His Ser Lys His
    50

<210> SEQ ID NO 79
<211> LENGTH: 57
<212> TYPE: PRT
<213> ORGANISM: Homo sapiens
<220> FEATURE:
<221> NAME/KEY: misc_feature
<223> OTHER INFORMATION: Incyte Clone No: 2009152

<400> SEQUENCE: 79

Met Lys Phe Tyr Ala Val Leu Leu Ser Ile Cys Leu Leu Leu Ser Cys
1               5                   10                  15

Trp Cys Ala Cys His Val Arg Asp Cys Asn Leu Ile Cys Leu Phe Ser
            20                  25                  30

Thr Val Lys Ala Ile Thr Arg Glu Leu Leu Gln Leu Pro Ser Tyr Val
```

```
                      35                  40                  45

Lys Arg Phe Phe Phe Asn Ser Leu Arg
    50                  55

<210> SEQ ID NO 80
<211> LENGTH: 52
<212> TYPE: PRT
<213> ORGANISM: Homo sapiens
<220> FEATURE:
<221> NAME/KEY: misc_feature
<223> OTHER INFORMATION: Incyte Clone No: 2061752

<400> SEQUENCE: 80

Met Gln Arg Leu Gly Lys Ala Pro Gly Thr Trp Gln Ala Ile Ser Lys
1               5                   10                  15

Cys Trp Leu Leu Leu Leu Leu Ser Leu Pro Phe Ser Gln Ser Ile Ile
            20                  25                  30

Ile Ser Leu Arg Ala Gly Thr Met Ser Tyr Leu Pro Leu Tyr Phe Pro
        35                  40                  45

Gln Tyr Phe Pro
    50

<210> SEQ ID NO 81
<211> LENGTH: 64
<212> TYPE: PRT
<213> ORGANISM: Homo sapiens
<220> FEATURE:
<221> NAME/KEY: misc_feature
<223> OTHER INFORMATION: Incyte Clone No: 2061933

<400> SEQUENCE: 81

Met Lys Leu Leu Leu Leu Lys Leu Asp Phe Phe Ile Leu Leu Gly Ser
1               5                   10                  15

Glu Ser Arg Cys Leu Val Asp Val Gln Tyr Val Ile Phe Phe Leu
            20                  25                  30

Ile Glu Cys Val His Leu Lys Ser Ser Leu Thr Phe Leu Glu Arg Leu
        35                  40                  45

Leu Ser Ile Asn Asn Gly Ile Leu Glu Glu Lys Trp Phe Phe Lys Ser
    50                  55                  60

<210> SEQ ID NO 82
<211> LENGTH: 65
<212> TYPE: PRT
<213> ORGANISM: Homo sapiens
<220> FEATURE:
<221> NAME/KEY: misc_feature
<223> OTHER INFORMATION: Incyte Clone No: 2081422

<400> SEQUENCE: 82

Met Lys Pro Leu Ile Pro Phe Leu Ser Pro Pro Leu Leu Pro Leu
1               5                   10                  15

Thr Phe Phe Leu Ser Ser Leu Leu Leu Ser Pro Leu Cys Arg Ala Leu
            20                  25                  30

Gly Thr Ser Gln Ala Val Pro Pro Leu Arg Ala Leu Ser Val Thr Asp
        35                  40                  45

Ala His Gly Ser Leu Leu Leu His Pro Lys Thr Leu Ala Cys Pro Cys
    50                  55                  60

Leu
65

<210> SEQ ID NO 83
<211> LENGTH: 56
```

-continued

```
<212> TYPE: PRT
<213> ORGANISM: Homo sapiens
<220> FEATURE:
<221> NAME/KEY: misc_feature
<223> OTHER INFORMATION: Incyte Clone No: 2101278

<400> SEQUENCE: 83

Met Arg Ala Asp Arg Leu Leu Pro Ile Ser Ala Leu Cys Leu Leu Tyr
1               5                  10                  15

Thr Pro Gly Gly Ala Leu Glu Pro Ala Gln Val Gly Tyr Thr Ile Phe
            20                  25                  30

Leu Asn Ser Ile Trp Leu Pro Ala Tyr Phe Phe His Leu Phe Thr Val
        35                  40                  45

Ile Ser Gly Val Phe Leu Phe Ile
    50                  55

<210> SEQ ID NO 84
<211> LENGTH: 120
<212> TYPE: PRT
<213> ORGANISM: Homo sapiens
<220> FEATURE:
<221> NAME/KEY: misc_feature
<223> OTHER INFORMATION: Incyte Clone No: 2121353

<400> SEQUENCE: 84

Met Pro Ala Leu Pro Pro Gly Phe Ser Gln Ala Gly Ser Cys Val Pro
1               5                  10                  15

Thr Gly Ser Ser Leu Val Leu Cys Leu Leu Ala Ala Ser Leu Leu Leu
            20                  25                  30

Phe Val Pro Thr Leu Ala Leu Leu Thr Gly Ala Thr Thr Cys Trp Cys
        35                  40                  45

Leu His Asn Lys Arg Leu Ala Leu Arg Pro Leu Ala Trp Gln Gly Leu
    50                  55                  60

Trp Gly Leu Val Ser Thr Arg Leu Ser His Gly Arg Thr Ser Phe Tyr
65                  70                  75                  80

Phe Asn Ser Leu Pro Leu Gln Thr Asn Ser Ser Thr Cys Gln Asn His
                85                  90                  95

Ser Trp Asp Ser Gly Ala Arg Ala Thr Ala Leu Ala Ser Gly Arg Thr
            100                 105                 110

Gln Glu Gly Gly Val Gly Ser Val
        115                 120

<210> SEQ ID NO 85
<211> LENGTH: 67
<212> TYPE: PRT
<213> ORGANISM: Homo sapiens
<220> FEATURE:
<221> NAME/KEY: misc_feature
<223> OTHER INFORMATION: Incyte Clone No: 2241736

<400> SEQUENCE: 85

Met Asn Ser Leu Val Leu Phe Leu Gly His Leu Gly Leu Leu Ile Lys
1               5                  10                  15

Asp Cys Val Leu Leu Phe Ala Met Ser Lys Val Ser Gln Lys Gln Lys
            20                  25                  30

Val Leu Gly Pro Phe Gly Ser Pro Glu Leu Glu Ser Leu Gly Ile Gly
        35                  40                  45

Pro Arg Tyr Leu His Phe His Arg Phe Leu Val Gly Asp Phe Leu Gln
    50                  55                  60

Ala Lys Val
65
```

<210> SEQ ID NO 86
<211> LENGTH: 62
<212> TYPE: PRT
<213> ORGANISM: Homo sapiens
<220> FEATURE:
<221> NAME/KEY: misc_feature
<223> OTHER INFORMATION: Incyte Clone No: 2271935

<400> SEQUENCE: 86

Met Ala Trp Leu Ser Phe Ala Ala Val Glu Met Thr Leu Leu His
1               5                   10                  15

Ser Ser Ser Leu Leu Ser Phe Ala Lys Val Val Leu Ser Leu Pro Glu
            20                  25                  30

Ile Arg Pro Phe Gly Asp Gly Asn Phe Ser Leu Lys Gln Ser Ser Lys
            35                  40                  45

Gln Asn Pro Asn Pro Ala Arg Val Gly Arg Lys Ser Met Phe
        50                  55                  60

<210> SEQ ID NO 87
<211> LENGTH: 75
<212> TYPE: PRT
<213> ORGANISM: Homo sapiens
<220> FEATURE:
<221> NAME/KEY: misc_feature
<223> OTHER INFORMATION: Incyte Clone No: 2295344

<400> SEQUENCE: 87

Met Met Ile Leu Leu Ser Leu Leu Val Ala Leu Ile Ser Val Ser Leu
1               5                   10                  15

Val Phe Leu Gly Leu Val Arg Phe Ser Arg Glu Asp Phe Ser Phe Pro
            20                  25                  30

Leu Trp Arg Glu Lys Ala Phe Tyr Gln His Ser Ser Ser Val Gly
            35                  40                  45

Glu Arg Leu Gln Ala Leu Arg Lys His Ala Phe Thr Leu Phe Gly Thr
        50                  55                  60

Ile Pro Leu Leu Val Thr Val Pro Gln Val Pro
65                  70                  75

<210> SEQ ID NO 88
<211> LENGTH: 80
<212> TYPE: PRT
<213> ORGANISM: Homo sapiens
<220> FEATURE:
<221> NAME/KEY: misc_feature
<223> OTHER INFORMATION: Incyte Clone No: 2303994

<400> SEQUENCE: 88

Met Asn Ser Ile Phe Phe Leu Ser Leu Cys Leu Pro Leu Trp Val Ser
1               5                   10                  15

Leu Leu Trp Ala Lys Pro Leu Glu Met His Lys Thr Ser Arg His Gly
            20                  25                  30

Phe Trp Gln Lys Leu His Asp Phe Lys Leu Ala Leu Leu Leu Leu Thr
            35                  40                  45

Phe His Arg Glu Lys Ile Phe Pro Leu Lys Lys Thr Gly Leu Val Ile
        50                  55                  60

Phe Ser Leu Val Ala Leu Ser Arg Asp Ile Ser Ala Leu His Tyr Thr
65                  70                  75                  80

<210> SEQ ID NO 89
<211> LENGTH: 50
<212> TYPE: PRT

```
<213> ORGANISM: Homo sapiens
<220> FEATURE:
<221> NAME/KEY: misc_feature
<223> OTHER INFORMATION: Incyte Clone No: 2497805

<400> SEQUENCE: 89

Met Arg Pro Ala Arg Leu Gly Pro Arg Cys Ser Asp Leu Asp Phe Gly
1               5                   10                  15

Leu Val Leu Ser Ser Trp Leu Arg Leu Ala Arg Cys Pro Leu Glu Ser
            20                  25                  30

Ser Phe Gly Phe Ala Phe Phe Val Cys Leu Phe Ser Pro Asn Phe Cys
            35                  40                  45

Gln Thr
     50

<210> SEQ ID NO 90
<211> LENGTH: 116
<212> TYPE: PRT
<213> ORGANISM: Homo sapiens
<220> FEATURE:
<221> NAME/KEY: misc_feature
<223> OTHER INFORMATION: Incyte Clone No: 2646362

<400> SEQUENCE: 90

Met Trp Trp Ala Leu Cys Ser Met Leu Pro Leu Gly Cys Ala Cys
1               5                   10                  15

Ser Ser Gly Cys Trp Gly Ser Gly Pro Thr Pro Leu Leu Ala Glu Pro
            20                  25                  30

Thr Phe Leu Cys Val Ser Ser Arg Pro His Asn Pro Leu Ser Phe Leu
            35                  40                  45

Ser Val Leu Pro Cys Ser Arg Gly Pro Gly Pro Ser Gly Leu Gln Gly
        50                  55                  60

Asp Gly Ala Gly Leu Pro Ala His Leu Gly Pro Leu Ser Cys Ile Cys
65                  70                  75                  80

Leu Pro Ser Leu Leu Cys Asp Leu Gly Glu Arg Gln Cys Pro Leu Trp
                85                  90                  95

Ala Val Arg Ser Thr Gln Cys Leu Ile Ala Gly Lys Lys Val Leu Gln
            100                 105                 110

Arg Leu Cys Pro
        115

<210> SEQ ID NO 91
<211> LENGTH: 67
<212> TYPE: PRT
<213> ORGANISM: Homo sapiens
<220> FEATURE:
<221> NAME/KEY: misc_feature
<223> OTHER INFORMATION: Incyte Clone No: 2657146

<400> SEQUENCE: 91

Met Ile Cys Gln Cys Leu Arg Leu Leu Val Leu Val Thr Leu Leu
1               5                   10                  15

Ile Cys Phe Ser Pro Asp Arg Leu Thr Cys Pro Leu Asn Ser Ala Val
            20                  25                  30

Val Leu Ala Ser Tyr Ala Val Gln Cys Lys Ser Gln Arg Glu His Phe
            35                  40                  45

Thr Asp Gly Gln Val Val Leu Ile Ser Val Trp Arg Lys Ser Leu Val
        50                  55                  60

Pro Pro Ala
65
```

-continued

```
<210> SEQ ID NO 92
<211> LENGTH: 538
<212> TYPE: PRT
<213> ORGANISM: Homo sapiens
<220> FEATURE:
<221> NAME/KEY: misc_feature
<223> OTHER INFORMATION: Incyte Clone No: 2755786

<400> SEQUENCE: 92
```

Met Ala Gly Ala Arg Ala Ala Ala Ala Ser Ala Gly Ser Ser
1               5                   10                  15

Ala Ser Ser Gly Asn Gln Pro Gln Glu Leu Gly Leu Glu Leu
            20                  25                  30

Leu Glu Glu Phe Ser Arg Thr Gln Tyr Arg Ala Lys Asp Gly Ser Gly
            35                  40                  45

Thr Gly Gly Ser Lys Val Glu Arg Ile Glu Lys Arg Cys Leu Glu Leu
50                  55                  60

Phe Gly Arg Asp Tyr Cys Phe Ser Val Ile Pro Asn Thr Asn Gly Asp
65                  70                  75                  80

Ile Cys Gly His Tyr Pro Arg His Ile Val Phe Leu Glu Tyr Glu Ser
                85                  90                  95

Ser Glu Lys Glu Lys Asp Thr Phe Glu Ser Thr Val Gln Val Ser Lys
            100                 105                 110

Leu Gln Asp Leu Ile His Arg Ser Lys Met Ala Arg Cys Arg Gly Arg
            115                 120                 125

Phe Val Cys Pro Val Ile Leu Phe Lys Gly Lys His Ile Cys Arg Ser
130                 135                 140

Ala Thr Leu Ala Gly Trp Gly Glu Leu Tyr Gly Arg Ser Gly Tyr Asn
145                 150                 155                 160

Tyr Phe Phe Ser Gly Gly Ala Asp Asp Ala Trp Ala Asp Val Glu Asp
                165                 170                 175

Val Thr Glu Glu Asp Cys Ala Leu Arg Ser Gly Asp Thr His Leu Phe
            180                 185                 190

Asp Lys Val Arg Gly Tyr Asp Ile Lys Leu Leu Arg Tyr Leu Ser Val
            195                 200                 205

Lys Tyr Ile Cys Asp Leu Met Val Glu Asn Lys Val Lys Phe Gly
210                 215                 220

Met Asn Val Thr Ser Ser Glu Lys Val Asp Lys Ala Gln Arg Tyr Ala
225                 230                 235                 240

Asp Phe Thr Leu Leu Ser Ile Pro Tyr Pro Gly Cys Glu Phe Lys
                245                 250                 255

Glu Tyr Lys Asp Arg Asp Tyr Met Ala Glu Gly Leu Ile Phe Asn Trp
            260                 265                 270

Lys Gln Asp Tyr Val Asp Ala Pro Leu Ser Ile Pro Asp Phe Leu Thr
            275                 280                 285

His Ser Leu Asn Ile Asp Trp Ser Gln Tyr Gln Cys Trp Asp Leu Val
            290                 295                 300

Gln Gln Thr Gln Asn Tyr Leu Lys Leu Leu Ser Leu Val Asn Ser
305                 310                 315                 320

Asp Asp Asp Ser Gly Leu Leu Val His Cys Ile Ser Gly Trp Asp Arg
                325                 330                 335

Thr Pro Leu Phe Ile Ser Leu Leu Arg Leu Ser Leu Trp Ala Asp Gly
            340                 345                 350

Leu Ile His Thr Ser Leu Lys Pro Thr Glu Ile Leu Tyr Leu Thr Val
            355                 360                 365

-continued

```
Ala Tyr Asp Trp Phe Leu Phe Gly His Met Leu Val Asp Arg Leu Ser
    370                 375                 380

Lys Gly Glu Glu Ile Phe Phe Cys Phe Asn Phe Leu Lys His Ile
385                 390                 395                 400

Thr Ser Glu Glu Phe Ser Ala Leu Lys Thr Gln Arg Arg Lys Ser Leu
                405                 410                 415

Pro Ala Arg Asp Gly Gly Phe Thr Leu Glu Asp Ile Cys Met Leu Arg
            420                 425                 430

Arg Lys Asp Arg Gly Ser Thr Thr Ser Leu Gly Ser Asp Phe Ser Leu
        435                 440                 445

Val Met Glu Ser Ser Pro Gly Ala Thr Gly Ser Phe Tyr Glu Ala
    450                 455                 460

Val Glu Leu Val Pro Ala Gly Ala Pro Thr Gln Ala Ala Trp Leu Ala
465                 470                 475                 480

Ala Leu Ser Asp Arg Glu Thr Arg Leu Gln Glu Val Arg Ser Ala Phe
                485                 490                 495

Leu Ala Ala Tyr Ser Ser Thr Val Gly Leu Arg Ala Val Ala Pro Ser
            500                 505                 510

Pro Ser Gly Ala Ile Gly Gly Leu Leu Glu Gln Phe Ala Arg Gly Val
        515                 520                 525

Gly Leu Arg Ser Ile Ser Ser Asn Ala Leu
    530                 535

<210> SEQ ID NO 93
<211> LENGTH: 58
<212> TYPE: PRT
<213> ORGANISM: Homo sapiens
<220> FEATURE:
<221> NAME/KEY: misc_feature
<223> OTHER INFORMATION: Incyte Clone No: 2831245

<400> SEQUENCE: 93

Met Glu Met Lys Gly Ser Arg Val Trp Leu Leu Leu Phe Met Trp
1               5                   10                  15

Lys Ala Arg Pro Thr Phe Phe Gln Ser Cys Val Val Pro Phe Ile Leu
                20                  25                  30

Ser Pro Gln Asn Cys Val Gln Thr His Ser Leu Gly Pro Gly Val Trp
            35                  40                  45

Leu Gly Val Phe Pro Ser Gly Ser Leu His
        50                  55

<210> SEQ ID NO 94
<211> LENGTH: 119
<212> TYPE: PRT
<213> ORGANISM: Homo sapiens
<220> FEATURE:
<221> NAME/KEY: misc_feature
<223> OTHER INFORMATION: Incyte Clone No: 3116250

<400> SEQUENCE: 94

Met Lys Val Leu Ile Ser Ser Leu Leu Leu Leu Pro Leu Met Leu
1               5                   10                  15

Met Ser Met Val Ser Ser Ser Leu Asn Pro Gly Val Ala Arg Gly His
                20                  25                  30

Arg Asp Arg Gly Gln Ala Ser Arg Trp Leu Gln Glu Gly Gly Gln
            35                  40                  45

Glu Cys Glu Cys Lys Asp Trp Phe Leu Arg Ala Pro Arg Arg Lys Phe
        50                  55                  60

Met Thr Val Ser Gly Leu Pro Lys Lys Gln Cys Pro Cys Asp His Phe
```

```
                65                  70                  75                  80
Lys Gly Asn Val Lys Lys Thr Arg His Gln Arg His Arg Lys Pro
                    85                  90                  95

Asn Lys His Ser Arg Ala Cys Gln Gln Phe Leu Lys Gln Cys Gln Leu
                100                 105                 110

Arg Ser Phe Ala Leu Pro Leu
            115

<210> SEQ ID NO 95
<211> LENGTH: 128
<212> TYPE: PRT
<213> ORGANISM: Homo sapiens
<220> FEATURE:
<221> NAME/KEY: misc_feature
<223> OTHER INFORMATION: Incyte Clone No: 3129630

<400> SEQUENCE: 95

Met Ala Tyr Ser Thr Val Gln Arg Val Ala Leu Ala Ser Gly Leu Val
1               5                   10                  15

Leu Ala Leu Ser Leu Leu Leu Pro Lys Ala Phe Leu Ser Arg Gly Lys
                20                  25                  30

Arg Gln Glu Pro Pro Thr Pro Glu Gly Lys Leu Gly Arg Phe Pro
            35                  40                  45

Pro Met Met His His Gln Ala Pro Ser Asp Gly Gln Thr Pro Gly
        50                  55                  60

Ala Arg Phe Gln Arg Ser His Leu Ala Glu Ala Phe Ala Lys Ala Lys
65                  70                  75                  80

Gly Ser Gly Gly Gly Ala Gly Gly Gly Ser Gly Arg Gly Leu Met
                85                  90                  95

Gly Gln Ile Ile Pro Ile Tyr Gly Phe Gly Ile Phe Leu Tyr Ile Leu
                100                 105                 110

Tyr Ile Leu Phe Lys Val Ser Arg Ile Ile Leu Ile Ile Leu His Gln
            115                 120                 125

<210> SEQ ID NO 96
<211> LENGTH: 124
<212> TYPE: PRT
<213> ORGANISM: Homo sapiens
<220> FEATURE:
<221> NAME/KEY: misc_feature
<223> OTHER INFORMATION: Incyte Clone No: 007632

<400> SEQUENCE: 96

Met Tyr Lys Leu Ala Ser Cys Cys Leu Leu Phe Ile Gly Phe Leu Asn
1               5                   10                  15

Pro Leu Leu Ser Leu Pro Leu Leu Asp Ser Arg Glu Ile Ser Phe Gln
                20                  25                  30

Leu Ser Ala Pro His Glu Asp Ala Arg Leu Thr Pro Glu Glu Leu Glu
            35                  40                  45

Arg Ala Ser Leu Leu Gln Ile Leu Pro Glu Met Leu Gly Ala Glu Arg
        50                  55                  60

Gly Asp Ile Leu Arg Lys Ala Asp Ser Ser Thr Asn Ile Phe Asn Pro
65                  70                  75                  80

Arg Gly Asn Leu Arg Lys Phe Gln Asp Phe Ser Gly Gln Asp Pro Asn
                85                  90                  95

Ile Leu Leu Ser His Leu Leu Ala Arg Ile Trp Lys Pro Tyr Lys Lys
                100                 105                 110

Arg Glu Thr Pro Asp Cys Phe Trp Lys Tyr Cys Val
            115                 120
```

```
<210> SEQ ID NO 97
<211> LENGTH: 182
<212> TYPE: PRT
<213> ORGANISM: Homo sapiens
<220> FEATURE:
<221> NAME/KEY: misc_feature
<223> OTHER INFORMATION: Incyte Clone No: 1236968

<400> SEQUENCE: 97

Met Trp Pro Leu Ser Ser Asp Ser Ser Trp Ser Leu Trp Ile Ser Thr
1               5                   10                  15

Gly Met Ala Pro Ala Pro Ser Ser Ser Thr Arg Ser Phe Ser Glu Ser
            20                  25                  30

Leu Lys Gln Lys Leu Val Arg Val Leu Glu Glu Asn Leu Ile Leu Ser
        35                  40                  45

Glu Lys Ile Gln Gln Leu Glu Glu Gly Ala Ala Ile Ser Ile Val Ser
    50                  55                  60

Gly Gln Gln Ser His Thr Tyr Asp Asp Leu Leu His Lys Asn Gln Gln
65                  70                  75                  80

Leu Thr Met Gln Val Ala Cys Leu Asn Gln Glu Leu Ala Gln Leu Lys
                85                  90                  95

Lys Leu Glu Lys Thr Val Ala Ile Leu His Glu Ser Gln Arg Ser Leu
            100                 105                 110

Val Val Thr Asn Glu Tyr Leu Leu Gln Gln Leu Asn Lys Glu Pro Lys
        115                 120                 125

Gly Tyr Ser Gly Lys Ala Leu Leu Pro Pro Glu Lys Gly His His Leu
    130                 135                 140

Gly Arg Ser Ser Pro Phe Gly Lys Ser Thr Leu Ser Ser Ser Ser Pro
145                 150                 155                 160

Val Ala His Glu Thr Gly Gln Tyr Leu Ile Gln Ser Val Leu Asp Ala
                165                 170                 175

Ala Pro Glu Pro Gly Leu
            180

<210> SEQ ID NO 98
<211> LENGTH: 237
<212> TYPE: PRT
<213> ORGANISM: Homo sapiens
<220> FEATURE:
<221> NAME/KEY: misc_feature
<223> OTHER INFORMATION: Incyte Clone No: 1334153

<400> SEQUENCE: 98

Met Lys Gly Ile Leu Val Ala Gly Ile Thr Ala Val Leu Val Ala Ala
1               5                   10                  15

Val Glu Ser Leu Ser Cys Val Pro Cys Asn Ser Trp Glu Lys Ser Cys
            20                  25                  30

Val Asn Ser Ile Ala Ser Glu Cys Pro Ser His Ala Asn Thr Ser Cys
        35                  40                  45

Ile Ser Ser Ser Ala Ser Ser Leu Glu Thr Pro Val Arg Leu Tyr
    50                  55                  60

Gln Asn Met Phe Cys Ser Ala Glu Asn Cys Ser Glu Glu Thr His Ile
65                  70                  75                  80

Thr Ala Phe Thr Val His Val Ser Ala Glu Glu His Phe His Phe Val
                85                  90                  95

Ser Gln Cys Cys Gln Gly Lys Gly Cys Ser Asn Thr Ser Asp Ala Leu
            100                 105                 110
```

-continued

```
Asp Pro Pro Leu Lys Asn Val Ser Ser Asn Ala Glu Cys Pro Ala Cys
        115                 120                 125

Tyr Glu Ser Asn Gly Thr Ser Cys Arg Gly Lys Pro Trp Lys Cys Tyr
    130                 135                 140

Glu Glu Glu Gln Cys Val Phe Leu Val Ala Glu Leu Lys Asn Asp Ile
145                 150                 155                 160

Glu Ser Lys Ser Leu Val Leu Lys Gly Cys Ser Asn Val Ser Asn Ala
                165                 170                 175

Thr Cys Gln Phe Leu Ser Gly Glu Asn Lys Thr Leu Gly Gly Val Ile
            180                 185                 190

Phe Arg Lys Phe Glu Cys Ala Asn Val Asn Ser Leu Thr Pro Thr Ser
        195                 200                 205

Ala Pro Thr Thr Ser His Asn Val Gly Ser Lys Ala Ser Leu Tyr Leu
    210                 215                 220

Leu Ala Leu Ala Ser Leu Leu Leu Arg Gly Leu Leu Pro
225                 230                 235
```

<210> SEQ ID NO 99
<211> LENGTH: 160
<212> TYPE: PRT
<213> ORGANISM: Homo sapiens
<220> FEATURE:
<221> NAME/KEY: misc_feature
<223> OTHER INFORMATION: Incyte Clone No: 1396975

<400> SEQUENCE: 99

```
Met Arg Pro Gly Pro Met Leu Gln Ala Arg Val Ser Ile Pro Ala Ala
1               5                   10                  15

Leu Gly Thr Leu Phe Pro Arg Pro Gly Trp Ala Pro Gly Glu Val Ser
                20                  25                  30

Ser Glu Ile Ser Ser Arg Asp Leu Leu Asn Pro His Pro Ser Thr Pro
            35                  40                  45

Ser Cys Cys Ser Gln Ser Trp Ser Pro Met Ser Val Leu Glu Pro Asp
        50                  55                  60

Ser Arg Gly Pro Pro Ile Ser Leu Thr His Thr Gly Ile His Thr
65                  70                  75                  80

Pro Gln Lys Thr Ser Gln Met Arg Pro Asp Ser Gly Ser Arg Gly Met
                85                  90                  95

Cys Phe Cys Pro Cys Lys Gly Phe Gly Gly Gly Asn Ile Val Glu
            100                 105                 110

Ala Gly Lys Ser Pro Gln Thr Cys Ala His Ala Pro Pro Ala Leu Arg
        115                 120                 125

Phe His Ser Ala Phe Ser Glu Cys Pro Cys Cys Thr Gln Thr Thr Gly
    130                 135                 140

Gln Glu Arg Pro Ser Leu Pro Leu Gln Pro Leu Ser Leu Pro Phe Asn
145                 150                 155                 160
```

<210> SEQ ID NO 100
<211> LENGTH: 148
<212> TYPE: PRT
<213> ORGANISM: Homo sapiens
<220> FEATURE:
<221> NAME/KEY: misc_feature
<223> OTHER INFORMATION: Incyte Clone No: 1501749

<400> SEQUENCE: 100

```
Met Ala Ala Ser Pro Ala Arg Pro Ala Val Leu Ala Leu Thr Gly Leu
1               5                   10                  15

Ala Leu Leu Leu Leu Leu Cys Trp Gly Pro Gly Gly Ile Ser Gly Asn
```

-continued

```
                20                  25                  30
Lys Leu Lys Leu Met Leu Gln Lys Arg Glu Ala Pro Val Pro Thr Lys
             35                  40                  45

Thr Lys Val Ala Val Asp Glu Asn Lys Ala Lys Glu Phe Leu Gly Ser
 50                  55                  60

Leu Lys Arg Gln Lys Arg Gln Leu Trp Asp Arg Thr Arg Pro Glu Val
 65                  70                  75                  80

Gln Gln Trp Tyr Gln Gln Phe Leu Tyr Met Gly Phe Asp Glu Ala Lys
                 85                  90                  95

Phe Glu Asp Asp Ile Thr Tyr Trp Leu Asn Arg Asp Arg Asn Gly His
                100                 105                 110

Glu Tyr Tyr Gly Asp Tyr Tyr Gln Arg His Tyr Asp Glu Asp Ser Ala
            115                 120                 125

Ile Gly Pro Arg Ser Pro Tyr Gly Phe Arg His Gly Ala Ser Val Asn
130                 135                 140

Tyr Asp Asp Tyr
145

<210> SEQ ID NO 101
<211> LENGTH: 170
<212> TYPE: PRT
<213> ORGANISM: Homo sapiens
<220> FEATURE:
<221> NAME/KEY: misc_feature
<223> OTHER INFORMATION: Incyte Clone No: 1575240

<400> SEQUENCE: 101

Met Thr Pro Thr Lys Arg Glu Pro Ala Ala Pro Leu Leu Leu Arg
 1               5                  10                  15

Val Leu Pro Gln Leu Ser Ala Met Ser Leu Arg Leu Ser Thr Arg Arg
                20                  25                  30

Glu Asp Met Ile Gly Gln Thr Ser Gly Met Cys Ser Phe Cys Ser Phe
             35                  40                  45

Gln Asn Met Arg Gly Glu Ser Ile Trp Leu Leu Cys Leu Glu Glu Glu
 50                  55                  60

Gly Ala Gly Leu Cys Gln Asn Ser Leu Asp Lys Arg Phe Ser Gln Lys
 65                  70                  75                  80

Glu Gly Cys Ser Asp Asp Lys Ser Pro Leu His His Phe Pro Trp Leu
                 85                  90                  95

Ser Asp Ala Pro Pro Ser Ser His Ala Arg Thr Ser Glu Ile Arg Leu
                100                 105                 110

Pro Pro Asp Ile Thr Gln Pro Cys Leu Thr Lys Arg Gln Trp Phe Ile
            115                 120                 125

Pro Ser Leu Gly Glu Lys Arg Gly Asn Ala Lys Leu Leu His Gln Leu
        130                 135                 140

Leu Ile Leu Leu Pro Ala Arg Asn Pro Gly Tyr Leu Gln Val Ser Leu
145                 150                 155                 160

Pro Leu Val Trp Ser Trp Leu Ser Leu Phe
                165                 170

<210> SEQ ID NO 102
<211> LENGTH: 150
<212> TYPE: PRT
<213> ORGANISM: Homo sapiens
<220> FEATURE:
<221> NAME/KEY: misc_feature
<223> OTHER INFORMATION: Incyte Clone No: 1647884

<400> SEQUENCE: 102
```

```
Met Gly Ala Ala Ala Trp Ala Arg Pro Leu Ser Val Ser Phe Leu Leu
1               5                   10                  15

Leu Leu Leu Pro Leu Pro Gly Met Pro Ala Gly Ser Trp Asp Pro Ala
            20                  25                  30

Gly Tyr Leu Leu Tyr Cys Pro Cys Met Gly Lys Ala Ser Gln Ala Leu
                35                  40                  45

Cys Ser Asp Gly Glu Thr Glu Ala Gly Arg Lys Ala Thr Pro Gln
    50                  55                  60

Met Arg Pro Glu Thr Pro Ser Gln Val Gln Gly Arg Thr Ser Glu Arg
65              70                  75                  80

Asp Gly Ala Cys Ser Ser Pro Leu Cys Leu Ser Cys Lys Gly Thr Glu
                85                  90                  95

Gly Pro Thr Cys Pro Thr Phe His Leu Thr Asp Glu Lys Thr Glu Ala
            100                 105                 110

Gly Arg Gly Tyr Val Thr Cys Leu Arg Ser Lys Pro Val Gln Gly Pro
            115                 120                 125

Val Asn Gly Val Ser Gly Ala Gly Leu Asp Val Thr Asp Pro Arg Trp
        130                 135                 140

Leu Leu Val Ile Phe His
145             150
```

<210> SEQ ID NO 103
<211> LENGTH: 142
<212> TYPE: PRT
<213> ORGANISM: Homo sapiens
<220> FEATURE:
<221> NAME/KEY: misc_feature
<223> OTHER INFORMATION: Incyte Clone No: 1661144

<400> SEQUENCE: 103

```
Met Gly Cys Leu Val Trp Gly Pro Ser Trp Pro Pro Leu Ser Leu Leu
1               5                   10                  15

Ala Ser Leu Leu His Ser Gly Ile Ala Gly Arg Cys Leu Leu Cys Leu
            20                  25                  30

Phe Lys Gly Leu Ala Ala Ala Ala Ser Leu Gln Ile Arg Asp Leu Ala
            35                  40                  45

Ser Arg Leu Thr Thr Gly Pro Arg Thr Cys Arg Val Gln Pro Pro Pro
    50                  55                  60

His Pro Gln Ser Ser Pro Pro Trp Pro Gly Pro Gly Ala Glu Thr
65              70                  75                  80

Cys Arg Pro Leu Ser Arg Thr Val Gly Val Cys Pro Ser Asp Trp
                85                  90                  95

Pro Val Ser Trp Leu Leu Leu Pro Pro Leu Pro Glu Val Thr Cys
            100                 105                 110

Ser Cys Pro Arg Ile Lys Ala Arg Pro Glu Arg Thr Pro Glu Leu Leu
            115                 120                 125

Cys Ala Trp Gly Gly Arg Gly Lys His Ser Gln Leu Val Ala
        130                 135                 140
```

<210> SEQ ID NO 104
<211> LENGTH: 110
<212> TYPE: PRT
<213> ORGANISM: Homo sapiens
<220> FEATURE:
<221> NAME/KEY: misc_feature
<223> OTHER INFORMATION: Incyte Clone No: 1685409

<400> SEQUENCE: 104

```
Met Glu Thr Gly Arg Leu Leu Ser Leu Ser Ser Pro Leu Val Leu
1               5                   10                  15

Leu Gly Trp Glu Tyr Ser Ser Gln Thr Leu Asn Leu Val Pro Ser Thr
            20                  25                  30

Ser Ile Leu Ser Phe Val Pro Phe Ile Pro Leu His Leu Val Leu Phe
            35                  40                  45

Ala Leu Trp Tyr Leu Pro Val Pro His His Leu Tyr Pro Gln Gly Leu
50                  55                  60

Gly Asp His Ala Ala Glu Ala Glu Lys Gly Lys Arg Glu Glu Gly Gly
65                  70                  75                  80

Thr Gln Val Ala Leu Trp Leu Arg Val Gln Pro Ser Cys Pro Ser Pro
                85                  90                  95

Val Cys Leu Glu Pro Val Pro Pro Arg Ser Arg Phe Leu Leu
            100                 105                 110

<210> SEQ ID NO 105
<211> LENGTH: 120
<212> TYPE: PRT
<213> ORGANISM: Homo sapiens
<220> FEATURE:
<221> NAME/KEY: misc_feature
<223> OTHER INFORMATION: Incyte Clone No: 1731419

<400> SEQUENCE: 105

Met Ser Arg Ala Gly Met Leu Gly Val Val Cys Ala Leu Leu Val Trp
1               5                   10                  15

Ala Tyr Leu Ala Val Gly Lys Leu Val Val Arg Met Thr Phe Thr Glu
            20                  25                  30

Leu Cys Thr His His Pro Trp Ser Leu Arg Cys Glu Ser Phe Cys Arg
            35                  40                  45

Ser Arg Val Thr Ala Cys Leu Pro Ala Pro Ala Pro Trp Leu Arg Pro
50                  55                  60

Phe Leu Cys Pro Met Leu Phe Ser Asp Arg Asn Pro Val Glu Cys His
65                  70                  75                  80

Leu Phe Gly Glu Ala Val Ser Asp Pro Val Cys Lys Gly Leu Leu Pro
                85                  90                  95

His Tyr Phe Trp His Pro Thr Phe Pro Val Lys Ala Asn Cys Leu
            100                 105                 110

Val Ser Phe Cys Pro Thr Thr Val
            115                 120

<210> SEQ ID NO 106
<211> LENGTH: 135
<212> TYPE: PRT
<213> ORGANISM: Homo sapiens
<220> FEATURE:
<221> NAME/KEY: misc_feature
<223> OTHER INFORMATION: Incyte Clone No: 2650265

<400> SEQUENCE: 106

Met Ala Arg Phe Trp Val Cys Val Ala Gly Ala Gly Phe Phe Leu Ala
1               5                   10                  15

Phe Leu Val Leu His Ser Arg Phe Cys Gly Ser Pro Val Leu Arg Asn
            20                  25                  30

Phe Thr Phe Ala Val Ser Trp Thr Glu Lys Ile Leu Tyr Arg Leu
            35                  40                  45

Asp Val Gly Trp Pro Lys His Pro Glu Tyr Pro Thr Gly Thr Thr Phe
50                  55                  60

Cys Val Ala Val Asp Ser Leu Asn Gly Leu Val Tyr Ile Gly Gln Arg
```

-continued

```
                65                  70                  75                  80
Gly Asp Asn Ile Pro Lys Ile Leu Val Phe Thr Glu Asp Gly Tyr Phe
                    85                  90                  95

Leu Arg Ala Trp Asn Tyr Thr Val Asp Thr Pro His Gly Ile Phe Ala
                100                 105                 110

Ala Ser Thr Leu Tyr Glu Gln Ser Val Trp Ile Thr Asp Val Gly Ser
                115                 120                 125

Gly Met Tyr Ser Asn Ile Tyr
            130                 135

<210> SEQ ID NO 107
<211> LENGTH: 301
<212> TYPE: PRT
<213> ORGANISM: Homo sapiens
<220> FEATURE:
<221> NAME/KEY: misc_feature
<223> OTHER INFORMATION: Incyte Clone No: 2677129

<400> SEQUENCE: 107

Met Leu Met Ile Ile Ile Glu Pro Phe Ser Val Leu Ile Leu Phe
1               5                   10                  15

Lys Ser Gly Ile Leu Ala Asp Phe Phe Ala Leu Leu Leu Ile Asn
                20                  25                  30

Phe Phe Leu Val Ser Phe Phe Leu Ala Tyr Pro Leu Phe Asn Asn Gln
            35                  40                  45

Ile Asn Ser Arg Ser Met Asn Glu Ile Lys Asn Leu Gln Tyr Leu Pro
        50                  55                  60

Arg Thr Ser Glu Pro Arg Glu Val Leu Phe Glu Asp Arg Thr Arg Ala
65                  70                  75                  80

His Ala Asp His Val Gly Gln Gly Phe Asp Trp Gln Ser Thr Ala Ala
                85                  90                  95

Val Gly Val Leu Lys Ala Val Gln Phe Gly Glu Trp Ser Asp Gln Pro
                100                 105                 110

Arg Ile Thr Lys Asp Val Ile Cys Phe His Ala Glu Asp Phe Thr Asp
            115                 120                 125

Val Val Gln Arg Leu Gln Leu Asp Leu His Glu Pro Pro Val Ser Gln
        130                 135                 140

Cys Val Gln Trp Val Asp Glu Ala Lys Leu Asn Gln Met Arg Arg Glu
145                 150                 155                 160

Gly Ile Arg Tyr Ala Arg Ile Gln Leu Cys Asp Asn Asp Ile Tyr Phe
                165                 170                 175

Ile Pro Arg Asn Val Ile His Gln Phe Lys Thr Val Ser Ala Val Cys
                180                 185                 190

Ser Leu Ala Trp His Ile Arg Leu Lys Gln Tyr His Pro Val Val Glu
            195                 200                 205

Ala Thr Gln Asn Thr Glu Ser Asn Ser Asn Met Asp Cys Gly Leu Thr
        210                 215                 220

Gly Lys Arg Glu Leu Glu Val Asp Ser Gln Cys Val Arg Ile Lys Thr
225                 230                 235                 240

Glu Ser Glu Glu Ala Cys Thr Glu Ile Gln Leu Leu Thr Thr Ala Ser
                245                 250                 255

Ser Ser Phe Pro Pro Ala Ser Glu Leu Asn Leu Gln Gln Asp Gln Lys
            260                 265                 270

Thr Gln Pro Ile Pro Val Leu Lys Val Glu Ser Arg Leu Asp Ser Asp
        275                 280                 285

Gln Gln His Asn Leu Gln Glu His Ser Thr Thr Ser Val
```

290                 295                 300

<210> SEQ ID NO 108
<211> LENGTH: 103
<212> TYPE: PRT
<213> ORGANISM: Homo sapiens
<220> FEATURE:
<221> NAME/KEY: misc_feature
<223> OTHER INFORMATION: Incyte Clone No: 3151073

<400> SEQUENCE: 108

Met Ser Phe Val Pro Gly Leu Leu Cys Phe Val Leu Leu Leu Cys
1               5                   10                  15

Val Ser Pro Val Tyr Leu Pro Ser Arg Ser Pro Ser Thr Phe Pro Ile
                20                  25                  30

Ser Glu Pro Leu Ser Phe Ile Gly Met Ser Ala Trp Pro Gln Cys Ser
            35                  40                  45

Pro Ile Tyr Ser Gln Thr Pro Gly Leu Ala Tyr Glu Pro Ser Ser Phe
        50                  55                  60

Pro Lys Arg Arg Tyr Trp Val Cys Thr Leu His Glu Ile Lys Trp Glu
65                  70                  75                  80

Cys Pro Arg Ser Arg Arg Thr Ser Asp Ala Val His Ala Asn Lys Leu
                85                  90                  95

Gly Leu Pro Leu Lys Ile Ile
                100

<210> SEQ ID NO 109
<211> LENGTH: 95
<212> TYPE: PRT
<213> ORGANISM: Homo sapiens
<220> FEATURE:
<221> NAME/KEY: misc_feature
<223> OTHER INFORMATION: Incyte Clone No: 3170095

<400> SEQUENCE: 109

Met Lys Phe Leu Leu Leu Val Leu Ala Ala Leu Gly Phe Leu Thr Gln
1               5                   10                  15

Val Ile Pro Ala Ser Ala Gly Gly Ser Lys Cys Val Ser Asn Thr Pro
                20                  25                  30

Gly Tyr Cys Arg Thr Cys Cys His Trp Gly Glu Thr Ala Leu Phe Met
            35                  40                  45

Cys Asn Ala Ser Arg Lys Cys Cys Ile Ser Tyr Ser Phe Leu Pro Lys
        50                  55                  60

Pro Asp Leu Pro Gln Leu Ile Gly Asn His Trp Gln Ser Arg Arg Arg
65                  70                  75                  80

Asn Thr Gln Arg Lys Asp Lys Lys Gln Gln Thr Thr Val Thr Ser
                85                  90                  95

<210> SEQ ID NO 110
<211> LENGTH: 113
<212> TYPE: PRT
<213> ORGANISM: Homo sapiens
<220> FEATURE:
<221> NAME/KEY: misc_feature
<223> OTHER INFORMATION: Incyte Clone No: 3475168

<400> SEQUENCE: 110

Met Ser Pro Ser Pro Arg Trp Gly Phe Leu Cys Val Leu Phe Thr Ala
1               5                   10                  15

Val His Pro Ala Pro Ser Thr Ala Pro Val Gln Asp Lys Cys Pro Val
                20                  25                  30

-continued

```
Asn Thr Trp Glu Ala Met Gln Ala Ser Ser Gln Gln Leu Leu Gln Thr
         35                  40                  45

Asp Pro Arg Pro Lys Pro Phe Leu Leu Pro Pro Pro Pro Leu Leu
 50                  55                  60

Leu Ile Ser Ala Gly Thr Glu Val Ser Ser Leu Val Phe Gln Lys Ser
 65                  70                  75                  80

Pro Leu His Thr Gln Pro Glu Gly Ala Ile Lys Thr Ala Gly Gln Pro
                 85                  90                  95

Thr Ser Val His Ser Lys Val Leu Ser Lys Gly Ser Leu Leu Leu Gly
                100                 105                 110

Glu

<210> SEQ ID NO 111
<211> LENGTH: 234
<212> TYPE: PRT
<213> ORGANISM: Homo sapiens
<220> FEATURE:
<221> NAME/KEY: misc_feature
<223> OTHER INFORMATION: Incyte Clone No: 3836893

<400> SEQUENCE: 111

Met Arg Lys Thr Arg Leu Trp Gly Leu Leu Trp Met Leu Phe Val Ser
 1               5                  10                  15

Glu Leu Arg Ala Ala Thr Lys Leu Thr Glu Glu Lys Tyr Glu Leu Lys
                 20                  25                  30

Glu Gly Gln Thr Leu Asp Val Lys Cys Asp Tyr Thr Leu Glu Lys Phe
                 35                  40                  45

Ala Ser Ser Gln Lys Ala Trp Gln Ile Ile Arg Asp Gly Glu Met Pro
 50                  55                  60

Lys Thr Leu Ala Cys Thr Glu Arg Pro Ser Lys Asn Ser His Pro Val
 65                  70                  75                  80

Gln Val Gly Arg Ile Ile Leu Glu Asp Tyr His Asp His Gly Leu Leu
                 85                  90                  95

Arg Val Arg Met Val Asn Leu Gln Val Glu Asp Ser Gly Leu Tyr Gln
                100                 105                 110

Cys Val Ile Tyr Gln Pro Pro Lys Glu Pro His Met Leu Phe Asp Arg
                115                 120                 125

Ile Arg Leu Val Val Thr Lys Gly Phe Ser Gly Thr Pro Gly Ser Asn
130                 135                 140

Glu Asn Ser Thr Gln Asn Val Tyr Lys Ile Pro Pro Thr Thr Thr Lys
145                 150                 155                 160

Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
                180                 185                 190

Thr Asn Val Thr Asp Ile Ile Arg Val Pro Val Phe Asn Ile Val Ile
                195                 200                 205

Leu Leu Ala Gly Gly Phe Leu Ser Lys Ser Leu Val Phe Ser Val Leu
210                 215                 220

Phe Ala Val Thr Leu Arg Ser Phe Val Pro
225                 230

<210> SEQ ID NO 112
<211> LENGTH: 119
<212> TYPE: PRT
<213> ORGANISM: Homo sapiens
<220> FEATURE:
<221> NAME/KEY: misc_feature
```

<223> OTHER INFORMATION: Incyte Clone No: 4072159

<400> SEQUENCE: 112

Met Val Leu Pro Leu Pro Trp Leu Ser Arg Tyr His Phe Leu Arg Leu
1               5                   10                  15

Leu Leu Pro Ser Trp Ser Leu Ala Pro Gln Gly Ser His Gly Cys Cys
            20                  25                  30

Ser Gln Asn Pro Lys Ala Ser Met Glu Glu Gln Thr Asn Ser Arg Gly
        35                  40                  45

Asn Gly Lys Met Thr Ser Pro Pro Arg Gly Pro Gly Thr His Arg Thr
    50                  55                  60

Ala Glu Leu Ala Arg Ala Glu Glu Leu Leu Glu Gln Gln Leu Glu Leu
65                  70                  75                  80

Tyr Gln Ala Leu Leu Glu Gly Gln Glu Gly Ala Trp Glu Ala Gln Ala
                85                  90                  95

Leu Val Leu Lys Ile Gln Lys Leu Lys Glu Gln Met Arg Arg His Gln
            100                 105                 110

Glu Ser Leu Gly Gly Gly Ala
        115

<210> SEQ ID NO 113
<211> LENGTH: 200
<212> TYPE: PRT
<213> ORGANISM: Homo sapiens
<220> FEATURE:
<221> NAME/KEY: misc_feature
<223> OTHER INFORMATION: Incyte Clone No: 1003916

<400> SEQUENCE: 113

Met Ala Ser Ser Leu Thr Cys Thr Gly Val Ile Trp Ala Leu Leu Ser
1               5                   10                  15

Phe Leu Cys Ala Ala Thr Ser Cys Val Gly Phe Phe Met Pro Tyr Trp
            20                  25                  30

Leu Trp Gly Ser Gln Leu Gly Lys Pro Val Ser Phe Gly Thr Phe Arg
        35                  40                  45

Arg Cys Ser Tyr Pro Val His Asp Glu Ser Arg Gln Met Met Val Met
    50                  55                  60

Val Glu Glu Cys Gly Arg Tyr Ala Ser Phe Gln Gly Ile Pro Ser Ala
65                  70                  75                  80

Glu Trp Arg Ile Cys Thr Ile Val Thr Gly Leu Gly Cys Gly Leu Leu
                85                  90                  95

Leu Leu Val Ala Leu Thr Ala Leu Met Gly Cys Cys Val Ser Asp Leu
            100                 105                 110

Ile Ser Arg Thr Val Gly Arg Val Ala Gly Gly Ile Gln Phe Leu Gly
        115                 120                 125

Gly Leu Leu Ile Gly Ala Gly Cys Ala Leu Tyr Pro Leu Gly Trp Asp
    130                 135                 140

Ser Glu Glu Val Arg Gln Thr Cys Gly Tyr Thr Ser Gly Gln Phe Asp
145                 150                 155                 160

Leu Gly Lys Cys Glu Ile Gly Trp Ala Tyr Tyr Cys Thr Gly Ala Gly
                165                 170                 175

Ala Thr Ala Ala Met Leu Leu Cys Thr Trp Leu Ala Cys Phe Ser Gly
            180                 185                 190

Lys Lys Gln Lys His Tyr Pro Tyr
        195                 200

<210> SEQ ID NO 114

```
<211> LENGTH: 225
<212> TYPE: PRT
<213> ORGANISM: Homo sapiens
<220> FEATURE:
<221> NAME/KEY: misc_feature
<223> OTHER INFORMATION: Incyte Clone No: 2093492

<400> SEQUENCE: 114

Met Gly Phe Arg Leu Glu Gly Ile Phe Pro Ala Ala Leu Leu Pro Leu
1               5                   10                  15

Leu Leu Thr Met Ile Leu Phe Leu Gly Pro Leu Met Gln Leu Ser Met
            20                  25                  30

Asp Cys Pro Cys Asp Leu Ala Asp Gly Leu Lys Val Val Leu Ala Pro
        35                  40                  45

Arg Ser Trp Ala Arg Cys Leu Thr Asp Met Arg Trp Leu Arg Asn Gln
    50                  55                  60

Val Ile Ala Pro Leu Thr Glu Glu Leu Val Phe Arg Ala Cys Met Leu
65                  70                  75                  80

Pro Met Leu Ala Pro Cys Met Gly Leu Gly Pro Ala Val Phe Thr Cys
                85                  90                  95

Pro Leu Phe Phe Gly Val Ala His Phe His His Ile Ile Glu Gln Leu
            100                 105                 110

Arg Phe Arg Gln Ser Ser Val Gly Asn Ile Phe Leu Ser Ala Ala Phe
        115                 120                 125

Gln Phe Ser Tyr Thr Ala Val Phe Gly Ala Tyr Thr Ala Phe Leu Phe
    130                 135                 140

Ile Arg Thr Gly His Leu Ile Gly Pro Val Leu Cys His Ser Phe Cys
145                 150                 155                 160

Asn Tyr Met Gly Phe Pro Ala Val Cys Ala Ala Leu Glu His Pro Gln
                165                 170                 175

Arg Arg Pro Leu Leu Ala Gly Tyr Ala Leu Gly Val Gly Leu Phe Leu
            180                 185                 190

Leu Leu Leu Gln Pro Leu Thr Asp Pro Lys Leu Tyr Gly Ser Leu Pro
        195                 200                 205

Leu Cys Val Leu Leu Glu Arg Ala Gly Asp Ser Glu Ala Pro Leu Cys
    210                 215                 220

Ser
225

<210> SEQ ID NO 115
<211> LENGTH: 155
<212> TYPE: PRT
<213> ORGANISM: Homo sapiens
<220> FEATURE:
<221> NAME/KEY: misc_feature
<223> OTHER INFORMATION: Incyte Clone No: 2108789

<400> SEQUENCE: 115

Met Ser Gly Leu Leu Ile Pro Pro Leu Pro Gly Trp Val Leu Gly Pro
1               5                   10                  15

Leu Met Trp Ala Cys Arg Pro Pro Gln Asp Glu Pro Ser Gly Thr Asp
            20                  25                  30

Pro Pro Pro Pro Arg Leu Gln Pro His His Val Ser Gly Leu Gly Leu
        35                  40                  45

Gly Gln Ala Trp Ala Gln Ser Trp Ala Pro Arg Gly Ser Pro Pro Leu
    50                  55                  60

Thr Trp Leu Leu Pro Thr Leu Pro Leu Lys Asp Gly Pro Ala Ala Arg
65                  70                  75                  80
```

-continued

```
Leu Pro Pro Pro Pro His Thr Thr Leu Gly Gly Leu Ser His Pro Pro
             85                  90                  95

Gln Pro Arg Ser Ala Gln Thr Asp Pro His Ser Ile Pro Arg Pro Ala
            100                 105                 110

Ala Gln Val Arg Gly Pro Val Leu Pro Gly Ala Trp Ala Thr Pro Tyr
        115                 120                 125

Ala Ile Ser Ser Glu Gln Pro Gly Pro Thr Asp Pro His Ala Leu Ser
        130                 135                 140

Tyr Val Pro Phe Ser Pro Asp Phe Phe Cys Thr
145                 150                 155

<210> SEQ ID NO 116
<211> LENGTH: 468
<212> TYPE: PRT
<213> ORGANISM: Homo sapiens
<220> FEATURE:
<221> NAME/KEY: misc_feature
<223> OTHER INFORMATION: Incyte Clone No: 2171401

<400> SEQUENCE: 116

Met Gly Arg Gly Trp Gly Phe Leu Phe Gly Leu Leu Gly Ala Val Trp
1               5                  10                  15

Leu Leu Ser Ser Gly His Gly Glu Glu Gln Pro Pro Glu Thr Ala Ala
            20                  25                  30

Gln Arg Cys Phe Cys Gln Val Ser Gly Tyr Leu Asp Asp Cys Thr Cys
        35                  40                  45

Asp Val Glu Thr Ile Asp Arg Phe Asn Asn Tyr Arg Leu Phe Pro Arg
    50                  55                  60

Leu Gln Lys Leu Leu Glu Ser Asp Tyr Phe Arg Tyr Tyr Lys Val Asn
65                  70                  75                  80

Leu Lys Arg Pro Cys Pro Phe Trp Asn Asp Ile Ser Gln Cys Gly Arg
                85                  90                  95

Arg Asp Cys Ala Val Lys Pro Cys Gln Ser Asp Glu Val Pro Asp Gly
            100                 105                 110

Ile Lys Ser Ala Ser Tyr Lys Tyr Ser Glu Glu Ala Asn Asn Leu Ile
        115                 120                 125

Glu Glu Cys Glu Gln Ala Glu Arg Leu Gly Ala Val Asp Glu Ser Leu
    130                 135                 140

Ser Glu Glu Thr Gln Lys Ala Val Leu Gln Trp Thr Lys His Asp Asp
145                 150                 155                 160

Ser Ser Asp Asn Phe Cys Glu Ala Asp Asp Ile Gln Ser Pro Glu Ala
                165                 170                 175

Glu Tyr Val Asp Leu Leu Leu Asn Pro Glu Arg Tyr Thr Gly Tyr Lys
            180                 185                 190

Gly Pro Asp Ala Trp Lys Ile Trp Asn Val Ile Tyr Glu Glu Asn Cys
        195                 200                 205

Phe Lys Pro Gln Thr Ile Lys Arg Pro Leu Asn Pro Leu Ala Ser Gly
    210                 215                 220

Gln Gly Thr Ser Glu Glu Asn Thr Phe Tyr Ser Trp Leu Glu Gly Leu
225                 230                 235                 240

Cys Val Glu Lys Arg Ala Phe Tyr Arg Leu Ile Ser Gly Leu His Ala
                245                 250                 255

Ser Ile Asn Val His Leu Ser Ala Arg Tyr Leu Leu Gln Glu Thr Trp
            260                 265                 270

Leu Glu Lys Lys Trp Gly His Asn Ile Thr Glu Phe Gln Gln Arg Phe
        275                 280                 285
```

```
Asp Gly Ile Leu Thr Glu Gly Glu Gly Pro Arg Arg Leu Lys Asn Leu
    290                 295                 300

Tyr Phe Leu Tyr Leu Ile Glu Leu Arg Ala Leu Ser Lys Val Leu Pro
305                 310                 315                 320

Phe Phe Glu Arg Pro Asp Phe Gln Leu Phe Thr Gly Asn Lys Ile Gln
            325                 330                 335

Asp Glu Glu Asn Lys Met Leu Leu Leu Glu Ile Leu His Glu Ile Lys
            340                 345                 350

Ser Phe Pro Leu His Phe Asp Glu Asn Ser Phe Phe Ala Gly Asp Lys
            355                 360                 365

Lys Glu Ala His Lys Leu Lys Glu Asp Phe Arg Leu His Phe Arg Asn
    370                 375                 380

Ile Ser Arg Ile Met Asp Cys Val Gly Cys Phe Lys Cys Arg Leu Trp
385                 390                 395                 400

Gly Lys Leu Gln Thr Gln Gly Leu Gly Thr Ala Leu Lys Ile Leu Phe
            405                 410                 415

Ser Glu Lys Leu Ile Ala Asn Met Pro Glu Ser Gly Pro Ser Tyr Glu
            420                 425                 430

Phe His Leu Thr Arg Gln Glu Ile Val Ser Leu Phe Asn Ala Phe Gly
            435                 440                 445

Arg Ile Ser Thr Ser Val Lys Glu Leu Glu Asn Phe Arg Asn Leu Leu
    450                 455                 460

Gln Asn Ile His
465

<210> SEQ ID NO 117
<211> LENGTH: 403
<212> TYPE: PRT
<213> ORGANISM: Homo sapiens
<220> FEATURE:
<221> NAME/KEY: misc_feature
<223> OTHER INFORMATION: Incyte Clone No: 2212530

<400> SEQUENCE: 117

Met Ser Thr Ser Thr Ser Pro Ala Ala Met Leu Leu Arg Arg Leu Arg
1               5                   10                  15

Arg Leu Ser Trp Gly Ser Thr Ala Val Gln Leu Phe Ile Leu Thr Val
            20                  25                  30

Val Thr Phe Gly Leu Leu Ala Pro Leu Ala Cys His Arg Leu Leu His
            35                  40                  45

Ser Tyr Phe Tyr Leu Arg His Trp His Leu Asn Gln Met Ser Gln Glu
        50                  55                  60

Phe Leu Gln Gln Ser Leu Lys Glu Gly Glu Ala Ala Leu His Tyr Phe
65                  70                  75                  80

Glu Glu Leu Pro Ser Ala Asn Gly Ser Val Pro Ile Val Trp Gln Ala
            85                  90                  95

Thr Pro Arg Pro Trp Leu Val Ile Thr Ile Thr Val Asp Arg Gln
            100                 105                 110

Pro Gly Phe His Tyr Val Leu Gln Val Val Ser Gln Phe His Arg Leu
            115                 120                 125

Leu Gln Gln Cys Gly Pro Gln Cys Glu Gly His Gln Leu Phe Leu Cys
        130                 135                 140

Asn Val Glu Arg Ser Val Ser His Phe Asp Ala Lys Leu Leu Ser Lys
145                 150                 155                 160

Tyr Val Pro Val Ala Asn Arg Tyr Glu Gly Thr Glu Asp Asp Tyr Gly
            165                 170                 175
```

```
Asp Asp Pro Ser Thr Asn Ser Phe Glu Lys Glu Lys Gln Asp Tyr Val
            180                 185                 190

Tyr Cys Leu Glu Ser Ser Leu Gln Thr Tyr Asn Pro Asp Tyr Val Leu
        195                 200                 205

Met Val Glu Asp Asp Ala Val Pro Glu Glu Gln Ile Phe Pro Val Leu
    210                 215                 220

Glu His Leu Leu Arg Ala Arg Phe Ser Glu Pro His Leu Arg Asp Ala
225                 230                 235                 240

Leu Tyr Leu Lys Leu Tyr His Pro Glu Arg Leu Gln His Tyr Ile Asn
                245                 250                 255

Pro Glu Pro Met Arg Ile Leu Glu Trp Val Gly Val Gly Met Leu Leu
                260                 265                 270

Gly Pro Leu Leu Thr Trp Ile Tyr Met Arg Phe Ala Ser Arg Pro Gly
            275                 280                 285

Phe Ser Trp Pro Val Met Leu Phe Phe Ser Leu Tyr Ser Met Gly Leu
        290                 295                 300

Val Glu Leu Val Gly Arg His Tyr Phe Leu Glu Leu Arg Arg Leu Ser
305                 310                 315                 320

Pro Ser Leu Tyr Ser Val Val Pro Ala Ser Gln Cys Cys Thr Pro Ala
                325                 330                 335

Met Leu Phe Pro Ala Pro Ala Ala Arg Arg Thr Leu Thr Tyr Leu Ser
            340                 345                 350

Gln Val Tyr Cys His Lys Gly Phe Gly Lys Asp Met Ala Leu Tyr Ser
        355                 360                 365

Leu Leu Arg Ala Lys Gly Glu Arg Ala Tyr Val Val Glu Pro Asn Leu
370                 375                 380

Val Lys His Ile Gly Leu Phe Ser Ser Leu Arg Tyr Asn Phe His Pro
385                 390                 395                 400

Ser Leu Leu

<210> SEQ ID NO 118
<211> LENGTH: 131
<212> TYPE: PRT
<213> ORGANISM: Homo sapiens
<220> FEATURE:
<221> NAME/KEY: misc_feature
<223> OTHER INFORMATION: Incyte Clone No: 2253036

<400> SEQUENCE: 118

Met Glu Arg Cys Phe His Cys Phe Pro Val His Leu Val Phe Asn Leu
1               5                   10                  15

Val Gln Ser Phe Ser Pro Ile Ser Gly Val Glu Ser Cys Leu Leu Pro
                20                  25                  30

Gln Cys Asp Lys Cys Trp Pro Met Val Tyr Arg Ser Cys Asp Ala Ser
            35                  40                  45

Arg Gly Leu Val Asn Ala Cys Ile Leu Gly Phe Val Leu Leu Glu Cys
        50                  55                  60

Ser Phe Val Gly Ala Leu Asn Asn Tyr Val Arg Ser Leu Ala Thr Leu
65                  70                  75                  80

Leu Glu Arg Thr His Gly Gly Lys Arg Leu Lys Leu Cys Glu Glu Ser
                85                  90                  95

Gln Ala Ser His Pro Ser Phe Ser Ala Glu Pro Arg His Gln Pro Thr
            100                 105                 110

Cys Gln Leu Asn Ala Thr Val Arg Val Ile Thr Ser Lys Ile Thr Arg
        115                 120                 125

Lys Thr Thr
```

<210> SEQ ID NO 119
<211> LENGTH: 556
<212> TYPE: PRT
<213> ORGANISM: Homo sapiens
<220> FEATURE:
<221> NAME/KEY: misc_feature
<223> OTHER INFORMATION: Incyte Clone No: 2280161

<400> SEQUENCE: 119

Met Ala Ala Ala Trp Leu Gln Val Leu Pro Val Ile Leu Leu Leu
1               5                   10                  15

Leu Gly Ala His Pro Ser Pro Leu Ser Phe Phe Ser Ala Gly Pro Ala
                20                  25                  30

Thr Val Ala Ala Ala Asp Arg Ser Lys Trp His Ile Pro Ile Pro Ser
            35                  40                  45

Gly Lys Asn Tyr Phe Ser Phe Gly Lys Ile Leu Phe Arg Asn Thr Thr
50                  55                  60

Ile Phe Leu Lys Phe Asp Gly Glu Pro Cys Asp Leu Ser Leu Asn Ile
65                  70                  75                  80

Thr Trp Tyr Leu Lys Ser Ala Asp Cys Tyr Asn Glu Ile Tyr Asn Phe
                85                  90                  95

Lys Ala Glu Glu Val Glu Leu Tyr Leu Glu Lys Leu Lys Glu Lys Arg
            100                 105                 110

Gly Leu Ser Gly Lys Tyr Gln Thr Ser Ser Lys Leu Phe Gln Asn Cys
        115                 120                 125

Ser Glu Leu Phe Lys Thr Gln Thr Phe Ser Gly Asp Phe Met His Arg
    130                 135                 140

Leu Pro Leu Leu Gly Glu Lys Gln Glu Ala Lys Glu Asn Gly Thr Asn
145                 150                 155                 160

Leu Thr Phe Ile Gly Asp Lys Thr Ala Met His Glu Pro Leu Gln Thr
                165                 170                 175

Trp Gln Asp Ala Pro Tyr Ile Phe Ile Val His Ile Gly Ile Ser Ser
            180                 185                 190

Ser Lys Glu Ser Ser Lys Glu Asn Ser Leu Ser Asn Leu Phe Thr Met
        195                 200                 205

Thr Val Glu Val Lys Gly Pro Tyr Glu Tyr Leu Thr Leu Glu Asp Tyr
    210                 215                 220

Pro Leu Met Ile Phe Phe Met Val Met Cys Ile Val Tyr Val Leu Phe
225                 230                 235                 240

Gly Val Leu Trp Leu Ala Trp Ser Ala Cys Tyr Trp Arg Asp Leu Leu
                245                 250                 255

Arg Ile Gln Phe Trp Ile Gly Ala Val Ile Phe Leu Gly Met Leu Glu
            260                 265                 270

Lys Ala Val Phe Tyr Ala Glu Phe Gln Asn Ile Arg Tyr Lys Gly Glu
        275                 280                 285

Ser Val Gln Gly Ala Leu Ile Leu Ala Glu Leu Leu Ser Ala Val Lys
    290                 295                 300

Arg Ser Leu Ala Arg Thr Leu Val Ile Ile Val Ser Leu Gly Tyr Gly
305                 310                 315                 320

Ile Val Lys Pro Arg Leu Gly Val Thr Leu His Lys Val Val Ala
                325                 330                 335

Gly Ala Leu Tyr Leu Leu Phe Ser Gly Met Glu Gly Val Leu Arg Val
            340                 345                 350

Thr Gly Tyr Phe Ser Tyr Pro Leu Thr Leu Ile Val Asn Leu Ala Leu

```
            355                 360                 365
Ser Ala Val Asp Ala Cys Val Ile Leu Trp Ile Phe Ile Ser Leu Thr
    370                 375                 380

Gln Thr Met Lys Leu Leu Lys Leu Arg Arg Asn Ile Val Lys Leu Ser
385                 390                 395                 400

Leu Tyr Arg His Phe Thr Asn Thr Leu Ile Leu Ala Val Ala Ala Ser
                405                 410                 415

Ile Val Phe Ile Ile Trp Thr Thr Met Lys Phe Arg Ile Val Thr Cys
            420                 425                 430

Gln Ser Asp Trp Arg Glu Leu Trp Val Asp Asp Ala Ile Trp Arg Leu
        435                 440                 445

Leu Phe Ser Met Ile Leu Phe Val Ile Met Val Leu Trp Arg Pro Ser
    450                 455                 460

Ala Asn Asn Gln Arg Phe Ala Phe Ser Pro Leu Ser Glu Glu Glu Glu
465                 470                 475                 480

Glu Asp Glu Gln Lys Glu Pro Met Leu Lys Glu Ser Phe Glu Gly Met
                485                 490                 495

Lys Met Arg Ser Thr Lys Gln Glu Pro Asn Gly Asn Ser Lys Val Asn
            500                 505                 510

Lys Ala Gln Glu Asp Asp Leu Lys Trp Val Glu Glu Asn Val Pro Ser
        515                 520                 525

Ser Val Thr Asp Val Ala Leu Pro Ala Leu Leu Asp Ser Asp Glu Glu
    530                 535                 540

Arg Met Ile Thr His Phe Glu Arg Ser Lys Met Glu
545                 550                 555

<210> SEQ ID NO 120
<211> LENGTH: 514
<212> TYPE: PRT
<213> ORGANISM: Homo sapiens
<220> FEATURE:
<221> NAME/KEY: misc_feature
<223> OTHER INFORMATION: Incyte Clone No: 2287485

<400> SEQUENCE: 120

Met Ser Trp Pro Arg Arg Leu Leu Leu Arg Tyr Leu Phe Pro Ala Leu
1               5                   10                  15

Leu Leu His Gly Leu Gly Glu Gly Ser Ala Leu Leu His Pro Asp Ser
            20                  25                  30

Arg Ser His Pro Arg Ser Leu Glu Lys Ser Ala Trp Arg Ala Phe Lys
        35                  40                  45

Glu Ser Gln Cys His His Met Leu Lys His Leu His Asn Gly Ala Arg
    50                  55                  60

Ile Thr Val Gln Met Pro Pro Thr Ile Glu Gly His Trp Val Ser Thr
65                  70                  75                  80

Gly Cys Glu Val Arg Ser Gly Pro Glu Phe Ile Thr Arg Ser Tyr Arg
                85                  90                  95

Phe Tyr His Asn Asn Thr Phe Lys Ala Tyr Gln Phe Tyr Tyr Gly Ser
            100                 105                 110

Asn Arg Cys Thr Asn Pro Thr Tyr Thr Leu Ile Ile Arg Gly Lys Ile
        115                 120                 125

Arg Leu Arg Gln Ala Ser Trp Ile Ile Arg Gly Thr Glu Ala Asp
    130                 135                 140

Tyr Gln Leu His Asn Val Gln Val Ile Cys His Thr Glu Ala Val Ala
145                 150                 155                 160

Glu Lys Leu Gly Gln Gln Val Asn Arg Thr Cys Pro Gly Phe Leu Ala
```

-continued

```
                165                 170                 175
Asp Gly Gly Pro Trp Val Gln Asp Val Ala Tyr Asp Leu Trp Arg Glu
            180                 185                 190

Glu Asn Gly Cys Glu Cys Thr Lys Ala Val Asn Phe Ala Met His Glu
        195                 200                 205

Leu Gln Leu Ile Arg Val Glu Lys Gln Tyr Leu His His Asn Leu Asp
    210                 215                 220

His Leu Val Glu Glu Leu Phe Leu Gly Asp Ile His Thr Asp Ala Thr
225                 230                 235                 240

Gln Arg Met Phe Tyr Arg Pro Ser Ser Tyr Gln Pro Pro Leu Gln Asn
                245                 250                 255

Ala Lys Asn His Asp His Ala Cys Ile Ala Cys Arg Ile Ile Tyr Arg
            260                 265                 270

Ser Asp Glu His His Pro Pro Ile Leu Pro Pro Lys Ala Asp Leu Thr
        275                 280                 285

Ile Gly Leu His Gly Glu Trp Val Ser Gln Arg Cys Glu Val Arg Pro
    290                 295                 300

Glu Val Leu Phe Leu Thr Arg His Phe Ile Phe His Asp Asn Asn Asn
305                 310                 315                 320

Thr Trp Glu Gly His Tyr Tyr His Tyr Ser Asp Pro Val Cys Lys His
                325                 330                 335

Pro Thr Phe Ser Ile Tyr Ala Arg Gly Arg Tyr Ser Arg Gly Val Leu
            340                 345                 350

Ser Ser Arg Val Met Gly Gly Thr Glu Phe Val Phe Lys Val Asn His
        355                 360                 365

Met Lys Val Thr Pro Met Asp Ala Ala Thr Ala Ser Leu Leu Asn Val
    370                 375                 380

Phe Asn Gly Asn Glu Cys Gly Ala Glu Gly Ser Trp Gln Val Gly Ile
385                 390                 395                 400

Gln Gln Asp Val Thr His Thr Asn Gly Cys Val Ala Leu Gly Ile Lys
                405                 410                 415

Leu Pro His Thr Glu Tyr Glu Ile Phe Lys Met Glu Gln Asp Ala Arg
            420                 425                 430

Gly Arg Tyr Leu Leu Phe Asn Gly Gln Arg Pro Ser Asp Gly Ser Ser
        435                 440                 445

Pro Asp Arg Pro Glu Lys Arg Ala Thr Ser Tyr Gln Met Pro Leu Val
    450                 455                 460

Gln Cys Ala Ser Ser Ser Pro Arg Ala Glu Asp Leu Ala Glu Asp Ser
465                 470                 475                 480

Gly Ser Ser Leu Tyr Gly Arg Ala Pro Gly Arg His Thr Trp Ser Leu
                485                 490                 495

Leu Leu Ala Ala Leu Ala Cys Leu Val Pro Leu Leu His Trp Asn Ile
            500                 505                 510

Arg Arg
```

<210> SEQ ID NO 121
<211> LENGTH: 109
<212> TYPE: PRT
<213> ORGANISM: Homo sapiens
<220> FEATURE:
<221> NAME/KEY: misc_feature
<223> OTHER INFORMATION: Incyte Clone No: 2380344

<400> SEQUENCE: 121

```
Met Leu Trp Trp Leu Val Leu Leu Leu Pro Thr Leu Lys Ser Val
1               5                   10                  15
```

```
Phe Cys Ser Leu Val Thr Ser Leu Tyr Leu Pro Asn Thr Glu Asp Leu
                20                  25                  30

Ser Leu Trp Leu Trp Pro Lys Pro Asp Leu His Ser Gly Thr Arg Thr
            35                  40                  45

Glu Val Ser Thr His Thr Val Pro Ser Lys Pro Gly Thr Ala Ser Pro
        50                  55                  60

Cys Trp Pro Leu Ala Gly Ala Val Pro Ser Pro Thr Val Ser Arg Leu
65                  70                  75                  80

Glu Ala Leu Thr Arg Ala Val Gln Val Ala Glu Pro Leu Gly Ser Cys
                85                  90                  95

Gly Phe Gln Gly Gly Pro Cys Pro Gly Arg Arg Arg Asp
                100                 105

<210> SEQ ID NO 122
<211> LENGTH: 431
<212> TYPE: PRT
<213> ORGANISM: Homo sapiens
<220> FEATURE:
<221> NAME/KEY: misc_feature
<223> OTHER INFORMATION: Incyte Clone No: 2383171

<400> SEQUENCE: 122

Met Ser Trp Val Gln Ala Thr Leu Leu Ala Arg Gly Leu Cys Arg Ala
1               5                   10                  15

Trp Gly Gly Thr Cys Gly Ala Ala Leu Thr Gly Thr Ser Ile Ser Gln
                20                  25                  30

Val Pro Arg Arg Leu Pro Arg Gly Leu His Cys Ser Ala Ala Ala His
            35                  40                  45

Ser Ser Glu Gln Ser Leu Val Pro Ser Pro Glu Pro Arg Gln Arg
        50                  55                  60

Pro Thr Lys Ala Leu Val Pro Phe Glu Asp Leu Phe Gly Gln Ala Pro
65                  70                  75                  80

Gly Gly Glu Arg Asp Lys Ala Ser Phe Leu Gln Thr Val Gln Lys Phe
                85                  90                  95

Ala Glu His Ser Val Arg Lys Arg Gly His Ile Asp Phe Ile Tyr Leu
                100                 105                 110

Ala Leu Arg Lys Met Arg Glu Tyr Gly Val Glu Arg Asp Leu Ala Val
            115                 120                 125

Tyr Asn Gln Leu Leu Asn Ile Phe Pro Lys Glu Val Phe Arg Pro Arg
        130                 135                 140

Asn Ile Ile Gln Arg Ile Phe Val His Tyr Pro Arg Gln Gln Glu Cys
145                 150                 155                 160

Gly Ile Ala Val Leu Glu Gln Met Glu Asn His Gly Val Met Pro Asn
                165                 170                 175

Lys Glu Thr Glu Phe Leu Leu Ile Gln Ile Phe Gly Arg Lys Ser Tyr
                180                 185                 190

Pro Met Leu Lys Leu Val Arg Leu Lys Leu Trp Phe Pro Arg Phe Met
            195                 200                 205

Asn Val Asn Pro Phe Pro Val Pro Arg Asp Leu Pro Gln Asp Pro Val
        210                 215                 220

Glu Leu Ala Met Phe Gly Leu Arg His Met Glu Pro Asp Leu Ser Ala
225                 230                 235                 240

Arg Val Thr Ile Tyr Gln Val Pro Leu Pro Lys Asp Ser Thr Gly Ala
                245                 250                 255

Ala Asp Pro Pro Gln Pro His Ile Val Gly Ile Gln Ser Pro Asp Gln
                260                 265                 270
```

```
Gln Ala Ala Leu Ala Arg His Asn Pro Ala Arg Pro Val Phe Val Glu
            275                 280                 285
Gly Pro Phe Ser Leu Trp Leu Arg Asn Lys Cys Val Tyr Tyr His Ile
290                 295                 300
Leu Arg Ala Asp Leu Leu Pro Pro Glu Glu Arg Val Glu Glu Glu Thr
305                 310                 315                 320
Pro Glu Glu Trp Asn Leu Tyr Tyr Pro Met Gln Leu Asp Leu Glu Tyr
                325                 330                 335
Val Arg Ser Gly Trp Asp Asn Tyr Glu Phe Asp Ile Asn Glu Val Glu
            340                 345                 350
Glu Gly Pro Val Phe Ala Met Cys Met Ala Gly Ala His Asp Gln Ala
        355                 360                 365
Thr Met Ala Lys Trp Ile Gln Gly Leu Gln Glu Thr Asn Pro Thr Leu
370                 375                 380
Ala Gln Ile Pro Val Val Phe Arg Leu Ala Gly Ser Thr Arg Glu Leu
385                 390                 395                 400
Gln Thr Ser Ser Ala Gly Leu Glu Glu Pro Pro Leu Pro Glu Asp His
                405                 410                 415
Gln Glu Glu Asp Asp Asn Leu Gln Arg Gln Gln Gln Gly Gln Ser
            420                 425                 430

<210> SEQ ID NO 123
<211> LENGTH: 142
<212> TYPE: PRT
<213> ORGANISM: Homo sapiens
<220> FEATURE:
<221> NAME/KEY: misc_feature
<223> OTHER INFORMATION: Incyte Clone No: 2396046

<400> SEQUENCE: 123

Met Leu Leu Gly Val Arg Ala Val Pro Leu Cys Ser Ala Trp Gln Gly
1               5                   10                  15
Ala Val Gly Leu Val Ser Leu Ala Ile Ser Ile Cys Lys His Gly Leu
            20                  25                  30
Ser Ser Gln Gln Asn Leu Val Pro Gly Lys Ser Asn Val Pro Lys Ala
        35                  40                  45
Ser Asp Met Pro Arg Cys Pro Pro Val Phe Gln Ser Pro Asn Leu Thr
    50                  55                  60
Pro Phe Pro His His Thr Lys His Thr Ser Gln Gly Ser His Leu Gly
65                  70                  75                  80
Val Pro Pro Pro Ala Pro Met Pro Trp Cys Pro Gln Ala Gln Gly Phe
                85                  90                  95
Gly Leu Ser Cys Gln Ser Leu Asp Ala Phe Glu Gly Gln Leu Gly Cys
            100                 105                 110
Gly Trp Gly Val Gln Ala Ala Gly Glu Pro Arg Leu Arg Ile Ile His
        115                 120                 125
Thr Leu Leu Phe Gly Ala Phe Val Glu Val Ser Arg Ile Pro
    130                 135                 140

<210> SEQ ID NO 124
<211> LENGTH: 643
<212> TYPE: PRT
<213> ORGANISM: Homo sapiens
<220> FEATURE:
<221> NAME/KEY: misc_feature
<223> OTHER INFORMATION: Incyte Clone No: 2456587

<400> SEQUENCE: 124
```

-continued

```
Met Glu Cys Cys Arg Ala Thr Pro Gly Thr Leu Leu Leu Phe Leu
1               5                   10                  15

Ala Phe Leu Leu Leu Ser Ser Arg Thr Ala Arg Ser Glu Glu Asp Arg
            20                  25                  30

Asp Gly Leu Trp Asp Ala Trp Gly Pro Trp Ser Glu Cys Ser Arg Thr
            35                  40                  45

Cys Gly Gly Gly Ala Ser Tyr Ser Leu Arg Arg Cys Leu Ser Ser Lys
        50                  55                  60

Ser Cys Glu Gly Arg Asn Ile Arg Tyr Arg Thr Cys Ser Asn Val Asp
65                  70                  75                  80

Cys Pro Pro Glu Ala Gly Asp Phe Arg Ala Gln Gln Cys Ser Ala His
                85                  90                  95

Asn Asp Val Lys His His Gly Gln Phe Tyr Glu Trp Leu Pro Val Ser
            100                 105                 110

Asn Asp Pro Asp Asn Pro Cys Ser Leu Lys Cys Gln Ala Lys Gly Thr
        115                 120                 125

Thr Leu Val Val Glu Leu Ala Pro Lys Val Leu Asp Gly Thr Arg Cys
    130                 135                 140

Tyr Thr Glu Ser Leu Asp Met Cys Ile Ser Gly Leu Cys Gln Ile Val
145                 150                 155                 160

Gly Cys Asp His Gln Leu Gly Ser Thr Val Lys Glu Asp Asn Cys Gly
                165                 170                 175

Val Cys Asn Gly Asp Gly Ser Thr Cys Arg Leu Val Arg Gly Gln Tyr
            180                 185                 190

Lys Ser Gln Leu Ser Ala Thr Lys Ser Asp Asp Thr Val Val Ala Ile
        195                 200                 205

Pro Tyr Gly Ser Arg His Ile Arg Leu Val Leu Lys Gly Pro Asp His
210                 215                 220

Leu Tyr Leu Glu Thr Lys Thr Leu Gln Gly Thr Lys Gly Glu Asn Ser
225                 230                 235                 240

Leu Ser Ser Thr Gly Thr Phe Leu Val Asp Asn Ser Ser Val Asp Phe
                245                 250                 255

Gln Lys Phe Pro Asp Lys Glu Ile Leu Arg Met Ala Gly Pro Leu Thr
            260                 265                 270

Ala Asp Phe Ile Val Lys Ile Arg Asn Ser Gly Ser Ala Asp Ser Thr
        275                 280                 285

Val Gln Phe Ile Phe Tyr Gln Pro Ile Ile His Arg Trp Arg Glu Thr
    290                 295                 300

Asp Phe Phe Pro Cys Ser Ala Thr Cys Gly Gly Gly Tyr Gln Leu Thr
305                 310                 315                 320

Ser Ala Glu Cys Tyr Asp Leu Arg Ser Asn Arg Val Val Ala Asp Gln
                325                 330                 335

Tyr Cys His Tyr Tyr Pro Glu Asn Ile Lys Pro Lys Pro Lys Leu Gln
            340                 345                 350

Glu Cys Asn Leu Asp Pro Cys Pro Ala Ser Asp Gly Tyr Lys Gln Ile
        355                 360                 365

Met Pro Tyr Asp Leu Tyr His Pro Leu Pro Arg Trp Glu Ala Thr Pro
    370                 375                 380

Trp Thr Ala Cys Ser Ser Ser Cys Gly Gly Gly Ile Gln Ser Arg Ala
385                 390                 395                 400

Val Ser Cys Val Glu Glu Asp Ile Gln Gly His Val Thr Ser Val Glu
                405                 410                 415

Glu Trp Lys Cys Met Tyr Thr Pro Lys Met Pro Ile Ala Gln Pro Cys
            420                 425                 430
```

```
Asn Ile Phe Asp Cys Pro Lys Trp Leu Ala Gln Glu Trp Ser Pro Cys
            435                 440                 445
Thr Val Thr Cys Gly Gln Gly Leu Arg Tyr Arg Val Val Leu Cys Ile
    450                 455                 460
Asp His Arg Gly Met His Thr Gly Gly Cys Ser Pro Lys Thr Lys Pro
465                 470                 475                 480
His Ile Lys Glu Glu Cys Ile Val Pro Thr Pro Cys Tyr Lys Pro Lys
            485                 490                 495
Glu Lys Leu Pro Val Glu Ala Lys Leu Pro Trp Phe Lys Gln Ala Gln
            500                 505                 510
Glu Leu Glu Glu Gly Ala Ala Val Ser Glu Glu Pro Ser Phe Ile Pro
            515                 520                 525
Glu Ala Trp Ser Ala Cys Thr Val Thr Cys Gly Val Gly Thr Gln Val
            530                 535                 540
Arg Ile Val Arg Cys Gln Val Leu Leu Ser Phe Ser Gln Ser Val Ala
545                 550                 555                 560
Asp Leu Pro Ile Asp Glu Cys Glu Gly Pro Lys Pro Ala Ser Gln Arg
                565                 570                 575
Ala Cys Tyr Ala Gly Pro Cys Ser Gly Glu Ile Pro Glu Phe Asn Pro
            580                 585                 590
Asp Glu Thr Asp Gly Leu Phe Gly Gly Leu Gln Asp Phe Asp Glu Leu
            595                 600                 605
Tyr Asp Trp Glu Tyr Glu Gly Phe Thr Lys Cys Ser Glu Ser Cys Gly
            610                 615                 620
Gly Gly Val Gln Glu Ala Val Val Ser Cys Leu Asn Lys Gln Thr Arg
625                 630                 635                 640
Glu Pro Cys

<210> SEQ ID NO 125
<211> LENGTH: 568
<212> TYPE: PRT
<213> ORGANISM: Homo sapiens
<220> FEATURE:
<221> NAME/KEY: misc_feature
<223> OTHER INFORMATION: Incyte Clone No: 2484813

<400> SEQUENCE: 125

Met Val Leu Leu His Trp Cys Leu Leu Trp Leu Leu Phe Pro Leu Ser
1               5                   10                  15
Ser Arg Thr Gln Lys Leu Pro Thr Arg Asp Glu Glu Leu Phe Gln Met
            20                  25                  30
Gln Ile Arg Asp Lys Ala Phe Phe His Asp Ser Ser Val Ile Pro Asp
        35                  40                  45
Gly Ala Glu Ile Ser Ser Tyr Leu Phe Arg Asp Thr Pro Lys Arg Tyr
    50                  55                  60
Phe Phe Val Val Glu Glu Asp Asn Thr Pro Leu Ser Val Thr Val Thr
65                  70                  75                  80
Pro Cys Asp Ala Pro Leu Glu Trp Lys Leu Ser Leu Gln Glu Leu Pro
            85                  90                  95
Glu Asp Arg Ser Gly Glu Gly Ser Gly Asp Leu Glu Pro Leu Glu Gln
            100                 105                 110
Gln Lys Gln Gln Ile Ile Asn Glu Glu Gly Thr Glu Leu Phe Ser Tyr
        115                 120                 125
Lys Gly Asn Asp Val Glu Tyr Phe Ile Ser Ser Ser Pro Ser Gly
    130                 135                 140
```

```
-continued

Leu Tyr Gln Leu Asp Leu Leu Ser Thr Glu Lys Asp Thr His Phe Lys
145                 150                 155                 160

Val Tyr Ala Thr Thr Thr Pro Glu Ser Asp Gln Pro Tyr Pro Glu Leu
            165                 170                 175

Pro Tyr Asp Pro Arg Val Asp Val Thr Ser Leu Gly Arg Thr Thr Val
        180                 185                 190

Thr Leu Ala Trp Lys Pro Ser Pro Thr Ala Ser Leu Leu Lys Gln Pro
    195                 200                 205

Ile Gln Tyr Cys Val Val Ile Asn Lys Glu His Asn Phe Lys Ser Leu
210                 215                 220

Cys Ala Val Glu Ala Lys Leu Ser Ala Asp Asp Ala Phe Met Met Ala
225                 230                 235                 240

Pro Lys Pro Gly Leu Asp Phe Ser Pro Phe Asp Phe Ala His Phe Gly
                245                 250                 255

Phe Pro Ser Asp Asn Ser Gly Lys Glu Arg Ser Phe Gln Ala Lys Pro
            260                 265                 270

Ser Pro Lys Leu Gly Arg His Val Tyr Ser Arg Pro Lys Val Asp Ile
        275                 280                 285

Gln Lys Ile Cys Ile Gly Asn Lys Asn Ile Phe Thr Val Ser Asp Leu
290                 295                 300

Lys Pro Asp Thr Gln Tyr Tyr Phe Asp Val Phe Val Val Asn Ile Asn
305                 310                 315                 320

Ser Asn Met Ser Thr Ala Tyr Val Gly Thr Phe Ala Arg Thr Lys Glu
                325                 330                 335

Glu Ala Lys Gln Lys Thr Val Glu Leu Lys Asp Gly Lys Ile Thr Asp
            340                 345                 350

Val Phe Val Lys Arg Lys Gly Ala Lys Phe Leu Arg Phe Ala Pro Val
        355                 360                 365

Ser Ser His Gln Lys Val Thr Phe Phe Ile His Ser Cys Leu Asp Ala
370                 375                 380

Val Gln Ile Gln Val Arg Arg Asp Gly Lys Leu Leu Leu Ser Gln Asn
385                 390                 395                 400

Val Glu Gly Ile Gln Gln Phe Gln Leu Arg Gly Lys Pro Lys Ala Lys
                405                 410                 415

Tyr Leu Val Arg Leu Lys Gly Asn Lys Lys Gly Ala Ser Met Leu Lys
            420                 425                 430

Ile Leu Ala Thr Thr Arg Pro Thr Lys Gln Ser Phe Pro Ser Leu Pro
        435                 440                 445

Glu Asp Thr Arg Ile Lys Ala Phe Asp Lys Leu Arg Thr Cys Ser Ser
450                 455                 460

Ala Thr Val Ala Trp Leu Gly Thr Gln Glu Arg Asn Lys Phe Cys Ile
465                 470                 475                 480

Tyr Lys Lys Glu Val Asp Asp Asn Tyr Asn Glu Asp Gln Lys Lys Arg
                485                 490                 495

Glu Gln Asn Gln Cys Leu Gly Pro Asp Ile Arg Lys Lys Ser Glu Lys
            500                 505                 510

Val Leu Cys Lys Tyr Phe His Ser Gln Asn Leu Gln Lys Ala Val Thr
        515                 520                 525

Thr Glu Thr Ile Lys Gly Leu Gln Pro Gly Lys Ser Tyr Leu Leu Asp
530                 535                 540

Val Tyr Val Ile Gly His Gly His Ser Val Lys Tyr Gln Ser Lys
545                 550                 555                 560

Val Val Lys Thr Arg Lys Phe Cys
                565
```

<210> SEQ ID NO 126
<211> LENGTH: 125
<212> TYPE: PRT
<213> ORGANISM: Homo sapiens
<220> FEATURE:
<221> NAME/KEY: misc_feature
<223> OTHER INFORMATION: Incyte Clone No: 2493851

<400> SEQUENCE: 126

Met Trp Leu Val Gly Pro Ser Phe Leu Ser Cys Pro Leu Gly Lys Val
1               5                   10                  15

Pro Pro Ala Gly Leu Leu Ala Gly Ser Ser Arg Gly Ala Arg
            20                  25                  30

Arg Pro Ala Thr Pro Arg His Trp Ser Ser Thr Thr Pro Gly Leu Arg
            35                  40                  45

Leu Glu Ala Pro Leu Cys Gln Leu Cys Pro Leu Gly Gly Thr Arg Gln
        50                  55                  60

Asp Cys Gln Pro Leu Ser Trp Gln Val Thr Ser Ala Phe Lys Leu Thr
65                  70                  75                  80

Val Pro Ser Pro Phe His Ala Pro Pro Arg Ser Trp Ser Cys Leu Leu
                85                  90                  95

Leu Gly Ile Phe Pro Gly Gln Ala Leu Ala Leu Glu Pro Trp His Leu
            100                 105                 110

Phe Leu Gly Ser Met Leu Pro Arg Cys Asp Gly Glu Cys
        115                 120                 125

<210> SEQ ID NO 127
<211> LENGTH: 196
<212> TYPE: PRT
<213> ORGANISM: Homo sapiens
<220> FEATURE:
<221> NAME/KEY: misc_feature
<223> OTHER INFORMATION: Incyte Clone No: 2495719

<400> SEQUENCE: 127

Met Ala Ala Leu Lys Ala Leu Val Ser Gly Cys Gly Arg Leu Leu Arg
1               5                   10                  15

Gly Leu Leu Ala Gly Pro Ala Ala Thr Ser Trp Ser Arg Leu Pro Ala
            20                  25                  30

Arg Gly Phe Arg Glu Val Val Glu Thr Gln Gly Lys Thr Thr Ile
            35                  40                  45

Ile Glu Gly Arg Ile Thr Ala Thr Pro Lys Gly Ser Pro Asn Pro Pro
        50                  55                  60

Asn Pro Ser Gly Gln Cys Pro Ile Cys Arg Trp Asn Leu Lys His Lys
65                  70                  75                  80

Tyr Asn Tyr Asp Asp Val Leu Leu Ser Gln Phe Ile Arg Pro His
                85                  90                  95

Gly Gly Met Leu Pro Arg Lys Ile Thr Gly Leu Cys Gln Glu His
            100                 105                 110

Arg Lys Ile Glu Glu Cys Val Lys Met Ala His Arg Ala Gly Leu Leu
        115                 120                 125

Pro Asn His Arg Pro Arg Leu Pro Glu Gly Val Val Pro Lys Ser Lys
    130                 135                 140

Pro Gln Leu Asn Arg Tyr Leu Thr Arg Trp Ala Pro Gly Ser Val Lys
145                 150                 155                 160

Pro Ile Tyr Lys Lys Gly Pro Arg Trp Asn Arg Val Arg Met Pro Val
                165                 170                 175

-continued

```
Gly Ser Pro Leu Leu Arg Asp Asn Val Cys Tyr Ser Arg Thr Pro Trp
            180                 185                 190

Lys Leu Tyr His
        195

<210> SEQ ID NO 128
<211> LENGTH: 214
<212> TYPE: PRT
<213> ORGANISM: Homo sapiens
<220> FEATURE:
<221> NAME/KEY: misc_feature
<223> OTHER INFORMATION: Incyte Clone No: 2614153

<400> SEQUENCE: 128

Met Val Leu Gly Gly Cys Pro Val Ser Tyr Leu Leu Cys Gly Gln
1               5                   10                  15

Ala Ala Leu Leu Leu Gly Asn Leu Leu Leu His Cys Val Ser Arg
                20                  25                  30

Ser His Ser Gln Asn Ala Thr Ala Glu Pro Glu Leu Thr Ser Ala Gly
            35                  40                  45

Ala Ala Gln Pro Glu Gly Pro Gly Ala Ala Ser Trp Glu Tyr Gly
        50                  55                  60

Asp Pro His Ser Pro Val Ile Leu Cys Ser Tyr Leu Pro Asp Glu Phe
65                  70                  75                  80

Ile Glu Cys Glu Asp Pro Val Asp His Val Gly Asn Ala Thr Ala Ser
                85                  90                  95

Gln Glu Leu Gly Tyr Gly Cys Leu Lys Phe Gly Gly Gln Ala Tyr Ser
            100                 105                 110

Asp Val Glu His Thr Ser Val Gln Cys His Ala Leu Asp Gly Ile Glu
        115                 120                 125

Cys Ala Ser Pro Arg Thr Phe Leu Arg Glu Asn Lys Pro Cys Ile Lys
    130                 135                 140

Tyr Thr Gly His Tyr Phe Ile Thr Thr Leu Leu Tyr Ser Phe Phe Leu
145                 150                 155                 160

Gly Cys Phe Gly Val Asp Arg Phe Cys Leu Gly His Thr Gly Thr Ala
                165                 170                 175

Val Gly Lys Leu Leu Thr Leu Gly Leu Gly Ile Trp Trp Phe Val
            180                 185                 190

Asp Leu Ile Leu Leu Ile Thr Gly Gly Leu Met Pro Ser Asp Gly Ser
        195                 200                 205

Asn Trp Cys Thr Val Tyr
    210

<210> SEQ ID NO 129
<211> LENGTH: 88
<212> TYPE: PRT
<213> ORGANISM: Homo sapiens
<220> FEATURE:
<221> NAME/KEY: misc_feature
<223> OTHER INFORMATION: Incyte Clone No: 2655184

<400> SEQUENCE: 129

Met Ala Cys Phe Ser Phe Phe Leu Cys Phe Leu Val His Leu Leu Ile
1               5                   10                  15

Lys Met Asn Pro Val Thr Glu Ser Pro Ser Cys Leu Phe Ser Pro Pro
                20                  25                  30

Ser Glu Ser Ala Leu Ala Ser Gln Leu Ala Leu Ser Ala Ser Cys Asp
            35                  40                  45

Gln Arg Ala Pro Phe Ser Leu Ala Gly Val Val Ser His Asp Pro Gly
```

```
                50                  55                  60
Trp Pro Val Val Arg Leu His Arg Pro Leu Val Pro Glu His Ala Val
 65                  70                  75                  80

Phe Ser Gln Pro Ser Leu Gln Pro
                 85
```

<210> SEQ ID NO 130
<211> LENGTH: 260
<212> TYPE: PRT
<213> ORGANISM: Homo sapiens
<220> FEATURE:
<221> NAME/KEY: misc_feature
<223> OTHER INFORMATION: Incyte Clone No: 2848362

<400> SEQUENCE: 130

```
Met Pro Asp Pro Leu Phe Ser Ala Val Gln Gly Lys Asp Glu Ile Leu
 1               5                  10                  15

His Lys Ala Leu Cys Phe Cys Pro Trp Leu Gly Lys Gly Met Glu
                20                  25                  30

Pro Leu Arg Leu Leu Ile Leu Leu Phe Val Thr Glu Leu Ser Gly Ala
                35                  40                  45

His Asn Thr Thr Val Phe Gln Gly Val Ala Gly Gln Ser Leu Gln Val
     50                  55                  60

Ser Cys Pro Tyr Asp Ser Met Lys His Trp Gly Arg Arg Lys Ala Trp
 65                  70                  75                  80

Cys Arg Gln Leu Gly Glu Lys Gly Pro Cys Gln Arg Val Val Ser Thr
                85                  90                  95

His Asn Leu Trp Leu Leu Ser Phe Leu Arg Arg Trp Asn Gly Ser Thr
                100                 105                 110

Ala Ile Thr Asp Asp Thr Leu Gly Gly Thr Leu Thr Ile Thr Leu Arg
            115                 120                 125

Asn Leu Gln Pro His Asp Ala Gly Leu Tyr Gln Cys Gln Ser Leu His
        130                 135                 140

Gly Ser Glu Ala Asp Thr Leu Arg Lys Val Leu Val Glu Val Leu Ala
145                 150                 155                 160

Asp Pro Leu Asp His Arg Asp Ala Gly Asp Leu Trp Phe Pro Gly Glu
                165                 170                 175

Ser Glu Ser Phe Glu Asp Ala His Val Glu His Ser Ile Ser Arg Ser
                180                 185                 190

Leu Leu Glu Gly Glu Ile Pro Phe Pro Pro Thr Ser Ile Leu Leu Leu
            195                 200                 205

Leu Ala Cys Ile Phe Leu Ile Lys Ile Leu Ala Ala Ser Ala Leu Trp
        210                 215                 220

Ala Ala Ala Trp His Gly Gln Lys Pro Gly Thr His Pro Pro Ser Glu
225                 230                 235                 240

Leu Asp Cys Gly His Asp Pro Gly Tyr Gln Leu Gln Thr Leu Pro Gly
                245                 250                 255

Leu Arg Asp Thr
            260
```

<210> SEQ ID NO 131
<211> LENGTH: 295
<212> TYPE: PRT
<213> ORGANISM: Homo sapiens
<220> FEATURE:
<221> NAME/KEY: misc_feature
<223> OTHER INFORMATION: Incyte Clone No: 2849906

<400> SEQUENCE: 131

```
Met Gly Leu Pro Val Ser Trp Ala Pro Ala Leu Trp Val Leu Gly
1               5                   10                  15

Cys Cys Ala Leu Leu Leu Ser Leu Trp Ala Leu Cys Thr Ala Cys Arg
            20                  25                  30

Arg Pro Glu Asp Ala Val Ala Pro Arg Lys Arg Ala Arg Gln Arg
            35                  40                  45

Ala Arg Leu Gln Gly Ser Ala Thr Ala Glu Ala Ser Leu Leu Arg
50                      55                  60

Arg Thr His Leu Cys Ser Leu Ser Lys Ser Asp Thr Arg Leu His Glu
65                  70                  75                  80

Leu His Arg Gly Pro Arg Ser Ser Arg Ala Leu Arg Pro Ala Ser Met
                85                  90                  95

Asp Leu Leu Arg Pro His Trp Leu Glu Val Ser Arg Asp Ile Thr Gly
            100                 105                 110

Pro Gln Ala Ala Pro Ser Ala Phe Pro His Gln Glu Leu Pro Arg Ala
            115                 120                 125

Leu Pro Ala Ala Ala Thr Ala Gly Cys Ala Gly Leu Glu Ala Thr
130                 135                 140

Tyr Ser Asn Val Gly Leu Ala Ala Leu Pro Gly Val Ser Leu Ala Ala
145                 150                 155                 160

Ser Pro Val Val Ala Glu Tyr Ala Arg Val Gln Lys Arg Lys Gly Thr
                165                 170                 175

His Arg Ser Pro Gln Glu Pro Gln Gln Gly Lys Thr Glu Val Thr Pro
            180                 185                 190

Ala Ala Gln Val Asp Val Leu Tyr Ser Arg Val Cys Lys Pro Lys Arg
            195                 200                 205

Arg Asp Pro Gly Pro Thr Thr Asp Pro Leu Asp Pro Lys Gly Gln Gly
210                 215                 220

Ala Ile Leu Ala Leu Ala Gly Asp Leu Ala Tyr Gln Thr Leu Pro Leu
225                 230                 235                 240

Arg Ala Leu Asp Val Asp Ser Gly Pro Leu Glu Asn Val Tyr Glu Ser
            245                 250                 255

Ile Arg Glu Leu Gly Asp Pro Ala Gly Arg Ser Ser Thr Cys Gly Ala
            260                 265                 270

Gly Thr Pro Pro Ala Ser Ser Cys Pro Ser Leu Gly Arg Gly Trp Arg
            275                 280                 285

Pro Leu Pro Ala Ser Leu Pro
            290                 295

<210> SEQ ID NO 132
<211> LENGTH: 183
<212> TYPE: PRT
<213> ORGANISM: Homo sapiens
<220> FEATURE:
<221> NAME/KEY: misc_feature
<223> OTHER INFORMATION: Incyte Clone No: 2899137

<400> SEQUENCE: 132

Met Ala Ala Ser Met Ala Arg Gly Gly Val Ser Ala Arg Val Leu Leu
1               5                   10                  15

Gln Ala Ala Arg Gly Thr Trp Trp Asn Arg Pro Gly Gly Thr Ser Gly
            20                  25                  30

Ser Gly Glu Gly Val Ala Leu Gly Thr Thr Arg Lys Phe Gln Ala Thr
            35                  40                  45

Gly Ser Arg Pro Ala Gly Glu Glu Asp Ala Gly Gly Pro Glu Arg Pro
50                      55                  60
```

```
Gly Asp Val Val Asn Val Phe Val Asp Arg Ser Gly Gln Arg Ile
 65                  70                  75                  80

Pro Val Ser Gly Arg Val Gly Asp Asn Val Leu His Leu Ala Gln Arg
             85                  90                  95

His Gly Val Asp Leu Glu Gly Ala Cys Glu Ala Ser Leu Ala Cys Ser
        100                 105                 110

Thr Cys His Val Tyr Val Ser Glu Asp His Leu Asp Leu Leu Pro Pro
    115                 120                 125

Pro Glu Glu Arg Glu Asp Asp Met Leu Asp Met Ala Pro Leu Leu Gln
130                 135                 140

Glu Asn Ser Arg Leu Gly Cys Gln Ile Val Leu Thr Pro Glu Leu Glu
145                 150                 155                 160

Gly Ala Glu Phe Thr Leu Pro Lys Ile Thr Arg Asn Phe Tyr Val Asp
                165                 170                 175

Gly His Val Pro Lys Pro His
            180
```

<210> SEQ ID NO 133
<211> LENGTH: 113
<212> TYPE: PRT
<213> ORGANISM: Homo sapiens
<220> FEATURE:
<221> NAME/KEY: misc_feature
<223> OTHER INFORMATION: Incyte Clone No: 2986229

<400> SEQUENCE: 133

```
Met Trp Arg Lys Pro Asp Val Leu Tyr Ser Val Ile Pro Val Thr Ser
  1               5                  10                  15

Leu Phe Phe Leu Leu Ala Leu Asn Leu Pro Asp Val Phe Gly Leu Val
             20                  25                  30

Val Leu Pro Leu Glu Leu Lys Leu Arg Ile Phe Arg Leu Leu Asp Val
         35                  40                  45

Arg Ser Val Leu Ser Leu Ser Ala Val Cys Arg Asp Leu Phe Thr Ala
 50                  55                  60

Ser Asn Asp Pro Leu Leu Trp Arg Phe Leu Tyr Leu Arg Asp Phe Arg
 65                  70                  75                  80

Gly Asp Phe Arg Asn Asp Ile Phe Thr Arg Lys Gly Ser Tyr Cys Leu
             85                  90                  95

Asp Tyr Ser Ala His Gln Lys Phe Leu Val Val Gly Phe Phe Cys Cys
        100                 105                 110

Lys
```

<210> SEQ ID NO 134
<211> LENGTH: 160
<212> TYPE: PRT
<213> ORGANISM: Homo sapiens
<220> FEATURE:
<221> NAME/KEY: misc_feature
<223> OTHER INFORMATION: Incyte Clone No: 3222081

<400> SEQUENCE: 134

```
Met Gln Arg Val Ser Gly Leu Leu Ser Trp Thr Leu Ser Arg Val Leu
  1               5                  10                  15

Trp Leu Ser Gly Leu Ser Glu Pro Gly Ala Ala Arg Gln Pro Arg Ile
             20                  25                  30

Met Glu Glu Lys Ala Leu Glu Val Tyr Asp Leu Ile Arg Thr Ile Arg
         35                  40                  45

Asp Pro Glu Lys Pro Asn Thr Leu Glu Glu Leu Glu Val Val Ser Glu
```

```
                50               55                  60
Ser Cys Val Glu Val Gln Glu Ile Asn Glu Glu Tyr Leu Val Ile
65                  70                  75                  80

Ile Arg Phe Thr Pro Thr Val Pro His Cys Ser Leu Ala Thr Leu Ile
                85                  90                  95

Gly Leu Cys Leu Arg Val Lys Leu Gln Arg Cys Leu Pro Phe Lys His
            100                 105                 110

Lys Leu Glu Ile Tyr Ile Ser Glu Gly Thr His Ser Thr Glu Glu Asp
        115                 120                 125

Ile Asn Lys Gln Ile Asn Asp Lys Glu Arg Val Ala Ala Ala Met Glu
    130                 135                 140

Asn Pro Asn Leu Arg Glu Ile Val Glu Gln Cys Val Leu Glu Pro Asp
145                 150                 155                 160

<210> SEQ ID NO 135
<211> LENGTH: 865
<212> TYPE: DNA
<213> ORGANISM: Homo sapiens
<220> FEATURE:
<221> NAME/KEY: misc_feature
<223> OTHER INFORMATION: Incyte Clone No: 443531

<400> SEQUENCE: 135
attcctcaat tttccagtct cccttgagct aagtgtggcc ctatgactca cttccagcca       60
tgaaaacaag tgcaaatctg ttaggagtat gttctggggc aattttttgct ctcctgatga     120 agacaaaggc tgttgatcca ctgaacccac ccagacacta tgtggttttct tgaatgtcct    180 acgtacattt tgatggatta cccaaggact atctgatgaa gaataataga gacatataaa    240
tacatatggg ctcatccttg gcaaaataaa gtaatcctga agtaaattct aaggatgttc    300
tgaattgaca cctcttaagc acaaccgaat gtcctggtgg cttttgcctcc cactggggct    360 ttttggctct tgtttggccc cagcggctgc tgcagctctg tctgaattca cacaggagca    420
acatgatggt gctcagccct cgccgaagtg tcttgctgaa gagttgggag atgcttggac    480
tattcagata gaagccaact ggaagtacag ggcagtcaac acaaaccaga gaggcaaact    540
tttggccagt gagacatgga aagggagaag aaatacattc ttctttctcc cctagagtga    600
ggaccaacct gagtcccagt cacctggaat cccctcagac gagcgtccct tgagatccag    660
cacatggcag ccagcgtgct gacgattcct tcctgcctac tggctccttc ttatttctgc    720
ctccgtggaa ctgtattctc taatcaatat tagcacatac atattgcccc agactgtacc    780
tcctgggaac ccaggataaa gcactatcta aacattttgt cttggaattg taataaactt    840
caaaagaaaa atacaaaaaa aaaaa                                          865

<210> SEQ ID NO 136
<211> LENGTH: 706
<212> TYPE: DNA
<213> ORGANISM: Homo sapiens
<220> FEATURE:
<221> NAME/KEY: modified_base
<222> LOCATION: (11)..(12)
<223> OTHER INFORMATION: a, c, g, t, unknown, or other
<220> FEATURE:
<221> NAME/KEY: misc_feature
<223> OTHER INFORMATION: Incyte Clone No: 632860

<400> SEQUENCE: 136
cggaccgtgg nnttggtaaa gcccatttcc gaggattttta gggagaccta ggtggggcag      60
acactagaag tgtccagcct ccaagcccaa gagatgtggc cggcagggct gggcaggtcc     120
```

| | | |
|---|---|---|
| ttgctggctc agcctgctct ttgctccttc atgggacccc agtggatcct gcagttctgc | 180 |
| tcttggctgg aaccacgcca gcttcgctgg agctggactg agccgccttt tacattattg | 240 |
| gactctctcg ggttgagagc tgcccaggac tcctgcagtt tcaccaccct tgttcctttg | 300 |
| actcttgact catcattcat gaccgttaac gtggttccat ttgtatggac ttcttctttc | 360 |
| ttcagagcat ttcagtatcc tgttacctcc ccatgcagaa caaagaatac tccacttttg | 420 |
| atagatgggg ttaccaggat tcaggctaca tggcctgagg caaggtcaca acatgagtga | 480 |
| cagaatgtgt cctggaagcc aggcatcctc tggggtgtat ttggggcgct caacaaggct | 540 |
| tgatcgagct ttgggggtag atctagctat tccatgggga ttcttttcag aattgctgtt | 600 |
| ttcggtaact aattccatga ccaggtccat ggcattggat gacattgcgc tacactgttg | 660 |
| ctcacccggg tcacccgtcc tcacaggttg gatggcaagc atgttg | 706 |

<210> SEQ ID NO 137
<211> LENGTH: 801
<212> TYPE: DNA
<213> ORGANISM: Homo sapiens
<220> FEATURE:
<221> NAME/KEY: misc_feature
<223> OTHER INFORMATION: Incyte Clone No: 670010

<400> SEQUENCE: 137

| | | |
|---|---|---|
| acttctacat gggcctcctg ctgctggtgc tcttcctcag cctcctgccg gtggcctaca | 60 |
| ccatcatgtc cctcccaccc tcctttgact gcgggccgtt caggtgcaga gtctcagttg | 120 |
| cccgggagca cctcccctcc cgaggcagtc tgctcagagg gcctcggccc agaattccag | 180 |
| ttctggtttc atgccagcct gtaaaaggcc atggaacttt gggtgaatca ccgatgccat | 240 |
| ttaagagggt tttctgccag gatggaaatg ttaggtcgtt ctgtgtctgc gctgttcatt | 300 |
| tcagtagcca ccagccacct gtggccgttg agtgcttgaa atgaggaact gagaaaatta | 360 |
| atttctcatg tatttttctc atttatttat taattttaa ctgatagttg tacatatttg | 420 |
| ggggtacatg tgatatttgg atacatgtat acaatatata atgatcaaat cagggtaact | 480 |
| gggatatcca tcacatcaaa catttatttt ttattctttt tagacagagt ctcactctgt | 540 |
| cacccaggct ggagtgcagt ggtgccatct cagcttactg caacctctgc ctgccaggtt | 600 |
| caagcgattc tcatgcctcc acctcccaag tagctgggac tacaggcatg caccacaatg | 660 |
| cccaactaat ttttgtattt ttagtagaga cggggttttg ccatgttgcc caggctggcc | 720 |
| ttgaactcct ggcctcaaac aatccacttg cctcggcctc ccaaagtgtt atgattacag | 780 |
| gcgtgagcca ccgtgcctgg g | 801 |

<210> SEQ ID NO 138
<211> LENGTH: 664
<212> TYPE: DNA
<213> ORGANISM: Homo sapiens
<220> FEATURE:
<221> NAME/KEY: modified_base
<222> LOCATION: (505)
<223> OTHER INFORMATION: a, c, g, t, unknown, or other
<220> FEATURE:
<221> NAME/KEY: modified_base
<222> LOCATION: (518)
<223> OTHER INFORMATION: a, c, g, t, unknown, or other
<220> FEATURE:
<221> NAME/KEY: modified_base
<222> LOCATION: (527)
<223> OTHER INFORMATION: a, c, g, t, unknown, or other
<220> FEATURE:
<221> NAME/KEY: modified_base
<222> LOCATION: (540)
<223> OTHER INFORMATION: a, c, g, t, unknown, or other

```
<220> FEATURE:
<221> NAME/KEY: modified_base
<222> LOCATION: (565)..(566)
<223> OTHER INFORMATION: a, c, g, t, unknown, or other
<220> FEATURE:
<221> NAME/KEY: misc_feature
<223> OTHER INFORMATION: Incyte Clone No: 726498

<400> SEQUENCE: 138
cggacgcgtg ggctggaagg agctctggag tcggaatcag gatgtggagg ctgagaagaa      60
atctggctct accacctggg aaactggcat ggttgtattt gtcagtgttc agtcagggga     120
gcagagccat gatgagtctt acggaaataa ggttaaaaca tatgcttgaa atttggcatg     180
gcagacaagc cagagcttgt gaaaatctaa gaaaccaaac acgtgtagcc accaaagtgg     240
aaccacaaaa gggaagatct acagaaattt gttgccttgc tgtagttcca ttaaatgagg     300
ttgtgcagtc aagcatcttg tggtgggtct ggagctgttg ccagcatcag gaagacaagc     360
tgggtgctaa gtgaagaaat acacaatgta gaaactgtca ggcatctctg cccctggact     420
tcaccatatc tgatgatgtt ctcagagtca gggcactgct tcacttttcg cttccaaatc     480
tcacacaaaa ttctctgtta ggcanccccca gcttagancc ttacaantga ggggatcan     540 ggaaatggag tacccagata cccanngtga tatacttta tgccctcagt ttcttatctt      600
tcagtgggga taatatcctc ggatacaaaa gagtgtacat ataccctg tatttggtaa       660 acta                                                                  664

<210> SEQ ID NO 139
<211> LENGTH: 1241
<212> TYPE: DNA
<213> ORGANISM: Homo sapiens
<220> FEATURE:
<221> NAME/KEY: misc_feature
<223> OTHER INFORMATION: Incyte Clone No: 795064

<400> SEQUENCE: 139
ccaggcaata tctcaggata tggaagtttc tgggtttatt taccccctcag tgcccagagt     60 taaagtttca gaagagactt gtgcacataa gggcttcatc tcaagtgtat tgcagtaatg    120
gctgaatcgg ggttaacatc ccttccaggc acagcgagtt ggttctgctt tttgcctgta    180
agccaaagaa aagccacatc taaaaagcta ctactaaaag ccagaaagaa aagtggattt    240
gaactcagtg tcacagactc ttctgagtgt tttagggtca cagctagtgt aagaggcatg    300
aagaatagac atgcaaaagg gaacgggtgc accagagacc cctgttttgg ctgacagacc    360
atatgtccca ccagctgggg aatctgacaa gaggacatag gtggcactct ttttttaaag    420
ctatttattg tatctattt taaataaaat tgcccatcct cattcagctc ttagaacaaa     480
agcaaaaaac cctgtaaatc aggagatata agcacatctg cacccagaat aggcccatat    540
gatagggcaa ccctgagctt aaacaatgac atcttcaagg gtagaactaa tctgaaaccc    600
ccttccagcc tctggaagac actggcctgc atcagttaga gtcagagcaa gtgtcacttc    660
acagggaaaa gaaggattat atagacttcc tatccctaga gtttataaat gtcaactata    720 taaaaaagc tcaaaacagt gttaaaggaa tgaacagtag aattttaata ggctgtccaa     780
agaagccagg tctgctgtgg gcaagtatag cctaaccctta gtcttgtaaa ataagccaga    840
aagggttact gagccacctt aagctagtac ctatatagta ggcaaaaagt acagaaatag    900
atgcaataag tgtggtgagt ctttgagcct acgagtcatg ccaccagcca taagttgacc    960
tatcacttga gaacctcctc agcaaagatg ccagaaaaca ttcaatcaag ttggcaaatg  1020
acacagggag ctgccctct gaccatcttc ctggcaaacc tggactggaa gggccatttg   1080
```

| | |
|---|---|
| cagcactgtc ctggagctaa tacactgttt cactgcctct gccatataat gatgccagca | 1140 |
| ctagccagct ggtgggtatt tggaggaatc ctgcatgagg attgcccaat aaggggcagg | 1200 |
| tacacatacc tggcaaagtg atgatgatgt gaattgtttc c | 1241 |

<210> SEQ ID NO 140
<211> LENGTH: 750
<212> TYPE: DNA
<213> ORGANISM: Homo sapiens
<220> FEATURE:
<221> NAME/KEY: modified_base
<222> LOCATION: (570)
<223> OTHER INFORMATION: a, c, g, t, unknown, or other
<220> FEATURE:
<221> NAME/KEY: modified_base
<222> LOCATION: (641)
<223> OTHER INFORMATION: a, c, g, t, unknown, or other
<220> FEATURE:
<221> NAME/KEY: misc_feature
<223> OTHER INFORMATION: Incyte Clone No: 924925

<400> SEQUENCE: 140

| | |
|---|---|
| tggagtgggg agaagagcat acgccaggag cctcctgcct caaagtgctc ccctaagtct | 60 |
| tcttcctcct gtgctgacct cagggtggtc tgacccttcc ctcggtgtgg gggatgtggc | 120 |
| cctctcaggt gccactactt gctttctgct tccttctggt gaagtccacc tccaacatta | 180 |
| acctgcccac cccaccccg tcatccctgg agaattccag ctttgtcgta tctcagagag | 240 |
| ggaatctaat tgttttgggg gggcaaaaga aagcaacgtt taggtatcac ttctacttgg | 300 |
| accgcatgcc tttttatagc caaatttctg tgtatttcgt aaatggattt cgcgttaatg | 360 |
| gatatttatg taataactag acttctcaga ttattgtgag aagggtcagg ttggaagggg | 420 |
| tgtaggaaga cgggtgaggg gtagtttttt tctgtcctag tttttttttt ttttattgtc | 480 |
| atctctgagg tggactttgt cacctgtggt tattggggcc aagtggactc agctccgggg | 540 |
| gagaaggctt ctctgccatt tcggtccaan ggtgactgac acaggcgtac ttttttgggac | 600 |
| tgtggaagca tcagatgcca gcactgactt cagaccagca nttcgggcta gaggaagatg | 660 |
| ggacctttca ggatggaaat accttggact ttcttttggt ccctcggaaa cttgggcttt | 720 |
| ctctaccgac ttgcccagat ttcatttcac | 750 |

<210> SEQ ID NO 141
<211> LENGTH: 1235
<212> TYPE: DNA
<213> ORGANISM: Homo sapiens
<220> FEATURE:
<221> NAME/KEY: misc_feature
<223> OTHER INFORMATION: Incyte Clone No: 962390

<400> SEQUENCE: 141

| | |
|---|---|
| ccctcaggca gcccctccac aggacccctc tcctgcctgg acagtctgc tggtctcccc | 60 |
| gtcccctgga gaagaacaag gccatgggtc ggcccctgct gctgcccctg ctgctcctgc | 120 |
| tgcagccgcc agcatttctg cagcctggtg gctccacagg atctggtcca agctaccttt | 180 |
| atggggtcac tcaaccaaaa cacctctcag cctccatggg tggctctgtg gaaatcccct | 240 |
| tctccttcta ttaccctgg gagttagcca tagttcccaa cgtgagaata tcctggagac | 300 |
| ggggccactt ccacgggcag tccttctaca gcacaaggcc gccttccatt cacaaggatt | 360 |
| atgtgaaccg gctctttctg aactggacag agggtcagga gagcggcttc ctcaggatct | 420 |
| caaacctgcg gaaggaggac cagtctgtgt atttctgccg agtcgagctg gacacccgga | 480 |
| gatcagggag gcagcagttg cagtccatca aggggaccaa actcaccatc acccaggctg | 540 |

```
tcacaaccac caccacctgg aggcccagca gcacaaccac catagccggc ctcagggtca    600
cagaaagcaa agggcactca gaatcatggc acctaagtct ggacactgcc atcagggttg    660
cattggctgt cgctgtgctc aaaactgtca ttttgggact gctgtgcctc ctcctcctgt    720
ggtggaggag aaggaaaggt agcagggcgc caagcagtga cttctgacca acagagtgtg    780
gggagaaggg atgtgtatta gccccggagg acgtgatgtg agacccgctt gtgagtcctc    840
cacactcgtt ccccattggc aagatacatg gagagcaccc tgaggacctt taaaaggcaa    900
agccgcaagg cagaaggagg ctgggtccct gaatcaccga ctggaggaga gttacctaca    960
agagccttca tccaggagca tccacactgc aatgatatag gaatgaggtc tgaactccac   1020
tgaattaaac cactggcatt tgggggctgt ttattatagc agtgcaaaga gttcctttat   1080
cctccccaag gatggaaaaa tacaatttat tttgcttacc atacacccct tttctcctcg   1140
tccacatttt ccaatctgta tggtggctgt cttctatggc agaaggtttt ggggaataaa   1200
tagcgtgaaa tgctgctgac acttaaaaaa aaaaa                              1235

<210> SEQ ID NO 142
<211> LENGTH: 1834
<212> TYPE: DNA
<213> ORGANISM: Homo sapiens
<220> FEATURE:
<221> NAME/KEY: misc_feature
<223> OTHER INFORMATION: Incyte Clone No: 1259405

<400> SEQUENCE: 142
gacggaagtg cgggcggagg atccccagcc gggtcccaag cctgtgcctg tgcctgagcc     60
tgagcctgag cctgagcccg agccgggagc cggtcgcggg ggctccgggc tgtgggaccg    120
ctgggccccc agcgatggcg accctgtggg gaggccttct tcggcttggc tccttgctca    180
gcctgtcgtg cctggcgctt tccgtgctgc tgctggcgca gctgtcagac gccgccaaga    240
atttcgagga tgtcagatgt aaatgtatct gccctcccta taagaaaaat tctgggcata    300
tttataataa gaacatatct cagaaagatt gtgattgcct tcatgttgtg gagcccatgc    360
ctgtgcgggg gcctgatgta gaagcatact gtctacgctg tgaatgcaaa tatgaagaaa    420
gaagctctgt cacaatcaag gttaccatta taatttatct ctccattttg ggccttctac    480
ttctgtacat ggtatatctt actctggttg agcccatact gaagaggcgc ctctttggac    540
atgcacagtt gatacagagt gatgatgata ttggggatca ccagcctttt gcaaatgcac    600
acgatgtgct agcccgctcc cgcagtcgag ccaacgtgct gaacaaggta gaatatgcac    660
agcagcgctg gaagcttcaa gtccaagagc agcgaaagtc tgtctttgac cggcatgttg    720
tcctcagcta attgggaatt gaattcaagg tgactagaaa gaaacaggca gacaactgga    780
aagaactgac tgggttttgc tgggtttcat tttaataccct tgttgatttc accaactgtt    840 gctgaagat tcaaaactgg aagcaaaaac ttgcttgatt ttttttcctt gttaacgtaa    900
taatagagac attttaaaa gcacacagct caaagtcagc caataagtct tttcctattt     960 gtgacttta ctaataaaaa taaatctgcc tgtaaattat cttgaagtcc tttacctgga    1020
acaagcactc tctttttcac cacatagttt taacttgact ttcaagataa ttttcagggt   1080
ttttgttgtt gttgtttttt gtttgtttgt tttggtggga gaggggaggg atgcctggga   1140
agtggttaac aactttttttc aagtcacttt actaaacaaa cttttgtaaa tagaccttac   1200
cttctatttt cgagtttcat ttatattttg cagtgtagcc agcctcatca aagagctgac   1260
ttactcattt gacttttgca ctgactgtgt tatctgggta tctgctgtgt ctgcacttca   1320
```

| | |
|---|---|
| tggtaaacgg gatctaaaat gcctggtggc ttttcacaaa aagcagattt tcttcatgta | 1380 |
| ctgtgatgtc tgatgcaatg catcctagaa caaactggcc atttgctagt ttactctaaa | 1440 |
| gactaaacat agtcttggtg tgtgtggtct tactcatctt ctagtacctt taaggacaaa | 1500 |
| tcctaaggac ttggacactt gcaataaaga aattttattt taaacccaag cctccctgga | 1560 |
| ttgataatat atacacattt gtcagcattt ccggtcgtgg tgagaggcag ctgtttgagc | 1620 |
| tccaatgtgt gcagctttga actagggctg gggttgtggg tgcctcttct gaaaggtcta | 1680 |
| accattattg gataactggc ttttttcttc ctctttggaa tgtaacaata aaaataattt | 1740 |
| ttgaaacatc catcagtgta tctatctatg tctcctagtt ttttcctcct ccctcttttg | 1800 |
| ctgtataatg agagagaaga tctgatgaga taac | 1834 |

<210> SEQ ID NO 143
<211> LENGTH: 1722
<212> TYPE: DNA
<213> ORGANISM: Homo sapiens
<220> FEATURE:
<221> NAME/KEY: misc_feature
<223> OTHER INFORMATION: Incyte Clone No: 1297384

<400> SEQUENCE: 143

| | |
|---|---|
| tacgagaccc ggccgcaccc cgagtcacac aggcccccgg ggccacggcg ttcgtctctc | 60 |
| ctgtgctgtc ctcaggcctc cgctcctgtt ttggtggccc aggctctccc ctgccccatc | 120 |
| ctcgctcccc cacctccttg ggtcatgccc acccacccctt tcctgcctcc tccgtgtgaa | 180 |
| gacatccaac atccacgtga cttttccagc tccattttta aacagtgact gagattctag | 240 |
| aaaaactggc tgctaactgg cctgagccag gcaacactga ttccaatccc tcctccttt | 300 |
| ttaagttatt tgatggaaga ctcacctaat ttgtgacctg aaactgttga agaaatagag | 360 |
| aggaggggggc ccgttgatta cagagagcat ttgggatttt gtttggtttg gagatgatgc | 420 |
| ctaggttact gggtttgggg ggattgtttt cttttggggg ccttcccctt ttactccttt | 480 |
| tcttccagag atcaagagct tctcttgcat cttcttccac tgggctctgg attaatcaat | 540 |
| tacccaaagg ctgcacctgc cgtgttgtct gggcttgcat cccagatgtg ttggagtatg | 600 |
| catggatgta gtgctttta gaggagccac tgggcaaggc caccaagaac aaatgcatga | 660 |
| cattttatag ccaaggacgc ctcgctaaag tcttatgggc gtcccctggg gttggggggg | 720 |
| cacaaggttt tggaggaaga agacaacttc cctcattcca tcatcaccat ctcttttctca | 780 |
| ctaggttctt tctagttttc aagcaatagt tctagcctgc cttggacaag ggggcccag | 840 |
| ttaaacaaac tacccatcca tgaggtgcca ggcagtcaaa acagaagct tccccgactt | 900 |
| gtgagtccct gagatgtgct cttgttgttt ggcatttggg gtgacaggga gtgacccaga | 960 |
| ggccaccact gcttttcatg caggagttac agacactggt ttcttggaaa atggagagaa | 1020 |
| gcgcactttg cacagacgtc gtcaattaag tcccaatttg ccacttggta ttgagtacac | 1080 |
| tggaccctga ccactggctc ttgggcaaac gtccttcctc acggggcgcc tccgccaagc | 1140 |
| cggcccagct gcacccctcc cttcctggag ggatggccag ggaaggagaa acagagaac | 1200 |
| tgacacctt gaaaccacag aatgtgttac atgcagactc gctcaagggc ataagttatt | 1260 |
| gtgaacgttt ttgccaatca ctgctcaaca gccctgctag attttgtatg atgctgaatt | 1320 |
| attatgcaga ctaattccac ccagttgaga cacaccatgc ttgttcactt gtatttattg | 1380 |
| aaactgtgga ttcttgcccg tgctgtccct tgtatttact ttaagcactg atcacttatc | 1440 |
| attcattcgg tatggttttc cctgtccctt gtacacattc tggtatgaat ttgtaaaaat | 1500 |
| aacctgctac aaattggttg aatgtttctg tctgtggtgc gaaccagcat taacggatgg | 1560 |

```
ggcacgtgcc caactgagga acaggagaag aaatcaccaa tttgggctct cagagctaag    1620
acacacttat tgattctgtt gcacattttg cactggttta tggcgattgt tttcttggac    1680
ggatagtgta aaataaactt ctctgttctc taaaaaaaaa aa                       1722
```

<210> SEQ ID NO 144
<211> LENGTH: 1741
<212> TYPE: DNA
<213> ORGANISM: Homo sapiens
<220> FEATURE:
<221> NAME/KEY: misc_feature
<223> OTHER INFORMATION: Incyte Clone No: 1299627

<400> SEQUENCE: 144

```
ttcgctccaa gcctcaggcc accggcttgg atggacgctc cgaggctacc cgtgcgtcca      60
ggggtcttgc ttccgaagtt ggtcctgctc tttgtctacg cagatgattg ccttgctcag     120
tgtggcaaag attgcaaatc ttactgctgt gatggaacca cgccctactg ttgctcctac     180
tacgcttata ttgggaatat cctctcgggc actgcaattg cgggcattgt ttttggaata     240
gtatttatca tggggtcat tgctgggatt gccatatgca tctgcatgtg catgaagaac      300
cacagggcga cccgcgtggg catcctcagg acgactcaca tcaacaccgt ctcctcctat     360
cctggaccac caccctacgg tcacgaccac gagatggaat actgtgcaga cttgcctcct     420
ccatactccc ccacccaca gggtccagca cagcgttctc caccccctcc ttatcctgga      480
aacgcaagga ataatctat ctcccagaac agaacatgtg ccaatgggcg atcttgcctg      540
gaataaaatg cctctactca gaaacaggca ggaaagaatt gctccaagga atactttttg     600
gggtcagata atgtgtcagg tggaatatcc ctgctaggag atataggatt tctactctgc     660
tcaaagctga cccatctgg agtattaatg tttggttcta tggaaccaca ttttaagaga      720
tctgctgatc cacctaagca cattcaggga agagtaatgt aattgacaaa atatctgata     780
atcatgttgt ttaagggcta ggtgaagaaa gtttcagtat tgatcctgga aaaaagaag     840 atctaagtag gatgggagaa tgatttggcc cacacaagga agcaacttta ttctatatag     900
ctttaaaagt cagaactaga attgttcatt cttttcattca tcaataaatg tattttgagt     960
gcctaagagt ttactatgtg cctagcactg tttgaggtcc tgatggaagt tacaggatgg    1020
gtactctggt tttagtacaa gaaagagcaa tgactagatt gctttgtgaa gctcttggta    1080
gagacacgct ccagaaggga taacaaaatc aaatagtaga tgggttcatt gggcctcaga    1140
agttctgctc gtatttagg tgggtgtgaa gtgaatttct atatgtccag gagtgaatac     1200
aacagaaaga gttggatctt atttatttaa ttagggagtt aaaacaagac caaaaagact    1260
caacagccgc ttgaagccaa gaactcttca atgccagcta ctgccaccta aaaatcatct    1320
ggctttatag tggatcagaa taaaggttat tctaactgtg gggagaaaaa aaaaattgta    1380
tcaagttcca caggtagcag acacttcact tccaagtaaa agatgagaaa tcaattattc    1440
ccacaggatt ttaggtcagg gagcaaaaat ctcagaactt gaccatgaag atacacaaca    1500
gactcgcaaa aataaagtgg gaaatgaagt tcagattccc ttctgtagat ttccttaaaa    1560
ctattatttt tttcttcttc gtaaaatttt gataatctgt tctcttaaaa aagttaatga    1620
cacaattaag atactgacat caaattgttg ccttttacca aaatgcaaat tttatgaagt    1680
gcctaccttt atatgtataa agcatttaat aaataattct aatgtgccat aaaaaaaaaa    1740
a                                                                     1741
```

<210> SEQ ID NO 145

```
<211> LENGTH: 997
<212> TYPE: DNA
<213> ORGANISM: Homo sapiens
<220> FEATURE:
<221> NAME/KEY: modified_base
<222> LOCATION: (973)
<223> OTHER INFORMATION: a, c, g, t, unknown, or other
<220> FEATURE:
<221> NAME/KEY: misc_feature
<223> OTHER INFORMATION: Incyte Clone No: 1306026

<400> SEQUENCE: 145
ggacaaccgt tgctgggtgt cccagggcct gaggcaggac ggtactccgc tgacaccttc      60
cctttcggcc ttgaggttcc cagcctggtg gccccaggac gttccggtcg catggcagag     120
tgctacggac gacgcctatg aagcccttag tccttctagt tgcgcttttg ctatggcctt     180
cgtctgtgcc ggcttatccg agcataactg tgacacctga tgaagagcaa aacttgaatc     240
attatataca agttttagag aacctagtac gaagtgttcc ctctggggag ccaggtcgtg     300
agaaaaaatc taactctcca aaacatgttt attctatagc atcaaaggga tcaaaattta     360
aggagctagt tacacatgga gacgcttcaa ctgagaatga tgttttaacc aatcctatca     420
gtgaagaaac tacaactttc cctacaggag gcttcacacc ggaaatagga agaaaaaac      480
acacggaaag taccccattc tggtcgatca aaccaaacaa tgtttccatt gttttgcatg     540
cagaggaacc ttatattgaa aatgaagagc cagagccaga gccggagcca gctgcaaaac     600
aaactgaggc accaagaatg ttgccagttg ttactgaatc atctacaagt ccatatgtta     660
cctcatacaa gtcacctgtc accactttag ataagagcac tggcattgag atctctacag     720
aatcagaaga tgttcctcag ctctcaggtg aaactgcgat agaaaaaccc gagagttgga     780
agcaccagag agtgggatat gatgcatttg aaaaaaattt agtattaatc acaatgcaca     840
ggcacttcta gtgacacagc acccagctat agagagatat gaaggggtac gagctcgaat     900
tcgaatcatg tcatagctgt ttcctgtgtg aattggtatc gctcacaatg cacacacata     960
cgagcggaag ctnaattggt aagcgggggt gccatga                              997

<210> SEQ ID NO 146
<211> LENGTH: 981
<212> TYPE: DNA
<213> ORGANISM: Homo sapiens
<220> FEATURE:
<221> NAME/KEY: misc_feature
<223> OTHER INFORMATION: Incyte Clone No: 1316219

<400> SEQUENCE: 146
gttttaaatt tacttaataa atataaaata ttgtatgttc ttaacttgaa gctcatattt      60
tcaagtaatt ccttgtctgg aattttctgt tgatctcatg ggtactaaga aacgaaatat     120
tctgttcatt ttcattttta aagaatatcg ataacttgat gacccagaa ggagttggcc     180
ttaccactgc cttacgtgtt ctctgtaatg ttgcatgccc accacctcct gttgaaggtc     240
aacagaaaga tctgaaatgg aatcttgccg ttattcagct ttttctgct gaaggaatgg      300
acacgtttat tcgagttctg caaaaattga acagtattct gactcagcct tggaggctcc     360
atgtcaacat ggggactacc cttcacagag ttactactat ttcaatggct cgctgcacac     420
tcactcttct taaactatg ttaacggaac tcctgagagg tggatccttt gagtttaagg      480
acatgcgtgt tccttcagcg cttgttactt tacatatgct cctgtgctct atcccctct     540
caggtcgttt ggatagtgat gaacagaaaa ttcagaatga tatcattgat attttactga     600
cttttacaca aggagttaat gaaaaactca caatctcaga agagactctg gccaataata     660
```

```
cttggtctttt aatgttaaaa gaagttctttt cttcaatctt gaaggttcct gaaggatttt      720
tttctggact catactcctt tcagagctgc tgcctcttcc attgcccatg caaacaactc       780
aggtatcact tccatataac atgcatctta taaatgactg cagtaacact ttttaaaaag       840
ccagtgattt tgttaaaaaa caaaaaccct catctccctt cctcccaaaa agacataaaa       900
taaccggatg aggggagat aaaactgaaa caagttggtc attgaggaaa tatgggggta        960 aaaatttaa ataaattttt g                                                  981
```

<210> SEQ ID NO 147
<211> LENGTH: 526
<212> TYPE: DNA
<213> ORGANISM: Homo sapiens
<220> FEATURE:
<221> NAME/KEY: misc_feature
<223> OTHER INFORMATION: Incyte Clone No: 1329031

<400> SEQUENCE: 147

```
ctgcaggccc acctgtctgc aacccagctg aggccatgcc ctccccaggg accgtctgca        60
gcctcctgct cctcggcatg ctctggctgg acttggccat ggcaggctcc agcttcctga      120
gccctgaaca ccagagagtc cagcagagaa aggagtcgaa gaagccacca gccaagctgc      180
agccccgagc tctagcaggc tggctccgcc cggaagatgg aggtcaagca gaaggggcag      240
aggatgaact ggaagtccgg ttcaacgccc cctttgatgt tggaatcaag ctgtcagggg      300
ttcagtacca gcagcacagc caggccctgg ggaagtttct tcaggacatc ctctgggaag      360
aggccaaaga ggccccagcc gacaagtgat cgcccacaag ccttactcac ctctctctaa      420
gtttagaagc gctcatctgg ctttttcgctt gcttctgcag caactcccac gactgttgta    480
caagctcagg aggcgaataa atgttccaac ctggtaaaaa aaaaaa                     526
```

<210> SEQ ID NO 148
<211> LENGTH: 2090
<212> TYPE: DNA
<213> ORGANISM: Homo sapiens
<220> FEATURE:
<221> NAME/KEY: misc_feature
<223> OTHER INFORMATION: Incyte Clone No: 1483050

<400> SEQUENCE: 148

```
gaggcgcggg gagagtaggg tgctgtggtc tgagctagag ggtgaagctg gcggagcagg        60
aggatgggcg tatgcaggtg atagactaga gaacaagacc tctgtctccg tagcatcctg      120
gagcagtctg aatgccagaa tggataaccg ttttgctaca gcatttgtaa ttgcttgtgt      180
gcttagcctc atttccacca tctacatggc agcctccatt ggcacagact tctggtatga      240
atatcgaagt ccagttcaag aaaattccag tgatttgaat aaaagcatct gggatgaatt      300
cattagtgat gaggcagatg aaaagactta taatgatgca cttttttcgat acaatggcac      360 agtgggattg tggagacggt gtatcaccat acccaaaaac atgcattggt atagcccacc      420
agaaaggaca gagtcatttg atgtggtcac aaaatgtgtg agtttcacac taactgagca      480
gttcatggag aaatttgttg atcccggaaa ccacaatagc gggattgatc tccttaggac      540
ctatctttgg cgttgccagt ccttttacc ttttgtgagt ttaggtttga tgtgctttgg       600
ggctttgatc ggactttgtg cttgcatttg ccgaagctta tatcccacca ttgccacggg      660
cattctccat ctccttgcag gtctgtgtac actgggctca gtaagttgtt atgttgctgg      720
aattgaacta ctccaccaga aactagagct ccctgacaat gtatccggtg aatttggatg      780
gtccttctgc ctggcttgtg tctctgctcc cttacagttc atggcttctg ctctcttcat      840
```

```
ctgggctgct cacaccaacc ggaaagagta caccttaatg aaggcatatc gtgtggcatg    900
agcaagaaac tgcctgcttt acaattgcca tttttatttt tttaaaataa tactgatatt    960
ttccccacct ctcaattgtt tttaattttt atttgtggat ataccatttt attatgaaaa   1020
tctattttat ttatacacat tcaccactaa atacacactt aataccacta aaatttatgt   1080
ggtttacttt aagcgatgcc atcttccaaa taaactaatc taggtctaga cagaaagaaa   1140
tggatagaga cttgacacaa atttatgaaa gaaaattggg agtaggaatg tgaccgaaaa   1200
caagttgtgc taatgtctgt tagactttcc agtaaaacta agtaactgt atctgttcaa    1260 ctaaaaactc tatattagtt tctttgggaa acctctcatc gtcaaaactt tatgttcact   1320
ttgctgttgt agatagccag tcaaccagca gtattagtgc tgttttcaaa gatttaagct   1380
ctataaaatt gggaaattat ctaagatcat tttccctaag cattgacaca tagcttcatc   1440
tgaggtgaga tatggcagct gttttgtatct gcactgtgtc tgtctacaaa aagtgaaaaa   1500
tacagtgttt acttgaaatt ttaactttgt aactgcaaga attccagttc agccgggcga   1560
ggattagtat tattttttaac tctccgtaag attttcagta ccaccaaatt gttttggatt   1620
ttttttcttt cctcttcaca taccagggtt attaaaagtg tgctttcttt ttacattata   1680
ttacagttac aaggtaaaat tcctcaactg ctatttattt attccagccc agtactataa   1740
agaacgtttc accataatga ccctccagag ctgggaaacc taccacaaga tctaaagttc   1800
tggctgtcca ttaacctcca actatggtct ttatttcttg tggtaatatg atgtgccttt    1860
ccttgcctaa atcccttcct ggtgtgtatc aacattattt aatgtcttct aattcagtca   1920 ttttttata agtatgtcta taaacattga actttaaaaa acttatttat ttattccact    1980
actgtagcaa ttgacagatt aaaaaaatgt aacttcataa tttcttacca taacctcaat    2040 gtcttttta aaaataaaa ttaaaaatga aaagagactc aaaaaaaaaa                2090
```

<210> SEQ ID NO 149
<211> LENGTH: 2403
<212> TYPE: DNA
<213> ORGANISM: Homo sapiens
<220> FEATURE:
<221> NAME/KEY: misc_feature
<223> OTHER INFORMATION: Incyte Clone No: 1514160

<400> SEQUENCE: 149

```
gggagagagc agcagagacc tcatcagcag accaaggaag tggtgggtgc tccccctccc     60
taagctccag ggtccctgaa tcttctgaaa tctcaaatga gtggaggcct cctggggtgg    120
cctgtcctgc aggggccctg gaatgggggc aagcagctgg gtgggcagaa tgcagagtag    180
actcggggga ggatcctttc actttccgct tcccctttctg atgcatggag gatggtgtga   240
gcttttcagc aggcccggaa aggtacgcag gtgacgcctt agcagccccg cagctggtgc    300
tctgccccgc ggtactggcg ccatcagggc ctcccttgcc cgcctgagag cagcagcagt    360
ctctgtcatc ccgtcgcccc ttaccccca ccccaggcca ctgggcccct cccacaccac     420
ctggggagct gagaagagga ggctggagta agggaggact tgatcatcca agaaatactt    480
tttattgctg ggagtcttct gaacctcacc aaactgaggc cagagctgag ctcctggggg    540
agttaattca gaggggagag gccagcacct ccctcctcca tcgctcgctg tgtgccttaa    600
actccatctc atgtccctcc ccatcccctg gctttccctc cctccttgcc ccatcctggg    660
ccagccagca gggctcctcc tctggctctt cagacctttc agccagtgct gtcagtgccc    720
ctgggaggga agggcatccc tgaggcaccc gaatggtccc tcagggtgca gggaggcaga   780
agcctggcca cagaggagcc tcctaaggca gcagctgcag caagcgcacc ctctccccac   840
```

```
tctccccacg ccagagcggc ttccagagca gatgctgttt ccatcctcct cgtcaaaacc      900
attctcgctg ctgagcttga caatctgggc aaggcttgtg gggcgcttga caaacagaat      960
ctgccctgtg ccgcctggtt ccgtggcctc cagcatgagc ctgcaggcag ggcgctgcgg     1020
gaacccagtt gtgctgcccc agcccatgcc tccgggtctg ctgtgcatga atgagtgctc     1080
acttgtcccg ggtttaggac gtggtcaagt gaacagcagg gtctaactgt gcttacttag     1140
cccagttcaa acagaacaaa ggaaaaatat agaaagcaac atctgttgat catttaggtt     1200
ttttttaaa ccaccatgtc actttgagtc cttcatgggt ttttgaacag catttatcaa      1260
gaagaaaatg tgggcttttt cccctctccc gtgttttgtt tgtcctgtag atagagggag     1320
gaaagccgtg cagtggcagg cgggaccccc tctggtggcg ggaccccctc ttgcggtggt     1380
cttgcgggc cagccgggac ctgtcacttt attatttaag gagtgtgtgt gtagagtcgc      1440
tggcttatta acagtattgt gtgtgggttg ggttttagt ttgttccttc ttttgaagt       1500
cccttcattt caatccttga ctctctctcc ccttcccttg cccagctctg ttgaatgctg     1560
ctgtgcgcgt gtgagggccg ctctgcacac agggcccttg ggttgtgtga actgaaattc     1620
tccctgtatt tgtgagactc gcaggagtcc ccatctgtag cacaggcaat gccagtgcca     1680
tgctgcagcc tcagaaacca ggcctctcac tccagcagca ggcagaaccg tgtctgtggt     1740
cgggtgctgt ccacagctct gtctgccttg ttctttgggct tgagctggat agaggtgggg   1800
tctcttcacc ttccctgaat tcagaacaga ccctgtgcct ggccccagtg tgcccaggca    1860
attccccagg ccctcattgg gagcccttgg tgttctgagc agcagggccc aggcagcaca    1920
tgagcagtgc ccaggggctc cctgcgtgag gacggcaagg tgcgatgtat gtctaactta    1980
ttgatggcag gcagccccct gtgccccta agcctggccc tggttattgc tgagctctgt    2040
gctcagtgct gcggcctggc cgtggctcgt ctgttccttt ggggggcccg ggcgggttgt    2100
gggaatcagt cttcacagac agacgtgagc caggcggagg actcgttcct tgcagaggtc    2160
agtcctcacc tgcaggtgtc ggggtggggg ggggcaagga ggggcaggca cacaccatgt    2220
ctgacctgaa cccgattctg gggagcatct tcccgctccg gccccacgac ctccacaggg    2280
ttacattgta atatatatgc cccagctaac ctgtctgatg gtggcatctt cctgcagaca    2340
tttcaaacat gtaacttta tatgaaaaaa aataaacaca gatgaaagct gaaaaaaaaa    2400
aaa                                                                 2403
```

<210> SEQ ID NO 150
<211> LENGTH: 431
<212> TYPE: DNA
<213> ORGANISM: Homo sapiens
<220> FEATURE:
<221> NAME/KEY: misc_feature
<223> OTHER INFORMATION: Incyte Clone No: 1603403

<400> SEQUENCE: 150

```
ggccaccggg acttcagtgt ctcctccatc ccaggagcgc agtggccact atggggtctg       60
ggctgcccct tgtcctcctc ttgaccctcc ttggcagctc acatggaaca gggccgggta      120
tgactttgca actgaagctg aaggagtctt ttctgacaaa ttcctcctat gagtccagct      180
tcctggaatt gcttgaaaag ctctgcctcc tcctccatct cccttcaggg accagcgtca      240
ccctccacca tgcaagatct caacaccatg ttgtctgcaa cacatgacag ccattgaagc      300
ctgtgtcctt cttggcccgg cttttgggc cggggatgca ggaggcaggc ccgaccctg       360
tctttcagca ggcccccacc ctcctgagtg gcaataaata aaattcggta tgctgaattc      420
```
aaaaaaaaaa a                                                                      431

<210> SEQ ID NO 151
<211> LENGTH: 2109
<212> TYPE: DNA
<213> ORGANISM: Homo sapiens
<220> FEATURE:
<221> NAME/KEY: misc_feature
<223> OTHER INFORMATION: Incyte Clone No: 1652303

<400> SEQUENCE: 151

| | | | | | |
|---|---|---|---|---|---|
| tttgtagcca | agtgggagct | attttctttt | ttgtgcatat | agatatttct | taaatgaagc |    60 |
| tgctttcttg | tcttttattt | ctaaaagccc | ccttataccc | cactttgtgc | agcaaagatc |   120 |
| cccgtgcagg | tcacagcctg | atttgtggcc | aggctggaca | aattcctgag | gcacaacttg |   180 |
| gcttcagttc | agatttcaag | ctgtgttggt | gttgggacca | gcagaaggca | aacgtccagc |   240 |
| caacacacag | gactgtaaga | ggactctgag | ctacgtgccc | tgtgaagacc | cccaggcttt |   300 |
| gtcataggag | gtcgttcagc | ttccccaaag | tcagaggtga | tttgatttgg | ggaagactga |   360 |
| atattcacac | ctaagtcgtg | agcatatcct | gagttttact | tccttatggc | ttgccctcca |   420 |
| agttctctct | ctcatacaca | cacacaccct | tgctccagaa | tcaccagaca | cctccatggc |   480 |
| tccagctatg | ggaacagctg | cattgggggct | gcctttctgt | ttggcttagg | aacttctgtg |   540 |
| cttcttgtgg | ctccactcgc | gaggcagctc | ggaggtgtgg | actccgattg | ggctgcaggc |   600 |
| agctctggga | cggcacaggg | cgggcgctct | gatcagctcg | tgtaaaacac | accgtcttct |   660 |
| tggcctcctg | gccagtcttt | ctgcgaatag | tcctctccct | ggccagttga | atgggggaag |   720 |
| ctgctggcac | aggaaggaga | ggcgatcccg | gctgaggctt | aggaaattgc | tggagccggc |   780 |
| tccaagcaga | taattcactg | ggaggttttt | cagagtcaaa | catcattctg | cctgtgttgg |   840 |
| gggccaggtg | tgtcacacaa | gcatctcaaa | gtcaaaagcc | atctggggct | gctgcttctc |   900 |
| tttctcaggc | tctggggaaa | ggaatctccc | tctcctctca | cttgattcca | agtgtggttg |   960 |
| aattgtctgg | agcactggga | cttttttttct | cttttccttg | atggaccaac | agtgcaaatg |  1020 |
| caatctcgcc | atttaacttt | caggtcgatt | tcctttcctg | atcagacatc | tttgtgcccc |  1080 |
| ctttaggaag | gaaaagaata | cacctacgat | gtgccaggca | ctgtgttagg | cgcttttata |  1140 |
| tagatcctcg | ttaggatgag | actaagggat | gaggacatct | ctttataaaa | ggcccctaag |  1200 |
| taatggataa | acagaaacac | ttagaggtga | gaaggtctgt | cttcaagatc | caaggtaaga |  1260 |
| ttgccttcag | tctgatgttt | gttctcaagg | acttatcccc | tacaatattc | tcccactcca |  1320 |
| tacttctcct | tctaccccac | catgtgctcc | cgtgcactcc | tcagatggtc | agagggtaa |  1380 |
| cccaagtcct | tagagaattt | ggggaccaat | agaatatgtg | atgtgtgaat | tttcttaaa |  1440 |
| aaacttaagg | agtctttgct | accttctgct | tgttgagttg | ttttggcatt | catattaaaa |  1500 |
| gccagcatct | cactatttat | tgacaggttg | ggctgtgtgt | gtgcgcatgt | gtgtatacat |  1560 |
| ttccaggcgt | gcctgtgtcc | tgtagctttt | taaaaggaaa | cccagtcatc | ccactatgaa |  1620 |
| tctggcatct | tcttatgctt | ctagtgtttt | ggccatacat | caaccaaggg | gtttaattta |  1680 |
| tccaatgctt | gacgacatgt | tcaggagggg | ctggatcaaa | ttttgagagg | gttatgggaa |  1740 |
| agggaggggg | agaagaaatt | gacatttatt | ttattattta | ttttaaatgt | ttacatcttc |  1800 |
| tttatgttgt | atcaagcctg | aatagaaact | gatagcatta | aaatactccg | ttcctctctc |  1860 |
| tcttctcgct | tcctttttttt | tttttttttaa | atttaggata | acacatttt | gtttctaaag |  1920 |
| tgatttgtga | tttgtgctgt | ataaactgta | taaaaggttc | tgttttttaaa | ggtggatttt |  1980 |
| cattcctctg | gggacagtgg | tcgccaagac | atctacattg | taagagaaca | cagtggaaga |  2040 |

```
tcctgtcctg attctcaaaa attattttct ctgtatgatt aaaagtttat tccatttaaa    2100
aaaaaaaaa                                                            2109

<210> SEQ ID NO 152
<211> LENGTH: 1114
<212> TYPE: DNA
<213> ORGANISM: Homo sapiens
<220> FEATURE:
<221> NAME/KEY: misc_feature
<223> OTHER INFORMATION: Incyte Clone No: 1693358

<400> SEQUENCE: 152
ggccggagca gctgtcaggc tgaagtcctg cgagcgacgc gcggcggggc ggcgagagga      60
aacgcggcgc cgggccgggc cgggccctgg agatggtccc cggcgccgcg ggctggtgtt     120
gtctcgtgct ctggctcccc gcgtgcgtcg cggcccacgg cttccgtatc catgattatt     180
tgtactttca agtgctgagt cctggggaca ttcgatacat cttcacagcc acacctgcca     240
aggactttgg tggtatcttt cacacaaggt atgagcagat tcaccttgtc cccgctgaac     300
ctccagaggc ctgcggggaa ctcagcaacg gtttcttcat ccaggaccag attgctctgg     360
tggagagggg gggctgctcc ttcctctcca agactcgggt ggtccaggag cacggcgggc     420
gggcggtgat catctctgac aacgcagttg acaatgacag cttctacgtg gagatgatcc     480
aggacagtac ccagcgcaca gctgacatcc ccgccctctt cctgctcggc cgagacggct     540
acatgatccg ccgctctctg aacagcatg ggctgccatg ggccatcatt ccatcccag      600 tcaatgtcac cagcatcccc acctttgagc tgctgcaacc gccctggacc ttctggtaga    660
agagtttgtc ccacattcca gccataagtg actctgagct gggaaggga aacccaggaa     720 ttttgctact tggaatttgg agatagcatc tggggacaag tggagccagg tagaggaaaa    780
gggtttgggc gttgctaggc tgaaagggaa gccacaccac tggccttccc ttccccaggg    840
cccccaaggg tgtctcatgc tacaagaaga ggcaagagac aggccccagg gcttctggct    900
agaacccgaa acaaaaggag ctgaaggcag gtggcctgag agccatctgt gacctgtcac    960
actcacctgg ctccagcctc ccctacccag ggtctctgca cagtgacctt cacagcagtt   1020
gttggagtgg tttaaagagc tggtgtttgg ggactcaata aaccctcact gacttttag    1080 caataaagct tctcatcagg gttaaaaaaa aaaa                                1114

<210> SEQ ID NO 153
<211> LENGTH: 2192
<212> TYPE: DNA
<213> ORGANISM: Homo sapiens
<220> FEATURE:
<221> NAME/KEY: misc_feature
<223> OTHER INFORMATION: Incyte Clone No: 1707711

<400> SEQUENCE: 153
ggaactcatg agccaacagc tgaagaaacc cattgctaca gcttccagtt gaatgccggg     60
gagaaacctg tccaatttta gcaggtttga agggaggatc ttcttcagtt gtagtttgga    120
aggttccttg gtgtggctca tgaaatcaca gagctcagag ataccatctt gagaaatcct    180
ccttggtatc atgaaactgg agcagaggaa ttgcaattta gcaggaggtc ctctactggt    240
gataccctca ccttggggta tggtcctaa cccagaccca gggtctggaa gcttaatgtt    300
gagttggtga ctccagcctc tttctcctgg aggtcacaag atgatgattg cgtagatgtt    360
gcctggtgca aagtgcccca acagcaata gaaaggcata tgtataacca aactccaagt    420
gataaccaga cccatctctc ctccaccttg acaaaagcag attatagtat acaaggtagg    480
```

```
aattcctgtc ctatttgaga tgaactatat cctgtacctc tgtgctctgt gtctgcatga      540
aggctcagcc tttagaggca ctccttctag ttgcattagt actgtctttc tgtggagttt      600
ggtttgaaga ctggctcagc aagtggaggt ttcaatgtat ttttcagttg gctcatcagc      660
cagcattggt gaatattcag tttaggggaa cagttctagg gagtgagaca tttttgggag      720
cagaggaaaa ctctgctgat gttcggtcct ggcaaacatt gagttatttt gagctgtgaa      780
ggcagtcgtc tctgttacac agtggcagct cttgagttat gcactgtgaa gaatgagaag      840
ggaaaagcaa aaattatcct tgtgaaatat ctgctgattg tgccctactc tttgcacctg      900
acttttccta gttgtcctgg tgctaacaca ggagctacac cttgatcctc tcctggcatg      960
aaaataaaac aaaggttttc gttgttgttg ttccattgcc catttccccc atgttgtctt     1020
tcccttggct gatgcctcct ctgggtcaca ttgcttctta tcctgaacac ttgacacctt     1080
gagggtagaa tttagcgttt ggttttttacc tcctagcata tgctgtttgg tatgtgaggg     1140
tttcagtaca aatgctgctg tctatttctg tgcacttaac aatggaaccc aaacagaaga     1200
gaataaagcc ttgataccaa aattgggaaa gaacatgtgt ccatttggac caaacgttgt     1260 tggttttttaa aaaattttat tttgtttttt tgttttttgtt tttgttttttt ttcatcttaa     1320 tatgtaccag tggcacttaa ccaaaagata cagtgatata gccatgtact gtgggtggga     1380
cagatacagt ctccttggcc tataatgaaa ccactaggac tttatacagt tttccttaat     1440
ttgttgacat ataaatggta aattatattt aggcttatcc tgttttgaaa tgatggtagt     1500
catctttctt actgctactt tcatgttgct ttctagaaaa cagcatttca ttccaaaata     1560
actaggatct gcatttagaa caagaatcat tatttgtcct gacctttttca gtcctacaga     1620 gacgcatctg tggttctttt gtacttgcca tagatgtaac ctaaaaagtt ttggcatatt     1680
taggtcagcc tagcggaact tttttttttca tttaaatgga gctgaataat ggagattttg     1740
tgtctgcaaa attcctgaga tcattgaaaa agtaacaagc tgttccttgt ttctgataca     1800
taaaattatt ttaagcattt tatcaatcat taaaatttac tgccagttgt gagtggcttt     1860
ttaattaact tgtctttcat tgcacttcac tctgcctgtt ttcaagggga gtaagattgg     1920
taacatttgg ggagactgta tctgtctact tagcgtggct gttttgaggg actgtcccat     1980
cagtgaacaa actgcatggc cttggagaga gactctgggc tcttggctca gatgtgttca     2040
tcaaatactc ctttcagagc tgttgtgggt gtaagtgaca tgatgtggcc aaaaatccaa     2100
actgtgcagt tgcgttgtga caaacatgca atgtgctgta aaaattcaat acagtttaaa     2160
taaaatctct atattagtgc tgaaaaaaaa aa                                  2192
```

<210> SEQ ID NO 154
<211> LENGTH: 913
<212> TYPE: DNA
<213> ORGANISM: Homo sapiens
<220> FEATURE:
<221> NAME/KEY: misc_feature
<223> OTHER INFORMATION: Incyte Clone No: 1738735

<400> SEQUENCE: 154

```
ctcgagcggc tcgagagcgg ggcaaactgc ttggcacctc ttcaataggt gacattcaat       60
gatagatctc tggcttcctg ctctgtttgt tctggttgcc ctggaaagcc tgctgctcag      120
cccatgcccc gggacttcct ccaccctcac caggacattc tttccatctc ttgtctcctg      180
tgtgcaagtc cctttctcct ggattccatg tcttgaatgt ttcttaattt acttcctcat      240
tttggcagag gatgtcctcc agttgttttc tgggaatgct aatatgcaag tgaaccagtg      300
```

```
acctgcagtt ctgcccacac agggttaata accaatcaga ttctctcttt tcaagatggt    360
taacataaca gacaccaaga aagggaagag gagccgacag cagaggggga agctgaaaag    420
acgcacaaag aatggccata aaagatatga gcaaccccag cttcccagac agtcactttt    480
cccagtggtc atacctggtc tggaagattc cccatcatct cgaataaagc tgttgttgct    540
tttaactcca tggagagacc gaatggagtg agcccagcag gcatgctgg  gcaagagagg    600 tcccccgagt cccaaataag aatttcaact agtataaaac gaggcagcga acccacacgt    660
ggaagtctga taccgcttgc agaagggaat tgaatagatg tctccctatt ggtaaggatg    720
tggttttatt gacttgaaat aacaaagccc gcaagcaaca actgatcatc cgcgggatgc    780
tgccacaagg aataattgag cactcattca gacacagggg aaaccactgc ctctttcagt    840
cttctcccca gattccaaca gtcagtgtta cagcatttca ccttgttcac ctccctgaga    900
agacgttgca ggg                                                      913

<210> SEQ ID NO 155
<211> LENGTH: 480
<212> TYPE: DNA
<213> ORGANISM: Homo sapiens
<220> FEATURE:
<221> NAME/KEY: misc_feature
<223> OTHER INFORMATION: Incyte Clone No: 1749147

<400> SEQUENCE: 155
cttctgttca ggctgggatt acaggtgtga gccgctgcgc tcggccttct ttgattttat     60
attattagga gcaaaagtaa atgaagccca ggaaaacacc tttgggaaca aactcttcct    120
ttgatggaaa atgcagaggc ccttcctctc tgtgccgtgc ttgctcctct tacctgcccg    180
ggtggtttgg ggtgttggt gtttcctccc tggagaagat gggggaggct gtcccactcc    240
cagctctggc agaatcaagc tgttgcagca gtgccttctt catccttcct tacgatcaat    300
cacagtctcc agaagatcag ctcaattgct gtgcaggtta aaactacaga accacatccc    360
aaaggtacct ggtaagaatg tttgaaagat cttccatttc taggaacccc agtcctgctt    420
ctccgcaatg gcacatgctt ccactccatc catactgcag tcgtcaaata aacagatatg    480

<210> SEQ ID NO 156
<211> LENGTH: 545
<212> TYPE: DNA
<213> ORGANISM: Homo sapiens
<220> FEATURE:
<221> NAME/KEY: misc_feature
<223> OTHER INFORMATION: Incyte Clone No: 1817722

<400> SEQUENCE: 156
caggctatta agaaaggcgg acccatgcac atgattttaa aggttctgac aactgcattg     60
ctgttacaag ctgcttcagc tttagctaat tacattcatt tctccagtta ctccaaagat    120
ggaatagggg taccatttat gggaagtttg gcagaatttt ttgacatcgc ttcccaaatt    180
cagatgttat acttactttt gagtctatgc atgggttgga caatagtcag aatgaagaag    240
tctcaaagca gacctctcca gtgggattct acacctgcat ccactggcat tgcagtattc    300
attgtcatga cacagagtgt tttgctactt tgggaacagt ttgaagatat cagtcatcat    360
agctaccatt cacaccacaa cttagcaggg atcctcctaa ttgttctaag aatttgccta    420
gcattgtcat taggctgtgg actctatcag atcatcacag tggagagaag tacactcaaa    480
agggagttct acatcacatt tgccaaagta tgggtttgga aagaaaatgg tttattctga    540
ttatc                                                               545
```

<210> SEQ ID NO 157
<211> LENGTH: 1746
<212> TYPE: DNA
<213> ORGANISM: Homo sapiens
<220> FEATURE:
<221> NAME/KEY: misc_feature
<223> OTHER INFORMATION: Incyte Clone No: 1831290

<400> SEQUENCE: 157

```
ttggcatcag cttgggcagg tgtgcgggct caggatgggg cggccgtggt gaggaaccct      60
ggactctcag catcacaaga ggcaacacca ggagccaaca tgagctcggg gactgaactg     120
ctgtggcccg agcagcgct gctggtgctg ttggggtgg cagccagtct gtgtgtgcgc       180
tgctcacgcc aggtgcaaa gaggtcagag aaaatctacc agcagagaag tctgcgtgag      240
gaccaacaga gctttacggg gtcccggacc tactccttgg tcgggcaggc atggccagga     300
cccctggcgg acatggcacc cacaaggaag acaagctgt tgcaattcta ccccagcctg      360
gaggatccag catcttccag gtaccagaac ttcagcaaag gaagcagaca cgggtcggag    420
gaagcctaca tagaccccat tgccatggag tattacaact ggggggcggtt ctcgaagccc    480
ccagaagatg atgatgccaa ttcctacgag aatgtgctca tttgcaagca gaaaaccaca    540
gagacaggtg cccagcagga gggcataggt ggcctctgca gagggaccct cagcctgtca    600
ctggccctga agactggccc cacttctggt ctctgtccct ctgcctcccc ggaagaagat    660
gaggaatctg aggattatca gaactcagca tccatccatc agtggcgcga gtccaggaag    720
gtcatggggc aactccagag agaagcatcc cctggcccgg tggaagccc agacgaggag     780
gacggggaac cggattacgt gaatggggag gtggcagcca cagaagccta ggcagacca    840
agaagaaagg agccaaggca agagggacc actgtgctca tggacccatc gctgccttcc    900
aaggaccatt tcccagagct actcaacttt taagcccctg ccatggttgc tcctggaagg    960
agaaccagcc accctgagga ccacctggcc atgcgtgcac agcctgggaa aagacagtta   1020
ctcacgggag ctgcaggccc gtcaccaagc cctctcccga cccaggcttt gtggggcagg   1080
cacctggtac caagggtaac ccggctcctg gtatggacgg atgcgcagga tttaggataa   1140
gctgtcaccc agtccccata acaaaaccac tgtccaacac tggtatctgt gttcttttgt   1200
gctatgaatt tggattccta attgctattg ttggttgctg gggttttaaa tgattgataa   1260
gcttgtacag ttaacttata gaggggagc catatttaac attctggatt tcagagtaga   1320
gatttctgtg ttgtctccta gaaagcatta catgtagttt atttcagcat ccttgttggg   1380
tggggccctg gctctcttcc cctttggtgg gacctcccct ttctttgggc ttcagttcac   1440
tcaggaagaa atgaggctgt cgccatcttt atgtgcttcc agtggaaatg tcacttgcta   1500
cagacaatag tgcatgagag tctagagaag tagtgaccag aacagggcag agtaggtccc   1560
ctccatggcc ctgaatcctc ctctgctcca gggctggcct ctgcagagct gattaaacag   1620
tgttgtgact gtctcatggg aagagctggg gcccagaggg accttgagtc agaaatgttg   1680
ccagaaaaag tatctcctcc aaccaaaaca tctcaataaa accattttag ttgaaaaaaa   1740
aaaaaa                                                              1746
```

<210> SEQ ID NO 158
<211> LENGTH: 2011
<212> TYPE: DNA
<213> ORGANISM: Homo sapiens
<220> FEATURE:
<221> NAME/KEY: misc_feature
<223> OTHER INFORMATION: Incyte Clone No: 1831477

<400> SEQUENCE: 158

```
ggagcacggc gctggggccg cccgcagcgc tcactcgctc gcactcagtc gcgggaggct      60
tccccgcgcc ggccgcgtcc cgcccgctcc ccggcaccag aagttcctct gcgcgtccga     120
cggcgacatg ggcgtcccca cggccccgga ggccggcagc tggcgctggg gatccctgct     180
cttcgctctc ttcctggctg cgtccctagg tccggtggca gccttcaagg tcgccacgcc     240
gtattccctg tatgtctgtc ccaggggca gaacgtcacc ctcacctgca ggctcttggg     300
ccctgtggac aaagggcacg atgtgacctt ctacaagacg tggtaccgca gctcgagggg     360
cgaggtgcag acctgctcag agcgccggcc catccgcaac ctcacgttcc aggaccttca     420
cctgcaccat ggaggccacc aggctgccaa caccagccac gacctggctc agcgccacgg     480
gctggagtcg gcctccgacc accatggcaa cttctccatc accatgcgca acctgaccct     540
gctggatagc ggcctctact gctgcctggt ggtggagatc aggcaccacc actcggagca     600
cagggtccat ggtgccatgg agctgcaggt gcagacaggc aaagatgcac catccaactg     660
tgtggtgtac ccatcctcct cccaggagag tgaaaacatc acggctgcag ccctggctac     720
gggtgcctgc atcgtaggaa tcctctgcct cccctcatc ctgctcctgg tctacaagca     780
aaggcaggca gcctccaacc gccgtgccca ggagctggtg cggatggaca gcaacattca     840
agggattgaa acccccggct tgaagcctc accacctgcc caggggatac ccgaggccaa     900
agtcaggcac cccctgtcct atgtggccca gcggcagcct tctgagtctg gcggcatct     960
gctttcggag cccagcaccc ccctgtctcc tccaggcccc ggagacgtct tcttcccatc    1020
cctggaccct gtccctgact ctccaaactt tgaggtcatc tagcccagct gggggacagt    1080
gggctgttgt ggctgggtct ggggcaggtg catttgagcc agggctggct ctgtgagtgg    1140
cctccttggc ctcggccctg gttccctccc tcctgctctg ggctcagata ctgtgacatc    1200
ccagaagccc agcccctcaa cccctctgga tgctacatgg ggatgctgga cggctcagcc    1260
cctgttccaa ggattttggg gtgctgagat tctcccctag agacctgaaa ttcaccagct    1320
acagatgcca aatgacttac atcttaagaa gtctcagaac gtccagccct tcagcagctc    1380
tcgttctgag acatgagcct tgggatgtgg cagcatcagt gggacaagat ggacactggg    1440
ccaccctccc aggcaccaga cacagggcac ggtggagaga cttctccccc gtggccgcct    1500
tggctccccc gttttgcccg aggctgctct tctgtcagac ttcctctttg taccacagtg    1560
gctctggggc caggcctgcc tgcccactgg ccatcgccac cttccccagc tgcctcctac    1620
cagcagtttc tctgaagatc tgtcaacagg ttaagtcaat ctggggcttc cactgcctgc    1680
attccagtcc ccagagcttg gtggtcccga aacgggaagt acatattggg gcatggtggc    1740
ctccgtgagc aaatggtgtc ttgggcaatc tgaggccagg acagatgttg ccccacccac    1800
tggagatggt gctgagggag gtgggtgggg ccttctggga aggtgagtgg agaggggcac    1860
ctgccccccg ccctccccat ccctactcc cactgctcag cgcgggccat tgcaagggtg    1920
ccacacaatg tcttgtccac cctgggacac ttctgagtat gaagcgggat gctattaaaa    1980
actacatggg gaaacaggtg caaaaaaaaa a                                  2011
```

<210> SEQ ID NO 159
<211> LENGTH: 480
<212> TYPE: DNA
<213> ORGANISM: Homo sapiens
<220> FEATURE:
<221> NAME/KEY: modified_base
<222> LOCATION: (440)
<223> OTHER INFORMATION: a, c, g, t, unknown, or other
<220> FEATURE:

```
<221> NAME/KEY: misc_feature
<223> OTHER INFORMATION: Incyte Clone No: 1841607

<400> SEQUENCE: 159
cccacgcgtc cgaaaagaaa agaaaaaaga aaatggcctc atcttgtttc agcctcagtt      60
ttcctcccct cagtctggct gggagcttag ctctttgggg tcattgctgt gtcaggctgg     120
gttgttcctt ttggtctgtt tctgccatgg cccagcgcct tccctctcag aatacataca     180
atccccccct ctgctgggcg tggtgactca tgtctataat cccagctctt tgggaggcca     240
gggcgggtgg atcacttgag cctaggagtt cgaaaccagc ctgagcaaca tggtgaaagc     300
ccatctctac gaaaaatgca aaagttagcc aggcatggtg gtgcacgtct gtagacccag     360
ctacttggga ggctgaggca ggaggatcct tgagcccagg aggcagaagc tgcagtgagc     420
tgtgatcgca ccactgctcn tcagcctggc gacagagcga gattccctca aaaaaaaaaa     480

<210> SEQ ID NO 160
<211> LENGTH: 542
<212> TYPE: DNA
<213> ORGANISM: Homo sapiens
<220> FEATURE:
<221> NAME/KEY: misc_feature
<223> OTHER INFORMATION: Incyte Clone No: 1852391

<400> SEQUENCE: 160
ttgaatcaac ataatgtatg tgaaagggct tagtccatga ttgggtgctt aatatgcccg      60
tgttgctggg gtgagccaaa gggatgaagt tggcagtgct tgctctgtcg tggagcagtc     120
cccacgtggg aaggccagcg ggaaaccagg cctgctgaag tctccagcgc tggaagcctc     180
acggggttta ggaaggagcc ttgggagcag ctcctcagag cacagttgta cctcaattgt     240
ggattttaga tgtttctgct tctcaatgtt ctctcttttt tcctgcctgc ttgcctgcct     300
tttggacctc ttgctgtcta gggtggcaga tgaagctttc tacaaacaac ccttcgctga     360
cgtgattggt tatgtgtatg ttgcaaaact aattcctttt tctacatctg attctttcta     420
cttttgttta gagttaatgc tccttttatg tcaccagttg ctttgctttt taaattattt     480
caaattggca ctttgggggc tgcctaagaa ttgataagcg gggtatgatc tgttgatgaa     540
tc                                                                    542

<210> SEQ ID NO 161
<211> LENGTH: 1066
<212> TYPE: DNA
<213> ORGANISM: Homo sapiens
<220> FEATURE:
<221> NAME/KEY: misc_feature
<223> OTHER INFORMATION: Incyte Clone No: 1854555

<400> SEQUENCE: 161
ttaggctttc tgtatttgtc tgaatgcttt cacgggagtg tgtcgcactg gagcacagag      60
gacactcgat cgtgcggcgc gcagggcggg gggccgccgc tgcctccccg cgggatggct     120
ggcactgtgc tcggagtcgg tgcgggcgtg ttcatcttag ccctgctctg ggtggcagtg     180
ctgctgctgt gtgtgctgct gtccagagcc tccgggcgg cgaggttctc tgtcattttt     240
ttattcttcg gtgctgtgat catcacatca gttctgttgc ttttcccgcg agctggtgaa     300
ttcccagccc cagaagtgga agttaagatt gtggatgact ttttcattgg ccgctatgtc     360
ctgctggctt tccttagtgc catcttcctt ggaggcctct tcttggtttt aatccattat     420
gttctggagc cgatctatgc caaaccactg cactcctact gaccactctt caggaaaacg     480
aaaacctgtt ctctccttca ttgtgatgac attgatgagc aggaaggcac tattcagagc     540
```

```
cttgttttga cagccctcat gccttaaggt tagaggagta tctgtccatc actaagacaa    600
atctctggag tcctggcttc cagaaacagg attgccaaat tgtccctgtg gggctagatt    660
cttaccagct taagaaggat attgctatct tcttagtacc cgtacctag gatttccaac     720 tgttttgaaa gggaaatagt aacagtgatc tgcttagagt ggattttcac tcaagtcctt    780
agtaagtgga ttttggggaa aaagcacat gggcttctgg ttcttttga taatatataa     840 aattattcat tatgaggttg cagttgtttg caaaggagag gcactcaaat ttgaaaggtt    900
attttaatgt gataatttgg aagacttact cagatgttgg tcattgacca ctctgtgcat    960
atatttctgc agagctctgt gaaggcaatg agtgtcactt ccctctgctc taataaagca    1020
ataaataata gctaaagggc tgactttcac ttcgaaaaaa aaaaaa                   1066

<210> SEQ ID NO 162
<211> LENGTH: 1173
<212> TYPE: DNA
<213> ORGANISM: Homo sapiens
<220> FEATURE:
<221> NAME/KEY: misc_feature
<223> OTHER INFORMATION: Incyte Clone No: 1855755

<400> SEQUENCE: 162
gtctcgctcc tgcccagccc gggcggctgc ccttgggtgc tcccttccct gcccgacacc     60
cagaccgacc ttgaccgccc acctggcagg agcaggacag gacggccgga cgcggccatg    120
gccgagctcc cggggccctt tctctgcggg gccctgctag gcttcctgtg cctgagtggg    180
ctggccgtgg aggtgaaggt acccacagag ccgctgagca cgcccctggg gaagacagcc    240
gagctgacct gcacctacag cacgtcggtg ggagacagct tcgccctgga gtggagcttt    300
gtgcagcctg ggaaacccat ctctgagtcc catccaatcc tgtacttcac caatggccat    360
ctgtatccaa ctggttctaa gtcaaagcgg gtcagcctgc ttcagaaccc ccccacagtg    420
ggggtggcca cactgaaact gactgacgtc cacccctcag atactggaac ctacctctgc    480
caagtcaaca acccaccaga tttctacacc aatgggttgg ggctaatcaa ccttactgtg    540
ctggttcccc ccagtaatcc cttatgcagt cagagtggac aaacctctgt gggaggctct    600
actgcactga gatgcagctc ttccgagggg gctcctaagc cagtgtacaa ctgggtgcgt    660
cttggaactt ttcctacacc ttctcctggc agcatggttc aagatgaggt gtctggccag    720
ctcattctca ccaacctctc cctgacctcc tcgggcacct accgctgtgt ggccaccaac    780
cagatgggca gtgcatcctg tgagctgacc ctctctgtga ccgaaccctc caaggccga    840 gtggccggag ctctgattgg ggtgctcctg ggcgtgctgt tgctgtcagt tgctgcgttc    900
tgcctggtca ggttccagaa agagagggg aagaagccca aggagacata tgggggtagt    960
gaccttcggg aggatgccat cgctcctggg atctctgagc acacttgtat gagggctgat   1020
tctagcaagg ggttcctgga aagaccctcg tctgccagca ccgtgacgac caccaagtcc   1080
aagctcccta tggtcgtgtg acttctcccg atccctgagg gcggtgaggg ggaatatcaa   1140
taattaaagt ctgtgggtac caaaaaaaaa aaa                                1173

<210> SEQ ID NO 163
<211> LENGTH: 890
<212> TYPE: DNA
<213> ORGANISM: Homo sapiens
<220> FEATURE:
<221> NAME/KEY: misc_feature
<223> OTHER INFORMATION: Incyte Clone No: 1861434

<400> SEQUENCE: 163
```

```
ctcgagccgg agagatcctc taccgcagtc gtttgaggag gcggaactga agttttttct      60
taattatcat gtgacgggtt ctggatttaa tgggggaaa agggcggaaa aggacaagga      120
tccaaactgg cgaatttgct gatcttcgcg tccctctccg ctttccggcc ggcagcgctg      180
ccagggtata tttcctttt tccgatcctg caacagcctc tttaaactgt ttaaatgaga      240
atgtccttgg ctcagagagt actactcacc tggcttttca cactactctt cttgatcatg      300
ttggtgttga aactggatga gaaagcacct tggaactggt tcctcatatt cattccagtc      360
tggatatttg atactatcct tcttgtcctg ctgattgtga aaatggctgg gcggtgtaag      420
tctggctttg accctcgaca tggatcacac aatattaaaa aaaaagcctg gtacctcatt      480
gcaatgttac ttaaattagc cttctgcctc gcactctgtg ctaaactgga acagtttact      540
accatgaatc tatcctatgt cttcattcct ttatgggcct tgctggctgg ggctttaaca      600
gaactcggat ataatgtctt ttttgtgaga gactgacttc taagtacatc atctcctttc      660
tattgctgtt caacaagtta ccattaaagt gttctgaatc tgtcaagctt caagaatacc      720
agagaactga gggaaaatac caaatgtagt tttatactac ttccataaaa caggattggt      780
gaatcacgga cttctagtca acctacagct taattattca gcatttgagt tattgagatc      840
cttattatct ctatgtaaat aaagtttgtt ttggacctca aaaaaaaaa      890

<210> SEQ ID NO 164
<211> LENGTH: 806
<212> TYPE: DNA
<213> ORGANISM: Homo sapiens
<220> FEATURE:
<221> NAME/KEY: misc_feature
<223> OTHER INFORMATION: Incyte Clone No: 1872334

<400> SEQUENCE: 164
tgcatcagtg cccaggcaag cccaggagtt gacatttctc tgcccagcca tgggcctcac      60
cctgctcttg ctgctgctcc tgggactaga aggtcagggc atagttggca gcctccctga      120
ggtgctgcag gcacccgtgg gaagctccat tctggtgcag tgccactaca ggctccagga      180
tgtcaaagct cagaaggtgt ggtgccggtt cttgccggag gggtgccagc ccctggtgtc      240
ctcagctgtg gatcgcagag ctccagcggg caggcgtacg tttctcacag acctgggtgg      300
gggcctgctg caggtggaaa tggttaccct gcaggaagag gatgctggcg agtatggctg      360
catggtggat ggggccaggg ggccccagat tttgcacaga gtctctctga acatactgcc      420
cccaggtgag ttatcctagg ccagctacca ccccttagac ctaccctccc cacccccgcc      480
tattgccagg gctcatgggt tcttgaggag tgggggcccc tggggaggag gcattccaag      540
gagatatcct cttgacagct ctgcaggag cggaaaccaa actgggtggg aagtctgaga      600
taaatcagct gaaaaccatc cctttccccc ttccacacta ctgcgcttcc ccacaggaag      660
gcatgtcctt cccactccag ggacttggcc tcttcttcca gcattttcaa catacttgat      720
gctaacttat tttttaatta gaaatatttt aaacaatgtt gaatctgagt gtataaaaca      780
gaataatttt tgtagctcca gtgttt                                           806

<210> SEQ ID NO 165
<211> LENGTH: 1923
<212> TYPE: DNA
<213> ORGANISM: Homo sapiens
<220> FEATURE:
<221> NAME/KEY: misc_feature
<223> OTHER INFORMATION: Incyte Clone No: 1877230

<400> SEQUENCE: 165
```
tggccggcaa gcagggctgc agtcacgggg cggcgcggag ggccccagcc cagtcagggg      60
tgtggccgcc gccaccgtaa ggctaggccg cgagcttagt cctgggagcc gcctccgtcg     120
ccgccgtcag agccgcccta tcagattatc ttaacaagaa aaccaactgg aaaaaaaaat     180
gaaattcctt atcttcgcat ttttcggtgg tgttcacctt ttatccctgt gctctgggaa     240
agctatatgc aagaatggca tctctaagag gacttttgaa gaaataaaag aagaaatagc     300
cagctgtgga gatgttgcta aagcaatcat caacctagct gtttatggta aagcccagaa     360
cagatcctat gagcgattgg cacttctggt tgatactgtt ggacccagac tgagtggctc     420
caagaaccta gaaaaagcca tccaaattat gtaccaaaac ctgcagcaag atgggctgga     480
gaaagttcac ctggagccag tgagaatacc ccactgggag aggggagaag aatcagctgt     540
gatgctggag ccaagaattc ataagatagc catcctgggt cttggcagca gcattgggac     600
tcctccagaa ggcattacag cagaagttct ggtggtgacc tctttcgatg aactgcagag     660
aagggcctca gaagcaagag ggaagattgt tgtttataac caaccttaca tcaactactc     720
aaggacggtg caataccgaa cgcaggggc ggtggaagct gccaaggttg ggctttggc      780 atctctcatt cgatccgtgg cctccttctc catctacagt cctcacacag gtattcagga     840
ataccaggat ggcgtgccca agattccaac agcctgtatt acggtggaag atgcagaaat     900
gatgtcaaga atggcttctc atgggatcaa aattgtcatt cagctaaaga tgggggcaaa     960
gacctaccca gatactgatt ccttcaacac tgtagcagag atcactggga gcaaatatcc    1020
agaacaggtt gtactggtca gtggacatct ggacagctgg gatgttgggc agggtgccat    1080
ggatgatggc ggtggagcct ttatatcatg ggaagcactc tcacttatta agatcttgg     1140 gctgcgtcca aagaggactc tgcggctggt gctctggact gcagaagaac aaggtggagt    1200
tggtgccttc cagtattatc agttacacaa ggtaaatatt ccaactaca gtctggtgat     1260 ggagtctgac gcaggaacct tcttacccac tgggctgcaa ttcactggca gtgaaaaggc    1320
cagggccatc atggaggagg ttatgagcct gctgcagccc ctcaatatca ctcaggtcct    1380
gagccatgga aagggacag acatcaactt ttggatccaa gctggagtgc ctggagccag    1440
tctacttgat gacttataca gtatttctt cttccatcac tcccacggag acaccatgac    1500
tgtcatggat ccaaagcaga tgaatgttgc tgctgctgtt tgggctgttg tttcttatgt    1560
tgttgcagac atggaagaaa tgctgcctag gtcctagaaa cagtaagaaa gaaacgtttt    1620
catgcttctg gccaggaatc ctgggtctgc aactttggaa aactcctctt cacataacaa    1680
tttcatccaa ttcatcttca aagcacaact ctatttcatg ctttctgtta ttatctttct    1740
tgatactttc caaattctct gattctagaa aaaggaatca ttctcccctc cctcccacca    1800
catagaatca acatatggta gggattacag tgggggcatt tctttatatc acctcttaaa    1860
aacattgttt ccactttaaa agtaaacact taataaattt ttggaagatc aaaaaaaaaa    1920
aaa                                                                  1923

<210> SEQ ID NO 166
<211> LENGTH: 518
<212> TYPE: DNA
<213> ORGANISM: Homo sapiens
<220> FEATURE:
<221> NAME/KEY: misc_feature
<223> OTHER INFORMATION: Incyte Clone No: 1877885

<400> SEQUENCE: 166
ttgacaccag cagggtgaca tccgctattg ctacttctct gctcccccac agttcctctg      60

| | |
|---|---|
| gacttctctg gaccacagtc ctctgccaga cccctgccag accccagtcc accatgatcc | 120 |
| atctgggtca catcctcttc ctgcttttgc tcccagtggc tgcagctcag acgactccag | 180 |
| gagagagatc atcactccct gccttttacc ctggcacttc aggctcttgt tccggatgtg | 240 |
| ggtccctctc tctgccgctc ctggcaggcc tcgtggctgc tgatgcggtg gcatcgctgc | 300 |
| tcatcgtggg ggcggtgttc ctgtgcgcac gcccacgccg cagccccgcc caagaagatg | 360 |
| gcaaagtcta catcaacatg ccaggcaggg gctgacccctc ctgcagcttg gacctttgac | 420 |
| ttctgacccct ctcatcctgg atggtgtgtg gtggcacagg aaccccgcc ccaacttttg | 480 |
| gattgtaata aaacaattga aacaccaaaa aaaaaaaa | 518 |

```
<210> SEQ ID NO 167
<211> LENGTH: 1631
<212> TYPE: DNA
<213> ORGANISM: Homo sapiens
<220> FEATURE:
<221> NAME/KEY: misc_feature
<223> OTHER INFORMATION: Incyte Clone No: 1889269

<400> SEQUENCE: 167
```

| | |
|---|---|
| gcgagctctc agcgggagcc gagacggtgc agggccggag aagcaccttc actcccagcc | 60 |
| tgcgccccga tgctgcgcgt tctgtgcctc ctgcgcccct ggaggcccct tcgggcccgc | 120 |
| ggctgcgctt ccgacgggc ggccggggc tcagagatcc aagtgcgcgc cctgcgggt | 180 |
| ccggaccaag gctgtaggtt ccatgaggac aggccttgag tctgtcctgg tctctggaat | 240 |
| cacggtgtct agtagaggcc agcacacagc aaatatataa atgtacaaat gagtgaatga | 300 |
| agagaatctg attggcctta aggaacttac gcacttaaaa taattgggca gaagagaagc | 360 |
| agtgaaggag tgcagaggca tcacctgaaa gtttacaagt ccttccactt tctctctgag | 420 |
| gcagaaagag caagggtttt tctctccatt ttatggttgg gaaaattgag gcctgcctga | 480 |
| gtgtgtgact tgtggcaagt cactctggtc atctagggca gaggctcccc agatcccagg | 540 |
| cctcctgcct ccagtcccca gcccgcagcc caggattagg cagagccagc tgctttcccg | 600 |
| tggctgccct gactccttac agggatcact gagattctga tgaacagacc ttctgcccgc | 660 |
| aatgccttgg ggaatgtctt cgtcagtgag ctgctggaaa ctctggccca gctgcgggag | 720 |
| gaccggcaag tgcgtgtcct gctcttcaga agtggagtga agggcgtgtt ctgtgcaggt | 780 |
| gcagacctga aggagcggga acagatgagt gaagcagagg tgggggtgtt tgtccagcga | 840 |
| ctccggggcc tgatgaatga catcggtgag gatctgggtg tagggtggag gaggggggttt | 900 |
| ggggggtccct gccgatgaca gtcccgctac ccccaccagc atctaaggag agtcttcttt | 960 |
| ctgtttggag ttctgtgata agacagatga ctcacccagg gggatggagg aggatgaccg | 1020 |
| agggcagttc tctcagagag ggagttctgg ctcttcagct tttgtgtccc gccccaccct | 1080 |
| cagggttcaa gcctggccat tccaaagcag ttaagtttcc ccaagcatgc tttcaagttt | 1140 |
| tgacaattgc tgttaccttt gcctgagata cccttcttg gttacttgaa cttttacttg | 1200 |
| tccttcaagc cctccagtac ctcctcctcc aggaagcctt cccaacccac cctctgagct | 1260 |
| ttttattgga gcactgatga tcctgggtca ataatgcctg atacacattt gtcttcccca | 1320 |
| tgagactgag ccccatggga acaaaggcta tgtctgattc attctgtgtt cccagttccc | 1380 |
| agcacccagc acagggcttg gcacaaagaa agggaggccc cagggaggcc agcggattag | 1440 |
| gcctgaacag ggatcatcca gcccatcctc ccattcctct ccctggctg attctgtaac | 1500 |
| tttccctaaa gggaaaattg gcttctgaga taacctggct gcgggaagca gaggttgtcg | 1560 |
| tgagcagaga ttgtgccatt gcactccagc ctgggcaaca acagcgagac tccatctcaa | 1620 |

```
aaaaaaaaaa a                                                        1631

<210> SEQ ID NO 168
<211> LENGTH: 1548
<212> TYPE: DNA
<213> ORGANISM: Homo sapiens
<220> FEATURE:
<221> NAME/KEY: misc_feature
<223> OTHER INFORMATION: Incyte Clone No: 1890243

<400> SEQUENCE: 168
atgcgctcca gcagcctgtt tgggaagcag cagtctctcc ttcagatact gtgggactca     60
tgctggagag gagccgccca cttccaggac ctgtgaataa gggctaatga tgagggttgg    120
tggggctctc tgtggggcaa aaaggtggta tggggttag cactggctct cgttctcacc     180
ggagaaggaa gtgttctagt gtggtttagg aaacatgtgg ataaagggaa ccatgaaaat    240
gagaggagga aagacatcca gatcagctgt tttgcctgtt gctcagttga ctctgattgc    300
atcctgtttt cctaattccc agactgttct gggcacggaa gggaccctgg atgtggagtc    360 ttccccttg gccctcctca ctggcctctg ggctagccca gagtccctta gcttgtacct    420
cgtaacactc ctgtgtgtct gtccagcctt gcagtcatgt caaggccagc aagctgatgt    480
gactcttgcc ccatgcgaga tatttatacc tcaaacactg gcctgtgagc cctttccaag    540
tcagtggaga gccctgaaag gagcctcact tgaatccagc tcagtgctct gggtggcccc    600
ctgcaggtgg cccctgaccc tgcgttcag cagggtccac ctgtgagcag gcccgccctg     660
gggcctcttc ctggatgtgc cctctctgag ttctgtgctg tctcttggag gcagggccca    720
ggagaacaaa gtgtggaggc ctcggggagt ggcttttcca gctctcatgc cccgcagtgt    780
ggaacaaggc agaaaaggat cctaggaaat aagtctcttg gcggtccctg agagtcctgc    840
tgaaatccag ccagtgtttt tgtggtatg agaacaggca aaagagatg ccccgagata     900 gaagggggagc cttgtgtttc tttcctgcag acgtgagatg aacactggag tgggcagagg    960
tggcccagga ccatggcacc cttagagtgc agaagctggg gggagaggct gcttcgaagg   1020
gcaggactgg ggataatcag aacctgcctg tcacctcagg gcatcactga caaacatt     1080 cctgatggga actcctgcgg cagagcccag gctggggaag tgaactaccc agggcagccc   1140
ctttgtggcc caggataatc aacactgttc tctctgtacc atgagctcct ccaggagatt   1200
atttaagtgt attgtatcat tggttttctg tgattgtcat aacattgttt tgttattgt    1260 tggtgctgtt gttatttat attgtaattt cagtttgcct ctactggaga atctcagcag    1320
gggtttcagc ctgactgtct ccctttctct accagactct acctctgaat gtgctgggaa   1380
cctcttggag cctgtcagga actcctcact gtttaaatat ttatttattg tgacaaatgg   1440
agctggtttc ctagatatga atgatgtttg caatccccat tttcctgttt cagcatgtta   1500
tattcttata aaataaaagc aaaagtcaaa tatgaaaaaa aaaaaaaa                 1548

<210> SEQ ID NO 169
<211> LENGTH: 616
<212> TYPE: DNA
<213> ORGANISM: Homo sapiens
<220> FEATURE:
<221> NAME/KEY: misc_feature
<223> OTHER INFORMATION: Incyte Clone No: 1900433

<400> SEQUENCE: 169
gccagctcag gtgagccctc gccaaggtga cctcgcagga cactggtgaa ggagcagtga     60
ggaacctgca gagtcacaca gttgctgacc aattgagctg tgagcctgga gcagatccgt    120
```

```
gggctgcaga ccccgcccc agtgcctctc ccctgcagc cctgcccctc gaactgtgac      180
atggagagag tgaccctggc ccttctccta ctggcaggcc tgactgcctt ggaagccaat      240
gacccatttg ccaataaaga cgatcccttc tactatgact ggaaaaacct gcagctgagc      300
ggactgatct gcggagggct cctggccatt gctgggatcg cggcagttct gagtggcaaa      360
tgcaaataca agagcagcca gaagcagcac agtcctgtac ctgagaaggc catcccactc      420
atcactccag gctctgccac tacttgctga gcacaggact ggcctccagg gatggcctga      480
agcctaacac tggcccccag cacctcctcc cctgggaggc cttatcctca aggaaggact      540
tctctccaag ggcaggctgt taggcccctt tctgatcagg aggcttcttt atgaattaaa      600
ctcgccccac caccc                                                      616
```

<210> SEQ ID NO 170
<211> LENGTH: 1981
<212> TYPE: DNA
<213> ORGANISM: Homo sapiens
<220> FEATURE:
<221> NAME/KEY: misc_feature
<223> OTHER INFORMATION: Incyte Clone No: 1909441

<400> SEQUENCE: 170

```
cagaacttct ttttgacacc atagattctt ctgaggtcaa cgttgcaaaa agcatagcaa       60
agtttcttcg aaatgttaga tatcgttatc aaccactatt agaaagatgt aataacgtat      120
ttttaagtaa tgtggaccac cttgatttgg attccatcag taaatacttt agtgtataca      180
aatttctaca atttaatagt tttgaattta ttataatggc taaaagaag ctaactgaaa       240 tgattcctct gtgtaatcat cctgctagct ttgtaaaatt gttttgtagca ttgggaccca     300 ttgcaggacc tgaagaaaag aaacaactta aatcaactat gttattgatg tcagaggacc      360
taactggcga gcaagccctg gcagtgttgg gagcaatggg agatatggaa agcagaaact      420
catgtctgat taaaagagtt acttcagttc tgcataaaca tttggatggc tataaaccat      480
tagagttgtt gaagataact caagaattga cttttctgca tttccaaagg aaggagtttt      540 ttgcgaaaact tagagaatta ctgcttagtt atttgaaaaa tagtttcata ccaactgagg     600
tgtctgttct ggtccgtgct atttccctgc tcccttctcc tcacttggac gaagtgggga     660
tatcccgaat tgaagccgtt ttaccacagt gtgacctaaa taacctgagt agttttgcca     720
catctgtttt aagatggatt cagcatgatc acatgtattt ggataatatg actgcgaaac      780
aactgaaact acttcaaaaa ttagatcact atggtcgtca gagactacaa cacagcaaca     840
gtttggatct gttacggaag gaacttaaat ctctcaaagg aaacacgttt cctgagtcac      900
ttcttgaaga aatgattgct actttacagc atttcatgga tgatattaat tacataaatg     960
ttggggagat tgcatctttt atttctagta ctgattacct cagtactttg ctactagata     1020
ggatagcctc agtggctgtt cagcagattg aaaagatcca tccttttaca atccctgcta     1080
ttattcgtcc attcagcgta ttgaactatg atccacctca aagggatgaa tttttgggaa     1140
cttgcgtgca acatcttaat tcttacttag gtatattgga tccttttata ttagtgtttc     1200
ttggtttctc tttggccaca cttgaatatt ttccagaaga tctgctaaag gcaattttta     1260
acatcaaatt cttagctaga ttggattctc aacttgaaat tttatctcca tctcgaagtg     1320
caagagtcca gtttcatctt atggagttaa atagatcagt ctgcttggaa tgccctgagt     1380
ttcagattcc atggtttcat gaccgcttct gtcaacaata taataaaggt attggtggca     1440
tggatggaac acaacagcag attttttaaaa tgttagcaga ggtactagga ggaatcaatt     1500
```

```
gtgtaaaagc ctcggttctt acgccttatt accacaaagt agattttgag tgtatcttgg    1560
ataaaagaaa aaaacctctt ccgtatggaa gccataatat agcattggga caactaccag    1620
aaatgccctg ggaatcaaat atcgaaatag ttggatcaag gctgccacca ggggctgaaa    1680
ggattgcttt ggaattttg  gattcaaaag cactttgtag aaatatccct cacatgaaag    1740
gaaaatctgc tatgaaaaaa cgacatttgg aaattctggg gtatcgtgta attcagattt    1800
cccagtttga atggaactct atggcactgt caacaaagga tgctcggatg gactacctga    1860
gagaatgtat atttggagaa gtcaagtcat gtttgtagtt tttatttaaa atgaatgtta    1920
tcgtgtgtta catttggacc tattttaata aagtggcctg tctcaattaa aaaaaaaaaa    1980
g                                                                   1981

<210> SEQ ID NO 171
<211> LENGTH: 1492
<212> TYPE: DNA
<213> ORGANISM: Homo sapiens
<220> FEATURE:
<221> NAME/KEY: misc_feature
<223> OTHER INFORMATION: Incyte Clone No: 1932226

<400> SEQUENCE: 171
cttctgggtg aggagtttga gcttggctgg gtccagggcc cagcactgac tcccgtccct      60
gaggaggagg aagaagagga agagggggct ccgattggga cccctaggga tcctggagat     120
ggttgtcctt cccccgacat ccctcctgaa ccccctccaa cacacctgag gccctgccct     180
gccagccagc tccctggact cctgtcccat ggcctcctgg ccggcctctc ctttgcagtg     240
gggtcctcct ctggcctcct gcccctcctg ctgctgctgc tgcttccatt gctggcagcc     300
cagggtgggg gtggcctgca ggcagcgctg ctggcccttg aggtggggct ggtgggtctg     360
ggggcctcct acctgctcct ttgtacagcc ctgcacctgc cctccagtct tttcctactc     420
ctggcccagg gtaccgcact gggggccgtc ctgggcctga gctggcgccg aggcctcatg     480
ggtgttcccc tgggccttgg agctgcctgg ctcttagctt ggccaggcct agctctacct     540
ctggtggcta tggcagcggg gggcagatgg gtgcggcagc agggcccccg ggtgcgccgg     600
ggcatatctc gactctggtt gcgggttctg ctgcgcctgt cacccatggc cttccgggcc     660
ctgcagggct gtggggctgt gggggaccgg ggtctgtttg cactgtaccc caaaaccaac     720
aaggatggct tccgcagccg cctgcccgtc cctgggcccc ggcggcgtaa tccccgcacc     780
acccaacacc cattagctct gttggcaagg gtctgggtcc tgtgcaaggg ctggaactgg     840
cgtctggcac gggccagcca gggtttagca tcccacttgc ccccgtgggc catccacaca     900
ctggccagct ggggcctgct tcggggtgaa cggcccaccc gaatccccg  gctactacca     960 cgcagccagc gccagctagg gcccctgcc  tcccgccagc cactgccagg gactctagcc    1020
gggcggaggt cacgcacccg ccagtcccgg gccctgcccc cctggaggta gctgactcca    1080
gcccttccag cccaaatcta gagcattgag cactttatct cccacgactc agtgaagttt    1140
ctccagtccc tagtcctctc ttttcaccca ccttcctcag tttgctcact taccccaggc    1200
ccagcccttc ggacctctag acaggcagcc tcctcagctg tggagtccag cagtcactct    1260
gtgttctcct ggcgctcctc ccctaagtta ttgctgttcg cccgctgtgt gtgctcatcc    1320
tcaccctcat tgactcaggc ctggggccag gggtggtgga gggtgggaag agtcatgttt    1380
tttttctcct ctttgatttt gtttttctgt ctcccttcca acctgtcccc ttccccccac    1440
caaaaaaaga aaaagacaaa cacaaataaa atatctgagc ggaaaaaaaa aa            1492
```

```
<210> SEQ ID NO 172
<211> LENGTH: 1613
<212> TYPE: DNA
<213> ORGANISM: Homo sapiens
<220> FEATURE:
<221> NAME/KEY: misc_feature
<223> OTHER INFORMATION: Incyte Clone No: 1932647

<400> SEQUENCE: 172
ctcggaattc ggctcgagac gggtcatgag cgcggtatta ctgctggccc tcctggggtt      60
catcctccca ctgccaggag tgcaggcgct gctctgccag tttgggacag ttcagcatgt     120
gtggaaggtg tccgacctac cccggcaatg gaccectaag aacaccagct gcgacagcgg     180
cttggggtgc caggacacgt tgatgctcat tgagagcgga ccccaagtga gcctggtgct     240
ctccaagggc tgcacggagg ccaaggacca ggagccccgc gtcactgagc accggatggg     300
ccccggcctc tccctgatct cctacacctt cgtgtgccgc caggaggact ctgcaacaa      360 cctcgttaac tccctcccgc tttgggcccc acagccccca gcagacccag gatccttgag     420
gtgcccagtc tgcttgtcta tggaaggctg tctggagggg acaacagaag agatctgccc     480 caagggggacc acacactgtt atgatggcct cctcaggctc aggggaggag gcatcttctc     540
caatctgaga gtccagggat gcatgcccca gccaggttgc aacctgctca atgggacaca     600
ggaaattggg cccgtgggta tgactgagaa ctgcaatagg aaagattttc tgacctgtca     660 tcggggacc accattatga cacacggaaa cttggctcaa gaacccactg attggaccac     720
atcgaatacc gagatgtgcg aggtgggca ggtgtgtcag gagacgctgc tgctcataga     780
tgtaggactc acatcaaccc tggtggggac aaaaggctgc agcactgttg gggctcaaaa     840
ttcccagaag accaccatcc actcagcccc tcctggggtg cttgtggcct cctataccca     900
cttctgctcc tcggacctgt gcaatagtgc cagcagcagc agcgttctgc tgaactccct     960
ccctcctcaa gctgcccctg tcccaggaga ccggcagtgt cctacctgtg tgcagcccct    1020
tggaacctgt tcaagtggct cccccgaat gacctgcccc agggggcgcca ctcattgtta    1080 tgatgggtac attcatctct caggaggtgg gctgtccacc aaaatgagca ttcagggctg    1140
cgtggcccaa ccttccagct tcttgttgaa ccacaccaga caaatcggga tcttctctgc    1200
gcgtgagaag cgtgatgtgc agcctcctgc ctctcagcat gagggaggtg gggctgaggg    1260
cctggagtct ctcacttggg gggtggggct ggcactggcc ccagcgctgt ggtgggagt     1320 ggtttgccct tcctgctaac tctattaccc ccacgattct tcaccgctgc tgaccaccca    1380
cactcaacct ccctctgacc tcataaccta atggccttgg acaccagatt ctttcccatt    1440
ctgtccatga atcatcttcc ccacacacaa tcattcatat ctattcacct aacagcaaca    1500
ctggggagag cctggagcat ccggacttgc cctatgggag aggggacgct ggaggagtgg    1560
ctgcatgtat ctgataatac agaccctgtc ctttctccca aaaaaaaaaa aaa           1613

<210> SEQ ID NO 173
<211> LENGTH: 1622
<212> TYPE: DNA
<213> ORGANISM: Homo sapiens
<220> FEATURE:
<221> NAME/KEY: misc_feature
<223> OTHER INFORMATION: Incyte Clone No: 2124245

<400> SEQUENCE: 173
tgtcgcgccc gctggccggc tccgccctca cctcccggcc gcggctgccc tctgcccggg      60
ttgtccaaga tggagggcgc tccaccgggg tcgctcgccc tccggctcct gctgttcgtg     120
gcgctacccg cctccggctg gctgacgacg ggcgcccccg agccgccgcc gctgtccgga     180
```

```
gccccacagg acggcatcag aattaatgta actacactga aagatgatgg ggacatatct      240
aaacagcagg ttgttcttaa cataacctat gagagtggac aggtgtatgt aaatgactta      300
cctgtaaata gtggtgtaac ccgaataagc tgtcagactt tgatagtgaa gaatgaaaat      360
cttgaaaatt tggaggaaaa agaatatttt ggaattgtca gtgtaaggat tttagttcat      420
gagtggccta tgcatctggg ttccagtttg caactaattg tcattcaaga agaggtagta      480
gagattgatg gaaaacaagt tcagcaaaag gatgtcactg aaattgatat tttagttaag      540
aaccggggag tactcagaca ttcaaactat accctccctt tggaagaaag catgctctac      600
tctatttctc gagacagtga catttttattt acccttccta acctctccaa aaaagaaagt      660
gttagttcac tgcaaaccac tagccagtat cttatcagga atgtgaaaac cactgtagat      720
gaagatgttt tacctggcaa gttacctgaa actcctctca gagcagagcc gccatcttca      780
tataaggtaa tgtgtcagtg gatggaaaag tttagaaaag atctgtgtag gttctggagc      840
aacgttttcc cagtattctt tcagtttttg aacatcatgg tggttggaat tacaggagca      900
gctgtggtaa taaccatctt aaaggtgttt ttcccagttt ctgaatacaa aggaattctt      960
cagttggata aagtggacgt cataccttgtg acagctatca acttatatcc agatggtcca     1020
gagaaaagag ctgaaaacct tgaagataaa acatgtattt aaaacgccat ctcatatcat     1080
ggactccgaa gtagcctgtt gcctccaaat ttgccacttg aatataattt tctttaaatc     1140
gttaagaatc agtttataca ctagagaaat tgctaaactc taagactgcc tgaaaattga     1200
cctttacagt gccaagttaa agtttacctt attctcggcc gggtgcagtg gctcatgcct     1260
gtaatcccag actttggga ggccaatgcg ggcggatcac gaggtcagat caagaccatc     1320
ctgccaacat ggtgaaaccc tgtctctact aaaaaaaata aaaaaattag ctgggtgtgg     1380
cggtgcacgc ctgtagtccc agctacttgg gaggctgagg caggagaatt gcttgaaccc     1440
gggaggcgga ggctgcagtg agccaggatc acgccactgc actccagcct gggtgacaga     1500
gcgagactct gtttcaaaaa aaaaaaagtt gaccttattc tctaaagggg ctggctattc     1560
atatgatgaa ttgttaagga aaacttaaag tggacaagaa caggatgtga agagaggtga     1620
tg                                                                    1622
```

<210> SEQ ID NO 174
<211> LENGTH: 1320
<212> TYPE: DNA
<213> ORGANISM: Homo sapiens
<220> FEATURE:
<221> NAME/KEY: misc_feature
<223> OTHER INFORMATION: Incyte Clone No: 2132626

<400> SEQUENCE: 174

```
gcgtgaccca gctgcggccg gccagccatg gagactggag cgctgcggcg cccgcaactt       60
ctcccgttgc tgctgctgct ctgcggtggg tgtcccagag caggcggctg caacgagaca      120
ggcatgttgg agaggctgcc cctgtgtggg aaggctttcg cagacatgat gggcaaggtg      180
gacgtctgga gtggtgcaa cctgtccgag ttcatcgtgt actatgagag tttcaccaac      240
tgcaccgaga tggaggccaa tgtcgtgggc tgctactggc ccaaccccct ggcccagggc      300
ttcatcaccg gcatccacag gcagttcttc tccaactgca ccgtgacag gtccacttg      360 gaggacccc cagacgaggt tctcatcccg ctgatcgtta taccgtcgt tctgactgtc      420 gccatggctg gctggtggt gtggcgcagc aaacgcaccg acacgctgct gtgagggtcc      480
cggtgagatg gagtgggtca cacctggcaa gctggaagaa agttccctgg ggatgggaga      540
```

| | |
|---|---|
| gcgggtgggt gctgccaatc tccagctact gtggccacac cccacctggt catgggcaga | 600 |
| cccctccctt cctgggctga cctgctccct cgaggccagc ctgctccctg gctgaggctc | 660 |
| aggctatccg cccaagctct ttgctcattc tagggccagt ggaggaaaat gtgataaggc | 720 |
| cagagcttgt gtgctgggca cagaaatcac ctgctgcatc ctgtgctccg caggctgggc | 780 |
| cggagcctct gcccgcaggt ttctatgctg tttcttagca cagaatccag cctagcctta | 840 |
| gccgcagtct aggccctgct tggactagga ctccttgctt gaccccatct ctggttcctg | 900 |
| ccctggctcc tgcaccagcc ccagctcctg cctacatcca ggcagaaaga taggcagggg | 960 |
| ctcttggaag acgttccgtg ctgtgacctc cgagccctcc tggtgggaag acagctggaa | 1020 |
| aggctgggag gagaagggag gggttggggg ttcccaggag ccatgcgtgg cctgcagagt | 1080 |
| ccattccatc atgatgctgt gcccgctatg ggctgtgtcc atgaccagag gctggagtgg | 1140 |
| gggtgtgtta gagcccctca ccgggacttg ctgtgcggat ggggcctggg cctccttcct | 1200 |
| acagggctc ctctgtgggt gaggggccct ctggaatggc atcccatgag cttgtggcct | 1260 |
| ctatctgcta ccatctgtgt tttatctgag taaagttacc ttacttctgg aaaaaaaaaa | 1320 |

<210> SEQ ID NO 175
<211> LENGTH: 778
<212> TYPE: DNA
<213> ORGANISM: Homo sapiens
<220> FEATURE:
<221> NAME/KEY: misc_feature
<223> OTHER INFORMATION: Incyte Clone No: 2280639

<400> SEQUENCE: 175

| | |
|---|---|
| gcgctccctc gctggcggac ggctgggcgg cgggccgggc ccggggccgc ttggaatggc | 60 |
| gcctcctccg ccttcgcccc aactgcttct cctggcagcc ctcgcgaggc tcctgggtcc | 120 |
| cagcgaggtg atggctggac cggcggagga ggcgggagcc cattgtcccg agagcctgtg | 180 |
| gcctctgcct ccgcaggtgt caccaagagt gacctacaca cgagtgagcc cagggcaggc | 240 |
| tgaggatgtc accttcctct accaccctg tgcccatccc tggctgaagc tccagcttgc | 300 |
| cctcctggcc tatgcttgta tggctaaccc ttccctcacc cctgacttca gcctcacgca | 360 |
| ggatcggccc ctggtgctga ctgcatgggg gctggcgctg gagatggcct gggtagagcc | 420 |
| agcctgggct gccccactgg ctgatgagga gcggaggagg aagcagagga agaagaaggc | 480 |
| atggatctac tgtgaaagcc tttcagggcc tgctccctcc gagccaactc ccggtagagg | 540 |
| gaggctgtgc cgaagagggt gtgtgcaggc cctggctctg gcctttgctc tgcggactgg | 600 |
| cggcccctg gcacagaggt gacatctcaa gggcccaggc agccctcttc tagtggtgcc | 660 |
| aagacgcgga tgctgcgggc tgcacttggg tcccagccca ctcgctcagc cctgaggttt | 720 |
| ccctctgctt ccccagttag cttgatggcc aagcattcca tggcgggcta tcctggtt | 778 |

<210> SEQ ID NO 176
<211> LENGTH: 1477
<212> TYPE: DNA
<213> ORGANISM: Homo sapiens
<220> FEATURE:
<221> NAME/KEY: misc_feature
<223> OTHER INFORMATION: Incyte Clone No: 2292356

<400> SEQUENCE: 176

| | |
|---|---|
| cctggcctgg ctcgctgggg cctggggagc tgcccgtgct tccagcccag tctcccctg | 60 |
| gctgctgccg gctgctggcc actcccacct cccaggcctg gcgtgaggcc cacagctgct | 120 |
| gttgcacaac cctggtcatt gtgtgatggg gggaggcctg ggcctggccc gcccctctgc | 180 |

```
cagggcttca gaccccctgcc cagccccagt atctgaagga accacagtgg agccaagccc      240
gcgatgtgga gaactcaggc ttcaggagac cctggccctg ctcctggcgg ctccgggtgg      300
ctttcagctc tctctgcaac ctgagctggg ggaggagcca ggcctcatgc ccagggctgg      360
gagtggggag cctggtgtgc acgcgtgccc aggcctgcac gtggaccgac caggggaggg      420
gcccagagct ctggctgggt cacccgcacc ccgcccccat ctcctccaga gccaccccag      480
gaaaagcccg gctggacgag gtcatggctg ccgctgccct acaagcctg tccaccagcc       540 ctctccttct gggggcccca gttgcagcct tcagcccaga gcctggcctg gagccctgga      600 aggaggcccct ggtgcggccc ccaggcagct acagcagcag cagcaacagt ggagactggg     660
gatgggacct ggccagtgac cagtcctctc cgtccacccc gtcaccccca ctgcccccccg     720 aggcagccca ctttctgttt ggggagccca ccctgagaaa aaggaagagc ccggcccagg      780
tcatgttcca gtgtctgtgg aagagctgcg ggaaggtgct gagcacggcg tcggcgatgc      840
agagacacat ccgcctggtg cacctggggt gcggcgggggc ctggggtgcg gcggggcctg    900
cgggttggct ggggttgtta ggcccggcca ggccacccct tcagctccca ctggctggct    960
gtgtctcccg caggaggcag gcagagcctg agcagagtga tggtgaggag gacttctact   1020
acacagagct ggatgttggt gtggacacgc tgaccgacgg gctgtccagc ctgactccag   1080 tttttccccga gggcttccat gccagcttgc cttcccccgc cctgaagctc cgcagacttg   1140
gtgggacccg ccaaccccgc cagtaccccct gaggagcgcc gggatttagt cgaggtcctt   1200
tgtcggcgcc cacggggaat attaatagct cccggggggg gggaatactt ttgaaggcag   1260
ttgataaaaa attttccccc ccaaacagag ggaggcccga gaataaagaa ccctccggg    1320 aaaaaacaca gtgggagaca tagagttgat tctcctggg tgagaaaat ttgggtaaag      1380 cggcttcaag caatttcgca gagcaagatt tgcgggcgcc ggaacccata aggtggtaa     1440 aaccctgggg ggtccccaag aggggggaagc tcaaccc                             1477
```

<210> SEQ ID NO 177
<211> LENGTH: 682
<212> TYPE: DNA
<213> ORGANISM: Homo sapiens
<220> FEATURE:
<221> NAME/KEY: misc_feature
<223> OTHER INFORMATION: Incyte Clone No: 2349310

<400> SEQUENCE: 177

```
tctgaatgtt ttggtgaata aatctgttct tcagcaaccc tacctgcttc tccaaactgc       60
ctaaagagat ccagtactga tgacgctgtt cttccatctt tactccctgg aaactaacca      120
cgttgtcttc tttccttcac caccacccag gagctcagag atctaagctg ctttccatct      180
tttctcccag ccccaggaca ctgactctgt acaggatggg gccgtcctct tgcctccttc      240
tcatcctaat ccccttctc cagctgatca acctggggag tactcagtgt tccttagact      300
ccgttatgga taagaagatc aaggatgttc tcaacagtct agagtacagt ccctctccta     360
taagcaagaa gctctcgtgt gctagtgtca aaagccaagg cagaccgtcc tcctgccctg      420
ctgggatggc tgtcactggc tgtgcttgtg gctatggctg tggttcgtgg atgttcagc       480 tggaaaccac ctgccactgc cagtgcagtg tggtggactg gaccactgcc cgctgctgcc      540
acctgacctg acagggagga ggctgagaac tcagttttgt gaccatgaca gtaatgaaac      600
cagggtccca accaagaaat ctaactcaaa cgtcccactt catttgttcc attcctgatt      660
cttgggtaat aaagacaaac tt                                                 682
```

<210> SEQ ID NO 178
<211> LENGTH: 1508
<212> TYPE: DNA
<213> ORGANISM: Homo sapiens
<220> FEATURE:
<221> NAME/KEY: modified_base
<222> LOCATION: (11)
<223> OTHER INFORMATION: a, c, g, t, unknown, or other
<220> FEATURE:
<221> NAME/KEY: modified_base
<222> LOCATION: (139)
<223> OTHER INFORMATION: a, c, g, t, unknown, or other
<220> FEATURE:
<221> NAME/KEY: misc_feature
<223> OTHER INFORMATION: Incyte Clone No: 2373227

<400> SEQUENCE: 178

| | | | | | |
|---|---|---|---|---|---|
| gcgtaaccccc | ntgatctggt | gataaacgta | ttacccgctt | ttgagtgagc | tgataccgct | 60 |
| cgccgcagcc | gaacgaccga | gcgcagcgag | tcagtgagcg | agaaagcgga | agagcgccca | 120 |
| atacgcaaac | cgcttctcnc | cgcgcgttgg | ccgattcatt | aatcagcttg | cacgacaggt | 180 |
| ttcccgactg | gaaagcgggc | agtgagcgca | acgcaattaa | tgtgagttag | ctcactcccc | 240 |
| acccccttcc | ccgcgggcct | cggttcaaac | gacccggtgg | gtctacagcg | gaagggaggg | 300 |
| agcgaaggta | ggaggcaggg | cttgcctcac | tggccaccct | cccaaccca | agagcccagc | 360 |
| cccatggtcc | ccgccgccgg | cgcgctgctg | tgggtcctgc | tgctgaatct | gggtccccgg | 420 |
| gcggcggggg | cccaaggcct | gacccagact | ccgaccgaaa | tgcagcgggt | cagtttacgc | 480 |
| tttgggggcc | ccatgacccg | cagctaccgg | agcaccgccc | ggactggtct | tccccggaag | 540 |
| acaaggataa | tcctagagga | cgagaatgat | gccatggccg | acgccgaccg | cctggctgga | 600 |
| ccagcggctg | ccgagctctt | ggccgccacg | gtgtccaccg | gctttagccg | gtcgtccgcc | 660 |
| attaacgagg | aggatgggtc | ttcagaagag | ggggttgtga | ttaatgccgg | aaaggatagc | 720 |
| accagcagag | agcttcccag | tgcgactccc | aatacagcgg | ggagttccag | cacgaggttt | 780 |
| atagccaata | gtcaggagcc | tgaaatcagg | ctgacttcaa | gcctgccgcg | ctcccccggg | 840 |
| aggtctactg | aggacctgcc | aggctcgcag | gccaccctga | gccagtggtc | cacacctggg | 900 |
| tctaccccga | gccggtggcc | gtcaccctca | cccacagcca | tgccatctcc | tgaggatctg | 960 |
| cggctggtgc | tgatgccctg | gggcccgtgg | cactgccact | gcaagtcggg | caccatgagc | 1020 |
| cggagccggt | ctgggaagct | gcacggcctt | tccgggcgcc | ttcgagttgg | ggcgctgagc | 1080 |
| cagctccgca | cggagcacaa | gccttgcacc | tatcaacaat | gtccctgcaa | ccgacttcgg | 1140 |
| gaagagtgcc | ccctggacac | aagtctctgt | actgacacca | actgtgcctc | tcagagcacc | 1200 |
| accagtacca | ggaccaccac | tacccccttc | cccaccatcc | acctcagaag | cagtcccagc | 1260 |
| ctgccacccg | ccagccctg | cccagccctg | gcttttgga | aacgggtcag | gattggcctg | 1320 |
| gaggatattt | ggaatagcct | ctcttcagtg | ttcacagaga | tgcaaccaat | agacagaaac | 1380 |
| cagaggtaat | ggcccacttca | tccacatgag | gagatgtcag | tatctcaacc | tctcttgccc | 1440 |
| tttcaatcct | agcaccccact | agatattttt | agtacagaaa | acaaaactg | gaaaacaaaa | 1500 |
| aaaaaaaa | | | | | | 1508 |

<210> SEQ ID NO 179
<211> LENGTH: 558
<212> TYPE: DNA
<213> ORGANISM: Homo sapiens
<220> FEATURE:
<221> NAME/KEY: misc_feature
<223> OTHER INFORMATION: Incyte Clone No: 2457682

<400> SEQUENCE: 179

```
ggagaaagga tggccggcct ggcggcgcgg ttggtcctgc tagctggggc agcggcgctg      60
gcgagcggct cccagggcga ccgtgagccg gtgtaccgcg actgcgtact gcagtgcgaa     120
gagcagaact gctctggggg cgctctgaat cacttccgct cccgccagcc aatctacatg     180
agtctagcag gctggacctg tcgggacgac tgtaagtatg agtgtatgtg ggtcaccgtt     240
gggctctacc tccaggaagg tcacaaagtg cctcagttcc atggcaagtg gcccttctcc     300
cggttcctgt tctttcaaga gccggcatcg gccgtggcct cgtttctcaa tggcctggcc     360
agcctggtga tgctctgccg ctaccgcacc ttcgtgccag cctcctcccc catgtaccac     420
acctgtgtgg ccttcgcctg gctttctgga agatgacagc ctgtagctgc tgaaggaatc     480
agaggacaag ttcaggctgg actgaagacc cttggagcga gtcttcccca gttggggata     540
ctgcccccgc cctgctgg                                                   558

<210> SEQ ID NO 180
<211> LENGTH: 502
<212> TYPE: DNA
<213> ORGANISM: Homo sapiens
<220> FEATURE:
<221> NAME/KEY: misc_feature
<223> OTHER INFORMATION: Incyte Clone No: 2480426

<400> SEQUENCE: 180
cttggagtct gggaggagga aagcggagcc ggcagggagc gaaccaggac tggggtgacg      60
gcagggcagg gggcgcctgg ccggggagaa gcgcggggc tggagcacca ccaactggag     120
ggtccggagt agcgagcgcc ccgaaggagg ccatcgggga gccgggaggg gggactgcga     180
gaggaccccg gcgtccgggc tcccggtgcc agcgctatga ggccactcct cgtcctgctg     240
ctcctgggcc tggcggccgg ctcgccccca ctggacgaca caagatccc cagcctctgc     300 ccgggactgc cgggacctcg aggggacccc gggccgcgag gagaggcggg acccgcgggg     360
cccaccgggc tagccgggga gtgctcggtg cctccgcgat ccgccttcag cgccaagcgc     420
tccgagatcc gggtgcctcc gctgtctgac gcacccttgc cttcgaccgc gtgctggtga     480
acgagcaagg acattacgac gc                                              502

<210> SEQ ID NO 181
<211> LENGTH: 1659
<212> TYPE: DNA
<213> ORGANISM: Homo sapiens
<220> FEATURE:
<221> NAME/KEY: misc_feature
<223> OTHER INFORMATION: Incyte Clone No: 2503743

<400> SEQUENCE: 181
gctgtgcggc ggggcaggca tgggagccgc gcgctctctc ccggcgccca cacctgtctg      60
agcggcgcac gagccgcggc ccgggcgggc tgctcggcgc ggaacagtgc tcggcatggc     120
agggattcca gggctcctct tccttctctt ctttctgctc tgtgctgttg ggcaagtgag     180
cccttacagt gcccctggaa aacccacttg gcctgcatac cgcctccctg tcgtcttgcc     240
ccagtctacc ctcaatttag ccaagccaga cttttggagcc gaagccaaat tagaagtatc     300
ttcttcatgt ggaccccagt gtcataaggg aactccactg cccacttacg aagaggccaa     360
gcaatatctg tcttatgaaa cgctctatgc caatggcagc gcacagaga cgcaggtggg     420 catctacatc ctcagcagta gtggagatgg ggcccaacac cgagactcag ggtcttcagg     480
aaagtctcga aggaagcggc agatttatgg ctatgacagc aggttcagca ttttttgggaa     540 ggacttcctg ctcaactacc ctttctcaac atcagtgaag ttatccacgg gctgcaccgg     600
```

```
caccctggtg gcagagaagc atgtcctcac agctgcccac tgcatacacg atggaaaaac    660
ctatgtgaaa ggaacccaga agcttcgagt gggcttccta aagcccaagt ttaaagatgg    720
tggtcgaggg gccaacgact ccacttcagc catgcccgag cagatgaaat ttcagtggat    780
ccgggtgaaa cgcacccatg tgcccaaggg ttggatcaag ggcaatgcca atgacatcgg    840
catggattat gattatgccc tcctggaact caaaaagccc cacaagagaa aatttatgaa    900
gattggggtg agccctcctg ctaagcagct gccagggggc agaattcact tctctggtta    960
tgacaatgac cgaccaggca atttggtgta tcgcttctgt gacgtcaaag acgagaccta   1020
tgacttgctc taccagcaat gcgatgccca gccaggggc agcgggtctg ggtctatgt    1080 gaggatgtgg aagagacagc agcagaagtg ggagcgaaaa attattggca ttttttcagg   1140
gcaccagtgg gtggacatga atggttcccc acaggatttc aacgtggctg tcagaatcac   1200
tcctctcaaa tatgcccaga tttgctattg gattaaagga aactacctgg attgtaggga   1260
ggggtgacac agtgttccct cctggcagca attaagggtc ttcatgttct tattttagga   1320
gaggccaaat tgttttttgt cattggcgtg cacacgtgtg tgtgtgtgtg tgtgtgtgtg   1380
taaggtgtct tataatcttt tacctatttc ttacaattgc aagatgactg gctttactat   1440
ttgaaaactg gtttgtgtat catatcatat atcatttaag cagtttgaag gcatactttt   1500
gcatagaaat aaaaaaaata ctgatttggg gcaatgagga atatttgaca attaagttaa   1560
tcttcacgtt tttgcaaact ttgatttta tttcatctga acttgtttca aagatttata   1620
ttaaatattt ggcatacaag agatatgaaa aaaaaaaa                          1659

<210> SEQ ID NO 182
<211> LENGTH: 2015
<212> TYPE: DNA
<213> ORGANISM: Homo sapiens
<220> FEATURE:
<221> NAME/KEY: misc_feature
<223> OTHER INFORMATION: Incyte Clone No: 2537684

<400> SEQUENCE: 182
aaaaacaaag gcaatgcatt ggcaagcctc acagcacaga gtgaccgctg cctggcgttc     60
cccagcactc ggtgtggaaa ggcccctacc tgctgtaaga ttatgggtcc atgaaagcag    120
taagctggac acagaggtgt agtgtgcggg acagagggcc ttgcagatgc ctttctgttg    180
gtgttttagt gttaaaatac ggagagtatg gaactcttca cctccatttt ctcagcggct    240
gtgaagcagc ctcctagctt cggaagtacg gacactacgt cgcgttttca agcgtgtctg    300
ttctgcaggt aacagcatca agctgcacgt ggaagcatct cgcggttttc tagaaacagg    360
cattttctta tccctctccc gctccttttt ccacaaaggt gaatttcata aatgtaatac    420
tagtaaagtg aatgaattac tgagtttata cagaaattta ggtaacttct cctttagtct    480
caagagcgag tcttgctttt taatgggtgc cgtttatgtt gctgcccgcc ctgtgtgcct    540
ggctcctctg ggtgccttgg tgtctgctgg tggctggcag tgggcgcagc ggaggagagt    600
tgtgctgcag ctcatacggt gtgtctgtca tctcagtctg gagtaaatgc agtgtctgcc    660
ggtgtctgat gggttctgtc cctcgtattt tctttgcctt ctatcccatt gcctggctac    720
cgctgcctgg cagccaaggg tgttggtcgc gaagctggga gtggcctctg gtggagcctg    780
catcttgtct cgtctgcctc tgctttacat ttggtgtact ttcgggcgtg gtggcagtaa    840
aatgacaccg tgattgagct tgtcagcaga gctgaaagag aaagtagaag gatgtgcatt    900
gtttcttgta agatatcttg catgtatctg tgtattcaaa ttcaaacaga gatggtttgt    960
```

-continued

| | |
|---|---|
| ccatttgtcc actgagaaat tataaactag ggacaagggg gaggaaaagt actgaaatac | 1020 |
| agtttatgaa gcaagtgtgt ctcgggctgt gcttgtccca ggagcccag cagcatctga | 1080 |
| actgaggctt cttcagtcct gcaggaacag gatcatctgt ctcagcggtg ggcagatgtt | 1140 |
| ttcatagaca gccagggagt aaacactgtt ggctctgtgg gctgtatggt ctctgccata | 1200 |
| aatagtacag agatgtggct gtgtctagta caacttttag acacagaaat ctgaatgaca | 1260 |
| tatattgttc tgtgtcaaga aacttagatt ttttttttaa ctatttaaaa acgtgaaacc | 1320 |
| tattcttagc tcacaggcca tggagaagct ggtggggacc agacccagct ccttagctgg | 1380 |
| ctgggctggg gagggggcag tgacagtggc agctgctact cactgctcag tgtggaaaac | 1440 |
| acaggacttg gcaatcacag cccgcagaac catcatgtgt ggcagaagcc tgagggatgc | 1500 |
| ggtttcttgc ccacgtgctc tgttcatttt ctgttgtttt tctgcactta aagaattcac | 1560 |
| atggaagcat gttttataaa atgaattacc agagaaacag agatgggccg agattctcag | 1620 |
| aaatggtccc atgtgaccaa gttctgctgt ttgggtgaca gtgctttgaa gatctccttt | 1680 |
| gaggatgtgc agtctttttt ttttttttt tttgagatgg agtttgttgc ccaggctgga | 1740 |
| gtgagtggca cagtctcggc tcactgcaac ctccacctcc tgggttcaag cagttctcgt | 1800 |
| gccgcagcct cccaagtagc tgggactaca ggcatgcgcc accacgccag gctaatttt | 1860 |
| gtatttttag tagagatggg gtttcaccat gtctcaaact cctgacctca ggcgatccac | 1920 |
| ccacctcagc gtcccaaagt gctggggata tagggtgac cacccgcacc tgcgccaaga | 1980 |
| gtgggctttt aattagggac aaatccaatg gaagg | 2015 |

<210> SEQ ID NO 183
<211> LENGTH: 740
<212> TYPE: DNA
<213> ORGANISM: Homo sapiens
<220> FEATURE:
<221> NAME/KEY: misc_feature
<223> OTHER INFORMATION: Incyte Clone No: 2593853

<400> SEQUENCE: 183

| | |
|---|---|
| ctgctttcgt gaagacaaga tgaagttcac aattgtctttt gctggacttc ttggagtctt | 60 |
| tctagctcct gccctagcta actataatat caacgtcaat gatgacaaca acaatgctgg | 120 |
| aagtgggcag cagtcagtga gtgtcaacaa tgaacacaat gtggccaatg ttgacaataa | 180 |
| caacggatgg gactcctgga attccatctg ggattatgga aatggctttg ctgcaaccag | 240 |
| actctttcaa aagaagacat gcattgtgca caaaatgaac aaggaagtca tgccctccat | 300 |
| tcaatcccct gatgcactgg tcaaggaaaa gaagcttcag ggtaagggac caggaggacc | 360 |
| acctcccaag ggcctgatgt actcagtcaa cccaaacaaa gtcgatgacc tgagcaagtt | 420 |
| cggaaaaaac attgcaaaca tgtgtcgtgg gattccaaca tacatggctg aggagatgca | 480 |
| agaggcaagc ctgttttttt actcaggaac gtgctacacg accagtgtac tatggattgt | 540 |
| ggacatttcc ttctgtggag acacggtgga gaactaaaca atttttaaa gccactatgg | 600 |
| atttagtcat ctgaatatgc tgtgcagaaa aaatatgggc tccagtggtt tttaccatgt | 660 |
| cattctgaaa tttttctcta ctagttatgt ttgatttctt taagtttcaa taaaatcatt | 720 |
| tagcattgaa aaaaaaaaaa | 740 |

<210> SEQ ID NO 184
<211> LENGTH: 748
<212> TYPE: DNA
<213> ORGANISM: Homo sapiens
<220> FEATURE:
<221> NAME/KEY: misc_feature
<223> OTHER INFORMATION: Incyte Clone No: 2622354

<400> SEQUENCE: 184

| ctgcaaccac ccagagccat ggctccccga ggctgcatcg tagctgtctt tgccattttc | 60 |
| tgcatctcca ggctcctctg ctcacacgga gccccagtgg cccccatgac tccttacctg | 120 |
| atgctgtgcc agccacacaa gagatgtggg gacaagttct acgaccccct gcagcactgt | 180 |
| tgctatgatg atgccgtcgt gcccttggcc aggacccaga cgtgtggaaa ctgcaccttc | 240 |
| agagtctgct ttgagcagtg ctgcccctgg accttcatgg tgaagctgat aaaccagaac | 300 |
| tgcgactcag cccggacctc ggatgacagg ctttgtcgca gtgtcagcta atggaacatc | 360 |
| aggggaacga tgactcctgg attctccttc ctgggtgggc ctggagaaag aggctggtgt | 420 |
| tacctgagat ctgggatgct gagtggctgt ttggggccca gagaaacaca cactcaactg | 480 |
| cccacttcat tctgtgacct gtctgaggcc caccctgcag ctgccctgag gaggcccaca | 540 |
| ggtcccctte tagaattctg dacagcatga datgcgtgtg ctgatggggg cccagggact | 600 |
| ctgaaccctc ctgatgaccc ctatggccaa catcaacccg gcaccacccc aaggctggct | 660 |
| gggaacccctt cacccttctg tgagattttc catcatctca agttctcttc tatccaggag | 720 |
| caaagcacag gatcataata aatttatg | 748 |

<210> SEQ ID NO 185
<211> LENGTH: 648
<212> TYPE: DNA
<213> ORGANISM: Homo sapiens
<220> FEATURE:
<221> NAME/KEY: misc_feature
<223> OTHER INFORMATION: Incyte Clone No: 2641377

<400> SEQUENCE: 185

| cggctcgagg atccccaagt ctctgaccca ccttcctgcc tgctcctctc ctcccacatt | 60 |
| ggctcagatt ctttccccgc tgtctgtggg tccacactcc cagtggcacc tccaggagag | 120 |
| aatctgattg gctcagttcg ccagataact caactttccc attggctacc tttgggtcag | 180 |
| gtgatctcca ctagacctat cgcctatgcc tgatggtggg tcacatggtg caaatgttgc | 240 |
| ctgagagctt agtggattag ggatgtggct gggctcatgg ttgacgtccc tgctgctgag | 300 |
| cccttacggg tcaggctggg agaaggtacc atgttgtgtg actggtcatt tgaggtcttg | 360 |
| cagctgttgc ttgctgggct tggcaggtgt tcaaagtgac catttttctg aagggttttt | 420 |
| ttctgagtat tcctcagatg tactcccctg gggccgacgg tctttccttc cacagggcga | 480 |
| tgcttcccta cttgcttgtg aatgtttcct tcatctccag gttgtctggg gacaattctg | 540 |
| tcttttggag gcctgggcag gatttacaga gggctccatg ccagctcctt cctgccgggt | 600 |
| ccacttctgg tgtagggtaa acacctgcgc attcatgtcc tagtgttg | 648 |

<210> SEQ ID NO 186
<211> LENGTH: 2110
<212> TYPE: DNA
<213> ORGANISM: Homo sapiens
<220> FEATURE:
<221> NAME/KEY: modified_base
<222> LOCATION: (1932)
<223> OTHER INFORMATION: a, c, g, t, unknown, or other
<220> FEATURE:
<221> NAME/KEY: misc_feature
<223> OTHER INFORMATION: Incyte Clone No: 2674857

<400> SEQUENCE: 186

| cggcggccat ctttactcag ggcacagagg gtctctgcgg ccgtagcggc cggggctgcg | 60 |

```
gtagccactt tagatttggg caaggacttt agattcgggc tctgttctgt ttccgccgtc      120
ctgcttcctg ccgaggctgg cccaggcagc cgcgcttcga aggacgccgc cgggagctgc      180
ggacatgcgt ggagtggcag tgctaacggc tggtgtctcg cactgttggc ctgtgaaggt      240
acgtgaagct gaaagcctgg aatggctgga aaggggtcat caggcaggcg ccccctgctg      300
ctggggctgc tggtggccgt agccactgtc cacctggtca tctgtcccta caccaaagtg      360
gaggagagct tcaacctgca ggccacacat gacctgctct accactggca agacctggag      420
cagtacgacc atcttgagtt ccccggagtc gtccccagga cgttcctcgg gccagtggtg      480
atcgcagtgt tctccagccc cgcggtttac gtgctttcgc tgttagaaat gtccaagttt      540
tactctcagc taatagttag aggagtgctt ggactcggcg tgattttttgg actctggacg      600 ttacaaaagg aagtgagacg gcacttcggg gccatggtgg ccaccatgtt ctgctgggtg      660
acggccatgc agttccacct gatgttctac tgcacgcgga cactgcccaa tgtgctggcc      720
ctgcctgtag tcctgctggc cctcgcggcc tggctgcggc acgagtgggc ccgcttcatc      780
tggctgtcag ccttcgccat catcgtgttc agggtggagc tgtgcctgtt cctgggcctc      840
ctgctgctgc tggccttggg caaccgaaag gtttctgtag tcagagccct tcgccacgcc      900
gtcccggcag ggatcctctg tttaggactg acggttgctg tggactctta tttttggcgg      960
cagctcactt ggccggaagg aaaggtgctt tggtacaaca ctgtcctgaa caaaagctcc     1020
aactggggga cctcccgct gctgtggtac ttctactcag ccctgccccg cggcctgggc     1080
tgcagcctgc tcttcatccc cctgggcttg gtagacagaa ggacgcacgc gccgacggtg     1140
ctggcactgg gcttcatggc actctactcc ctcctgccac acaaggagct acgcttcatc     1200
atctatgcct tccccatgct caacatcacg gctgccagag gctgctccta cctgctgaat     1260
aactataaaa agtcttggct gtacaaagcg gggtctctgc ttgtgatcgg acacctcgtg     1320
gtgaatgccg cctactcagc cacggccctg tatgtgtccc atttcaacta cccaggtggc     1380
gtcgcaatgc agaggctgca ccagctggtg ccccccccaga cagacgtcct tctgcacatt     1440
gacgtggcag ccgcccagac aggtgtgtct cggtttctcc aagtcaacag cgcctggagg     1500
tacgacaaga gggaggatgt gcagccgggg acaggcatgc tggcatacac acacatcctc     1560
atggaggcgg cccctgggct cctggcccct tacagggaca caccgggt cctggccagc      1620 gtcgtgggga ccacaggtgt gagtctgaac ctgacccaac tgccccctt caacgtccac     1680 ctgcagacaa agctggtgct tctggagagg ctcccccggc cgtcctgagg gggaccaggc     1740
agccctcagc agccacaggc cttcaggag ctgttatcac taccagtttc tggcacaatt      1800
ccagcacaat tatgcaatt cagagaagca agtcaaagga ctggggcacc tgcctctgac     1860
agacaccaga ccaggtccag ggcctcctcc cacagcctca gctgggggct cttcagcaac     1920
caaagaacga angggccccc aagttctttg tttgggcacc cccggggta agcccacttg      1980 cccccaaggg tttgatgggg ttgggcccag cttccagggg cttccctg gccgggttt        2040 gacttgttcc ggccccagga ttcaagggtt ggcccaattt cccattgaac ttaaatttcc     2100
agggaaaggc                                                           2110
```

<210> SEQ ID NO 187
<211> LENGTH: 773
<212> TYPE: DNA
<213> ORGANISM: Homo sapiens
<220> FEATURE:
<221> NAME/KEY: misc_feature
<223> OTHER INFORMATION: Incyte Clone No: 2758485

<400> SEQUENCE: 187

```
cccggagccg ggagggagg gagcgaggtt cggacaccgg cggcggctgc ctggcctttc        60
catgagcccg cggcggaccc tcccgcgccc cctctcgctc tgcctctccc tctgcctctg       120
cctctgcctg gccgcggctc tgggaagtgc gcagtccggg tcgtgtaggg ataaaaagaa       180
ctgtaaggtg gtcttttccc agcaggaact gaggaagcgg ctaacacccc tgcagtacca       240
tgtcactcag gagaaaggga ccgaaagtgc ctttgaagga gaatacacac atcacaaaga       300
tcctggaata tataaatgtg ttgtttgtgg aactccattg tttaagtcag aaaccaaatt       360
tgactccggt tcaggttggc cttcattcca cgatgtgatc aattctgagg caatcacatt       420
cacagatgac ttttcctatg ggatgcacag ggtggaaaca agctgctctc agtgtggtgc       480
tcaccttggg cacattttg atgatgggcc tcgtccaact gggaaaagat actgcataaa        540
ttcggctgcc ttgtctttta cacctgcgga tagcagtggc accgccgagg gaggcagtgg       600
ggtcgccagc ccggcccagg cagacaaagc ggactctgag agtaatggag agtgatggaa       660
acaaagtgta cttaatgcac agcttattaa aaagatcaaa attgttatcc taatagatat       720
attttttcaa aaactataag ggcagttttg tgctattgta attttcctc ctt               773
```

```
<210> SEQ ID NO 188
<211> LENGTH: 714
<212> TYPE: DNA
<213> ORGANISM: Homo sapiens
<220> FEATURE:
<221> NAME/KEY: misc_feature
<223> OTHER INFORMATION: Incyte Clone No: 2763296

<400> SEQUENCE: 188
```

```
gggagcctcc cacgctctcc agctcactcg gcaggcagcg gggaccaggg ctggcaggtt        60
aagcctctgg gggtggatcc tgaaaggtgg tccagccgcc tggccctgcg tgggaccctc       120
cacctggcag caggtggtga cttccaagag tgactccgtc ggaggaaaat gactccccag       180
tcgctgctgc agacgacact gttcctgctg agtctgctct tcctggtcca aggtgcccac       240
ggcaggggcc acagggaaga cttcgcttc tgcagccagc ggaaccagac acacaggagc        300
agcctccact actactggtc catgcggctg caggcccggg gtggccctc ccctctgaag         360 agcaactcag acagcgccag gctccccatc agctcgggca gcacctcgtc cagccgcatc       420
taggcctcca gcccacctgc ccatgtaatg aagcagagat gcggcctcgt cgcacactgc       480
ctgtagcccc cgaacccggc ccagcccag gccagtaagc cgcagacttt agaaagccca        540
acgaccatgg agagatgggc cgttgccatg gtggacggac tcccgggctg ggcttttgag       600
attggcttag gggctactcg gctctcactc agctcccacg ggactcaaga atgcggcgcc       660
atgctgcctt aggtactgtc cccacatctg tcccaaccca gctggaggcc tggt             714
```

```
<210> SEQ ID NO 189
<211> LENGTH: 609
<212> TYPE: DNA
<213> ORGANISM: Homo sapiens
<220> FEATURE:
<221> NAME/KEY: misc_feature
<223> OTHER INFORMATION: Incyte Clone No: 2779436

<400> SEQUENCE: 189
```

```
cggccagggc gccgacagcc cgacctcacc aggagaacat gcagctcggc actgggctcc        60
tgctggccgc cgtcctgagc ctgcagctgg ctgcagccga agccatatgg tgtcaccagt       120
gcacgggctt cggagggtgc tcccatggat ccagatgcct gagggactcc acccactgtg       180
tcaccactgc cacccgggtc ctcagcaaca ccgaggattt gcctctggtc accaagatgt       240
```

```
gccacatagg ctgccccgat atccccagcc tgggcctggg cccctacgta tccatcgctt    300
gctgccagac cagcctctgc aaccatgact gacggctgcc ctcctccagg cccccggacg    360
ctcagccccc acagccccca cagcctgcgc cagggctca cggccgcccc tcctcgaga     420 ctggccagcc cacctctccc ggcctctgca gccaccgtcc agcaccgctt gtcctaggga    480
agtcctgcgt ggagtcttgc ctcaatctgc tgccgtccaa gcctgggcc catcgtgcct    540 gccgcccctt caggtcccga cctccccaca ataaaatgtg attggatcgt gtggtacaaa    600
aaaaaaaac                                                            609

<210> SEQ ID NO 190
<211> LENGTH: 1088
<212> TYPE: DNA
<213> ORGANISM: Homo sapiens
<220> FEATURE:
<221> NAME/KEY: misc_feature
<223> OTHER INFORMATION: Incyte Clone No: 2808528

<400> SEQUENCE: 190
tgtagaagac agcggcgttg ccatggcggc gtctctgggg caggtgttgg ctctggtgct     60
ggtggccgct ctgtgggtg gcacgcagcc gctgctgaag cgggcctccg ccggcctgca    120
gcgggttcat gagccgacct gggcccagca gttgctacag gagatgaaga ccctcttctt    180
gaatactgag tacctgatgc cctttctcct caaccagtgt ggatcccttc tctattacct    240
caccttggca tcgacagatc tgaccctggc tgtgcccatc tgtaactctc tggctatcat    300
cttcacactg attgttggga aggcccttgg agaagatatt ggtggaaaac gagcagttgc    360
tggcatggtg ctcaccgtga taggaatttc actctgcatc acaagctcag tgagtaagac    420 ccagggggcaa cagtctaccc tttgagtggg ccgaacccac ttccagctct gctgcctcca    480
ggaagcccct gggccatgaa gtgctggcag tgagcggatg gacctagcac ttcccctctc    540
tggccttagc ttcctcctct cttatgggga taacagctac ctcatggatc acaataagag    600
aacaagagtg aaagagtttt gtaaccttca agtgctgttc agctgcgggg atttagcaca    660
ggagactcta cgctcaccct cagcaacctt tctgccccag cagctctctt cctgctaaca    720
tctcaggctc ccagcccagc caccattact gtggcctgat ctggactatc atggtggcag    780
gttccatgga ctgcagaact ccagctgcat ggaaagggcc agctgcagac tttgagccag    840
aaatgcaaac gggaggcctc tgggactcag tcagagcgct ttggctgaat gaggggtgga    900
accgagggaa gaaggtgcgt cggagtggca gatgcaggaa atgagctgtc tattagcctt    960
gcctgcccca cccatgaggt aggcagaaat cctcactgcc agcccctctt aaacaggtag   1020
agagctgtga gccccagccc cacctgactc agcacacct ggcgagtagt agctgtcaat   1080
aaagctat                                                            1088

<210> SEQ ID NO 191
<211> LENGTH: 1377
<212> TYPE: DNA
<213> ORGANISM: Homo sapiens
<220> FEATURE:
<221> NAME/KEY: misc_feature
<223> OTHER INFORMATION: Incyte Clone No: 2809230

<400> SEQUENCE: 191
gcgggacttc ctgtgtcgta tttccaagga ctccaaagcg aggccgggga ctgaaggtgt     60
gggtgtcgag ccctctggca gagggttaac ctgggtcaaa tgcacggatt ctcacctcgt    120
acagttacgc tctcccgcgg cacgtccgcg aggacttgaa gtcctgagcg ctcaagtttg    180
```

| | |
|---|---|
| tccgtaggtc gagagaaggc catggaggtg ccgccaccgg caccgcggag ctttctctgt | 240 |
| agagcattgt gcctatttcc ccgagtcttt gctgccgaag ctgtgactgc cgattcggaa | 300 |
| gtccttgagg agcgtcagaa gcggcttccc tacgtcccag agccctatta cccggaatct | 360 |
| ggatgggacc gcctccggga gctgtttggc aaagatgaac agcagagaat tcaaaggac | 420 |
| cttgctaata tctgtaagac ggcagctaca gcaggcatca ttggctgggt gtatggggga | 480 |
| ataccagctt ttattcatgc taaacaacaa tacattgagc agagccaggc agaaattat | 540 |
| cataaccggt ttgatgctgt gcaatctgca catcgtgctg ccacgcgagg cttcattcgt | 600 |
| tatggctggc gctggggttg gagaactgca gtgtttgtca ctatattcaa cacagtgaac | 660 |
| actagtctga atgtataccg aaataaagat gccttaagcc attttgtaat tgcaggagct | 720 |
| gtcacgggaa gtcttttag gataaacgta ggcctgcgtg gcctggtggc tggtggcata | 780 |
| attggagcct tgctgggcac tcctgtagga ggcctgctga tggcatttca gaagtactct | 840 |
| ggtgagactg ttcaggaaag aaaacagaag gatcgaaagg cactccatga gctaaaactg | 900 |
| gaagagtgga aaggcagact acaagttact gagcacctcc ctgagaaaat tgaaagtagt | 960 |
| ttacaggaag atgaacctga gaatgatgct aagaaaattg aagcactgct aaaccttcct | 1020 |
| agaaaccctt cagtaataga taaacaagac aaggactgaa agtgctctga acttgaaact | 1080 |
| cactggagag ctgaagggag ctgccatgtc cgatgaatgc aacagacag gccactcttt | 1140 |
| ggtcagcctg ctgacaaatt taagtgctgg tacctgtggt ggcagtggct tgctcttgtc | 1200 |
| tttttctttt cttttaact aagaatgggg ctgttgtact ctcactttac ttatccttaa | 1260 |
| atttaaatac atacttatgt ttgtattaat ctatcaatat atgcatacat gaatatatcc | 1320 |
| acccacctag attttaagca gtaaataaaa catttcgcaa aagattaaaa aaaaaaa | 1377 |

<210> SEQ ID NO 192
<211> LENGTH: 985
<212> TYPE: DNA
<213> ORGANISM: Homo sapiens
<220> FEATURE:
<221> NAME/KEY: misc_feature
<223> OTHER INFORMATION: Incyte Clone No: 2816821

<400> SEQUENCE: 192

| | |
|---|---|
| gcgggcccgc gagtccgaga cctgtcccag gagctccagc tcacgtgacc tgtcactgcc | 60 |
| tcccgccgcc tcctgcccgc gccatgaccc agccggtgcc ccggctctcc gtgcccgccg | 120 |
| cgctggccct gggctcagcc gcactgggcg ccgccttcgc cactggcctc ttcctgggga | 180 |
| ggcggtgccc cccatggcga ggccggcgag agcagtgcct gcttcccccc gaggacagcc | 240 |
| gcctgtggca gtatcttctg agccgctcca tgcgggagca cccggcgctg cgaagcctga | 300 |
| ggctgctgac cctggagcag ccgcaggggg attctatgat gacctgcgag caggcccagc | 360 |
| tcttggccaa cctggcgcgg ctcatccagg ccaagaaggc gctggacctg gcaccttca | 420 |
| cgggctactc cgccctggcc ctggccctgg cgctgcccgc ggacgggcgc gtggtgacct | 480 |
| gcgaggtgga cgcgcagccc ccggagctgg acggcccct gtggaggcag gccgaggcgg | 540 |
| agcacaagat cgacctccgg ctgaagcccg ccttggagac cctggacgag ctgctggcgg | 600 |
| cgggcgaggc cggcaccttc gacgtggccg tggtggatgc ggacaaggag aactgctccg | 660 |
| cctactacga gcgctgcctg cagctgctgc gacccggagg catcctcgcc gtcctcagag | 720 |
| tcctgtggcg cgggaaggtg ctgcaacctc gaaagggga cgtggcggcc gagtgtgtgc | 780 |
| gaaacctaaa cgaacgcatc cggcgggacg tcagggtcta catcagcctc ctgccctgg | 840 |

```
gcgatggact caccttggcc ttcaagatct agggctggcc cctagtgagt gggctcgagg    900
gagggttgcc tgggaacccc aggaattgac cctgagtttt aaattcgaaa ataaagtggg    960
gctgggacac acgaaaaaaa aaaaa                                          985
```

<210> SEQ ID NO 193
<211> LENGTH: 1310
<212> TYPE: DNA
<213> ORGANISM: Homo sapiens
<220> FEATURE:
<221> NAME/KEY: misc_feature
<223> OTHER INFORMATION: Incyte Clone No: 2817268

<400> SEQUENCE: 193

```
cccacgcgtc cgggttcacg taaagacagc gagatcctga gggccagccg ggaaggaggc     60
gtggatatgg agctggctgc tgccaagtcc ggggcccgcg ccgctgccta gcgcgtcctg    120
gggactctgt ggggacgcgc cccgcgccgc ggctcgggga cccgtagagc ccggcgctgc    180
gcgcatggcc ctgctctcgc gccccgcgct caccctcctg ctcctcctca tggccgctgt    240
tgtcaggtgc caggagcagg cccagaccac cgactggaga gccaccctga gaccatccg    300 gaacggcgtt cataagatag acacgtacct gaacgccgcc ttggacctcc tgggaggcga    360
ggacggtctc tgccagtata aatgcagtga cggatctaag cctttcccac gttatggtta    420
taaaccctcc ccaccgaatg gatgtggctc tccactgttt ggtgttcatc ttaacattgg    480
tatcccttcc ctgacaaagt gttgcaacca acacgacagg tgctatgaaa cctgtggcaa    540
aagcaagaat gactgtgatg aagaattcca gtattgcctc tccaagatct gccgagatgt    600
acagaaaaca ctaggactaa ctcagcatgt tcaggcatgt gaaacaacag tggagctctt    660
gtttgacagt gttatacatt taggttgtaa accatatctg gacagccaac gagccgcatg    720
caggtgtcat tatgaagaaa aaactgatct ttaaaggaga tgccgacagc tagtgacaga    780
tgaagatgga agaacataac cttgacaaa taactaatgt ttttacaaca taaaactgtc    840
ttatttttgt gaaaggatta ttttgagacc ttaaaataat ttatatcttg atgttaaaac    900
ctcaaagcaa aaaagtgag ggagatagtg agggaggc acgcttgtct tctcaggtat    960
cttccccagc attgctccct tacttagtat gccaaatgtc ttgaccaata tcaaaaacaa   1020
gtgcttgttt agcggagaat tttgaaaaga ggaatatata actcaatttt cacaaccaca   1080
tttaccaaaa aaagagatca aatataaaat tcatcataat gtctgttcaa cattatctta   1140
tttggaaaat ggggaaatta tcacttacaa gtatttgttt actatgaaat tttaaataca   1200
catttatgcc tagaaggaac ggactttttt tttctatttt aattacacat aatatgtaat   1260
taaagtacaa cataatatgt tgtttctctg tagcccgttg agcatatgag               1310
```

<210> SEQ ID NO 194
<211> LENGTH: 914
<212> TYPE: DNA
<213> ORGANISM: Homo sapiens
<220> FEATURE:
<221> NAME/KEY: misc_feature
<223> OTHER INFORMATION: Incyte Clone No: 2923165

<400> SEQUENCE: 194

```
cggtggccat gactgcggcc gtgttcttcg gctgcgcctt cattgccttc gggcctgcgc     60 tcgccctta tgtcttcacc atcgccaccg agccgttgcg tatcatcttc ctcatcgccg    120
gagctttctt ctggttggtg tctctactga tttcgtccct tgtttggttc atggcaagag    180
tcattattga caacaaagat ggaccaacac agaaatatct gctgatcttt ggagcgtttg    240
```

```
tctctgtcta tatccaagaa atgttccgat ttgcatatta taaactctta aaaaaagcca      300
gtgaaggttt gaagagtata aacccaggtg agacagcacc ctctatgcga ctgctggcct      360
atgtttctgg cttgggcttt ggaatcatga gtggagtatt ttcctttgtg aatacccctat    420 ctgactcctt ggggccaggc acagtgggca ttcatgagga ttctcctcaa ttcttccttt     480
attcagcttt catgacgctg gtcattatct tgctgcatgt attctggggc attgtatttt     540
ttgatggctg tgagaagaaa aagtggggca tcctccttat cgttctcctg acccacctgc    600
tggtgtcagc ccagaccttc ataagttctt attatggaat aaacctggcg tcagcattta    660
taatcctggt gctcatgggc acctgggcat tcttagctgc gggaggcagc tgccgaagcc    720
tgaaactctg cctgctctgc aagacaaga actttcttct ttacaaccag cgctccagat     780
aacctcaggg aaccagcact tcccaaaccg cagactacat ctttagagga agcacaactg    840 tgccttttc tgaaaatccc ttttctggt ggaattgaga agaaataaa actatgcaga      900 tatgaaaaaa aaaa                                                       914

<210> SEQ ID NO 195
<211> LENGTH: 606
<212> TYPE: DNA
<213> ORGANISM: Homo sapiens
<220> FEATURE:
<221> NAME/KEY: misc_feature
<223> OTHER INFORMATION: Incyte Clone No: 2949822

<400> SEQUENCE: 195 tttttttaata atgccttta gttggatggt aattatcctg ggttttctat gtggattatc     60
aggtcagctt caaataatga acaccctctc ttctcttcca attgtttac ttgtttcttc    120 ttcttgtctt atattagcca gaatgtcata tagtatattg accagtagct atggtggtgg   180 cgttttatc ttattggact taaaagaaa tacatcaaaa gtttctccat taatgatgat    240
gtttgctata gggcattgat agatagcctt caaaagtta agaaagttct tttctttcta    300
gtcttcaagg ttaaaagtt tttaaagatc ttaattgaat gtgaactta tcaaatgcct     360 ttgtgatgtc tatggagata atcatgtatt tgcttcttta atacattcct gtggtgaaat   420
atgtgaataa gtgttctgat attgaattat ctttgcattt ctagaataag ccctaataag    480
tactattcaa ggtattttc tcaaacacct gattggactc tgtaagctca tatttcattg    540 agtggattc cttctatgtt tgtcagtgca attgcgctat aattcgcgtt gctgtcctca    600
tctgaa                                                                606

<210> SEQ ID NO 196
<211> LENGTH: 893
<212> TYPE: DNA
<213> ORGANISM: Homo sapiens
<220> FEATURE:
<221> NAME/KEY: misc_feature
<223> OTHER INFORMATION: Incyte Clone No: 2992192

<400> SEQUENCE: 196 ccacccgga gtcggctgg ccatggcggc gccttggagg cgatggccca cggggctgct     60
agccgtgctg cggcccctgc tcacctgccg gccccctgcaa ggcacgacgc tgcaacggga   120
tgtgctgctc tttgagcatg atcgggggcg cttcttcacc atcctcgggc tgttctgcgc   180
gggccagggc gtcttctggg cttccatggc tgtggcagcc gtgtcccggc cccggttcc    240 ggtgcagcct ctggatgcgg aggtcccaaa tcgtggcccc ttcgacctgc gctccgcgct    300
ctggcgctac ggtctggccg tcggctgcgg cgccatcgga gccctcgtac tcggtgctgg   360
```

-continued

| | |
|---|---|
| tcttctcttc tctctccggt ctgtgcgctc agtggtgctt cgagctggag ggcagcaggt | 420 |
| gaccctcacc actcatgccc cctttggctt ggggggcccat ttcacagttc ctttgaagca | 480 |
| ggtatcttgc atggcccacc ggggtgaagt ccctgccatg ctacctctga aagtcaaagg | 540 |
| ccgacgcttc tatttcctct tggacaaaac tggacacttc cctaacacaa aactctttga | 600 |
| caatactgtg ggtgcctacc ggagcttgtg aagaaatgac ctcaagtcac tcacctctcc | 660 |
| aagaggagga taaaaactga accttgggga gccaggtgtg ttggttcaca cctgttgtaa | 720 |
| tcccagcact ttgggagggt gaggcaggag cactgctcga gcccaggctg gcaacatag | 780 |
| cgagaccttg tctctattta caaaaaaaaa aacaaaaaaa aacgccaatc ttagaatgga | 840 |
| gtaacaacca gggtcacaca aggaggtcaa gattcattaa caacaaataa agg | 893 |

<210> SEQ ID NO 197
<211> LENGTH: 1730
<212> TYPE: DNA
<213> ORGANISM: Homo sapiens
<220> FEATURE:
<221> NAME/KEY: misc_feature
<223> OTHER INFORMATION: Incyte Clone No: 2992458

<400> SEQUENCE: 197

| | |
|---|---|
| ggccagaggc tgcccggctc ccggaagcag gctgtgaggg gcgggagcgc tgctggaacc | 60 |
| cgagccggag ccggagccac agcggggagg gtggcctggc ggcctggagc cggacgtgtc | 120 |
| cggggcgtcc ccgcagaccg gggcagcagg tcgtccgggg gcccaccatg ctggtgactg | 180 |
| cctaccttgc ttttgtaggc ctcctggcct cctgcctggg gctggaactg tcaagatgcc | 240 |
| gggctaaacc ccctggaagg gcctgcagca atccctcctt ccttcggttt caactggact | 300 |
| tctatcaggt ctacttcctg gccctggcag ctgattggct tcaggccccc tacctctata | 360 |
| aactctacca gcattactac ttcctggaag gtcaaattgc catcctctat gtctgtggcc | 420 |
| ttgcctctac agtcctcttt ggcctagtgg cctcctccct tgtggattgg ctgggtcgca | 480 |
| agaattcttg tgtcctcttc tccctgactt actcactatg ctgcttaacc aaactctctc | 540 |
| aagactactt tgtgctgcta gtggggcgag cacttggtgg gctgtccaca gccctgctct | 600 |
| tctcagcctt cgaggcctgg tatatccatg agcacgtgga acggcatgac ttccctgctg | 660 |
| agtggatccc agctacccttt gctcgagctg ccttctggaa ccatgtgctg gctgtagtgg | 720 |
| caggtgtggc agctgaggct gtagccagct ggatagggct ggggcctgta gcgcccttttg | 780 |
| tggctgccat ccctctcctg gctctggcag gggccttggc ccttcgaaac tgggggggaga | 840 |
| actatgaccg gcagcgtgcc ttctcaagga cctgtgctgg aggcctgcgc tgcctcctgt | 900 |
| cggaccgccg cgtgctgctg ttgggcacca tacaagctct atttgagagt gtcatcttca | 960 |
| tcttttgtctt cctctggaca cctgtgctgg acccacacgg ggcccctctg ggcattatct | 1020 |
| tctccagctt catggcagcc agcctgcttg ctcttccct gtaccgtatc gccacctcca | 1080 |
| agaggtacca ccttcagccc atgcacctgc tgtcccttgc tgtgctcatc gtcgtcttct | 1140 |
| ctctcttcat gttgactttc tctaccagcc caggccagga gagtccggtg gagtccttca | 1200 |
| tagccttttct acttattgag ttggcttgtg gattatactt tcccagcatg agcttcctac | 1260 |
| ggagaaaggt gatccctgag acagagcagg ctggtgtact caactggttc cgggtacctc | 1320 |
| tgcactcact ggcttgccta gggctccttg tcctccatga cagtgatcga aaaacaggca | 1380 |
| ctcggaatat gttcagcatt tgctctgctg tcatggtgat ggctctgctg gcagtggtgg | 1440 |
| gactcttcac cgtggtaagg catgatgctg agctgcgggt accttcacct actgaggagc | 1500 |
| cctatgcccc tgagctgtaa ccccactcca ggacaagata gctgggacag actcttgaat | 1560 |

```
tccagctatc cgggattgta cagatctctc tgtgactgac tttgtgactg tcctgtggtt    1620
tctcctgcca ttgctttgtg tttgggagga catgatgggg gtgatggact ggaaagaagg    1680
tgccaaaagt tccctctgtg ttactcccat ttagaaaata aacacttttta              1730
```

<210> SEQ ID NO 198
<211> LENGTH: 2029
<212> TYPE: DNA
<213> ORGANISM: Homo sapiens
<220> FEATURE:
<221> NAME/KEY: misc_feature
<223> OTHER INFORMATION: Incyte Clone No: 3044710

<400> SEQUENCE: 198

```
ccttgacaag tcagaagctt gaaagcaggg aaatccggat gtctcggtta tgaagtggag      60
cagtgagtgt gagcctcaac atagttccag aactctccat ccggactagt tattgagcat     120
ctgcctctca tatcaccagt ggccatctga ggtgtttccc tggctctgaa ggggtaggca     180
cgatggccag gtgcttcagc ctggtgttgc ttctcacttc catctggacc acgaggctcc     240
tggtccaagg ctcttttgcgt gcagaagagc tttccatcca ggtgtcatgc agaattatgg    300
ggatcaccct tgtgagcaaa aaggcgaacc agcagctgaa tttcacagaa gctaaggagg     360
cctgtaggct gctgggacta agtttggccg gcaaggacca agttgaaaca gccttgaaag     420
ctagctttga aacttgcagc tatggctggg ttggagatgg attcgtggtc atctctagga     480
ttagcccaaa ccccaagtgt gggaaaaatg gggtgggtgt cctgatttgg aaggttccag     540
tgagccgaca gtttgcagcc tattgttaca actcatctga tacttggact aactcgtgca     600
ttccagaaat tataccacc aaagatccca tattcaacac tcaaactgca acacaaacaa      660
cagaatttat tgtcagtgac agtacctact cggtggcatc cccttactct acaatacctg     720
cccctactac tactcctcct gctccagctt ccacttctat tccacggaga aaaaattga     780 tttgtgtcac agaagttttt atggaaacta gcaccatgtc tacagaaact gaaccatttg     840
ttgaaaataa agcagcattc aagaatgaag ctgctgggtt tggaggtgtc cccacggctc     900
tgctagtgct tgctctcctc ttctttggtg ctgcagctgg tcttggattt tgctatgtca     960
aaaggtatgt gaaggccttc ccttttacaa acaagaatca gcagaaggaa atgatcgaaa    1020
ccaaagtagt aaaggaggag aaggccaatg atagcaaccc taatgaggaa tcaaagaaaa    1080
ctgataaaaa cccagaagag tccaagagtc caagcaaaac taccgtgcga tgcctggaag    1140
ctgaagttta tgatgagacag aaatgaggag acacacctga ggctggtttc tttcatgctc    1200
cttaccctgc cccagctggg gaaatcaaaa gggccaaaga accaaagaag aaagtccacc    1260
cttggttcct aactggaatc agctcaggac tgccattgga ctatgagtg caccaaagag     1320 aatgcccttc tccttattgt aaccctgtct ggatcctatc ctcctacctc caaagcttcc    1380 cacgccttt ctagcctggc tatgtcctaa taatatccca ctgggagaaa ggagttttgc     1440
aaagtgcaag gacctaaaac atctcatcag tatccagtgg taaaaaggcc tcctggctgt    1500
ctgaggctag gtgggttgaa agccaaggag tcactgagac caaggctttc tctactgatt    1560
ccgcagctca gacccttct tcagctctga aagagaaaca cgtatcccac ctgacatgtc     1620
cttctgagcc cggtaagagc aaaagaatgg cagaaaagtt tagcccctga aagccatgga    1680
gattctcata acttgagacc taatctctgt aaagctaaaa taaagaaata gaacaaggct    1740
gaggatacga cagtacactg tcagcaggga ctgtaaacac agacagggtc aaagtgtttt    1800
ctctgaacac attgagttgg aatcactgtt tagaacacac acacttactt tttctggtct    1860
```

-continued

| | |
|---|---|
| ctaccactgc tgatattttc tctaggaaat atacttttac aagtaacaaa aataaaaact | 1920 |
| cttataaatt tctatttta tctgagttac agaaatgatt actaaggaag attactcagt | 1980 |
| aatttgttta aaagtaata aaattcaaca aacatttaaa aaaaaaaaa | 2029 |

<210> SEQ ID NO 199
<211> LENGTH: 543
<212> TYPE: DNA
<213> ORGANISM: Homo sapiens
<220> FEATURE:
<221> NAME/KEY: misc_feature
<223> OTHER INFORMATION: Incyte Clone No: 3120415

<400> SEQUENCE: 199

| | |
|---|---|
| ccggcgctgg aggggcgagg accgggtata agaagcctcg tggccttgcc cgggcagccg | 60 |
| caggttcccc gcgcgccccg agccccgcg ccatgaagct cgccgccctc ctggggctct | 120 |
| gcgtggccct gtcctgcagc tccgctgctg cttttcttagt gggctcggcc aagcctgtgg | 180 |
| cccagcctgt cgctgcgctg gagtcggcgg cggaggccgg ggccgggacc ctggccaacc | 240 |
| ccctcggcac cctcaacccg ctgaagctcc tgctgagcag cctgggcatc cccgtgaacc | 300 |
| acctcataga gggctcccag aagtgtgtgg ctgagctggg tccccaggcc gtgggggccg | 360 |
| tgaaggccct gaaggccctg ctgggggccc tgacagtgtt tggctgagcc gagactggag | 420 |
| catctcacc tgaggacaag acgctgccca ccgcgaggg ctgaaaaccc cgccgcgggg | 480 |
| aggaccgtcc atccccttcc cccggcccct ctcaataaac gtggttaaga gcaaaaaaaa | 540 |
| aaa | 543 |

<210> SEQ ID NO 200
<211> LENGTH: 531
<212> TYPE: DNA
<213> ORGANISM: Homo sapiens
<220> FEATURE:
<221> NAME/KEY: misc_feature
<223> OTHER INFORMATION: Incyte Clone No: 126758

<400> SEQUENCE: 200

| | |
|---|---|
| gcaagtggaa ccactggctt ggtggatttt gctagatttt tctgattttt aaactcctga | 60 |
| aaaatatccc agataactgt catgaagctg gtaactatct tcctgctggt gaccatcagc | 120 |
| cttttgtagtt actctgctac tgccttcctc atcaacaaag tgccccttcc tgttgacaag | 180 |
| ttggcacctt tacctctgga caacattctt cccttatgg atccattaaa gcttcttctg | 240 |
| aaaactctgg gcatttctgt tgagcacctt gtggagggc taaggaagtg tgtaaatgag | 300 |
| ctgggaccag aggcttctga agctgtgaag aaactgctgg aggcgctatc acacttggtg | 360 |
| tgacatcaag ataaagagcg gaggtggatg gggatgaag atgatgctcc tatcctccct | 420 |
| gcctgaaacc tgttctacca attatagatc aaatgcccta aaatgtagtg acccgtgaaa | 480 |
| aggacaaata aagcaatgaa tacatttaaa ctcagaccat cgaatggaaa a | 531 |

<210> SEQ ID NO 201
<211> LENGTH: 491
<212> TYPE: DNA
<213> ORGANISM: Homo sapiens
<220> FEATURE:
<221> NAME/KEY: misc_feature
<223> OTHER INFORMATION: Incyte Clone No: 674760

<400> SEQUENCE: 201

| | |
|---|---|
| cttctcccat gactgccggc cagtttcctg cacttgtttc tctcgcttta ttgctggacg | 60 |
| gtgggagaag ggcaagtgca agacggaatc gagggcacct ctgggtgttc tgtacctctt | 120 |

```
ttcttcttgc accttgggaa gtggaggacg tgggatggaa gaagggcctg gacctccctc      180
cttcctcctc cccaccttct cctaaggagc ttgccctgca gtaagcccca actttccctt      240
cctcttttcc ctctatcaga gtcgtcgccc accccccttt cccaccgctc ccctaccccc      300
gccttcctgc caagccgagg gcgacggtga tccccagctt agtaagaaaa gtaaataggc      360
cgggcgcggt agctcacgcc tggaatccca gcactgtggg aggccgaggc gggcggatcg      420
cttgagccca ggagatcagg ttggagacag cctaggcaac atggcgaaac cctgtctcta      480
caaaaaaaaa a                                                           491
```

<210> SEQ ID NO 202
<211> LENGTH: 1551
<212> TYPE: DNA
<213> ORGANISM: Homo sapiens
<220> FEATURE:
<221> NAME/KEY: misc_feature
<223> OTHER INFORMATION: Incyte Clone No: 1229438

<400> SEQUENCE: 202

```
ccgggggggcc ggcggcggcc cgggcgggac gatgaagcgg cagaacgtgc gcacgctggc     60
gctcatcgtg tgcaccttca cctacctgct ggtgggcgcc gcggtcttcg acgcgctgga    120
gtcggagccc gagctgatcg agcggcagcg gctggagctg cggcagcagg agctgcgggc    180
gcgctacaac ctcagccagg gcggctacga ggagctggag cgcgtcgtgc tgcgcctcaa    240
gccgcacaag gccggcgtgc agtggcgctt cgccggctcc ttctacttcg ccatcaccgt    300
catcaccacc atcggctacg ggcacgcggc acccagcacg gatggcggca aggtgttctg    360
catgttctac gcgctgctgg gcatcccgct cacgctcgtc atgttccaga gcctgggcga    420
gcgcatcaac accttggtga ggtacctgct gcaccgcgcg aagaaggggc tgggcatgcg    480
gcgcgccgac gtgtccatgg ccaacatggt gctcatcggc ttcttctcgt gcatcagcac    540
gctgtgcatc ggcgccgccg ccttctccca ctacgagcac tggaccttct tccaggccta    600
ctactactgc ttcatcaccc tcaccaccat cggcttcggc gactacgtgg cgctgcagaa    660
ggaccaggcc ctgcagacgc agccgcagta cgtggccttc agcttcgtct acatccttac    720
gggcctcacg gtcatcggcg ccttcctcaa cctcgtggtg ctgcgcttca tgaccatgaa    780
cgccgaggac gagaagcgcg acgccgagca ccgcgcgctc tcacgcgca acgggcaggc    840 gggcggcggc ggaggggggtg gcagcgcgca cactacggac accgcctcat ccacggcggc    900
agcgggcggc ggcggcttcc gcaacgtcta cgcggaggtg ctgcacttcc agtccatgtg    960
ctcgtgcctg tggtacaaga gccgcgagaa gctgcagtac tccatcccca tgatcatccc   1020
gcgggacctc tccacgtccg acacgtgcgt ggagcagagc cactcgtcgc gggagggggg   1080
cggccgctac agcgacacgc cctcgcgacg ctgcctgtgc agcggggcgc cacgctccgc   1140
catcagctcg gtgtccacgg gtctgcacag cctgtccacc ttccgcgcc tcatgaagcg   1200 caggagctcc gtgtgactgc cccgagggac ctggagcacc tgggggcgcg gcggggggac   1260
ccctgctggg aggccaggag actgcccctg ctgccttctg cccagtggga ccccgcacaa   1320
catccctcac cactctcccc cagcaccccc atctccgact gtgcctgctt gcaccagccg   1380
gcaggaggcc gggctctgag gacccctggg gccccatcg gagccctgca aattccgaga   1440
aatgtgaaac ttggtggggt cagggaggaa aggcagaagc tgggagcctc ccttcccttt   1500
gaaaatctaa gaagctccca gtcctcagag accctgctgg tacccagact a            1551
```

<210> SEQ ID NO 203

```
<211> LENGTH: 936
<212> TYPE: DNA
<213> ORGANISM: Homo sapiens
<220> FEATURE:
<221> NAME/KEY: misc_feature
<223> OTHER INFORMATION: Incyte Clone No: 1236935

<400> SEQUENCE: 203
gtcagtttag tgtttgtggc attcccgctg cttttatggc acttcagtca ttttttagca      60
cacttccatc catactacat gtgtccttt ttcccttaa cttctctaat tgtgtttctt       120
atcctttct ttaaaaccat tgcttcatct gggagtggtg gttcatgcct tggcctccca      180
aagtgctggg attacaggcg tgagcaccgc gcccggccaa ctatagtgtt ttcaaaacat     240
gtgtacacat actctatgag gatgcaaatt gagatttcaa caaatatttc tcagtgactt     300
acataaagcc gtgctttatc ttggcgctta gatgaatttt gtttggttgg ttttggtttt    360
ggttttacat atatcctagg aacatagcag gtgatataga gtggtaaaga gcacacgtcc    420
actgttagta ggtattttta tgcacttgtt ttctcatcta taaataagg ataaaattag     480
tgcctacctc acaggatatt agggagatgg agagaatgct cagaacacaa cagggcctag   540
cacagaggaa gcacaatgct gaggaacgag aaactgcacc tgtaaattct gcagtcactt    600
taaattataa aacgagtatt tgatgtatga tcataacttt gctaagaagc catcagttat   660
aatggatgca tgaactgtag ccatccagtg agtagtgacc aggatggagg agctttatgg   720
agggggaaga aggaacctc aaagctttcc gattcatttt gaatcatgag atgtctacat    780
gtaaaaattc tgccttggta aactttgttt ataatgtttt agataatgca ttcacatggt   840
tcagatgtat gaatgtgata tattagttat ttgtttataa atatatattt tataaacata   900
tttataaata tataaatata tatttgggga acatat                             936

<210> SEQ ID NO 204
<211> LENGTH: 432
<212> TYPE: DNA
<213> ORGANISM: Homo sapiens
<220> FEATURE:
<221> NAME/KEY: misc_feature
<223> OTHER INFORMATION: Incyte Clone No: 1359283

<400> SEQUENCE: 204
cgctgtcctg ctaaagcaga ggatcacagc tttaataaag accctaaata tttatcttgc      60
ctgtggtcat gtatagctga acaatgcaca gcgaactcat ttagttttcca tgcgcttaac  120
tgggctaact ctgcttttga gcctaatgga aagcttgggg caggtggagg accggttctt   180
tagcactcac agacgattcc cacaccacac tccatatcc ggtcttctct gccgagaatt     240
ctccctgccc aagaggtctg gggtgccctg gacacgtgtg ctcatctcct gtatttggag    300
atctggggct gggaagagaa tgtaaagcaa cctaaacagt aatttaagaa tggagaaaat   360
gggactaaat tattcagaca cgtttgagtg cctactcgct agcaggcatt ttccgctgcc   420
tataattatg ag                                                        432

<210> SEQ ID NO 205
<211> LENGTH: 971
<212> TYPE: DNA
<213> ORGANISM: Homo sapiens
<220> FEATURE:
<221> NAME/KEY: misc_feature
<223> OTHER INFORMATION: Incyte Clone No: 1450703

<400> SEQUENCE: 205
gggagagagg ataaatagca gcgtggcttc cctggctcct ctctgcatcc ttcccgacct      60
```

```
tcccagcaat atgcatcttg cacgtctggt cggctcctgc tccctccttc tgctactggg      120
ggccctgtct ggatgggcgg ccagcgatga ccccattgag aaggtcattg aagggatcaa      180
ccgagggctg agcaatgcag agagagaggt gggcaaggcc ctggatggca tcaacagtgg      240
aatcacgcat gccggaaggg aagtggagaa ggttttcaac ggacttagca acatggggag      300
ccacaccggc aaggagttgg acaaaggcgt ccaggggctc aaccacggca tggacaaggt      360
tgcccatgag atcaaccatg gtattggaca agcaggaaag gaagcagaga gcttggcca       420 tggggtcaac aacgctgctg acaggccgg aaggaagca gacaaagcgg tccaagggtt        480
ccacactggg gtccaccagg ctgggaagga agcagagaaa cttggccaag gggtcaacca      540
tgctgctgac caggctggaa aggaagtgga gaagcttggc caaggtgccc accatgctgc      600
tggccaggcc gggaaggagc tgcagaatgc tcataatggg gtcaaccaag ccagcaagga      660
ggccaaccag ctgctgaatg caaccatca aagcggatct tccagccatc aaggagggc        720 cacaaccacg ccgttagcct ctggggcctc ggtcaacacg cctttcatca accttcccgc      780
cctgtggagg agcgtcgcca acatcatgcc ctaaactggc atccggcctt gctgggagaa      840
taatgtcgcc gttgtcacat cagctgacat gacctggagg ggttgggggt gggggacagg      900
tttctgaaat ccctgaaggg ggttgtactg ggatttgtga ataaacttga tacactaaaa      960
aaaaaaaaaa a                                                            971

<210> SEQ ID NO 206
<211> LENGTH: 1832
<212> TYPE: DNA
<213> ORGANISM: Homo sapiens
<220> FEATURE:
<221> NAME/KEY: misc_feature
<223> OTHER INFORMATION: Incyte Clone No: 1910668

<400> SEQUENCE: 206
cccagtttta tctgctcctg agactgagcc cagatcccca aatctaatct gatttacagt       60
tcaaggaagc tgatggggag ctgggcctta cccctgatgt aggaggggca cacagctggg      120
ggtgcagagc ccacctgggt acctgacccc caggggatga aaatgcaagg gtgagtctgc      180
ttgggcctga gagtttgatc tgcaggggca ggctcatctt ttctctcccc tgccttctcc      240
tccttctctc cccagagccc ccttgagccc ctctgcctat gtccctctgc ctcctcccca      300
tgcccccagt tgctgtggct tgattctgct accctgaccc caccatgtgc caggtggcat      360
ctgccttact gccttccctg aggagctggg acatgctggg cagttgtcag atgtaaaggc      420
acagctggag cagagggcat gtcagtaatg attggtccct ggggaaggtc tggctggctc      480
cagcacagtg aggcatttag gtatctctcg gtgaccgttg gattcctgga agcagtagct      540
gttctgtttg gatctggtag gacagggctc agagggctag gcacggaggg aaggtcagag      600
gagaaggcag gcaggcccca gtgagagggg agcatgcctt cccccacccct ggcttgctct      660 tggtcacagg gcggttctgg gcacttgaac tcagggccga agcagaagca caggcccagt      720
cctggctgca agcacaatag cctgaatggg atttcaggtt aggcagggtg ggaggggagg      780
ctctctggct ttagttttgt tttgttttcc aaatcaaggt aacttgctcc cttctgccta      840
caggccttgg tcttggcttg tcctcaccca gtcggaactc cctaccactt tcaggagagt      900
ggttttaggc ccgtggggct gttctgttcc aagcagtgtg agaacatggc tggtagaggc      960
tctagctgtg tgcggggcct gaaggggagt gggttctcgc ccaaagagca tctgcccatt     1020
tcccaccttc ccttctccca ccagaagctt gcctgagctg tttggacaaa aatccaaacc     1080
```

```
ccacttggct actctggcct ggcttcagct tggaacccaa tacctaggct tacaggccat    1140
cctgagccag gggcctctgg aaattctctt cctgatggtc ctttaggttt gggcacaaaa    1200
tataattgcc tctcccctct cccatttct ctcttgggag caatggtcac agtccctggt     1260
acctgaaaag gtacctaggt ctaggcccct cttcccttc ccttcctctc ccctacccca    1320
gaactttggc tcccttccc ttctctctct ggtagctcca ggaggcctgt gatccagctc     1380
cctgcctagc atccatgacc tgttggatgt tacctccaat cagtttcctg tcctacctgc    1440
ctctttggct tggacctata tggccatgct ctggctctac ccttgggaag cctgatcccg    1500
gtgtgtggcc cagcttgttc aggccctggg atgctgcatc tccaggcaac tatgcacttt    1560
cccggggaga gaaccagtat gagaagtggg ggcagggcac acattcatct ttgtaggaag    1620
gtctggcctg gggtcgggtg aaggagggcc caggtcagtt ctggggtccc agtgacctgc    1680
tttgccattc tcctggtgcc gctgctgctc cctgtttctg gagctggatg ttccccagct    1740
ggcagttgag ctgcctgagc caatgtgtct gtctttggta actgagtgaa ccataataaa    1800
ggggaacatt tggccctgtg aaaaaaaaaa aa                                  1832

<210> SEQ ID NO 207
<211> LENGTH: 567
<212> TYPE: DNA
<213> ORGANISM: Homo sapiens
<220> FEATURE:
<221> NAME/KEY: misc_feature
<223> OTHER INFORMATION: Incyte Clone No: 1955143

<400> SEQUENCE: 207
catagatcca taaatcatca tctgttgcaa aaaagcacat taattgattg gttgaatggg      60
gagattgaga tatttctttt ctcttcttct gctcaggtgg gggcaacttt tgggggcaga     120
tgagttctgt tgccacaaaa gttatatagc acatttggtt tgcactgaat cagcgattct     180
caatcctggc catgctttag aattatacaa gaaaaatctt caagtatcaa tactcagtcc     240
ctatcctact gatccaattc atctatgata aagccagagc attgattttt aagttctgca     300
agtgattcta atatacagcc aaggctaaga actactgata tgttccaaac actcctattt     360
tggagataaa gaagttgagg ctgaggatga gaccttagca cataaagttc cataactagt     420
aacagaccga agttctgtcc ttacaaataa aaaaaaaaag gggcggccgc cgacttagtg     480
gagcttcgtc ggccccggga atttatttcc cggaccggta ccttgcaggg ggttccaagc     540
ttttcactct atagtggagg ccgtatt                                         567

<210> SEQ ID NO 208
<211> LENGTH: 1303
<212> TYPE: DNA
<213> ORGANISM: Homo sapiens
<220> FEATURE:
<221> NAME/KEY: misc_feature
<223> OTHER INFORMATION: Incyte Clone No: 1961637

<400> SEQUENCE: 208
gggggacaat tccacccact cgagggctgc cccctcttcc ttagcagacg aaccagtaat      60
gggggcaagg ctggggcatc ccagcccaca caccctggat gcccagcaag gccacagaaa     120
gagcctgatg tccatgatcc aggtggctct gagaagcttg gcctgacac ctgagcctgc      180 ggccggtact cctgccttct ccccatctat ccccaaggcc tctgcctctc agcctcttcc     240
atggtcggtt taggctgctg agttttctgt gcttccccaa gaaccagtgg gatcaatgcc     300
ggcggcctct gtgatggttg ctgactaatc cgggatttca tgagtcagag gcaccacccc    360
```

```
tcaccccagc tgcctgctgc ttctgacgga tcttggtgct caggctgcct ggctctccga    420
gtgaggacgc agcctccata tttggtgcac tcaggcatgg ctgggacaag ccagctgccc    480
cagggttctt ccctggtga ttctcgcctg ctttctcatc tcaggggagg cagtggcacc    540
```
(Note: line 540 shows "ccctggtga" — 9 letters in that block as printed.)

```
tccctctccc tgctgacatg aagagagcta tgatatgcca ctgctgccaa ctcatcctct    600
gcccccacct cgaaacccac agtccccagt ggagggccac tactcatccc cattggtttc    660
ccaggggagg ggtgttgtct ggaagggcag gttcagatgc agccttccag atttagaggc    720
actgggagga cagtggctga gtggaggcgc ccagacctgg gcaggcagca ggctcaggcc    780
cacaccttgt gattttgaa accaaagccc agaagatgat gtttacttct ctctcctgg    840
```
```
ctctgccctt cttactgcaa accatgctgt gccttagggc ccttctcata gctgttcctc    900
atggccatga ctggaacagg gatgcaacct ctttctacac aagcacagtt agttgggtga    960
agtctttttt tttgtttgtt ttagacggag tttcactctt gttgcccagg ctggagtgaa   1020
gtggcgtgac cttggctcac tgcaacctcc aggccagcct cagcctccct agtagctggg   1080
actacaggca cccactacca cgcctggcta attctttgta ttttagtag atgggggtt    1140 tgaccgtgtt agccaggatg gtctcgatct cctgacctcg tgatccaccc acctcggcct   1200
cccaaagtgc tgggattata ggtgtgagcc accgcgccgg gccggttgct ggcatcttaa   1260
tgttctgtag gtggaatatt ccaataaac acaaggtcgc cac                      1303
```

<210> SEQ ID NO 209
<211> LENGTH: 1355
<212> TYPE: DNA
<213> ORGANISM: Homo sapiens
<220> FEATURE:
<221> NAME/KEY: misc_feature
<223> OTHER INFORMATION: Incyte Clone No: 1990762

<400> SEQUENCE: 209

```
gcagctcttt tctggaaatt ctcagggga tgtatctgaa gctccaggtc tctgagatac     60 tctgagggc ccgaccttgt ggagatgtgg ccaaccacat gggcctggag ctgggttcaa    120
accctgactt tggcactact tattagctgt gtgaccttgg acagttaat taccactctg    180 caggtcagtt tcctcatctg tgagatggat gtaataatag ggtgtgatga gatgatccct    240
agtgagtcat tggtgttgct gtggccacca ccattgttgt tactgggaga gttttggatt    300
tggaatcccg tgagcaggat tctattctgg ctgtgccatg tgccagctgg gcagctgtag    360
gaagtcactt cctctctgag ccttcacttc ccagtctcta aactgggct cacaaatgtc    420 gcattgcagt ttgggggtgg atcttttgta agaatggaca gaaaaagat ggtcaactgt     480 aatgtgtggt gcatcgtgag ctgtcactcc cgtgtgccct ggtctcctgc tggcctcact    540
gtggtttgac tcagacttgg actttcctgg aattctgaac tttgcctctc taagcaaagc    600
cccgccaggg ggtacactct gccttgtttt ccatggtgcc gtgtttccag ccctatccaa    660
caactggctt ctgatcggct gcttttttcac actgctgttc ctgcaaggct gtgtggcccc    720
atggttaagg gtgagggttc tgcaaggggtc agccagatgc gagttccggt cctaggtcca    780
ccacttactg gtcaggtgac ctcaagtaag ttgcctaacc aaggcttaac ctcttaggag    840
ctcagttttt cttcctgtaa aatggggata ataatagtac ctacctcagg gaataggggg    900
atgaaaaatg gtcttatgaa atcccctgg ccctaactgg caaaagccaa ctcagttaac    960
ggggctccat tatcactgtt gggacctggg cttgtgggag ctcaggagtc ttctcagacc   1020
tcctcattgc tgtgccaggt ggaggaggtg tttgtattta ctgagagcaa ttgggccaat   1080
ggcccatagt ccttgagcac ccagctgacc caggccacag aggctgctca tcttggtctg   1140
```

| | |
|---|---|
| gtgaccacag gaggctgtgg ctgttgggat gaccctcccc agtgttgtta acaacagtcc | 1200 |
| caggccatgt cctgctggcc ttgagttccc ctgtcctctt gtgaatgtcc ctagagccat | 1260 |
| ggcctcaagg ttcctgaagt tcccaataat gtgacatgct gcccagacct cactacactc | 1320 |
| cttttttatt ttgagcctgg gtgacagagc aagac | 1355 |

<210> SEQ ID NO 210
<211> LENGTH: 776
<212> TYPE: DNA
<213> ORGANISM: Homo sapiens
<220> FEATURE:
<221> NAME/KEY: misc_feature
<223> OTHER INFORMATION: Incyte Clone No: 1994131

<400> SEQUENCE: 210

| | |
|---|---|
| gttcactgcc atattcctag ggacaagtaa agttccctgt atattgtagg agctaagtgt | 60 |
| tgaatgaatg aatggtggct gctattattg cttcaccttc accctccaag agtaatctcc | 120 |
| ccattctggt ttatagtttc tgtgctcact gcttgtgata atcgtaagta tatattgttg | 180 |
| agaacagtgc ctgttttctc tttccctgaa aacacatact ttgacgttgg ctgacatagt | 240 |
| tcactcagct gttcctaacc actgatccct ctgtatcaca ggtatctcgg gggagctttg | 300 |
| tgccttgatg gatcaagttc atcatatgca gcactcaaaa tggcagcatc cttcggacct | 360 |
| caccacgcga aactacgccc gccgacagaa acatctgcaa agatacagtc tgactcagtg | 420 |
| ggttgacagg aacatgcgaa gccaccatcg gttccagcgt ctcccagact tctcgtacag | 480 |
| ttaatttgtg tcatcccatc agcaatgaag gtccctatcc agggtcctgc ttggagcagc | 540 |
| atttcatgtt cttttgctgt tttgtgcttt gccgattttg gatttttattt ttcacaaaat | 600 |
| ttttatttaa aaaactcgtc accttttgga aatgcccatt gccgacttga attttttgt | 660 |
| atggagtccc cctgattttg tgtgtgtgtg tctgtgttta agcacgcgtt cggttggtat | 720 |
| agttttttat atgtattttt acattaaatt gaaggtagct gcctcctgga aagcag | 776 |

<210> SEQ ID NO 211
<211> LENGTH: 817
<212> TYPE: DNA
<213> ORGANISM: Homo sapiens
<220> FEATURE:
<221> NAME/KEY: misc_feature
<223> OTHER INFORMATION: Incyte Clone No: 1997745

<400> SEQUENCE: 211

| | |
|---|---|
| ggaggcgtta gaggagctgc cttcggaggc tcagggagtc cctttggagc tggttgtttc | 60 |
| cttggccctg cagcgcactg ctcggggctc ccaaggaggt tgtgtgtatg gttcttaatt | 120 |
| catcaggaca aagaccccca gcatgtgtgt accctgggac ccgatttctc tgggcccaca | 180 |
| tctatctcca atacctcagc ctcagatcag accctttctt ttttgtcttt cttctcttaa | 240 |
| ttttttaaatg cctcttttct tgagcattcc atctctcttt ttgaccctct caggactggg | 300 |
| cttagctgtc cagagccctg ccggagggtg ctggggctg tccctctgca ggcactgtgt | 360 |
| tttcctcagg ggctgtcctc agaacacccc tcctgctccc tggggctcct cagggagcca | 420 |
| tttcagctgg agtctcaggt ctcaaaaaca acttctccag gaggccaaaa aaagactggg | 480 |
| ttggcttctg gtcctcatga tggctttat cctcctggga cactttgggt atattcatgg | 540 |
| gcattgtttc catctgtctt ttctacctgt gccacccctg ccctgattcc acggctgcct | 600 |
| caggcaggca ggcaaggagc taggccggtg cccggccctg gcagcaaggg gtctttgtgc | 660 |
| agttggagat gctgccgttg tggcagagcg tcctgcagcc ccgcttccat cagcaggctc | 720 |

```
tggggtgggg gctttgcagg ggatgctctc tgatgtttgt tccgttgttt aaataaaatg      780
cacttatttt tgttttttt tttgcaaaaa aaaaaaa                                817

<210> SEQ ID NO 212
<211> LENGTH: 484
<212> TYPE: DNA
<213> ORGANISM: Homo sapiens
<220> FEATURE:
<221> NAME/KEY: misc_feature
<223> OTHER INFORMATION: Incyte Clone No: 2009035

<400> SEQUENCE: 212
ttttctttta tatgtattat taaatgactg ttactctaca acatatggt tgttatttt        60 acttttttgga taccattata gtgtaggcat ttcccaggtt tttttggtaa caccatttc     120 ttaatgatat gatgttgcag ccagtggatt tattacagtc ttacttatta ttgctctact    180
gttggtcctt tagtttgctt ttcactcttc tatgtaatgc tgtaagaaat gactttttcc    240
ataaactatt ttccatatat tggatgtata atttaacaca ttctaaacat taatgttaaa    300
acagacataa agcataaaaa ccgagatata tatttgatca tataaaaatt taagctgggc    360
acagtggctc ataccctgta tcccagcact ttgggaggcc aaggtggggg tagactggtt    420
gagctcaggg gttcaagacc agcctgggaa catggtgaaa cccaactcta ccaaaaaaaa    480
aaaa                                                                 484

<210> SEQ ID NO 213
<211> LENGTH: 509
<212> TYPE: DNA
<213> ORGANISM: Homo sapiens
<220> FEATURE:
<221> NAME/KEY: misc_feature
<223> OTHER INFORMATION: Incyte Clone No: 2009152

<400> SEQUENCE: 213
cccagtttat taccattaga ccataccttt ttgtccaatc atttaaaaca aattttata      60 taataagttt tatttgtatg taataaattt tattatataa aaataagttt taatatatat    120
tatataaaaa gttttaataa ataccctaata tattatttaa tatgataaaa cttatattaa   180
atgaaatttt atgctgttct cttgtcaatc tgtcttttgt tatcttgctg gtgtgcctgt    240
catgtgaggg actgcaatct gatatgccta ttttccacag tcaaagcaat tacaagagaa    300
ttgttacaat tacccagtta tgtcaagaga tttttttta attcactaag gtagagataa     360
ggagaatgta ttaaaatagg atattttaat tataaatgca tgactgggga gggggtattg    420 ttttgaata aaatatgagg ttatttgcca tgacaaaaaa aaaagaagt aggaaaatcc      480 catggaaatt tatgttcctt ctaacttt                                      509

<210> SEQ ID NO 214
<211> LENGTH: 1130
<212> TYPE: DNA
<213> ORGANISM: Homo sapiens
<220> FEATURE:
<221> NAME/KEY: misc_feature
<223> OTHER INFORMATION: Incyte Clone No: 2061752

<400> SEQUENCE: 214
ggatttatca cattctgcct tgaatcatag ggaacagcat gtgtagtgga atgaacacag      60
gcctctgaat ccaagatatg agtttaaatc ccagctttgg aggtggtac ttaaagtctc     120 agtgccttca ttcttcttcc tatataaagt agatattaca atatctaact tacagagtca    180
```

-continued

| | |
|---|---|
| ttgggagcta tacatgcagc gattgggtaa agcacctggc acatggcaag cgattagcaa | 240 |
| atgctggtta cttctacttc tttctcttcc cttttcccag tctatcataa tttccttgag | 300 |
| agcaggcacc atgtcttatt tacccttgta tttcccacag tacttcccat agtgagttac | 360 |
| ccttagtaaa tactcagtaa gttgaattga atttaaatta cctgtaagtc ttaaaatgtg | 420 |
| ggattaaatt aagaatatat tgtcctggaa atacccaaat gtctattgat ggatgaatgg | 480 |
| ataaacaaaa tgtggtatac acataatgga atattattca gccttaaaaa ggaatgaaat | 540 |
| tctgacatgt gctacaatat gatgaacctg aagacatta tatgtgaaat aagccagaca | 600 |
| gaaaaggaca aatactatat gattccactt atatgaagta cctagagtag tgtaattcat | 660 |
| agaaacagaa agtacaggtt gacatccaaa atctgaaatg agaaatgctc caaaaactga | 720 |
| aacttttca atgccgacac gatgctcaaa gaaaatgcta attggagcat ttcagatttt | 780 |
| ggattttgg atttgggatg ctcaactggc ataatgtgaa tattccaaac tctgaaaaaa | 840 |
| tctgaagtct aaaacacttc tggtctcaag gattttggat aaaggatact caatgtgcaa | 900 |
| catgtagaat ggtggttgca aggtgggagg agagaatgga gagttactgt ttaatgatac | 960 |
| aatgtttccg tttgggaaga tggaaagttt tggagatgtg tgatggttat ggttgcgcaa | 1020 |
| caatgggaag gtacttagta ctgcttaact gtgcacactt aaaaatggta aaaatgataa | 1080 |
| attttgtgta tgtcttaaaa cataaaaga agtttttaa aaaaaaaaa | 1130 |

<210> SEQ ID NO 215
<211> LENGTH: 1273
<212> TYPE: DNA
<213> ORGANISM: Homo sapiens
<220> FEATURE:
<221> NAME/KEY: misc_feature
<223> OTHER INFORMATION: Incyte Clone No: 2061933

<400> SEQUENCE: 215

| | |
|---|---|
| attttctccc ttcagcaagc actcattaag gagtgaggct gagtattta agatagagtg | 60 |
| agatctgtga gtgattgaaa ggtgatattt aaaaacttgg atttcattcc agtgtcaggt | 120 |
| ttgggtttta agttcctttg gtccagggaa gggtccaagc agccacagtt gcctaaatc | 180 |
| tccatcatta agtcttccag caaggttaag tgcagtatgg aaggagaagg gggaagagga | 240 |
| cggtaacggc cccacactcc aggctgagaa agagtaatta ggaggcctga ggaggggccg | 300 |
| aggaaaggct gttggggtgt gctggggttg gtacccgagc gccttcccct cacctcaacc | 360 |
| agagaagagc atccggttgc tttttaaagc tttagcctg ccctagcaag gacaaagcat | 420 |
| gttagattag agatgcttct gctgatcgca ggggttctta tttgaaaaca tctatgatgg | 480 |
| gggtggggtg ggaggagaca ggttgtggtt atgcaggaaa atcttgtcct aaaaatatat | 540 |
| gagtttgggg gtaaggggtg ggatagccaa gcaaaatcag taattatttt aaaatgaaca | 600 |
| tatgtatttt tattaacttt tagttaaata cagattttac aacgaggtca gcataagcct | 660 |
| aaatctatat agagggctaa ctcaggcatt gtcttgttta tttgtagact ggattaaaaa | 720 |
| caacctgtcc tgttttgtca gttcccagct tcttcgttta gaataaatta gaccaaaaga | 780 |
| agaaacgtgc ttgtctctgt atacccgcag aatgaagtta ctgttgttaa aactggattt | 840 |
| tttcatttta ctaggttccg aagagtccag atgcttggta gatgttcaat acgtgatttt | 900 |
| tttttaatt gaatgtgttc atttaaaatc ctccttaaca tttctagaaa gacttctttc | 960 |
| aataaataat ggaatcttag aggaaagtg gttttttaaa agctagggaa ctcctccact | 1020 |
| aaaagtaacc attggaaacc tcgaatgagg gctaaagttt taatcataag agaaaggca | 1080 |
| gcataatgaa atgtgtacac atacatagtc agtggtccat tttaggaagc cagtggcgtc | 1140 |

```
tgataaagaa atgttaagag tagtgaggtt gaggaaggaa attgtgggga tttgaaatat   1200
tctctttatg ttgtttctct tctgagtcat ggtaaaacaa taaattatca tctctaggtg   1260
gaaaaaaaaa aaa                                                       1273
```

<210> SEQ ID NO 216
<211> LENGTH: 1279
<212> TYPE: DNA
<213> ORGANISM: Homo sapiens
<220> FEATURE:
<221> NAME/KEY: misc_feature
<223> OTHER INFORMATION: Incyte Clone No: 2081422

<400> SEQUENCE: 216

```
ctttaacaga aggatggggg atagtcagat agtcggagga agtgggtgat ttgaacaagt     60
tcagagcagg gaggaaggct gtgttgggga cttccagctt gctctcctca tgcatgaagc    120
cactcattcc ctttctctct cccccacccc ttcttccct  cactttcttc ctttcctcac    180
ttctcctttc ccctctgtgc agagctcttg gcaccagtca agctgtccca cccctcaggg    240
ccctctcagt gactgatgcc catggctccc tcctcctaca cccaaagacc ctggcttgcc    300
catgtctctg atgagaattc aaagggagct gtgtttatat aacgtagagg gatttacctg    360
tggcttttcc tttactcact tcctcaaaac tgtacattta tggcatagga tgtcagtcct    420
aaaagtttta ttatcaaaac agtaggtggc aagtaattat tatcataaat ccagcaggtt    480
ctagagaagc caagttggag gagaaagcag gatagagtcc accatgacca ttgattgttg    540
ggcacattct ttctaagaaa cagattaatt ccattgtatc tgttctctgt tatcccatac    600
cagcttatga ttagagtctt gagctcacaa cttggtcctc taagaggtag tcagtggtca    660
gcgcttcagc ttgaccacag cgtttggttc tttctttaag tgttgtgttg taatgcttgg    720
attataaaag ccttaacacg gccccatttg atcagttccc tgccaactct tgtatcctca    780
tttcactaag ctttgttaca ctcactagac tgttaacaac ggagaaaaac ctgtgggtac    840
tgaatatgcc atatacaact tgctatttat tctgttccct gtttagaagg ccatggctac    900
ccttaactat ctgaactctt cctgtcctgt aagactgagc tcactggcaa tatcctatag    960
gctgctttcc ctaagcctcc ccatctttct tcctccctcc ttctacttct ctcctacctc   1020
cttttccctc tctcccctac tcacctgctt tccttttgcc cctcccacat cctcttcccc   1080
cttcttgtca tttttccatg tcaagaaatt tccagatata taggaatatg atggagaatg   1140
ctgacaggca gttctttgag tagtcaaatt aagatgtaat ggttgaattg tataatggca   1200
atcacataaa ctacatatat aaagcttcta gcttagtaaa ctctaaatgt gttttttaa    1260 actaaagaat gaggggggg                                                1279
```

<210> SEQ ID NO 217
<211> LENGTH: 899
<212> TYPE: DNA
<213> ORGANISM: Homo sapiens
<220> FEATURE:
<221> NAME/KEY: misc_feature
<223> OTHER INFORMATION: Incyte Clone No: 2101278

<400> SEQUENCE: 217

```
tggtttggga atgcttcgaa ttttattttt tctactccca attaatcagg agttgatgat     60
cccatgagca ggaccgcctc catgattggg gagcatgcac ttgtgactgc agggtaagag    120
tgggaagata ggtttgtgga gtggcaccga caggactgtg attgtgtgtg ggcctgcccc    180
acatttctct gggggatgct tatgtgagag tgggcccagt gaaagagtta ccaagccacc    240
```

| | |
|---|---|
| cacaccccta acactgttct ggatgagaga tgagagcaga ccggcttctc cccatcagtg | 300 |
| cattgtgcct gttgtacacc cctggaggag ccctggagcc agcccaggtg gggtacacaa | 360 |
| tcttttaaa ttccatatgg ttgccagctt atttctttca cttgtttact gtaatatctg | 420 |
| gcgtgttttt atttatctaa ttttgtattc agttataacc atggtagggg tagtgaatat | 480 |
| atgacaggtg taatccctgg tgctgcagtg gaccttcttt tcttttggac aagataatac | 540 |
| tgtgagtttc cctccttcct tccctctaat ttgttttcct tttttcccca gcctcttgca | 600 |
| tccccttctt ttctaccctg tcctacaact atcatatgca cagtcttctc tctttgtgtg | 660 |
| tgactgttac aaaatttcac ttttcaaaat cgaaatcagg tgtttgctca aatgagggga | 720 |
| gattttttt tttttttttt tttaaatgc tgagacttca gcagagtact ttccttttgg | 780 |
| tggtttcccc caaaaaccca tcagtctggg agagcattgg gagtggaaat catgttgcct | 840 |
| gggatgctgg tttctttgaa aattatataa aacgtatgta aaggtccccc ccatttggg | 899 |

<210> SEQ ID NO 218
<211> LENGTH: 645
<212> TYPE: DNA
<213> ORGANISM: Homo sapiens
<220> FEATURE:
<221> NAME/KEY: misc_feature
<223> OTHER INFORMATION: Incyte Clone No: 2121353

<400> SEQUENCE: 218

| | |
|---|---|
| caaagtgctg ggattacagg tatgagccac cgcaccgggc ctgttctatt tttctagtta | 60 |
| agggaactga agctcagaga ggtgtcacca gcaggtgttc attcccatgc cagccttgcc | 120 |
| ccccggcttt tcccaggcag gctcctgcgt gcccactggc tccagcctgg tcctctgtct | 180 |
| cttggctgct tcactcctgc tctttgtccc gactctggcc ctgcttacag gggccactac | 240 |
| ctgctggtgc ctccataaca agcgtctggc gttgagaccc ctggcatggc aggggctttg | 300 |
| gggtctggtt tccacaaggc ttagccatgg cagaacctcg ttttatttta actctttgcc | 360 |
| cctacaaaca aacagcagta cttgccagaa ccattcttgg gattcaggag ctcgggcgac | 420 |
| tgccttggcc tctggccgca cccaggaggg tggggttgga tctgtgtagt tgccaggccc | 480 |
| acacctgcca gcaggggct gactggatcc atgctttact gtgtttaatg ggggtaacag | 540 |
| gggtccctac agccctccca gctaaacatt tggaacaaaa caccagccct tttgtagtgg | 600 |
| atgcagaata aaattgttaa tccaatcacc tccaaaaaaa aaaaa | 645 |

<210> SEQ ID NO 219
<211> LENGTH: 703
<212> TYPE: DNA
<213> ORGANISM: Homo sapiens
<220> FEATURE:
<221> NAME/KEY: misc_feature
<223> OTHER INFORMATION: Incyte Clone No: 2241736

<400> SEQUENCE: 219

| | |
|---|---|
| ccacgcgtcc gctgtaaacc agaaaaatgt tggttatcta gaaaacttga gagagcatgt | 60 |
| agattaactt ttctctttgg agttctaaaa cattaactgg aaagattaga taatatacta | 120 |
| aatgtataca gaagtataca gactatacaa agactgaaac aagtcccttt tgcactacaa | 180 |
| ctctataaca ttaccgcaga aattttggtt ctatgtagca tggacctcct aaggaattct | 240 |
| gtttcttta gcattgagat ccctggtgct cttttttac ctcagaattg gtacaatcat | 300 |
| tattaaacgt taatttattt caaacttttt aattgaaaaa aggaaaggga aacttaattg | 360 |
| gggataaatt caggcatcat attattatga tagagtctcc tgagtggttc gtctataggt | 420 |

```
aatgaactca ttggtgttat ttcttggaca tcttggcctt ttaatcaaag actgtgtgct      480
gctatttgct atgagcaagg tttctcaaaa gcaaaaggtg cttggaccat ttggatcacc      540
tgagttagaa tctctaggta tagggcccag gtatctgcat tttcacaggt ttcttgtagg      600
tgactttctg caagctaaag tatgagaacc attggcttgg atgtagttct aaacttttag      660
gtctgtaaat cttgaaatct tgaactgaag gtcaactatt ggc                        703

<210> SEQ ID NO 220
<211> LENGTH: 536
<212> TYPE: DNA
<213> ORGANISM: Homo sapiens
<220> FEATURE:
<221> NAME/KEY: misc_feature
<223> OTHER INFORMATION: Incyte Clone No: 2271935

<400> SEQUENCE: 220
ctttcatcat aattaaagtg ctgtcaggga aaatggcatg gctgagtttt gctgctgttg       60
aaatgaccct cctcctccac tcctcttcgc ttctctcatt tgctaaagtg gtcctttctc      120
tgcctgaaat caggcccttt ggtgatgaaa attttagctt aaagcagagt tctaagcaga      180
atcctaaccc tgcgagggtg gggagaaaat caatgttttg agctggtgtc tgtttgcagc      240
gaggtgctgg tgaggccatt tcatcagga ggaacggtgg tggtggctac ttctgggctt       300
tagatccacg caaggtctcc taaatacaag tcactgtcat ggtacacaat ttagcaaaac      360
ttggaggctg atttttcccg ttgacttagc tagggtcagg aggaagctgt ttagaagtac      420
agaggttctg catctgggag ggtaaaatcc aaacgcctct catgctcaga gggaaagcat      480
gcctgcatgt ttactatcac tgctggccta cgtgcttgtg tgctgaattt agatgg          536

<210> SEQ ID NO 221
<211> LENGTH: 790
<212> TYPE: DNA
<213> ORGANISM: Homo sapiens
<220> FEATURE:
<221> NAME/KEY: misc_feature
<223> OTHER INFORMATION: Incyte Clone No: 2295344

<400> SEQUENCE: 221
tccgtccccg gccggtagat tttcttctct ttctaaggct aatggtggta gttttgtttt       60
ttgacgtttt cttataatga gttttcttt ataatttta atttatgctg taatgtttct        120
tatttacaat gttatctctt aaatctttga gtacattaca ttttctcccc tgataatctc      180
ttctaaatta ccttctctag ttggttttct tcccttcctt aatgttagcc attcttcagg      240
tgaaggttaa tcctcaatgt actcttcatg tttaagggga gggtctaaaa ccttgtgggt      300
aggacttacc aacggagttt cattgcatga tgatcttatt gagcttattg gtagcccta       360 tctcagtatc tttagttttt cttgggctgg tcagattttc aagagaagac ttttcatttc      420
ctttgtggag ggaaaaggcc ttttaccagc actcttcaag ctcagtaggg gaaagacttc      480
aagcactcag gaagcatgca ttcactttat ttggaacaat acccttactt gtaactgtgc      540
ctcaggtgcc atagtccaca gagacttctt ttacctgtcc agagaataaa attagttgtc      600 tgttgggta acaaaaagtg tggagctgaa gagggtacct ataaatgaag ttgttttctg       660
gccgggcgca gtggctcacg cctgtaatcc cagcacttcg ggaggccaag gtggagggat      720
cacttgagtc caggagtttg agaccagcct gggcaacata ctgagactcc gtctctccaa      780
aaaaaaaaaa                                                             790
```

```
<210> SEQ ID NO 222
<211> LENGTH: 1045
<212> TYPE: DNA
<213> ORGANISM: Homo sapiens
<220> FEATURE:
<221> NAME/KEY: misc_feature
<223> OTHER INFORMATION: Incyte Clone No: 2303994

<400> SEQUENCE: 222
gggaagttga ggctgcagtg aactatgatt ttaccactgc actccagctt gggcaacaag      60
atgagaccct gtctcaaaaa aaaaaaaaag ttttctagaa taagcaggat gattgtttaa     120
tttgaagatg aacaggaaaa ctagagtgca tttaaaatac tctgtcttca ttttaacatg     180
ttgaatggaa taactgcata tcaccatgag tttgttttgc ttttcataca gacttgtatg     240
tgtcatttga gtggtttcca gattggagcg aggttattct gatctaaatg aacagcattt     300
ttttccttag cctctgtttg ccactctggg tatctctcct atgggcaaag ccattagaaa     360
tgcataaaac ctcgagacat ggttttggc aaaaactcca tgactttaaa ctagctcttt      420
tactactgac cttttcacaga gaaaaaatat ttcccttgaa aaaaactggg cttgtcattt    480
tttcccttgt agctttaagc agagacataa gtgccttgca ttacacatag taaactttct     540
ttaaaaaaaa aaaaaaagat tttggagact accagggtaa gattccaact tgtccaaaag    600
ctttctggcc ttacatattt tattataaaa attctcaagt ctggtaatct tctatgtcag     660
agctagtgat ttcaaaaggt ttcacaattc cccaagacaa aagtgatttt cgttcattat     720
aataaggtta agtgatatgt gattcataac aattttgatg tgaagaaggg aaggacatca     780
ttgacttaat aatagtatca gtcggtgcaa cagttggcaa catgtgcctt cacactttac     840
cataaagaga cgggtttgag ggtttgcctt ctaaagtctg caacttcaag aaaaaaaatc     900
gacaccgtgg attgaccttc ccgggtccac taatataaag ccaataaagc ttaaaaacac    960
ctttggtaac ccatgtaatt taactccggt ccagtggccc tataattcca attaaaaatg    1020
gttcaatctc ttggaaaaaa aaaaa                                          1045

<210> SEQ ID NO 223
<211> LENGTH: 553
<212> TYPE: DNA
<213> ORGANISM: Homo sapiens
<220> FEATURE:
<221> NAME/KEY: misc_feature
<223> OTHER INFORMATION: Incyte Clone No: 2497805

<400> SEQUENCE: 223
ctggcagatc cggacgggca ggactgggtg tgtcccatga gagcacctcc ttcctggcct      60
ttcctgtgga ctttgtccca caccacctgc ctgggttcct tcctttagtc acttccagct     120
ccaggcacag cagttggtga ctccttggtg ggagccgtgt cccacccggt cctgatactg     180
ccgtcttctc tttcacagtc ctccaggctt gggccagcct tggggcagc agagcttctg      240 gggtgagtgt cgagatcctg tgtcctgaga gcggtagtca gggagagggc tggtcggggc     300
agggctgccc gggcaggaca caggatgcgg ccggccaggc tggggccaag gtgttcagac     360
ctggactttg ggctcgtgct ttcttcatgg ttgcgccttg ctcgctgtcc cttggagtct     420
tcatttggtt ttgctttttt tgtttgtttg ttttcaccta attttgcca gacttaagct      480 agttttgctg ccttttgaaa ctagtggaag aatcatttta ttcctgggga taatttgggg    540
gcttttgaat cca                                                       553

<210> SEQ ID NO 224
<211> LENGTH: 706
```

```
<212> TYPE: DNA
<213> ORGANISM: Homo sapiens
<220> FEATURE:
<221> NAME/KEY: misc_feature
<223> OTHER INFORMATION: Incyte Clone No: 2646362

<400> SEQUENCE: 224
ccgaccccca acctcaagtt gccgccggaa gagcggctca tctgaacgct ggggcctgct      60
gcagccacca acactgccca ggactgcggg ttgctggctt gtacaccgca gctgccaccg     120
agacaccagc tctgatggc tcaggaggac ttgtggggag aggctggggg cacccatgtg     180
gtgggctctg tgcagcatgt tgcctctgct tggctgtgcc tgcagctcag ggtgctgggg     240
ctcgggaccc accccctgc ttgcggaacc aacttttctc tgtgtgtcca gcaggcccca     300 caacccctc tcctttcttt cagttctccc atgcagccga ggcccgggcc cctcaggact     360
ccaaggagac ggtgcagggc tgcctgccca tctaggtccc ctctcctgca tctgtctccc     420
ttcattgctg tgtgacccttg gggaaaggca gtgccctctc tgggcagtca gatccaccca     480
gtgcttaata gcagggaaga aggtacttca aagactctgc ccctgaggtc aagagaggat     540
ggggctattc acttttatat atttatataa aattagtagt gagatgtaac aaaagcttta     600
ttggtgtgtt tgagctggtg ggtgccacat atttgggat ttgaagaagg aggtgagatg      660
tctggatggg gactgggatg ggtagaggat tcagtgatac tccgag                    706

<210> SEQ ID NO 225
<211> LENGTH: 509
<212> TYPE: DNA
<213> ORGANISM: Homo sapiens
<220> FEATURE:
<221> NAME/KEY: modified_base
<222> LOCATION: (492)
<223> OTHER INFORMATION: a, c, g, t, unknown, or other
<220> FEATURE:
<221> NAME/KEY: misc_feature
<223> OTHER INFORMATION: Incyte Clone No: 2657146

<400> SEQUENCE: 225 aaatttagt gtattacatt tgcctttact gttatgtgc agcataaagt tgcttttgtt       60
acaattcatg ttgttttgta atggttgatc aaagcaaaga aagacatgtg ttactacgca     120
tgatctgtca atgtttaagg ctgttgttgg ttcttgtgac tttgctaata tgttttctc     180 ctgacaggtt aacctgccct cttaactcag cagtggttct agcgtcctat gccgtacaat     240
gtaagtcaca aagggagcat ttcacggatg acaggttgt tctgatcagt gtgtggagaa     300
agtcactggt tcctcctgct tgaccaagtc cctcttcccc aggaatcctg ctgggcagca     360
tatctctggc tgtccagata tgtgtttcta ctcagactgg cactctcctg tagcatgggg     420
atgttagatt aaggaaggtg gttaaagggg aaagaatgaa tgaactgtgg tgtgaaattt     480
cttccaagga gnccatccga cagcagaca                                       509

<210> SEQ ID NO 226
<211> LENGTH: 2153
<212> TYPE: DNA
<213> ORGANISM: Homo sapiens
<220> FEATURE:
<221> NAME/KEY: misc_feature
<223> OTHER INFORMATION: Incyte Clone No: 2755786

<400> SEQUENCE: 226
gaaggcggtg gctgaggcgg ttccggaggt tctagtgtcg gagttgggtg caggcaggtg      60
ccatgggccc gcttgaggca cactgagggg acgcggggct gggccatggc cggcgctcgg     120
```

```
gccgccgccg ccgctgcctc ggcggggtcc tcggcctctt caggcaacca gccgcctcag      180
gagctggggc ttggggagct gctggaggag ttctcccgga ctcagtaccg ggccaaggat      240
ggcagcggga ccggcggctc taaggttgag cgcattgaga agagatgtct ggagctgttt      300
ggccgagact actgtttcag cgtgattcca aacacgaatg gggatatctg tggccactat      360
ccccggcaca tcgtgttcct ggagtatgag agttctgaga aggagaaaga cacgtttgag      420
agtaccgtac aggtgagcaa gttgcaagac ctcatccacc gcagcaagat ggcccggtgc      480
agaggacggt ttgtctgccc agtaatcctg ttcaagggca agcacatttg caggtcggcc      540
acactggctg gatggggaga gctgtatgga cgctcaggct acaactattt tttctcaggg      600
ggtgcagatg atgcctgggc agatgtggag gacgtcacgg aggaggactg tgctcttcga      660
agtggtgaca cgcatctttt tgataaggtc agaggctatg acatcaagct gcttcgatac      720
ctgtcagtca aatacatctg tgacctgatg gtggagaaca agaaggtgaa gtttggcatg      780
aatgtaacct cctctgagaa ggtggacaaa gcccagcgct atgccgactt cactctcctc      840
tccatcccgt atccaggctg tgaattttc aaggaatata aagatcggga ttacatggca      900
gaagggctca tatttaactg gaagcaggac tacgttgatg ccccattgag catccccgac      960
ttcctgactc actctctgaa cattgactgg agccagtatc agtgttggga tctggtgcaa     1020
caaacacaaa actacctgaa gctgctgctt ccttagttta acagtgatga tgacagcggg     1080
ctgctggtac actgtatctc aggctgggat cggaccccc tcttcatctc cctcctgcgc     1140
ctttccttgt gggctgatgg gctcatccac acgtccctga gcccactga gatcctctac     1200
ctcactgtgg cctatgactg gttcctcttc gggcacatgt tggtagatcg gctcagcaaa     1260
ggggaggaga ttttcttctt ctgcttcaat ttttgaagc atattcctc cgaggagttc     1320
tctgctctga agacccagag gaggaagagt ttgccagccc gggatggagg cttcaccctg     1380
gaagacatct gcatgctgag acgaaaggac cgtggcagca ccaccagcct tggcagcgac     1440
ttctccctgg tcatggagag ttccccagga gccactggga gcttcaccta tgaggccgtg     1500
gagctggtcc cagcaggagc gccaactcag gcagcttggc ttgcagccct gagtgatcga     1560
gagactcggc tgcaggaggt gcgctcagcc ttcttggctg cgtacagcag cacagtgggg     1620
cttcgggcag tagcccccag tccttccggt gccatcgggg gcctgctgga gcaatttgcc     1680
cgtggtgttg gactccggag catcagcagc aatgccttgt gaagaagcca gcccatgaca     1740
ttttcctgct cctctctcag ctgagcccctt agcagagaat caaagccatg cctggccgaa     1800
ggggtacttc caggtcaggg gaaatttcag tcccccatct ccatcatgaa catggcagcc     1860
ccaaagctga gcaaggccaa agacaggggtt ttccaacccc cagcctcttg actggtgacc     1920
accaccccctt cttgtcactg tctcccaccc accccatctt tgctgggatt cccatcaact     1980
ctcagaactg tgtggggttt ccctgggggcc ttgtggaagc catgacttca caaagaccct     2040
acctgtcagt tcttgtttct ggggaggagg gatcacctgc actgagaatg aggcagtttg     2100
acacagatca caaaataaaa tcaaagtctt tttgaatagc caaaaaaaa aaa             2153
```

<210> SEQ ID NO 227
<211> LENGTH: 791
<212> TYPE: DNA
<213> ORGANISM: Homo sapiens
<220> FEATURE:
<221> NAME/KEY: misc_feature
<223> OTHER INFORMATION: Incyte Clone No: 2831245

<400> SEQUENCE: 227

```
ttaactgagg actaagttga tctatgcagg gtctgagtcc aaaccctggt gtcaaggtgt       60
```

```
taagtgcaaa ttattattat tatttttaa agaaaacact cttgttacaa tttggacaga      120
gagaatggta tggagatgaa aggttctcgt gtatggcttt tgctcctatt tatgtggaaa      180 gcacgccta cattctttca aagctgtgtt gttcccttta ttctcagtcc ccagaattgt       240
gtgcaaacac actctcttgg cccaggggtt tggctgggtg tgtttccttc tggaagtctt      300
cactagcact cttgagttag ctggcaggag atcccttaaa accatttcca agcagttttt      360
ctcacttccc tatagggct aatcctgtac tttccacttc agttccagct gctgttgctt      420
gggaagaaac aaatttctgc tgtgttctca atctccagac ggtccatgaa atttaatgt       480 ataagaacaa agaggctggg cgcagtggct aacgcctgta atacctgcac tttgggaggc      540
tgaggtgggt ggatcacctg aggtcagaag ttcgagaaca gcctagccaa catggcgaaa      600
ccctgtctct actaaaaata ccaaatttgc tgaacgtgat ggtggggct gttaacccca       660 gtacttggga ggctgaggca ggaaatcgct gaactcggga agcaaaggtt gcattaaggg      720
tacgagctcg aattcggtat catgttaaaa ccgtttccgg gttaaattgg tatccgccca      780
caattcccac a                                                          791

<210> SEQ ID NO 228
<211> LENGTH: 870
<212> TYPE: DNA
<213> ORGANISM: Homo sapiens
<220> FEATURE:
<221> NAME/KEY: misc_feature
<223> OTHER INFORMATION: Incyte Clone No: 3116250

<400> SEQUENCE: 228
cctgttctcg ccctcaaatg ggaacgctgg cctgggacta aagcatagac caccaggctg      60
agtatcctga cctgagtcat ccccagggat caggagcctc cagcagggaa ccttccatta     120
tattcttcaa gcaacttaca gctgcaccga cagttgcgat gaaagttcta atctcttccc     180
tcctcctgtt gctgccacta atgctgatgt ccatggtctc tagcagcctg aatccagggg     240
tcgccagagg ccacagggac cgaggccagg cttctaggag atggctccag gaaggcggcc     300
aagaatgtga gtgcaaagat tggttcctga gagccccgag aagaaaattc atgacagtgt     360
ctgggctgcc aaagaagcag tgcccctgtg atcatttcaa gggcaatgtg aagaaaacaa     420
gacaccaaag gcaccacaga aagccaaaca agcattccag agcctgccag caatttctca     480
aacaatgtca gctaagaagc tttgctctgc ctttgtagga gctctgagcg cccactcttc     540
caattaaaca ttctcagcca agaagacagt gagcacacct accagacact cttcttctcc     600
cacctcactc tcccactgta cccaccccta aatcattcca gtgctctcaa aaagcatgtt     660
tttcaagatc attttgtttg ttgctctctc tagtgtcttc ttctctcgtc agtcttagcc     720
tgtgccctcc ccttacccag gcttaggctt aattacctga agattccag gaaactgtag      780 cttcctagct agtgtcattt aaccttaaat gcaatcagga agtagcaaa cagaagtcaa     840 taaatatttt taaatgtcac aaaaaaaaaa                                      870

<210> SEQ ID NO 229
<211> LENGTH: 764
<212> TYPE: DNA
<213> ORGANISM: Homo sapiens
<220> FEATURE:
<221> NAME/KEY: misc_feature
<223> OTHER INFORMATION: Incyte Clone No: 3129630

<400> SEQUENCE: 229
gcacctgcga ccaccgtgag cagtcatggc gtactccaca gtgcagagag tcgctctggc      60
```

```
ttctgggctt gtcctggctc tgtcgctgct gctgcccaag gccttcctgt cccgcgggaa    120
gcggcaggag ccgccgccga cacctgaagg aaaattgggc cgatttccac ctatgatgca    180
tcatcaccag gcaccctcag atggccgac tcctggggct cgtttccaga ggtctcacct     240
tgccgaggca tttgcaaagg ccaaaggatc aggtggaggt gctggaggag gaggtagtgg    300
aagaggtctg atgggcaga ttattccaat ctacggtttt gggattttt tatatatact      360 gtacattcta tttaaggtaa gtagaatcat cctaatcata ttacatcaat gaaaatctaa    420
tatggcgata aaatcattg tctacattaa aacttcttat agttcataaa attatttcaa     480
atccatcatc tctttaaatc ctgcctcctc ttcatgaggt acttaggata gccatgattt    540
cagtttcaca taagaatgtt tactcaatgt ttaagtgtgt tgccccaaaa ttcccaacta    600
acaaggcaga actagggac ttgaccttgg gacctttttg ggtcctaaac tccaggtaag     660
tataaacaat ttcaattggc ctttccccctt gccaagaaaa aaaaaaataa aggggcgggg   720
gggttccccg accccggaa tttccggaaa cccttggtaa aacc                      764
```

<210> SEQ ID NO 230
<211> LENGTH: 540
<212> TYPE: DNA
<213> ORGANISM: Homo sapiens
<220> FEATURE:
<221> NAME/KEY: misc_feature
<223> OTHER INFORMATION: Incyte Clone No: 007632

<400> SEQUENCE: 230

```
atcttgtggc gatcatgtat aagctggcct cctgctgttt gcttttcata ggattcttaa     60
atcctctctt atctcttcct ctccttgact ccagggaaat atcctttcaa ctctcagcac    120
ctcatgaaga cgcgcgctta actccggagg agctagaaag agcttcccctt ctacagatac   180 tgccagagat gctgggtgca gaaagagggg atattctcag gaaagcagac tcaagtacca    240
acatttttaa cccaagagga aatttgagaa agtttcagga tttctctgga caagatccta    300
acattttact gagtcatctt ttggccagaa tctggaaacc atacaagaaa cgtgagactc    360
ctgattgctt ctggaaatac tgtgtctgaa gtgaaataag catctgttag tcagctcaga    420
aacacccatc ttagaatatg aaaaataaca caatgcttga tttgaaaaca gtgtggagaa    480
aaactaggca aactacaccc tgttcattgt tacctggaaa ataaatcctc tatgttttgc    540
```

<210> SEQ ID NO 231
<211> LENGTH: 857
<212> TYPE: DNA
<213> ORGANISM: Homo sapiens
<220> FEATURE:
<221> NAME/KEY: misc_feature
<223> OTHER INFORMATION: Incyte Clone No: 1236968

<400> SEQUENCE: 231

```
cacatttgaa cgcgcatgga cttccttcta cctaaacttt cgaactttt ttagacacag      60 gaagtagcaa gaagggagat gccaagtgac aatcaccagg aagatgcctc tctctagtga    120
cctgggtagt ttgcacggtt tggctggaaa ccacagtccc cccatctctg ccagaacccc    180
ccatgtggcc actgtcctca gacagctcct ggagcttgtg gataagcact ggaatggctc    240
cggctccctc ctcctcaaca agaagtttct cggaaagttt gaagcaaaaa ctggtcagag    300
tgctggagga aaacctcatt ttgtcagaaa aaattcaaca gttggaggaa ggtgctgcca    360
tctcaattgt gagtgggcaa cagtcacata cttatgatga tcttctgcac aaaaaccaac    420
agctgaccat gcaggtggct tgcctgaacc aggagcttgc ccagctgaaa aagctggaga    480
```

```
agacagttgc cattctccat gaaagtcaga gatccctggt ggtaactaat gagtatctgc      540
tgcagcagct gaataaggag ccaaaaggtt attccgggaa agcgctcctg cctcctgaga      600
agggtcatca tctggggaga tcatcgccct ttgggaaaag cacgttgtct tcctcctcac      660
cagtggcaca tgagactggt cagtatctaa tacagagcgt cttggatgct gccccagagc      720
ctggcttata gagctagcat ggaactcaca ccacagcttc cctggtccac agaggctctc      780
accgccattg ccaccagtat ggtggtatgt actcacaaag attaagaaag aaatgtattc      840
tgattaaaaa aaaaaaa                                                    857

<210> SEQ ID NO 232
<211> LENGTH: 1010
<212> TYPE: DNA
<213> ORGANISM: Homo sapiens
<220> FEATURE:
<221> NAME/KEY: misc_feature
<223> OTHER INFORMATION: Incyte Clone No: 1334153

<400> SEQUENCE: 232
gggaaccacc ttctgtagga cagtcaccag gccagatcca gaaggcttga ggccctgtgg       60
tccccatcct tgggagaagt cagctccagc accatgaagg gcatcctcgt tgctggtatc      120
actgcagtgc ttgttgcagc tgtagaatct ctgagctgcg tgccgtgtaa ttcatgggaa      180
aaatcctgtg tcaacagcat tgcctctgaa tgtccctcac atgccaacac cagctgtatc      240
agctcctcag ccagctcctc tctagagaca ccagtcagat tataccagaa tatgttctgc      300
tcagcggaga actgcagtga ggagacacac attacagcct tcactgtcca cgtgtctgct      360
gaagaacact ttcattttgt aagccagtgc tgccaaggaa aggaatgcag caacaccagc      420
gatgccctgg accctcccct gaagaacgtg tccagcaacg cagagtgccc tgcttgttat      480
gaatctaatg gaacttcctg tcgtgggaag ccctggaaat gctatgaaga agaacagtgt      540
gtctttctag ttgcagaact taagaatgac attgagtcta agagtctcgt gctgaaaggc      600
tgttccaacg tcagtaacgc cacctgtcag ttcctgtctg gtgaaaacaa gactcttgga      660
ggagtcatct ttcgaaagtt tgagtgtgca aatgtaaaca gcttaacccc cacgtctgca      720
ccaaccactt cccacaacgt gggctccaaa gcttccctct acctcttggc ccttgccagc      780
ctccttcttc ggggactgct gccctgaggt cctggggctg cactttgccc agcacccccat     840 ttctgcttct ctgaggtcca gagcaccccc tgcggtgctg acaccctctt tccctgctct      900
gccccgttta actgcccagt aagtgggagt cacaggtctc caggcaatgc cgacagctgc      960
cttgttcttc attattaaag cactggttca ttcactgccc aaaaaaaaaa                1010

<210> SEQ ID NO 233
<211> LENGTH: 1981
<212> TYPE: DNA
<213> ORGANISM: Homo sapiens
<220> FEATURE:
<221> NAME/KEY: misc_feature
<223> OTHER INFORMATION: Incyte Clone No: 1396975

<400> SEQUENCE: 233
cagcactttg ggaggctggt ctcgaactcc tgatctcagg tgattcaccc gcctcagcct       60
tccaaagtgc tgggattata ggtgtgagcc accgcgcccg gcctggatct gttttcttag      120
cacgcagtga ggaatctttg tacttaaggc caggcaaca aagtcaagag gtcaaggtgt       180
agggccatga ggcctggacc tatgctgcag gcaagggttt ccatcccgc tgccctaggc       240 actctcttcc caaggccagg ttgggcacct ggggaggtca gttcagaaat atctagcaga      300
```

```
gacctcttaa accccatcc cagcacccca tcctgttgtt cccagagctg gtctcccatg    360
agtgtgctag agccagatag ccgtggcccc ccacccatct cactcacaca cacaggcatc    420
catacacccc agaagacttc ccaaatgagg ccagactcag ggtcacgggg aatgtgcttc    480
tgcccctgta agggctttgg ggaagggggc aacatagtag aggctggaaa gagcccccaa    540
acctgtgccc atgcccctcc agccctgcgt ttccattctg ccttctcaga gtgcccttgc    600
tgcacccaga ccaccggcca ggagagacct tctctcccac tccagcccct ctcactgccc    660
ttcaactaga gctttcacct ttttacattt cccttctgaa ggacacaaat ctgcttttct    720
gcccatacac tggcccaagg gctcacctaa cttgggaggg aaggggctgt tggtacaagg    780
atgattttct gttagactgc cattttgcac ggtctcccc ttcccatctg atgtgtcctg    840
cccctcagct ctttgcctta tctgtgtcac tgtcacttta gcaaaaatac agcggccatt    900
tgtatcagcc tctggtggtt gcttgtgagg tgggactctt gcgggaacag gtggactttg    960
ggaggagtgg gcagggaggg agtggtagtg gcagttctcg agctatctga ttaagccatt   1020
ccgttagttc agttgtgccc tggagggcag gggacagggt cagtatctct ggggctgcag   1080
gccctcttgc cttggccctc ctggcatggg gtaaccacca gctcagctct cctcctccag   1140 cttcctctc tctagcacac cccagccagg gcaaggatgc ccacgggcat agctacagca   1200 accctgcgg gatttggtgt ccacacccga gaggccaggc cagatgggaa agggattagc   1260
gcctcttccc tcacactctg ccaggctgcc gggagcttgg gccaggtcta aggtaatgag   1320
gtgctcctct tcctgctgga aaaccggac agactcagaa ccacaaaggc aggtgctgcc   1380
agcctggcgc cttcctctct gcttaggctg ggtgagcttg tccaggcctg tgcctcaccc   1440
cttctctctt ctaggctcag tgtatgctta atcaggcatg gtgcatcaga gcgggaagga   1500
gccatcaaca gtgtatactt ctggagcctt ctactgataa acagaggccc cagaagacga   1560
tttgacttac ctgagctccc agctgggact taaacccagg tgtgtctgag tcacaactct   1620
tcggggatgc cgtggtgagc tggggctgag ctcctgtatt cccactcccc caccccaccc   1680
ccactcctgc catatcaggg ctggtctctg tggactcagc ccagggctgc ctcctctttg   1740
tcaccccaaa gtggggcagc cagggacagc cagggtgtgt tcagaatggg ttcttcctgc   1800
agggcaggaa gggcagattg ttaaaggggc tgcggcccag accaccctgg tccctcctcc   1860
ggcagtgact cagacccaca ctgtgccgtg cagctgtgtg ccctgcacac ccgcttgacg   1920
gcgcactgct cacttctggg gggcccttc agaggcactt ttaaagcaaa taaacatttt   1980
a                                                                  1981

<210> SEQ ID NO 234
<211> LENGTH: 744
<212> TYPE: DNA
<213> ORGANISM: Homo sapiens
<220> FEATURE:
<221> NAME/KEY: misc_feature
<223> OTHER INFORMATION: Incyte Clone No: 1501749

<400> SEQUENCE: 234
gcgcccggtt ctccctcgca gcacctcgaa gtgcgcccct cgcctcctg ctcgcgcccc      60 gccgccatgg ctgcctcccc cgcgcggcct gctgtcctgg ccctgaccgg gctgcgctg     120 ctcctgctcc tgtgctgggg cccaggtggc ataagtggaa ataaactcaa gctgatgctt    180
caaaaacgag aagcacctgt tccaactaag actaaagtgg ccgttgatga gaataaagcc    240
aaagaattcc ttggcagcct gaagcgccag aagcggcagc tgtgggaccg gactcggccc    300
```

```
gaggtgcagc agtggtacca gcagtttctc tacatgggct ttgacgaagc gaaatttgaa    360
gatgacatca cctattggct aacagagatc gaaatggac atgaatacta tggcgattac     420
taccaacgtc actatgatga agactctgca attggtcccc ggagcccta cggctttagg     480
catggagcca gcgtcaacta cgatgactac taaccatgac ttgccacacg ctgtacaaga    540
agcaaatagc gattctcttc atgtatctcc taatgcctta cactacttgg tttctgattt    600
gctctatttc agcagatctt ttctacctac tttgtgtgat caaaaaagaa gagttaaaac    660
aacacatgta aatgcctttt gatatttcat gggaatgcct ctcatttaaa aatagaaata    720
aagcattttg ttaaaaaaaa aaaa                                           744

<210> SEQ ID NO 235
<211> LENGTH: 979
<212> TYPE: DNA
<213> ORGANISM: Homo sapiens
<220> FEATURE:
<221> NAME/KEY: misc_feature
<223> OTHER INFORMATION: Incyte Clone No: 1575240

<400> SEQUENCE: 235
gggatgaagc ccagcaagtt cacagggatc cgggaagttg tgtggctgga aacccaggca    60
gggctgcacc acagggacca tttgctggag atgcagcact tgccacagcc accaccactg   120
acagcatgac acccacaaaa agggagcctc cagctgcacc cctgctgctg cgagtacttc   180
ctcagctgtc tgccatgagc ttaaggttaa gtaccaggag ggaggatatg attgggcaaa   240
cctcaggcat gtgttcattc tgtagcttcc agaacatgcg aggagagagc atctggctcc   300
tttgtctcga ggaggagggg gcaggactct gccagaactc actcgataaa agattttccc   360
aaaaggaagg gtgttcagat gacaaaagtc cactacacca ctttccttgg ctatctgatg   420
caccccatc ttcccatgcg cgcacctcag aaatcaggct cccacctgac ataacacaac    480
catgcctcac aaaaagacag tggtttatcc cttccctagg agaaaagaga ggcaatgcca   540
agctgcttca tcaactgtta atacttcttc cagcccgcaa cccaggatat ctgcaggtgt   600
ctctcccctct ggtttggtca tggctctctc tgttctagaa tgtatgggtt aaagtcggct  660
gccacaccat gccctcggca gtgtggtcca aggaccctg agggtcctca aggtccttcc    720
tttcccaacc ccacgtggtt tcttcagtc aggataccat actgcaacag accgaaggcg    780
gaagcagcta tgaggatgca gcagccttct gttaagccag gctttaagga tctgcaaaaa   840
tgtaaaacga tgccactcct actgatgaaa tatattgttt tggaaaatat aggtttaaaa    900
atttttttaa ggtaacatgt aatggatgta tagtcttcaa atggatgaat aaatgttttt    960
cagagttaaa aaaaaaaaa                                                 979

<210> SEQ ID NO 236
<211> LENGTH: 760
<212> TYPE: DNA
<213> ORGANISM: Homo sapiens
<220> FEATURE:
<221> NAME/KEY: misc_feature
<223> OTHER INFORMATION: Incyte Clone No: 1647884

<400> SEQUENCE: 236
cccgactgtg cgccgcggct ggctcgggtt cccgggccga catgggcgcc gccgcgtggg    60
cacggccgct gagcgtgtct ttcctgctgc tgcttctgcc gctcccgggg atgcccgcgg   120
gctcctggga cccggccggt tacctgctct actgcccctg catgggtaag gcctcccaag    180
ccctctgctc agatggagaa actgaggccg ggagaggaaa agccactcct cagatgcgcc   240
```

| | |
|---|---|
| cagagacacc ttcacaggtc caggagagaa cctcagagcg ggacggggca tgctcttctc | 300 |
| ctctctgcct tagttgcaag ggcacagagg ggccaacgtg tccaactttc catttgacag | 360 |
| atgagaaaac tgaggctggg agaggttacg tgacttgctt gaggtctaag ccagtccagg | 420 |
| gtccagtaaa tggagttagt ggggcaggac ttgatgtcac tgacccacgc tggctcctgg | 480 |
| tgattttca ttgattcagc aaatatttat ggggcaccta ttctgtgccg ggccctgttc | 540 |
| tctgtactgg gaataccgca gtgaataaga taaactccgt gtccttgtag agccttcatt | 600 |
| ttagttgggg aagacaaaca attgagaata gtaggccag gcgcggtggc tcacttctgt | 660 |
| aatcccacca ctttgagaga ccgaggcagg atcacttgaa gccaggagct cgagatcagc | 720 |
| ctaggcaaca tagtgaaaat ccaatctcaa aaaaaaaaa | 760 |

<210> SEQ ID NO 237
<211> LENGTH: 1080
<212> TYPE: DNA
<213> ORGANISM: Homo sapiens
<220> FEATURE:
<221> NAME/KEY: misc_feature
<223> OTHER INFORMATION: Incyte Clone No: 1661144

<400> SEQUENCE: 237

| | |
|---|---|
| tttttgtat ttttagtaga gatgggtcta accatgttgc ctaggctggt ctcgaactcc | 60 |
| tgagctcaag cgatcctctt gcctcaacct cccaaagtgc tgggattgca gctgtgagcc | 120 |
| accgcacccg gccgcattct tctaaatcac agtacatctg gttcccagtg cccaggctct | 180 |
| cagggcagag ggtccagtgt gatcactttg catggcctct ctcccctcct gagcttgtgc | 240 |
| cagggcccca gggctgacct ggagaaggaa aatggcagag ggtgaagatg gggtgtctgg | 300 |
| tttggggacc atcctggccc cccttgtcac tgttggcatc tcttctgcac agtggcattg | 360 |
| ctgggaggtg cttactgtgc ctattcaagg ggctggcagc cgcagcctca ctgcagatca | 420 |
| gggacttggc ttcccggttg accacaggtc caagaacctg cagggtccag cctccccccc | 480 |
| atccccagtc ttccccaccc tggcccggcc ctccaggtgc agaaacatgc aggcccctct | 540 |
| ccaggactgt gggaggagtg tgtccctcag actggcctgt gtcctggctc tcttaccac | 600 |
| ctcttccaga ggttgtcacc tgcagctgcc ccaggataaa ggcaaggcca gagaggactc | 660 |
| ctgaactcct gtgtgcctgg ggtggcaggg gcaaacatag ccaactggtg gcctgagcgg | 720 |
| ggccatggtg aggacaccct tggtggcttg tcccacatca agctgggagg tgacactgag | 780 |
| gatgcattag tctgcagcgt atgataaaaa cggcatttca ggccaggcgt ggtggctcat | 840 |
| gcctgtcacc ccagcacctt ggaggccga ggtgggcgga tcatatgagg tcaggacttt | 900 |
| gagaccagcc tggccaacat ggtgaaaact catctgtact aaaaaaacaa aaattatgtg | 960 |
| ggttggtggt gtgcgcctgt aatcccagct acttgggagg ctgaggcagg agaatcactt | 1020 |
| gaacctggga ggcggaggct acaacgagcc gaaattgcac cactgcactc cagcgctgat | 1080 |

<210> SEQ ID NO 238
<211> LENGTH: 1129
<212> TYPE: DNA
<213> ORGANISM: Homo sapiens
<220> FEATURE:
<221> NAME/KEY: misc_feature
<223> OTHER INFORMATION: Incyte Clone No: 1685409

<400> SEQUENCE: 238

| | |
|---|---|
| caacgtccga cagaacgagg ggacgtaacg gaggcaggtt ggagccgctg ccgtcgccat | 60 |
| gacccgcggt aaccagcgtg agctcgcccg ccagaagaat atgaaaaagc agagcgactc | 120 |

```
ggttaaggga aagcgccgag atgacgggct ttctgctgcc gcccgcaagc agaggtagcc    180
ccagggaggg gagggaaagg gacggtggag acctgggtta gaccaagggt tatagaagga    240
aagagagcta cctcagggct tgaatgtgga ctagtcgtga ggagcagagt gcattgcttc    300
ctctagggtt ttatttcctc cccaccctcc aaattgttag ctcacagcct tacaggaaag    360 gacggggcg gcgcctgcc ctcagtctga tttctgagcg tccctgggtc tgaccttaag    420
ggcaagggca gggagcttca catttcaaat acagttgtgg ttacggcagc ccagtacttt    480
tggccctcct tgctgttcgg ttctcctccc ttctcccaac ctcctcactg gtgttgctgg    540
gtgtggtcct caatacagaa tagagaccct tgggcctgtg tcaccagact tctgaccct    600 tgggcaacag ccagatggag actggtcgcc ttttgagcct cagctctctt cctcttgttc    660
tcctagggtg ggagtacagc agccaaacgc tgaacttagt cccatccact tccatcttat    720
cctttgtgcc cttcatcccc ctgcatcttg tcctttttgc cctctggtac ctcccagtgc    780
cccatcatct ctaccccag ggactcggag atcatgcagc agaagcagaa aaaggcaaac    840
gagaagaagg aggaacccaa gtagctttgt ggcttcgtgt ccaaccctct tgcccttcgc    900
ctgtgtgcct ggagccagtc ccaccacgct cgcgtttcct cctgtagtgc tcacaggtcc    960
cagcaccgat ggcattccct ttgccctgag tctgcagcgg gtccttttg tgcttccttc    1020 ccctcaggta gcctctctcc ccctgggcca ctcccggggg tgaggggtt accccttccc    1080 agtgtttttt attcctgtgg ggctcacccc aaagtattaa agtagctt              1129
```

<210> SEQ ID NO 239
<211> LENGTH: 2370
<212> TYPE: DNA
<213> ORGANISM: Homo sapiens
<220> FEATURE:
<221> NAME/KEY: modified_base
<222> LOCATION: (122)
<223> OTHER INFORMATION: a, c, g, t, unknown, or other
<220> FEATURE:
<221> NAME/KEY: modified_base
<222> LOCATION: (124)
<223> OTHER INFORMATION: a, c, g, t, unknown, or other
<220> FEATURE:
<221> NAME/KEY: misc_feature
<223> OTHER INFORMATION: Incyte Clone No: 1731419

<400> SEQUENCE: 239

```
agaaacttgg cccaagtttg tgacggttct gggtatgaaa gaagtcagtg tttcccaagt     60
gcctgccatg tgcgaggctc tgtgctgggg cgggtgcatg tgtgcgttgg gggcgtggac    120 angngggtg ggaaaggcct gtgacatttc ctctggtggt ttccacgaac ccaggcgtca    180
cccctcggtg gagataaagt ggagccaccc agctccaccg tgtctcagcc tggggtcggc    240
ctctgctgct tctggactca gtgaccctgg gctgtcaggg agcttctgag ccttggtttt    300
cctgtcgagt aagatggagg taatcgtgtc ttatgggtt gttttgaggg ttaaatgagc    360
tggtggctgt gtgggaaaga gctctgcctc ccgcagggag gaactgtgct gttcttatta    420
ttgtgaactt agtgacaagt gtggcactat tacccatttc cttgtctgcc cccaaccctg    480
gggtcttggg cagagaacag gagttcttgc cattttctcc cagctcccac cttgtgctgg    540
cttgcgggtg ctgaggtcat atttgctggg tgaaagggtg caggccagat atgagccagg    600
cctggcagag agggttttgg tcagcagtga tacctgcagt gttctctgca gttggtttgg    660
gctggccctg ctcctgagaa ctcctgggtt gtcccttcag gcaaccaggg aaggctcctt    720
ggagcagcag catctcccct taccactcgc cgacaccagc ttccgcctga cccagagaag    780
gagtttgggg acagccacag cacgtccagg gcttccaagg cagctggcag agccaatgag    840
```

```
gagaccccaa cacccatccg acggctgcag ctctccctga cgtgtgttac cgcagccctg    900
gtcccagccg ctgtgcttct cagggcctgc ctgcccagcc cgggtggata tggtgcccag    960
gcgggccccg gggacacaat gagggccatt ctcagagcca ggcagagcgt gtggggcagt   1020
cctgtcagtc ctatgtgcaa cagctgggat attgtttagg gagtgctggc atcaggccgg   1080
ggctctcctc ctctggccct gcccttt ggg atgagcaagc ccccaaaggc cttcctgggt   1140
tcctctggtg cacgtgccct ggagttaccc ttctgaagga ggtagacttg tcctcctgtc   1200
ctgggtgcct ggggtgcagg ggtgtgaatt gggctatgtc aagatatgct ggcagtact   1260 gtgaggtggg ggcagagggg agaaggtgtc ccaggaggag ccttcctgga ggggatgata   1320
gtccagcatg ttctgaagtg ggagtagggt gcggcaggag tagggtacca gagaatgagt   1380
gagtcaggca gcagcctcca ctgcgccttg gacacaggtg gccgacagtg tccacctgga   1440
ctggctttgc acccctt ctg aggtcacagt tgtgtcccct gaaaacttgg gcaggagcac   1500
ctgactggcc cagcttgggt catgcccta g gcccagcagt gcgggaggcc aggaaagtag   1560
gcttggggag gctggcctct cctccagttt gaagcatggc aggggttccg ggggaggctg   1620
ctggggggcc tgcgagcatg tccagagcag gaatgcttgg ggtggtgtgt gctttgctcg   1680
tctgggctta tctggccgtg gggaagctgg ttgtgcggat gacgttcact gagctgtgca   1740
cgcatcatcc atggagtctg cggtgtgagt ccttttgccg ctccagggtc acagcctgcc   1800
tccctgctcc agcccctgg ctgaggccct tcctctgccc catgctcttc tcagacagga   1860
atcctgtgga atgtcatctc tttggggagg ccgtctctga ccctgtatgc aaaggccttc   1920
tcccacatta tttttggcac cccactttct tccccgtgaa agcaaattgt ttggtgtctt   1980
tctgtcccac tacagtatag gcccggttca gacagaggcc ttgtccacta ggcctgcgct   2040
atctctgcgg agcccagcca agcaggggc caggcgaatc ttttgttaaa agaacaatgc   2100
gcgctgggca cagtgctcac gcctgtaatc ccagcacttt gggagtccga agctggagga   2160
tcacttgaac ccaagagttt gagaccaccc tgggcaacat aaggagaacc catctctaca   2220
caaaattagc tgggcgtggt ggtgtatgcc tgtagtccta gctacttggg aggctaaggt   2280
gggaggtggc tgaggtggga ggatcacttg agcctgggag gttgttgcag tgagagccat   2340
gatcgcgcta ctgggcaata gagcagaacc                                    2370
```

<210> SEQ ID NO 240
<211> LENGTH: 981
<212> TYPE: DNA
<213> ORGANISM: Homo sapiens
<220> FEATURE:
<221> NAME/KEY: misc_feature
<223> OTHER INFORMATION: Incyte Clone No: 2650265

<400> SEQUENCE: 240

```
cggactgccc tgagggcggg aaagggtggt cactgggtca gcccgaagca cctgacatga     60
gggcggggac cccgaaatgc acacgaagtc cggaactggt cttctgtgat tttcattcgc    120
cctggtctct gttcccttttc gtactcaaag ctcgtgcatc cagggagggg aaaccggaga    180
tagggtcttc gggccccggg cagaccctct gtgccgctgc aaaccgttgc agcctgaggc    240
tgtcaggtcc tcccccagac acctgcggac cctccctctc ctggcttccc gtctggtcat    300
ggcgagattc tgggtctgcg tagccggtgc tggcttcttt cttgcatttt tggttttgca    360
ttcgcgtttt tgtggctctc cagttttgag gaactttact tttgcagttt cctggagaac    420
tgagaaaatt ctttaccggc tggatgtggg ttggcctaag cacccagaat attttaccgg    480
```

```
aacaacattt tgtgttgcag ttgactccct caatggattg gtttacatag gtcaaagagg    540
ggataacatc ccaaagatat tagtgttcac agaggatgga tatttcctac gagcctggaa    600
ttatacagtt gacacacctc atggtatatt tgcagccagt actctatatg aacaatccgt    660
ctggatcacg gatgtaggaa gtggtatgta tagtaatatc tattaaatta tcttactgga    720
aatcacatct ttgcacatgt ccttgtttgt attgtttaaa atcagagttg ctgaatctaa    780
ttgtaatttc tttaacgatt catgaaatca catgttttta acaaacttta ttttgtactt    840
ctgtggaatt aagaaattta acaagggctg gacgccgtgc tcacgcctgt aatcccagca    900
ctttgggagg ccgaggcggg cggatcacga ggtcaggaga tcgagacgat cctggccaac    960
acggtgaaac ccccgtctcc a                                              981

<210> SEQ ID NO 241
<211> LENGTH: 1204
<212> TYPE: DNA
<213> ORGANISM: Homo sapiens
<220> FEATURE:
<221> NAME/KEY: misc_feature
<223> OTHER INFORMATION: Incyte Clone No: 2677129

<400> SEQUENCE: 241
aggagaggaa ggtaattaca ttaagcatta aatatagtg tgttaaatgc taatgatcat     60
aatcattgaa cccttctcag tcctcatctt atttaaatct ggtatttag cagactttt    120 tgccttactg ctattaatta attttttttt ggtctctttc ttccttgctt accctttgtt   180
taacaaccaa atcaactcta gatcaatgaa tgaaataaaa aatctccagt acctacctcg   240
gaccagtgaa ccccgcgaag ttctctttga agataggact agagctcatg ctgatcatgt   300
cggtcagggg tttgactggc agagtacggc tgctgttgga gttttgaaag ctgtacaatt   360
tggtgaatgg agtgaccaac ctcgcataac caaagatgtg atttgttttc atgctgagga   420
ttttactgat gttgtacaaa gacttcagtt agatcttcat gaacctccag tttcccagtg   480
cgtacagtgg gtagatgaag ctaaactaaa ccaaatgagg cgggaaggca ttcgttatgc   540
tagaattcag ctttgcgaca atgatatcta cttcatccct agaaatgtca ttcatcagtt   600
caaaacagtt tcggcggtgt gcagcttagc ctggcatata aggcttaaac agtaccaccc   660
tgttgtggaa gccactcaaa acacagaaag caattctaac atggactgtg gtttaactgg   720
aaagcgagaa ttagaagttg actcccaatg tgtgaggata aaaactgaat ctgaagaagc   780
atgcacagag attcagctgt taacaactgc ttcatcatct ttcccacctg catcagaact   840
taatctacag caagatcaga agactcagcc tattccagtt ttaaaagtgg aaagtagact   900
ggactctgac cagcaacaca atctgcaaga acattcaacc acttctgtgt gatatgtaca   960
tattcaaaca catttttta cttttttaaa ttttgatgtg aagttatagt tttataactg   1020
gcttaagtta agttttattg gagaaatctt gcctataatt ctataaagag aaatgacatt  1080
cacaaatgtc agcatatctt tttacacaga tatgcaagtt agagtgtatc tatccggtag  1140
tacgtatgta taagtggtct gcgcacttct gttttaaggg tgaggtacat ccatctctct  1200
cgag                                                               1204

<210> SEQ ID NO 242
<211> LENGTH: 784
<212> TYPE: DNA
<213> ORGANISM: Homo sapiens
<220> FEATURE:
<221> NAME/KEY: misc_feature
<223> OTHER INFORMATION: Incyte Clone No: 3151073
```

-continued

<400> SEQUENCE: 242

| cacagacaaa ccgtcaacag ctggtctcgc atgtcctttg ttcccggtct gctcttgtgt | 60 |
| ttcgttctcc tcctgtgtgt tagccctgtg taccttccct ctcgttcacc ctccacattt | 120 |
| cccatctctg agcccctcag ctttataggg atgtcagctt ggccccaatg tagtcccatt | 180 |
| tacagccaga ctcctggact tgcctatgag ccatcttcat ttccaaaaag gcgatattgg | 240 |
| gtatgtacat tgcatgaaat aaagtgggaa tgtcccagaa gcagaaggac atctgatgca | 300 |
| gtccacgcca ataaattggg cttacctttta aaaatcatct gaatatgcag gtcttagggc | 360 |
| agagaatata gacagcttaa gattttctaa actacaagtc ccacccaaaa tacggtattt | 420 |
| tcatgatttc ccaaaggttg accatcagca agactggata ttttttcagac ttaagatgac | 480 |
| tgttcagtag ctgatgttct ggaaaagatc tgggccttca ccatgaaatc ttaaatgtga | 540 |
| gcagttactg gatgttgaat ttgaaaccta ttcatttctt tttttaaaac aagcttggtc | 600 |
| atttctgtgc aatgctataa ttcggaacga aacaaagcac aatgttaata aggtagacac | 660 |
| taattcattc ctctgaagag agatctcttc cagacatttt aagccagggc aagaaatgtt | 720 |
| taaagatgtt ttctgcagtt gccgtagaaa cactccttag cagtcatctt ggctgttggt | 780 |
| aaaa | 784 |

<210> SEQ ID NO 243
<211> LENGTH: 426
<212> TYPE: DNA
<213> ORGANISM: Homo sapiens
<220> FEATURE:
<221> NAME/KEY: misc_feature
<223> OTHER INFORMATION: Incyte Clone No: 3170095

<400> SEQUENCE: 243

| ctccattaaa ccaccaccag ctccccaagc cacccctttca gccatgaagt tcctgctcct | 60 |
| ggtcttggca gccctcggat tcctgaccca ggtgatccca gccagtgcag gtgggtcaaa | 120 |
| atgtgtgagt aacaccccag gatactgcag gacatgttgc cactgggggg agacagcatt | 180 |
| gttcatgtgc aacgcttcca gaaaatgctg catcagctac tccttcctgc cgaagcctga | 240 |
| cctaccacag ctcatcggta accactggca atcaaggaga gaaacacac aaaggaaaga | 300 |
| caagaagcaa caaacgaccg taacatcata ataaccactg ctatcgcctc caccaactca | 360 |
| gagaaatatc atttccacag ttccaattcc tcctacattg ctgagtacta gccaaggctc | 420 |
| ctctttt | 426 |

<210> SEQ ID NO 244
<211> LENGTH: 1732
<212> TYPE: DNA
<213> ORGANISM: Homo sapiens
<220> FEATURE:
<221> NAME/KEY: modified_base
<222> LOCATION: (1651)
<223> OTHER INFORMATION: a, c, g, t, unknown, or other
<220> FEATURE:
<221> NAME/KEY: modified_base
<222> LOCATION: (1655)
<223> OTHER INFORMATION: a, c, g, t, unknown, or other
<220> FEATURE:
<221> NAME/KEY: misc_feature
<223> OTHER INFORMATION: Incyte Clone No: 3475168

<400> SEQUENCE: 244

| cgggaccaga gcacgttcct ggctgcagag gccacaagtc acgctgtctc tgagagtgga | 60 |
| atgtcaccat cgcccaggtg gggattttttg tgtgttttgt tcactgctgt acacccagcc | 120 |

-continued

| | | | | |
|---|---|---|---|---|
| cccagcacag | cgcctgtcca | ggacaagtgc | ccagtaaaca | cttgggaagc aatgcaagcg | 180 |
| tcctcccagc | agctcctgca | aacagacccc | cgacccaagc | ctttccttct gcctccactg | 240 |
| ccaccactgc | tgctcatctc | tgctggcaca | gaagtctctt | ccctggtctt ccagaaatcc | 300 |
| cctctccaca | ctcagccaga | gggagctatt | aaaactgcgg | gccagcccac atcagtccac | 360 |
| agcaaagtcc | tctctaaggg | atctctgttg | cttggagaat | aaaccctcgg attccttcct | 420 |
| tggctctcgg | ggcctcctct | ctgacctccc | tctgtctcct | ctcccagcct tcctcctcac | 480 |
| tcaccctcca | gccatgctgg | cttcctcctt | gctcctgaaa | cagcctgaga gccacactgc | 540 |
| cccgggccct | ttgcactggc | tgtttcctct | gcctggagca | cttctcctag gcatccacag | 600 |
| ggctccctcc | cacaactcct | tcgggtgccc | acatgggaag | ccatccctga ccaccccccc | 660 |
| gacttccttc | tgagcaaggt | agggtctttc | tacctagtca | tgagggcagg gattttttgtc | 720 |
| tgttgtgttc | tctgtgtgcc | cccagtgcca | tcccagtgcc | tggcagatgg taagtgctcg | 780 |
| acacacattg | gctgactgcc | tgaatgaaca | actctatgag | ccgatggcag ataaggacac | 840 |
| tgaggtcctc | tggggtaggt | gaccagccca | aggccacaca | gctggtctga gattaggcca | 900 |
| ggagaggagc | ccgggttggt | cacatcctgg | agttggcgtc | ttggaaactg catcaggaga | 960 |
| ataacaaaga | tgagacgcag | gctctaacaa | gtggatacca | gtgactctcg ccccgccagc | 1020 |
| cccagccctg | cagccttggg | cccttccagg | agtcatggtc | tgcctgcctg gggcattcca | 1080 |
| ggcttcgacc | caggtcctgc | actttctatt | ttgagcctct | tagtcctgag gactgtgtgt | 1140 |
| tcccagcagg | cggcgcgggc | cagaggctga | gcctgggtgt | ggctgtcacc ctatctgggg | 1200 |
| ccagagaccc | agattcccgg | gcccttaacc | tgttggctgc | tgagggctct ggcataagcc | 1260 |
| ctgttccctg | cttgattgtc | tccccttcaa | gcccctgccc | tggtatcgta tcggcccatc | 1320 |
| tcaccttgga | ttatatccct | gtttggcccc | atttgaatcc | tggctctgcc cctttccagc | 1380 |
| aatgtgacct | tgggcaagtc | acttcatctc | tctggtctca | gttcttcatc tggaaatggg | 1440 |
| acaataagag | tacctgtctc | tggccatgtg | tggtgactca | tgcctgtaac cccagcgctt | 1500 |
| tgggaagccg | agccgagaga | attgcttgag | accaggagtt | tgagatcagc cctgggcaac | 1560 |
| atagtgagac | ccctgtctct | acaaaattct | aaaaaaatta | gccggttgtg gtggtgtgtg | 1620 |
| cctgtagtcc | cagctattct | agaggctgag | ncggnaggat | tgcttgagcc cagcagtttg | 1680 |
| aggctgcagt | gagctatgat | tatgcccgtg | aaggccccccc | aaaaaaaaaa aa | 1732 |

<210> SEQ ID NO 245
<211> LENGTH: 918
<212> TYPE: DNA
<213> ORGANISM: Homo sapiens
<220> FEATURE:
<221> NAME/KEY: misc_feature
<223> OTHER INFORMATION: Incyte Clone No: 3836893

<400> SEQUENCE: 245

| | | | | |
|---|---|---|---|---|
| agcctctagg | tcattgtggt | gccttgtagc | tgtcccggga | gccctcagca gcagttggag | 60 |
| ctggtgcaca | ggaaggatga | ggaagaccag | gctctggggg | ctgctgtgga tgctctttgt | 120 |
| ctcagaactc | cgagctgcaa | ctaaattaac | tgaggaaaag | tatgaactga agaggggca | 180 |
| gaccctggat | gtgaaatgtg | actacacgct | agagaagttt | gccagcagcc agaaagcttg | 240 |
| gcagataata | agggacggag | agatgcccaa | gaccctggca | tgcacagaga ggccttcaaa | 300 |
| gaattcccat | ccagtccaag | tggggaggat | catactagaa | gactaccatg atcatggttt | 360 |
| actgcgcgtc | cgaatggtca | accttcaagt | ggaagattct | ggactgtatc agtgtgtgat | 420 |
| ctaccagcct | cccaaggagc | ctcacatgct | gttcgatcgc | atccgcttgg tggtgaccaa | 480 |

```
gggtttttca gggacccctg gctccaatga gaattctacc cagaatgtgt ataagattcc    540
tcctaccacc actaaggcct tgtgcccact ctataccagc cccagaactg tgacccaagc    600
tccacccaag tcaactgccg atgtctccac tcctgactct gaaatcaacc ttacaaatgt    660
gacagatatc atcagggttc cggtgttcaa cattgtcatt ctcctggctg gtggattcct    720
gagtaagagc ctggtcttct ctgtcctgtt tgctgtcacg ctgaggtcat ttgtacccta    780
ggcccacgaa cccacgagaa tgtcctctga cttccagcca catccatctg gcagttgtgc    840
caagggagga gggaggaggt aaaaggcagg gagttaataa catgaattaa atctgtaatc    900
accagctaaa aaaaaaaa                                                  918

<210> SEQ ID NO 246
<211> LENGTH: 676
<212> TYPE: DNA
<213> ORGANISM: Homo sapiens
<220> FEATURE:
<221> NAME/KEY: misc_feature
<223> OTHER INFORMATION: Incyte Clone No: 4072159

<400> SEQUENCE: 246
gctcacacag ctcccggcca ggtcacccgc catggtcctc cctctgccct ggctctctcg     60
gtaccatttc cttcgcctcc ttctgccctc ctggtccttg caccccagg gctcccatgg    120 gtgctgctcc caaaacccca agcaagcat ggaagagcag accaactcca gaggaaatgg    180
gaagatgacg tcccctccca ggggccctgg gacccaccgc acagctgagc tggcccgagc    240
tgaagagttg ttggagcagc agctggagct gtaccaggcc ctccttgaag ggcaggaggg    300
agcctgggag gccaagccc tggtgctcaa gatccgaaag ctgaaggaac agatgaggag    360
gcaccaagag agccttggag gaggcgccta gtttccccc agtgcccaca gcaccctccg    420
gcactgaaaa tacacgcacc acccaccagg agccttggga tcataaacac cccagcgtct    480
tcccaggcca gagaaagtgg aagagaccac aaaccgcagg caattggcag gcagtggggg    540
agccagggct ctgcagtctt agtcccattc ccctttgatc tcacagcagg cagggcacca    600
caggccttac taggaattca ccctggacca tgccctaaaa taacctcacc ccaaatacaa    660
taaagggacg aggcaa                                                   676

<210> SEQ ID NO 247
<211> LENGTH: 2255
<212> TYPE: DNA
<213> ORGANISM: Homo sapiens
<220> FEATURE:
<221> NAME/KEY: misc_feature
<223> OTHER INFORMATION: Incyte Clone No: 1003916

<400> SEQUENCE: 247
ccggtgcgtc ctgggtctgt ctgcgcggag ttccccgggg cgcgaggaga ggggactgga     60
gaaagaggag ggccgggcag cggagggag gaggcggtgc gtgcctcgcc tgccaaaggg    120
agatccgctc ctctgcgtgc gatccccggc gcccgcccgc gcccacagcg ctccgccaga    180
gctgccgccg cggactcgcc gggagtgggg gtctccgctg gtgccagccc gcttctggag    240
accctccgcc tcctgccaac ccctgctctt ccaggtcggg cccgggggtt ctgcggctgt    300
tagggacaga ggcaaagaag ggcaggacgg tccggttttcc cgtggatgtt cccgcccgag    360
aaagacagca agttgtgtgt gcgcccggga cgcgggaggg aaggtagccg ccgcccgcca    420
gccatggacc atcatctta gtgcagagga tggaaagttg atgcccagta agactgaaga    480
tccattctgc attacggaac tgtggattat ctgtgggtcc ctggtgattt cacaccttca    540
```

```
ttcactcctg cagtccctga acacttactt ggggtcctca ttgccctatc tggtgaaaga      600
tggcatccag cctgacttgt actggagtaa tctgggcttt gctgtctttt ctttgtgctg      660
ccacctcctg cgtggggttc tttatgcctt actggctctg gggatcacag ctgggcaagc      720
ctgtgtcctt cggtaccttc cggaggtgct catatcctgt gcatgatgag agtcggcaga      780
tgatggtgat ggtggaggaa tgtgggcgct atgcctcctt ccagggcatc cccagcgcag      840
aatggaggat ctgcaccata gtgaccggcc tgggttgtgg cctcctcctc ctggtggcgc      900
tcactgccct catgggttgc tgtgtttccg acctcatctc caggacagtg gaagagtgg       960 ctggaggaat tcagtttctt gggggcttgt tgattggtgc tggctgtgcc ctctacccct     1020
tgggctggga cagtgaggaa gtccggcaga cttgtggcta cacttctggc cagtttgacc     1080
tggggaagtg tgaaatcggc tgggcctact actgcacggg agcaggtgcc actgccgcca     1140
tgctgctgtg cacgtggctg gcttgctttt cgggcaagaa acagaagcac tacccatact     1200
gagatggagc taccaagagc agacagagga gaagatgggc caaggggct tggagaggtc      1260 aaaacatcca cctaccttca aaggtgggaa tagtagttct aatccaatac aatgctaata     1320
aaatgaaacc cgataaaatc aggaacatga tataggaagg aaggattgta ggagatttgt     1380
gggggaaaaa aaaggagagt atagaatgat ggagaaaaat ggaccaaagg ctaaaaatat     1440
tgcagggcat cggtgtttc tattccacag agtattgtta atgtacaaca cacacacaca      1500
cacacacaca cacacacaca cacacacaca acaaatctac atatacaaac aagggtttgg     1560
gttttagttt ttttttttta aggtgaggac tcagaaaatc aaagggctag tagaaacagt     1620
gttatgttgg gaagcagggt accccaaag atgttccctg taggtcacgg cactcccaaa      1680
agcacacaag cacatacaga catatgcatc cccacacacg cctatgcaca aacgtggatt     1740
atcgcacaga ctgggaggtt tagtggtgca tttctcctct gttttctttt taatatacat     1800
ttaaaataca gtattatcac tttataaaac atacattaag cctaataaat ggaccaataa     1860
gccaaactat cagtatttg tatatcctgc ataaactcta atttagttcc tcaacatatt      1920
ttcagtgttt atgcagacct ttagagttaa gcctttgtat ttccatgtta ttccacaata     1980
tgcaatattt ctctgagtag cttctgctat gatattctta tgaagaaaag gggcaacttt     2040
ctgtccacta taggagagaa ttcagccgaa gatatgagag taatgagaga cattttccag     2100
tcattggatc gtgttttctt tgtccatta ttgtactgtg ctgtaccaca tttatttcta      2160
tattcatttt gtaaaaaatt taaaagtgct attttgtttg tatttgaaaa tctctgtgaa     2220
taaattctct ctttgatcaa tagcaaaaaa aaaaa                                2255

<210> SEQ ID NO 248
<211> LENGTH: 1223
<212> TYPE: DNA
<213> ORGANISM: Homo sapiens
<220> FEATURE:
<221> NAME/KEY: misc_feature
<223> OTHER INFORMATION: Incyte Clone No: 2093492

<400> SEQUENCE: 248
gacgcttcac cagcgtcctg gtggtgtcca gtctctcacc cctgtgcgtg ctgctctgga       60
gggaactcac aggcatccag ccaggcacat ccctgctcac cctgatgggc ttcaggctgg      120
agggcatttt cccagcggcg ctgctgcccc tgttgctgac catgattctt ttcctgggcc      180
cactgatgca gctctctatg gattgccctt gtgacctggc agatgggctg aaggttgtcc      240 tggcccccg ctcctgggcc cgctgcctca cagacatgcg ttggctgcgg aaccaagtga      300
```

-continued

| | |
|---|---|
| tcgccccgct gacagaggag ctggtgttcc gggcctgtat gctgcccatg ttagcaccgt | 360 |
| gcatgggcct gggccctgct gtgttcacct gcccgctctt ttttggagtt gcccattttc | 420 |
| accatattat tgagcagctg cgtttccgcc agagcagcgt ggggaacatc ttcttgtctg | 480 |
| ctgcgttcca gttctcctac acagctgtct tcggtgccta cactgctttc ctcttcatcc | 540 |
| gcacaggaca cctgattggg ccggttctct gccattcctt ctgcaattac atgggtttcc | 600 |
| cagctgtttg cgcggccttg gagcacccac agaggcggcc cctgctggca ggctatgccc | 660 |
| tgggtgtggg actcttcctg cttctgctcc agcccctcac ggaccccaag ctctacggca | 720 |
| gccttcccct ttgtgtgctt ttggagcggg caggggactc agaggctccc ctgtgctcct | 780 |
| gacctatgct cctggatacg ctatgaactc tcaccggctc cccagccctc cccaccaagg | 840 |
| ggtactgcag gggaagggct ggctggggtc cccgagatct caggaatttt tgtaggggat | 900 |
| tgaagccaga gctagttgcg tcccagggac caagagaaag aagcagatat ccaaagggtg | 960 |
| cagcccctt tgaaaggggt gtttacgagc agctgtgagt gaggggacaa ggggcaggtc | 1020 |
| ccaggagcca cacactccct tcctcacttt ggactgctgc ttctcttagc tcctctgcct | 1080 |
| ctgaaaagct gctcggggtt ttttatttat aaaacctctc cccaccccc accccccaac | 1140 |
| ttcctgggtt ttctcattgt cttttttgcat cagtactttg tattgggata ttaaagagat | 1200 |
| ttaacttggg taaaaaaaaa aaa | 1223 |

<210> SEQ ID NO 249
<211> LENGTH: 1188
<212> TYPE: DNA
<213> ORGANISM: Homo sapiens
<220> FEATURE:
<221> NAME/KEY: misc_feature
<223> OTHER INFORMATION: Incyte Clone No: 2108789

<400> SEQUENCE: 249

| | |
|---|---|
| gccctccca gcctgccaag aaaacggtag gggagcatga tggggccttt gaggcagggt | 60 |
| cgcagggaca agctcagctt taggcaccat ctgttcccat cgcgcctgct gctgtgaccc | 120 |
| gttttggaaa actggtgtgt accgaggcgc tgactgcacg gctgaccgcc tgctcgtgcc | 180 |
| ttcattctgc agcggcatgg tccctcccat tctggctcca cctgcagcct ccctgggtgg | 240 |
| cctaggctcc cccgaccaag agacctccct ctcatgatca ctggtacctg ggggcctgaa | 300 |
| ttctggcccc cggctcccca cacagctggg actggcctgg atggctgtcc tggtagcccc | 360 |
| tgcccaccct gacagaggga gctgggcctc ccctcatcct ctgtaactcc cgccttcacc | 420 |
| agactcgagg acaccctggc cctgctgagg catacagagc ttcagcccag cacagaagca | 480 |
| agacaaaatc agtggctctt agagtttaga aaacaagaca gactctcaga tgaaagatct | 540 |
| gacaagcacc gtggccagtc acagggagag acttgatgtc tggccttta attcctcctc | 600 |
| tgccagggtg gtcctggga cctctaatgt gggcatgtcg tccacccag dacgagccat | 660 |
| cagggacaga ccccccaccc ccaaggctgc agccacacca tgtttcaggc ttggggctgg | 720 |
| ggcaggcttg ggctcaatcc tgggcaccca ggggcagccc acccctaacc tggctcctac | 780 |
| ccaccttgcc cttgaaggat gggcctgctg cacgtctccc tcctccaccc cataccacac | 840 |
| tgggggtct gagccacccc cctcagcccc gttcggctca gaccgacccc cactccatcc | 900 |
| ccagacctgc agcacaagtg cgcgggcctg tcctcccagg ggcctgggcg actccatatg | 960 |
| caatcagtag cgagcagccc ggccccacag accctcatgc actctcttac gtgccattct | 1020 |
| ccccagactt ttttttgtact taatgtatga aagatccaaa ctaatattgc tgtaaaaagg | 1080 |
| agagacaaat taatatagct tattctataa atatatctgt atataaaggt ttctgtatat | 1140 |

```
tgtatagagc tgtgtataaa ctggatgtag aagcacaaaa aaaaaaaa            1188

<210> SEQ ID NO 250
<211> LENGTH: 1792
<212> TYPE: DNA
<213> ORGANISM: Homo sapiens
<220> FEATURE:
<221> NAME/KEY: misc_feature
<223> OTHER INFORMATION: Incyte Clone No: 2171401

<400> SEQUENCE: 250
cgccgctggg gccggcccgc acggcttcat ctgagggcgc acggcccgcg accgagcgtg     60
cggactggcc tcccaagcgt ggggcgacaa gctgccggag ctgcaatggg ccgcggctgg    120
ggattcttgt ttggcctcct gggcgccgtg tggctgctca gctcgggcca cggagaggag    180
cagcccccgg agacagcggc acagaggtgc ttctgccagg ttagtggtta cttggatgat    240
tgtacctgtg atgttgaaac cattgataga tttaataact acaggctttt cccaagacta    300
caaaaacttc ttgaaagtga ctactttagg tattacaagg taaacctgaa gaggccgtgt    360
cctttctgga atgacatcag ccagtgtgga agaagggact gtgctgtcaa accatgtcaa    420
tctgatgaag ttcctgatgg aattaaatct gcgagctaca agtattctga agaagccaat    480
aatctcattg aagaatgtga acaagctgaa cgacttggag cagtggatga atctctgagt    540
gaggaaacac agaaggctgt tcttcagtgg accaagcatg atgattcttc agataacttc    600
tgtgaagctg atgacattca gtcccctgaa gctgaatatg tagatttgct tcttaatcct    660
gagcgctaca ctggttacaa gggaccagat gcttggaaaa tatggaatgt catctacgaa    720
gaaaactgtt ttaagccaca gacaattaaa agaccttaa atcctttggc ttctggtcaa    780
gggacaagtg aagagaacac ttttacagt tggctagaag gtctctgtgt agaaaaaaga    840
gcattctaca gacttatatc tggcctacat gcaagcatta atgtgcattt gagtgcaaga    900
tatcttttac aagagacctg gttagaaaag aaatggggac acaacattac agaatttcaa    960
cagcgatttg atggaatttt gactgaagga gaaggtccaa gaaggcttaa gaacttgtat   1020
tttctctact aatagaact aagggctttta tccaaagtgt taccattctt cgagcgccca   1080
gattttcaac tcttactgg aaataaaatt caggatgagg aaaacaaaat gttacttctg   1140
gaaatacttc atgaaatcaa gtcatttcct ttgcattttg atgagaattc attttttgct   1200
ggggataaaa aagaagcaca caaactaaag gaggactttc gactgcattt tagaaatatt   1260
tcaagaatta tggattgtgt tggttgtttt aaatgtcgtc tgtggggaaa gcttcagact   1320 cagggttttgg gcactgctct gaagatctta ttttctgaga aattgatagc aaatatgcca   1380
gaaagtggac ctagttatga attccatcta accagacaag aaatagtatc attattcaac   1440
gcatttggaa gaattctac aagtgtgaaa gaattagaaa acttcaggaa cttgttacag   1500
aatattcatt aaagaaaaca agctgatatg tgcctgtttc tggacaatgg aggcgaaaga   1560
gtggaatttc attcaaaggc ataatagcaa tgacagtctt aagccaaaca ttttatataa   1620
agttgctttt gtaaaggaga attatattgt tttaagtaaa cacattttta aaaattgtgt   1680
taagtctatg tataatacta ctgtgagtaa aagtaatact ttaataatgt ggtacaaatt   1740
ttaaagttta atattgaata aaaggaggat tatcaaattc aaaaaaaaaa aa            1792

<210> SEQ ID NO 251
<211> LENGTH: 2005
<212> TYPE: DNA
<213> ORGANISM: Homo sapiens
<220> FEATURE:
```

<221> NAME/KEY: misc_feature
<223> OTHER INFORMATION: Incyte Clone No: 2212530

<400> SEQUENCE: 251

```
gcgaggcggg aggaggtgag gctccggcgc acacccaaac cgcgctgcgc ccgctccttc      60
cgggccccgg agatggcgcc tccaccggga tgagctagcc agcctgggca ataccagagg     120
cggccctcgg cgcgcgcagg ggaccgagct ggtcgcccca accgggtttg atttctgatg     180
actctggcct gagttccagg atggttttt cttgggacca gacatgaaca aaagttgacc     240
tcatgagcac ttcaacctct ccagctgcca tgctcctccg gaggctgcgg cgactctcct     300
ggggcagcac tgctgtccag ctcttcatcc taacagtggt gacgtttggc ctgctggccc     360
ccctggcctg tcaccgactt ctacactctt acttctatct gcgccattgg catctgaacc     420
aaatgagcca agagttcctg cagcaaagct tgaaagaggg tgaggctgcc ctccactatt     480
ttgaggagct tccctctgcc aatggctcag tgcccattgt ctggcaggcc acccccggc     540
cctggctggt gatcaccatc atcactgtgg acaggcagcc tggcttccac tacgtcctgc     600
aggttgtgtc ccagttccac cggcttcttc agcaatgtgg cccccagtgc gagggggcacc    660
aactcttcct gtgcaacgtg gagcgtagtg tgagccattt tgatgccaag ttgctctcca     720
agtatgtccc tgtggccaat cgctatgagg gcactgagga tgattatggt gatgacccct     780
cgaccaactc gtttgagaaa gagaagcagg actatgtcta ttgcctggag tcatccctgc     840
agacctacaa cccagactac gtcctgatgg tagaagacga tgctgtacca aagagcaga     900
tcttcccagt cttggagcac cttctgcggg ctcgcttctc tgagccacat ctcagagatg     960
cccttttatct caagctgtat caccccgaga ggctccagca ctacatcaat ccagagccca    1020
tgcggatcct ggaatgggtt ggtgtaggca tgttgctggg gcccttacta acctggatat    1080
acatgaggtt tgccagccgc ccagggttta gctggcctgt aatgctcttc ttctccctgt    1140
atagcatggg tctggtggag ctggtgggtc ggcactattt cctggaactg cggcggctga    1200
gtccttccct gtacagtgtg gttcctgcct ctcagtgttg caccccagcc atgctcttcc    1260
cggcacctgc ggcccgccgg accctcacct acctgtccca agtgtactgc acaagggct    1320
ttggcaagga catggcactg tactcgctgt tgagggccaa gggagagagg gcctatgtag    1380
tggagccgaa cctcgtgaaa cacatcgggc tcttctccag tctccggtac aactttcatc    1440
ccagtctcct ctagggtgcc aagagatgcc tttcggaagt tggccacttc ttgaagattc    1500
aaatatttat ctctttattt agacatggtt gcctgcaggt atttcactgt ttactgttgt    1560
tagagatata ggcactgggg cagctgagga acctcaatat gttaagagcc ttggctttgg    1620
tagcctcctg gcaggagcag cagtttgcca caggtccgga cctctcccct cacacagcca    1680
cactgcctca tgcagtctga cccacccagt gagggtgcat ttgaacactg attatattct    1740
ccatttgttt ttaagctctg cttttgtgtta gagcttgtga ctgccaaaaa ttttgtgcac    1800
agtgatatga ctgttttagg atcttaaggg tagaattttg tgaaaggtga gatcctttgg    1860
aattgagttc tttctcattg ggtatgaaaa tggatgtatg tttagaatat atgcccaacg    1920
aggcaggacc atgtggatag attccattg tttccttgac ctgatgtaat aaaaactgat    1980
aaaagccgtg cagtgcccgg catct                                           2005
```

<210> SEQ ID NO 252
<211> LENGTH: 471
<212> TYPE: DNA
<213> ORGANISM: Homo sapiens
<220> FEATURE:
<221> NAME/KEY: misc_feature
<223> OTHER INFORMATION: Incyte Clone No: 2253036

<400> SEQUENCE: 252

```
tgggtatgtc tcatggagag gtgctttcac tgcttccctg ttcacctagt cttcaatctg    60
gtccagagtt tcagccccat ctctggagtt gagtcctgcc ttctccctca atgtgacaaa   120
tgttggccaa tggtatatcg cagttgtgat gcaagcagag gcttggtaaa tgcctgcata   180
ctggggtttg tcctcttgga atgctcattt gtgggagccc tgaacaacta tgtaagaagt   240
ctggctaccc tgctggagag aacacatggt gggaagagac taaaattatg tgaagagagt   300
caggccagcc atcccagctt ctctgctgag ccccgccatc agccaacctg ccagctgaat   360
gcaaccgtaa gagtgatcac cagcaagatc actagaaaaa ccacctaact gagcccaccc   420
tggattgaac aatcataaac aaataaaatg gttattgttt taaaaaaaaa a            471
```

<210> SEQ ID NO 253
<211> LENGTH: 3775
<212> TYPE: DNA
<213> ORGANISM: Homo sapiens
<220> FEATURE:
<221> NAME/KEY: misc_feature
<223> OTHER INFORMATION: Incyte Clone No: 2280161

<400> SEQUENCE: 253

```
tccctgagag gtgtccactg atgtctcctc ctcatttcat ttagcagctc ttagtttgtg    60
aagaatctgt agatgctcaa agtataattg ccccagggaa tttatgctaa tcacaacctc   120
ttcttcagac accaagtcta ccttgaatgg gtttgctgtg atatggcact tcaggtctcc   180
tttccatct gccaatatca gactgcctgt gtccccagag catgaaatca gccttacagt   240
gcttggcttg cttgtgagga catccggaac ttcaaatctg gttttagag gagtctcttc   300
gttaatttta agcctgaaaa tgtttccttc tataccataa atttcagcca ggagaggaac   360
cttacttgct tcattgatga tttggaacct ggtgctgtct tcatctgttg tgactgaatc   420
caataatgcc cgataggtgg acttcttgga aagccactgt ttctgacgcc tgtaaaatgc   480
gatcttgtta cagtctctga aaatgttttt atctacagct tcatcttcaa cacttatttc   540
ctctttcact gctgcttcca tggcttctct gtcactccga ccagctccca gctctcagga   600
caagggccct gggcgatctt ttaaaaaagc cgattgggtg tctttctaaa attacaacca   660
gtacttcatc gtcaagtttc tgggaaggga gtcccctcca gattctcatg gagtgacaaa   720
tcttgactct tgctcctgga attttttcagg cccaaactag cgtttctaca atgatttatt   780
tggcaaattt gtcttgatta tgggtggctg atgaggaacg tgcttttgtt aggaaccgaa   840
actgggcggc ggtgagggcg tgtacgcaat gagtccggaa gagggtgaaa tgctttcggt   900
aggcactcca cggctgtgaa gatggcggcg gctgcgtggc ttcaggtgtt gcctgtcatt   960
cttctgcttc tgggagctca cccgtcacca ctgtcgtttt tcagtgcggg accggcaacc  1020
gtagctgctg ccgaccggtc caaatggcac attccgatac cgtcgggaaa aaattatttt  1080
agttttggaa agatcctctt cagaaatacc actatcttcc tgaagtttga tggagaacct  1140
tgtgacctgt ctttgaatat aacctggtat ctgaaaagcg ctgattgtta caatgaaatc  1200
tataacttca aggcagaaga agtagagttg tatttggaaa aacttaagga aaaagaggc   1260
ttgtctggga aatatcaaac atcatcaaaa ttgttccaga actgcagtga actctttaaa  1320
acacagacct tttctggaga ttttatgcat cgactgcctc ttttaggaga aaaacaggag  1380
gctaaggaga atggaacaaa ccttaccttt attggagaca aaaccgcaat gcatgaacca  1440
ttgcaaactt ggcaagatgc accatacatt tttattgtac atattggcat ttcatcctca  1500
```

```
aaggaatcat caaaagaaaa ttcactgagt aatcttttta ccatgactgt tgaagtgaag    1560
ggtccctatg aatacctcac acttgaagac tatcccttga tgattttttt catggtgatg    1620
tgtattgtat atgtcctgtt tggtgttctg tggctggcat ggtctgcctg ctactggaga    1680
gatctcctga gaattcagtt ttggattggt gctgtcatct tcctgggaat gcttgagaaa    1740
gctgtcttct atgcggaatt tcagaatatc cgatacaaag gagaatctgt ccagggtgct    1800
ttgatccttg cagagctgct ttcagcagtg aaacgctcac tggctcgaac cctggtcatc    1860
atagtcagtc tgggatatgg catcgtcaag ccacgccttg gagtcactct tcataaggtt    1920
gtagtagcag gagccctcta tcttttgttc tctggcatgg aaggggtcct cagagttact    1980
gggtattttt cttatccctt gactctgata gtaaacctgg ccctctcagc agttgacgcc    2040
tgtgttattt tatggatatt tattagcctg actcaaacaa tgaagctatt aaaacttcgg    2100
aggaacattg taaaactctc tttgtatcgg catttcacca acacgcttat tttggcagtg    2160
gcagcatcca ttgtgtttat catctggaca accatgaagt tcagaatagt gacatgtcag    2220
tcggactggc gggagctgtg ggtagacgat gccatctggc gcttgctgtt ctccatgatc    2280
ctctttgtca tcatggttct ctggcgacca tctgcaaaca accagaggtt tgccttttca    2340
ccattgtctg aggaagagga ggaggatgaa caaaaggagc ctatgctgaa agaaagcttt    2400
gaaggaatga aaatgagaag taccaaacaa gaacccaatg gaaatagtaa agttaacaaa    2460
gcacaggaag atgatttgaa gtgggtagaa gagaatgttc cttcttctgt gacagatgta    2520
gcacttccag cccttctgga ttcagatgag gaacgaatga tcacacactt tgaaaggtcc    2580
aaaatggagt aaggaatggg aagatttgca gttaaagatg gctaccatca gggaagagat    2640
cagcatctgt gtcagtcttc tgtacggctc catgggatta aaggaagcaa tgacatcctg    2700
atctgttcct tgatctttgg gcattggagt tggcgagagg tgtcagaaca agagaacat    2760 cttactgaaa acaagttcat aagatgagaa aaatctacga gcttcttatt tacaacactg    2820
ctgccccctt tcctcccaga ctctgacatg gatgttcatg caacttaagt gtgttgttcc    2880
tgaactttct gtaatgtttc atttttttaaa tctgacaaac taaaaagttt aacgtcttct    2940
aaaagattgt catcaacacc ataatatgta atctccagga gcaactgcct gtaattttta    3000
tttatttagg gagttacata ggtgatgggg gaaattgtta actacctttc attttcctgg    3060
gaagtcaagg ttacatcttg cagaggttgt tttgagaaaa aagggcccctt ctgagttaag    3120 gagccatagt tctatcaatg atcaaaagaa aaaaaaaaaa aagagaaact gttacagtat    3180
gattcagatc atttaaaaaa gcaaaatcaa gtgcaatttt gtttacaaat ggtgtatatt    3240
aaagattttt ctatttcaga tgtactttaa agagaaatat tagcttaact cttttgacat    3300
ctgctattgt gacacatccc attgctggca atgtggtgca cactccgaaa cttttaacta    3360
ctgttttgta agcctccaag ggtggcattg cagggtcctt aggcaatgtt ttgtttgcct    3420
ttatgcagag aggtgctcca agtgctgtga ttgagcaccg tgctagagga actgtaatgc    3480
ttcagaagtt gtagcttata caaaggaaac aggtcctgct ggcttaattt aaacagttat    3540
tgcatgaagt agcgtggagg ccctggactg ctgctcgttc tttaggatgg actgttctgg    3600
tatctggtat tggtttagag actgttaata agggacatca caaggtgatg ggattcattt    3660
gaagcactct atttctgttt taatggtttt atccaatttt gccttcccaa gattttgtt     3720 ctacataaaa agttcatgcc actttttaat ataaaaaaat ttaacaaaaa aaaaa          3775
```

<210> SEQ ID NO 254
<211> LENGTH: 1856

```
<212> TYPE: DNA
<213> ORGANISM: Homo sapiens
<220> FEATURE:
<221> NAME/KEY: misc_feature
<223> OTHER INFORMATION: Incyte Clone No: 2287485

<400> SEQUENCE: 254
cggccgcacc cggccggagc ggagggcaga gcgcgcgccc agttgcccgg gcaccaaatc      60
ggagcgcggc gtgcgggagg gcccagagca ggactggaaa tgtcctggcc gcgccgcctc     120
ctgctcagat acctgttccc ggccctcctg cttcacgggc tgggagaggg ttctgccctc     180
cttcatccag acagcaggtc tcatcctagg tccttagaga aaagtgcctg gagggctttt     240
aaggagtcac agtgccatca catgctcaaa catctccaca atggtgcaag gatcacagtg     300
cagatgccac ctacaatcga gggccactgg gtctccacag gctgtgaagt aaggtcaggc     360
ccagagttca tcacaaggtc ctacagattc taccacaata caccttcaa ggcctaccaa     420
ttttattatg gcagcaaccg gtgcacaaat cccactttata ctctcatcat ccggggcaag     480
atccgcctcc gccaggcctc ctggatcatc cgaggggca cggaagccga ctaccagctg     540
cacaacgtcc aggtgatctg ccacacagag gcggtggccg agaagctggg ccagcaggtg     600
aaccgcacat gcccgggctt cctcgcagac gggggtccct gggtgcagga cgtggcctat     660
gacctctggc gagaggagaa cggctgtgag tgcaccaagg ccgtgaactt tgccatgcat     720
gaacttcagc tcatccgggt ggagaagcag taccttcacc acaacctcga ccacctggtc     780
gaggagctct tccttggtga cattcacact gatgccaccc agaggatgtt ctaccggccc     840
tccagttacc agcccctct gcagaatgcc aagaaccacg accatgcctg catcgcctgt     900
cggatcatct atcggtcaga cgagcaccac cctcccatcc tgcccccaaa ggcagacctg     960
accatcggcc tgcacgggga gtgggtgagc cagcgctgtg aggtgcgccc cgaagtcctc    1020
ttcctcaccc gccacttcat cttccatgac aacaacaaca cctgggaggg ccactactac    1080
cactactcag acccggtgtg caagcacccc accttctcca tctacgcccg ggccgctac     1140
agccgcggcg tcctctcgtc cagggtcatg ggaggcaccg agttcgtgtt caaagtgaat    1200
cacatgaagg tcaccccat ggatgcggcc acagcctcac tgctcaacgt cttcaacggg    1260
aatgagtgcg gggccgaggg ctcctggcag gtgggcatcc agcaggatgt gacccacacc    1320
aatggctgcg tggccctggg catcaaacta cctcacacgg agtacgagat cttcaaaatg    1380
gaacaggatg cccgggggcg ctatctgctg ttcaacggtc agaggcccag cgacgggtcc    1440
agcccagaca ggccagagaa gagagccacg tcctaccaga tgcccttggt ccagtgtgcc    1500
tcctcttcgc cgagggcaga ggacctcgca gaagacagtg gaagcagcct gtatggccgg    1560
gccctggga ggcacacctg gtccctgctg ctggctgcac ttgcctgcct tgtccctctg    1620
ctgcattgga acatccgcag atagaagttt tagaaagttc tatttttcca aaccaggatt    1680
ccttactatt gacagatttt ctttaccaaa agaaaagaca tttattcttt tgatgcactt    1740
gaatgccaga gaactgtcct tcttttttctc ctctccctcc ctcccagccc ctgagtcatg    1800
aacagcaagg agtgtttgaa gtttctgctt tgaactccgt ccagcctgat ccctgg         1856

<210> SEQ ID NO 255
<211> LENGTH: 1545
<212> TYPE: DNA
<213> ORGANISM: Homo sapiens
<220> FEATURE:
<221> NAME/KEY: misc_feature
<223> OTHER INFORMATION: Incyte Clone No: 2380344

<400> SEQUENCE: 255
```

-continued

```
ggctggactg gaactcctgg tcccaagtga tccacccgcc tcagcctccc aaggtgctgt    60
gattataggt gtaagccacc gtgtctggcc tctgaacaac tttttcagca actaaaaaag   120
ccacaggagt tgaactgcta ggattctgac tatgctgtgg tggctagtgc tcctactcct   180
acctacatta aaatctgttt tttgttctct tgtaactagc ctttaccttc ctaacacaga   240
ggatctgtca ctgtggctct ggcccaaacc tgaccttcac tctggaacga aacagaggt    300 ttctacccac accgtcccct cgaagccggg acagcctca ccttgctggc ctctcgctgg    360
agcagtgccc tcaccaactg tctcacgtct ggaggcactg actcgggcag tgcaggtagc   420
tgagcctctt ggtagctgcg gctttcaagg tgggccttgc cctggccgta aagggattg    480 acaagcccga agatttcata ggcgatggct cccactgccc aggcatcagc cttgctgtag   540
tcaatcactg ccctggggcc aggacgggcc gtggacacct gctcagaagc agtgggtgag   600
acatcacgct gcccgcccat ctaacctttt catgtcctgc acatcacctg atccatgggc   660
taatctgaac tctgtcccaa ggaacccaga gcttgagtga gctgtggctc agacccagaa   720
ggggtctgct tagaccacct ggtttatgtg acaggacttg cattctcctg aacatgagg    780 gaacgccgga ggaaagcaaa gtggccaggg aaggaacttg tgccaaatta tgggtcagaa   840
aagatggagg tgttgggtta tcacaaggca tcgagtctcc tgcattcagt ggacatgtgg   900
gggaagggct gccgatggcg catgacacac tcgggactca cctctggggc catcagacag   960
ccgtttccgc cccgatccac gtaccagctg ctgaagggca actgcaggcc gatgctctca  1020 tcagccagge agcagccaaa atctgcgatc accagccagg gcagccgtc tgggaaggag   1080 caagcaaagt gaccatttct cctcccctcc ttccctctga gaggccctcc tatgtcccta  1140
ctaaagccac cagcaagaca tagctgacag gggctaatgg ctcagtgttg cccaggagg   1200 tcagcaaggc ctgagagctg atcagaaggg cctgctgtgc gaacacggaa atgcctccag  1260
tctctgtgcg cgatgccctg ttgaaccaga tggtccacgc cttccagcag ctgcagcagc  1320
atcatggcgg cgaggcgggg gctgggtgtg ttcacacaaa ggaagaagag tgacctccct  1380
ggaagaagat ggaattctgc cagcggccag gcttcaaacc tgaactgcac cgctggctcc  1440
tccctggctc tccagcctgc ccgcctactc tgcggctttt aagactttgc caatccccat  1500
agggagccag gtcctcaaaa taaacctgcc tctatataga cacat                  1545
```

<210> SEQ ID NO 256
<211> LENGTH: 1671
<212> TYPE: DNA
<213> ORGANISM: Homo sapiens
<220> FEATURE:
<221> NAME/KEY: misc_feature
<223> OTHER INFORMATION: Incyte Clone No: 2383171

<400> SEQUENCE: 256

```
gaattcggac gctctctggg ccaatatggc agcgcccagc aacaagacag agctggcctg    60
gagtccgcgg ctggccgcgt gagtaggtga ttgtctgaca agcagaggca tgagctgggt   120
ccaggccacc ctactggccc gaggcctctg tagggcctgg ggaggcacct gcggggccgc   180
cctcacagga acctccatct ctcaggtccc tcgccggctc cctcggggcc tccactgcag   240
cgcagctgcc catagctctg aacagtccct ggttcccagc ccaccggaac ccggcagag    300 gcccaccaag gctctggtgc cctttgagga cctgtttggg caggcgcctg gtggggaacg   360
ggacaaggcg agcttcctgc agacggtgca gaaatttgcg gagcacagcg tgcgtaagcg   420
gggccacatt gacttcatct acctggccct gcgcaagatg cgggagtatg gtgtcgagcg   480
```

```
ggacctggct gtgtacaacc agctgctcaa catcttcccc aaggaggtct tccggcctcg      540
caacatcatc cagcgcatct tcgtccacta ccctcggcag caggagtgtg ggattgctgt      600
cctggagcag atggagaacc acggtgtgat gcccaacaag gagacggagt tcctgctgat      660
tcagatcttt ggacgcaaaa gctaccccat gctcaagttg gtgcgcctga agctgtggtt      720
ccctcgattc atgaacgtca accccttccc agtgccccgg gacctgcccc aggaccctgt      780
ggagctggcc atgtttggcc tgcggcacat ggagcctgac cttagtgcca gggtcaccat      840
ctaccaggtt cctttgccca aagactcaac aggtgcagca gatccccccc agccccacat      900
cgtaggaatc cagagtcccg atcagcaggc cgccctggcc cgccacaatc cagcccggcc      960
tgtctttgtt gagggcccct tctccctgtg gctccgcaac aagtgtgtgt attaccacat     1020
cctcagagct gacttgctgc ccccggagga gagggaagtg aaagagacgc cggaggagtg     1080
gaacctctac tacccgatgc agctggacct ggagtatgtg aggagtggct gggacaacta     1140
cgagtttgac atcaatgaag tggaggaagg ccctgtcttc gccatgtgca tggcgggtgc     1200
tcatgaccag gcgacgatgg ctaagtggat ccagggcctg caggagacca acccaaccct     1260
ggcccagatc cccgtggtct tccgcctcgc cgggtccacc cgggagctcc agacatcctc     1320
tgcagggctg gaggagccgc ccctgcccga ggaccaccag gaagaagacg acaacctgca     1380
gcgacagcag cagggccaga gctagtctga gccggcgcga gggcacgggc tgtgccccga     1440
ggaggcggtg gactgaaggc atgagatgcc ctttgagtgt acagcaaatc aatgttttcc     1500
tgcttgggc tctcttccct catctctagc agtatggcat cccctcccca ggatctcggg     1560
ctgccagcga tgggcaggcg agacccctcc agaatctgca ggcgcctctg gttctccgaa     1620
ttcaaataaa aagggggcggg agcgctgttg gttgtgcgca aaaaaaaaa a              1671
```

<210> SEQ ID NO 257
<211> LENGTH: 792
<212> TYPE: DNA
<213> ORGANISM: Homo sapiens
<220> FEATURE:
<221> NAME/KEY: misc_feature
<223> OTHER INFORMATION: Incyte Clone No: 2396046

<400> SEQUENCE: 257

```
aattttaggg agaatgtggg ggggtggggt gttactttcc attttacaca tatttgtatt       60
ttcagatttt caacaataac agtattcaat acataatcag aaaaaagaga tgtggaggag      120
gaggagagaa acttcccaag gagctccctt gggtgctgct ggctcctaat tagtgtaacc      180
tgttaatcac atgttgctcg tgttagagc ggtccctctg tgctctgcct ggcagggcgc      240
tgttggcctg gtctccctcg ctatttctat ttgcaagcat gggctttctt cccagcagaa      300
tctggttcct gggaagagta atgttccaaa ggcctctgat atgcctcgat gccctcctgt      360
cttccagagc cccaacctca ctcccttttcc ccaccataca aaacacacct cccaggggtc      420
acatttgggg gtcccgccc ctgctccaat gccatggtgt cccaagcac agggctttgg      480
cctgagttgt cagtctctgg atgcatttga ggggcagcta gggtgtggct ggggggtcca      540
agcagctggg gagccgagac tcagaatcat tcacacactt ctatttggag cttttgtgga      600
agtttccaga attccataat attcacctcc tgaatggtgg ctgcccctta tcagccaggg      660
ctggggtttc cagtgccctc ggagagcttg ctttagagtc ttggagagac ggccatggtc      720
tgcgttttgta tgtctgtcac atcttaccat catcacaaat tgaatataca acattaccta     780
attgtgtgat ca                                                          792
```

```
<210> SEQ ID NO 258
<211> LENGTH: 3045
<212> TYPE: DNA
<213> ORGANISM: Homo sapiens
<220> FEATURE:
<221> NAME/KEY: misc_feature
<223> OTHER INFORMATION: Incyte Clone No: 2456587

<400> SEQUENCE: 258
```

| | | | | | |
|---|---|---|---|---|---|
| gtgagagggg | ctgatggaag | ctgataggca | ggactggagt | gttagcacca | gtactggatg | 60
| tgacagcagg | cagaggagca | cttagcagct | tattcagtgt | ccgattctga | ttccggcaag | 120
| gatccaagca | tggaatgctg | ccgtcgggca | actcctggca | cactgctcct | ctttctggct | 180
| ttcctgctcc | tgagttccag | gaccgcacgc | tccgaggagg | accgggacgg | cctatgggat | 240
| gcctggggcc | catggagtga | atgctcacgc | acctgcgggg | gaggggcctc | ctactctctg | 300
| aggcgctgcc | tgagcagcaa | gagctgtgaa | ggaagaaata | tccgatacag | aacatgcagt | 360
| aatgtggact | gcccaccaga | agcaggtgat | ttccgagctc | agcaatgctc | agctcataat | 420
| gatgtcaagc | accatggcca | gttttatgaa | tggcttcctg | tgtctaatga | ccctgacaac | 480
| ccatgttcac | tcaagtgcca | agccaaagga | acaaccctgg | ttgttgaact | agcacctaag | 540
| gtcttagatg | gtacgcgttg | ctatacagaa | tctttggata | tgtgcatcag | tggtttatgc | 600
| caaattgttg | gctgcgatca | ccagctggga | agcaccgtca | aggaagataa | ctgtggggtc | 660
| tgcaacggag | atgggtccac | ctgccggctg | gtccgagggc | agtataaatc | ccagctctcc | 720
| gcaaccaaat | cggatgatac | tgtggttgca | attccctatg | gaagtagaca | tattcgcctt | 780
| gtcttaaaag | gtcctgatca | cttatatctg | gaaaccaaaa | ccctccaggg | gactaaaggt | 840
| gaaaacagtc | tcagctccac | aggaactttc | cttgtggaca | attctagtgt | ggacttccag | 900
| aaatttccag | acaaagagat | actgagaatg | gctggaccac | tcacagcaga | tttcattgtc | 960
| aagattcgta | actcgggctc | cgctgacagt | acagtccagt | tcatcttcta | tcaacccatc | 1020
| atccaccgat | ggagggagac | ggatttcttt | ccttgctcag | caacctgtgg | aggaggttat | 1080
| cagctgacat | cggctgagtg | ctacgatctg | aggagcaacc | gtgtggttgc | tgaccaatac | 1140
| tgtcactatt | acccagagaa | catcaaaccc | aaacccaagc | ttcaggagtg | caacttggat | 1200
| ccttgtccag | ccagtgacgg | atacaagcag | atcatgcctt | atgacctcta | ccatccccctt | 1260
| cctcggtggg | aggccacccc | atggaccgcg | tgctcctcct | cgtgtggggg | gggcatccag | 1320
| agccgggcag | tttcctgtgt | ggaggaggac | atccagggc | atgtcacttc | agtggaagag | 1380
| tggaaatgca | tgtacacccc | taagatgccc | atcgcgcagc | cctgcaacat | ttttgactgc | 1440
| cctaaatggc | tggcacagga | gtggtctccg | tgcacagtga | cgtgtggcca | gggcctcaga | 1500
| taccgtgtgg | tcctctgcat | cgaccatcga | ggaatgcaca | caggaggctg | tagcccaaaa | 1560
| acaaagcccc | acataaaaga | ggaatgcatc | gtacccactc | cctgctataa | acccaaagag | 1620
| aaacttccag | tcgaggccaa | gttgccatgg | ttcaaacaag | ctcaagagct | agaagaagga | 1680
| gctgctgtgt | cagaggagcc | ctcgttcatc | ccagaggcct | ggtcggcctg | cacagtcacc | 1740
| tgtggtgtgg | ggaccccaggt | gcgaatagtc | aggtgccagg | tgctcctgtc | tttctctcag | 1800
| tccgtggctg | acctgcctat | tgacgagtgt | gaagggccca | agccagcatc | ccagcgtgcc | 1860
| tgttatgcag | gccatgcag | cggggaaatt | cctgagttca | acccagacga | gacagatggg | 1920
| ctctttggtg | gcctgcagga | tttcgacgag | ctgtatgact | gggagtatga | ggggttcacc | 1980
| aagtgctccg | agtcctgtgg | aggaggtgtc | caggaggctg | tggtgagctg | cttgaacaaa | 2040
| cagactcggg | agccttgctg | aggagaacct | gtgcgtgacc | accgccggcc | cccacagctc | 2100

```
ctgaagtcct gcaatttgga tccctgccca gcaagtcctg tcatctagga agaagcagta    2160
tcgactcagc atggaacgcc tgcaacgttc tttgttaggc aaccaagagg cctggcttct    2220
catcctgctg tcaccaacta gctctgtggc ctagggcgag gtgtctgccc tttatgtttc    2280
cacatctgca aagtgaactg gttgtacctg atgatctgag atcccatgac ttgctcacat    2340
gtcccatgat tctttatttt gtaggcagaa gcattaaaca gctactcctg ctgctgtgtg    2400
ctaatcattc ctgtaatttc tgttctgctt atttgccatt atttgaaaaa catgcaaaag    2460
ggtctttcta accacattcc tgtgttgtaa caacacccaa atgctgaggc agtgccgagg    2520
agtcagtgcc tgggacttgc ttaaaactgc tgggactcgt ggtccctaaa cccttctttg    2580
agcaccaaaa cgaataggac atgagatgtt acttctcatt ctcaaagtac taactatgtt    2640
taagttacaa aaggttaggt tatcctgtga ccctttgtt gactcacaga caagaacagt    2700
tgttgagctt aatgttgtcg catttgctcc agataaactc aattctctga tttcccacca    2760
gccaactgtc aagccaacag gcaagacctc tcactgggca cagccaggag tttcttgggt    2820
cgaccataca cattgaaaca tttgtagaag gttgctaatt gcaacaataa aggggaccaa    2880
agtataatgg cctaatctca tccaagagtc aaaacagatt ttccccctaa aaatgataat    2940
tgtatagagg tgcctttcct gtggaatatc tcactctgat gtcagagaaa aatctctcct    3000
tcccttctcc tggtgttcaa tgtgagacag aaaataaaat gtgtg              3045
```

```
<210> SEQ ID NO 259
<211> LENGTH: 2445
<212> TYPE: DNA
<213> ORGANISM: Homo sapiens
<220> FEATURE:
<221> NAME/KEY: misc_feature
<223> OTHER INFORMATION: Incyte Clone No: 2484813

<400> SEQUENCE: 259
```

```
gcatcttggc agggtccggg gacgtggact atttcgcaca ccacaccacg gggagggatt      60 ttttctatt tccctacga aaaacagatc ttttttaagga tggtgctgct ccactggtgc     120
ctgctgtggc tcctgttttcc actcagctca aggacccaga agttaccac ccggatgag      180 gaactttttc agatgcagat ccgggacaag gcatttttc atgattcgtc agtaattcca     240
gatggagctg aaattagcag ttatctcttt agagatacac ctaaaaggta tttcttgtg      300 gttgaagaag acaatactcc attatcagtc acagtgacgc cctgtgatgc gccttggag      360 tggaagctga gcctccagga gctgccagag gacaggagcg gggaaggctc aggtgatctg     420
gaacctcttg agcagcagaa gcagcagatc attaatgagg aaggcactga gttattctcc     480
tacaaaggca atgatgttga gtattttata tcgtctagtt ccccatccgg tttatatcag     540
ttggatcttc ttcaacaga gaaagacaca catttcaaag tatatgccac cacaactcca      600
gaatctgatc agccatacccc tgagttaccc tatgacccaa gagtagatgt gacctcactg    660
gggcgcacca cggtcacttt ggcctggaaa ccaagcccca ctgcctcttt gctgaaacaa    720
cccattcagt actgtgtggt catcaacaaa gagcacaatt tcaaagtct ctgtgcagtg      780 gaagcaaaac tgagtgcaga tgatgctttt atgatggcac cgaaacctgg tctgactttc   840 agccccttg acttttgccca ctttggattt ccttctgata attcaggtaa agaacgcagt     900
ttccaggcaa agccttctcc aaaactgggg cgtcatgtct actccaggcc caaggttgat    960
attcagaaaa tctgcatagg aaacaagaac atcttcaccg tctctgatct gaaaccccgac  1020 acgcagtact actttgacgt atttgtggtc aacatcaaca gcaacatgag caccgcttat    1080
gtaggtacct tgccaggac caaggaagaa gccaaacaga agacagtcga gctaaaagat    1140
```

```
gggaagataa cagatgtatt tgttaaaagg aagggagcaa agtttctacg gtttgctcca    1200
gtctcttctc accaaaaagt caccttcttt attcactctt gtctggatgc tgtccaaatc    1260
caagtgagaa gagatgggaa acttcttctg tctcagaatg tggaaggcat tcagcagttt    1320
cagcttagag gaaaacctaa agctaaatac ctcgttcgac tgaaaggaaa caagaaagga    1380
gcatctatgt tgaaaattct agctaccaca aggcctacta agcagtcatt tccctctctt    1440
cctgaagaca caagaatcaa agcctttgac aagctccgta cctgttcctc ggccaccgtg    1500
gcttggctag gcactcagga aaggaacaag ttttgcatct acaaaaaaga agtggatgat    1560
aactacaatg aagaccagaa gaaaagagag caaaaccaat gtctaggacc agatataagg    1620
aagaagtcag aaaaggtcct ctgtaaatat ttccacagtc aaaacctgca gaaagcagtg    1680
accacagaaa caattaaagg tcttcagcct ggcaaatctt acctgctgga tgtttatgtc    1740
ataggacatg gggggcactc tgtaaagtat cagagtaagg ttgtgaaaac tagaaagttc    1800
tgttagttac cttcttatag agatatatta tgtagaactc caggagggac attaaatcac    1860
tttaagtata aactgactac tcccacagtt gagagaagtt gtgacctgta cttgtactat    1920
ggaaggaagg atatcaacgt gtgtatattg atgtttatat aagtaactct tgaaggagac    1980
ttgttctagc gtgccccatg gtacctagtg tgtgtctgat gccggttggt gtcaaagata    2040
gagggcttct tgaaggaact tgccattcct tgctttgacc actgcatgaa ctgcttctaa    2100
attattttat tacctaaaaa tttaaaatat gccattcatt gcacacaccc acaaatgcaa    2160
atcattcctc tctatagatg ctaggatata tataaattat tttataaatt cttgttttaa    2220
atgtcagtgt ttctatgatt gtaaactatt aaattctttt cctattaaag tacagatcta    2280
atctaagtat tattaagttg atagccctct agtcagttat attgctattg taaattcttg    2340
tttgttgagt aaaatgttta aatactatat gtatctcatg tacaaagttg acatacatta    2400
tattcatgta cataaaatta aagagattag attatatagt gttca                   2445
```

<210> SEQ ID NO 260
<211> LENGTH: 672
<212> TYPE: DNA
<213> ORGANISM: Homo sapiens
<220> FEATURE:
<221> NAME/KEY: misc_feature
<223> OTHER INFORMATION: Incyte Clone No: 2493851

<400> SEQUENCE: 260

```
cccacgggcg cccagcctag gagtcgtccc ccaggcaatc cccagtactc ctgatgctgg      60
agagccagcc acactgcaca gtgccccggg ggcggtttct accaccctaa ggggtattct     120
tggctccagg catcagagtc catgtggctt gtggggccct catttctttc atgcccactg     180
gggaaggttc caccagcagg gctgttactg gcggggtcct ctgggagggg ggcaagaagg     240
ccagccacac caaggcactg gagctccacg actcctggcc ttcgattgga ggcccctctc     300
tgccagctct gccccttggg gggcaccagg caggactgcc agccgctctc ctggcaggtg     360
acatcagcct tcaagctcac tgtgccctca ccatttcatg ctcccccaag gtcctggtca     420
tgtcttctct tgggtatctt cccaggacag gcactggcac tggagccctg gcacttgttt     480
ctgggttcca tgcttcccag gtgtgatggt gaatgctgag tgtcagcttg actggattga     540
aggatgcaaa gtattgtcac tgggtgtgtc tgtgagggtg ttgccagagg agattcccat     600
ttgagtcagt gggctgggag aggcagaccc accctcaatc caggtgggca ccacctaatc     660
ggctgccagc aa                                                         672
```

<210> SEQ ID NO 261
<211> LENGTH: 1183
<212> TYPE: DNA
<213> ORGANISM: Homo sapiens
<220> FEATURE:
<221> NAME/KEY: misc_feature
<223> OTHER INFORMATION: Incyte Clone No: 2495719

<400> SEQUENCE: 261

| | | | | | |
|---|---|---|---|---|---|
| gagagaaatg | atgtgacagg | agcaagcgaa | ctacaacccc | gccccgccgt | tcctgcccca | 60 |
| ccactgcggc | ggcgggcgct | acgttccgga | agcggaaatg | gacgagaggt | cagggtaggt | 120 |
| ttttgaagat | ggcggccctc | aaggctctgg | tgtccggctg | tgggcggctt | ctccgtgggc | 180 |
| tactagcggg | cccggcagcg | accagctggt | ctcggcttcc | agctcgcggg | ttcagggaag | 240 |
| tggtggagac | ccaagaaggg | aagacaacta | taattgaagg | ccgtatcaca | gcgactccca | 300 |
| aggagagtcc | aaatcctcct | aacccctctg | gccagtgccc | catctgccgt | tggaacctga | 360 |
| agcacaagta | taactatgac | gatgttctgc | tgcttagcca | gttcatccgg | cctcatggag | 420 |
| gcatgctgcc | ccgaaagatc | acaggcctat | gccaggaaga | acaccgcaag | atcgaggagt | 480 |
| gtgtgaagat | ggcccaccga | gcaggtctat | taccaaatca | caggcctcgg | cttcctgaag | 540 |
| gagttgttcc | gaagagcaaa | ccccaactca | accggtacct | gacgcgctgg | gctcctggct | 600 |
| ccgtcaagcc | catctacaaa | aaaggccccc | gctggaacag | ggtgcgcatg | cccgtggggt | 660 |
| cacccctttct | gagggacaat | gtctgctact | caagaacacc | ttggaagctg | tatcactgac | 720 |
| agagagcagt | gcttccagag | ttcctcctgc | acctgtgctg | gggagtagga | ggcccactca | 780 |
| caagcccttg | gccacaacta | tactcctgtc | ccaccccacc | acgatggcct | ggtccctcca | 840 |
| acatgcatgg | acaggggaca | gtgggactaa | cttcagtacc | cttggcctgc | acagtagcaa | 900 |
| tgctgggagc | tagaggcagg | cagggcagtt | gggtcccttg | ccagctgcta | tggggcttag | 960 |
| gccatgctca | gtgctgggga | caggagtttt | gcccaacgca | gtgtcataaa | ctgggttcat | 1020 |
| gggcttaccc | attgggtgtg | cgctcactgc | ttgggaagtg | caggggggtcc | tgggcacatt | 1080 |
| gccagctggg | tgctgagcat | tgagtcactg | atctcttgtg | atggggccaa | tgagtcaatt | 1140 |
| gaattcatgg | gccaaacagg | tcccatcctc | ttcaaaaaaa | aaa | | 1183 |

<210> SEQ ID NO 262
<211> LENGTH: 1266
<212> TYPE: DNA
<213> ORGANISM: Homo sapiens
<220> FEATURE:
<221> NAME/KEY: misc_feature
<223> OTHER INFORMATION: Incyte Clone No: 2614153

<400> SEQUENCE: 262

| | | | | | |
|---|---|---|---|---|---|
| gcctgaccac | gcagttcttg | ggtctgtgct | gctggcctgg | ggttgtggtt | gaggccgggt | 60 |
| ctccgctcct | gtgcccggga | agatggtgct | aggtggttgc | ccggttagtt | acttacttct | 120 |
| gtgcggccag | gcggctttgc | tgctggggaa | tttacttctg | ctgcattgtg | tgtctcggag | 180 |
| ccactcgcaa | aatgcgaccg | ctgagcctga | gctcacatcc | gctggcgccg | cccagccgga | 240 |
| gggccccggg | ggtgctgcga | gctgggaata | tggcgacccc | cactctccgg | tcatcctctg | 300 |
| ctcttaccta | cctgatgaat | ttatagaatg | tgaagaccca | gtggatcatg | ttggaaatgc | 360 |
| aactgcatcc | caggaacttg | gttatggttg | tctcaagttc | ggcggtcagg | cctacagcga | 420 |
| cgtggaacac | acttcagtcc | agtgccatgc | cttagatgga | attgagtgtg | ccagtcctag | 480 |
| gacctttcta | cgagaaaata | aaccttgtat | aaagtatacc | ggacactact | tcataaccac | 540 |

-continued

```
tttactctac tccttcttcc tgggatgttt tggtgtggat cgattctgtt tgggacacac      600
tggcactgca gtagggaagc tgttgacgct tggaggactt gggatttggt ggtttgttga      660
ccttattttg ctaattactg gagggctgat gccaagtgat ggcagcaact ggtgcactgt      720
ttactaaaaa gagctgccat catggcccag ggaggcgggt gaaagctccg tcttctgaat      780
tcatctctac aggctcaaaa ctcctctttg atatcagacc tgatgttatt ttccttctttt     840 tggagggcat ttgtttggtt aagaaggctt ctttggactt tggaatttca acccagattt      900
taccttgcag acggaatgac aagcaaaaag tgttgtgggg aatcaaattt gttcctttcc      960
tcatgcacaa acataaagg atagtggcga gtttacaagc tgtggatggg tttccatagt      1020
cttcctttct gtacattgct atatcttcag tcctttggag caagtggacc taacaagttg      1080
agcaaaatga atatttggat ccatgttcct cttgtgaccc tgagtcttca tgcaaggaga      1140
tctgaagctg aacaatgaaa atcttcagca gaaatagaaa tggccgtgga ttgtaataca      1200
cactgaaatt ctgactttct gaatttaaat gtagaataaa ttttaccaac ttggaaaaaa      1260
aaaaaa                                                                 1266
```

<210> SEQ ID NO 263
<211> LENGTH: 1093
<212> TYPE: DNA
<213> ORGANISM: Homo sapiens
<220> FEATURE:
<221> NAME/KEY: misc_feature
<223> OTHER INFORMATION: Incyte Clone No: 2655184

<400> SEQUENCE: 263

```
gatggcttgt ttttcatttt ttttgtgctt tttggtccat ctattaataa aaatgaaccc      60
cgttacagag tcaccatcat gtctcttctc accaccctct gaatctgcat tagccagtca      120
actagccctt tcagcgtcat gtgaccagcg cgccccattc agcttggctg gtgtcgtttc      180
acatgaccca ggctgccag tcgtcaggtt gcaccgccct ttggttcccg agcatgctgt       240
tttctctcag ccttctctcc aaccttaacc aaatcggcag cagccacctc gaccgcccac      300
acattcctgg ccaatcagct cagctgttta tttaccaaat gtcttcacaa caactacagc      360
agcagccttc ggctaacaaa aaagcaggaa aaatccacaa caccccttc gccaaccaac       420 taaatccaac gcaacatctg gcaaaacctt tcagcaaat tcttcctggc cgtcagtccg       480
gcagcctcac ctcaccattt ctagcttgtt gaaacccaaa actaatctcc aagaaggaga     540
agcttctctc gcagccggag caggtccctt tctagagata ggagaagaga gagatcgctg     600
tctcgggaga gaaatcacaa gccgtcccga tccttctcta ggtctcgtag tcgatctagg    660
tcaaatgaaa ggaaatagaa gacagtttgc aagagaagtg gtgtacagga aattacttca    720
tttgacagga gtatgtacag aaaattcaag ttttgtttga gacttcataa gcttggtgca    780
tttttaagat gttttagctg ttcaaatctg tttgtctctt gaaacagtga cacaaaggtg    840
taattctcta tggtttgaaa tggatcatac gaggcatgta ataccaagaa ttgttacttt    900
acaatgttcc cttaagcaaa attgaatttg ctttgaactt ttagttatgc acagactgat   960
aataaacctc taacctgcc cagcggaagt gtgttttttt taaatttaaa tacagaacca     1020
ctggcaaaaa ttgaactaag atttacttt ttttccatag ctgggatata gggggatcc     1080 tctagagtcg acc                                                        1093
```

<210> SEQ ID NO 264
<211> LENGTH: 1056
<212> TYPE: DNA
<213> ORGANISM: Homo sapiens

```
<220> FEATURE:
<221> NAME/KEY: misc_feature
<223> OTHER INFORMATION: Incyte Clone No: 2848362

<400> SEQUENCE: 264
gcctgacatg cctgatcctc tcttttctgc agttcaaggg aaagacgaga tcttgcacaa      60
ggcactctgc ttctgccctt ggctggggaa gggtggcatg gagcctctcc ggctgctcat     120
cttactcttt gtcacagagc tgtccggagc cacaacacc acagtgttcc agggcgtggc     180
gggccagtcc ctgcaggtgt cttgcccta tgactccatg aagcactggg ggaggcgcaa     240
ggcctggtgc cgccagctgg gagagaaggg cccatgccag cgtgtggtca gcacgcacaa     300
cttgtggctg ctgtccttcc tgaggaggtg gaatgggagc acagccatca cagacgatac     360
cctgggtggc actctcacca ttacgctgcg gaatctacaa ccccatgatg cgggtctcta     420
ccagtgccag agcctccatg gcagtgaggc tgacaccctc aggaaggtcc tggtggaggt     480
gctggcagac cccctggatc accgggatgc tggagatctc tggttccccg gggagtctga     540
gagcttcgag gatgcccatg tggagcacag catctccagg agcctcttgg aaggagaaat     600
ccccttccca cccacttcca tccttctcct cctggcctgc atctttctca tcaagattct     660
agcagccagc gccctctggg ctgcagcctg gcatggacag aagccaggga cacatccacc     720
cagtgaactg gactgtggcc atgacccagg gtatcagctc caaactctgc cagggctgag     780
agacacgtga aggaagatga tgggaggaaa agcccaggag aagtcccacc agggaccagc     840
ccagcctgca tacttgccac ttggccacca ggactccttg ttctgctctg caagagact      900
actctgcctg aacactgctt ctcctggacc ctggaagcag ggactggttg agggagtggg     960
gaggtggtaa gaacacctga caacttctga atattggaca ttttaaacac ttacaaataa    1020
atccaagact gtcatattta gctggaaaaa aaaaaa                              1056

<210> SEQ ID NO 265
<211> LENGTH: 1183
<212> TYPE: DNA
<213> ORGANISM: Homo sapiens
<220> FEATURE:
<221> NAME/KEY: misc_feature
<223> OTHER INFORMATION: Incyte Clone No: 2849906

<400> SEQUENCE: 265
ggagctcagc cgagggctgc acaaagacct tcctggcctg ccccagacag agctgaggac      60
ccctggccgt gggcttgggc ctcggcttca caggatgggg ctgccagtgt cctgggcccc     120
tcctgccctc tgggttctag ggtgctgcgc cctgctcctc tcgctgtggg cgctgtgcac     180
agcctgccgc aggcccgagg acgtgtagc ccccaggaag agggcgcgga ggcagcgggc     240
gaggctgcag ggcagtgcga cggcggcgga agcgtcccta ctgaggcgga cccacctctg     300
ctccctcagc aagtcggaca ccagactgca cgagctgcac cggggccgc gcagcagcag     360
ggccctgcgg cctgccagca tggatctcct gcgcccacac tggctggagg tgtccaggga     420
catcaccgga ccgcaggcag ccccctctgc cttcccacac caggagctgc cccgggctct     480
gccggcagct gcagccaccg cagggtgcgc tggcctcgag gccacctatt ccaacgtggg     540
gctggcggcc cttccggggg tcagcctggc ggccagccct gtggtggccg agtatgcccg     600
cgtccagaag cgcaaaggga cccatcgcag tccccaagag ccacagcagg gaagactga     660
ggtgaccccg gccgctcagg tggacgtcct gtactccagg gtctgcaagc ctaaaaggag     720
ggacccagga cccaccacag acccgctgga ccccaagggc cagggagcga ttctggccct     780
ggcgggtgac ctggcctacc agaccctccc gctcagggcc ctggatgtgg acagcggccc     840
```

-continued

```
cctggaaaac gtgtatgaga gcatccggga gctggggac cctgctggca ggagcagcac      900
gtgcggggct gggacgcccc ctgcttccag ctgccccagc ctagggaggg gctggagacc      960
cctccctgcc tccctgccct gaacactcaa ggacctgtgc tccttcctcc agagtgaggc     1020
ccgtcccccg ccccgccccg cctcacagct gacagcgcca gtcccaggtc cccgggccgc     1080
cagcccgtga ggtccgtgag gtcctggccg ctctgacagc cgcggcctcc ccgggcatcc     1140
tagagaaggc ccgcgtctaa ataaagcgcc acgcagagtg atc                       1183
```

<210> SEQ ID NO 266
<211> LENGTH: 840
<212> TYPE: DNA
<213> ORGANISM: Homo sapiens
<220> FEATURE:
<221> NAME/KEY: misc_feature
<223> OTHER INFORMATION: Incyte Clone No: 2899137

<400> SEQUENCE: 266

```
gcatgtcatg gccgcctcca tggcccgggg aggcgtgagt gccagggttc tactgcaggc       60
tgccaggggc acctggtgga acagacctgg gggcacttcc gggtcggggg aggggtggc      120 gctggggaca accagaaagt ttcaagcgac aggctcgcgc ccggctggag aggaggacgc      180
gggcggcccg gagcggcccg gggacgtggt gaacgtggtg ttcgtagacc gctcaggcca      240
gcggatccca gtgagtggca gagtcgggga caatgttctt cacctggccc agcgccacgg      300
ggtggacctg gaaggggcct gtgaagcctc cctggcctgc tccacctgcc atgtgtatgt      360
gagtgaagac cacctggatc tcctgcctcc tcccgaggag agggaagacg acatgctaga      420
catggccccc ctcctccagg agaactcgcg gctgggctgc cagattgtgc tgacaccgga      480
gctggaagga gcggaattca ccctgcccaa gatcaccagg aacttctacg tggatggcca      540
tgtccccaag ccccactgac atgaacacct ggaccattcc acattgccat ggccccaggg      600
cccagattga gggaatagcc aggtgccagc cctgcccaga gtgcggacag gcccgggaga      660
gacgtggaag ccctgtgaa ggacaacacc cctgcttggg agagtccc atgtccaggc       720 tctggtgggg acagggcccc tagtggggtg gccttcccca ggcccctgag aatcagggtt      780
tgagtaggag tggactcata ttggagctgc aataaatcga taacacagga aaaaaaaaa      840
```

<210> SEQ ID NO 267
<211> LENGTH: 606
<212> TYPE: DNA
<213> ORGANISM: Homo sapiens
<220> FEATURE:
<221> NAME/KEY: misc_feature
<223> OTHER INFORMATION: Incyte Clone No: 2986229

<400> SEQUENCE: 267

```
aataatgttt gagacagaag agaccattgg ctagtattta gcaattatca tagttatttg       60
atttatatta aaaagcattt gtctttccac taaaacataa agggaataag ggcctagagt      120
tatatgagtt aatagtaatt atagtcaagc tggggttaaa aatttgttgt agatgatgca      180
tacttgggga taattaagag taccatctaa ttttctgtca ctttagaaag gaacaagtgg      240
caactttgtt gactatgtgg agaaagccag atgttcttta ctcagtaata cctgttactt      300 ctctttttt ccttttagca ctgaacctac cagatgtatt tgggttggtc gtcctcccat      360
tggaactgaa actacggatc ttccgacttc tggatgttcg ttccgtcttg tctttgtctg      420
cggtttgtcg tgacctcttt actgcttcaa atgacccact cctgtggagg ttttatatc      480 tgcgtgattt tcgaggtgat ttccgtaatg acatattcac aagaaagggc tcttattgtc      540
```

```
ttgattactc agctcaccaa aagtttttag ttgtaggatt tttctgttgc aaatgattac    600
aataaa                                                              606

<210> SEQ ID NO 268
<211> LENGTH: 1025
<212> TYPE: DNA
<213> ORGANISM: Homo sapiens
<220> FEATURE:
<221> NAME/KEY: misc_feature
<223> OTHER INFORMATION: Incyte Clone No: 3222081

<400> SEQUENCE: 268
gtccttcgag ctactccgtc tggccccgcc ttttctctgc tctcctgaac ctttaggctt     60
gtctcggccc atttgaagac caggaagttg atcaatcccg aggctgctga gagacggtgg    120
cgcgattggg acagtcgcca gggatggctg agcgtgaaga tgcagcgggt gtccgggctg    180
ctctcctgga cgctgagcag agtcctgtgg ctctccggcc tctctgagcc gggagctgcc    240
cggcagcccc ggatcatgga agagaaagcg ctagaggttt atgatttgat tagaactatc    300
cgggacccag aaaagcccaa tactttagaa gaactggaag tggtctcgga aagttgtgtg    360
gaagttcagg agataaatga agaagaatat ctggttatta tcaggttcac gccaacagta    420
cctcattgct ctttggcgac tcttattggg ctgtgcttaa gagtaaaact tcagcgatgt    480
ttaccattta aacataagtt ggaaatctac atttctgaag gaacccactc aacagaagaa    540
gacatcaata agcagataaa tgacaaagag cgagtggcag ctgcaatgga aaaccccaac    600
ttacgggaaa ttgtggaaca gtgtgtcctt gaacctgact gatagctgtt ttaagagcca    660
ctggcctgta attgtttgat atatttgttt aaactctttg tataatgtca gagactcatg    720
tttaatacat aggtgatttg tacctcagag catttttaa aggattcttt ccaagcgaga     780
tttaattata aggtagtacc taatttgttc aatgtataac attctcagga tttgtaacac    840
ttaaatgatc agacagaata atattttcta gttattatgt gtaagatgag ttgctatttt    900
tctgatgctc attctgatac aactattttt cgtgtcaaat atctactgtg cccaaatgta    960
ctcaatttaa atcattactc tgtaaaataa ataagcagat gattcttata atgaaaaaaa    1020
aaaaa                                                                1025

<210> SEQ ID NO 269
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 269

His His His His His His
1               5
```